US009944931B2

(12) United States Patent
Wucherpfennig et al.

(10) Patent No.: US 9,944,931 B2
(45) Date of Patent: Apr. 17, 2018

(54) METHODS AND COMPOSITIONS FOR REDUCING IMMUNOSUPRESSION BY TUMOR CELLS

(71) Applicants: Dana-Farber Cancer Institute, Inc., Boston, MA (US); The General Hospital Corporation, Boston, MA (US)

(72) Inventors: Kai W. Wucherpfennig, Brookline, MA (US); Glenn Dranoff, Sudbury, MA (US); Penghui Zhou, Quincy, MA (US); Donald Shaffer, Boston, MA (US); Nir Hacohen, Brookline, MA (US); Harvey I. Cantor, Wellesley, MA (US); Diana Alvarez Arias, Midland, MI (US)

(73) Assignees: Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/897,210

(22) PCT Filed: Jun. 10, 2014

(86) PCT No.: PCT/US2014/041739

§ 371 (c)(1),
(2) Date: Dec. 9, 2015

(87) PCT Pub. No.: WO2014/201021

PCT Pub. Date: Dec. 18, 2014

(65) Prior Publication Data

US 2016/0122766 A1 May 5, 2016

Related U.S. Application Data

(60) Provisional application No. 61/833,298, filed on Jun. 10, 2013, provisional application No. 61/921,303, (Continued)

(51) Int. Cl.
*A61K 35/14* (2015.01)
*C12N 15/113* (2010.01)

(Continued)

(52) U.S. Cl.
CPC .......... *C12N 15/1137* (2013.01); *A61K 35/17* (2013.01); *A61K 39/0011* (2013.01);

(Continued)

(58) Field of Classification Search
USPC .......................................... 536/24.5; 514/44
See application file for complete search history.

(56) References Cited

FOREIGN PATENT DOCUMENTS

| | | | |
|---|---|---|---|
| WO | WO 2012/079000 | A1 | 12/2011 |
| WO | WO 2012/038918 | A1 | 3/2012 |
| WO | WO 2013/121042 | A1 | 8/2013 |

OTHER PUBLICATIONS

Ashton, J.M., et al.; "Gene sets identified with oncogene cooperativity analysis regulate in vivo growth and survival of leukemia stem cells"; Cell Stem Cell, vol. 11; Sep. 7, 2012; pp. 359-372.

(Continued)

*Primary Examiner* — Terra C Gibbs
(74) *Attorney, Agent, or Firm* — Brinks Gilson & Lione

(57) ABSTRACT

The present disclosure provides, in part, methods of discovering immunotherapy targets in vivo, therapeutic compositions (e.g., shRNA, immunoresponsive cells expressing shRNA and/or a chimeric antigen receptors (CAR)), and methods of use thereof.

11 Claims, 38 Drawing Sheets

Related U.S. Application Data filed on Dec. 27, 2013, provisional application No. 61/929,821, filed on Jan. 21, 2014.

(51) Int. Cl.

| | |
|---|---|
| ***G01N 33/50*** | (2006.01) |
| ***A61K 35/17*** | (2015.01) |
| ***C12N 5/0783*** | (2010.01) |
| ***A61K 39/00*** | (2006.01) |
| ***C07K 14/725*** | (2006.01) |
| ***C07K 16/32*** | (2006.01) |
| ***C12Q 1/68*** | (2018.01) |

(52) U.S. Cl.

CPC .......... *C07K 14/7051* (2013.01); *C07K 16/32* (2013.01); *C12N 5/0638* (2013.01); *C12N 15/113* (2013.01); *C12Q 1/6886* (2013.01); *A61K 2039/5158* (2013.01); *A61K 2039/585* (2013.01); *C07K 2317/24* (2013.01); *C07K 2317/55* (2013.01); *C07K 2317/622* (2013.01); *C07K 2317/76* (2013.01); *C07K 2319/33* (2013.01); *C12N 2310/14* (2013.01); *C12N 2310/531* (2013.01); *C12N 2320/31* (2013.01); *C12N 2320/32* (2013.01); *C12Q 2600/178* (2013.01)

(56) References Cited

OTHER PUBLICATIONS

Barr, F.A. et al.; "Protein phosphatases and the regulation of mitosis"; Journal of Cell Science, vol. 124; Jul. 15, 2011; pp. 2323-2334.

Bellone, M., et al.; "Relevance of the tumor antigen in the validation of three vaccination strategies for melanoma"; Journal of immunology, vol. 165; Sep. 1, 2000; pp. 2651-2656.

Bollard, C.M. et al.; "T-cell therapy in the treatment of post-transplant lymphoproliferative disease"; Nat Rev Clin Oncol, vol. 9; Sep. 2012; pp. 510-519.

Brahmer, J.R., et al. "Safety and activity of anti-PD-L1 antibody in patients with advanced cancer"; The New England Journal of Medicine, vol. 366, No. 26; Jun. 28, 2012; pp. 2455-2465.

Chiang, C.W., et al.; "Protein phosphatase 2A dephosphorylation of phosphoserine 112 plays the gatekeeper role for BAD-mediated apoptosis"; Mol Cell Biol, vol. 23, Sep. 2003; pp. 6350-6362.

Doody, K.M. et al.; "T-cell protein tyrosine phosphatase is a key regulator in immune cell signaling: lessons from the knockout mouse model and implications in human disease"; Immunological reviews; vol. 228; Mar. 6, 2009; pp. 325-341.

Eichhorn, P. et al.; "A RNA interface screen identifies the protein phosphatase 2A subunit PR55gamma as a stress-sensitive inhibitor of c-SRC"; PLoS Genetics, vol. 3, Issue 12; Dec. 2007; pp. 2381-2394; XP009170430.

Fidler, I.J.; "Biological behavior of malignant melanoma cells correlated to their survival in vivo"; Cancer research, vol. 35; Jan. 1975; pp. 218-224.

Gabrilovich, D.I. et al.; "Myeloid-derived suppressor cells as regulators of the immune system"; Nature Reviews—Immunology, vol. 9; Mar. 2009; pp. 162-174.

Galon, J., et al.; "Type, density, and location of immune cells within human colorectal tumors predict clinical outcome"; Science, vol. 313, Sep. 29, 2006; pp. 1960-1964.

Gerber, S.A. et al.; "Absolute quantification of proteins and phosphoproteins from cell lysates by tandem MS"; PNAS, vol. 100; Jun. 10, 2003; pp. 6940-6945.

Gorer, P.A.; "Studies in antibody response of mice to tumour inoculation"; Br J Cancer, vol. 4; Dec. 1950; pp. 372-379.

Hamanishi, J., et al.; Programmed cell death 1 ligand 1 and tumor-infiltrating CD8+ T lymphocytes are prognostic factors of human ovarian cancer:; PNAS, vol. 104, No. 9; Feb. 27, 2007; pp. 3360-3365.

Han, Q., et.al.; "Multidimensional analysis of the frequencies and rates of cytokine secretion from single cells by quantitative microengraving"; Lab on a Chip, vol. 10; Apr. 8, 2010; pp. 1391-1400.

Hinterleitner, R. et al.; "Adoptive Transfer of siRNA Cblb-Silenced CD8+ T Lymphocytes Augments Tumor Vaccine Efficacy in a B16 Melanoma Model"; PLOS ONE, vol. 7, No. 9; Sep. 2012; p. e44295; XP055141808.

Hodi, F.S., et al.; "Improved Survival with Ipilimumab in Patients with Metastatic Melanoma"; New England Journal of Medicine, vol. 363, No. 8; Aug. 19, 2010; pp. 711-723.

Hogquist, K.A., et al.; "T cell receptor antagonist peptides induce positive selection"; Cell, vol. 76, pp. 17-27; Jan. 14, 1994.

Kalos M, et al.; "T Cells with Chimeric Antigen Receptors Have Potent Antitumor Effects and Can Establish Memory in Patients with Advanced Leukemia"; Science Translational Medicine, vol. 3, Issue 95; Aug. 10, 2011; 11 pages.

Koller, B.H. et al.; "Normal development of mice deficient in beta 2M, MHC class I proteins, and CD8+ T cells"; Science, vol. 248; Jun. 8, 1990; pp. 1227-1230.

Kurella, S., et al.; Transcriptional modulation of TCR, Notch and Wnt signaling pathways in SEB-anergized CD4+ T cells; Genes and Immunity, vol. 6; Jul. 21, 2005; pp. 596-608.

Lopes, A.R., et al.; "Bim-mediated deletion of antigen-specific CD8 T cells in patients unable to control HBV infection"; The Journal of clinical investigation, vol. 118; May 2008; pp. 1835-1845.

Luo, B., et al.; "Highly parallel identification of essential genes in cancer cells"; PNAS, vol. 105, No. 51; Dec. 23, 2008; pp. 20380-20385.

Macian, F., et al.; "Transcriptional mechanisms underlying lymphocyte tolerance"; Cell, vol. 109; Jun. 14, 2002; pp. 719-731.

Mahmoud, S.M., et al.; "Tumor-Infiltrating CD8+ Lymphocytes Predict Clinical Outcome in Breast Cancer"; Journal of Clinical Oncology, vol. 29, No. 15; May 20, 2011; pp. 1949-1955.

Milone et al.; "Chimeric Receptors Containing CD137 Signal Transduction Domains Mediate Enhanced Survival of T Cells and Increased Antileukemic Efficacy In Vivo"; Molecular Therapy, vol. 17; Apr. 21, 2009; pp. 1453-1464.

Mochida, S. et al.; "Greatwall phosphorylates an inhibitor of protein phosphatase 2A that is essential for mitosis"; Science, vol. 330, Nov. 25, 2010; pp. 1670-1673.

Muranski, P., et al.; "Tumor-specific Th17-polarized cells eradicate large established melanoma" Blood, vol. 112; Jul. 15, 2008; 362-373.

Overwijk, W.W., et al.; "Tumor regression and autoimmunity after reversal of a functionally tolerant state of self-reactive CD8+ T cells"; The Journal of experimental medicine, vol. 198; Aug. 18, 2003; pp. 569-580.

Pagès, F. et al; "In situ cytotoxic and memory T cells predict outcome in patients with early-stage colorectal cancer"; Journal of Clinical Oncology, vol. 27, No. 35; Dec. 10, 2009; pp. 5944-5951.

Paolino, M. et al.; "Cbl-b in T-cell activation"; Semin Immunopathol, vol. 32; Feb. 21, 2010; pp. 137-148.

Parish, I.A., et al.; "The molecular signature of CD8+ T cells undergoing deletional tolerance"; Blood, vol. 113; May 2009; pp. 4575-4585.

Restifo, N.P. et al.; "Adoptive immunotherapy for cancer: harnessing the T cell response"; Nature reviews—Immunology, vol. 12; Apr. 2012; pp. 269-281.

Riese, M.J. et al.; "Enhanced Effector Responses in Activated CD8+ T Cells Deficient in Diacylglycerol Kinases"; Cancer Research, vol. 73, No. 12; Apr. 10, 2013; pp. 3566-3577; XP055142357.

Shiao, S.L. et al.; "Immune microenvironments in solid tumors: new targets for therapy"; Genes & Development, vol. 25; Dec. 15, 2011; pp. 2559-2572.

Tamiya, T. et al.; "Suppressors of cytokine signaling (SOCS) proteins and JAK/STAT pathways: regulation of T-cell inflammation by SOCS1 and SOCS3"; Arteriosclerosis, Thrombosis, and Vascular Biology, vol. 31; May 2011; pp. 980-985.

(56) References Cited

OTHER PUBLICATIONS

Topalian, S.L. et al.; "Targeting the PD-1/B7-H1(PD-L1) pathway to activate anti-tumor immunity"; Current opinion in immunology, vol. 24; Apr. 2012; pp. 207-212.
Topalian, S.L., et al.; "Safety, activity, and immune correlates of anti-PD-1 antibody in cancer"; The New England Journal of Medicine, vol. 366, No. 26; Jun. 28, 2012; pp. 2443-2454.
Turtle, C.J., et al.; Engineered T cells for anti-cancer therapy. Current opinion in immunology, vol. 24, Oct. 2012; pp. 633-639.
Westbrook, T.F., et al.; :A genetic screen for candidate tumor suppressors identifies REST; Cell, vol. 121; Jun. 17, 2005; pp. 837-848.
Wherry, E.J., et al.; "Molecular signature of CD8+ T cell exhaustion during chronic viral infection"; Immunity, vol. 27; Oct. 2007; pp. 670-684.
Xu, T., et al.; Microarray analysis reveals differences in gene expression of circulating CD8(+) T cells in melanoma patients and healthy donors; Cancer research, vol. 64; May 15, 2004; pp. 3661-3667.
Zender, L., et al.; "An oncogenomics-based in vivo RNAi screen identifies tumor suppressors in liver cancer"; Cell, vol. 135; Nov. 26, 2008; pp. 852-864.
Zha, Y., et al.; "T cell anergy is reversed by active Ras and is regulated by diacylglycerol kinase-alpha"; Nat Immunol, vol. 7; Nov. 2006; 1166-1173.
Zheng, Y. et al.; "Molecular regulation of T-cell anergy"; EMBO Reports, vol. 9; Jan. 1, 2008; pp. 50-55.
Zhou, P. et al.; "In vivo discovery of immunotherapy targets in the tumour microenvironment"; Nature, vol. 506, No. 7486; Jan. 29, 2014; pp. 52-57; XP055141914.
International Search Report completed Dec. 17, 2014 for International Application No. PCT/US2014/041739.
Office Action dated Jan. 5, 2018 for Japanese Application No. 2016519595, including English translation.

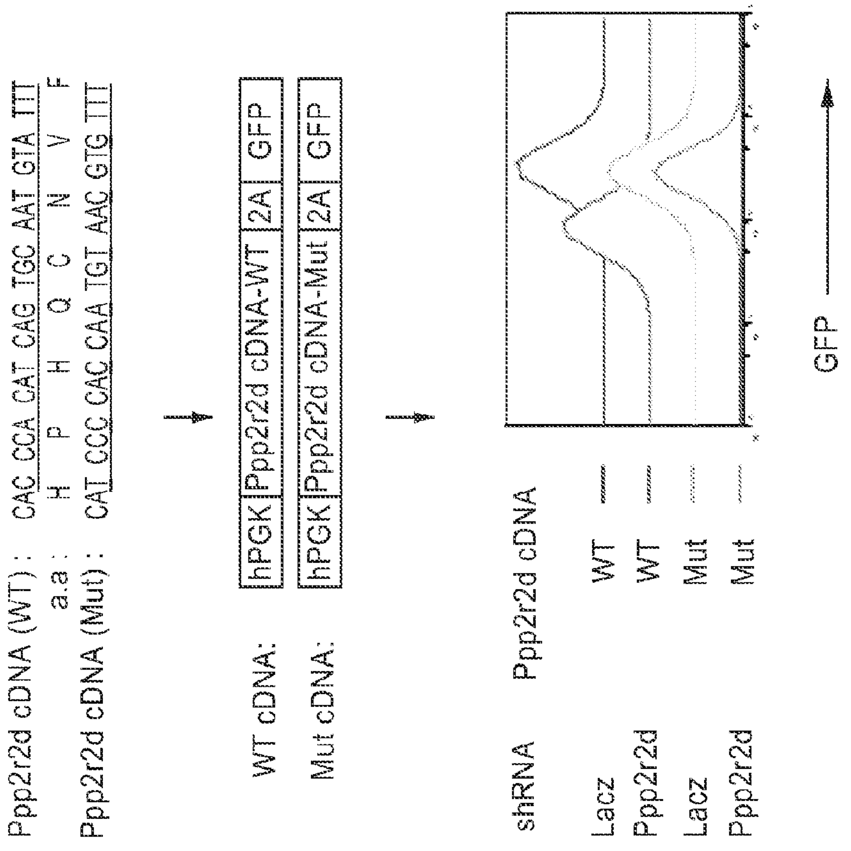

FIG. 10a

Ppp2r2d cDNA (WT):  CAC CCA CAT CAG TGC AAT GTA TTT
         a.a:         H   P   H   Q   C   N   V   F
Ppp2r2d cDNA (Mut):  CAT CCC CAC CAA TGT AAC GTG TTT

WT cDNA: [hPGK|Ppp2r2d cDNA-WT|2A|GFP]
Mut cDNA: [hPGK|Ppp2r2d cDNA-Mut|2A|GFP]

shRNA    Ppp2r2d cDNA
Lacz       WT
Ppp2r2d    WT
Lacz       Mut
Ppp2r2d    Mut

GFP →

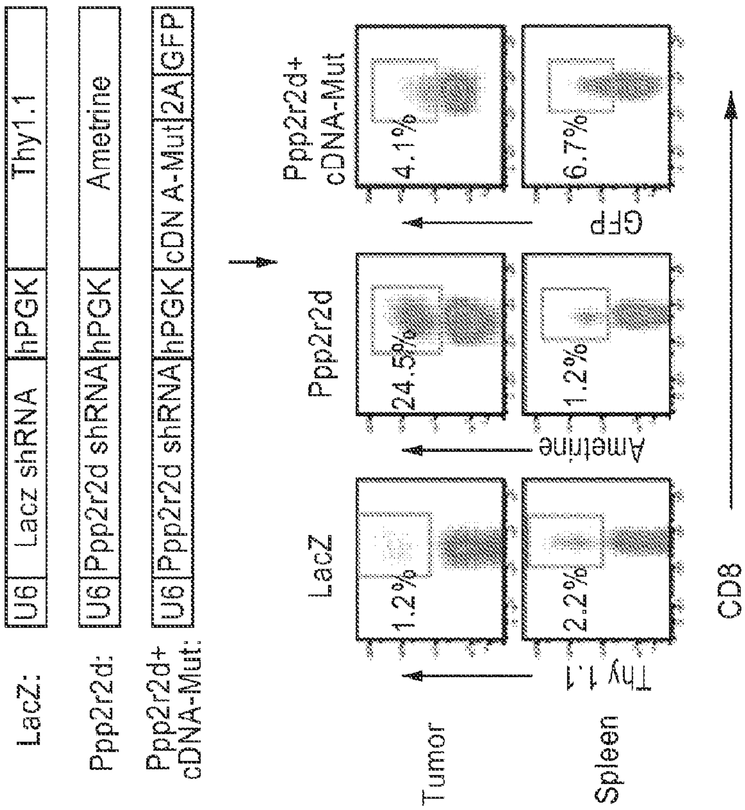

FIG. 10b

LacZ: [U6|Lacz shRNA|hPGK|Thy1.1]
Ppp2r2d: [U6|Ppp2r2d shRNA|hPGK|Ametrine]
Ppp2r2d+ cDNA-Mut: [U6|Ppp2r2d shRNA|hPGK|cDNA-Mut|2A|GFP]

Tumor / Spleen
LacZ: 1.2%, 2.2% (Thy1.1)
Ppp2r2d: 24.5%, 1.2% (Ametrine)
Ppp2r2d+ cDNA-Mut: 4.1%, 6.7% (GFP)

| Gene Symbol | Function | Enrichment Fold |
|---|---|---|
| Ppp2r2d | Regulatory subunit of PP2A phosphatase | 17.2 |
| Arhgap5 | Negative regulator of Rho GTPases | 15.7 |
| Alk | Anaplastic lymphoma kinase (translocation of nucleophosmin and ALK in ALCL) | 13.5 |
| Egr2 | Transcription factor involved in T cell unresponsiveness, expression of Cblb | 10.2 |
| Ptpn2 | Inhibitor of T cell and cytokine signaling | 7.4 |

| | Alk | Arhgap5 | Egr2 | Ppp2r2d | Ptpn2 |
|---|---|---|---|---|---|
| Alk | | 1.0E-31 | 5.6E-14 | ns | 1.9E-23 |
| Arhgap5 | | | 7.8E-07 | 9.5E-14 | 3.5E-16 |
| Egr2 | | | | 3.2E-08 | 3.3E-24 |
| Ppp2r2d | | | | | 1.6E-07 |
| Ptpn2 | | | | | |

METHODS AND COMPOSITIONS FOR REDUCING IMMUNOSUPRESSION BY TUMOR CELLS

RELATED APPLICATIONS

This application claims the benefit under 35 U.S.C. § 371 of International Application No. PCT/US2014/041739, filed Jun. 10, 2014, which claims priority to and the benefit of provisional application U.S. Ser. No. 61/929,821, filed Jan. 21, 2014, U.S. Ser. No. 61/921,303, filed Dec. 27, 2013 and U.S. Ser. No. 61/833,298, filed Jun. 10, 2013, the contents of which are incorporated herein by reference in their entireties.

GOVERNMENT SUPPORT

This invention was made with government support under grant numbers R01 CA173750, AI073861, and P30 CA014051 awarded by The National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Dec. 9, 2015, is named 14293-469 sequence listing_ST25.txt and is approximately 351 KB in size.

TECHNICAL FIELD

This invention relates to methods of discovering immunotherapy targets in vivo, therapeutic compositions that modulate immunotherapy targets (e.g., shRNA, immunoresponsive cells expressing shRNA and, in some cases a receptor targeting a cancer cell, e.g., a chimeric antigen receptors (CAR)), and related methods of use.

BACKGROUND

Cytotoxic T cells play a central role in immune-mediated control of cancers[1-3], and monoclonal antibodies that target inhibitory receptors on T cells can induce significant clinical benefit in patients with advanced disease[4-6]. For survival, tumors have developed numerous immunosuppressive mechanisms to promote their own growth and to successfully evade the host immune system, effectively blocking the activity of T cells in the tumor microenvironment. This is a central issue in oncology because strong infiltration by CD8 T cells, which have cytotoxic function against tumor cells, is associated with a favorable prognosis in multiple types of human cancer[1,3,8]. This natural defense mechanism is severely blunted in the majority of patients by multiple inhibitory signals emanating from the tumor, its stroma, regulatory T cells and myeloid cell populations.[9-11] Various molecular and cellular immunosuppressive mechanisms responsible for tumor evasion have been identified. Certain of these mechanisms target immune antitumor effector cells. However, many of the regulatory mechanisms that result in loss of T cell function within immunosuppressive tumors remain unknown. Improving on the limited success of cancer immunotherapy requires new approaches to inhibit immunosuppressive pathways initiated by tumor cells to evade the host immune system.

SUMMARY

The present disclosure provides targets for inhibiting immunosuppressive pathways used by tumor cells to inactivate and/or suppress immune cells.

The disclosure also provides compositions and methods related to shRNA with therapeutic potential.

The disclosure also provides immunoresponsive cells, including T cells (e.g., cells targeting a tumor antigen) expressing at least one shRNA or other nucleic acid molecule capable of silencing genes that inhibit T cell function.

The disclosure also provides immunoresponsive cells, including T cells, harboring at least one vector expressing a shRNA and at least one chimeric antigen receptor directed to a tumor antigen.

In some embodiments, the disclosure provides immunoresponsive cells having tumor specificity comprising a vector encoding a shRNA capable of silencing genes that inhibit T cell function. In some aspects, the shRNA sequence reduces the expression of a gene selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In another aspect, the shRNA comprises 15 contiguous nucleotides complementary to a nucleic acid sequence selected from the group consisting of SEQ ID NOs: 604-620 and 653-678. In some aspects, the immunoresponsive cell further comprises a vector encoding a tumor-specific T-cell receptor. In some aspects, the immunoresponsive cell is selected from the group consisting of a tumor-infiltrating lymphocyte (TIL), a Natural Killer T cell (NKT), a cytotoxic T lymphocyte (CTL), and a CD4 T cell.

In some embodiments, the immunoresponsive cell comprises a vector encoding a CAR, wherein the CAR comprises an antigen binding domain, a transmembrane domain, and a stimulatory domain. In some aspects, the antigen binding domain binds a tumor antigen or pathogen antigen. Exemplary tumor antigens include, for example, prostate-specific membrane antigen (PSMA), Carcinoembryonic Antigen (CEA), CD19, CD20, CD22, ROR1, mesothelin, CD333/IL3Ra, c-Met, Glycolipid F77, EGFRvIII, GD-2, NY-ESO-1 TCR, ERBB2, BIRC5, CEACAM5, WDR46, BAGE, CSAG2, DCT, MAGED4, GAGE1, GAGE2, GAGE3, GAGE4, GAGE5, GAGE6, GAGE7, GAGE5, IL13RA2, MAGEA1, MAGEA2, MAGEA3, MAGEA4, MAGEA6, MAGEA9, MAGEA10, MAGEA12, MAGEB1, MAGEB2, MAGEC2, TP53, TYR, TYRP1, SAGE1, SYCP1, SSX2, SSX4, KRAS, PRAME, NRAS, ACTN4, CTNNB1, CASP8, CDC27, CDK4, EEF2, FN1, HSPA1B, LPGAT1, ME1, HHAT, TRAPPC1, MUM3, MYO1B, PAPOLG, OS9, PTPRK, TPI1, ADFP, AFP, AIM2, ANXA2, ART4, CLCA2, CPSF1, PPIB, EPHA2, EPHA3, FGF5, CA9, TERT, MGAT5, CEL, F4.2, CAN, ETV6, BIRC7, CSF1, OGT, MUC1, MUC2, MUM1, CTAG1A, CTAG2, CTAG, MRPL28, FOLH1, RAGE, SFMBT1, KAAG1, SART1, TSPYL1, SART3, SOX10, TRG, WT1, TACSTD1, SILV, SCGB2A2, MC1R, MLANA, GPR143, OCA2, KLK3, SUPT7L, ARTC1, BRAF, CASP5, CDKN2A, UBXD5, EFTUD2, GPNMB, NFYC, PRDX5, ZUBR1, SIRT2, SNRPD1, HERV-K-MEL, CXorf61, CCDC110, VENTXP1, SPA17, KLK4, ANKRD30A, RAB38, CCND1, CYP1B1, MDM2, MMP2, ZNF395, RNF43, SCRN1, STEAP1, 707-AP, TGFBR2, PXDNL, AKAP13, PRTN3, PSCA, RHAMM, ACPP, ACRBP, LCK, RCVRN, RPS2, RPL10A, SLC45A3, BCL2L1, DKK1, ENAH, CSPG4, RGS5, BCR, BCR-ABL, ABL-BCR, DEK, DEK-CAN, ETV6-AML1, LDLR-FUT, NPM1-ALK1, PML-RARA, SYT-SSX1, SYT-SSX2, FLT3, ABL1, AML1, LDLR, FUT1, NPM1, ALK, PML1, RARA, SYT, SSX1, MSLN, UBE2V1, HNRPL, WHSC2, EIF4EBP1, WNK2, OAS3, BCL-2, MCL1, CTSH, ABCC3, BST2, MFGE8, TPBG, FMOD, XAGE1, RPSA, COTL1, CALR3, PA2G4, EZH2, FMNL1, HPSE, APC, UBE2A, BCAP31, TOP2A, TOP2B, ITGB8, RPA1, ABI2, CCNI, CDC2, SEPT2, STAT1, LRP1, ADAM17, JUP, DDR1, ITPR2, HMOX1, TPM4, BAAT, DNAJC8, TAPBP, LGALS3BP, PAGE4, PAK2, CDKN1A, PTHLH, SOX2, SOX11, TRPM8, TYMS, ATIC, PGK1, SOX4, TOR3A, TRGC2, BTBD2, SLBP, EGFR, IER3, TTK, LY6K, IGF2BP3, GPC3, SLC35A4, HSMD, H3F3A, ALDH1A1, MFI2, MMP14, SDCBP, PARP12, MET, CCNB1, PAX3-FKHR, PAX3, FOXO1, XBP1, SYND1, ETV5, HSPA1A, HMHA1, TRIM68, and any combination thereof. In some aspects, the antigen binding domain is an antigen-binding fragment of an antibody (e.g., Fab or a scFv). The intracellular domains of such CARs contain cytoplasmic signaling domains derived from the T cell receptor and costimulatory molecules.

In some embodiments, the vector is a plasmid, retroviral vector, or lentiviral vector.

In some embodiments, the disclosure provides isolated nucleic acid molecules encoding a shRNA sequence. In another embodiment, the disclosure provides isolated nucleic acid molecules encoding a CAR. In yet another embodiment, the disclosure provides isolated nucleic acid molecules encoding a CAR and a shRNA sequence. In some aspects, the isolated nucleic acid encodes a shRNA sequence reduces the expression of a gene selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, or Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In another aspect, the isolated nucleic acid encodes a shRNA comprising 15 contiguous nucleotides complementary a nucleic acid sequence selected from the group consisting of SEQ ID NOs: 604-620 and 653-678.

In some embodiments, the isolated nucleic acid encodes a CAR comprising an antigen binding domain, a transmembrane domain, a stimulatory domain, and a co-stimulatory domain. In some embodiments, the antigen binding domain is an antigen-binding fragment of an antibody (e.g., Fab or a scFv). In some embodiments, the antigen binding domain is a cytoplasmic signaling domain derived from the T cell receptor and costimulatory molecules.

In some embodiments, the antigen-binding domain binds tumor antigen (e.g., a tumor antigen associated with a solid tumor, lymphoid tumor, melanoma, carcinoma, sarcomas, adenocarcinoma, lymphoma, leukemia, kidney, breast, lung, bladder, colon, ovarian, prostate, pancreas, stomach, brain, head and neck, skin, uterine, testicular, glioma, esophagus, and liver cancer).

In some embodiments the disclosure provides vectors comprising an isolated nucleic acid encoding a shRNA sequence, an isolated nucleic acid encoding a CAR, or an isolated nucleic acid encoding a CAR and a shRNA sequence. In some aspects, the vector is a plasmid, lentiviral vector, retroviral vector, adenoviral vector, adeno-associated viral vector. The shRNA can be operably linked to RNA polymerase II promoter or an RNA polymerase III promoter.

In yet other embodiments, the invention provides compositions comprising immunoresponsive cells according to the invention, and a pharmaceutically acceptable carrier.

In some embodiments, the disclosure provides immunoresponsive cells transfected with a first vector encoding a CAR and a second vector encoding a shRNA sequence. In some aspects, the shRNA sequence reduces the expression of a gene selected from the group consisting of Ppp2r2d, Eif2ak3, Arhgap5, Smad2, Akap81, Rbks, Egr2, Dgka, Cblb, Map3k3, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In another aspect, the shRNA comprise 15 contiguous nucleotides complementary a nucleic acid sequence selected from the group consisting of SEQ ID NOs: 604-620 and 653-678. In some aspects, the immunoresponsive cell further comprises a vector encoding a tumor-specific T-cell receptor. In some aspects, the immunoresponsive cell is selected from the group consisting of a tumor-infiltrating lymphocyte (TIL), a Natural Killer T cell (NKT), a cytotoxic T lymphocyte (CTL), and a CD4 T cell.

In some embodiments, the disclosure provides methods for treating cancer in a subject, the method comprising administering to the subject an autologous T cell modified to express a tumor-specific T-cell receptor or CAR and an shRNA, wherein the shRNA sequence reduces the expression of a gene selected from the group consisting of Ppp2r2d, Eif2ak3, Arhgap5, Smad2, Akap81, Rbks, Egr2, Dgka, Cblb, Map3k3, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc. In some aspects, the shRNA sequence comprises 15 contiguous nucleotides complementary a nucleic acid sequence selected from the group consisting of: SEQ ID NOs: 604-620 and 653-678; and wherein the CAR comprises an antigen binding domain, a transmembrane domain, a stimulatory domain, and a co-stimulatory domain. In some aspects, the CAR comprises an antigen binding domain, a transmembrane domain, a stimulatory domain, and a co-stimulatory domain.

In some embodiments, the disclosure provides methods for treating cancer in a subject, the method comprising administering to the subject an autologous T cell modified to express a tumor-specific T-cell receptor or CAR and an shRNA of the invention. In yet another embodiment, the disclosure provides methods for treating cancer in a subject in need thereof by silencing genes that inhibit T cell function comprising administering to the subject an immunoresponsive cell comprising a vector, the vector encoding a tumor-specific T-cell receptor or a CAR and a shRNA sequence of the invention.

In some embodiments, the disclosure provides methods for identifying a gene that inhibits the function of an immunoresponsive T cell, the method comprising providing a population of immunoresponsive T cells harboring vectors expressing a shRNA, contacting the population of immunoresponsive T cells with an immunosuppressive tumor, determining whether a shRNA restores T cell function within the immunosuppressive tumor, and identifying a gene associated with a shRNA that restores T cell function within the tumor as a gene that inhibits the function of tumor-infiltrating T cells.

In some embodiments, the disclosure provides methods for increasing the immune response in a subject in need thereof, the method comprising administering a therapeutic agent that modulates the activity of a gene selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

In some cases the sequence encoding an shRNA comprises a first sequence comprising 15-25 (15, 16, 17, 18, 19, 20, 21, 22, 23, 24 or 25) nucleotides complementary to any of SEQ ID NOs: 604-620 or SEQ ID NOs: 653-678 and a second sequence that is the reverse complement of the first sequence with one or no mismatches (i.e., is perfectly complementary to the first sequence), and a third sequence of 5-9 nucleotides positioned between the first and second sequences.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. **10*a*** describes the generation of mutant Ppp2r2d cDNA with preserved protein sequence but disrupted shRNA binding site. EL4 cells were transduced with mutant or wild type Ppp2r2d cDNA on a vector also containing GFP. GFP-positive cells were sorted to purity and transduced with LacZ or Ppp2r2d shRNA vectors expressing a Thy1.1 reporter. shRNA-transduced (Thy1.1) cells were analyzed by flow cytometry for GFP expression. The Ppp2r2d shRNA reduced GFP levels when wild-type Ppp2r2d, but not when mutant Ppp2r2d was expressed. (SEQ ID NOS: 679-681 shown.)

FIG. **10*b*** demonstrates that expression of Ppp2r2d mutant cDNA prevents phenotype induced by Ppp2r2d shRNA. OT-I T cells were transduced with a vector encoding LacZ shRNA, Ppp2r2d shRNA or Ppp2r2d shRNA plus mutant Ppp2r2d cDNA. The different cell populations were normalized for transduction efficiency and co-injected into B16-Ova tumor bearing mice. The percentage of each T cell population in tumors and spleens was quantified by gating on $CD8^+V\alpha2^+V\beta5^+$ T cells; transduced cells were detected based on expression of Thy1.1 or Ametrine/GFP fluorescent reporters (representative data from 2 independent experiments, n=3 mice per experiment).

FIG. **10*c*** is a graph demonstrating real-time PCR analysis for Ppp2r2d expression in OT-I T cells transduced with LacZ shRNA, Ppp2r2d shRNA, and Ppp2r2d shRNA plus Ppp2r2d mutant cDNA. Data represent biological replicates (n=3), each value represents mean+/−s.d.

Figure 11:
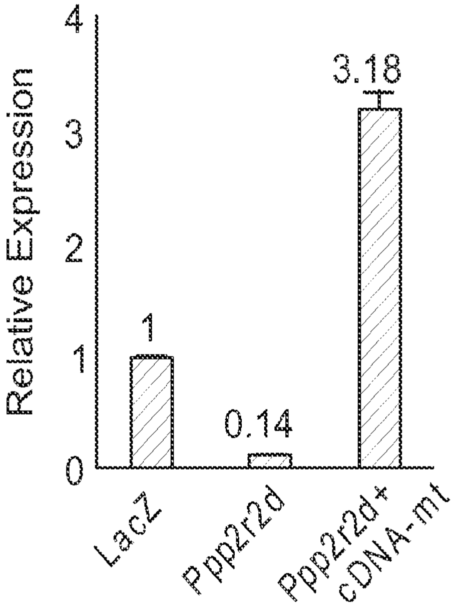

FIG. 11 is a graph demonstrating real-time qPCR analysis for Ppp2r2d mRNA levels in OT-I T cells transduced with LacZ shRNA or one of three Ppp2r2d shRNAs identified in the screen.

FIG. 12*a* is a table demonstrating enrichment of particular shRNAs in tumor versus spleen which was calculated based on deep sequencing results from the secondary screen.

Figure 12B:
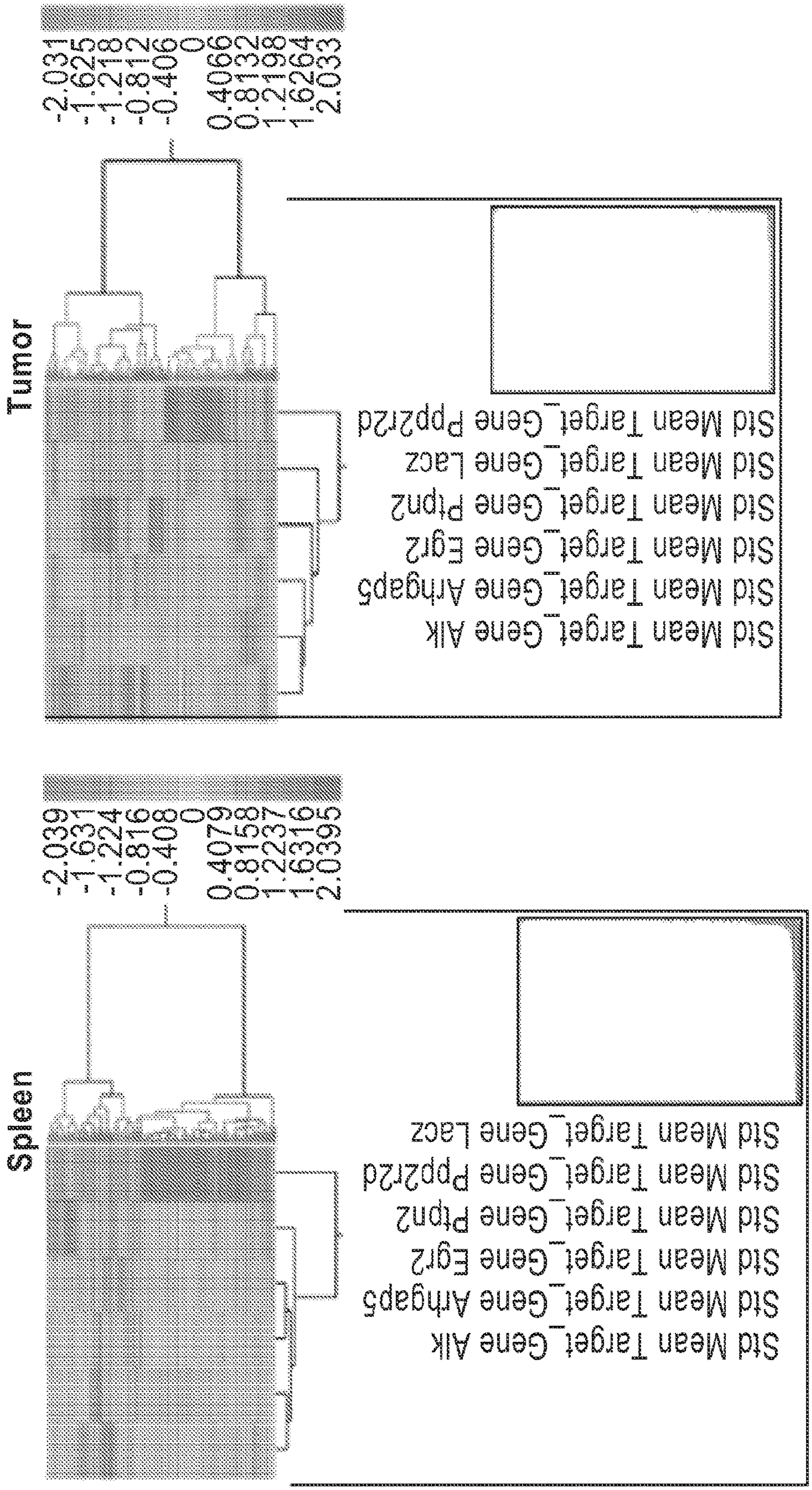

FIG. 12*b* demonstrates clustering of mean expression levels for mRNAs found to be significantly regulated by T cells in or tumors expressing the LacZ control shRNA or one of five experimental shRNAs. Significant expression differences were defined as an Anova p value<0.01 between T cells expressing LacZ control shRNA or one of five experimental shRNAs (Alk, Arhgap5, Egr2, Ptpn2 or Ppp2r2d) (JMP-Genomics 6.0, SAS Institute Inc.). mRNAs significantly regulated in one or more treatment groups are shown after clustering (Fast Ward).

Figure 12C:
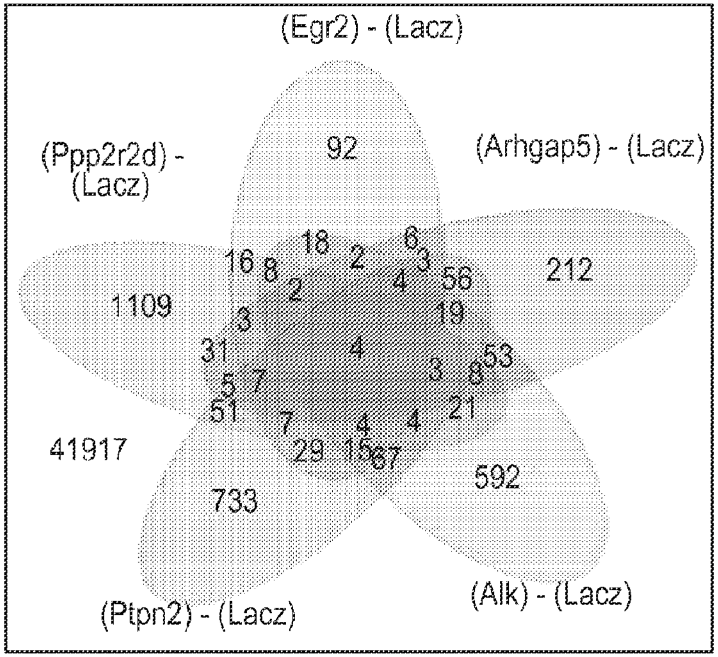

FIG. 12*c* is a Venn diagram showing overlaps between expression signatures by tumor-infiltrating T cells transduced with one of the five experimental shRNAs (signatures defined as an Anova p<0.01 as described above). Indicated are the numbers of overlapping probe IDs for any combination of the 5 signatures, as indicated by the overlapping ovals. The significance of the overlaps versus that expected by random chance (Fishers Exact Test) is shown in the accompanying table.

Figure 13A:
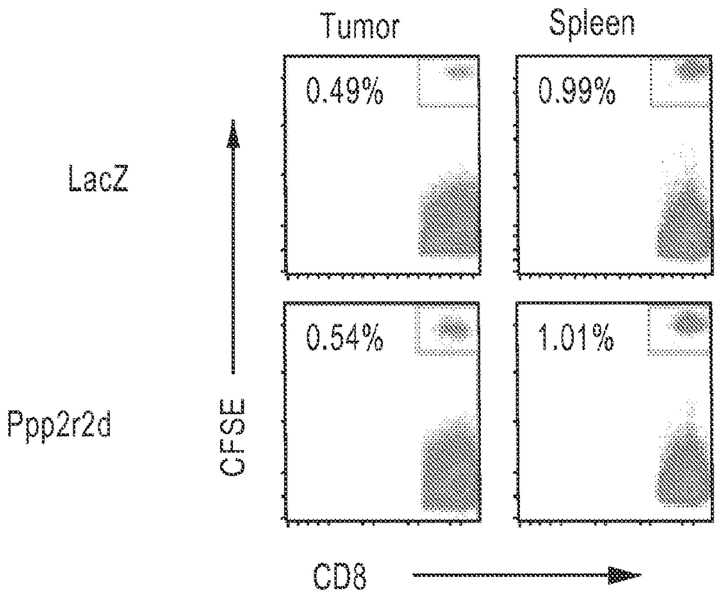

FIG. 13*a* is a set of graphs showing representative flow cytometry plots of demonstrating the frequency of Ppp2r2d or LacZ shRNA-transduced CD8 T cells in tumors on day 1.

Figure 13B:
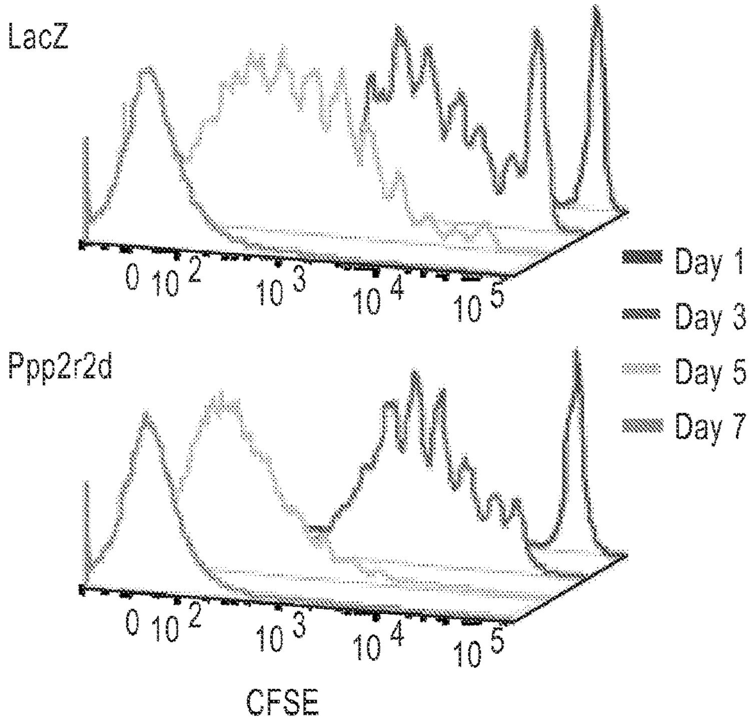

FIG. 13*b* are a pair of graphs demonstrating the degree of proliferation (based on CFSE dilution) by Ppp2r2d shRNA-transduced CD8 T cells compared to LacZ shRNA-transduced T cells in tumors on days 1, 3, 5, and 7.

Figure 13C:
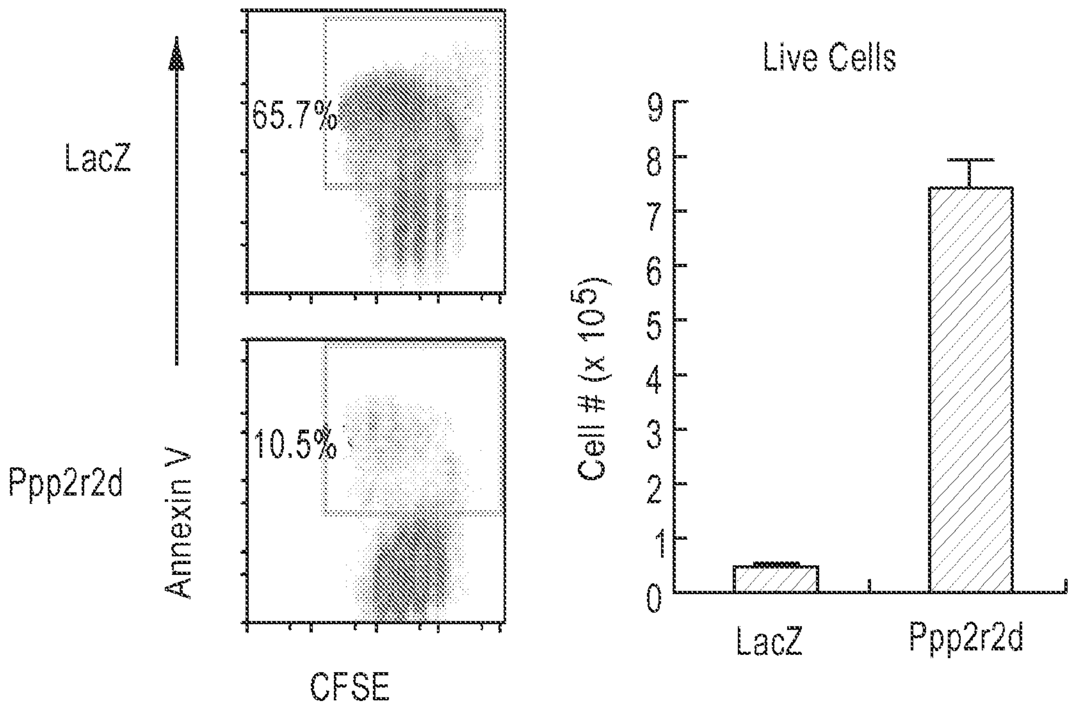

FIG. 13*c* is a set of graphs demonstrating that Ppp2r2d-silencing inhibits T cell apoptosis upon encounter of tumor cells. CFSE-labeled OT-I T cells were co-cultured with B16-Ova tumor cells for 72 hours. Cells were stained with CD8 and annexin V.

Figure 13D:
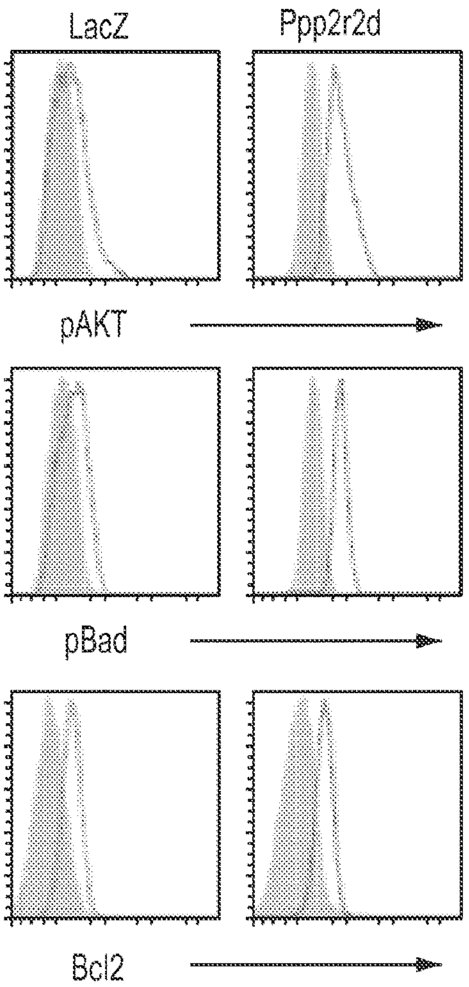

FIG. 13*d* is a set of graphs demonstrating intracellular staining for anti-apoptotic proteins. OT-I T cells expressing LacZ or Ppp2r2d shRNA were co-cultured with B16-Ova tumor cells for 48 hours and then stained with isotype control (grey) and phospho-AKT (Ser473), phospho-Bad (Ser 112) or Bcl-2 antibodies.

Figure 13E:
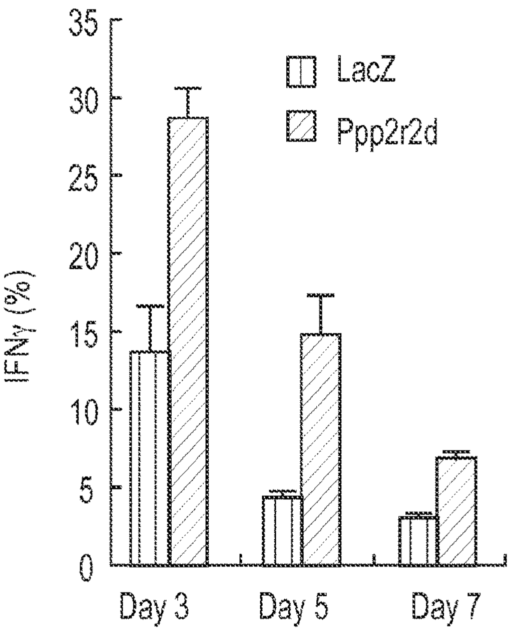

FIG. 13*e* is a graph demonstrating increased IFN-γ secretion by Ppp2r2d-silenced T cells. OT-I T cells isolated from B16-Ova tumor-bearing mice were assayed for IFN-γ expression by intracellular staining.

Figure 13F:
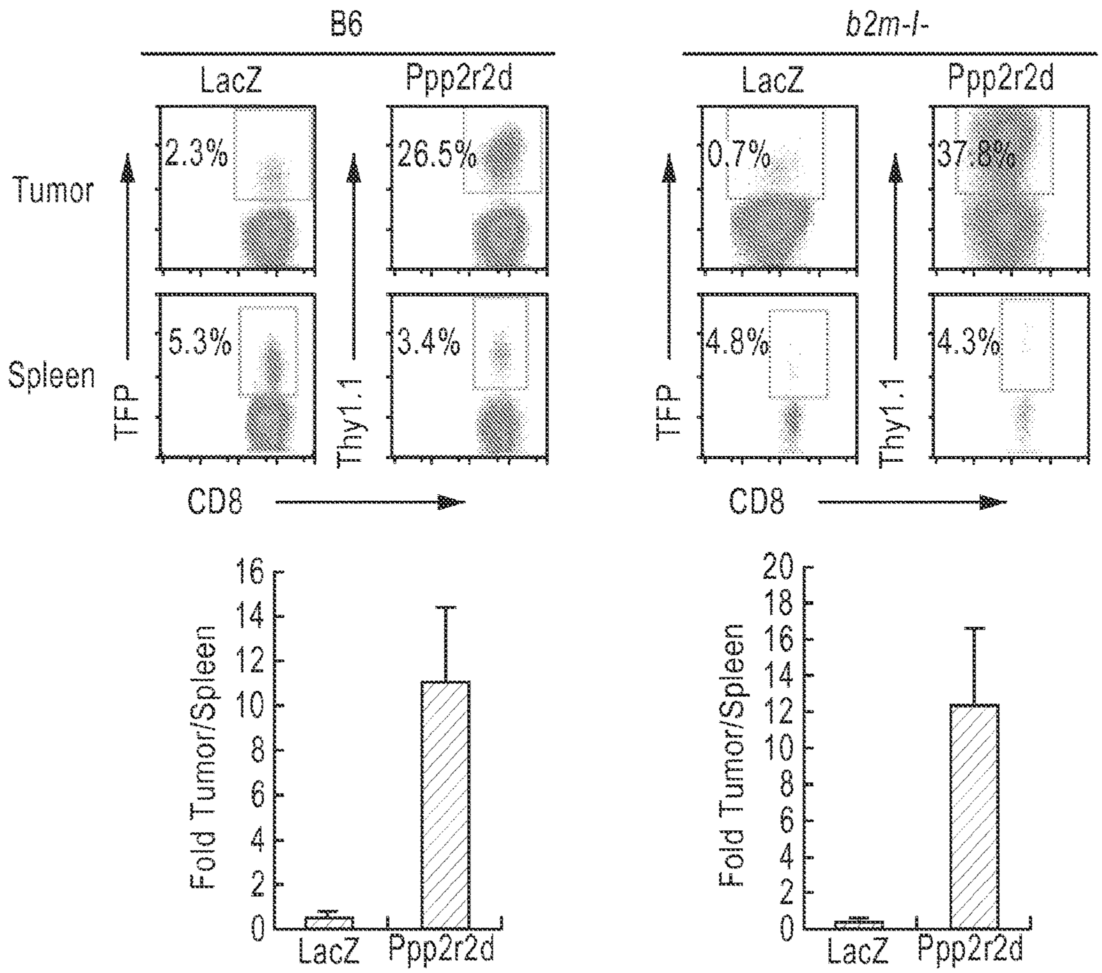

FIG. 13*f* is a set of graphs demonstrating Ppp2r2d-silenced T cells expand in tumors even without presentation of tumor antigens by professional antigen presenting cells. LacZ or Ppp2r2d shRNA-expressing OT-I T cells were transferred into day 14 B16-Ova tumor-bearing C57BL/6 or b2m−/− mice. shRNA-expressing T cells were identified based on expression of teal fluorescent protein (TFP) or Thy1.1 (fold enrichment in tumors compared to spleens).

Figure 13G:
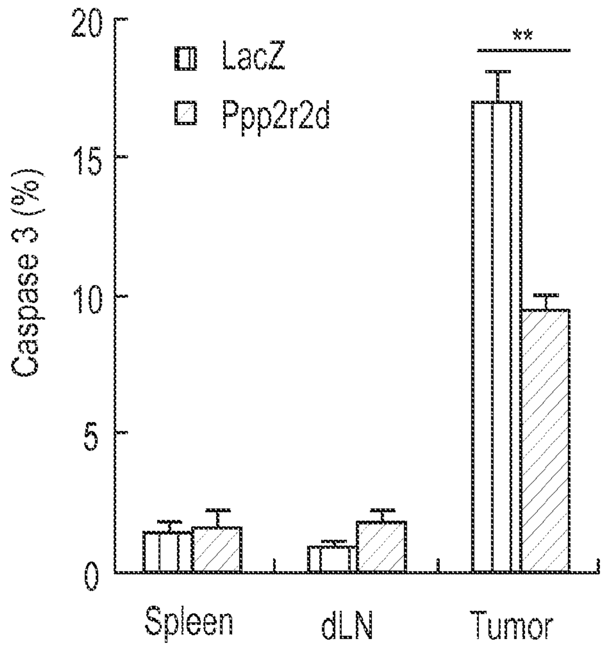

FIG. 13*g* is a graph demonstrating that Ppp2r2d-silencing inhibits T cell apoptosis upon encounter of tumor cells. CFSE-labeled OT-I T cells were co-cultured with B16-Ova tumor cells for 72 hours (activated caspase-3).

Figure 14:
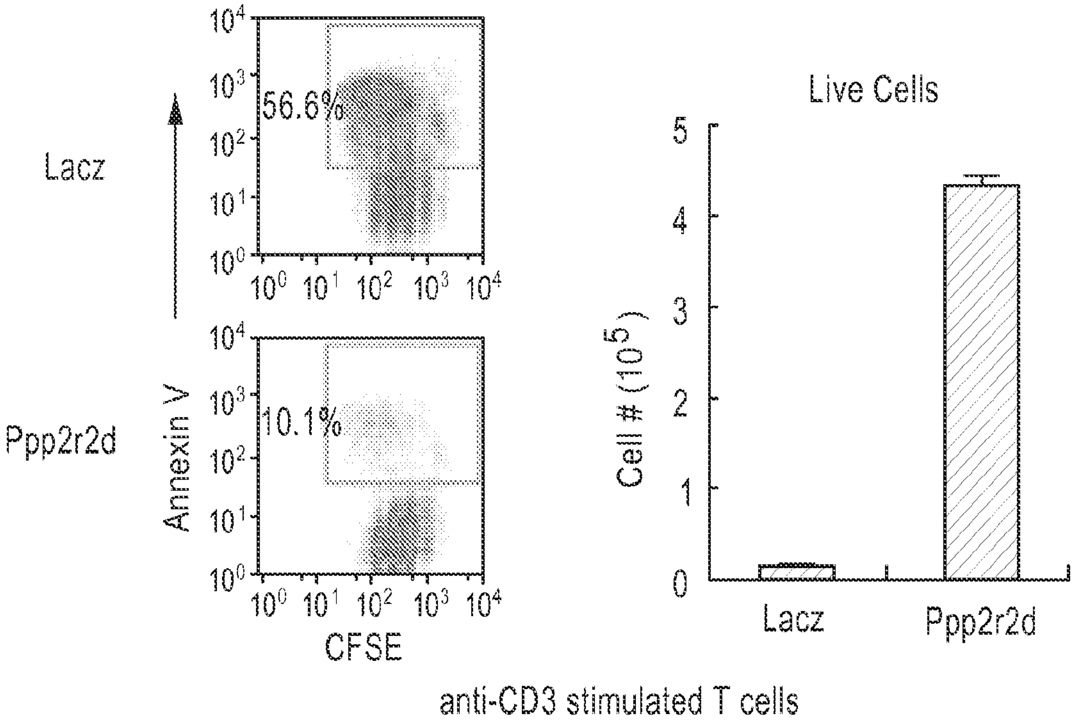

FIG. 14 is a set of graphs demonstrating OT-I T cells expressing LacZ or Ppp2r2d shRNAs labeled with CFSE and stimulated with CD3 antibody for 72 h. Cells were then stained with CD8 and annexin V and analyzed by flow cytometry.

Figure 15:
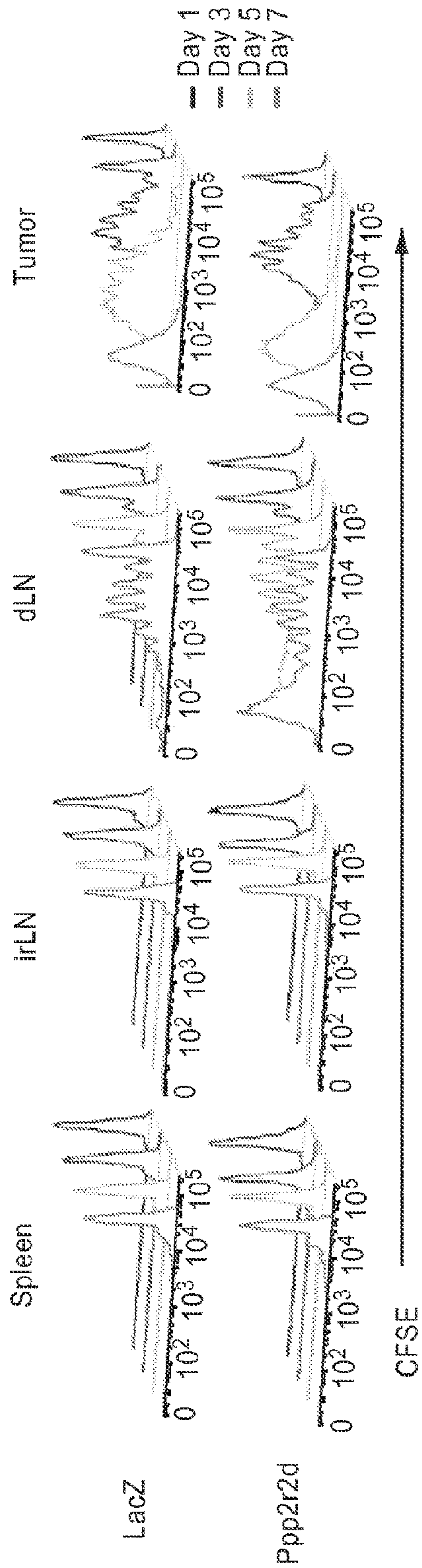

FIG. 15 is a set of graphs demonstrating accumulation of Ppp2r2d shRNA-expressing T cells in tumors and tumor-draining lymph nodes, but not other secondary lymphoid organs. OT-I T cells expressing Ppp2r2d or LacZ shRNAs were labeled with CF SE and injected into B16-Ova tumor-bearing mice. T cells were isolated from the indicated organs on days 1, 3, 5 and 7 to examine the extent of T cell accumulation based on dilution of the CSFE dye.

Figure 16A:
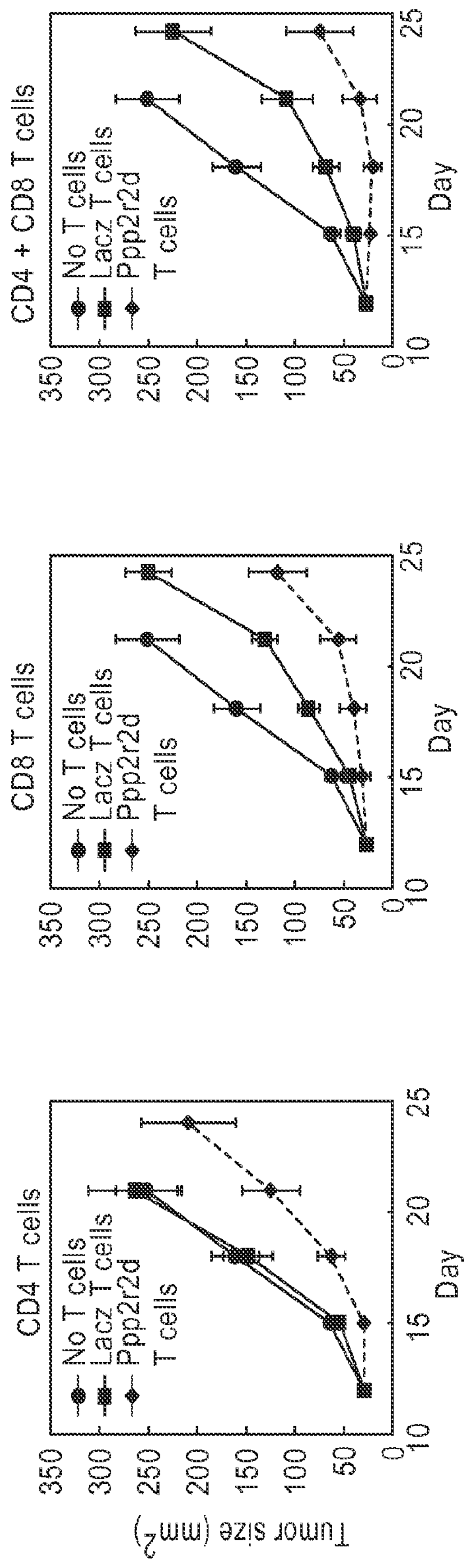
Figure 16B:
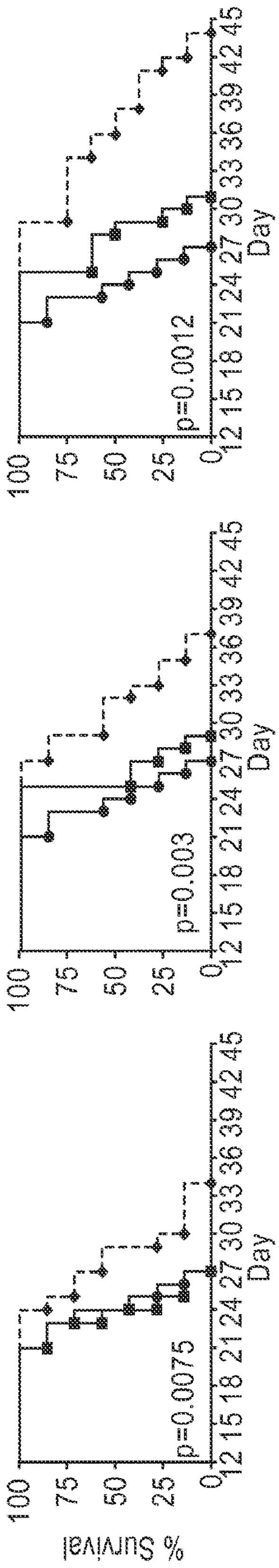
Figure 16C:
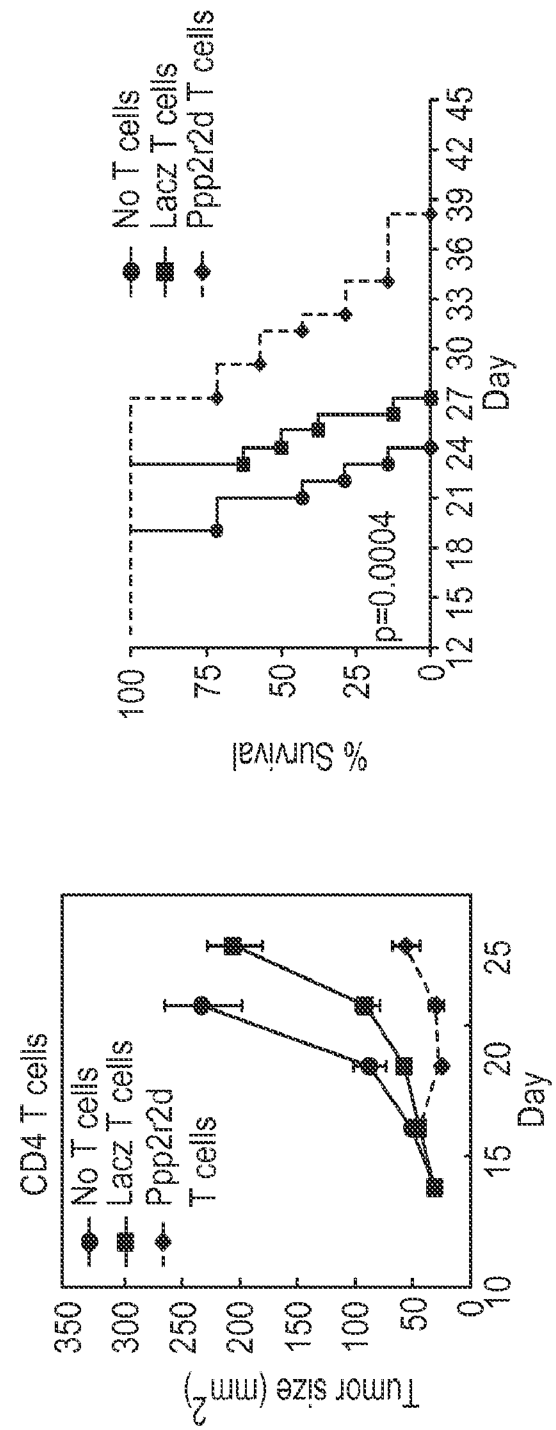

FIGS. 16*a-c* are a set of graphs demonstrating that the silencing of Ppp2r2d enhances anti-tumor activity of CD4 and CD8 T cells. T cells were activated with anti-CD3/CD28 beads, infected with lentiviruses driving LacZ or Ppp2r2d shRNA expression and injected into B16-Ova (a,b) or B16 (c) tumor-bearing mice. Tumor size was measured every three days following T cell transfer using calipers on the two longest axes. a,b $CD4^+$ TRP-1 and/or $CD8^+$ OT-I T cells ($2\times10^6$) were transferred (day 12 and 17) into mice bearing day 12 B16-Ova tumors. Tumor burden (a) and survival (b) were assessed. c, $CD4^+$ TRP-1 and $CD8^+$ pmel-1 T cells ($3\times10^6$ $CD4^+$ TRP-1 plus $3\times10^6$ $CD8^+$ pmel-1) were transferred (day 10 and 15) into mice with day 10 B16 tumors. Log-rank (Mantel-Cox) test was performed using GraphPad Prism version 6 comparing survival of mice treated with LacZ versus Ppp2r2d shRNA-expressing T cells.

Figure 17:
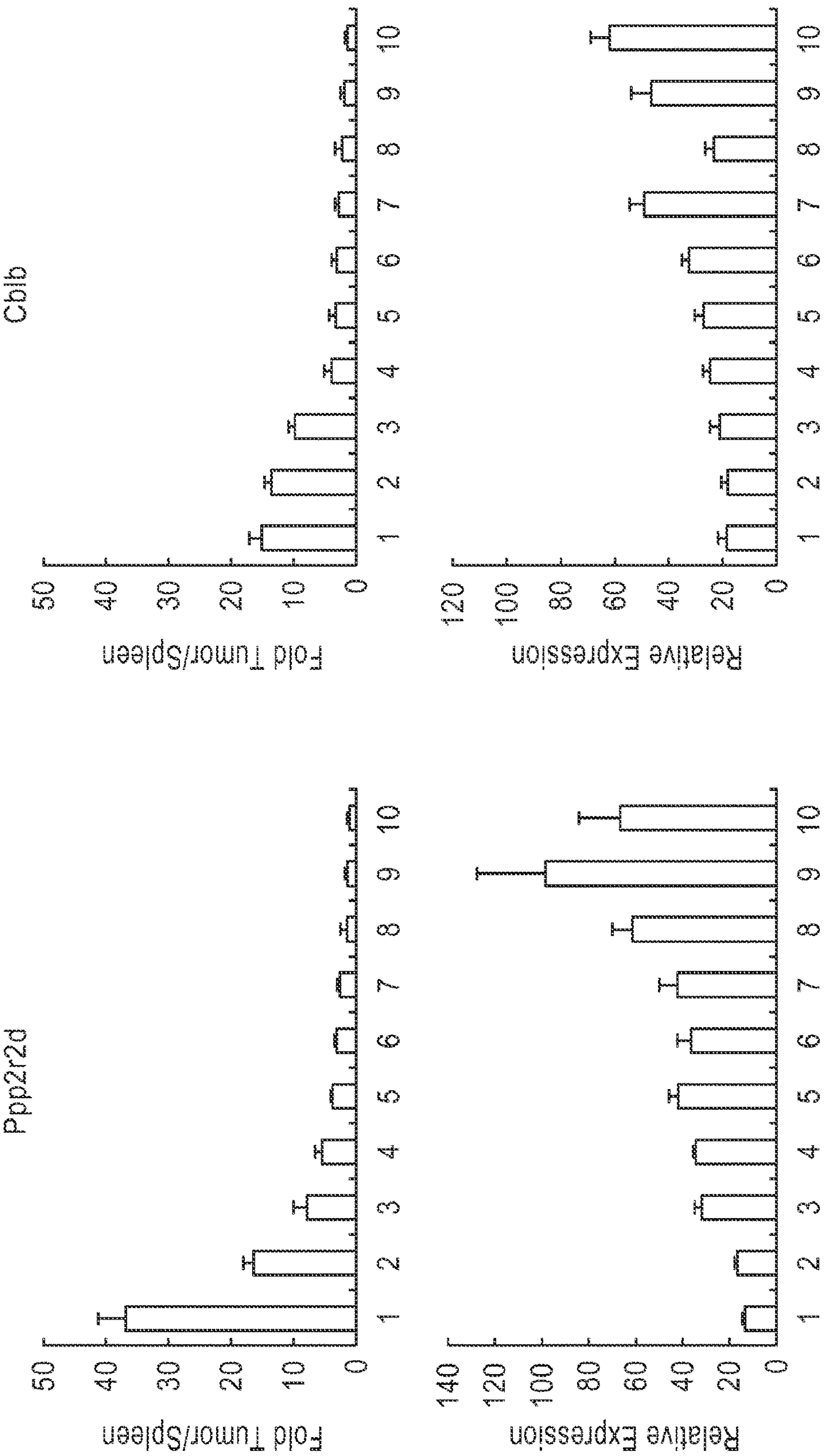

FIG. 17 is a set of graphs demonstrating FACS analysis of T cell enrichment in tumors compared to spleen for cells expressing a panel of Ppp2r2d or Cblb shRNAs (upper panels). Ppp2r2d and Cblb mRNA levels were measured by qPCR prior to T cell transfer (lower panels). Data represent biological replicates (n=3), each value represents mean+/−s.d.

Figure 18:
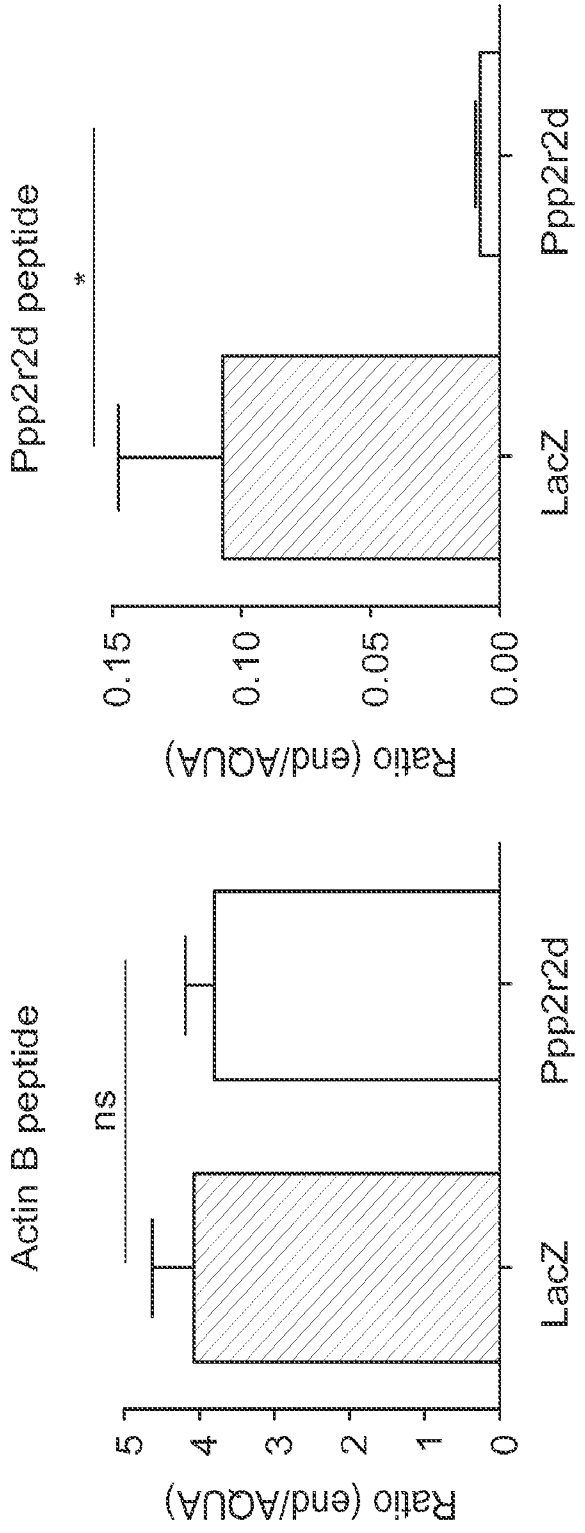

FIG. 18 is a set of graphs demonstrating Ppp2r2d protein quantification by mass spectrometry with labeled synthetic peptides (AQUA, ratio of endogenous to AQUA peptides). Representative data from two independent experiments (a-d); Two-sided student's t-test, * P<0.05, ** P<0.01; mean+/−s.d.

Figure 19:
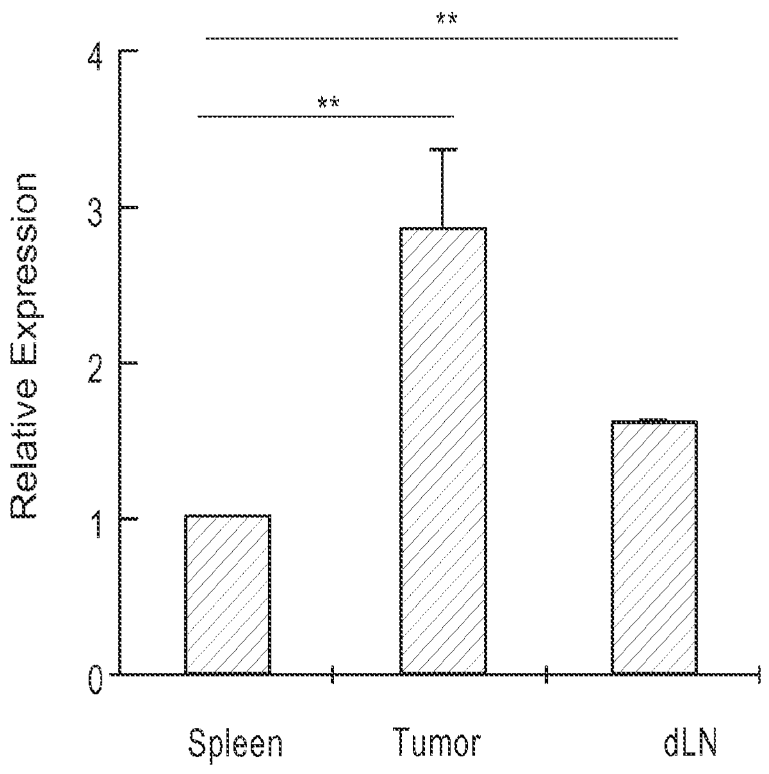

FIG. 19 is a graph demonstrating qPCR analysis for Ppp2r2d mRNA in tumor-infiltrating OT-I T cells (day 7).

Figure 20A:
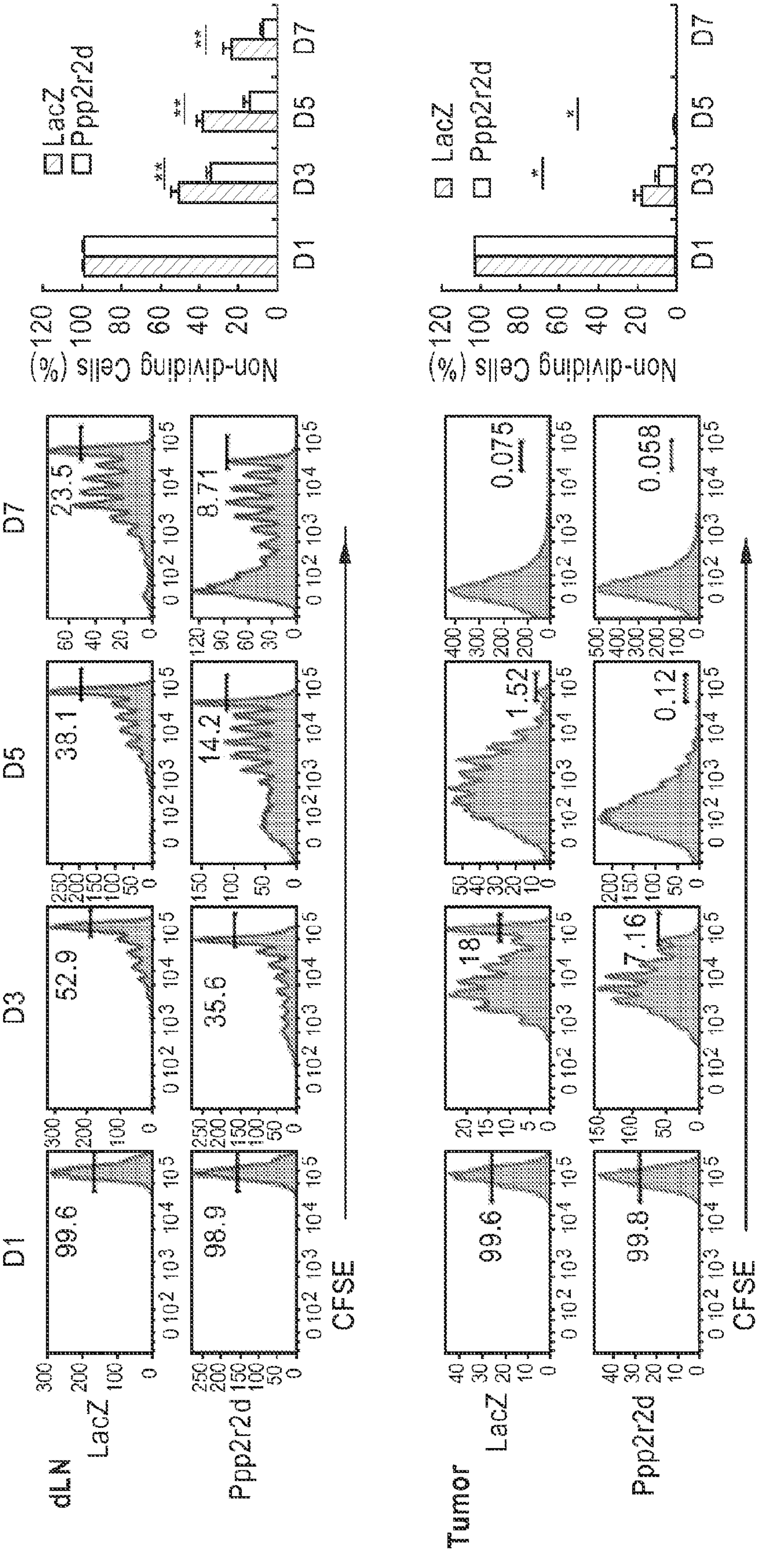

FIG. 20*a* are graphs showing representative flow cytometry plots demonstrating proliferation of Ppp2r2d shRNA-expressing T cells in tumors and tumor-draining lymph nodes. OTI T cells expressing Ppp2r2d or LacZ shRNAs were labeled with CFSE and injected into B16-Ova tumor-bearing mice. T cells were isolated from the indicated organs on days 1, 3, 5 and 7 to examine the extent of T cell proliferation based on CFSE dilution. T cells that had not diluted CFSE (nondividing cells) were quantified (right).

Figure 20B:
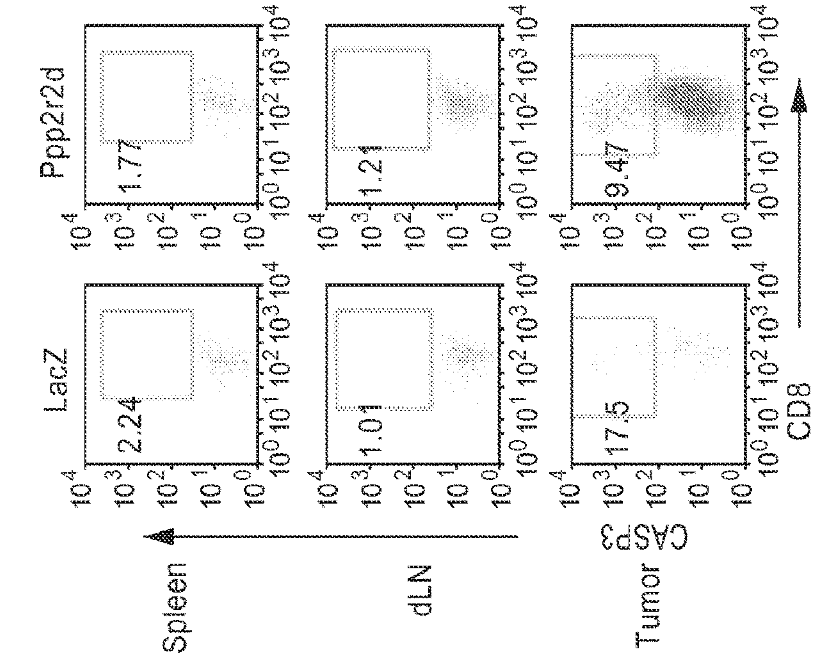

FIG. 20*b* are graphs showing representative flow cytometry plots demonstrating viability of tumor-infiltrating T cells. OT-I T cells expressing Pp2r2d or LacZ shRNAs were injected into B16-Ova tumor-bearing mice. T cells were isolated on day 7 and apoptosis was assessed by intracellular staining with an antibody specific for activated caspase-3 (some T cell death may have been caused by the isolation procedure from tumors).

Figure 20C:
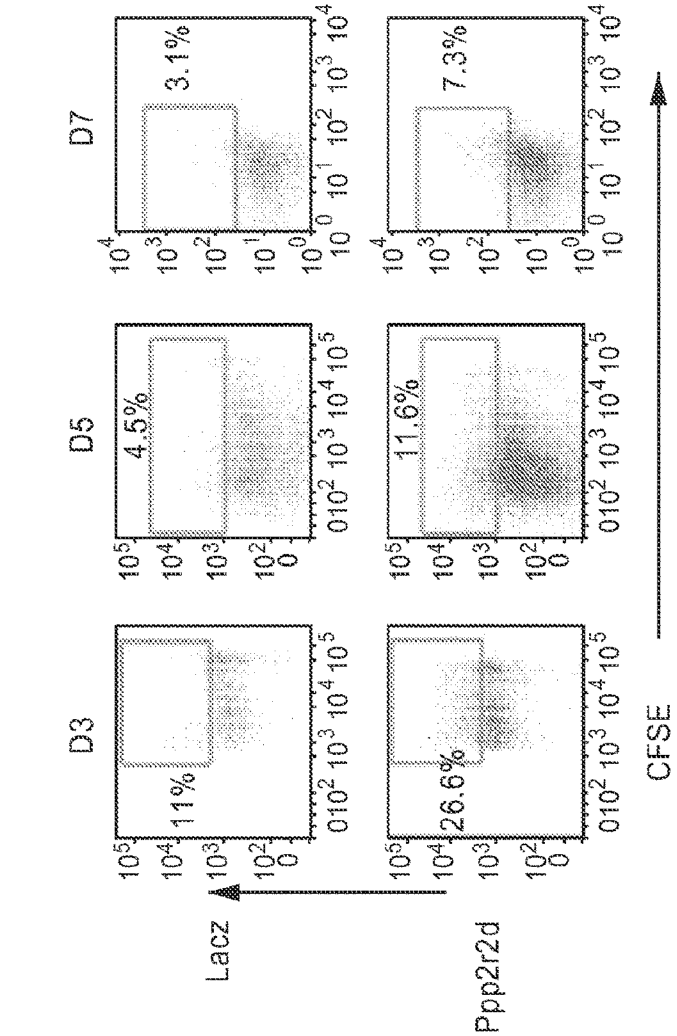

FIG. 20*c* are graphs showing representative flow cytometry plots demonstrating intracellularcytokine staining for IFNγ by LacZ and Ppp2r2d shRNA-expressing T cells harvested from B16-Ova tumors; T cells were labeled with CFSE prior to injection. Data for all experiments are representative of two independent trials. Statistical analysis was performed on biological replicates (n=3); * P<0.05, ** P<0.01, two-sided Student's t-test. Each value represents mean+/−s.d.

Figures 21A, 21B, 21C:
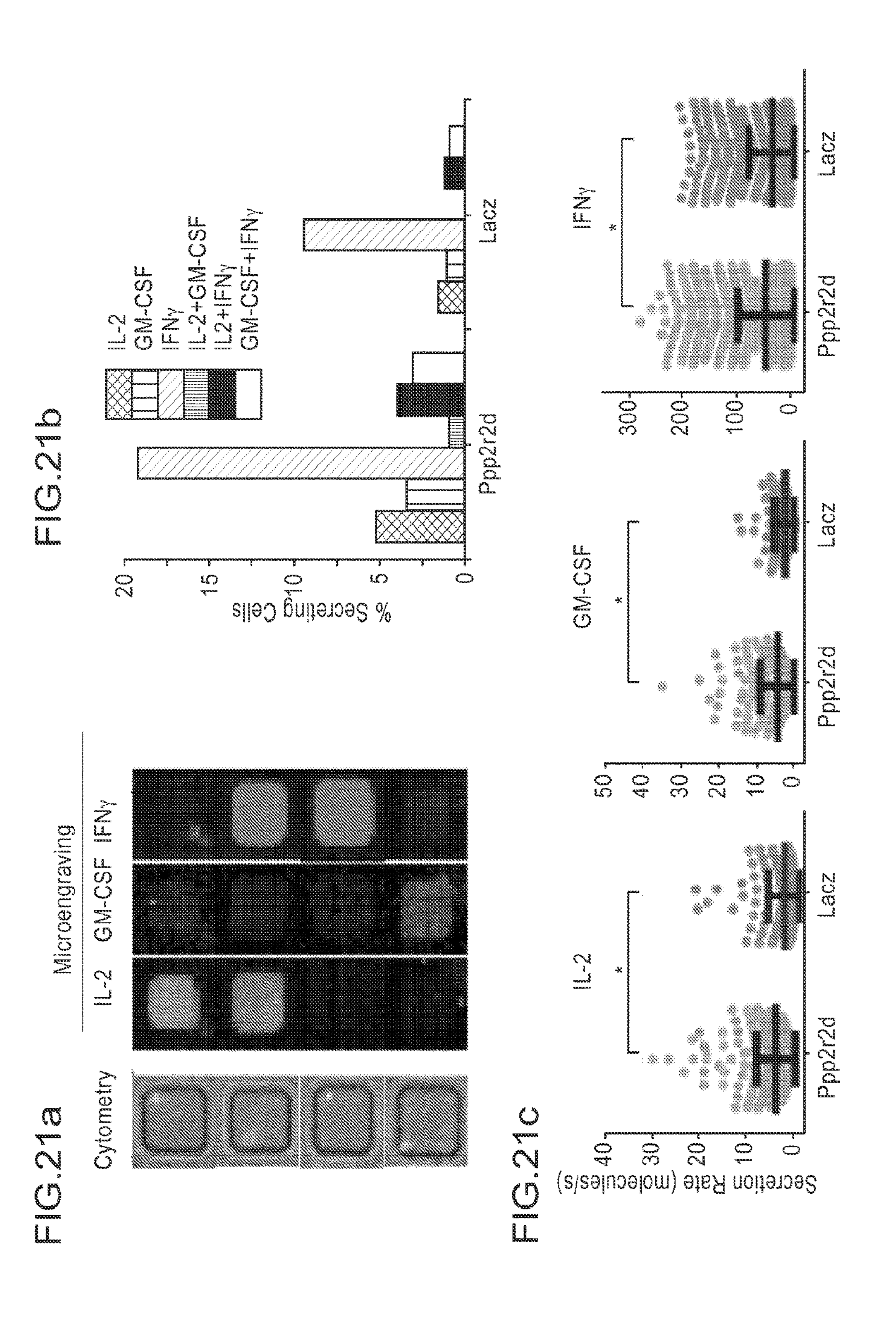

FIGS. 21*a-c* are a series of graphs demonstrating ex vivo analysis of cytokine production by tumor-infiltrating OT-I T cells at a single-cell level using a nanowell device (84,672 wells of picoliter volume). a, Representative single cells in nanowells and corresponding patterns of cytokine secretion. b, Percentage of T cells secreting indicated cytokines. c, Cytokine secretion rates calculated from standard curves (mean+/−s.d., Mann Whitney test * P<0.05).

Figure 22A:
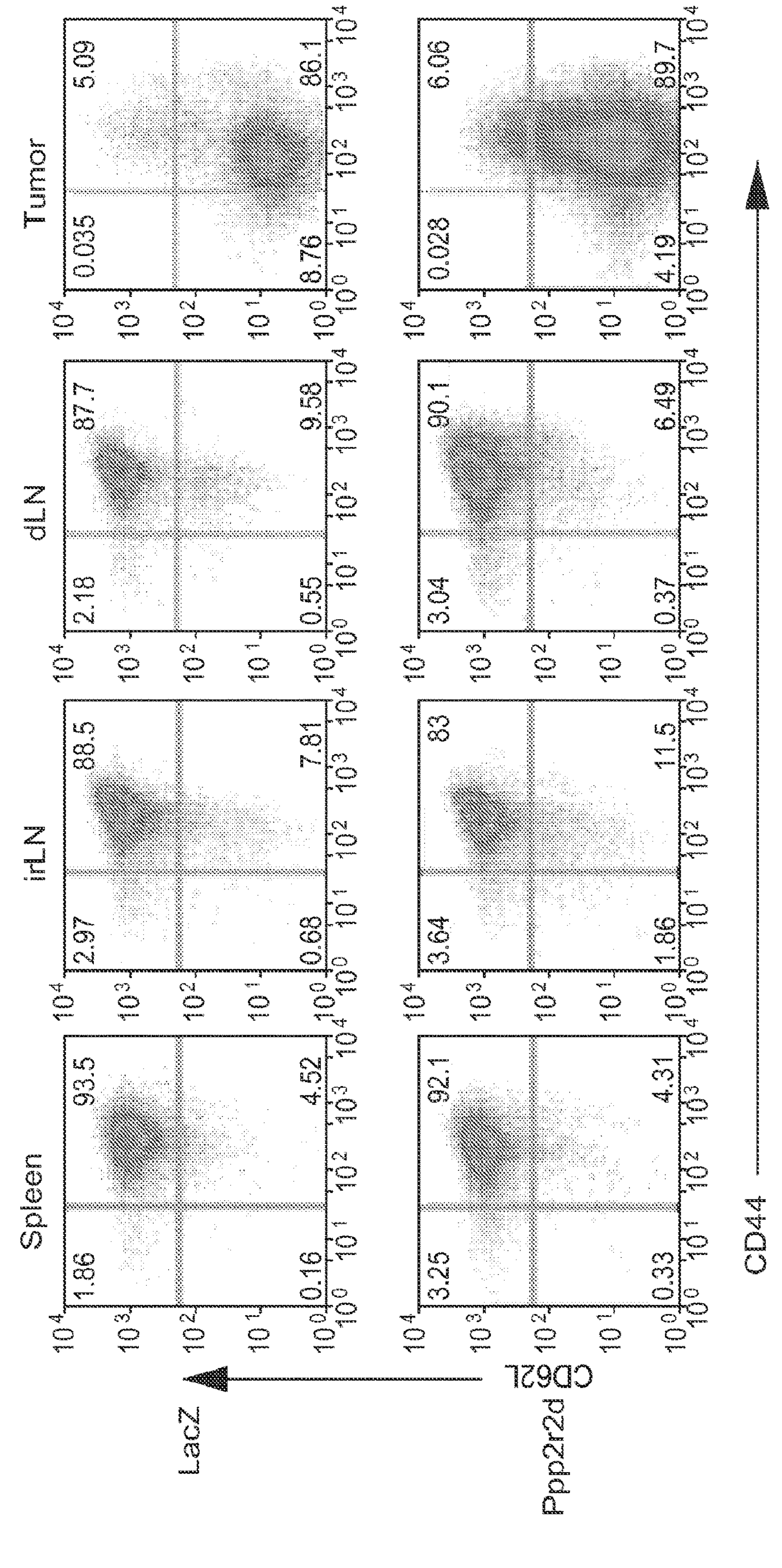

FIG. 22*a* is a set of graphs showing representative flow cytometry plots demonstrating that the majority of adoptively transferred OT-I cells have a memory phenotype in lymph nodes but an effector phenotype in tumors. Cytokine pre-treated cells expressing Ppp2r2d or LacZ shRNAs were injected into mice bearing day 14 B16-Ova tumors. On day 7 following transfer, T cells were harvested from the indicated organs and stained with CD62L and CD44 antibodies. FACS analysis of shRNA-expressing OT-I cells was performed by gating on CD8/Thy1.1 double-positive cells.

Figure 22B:
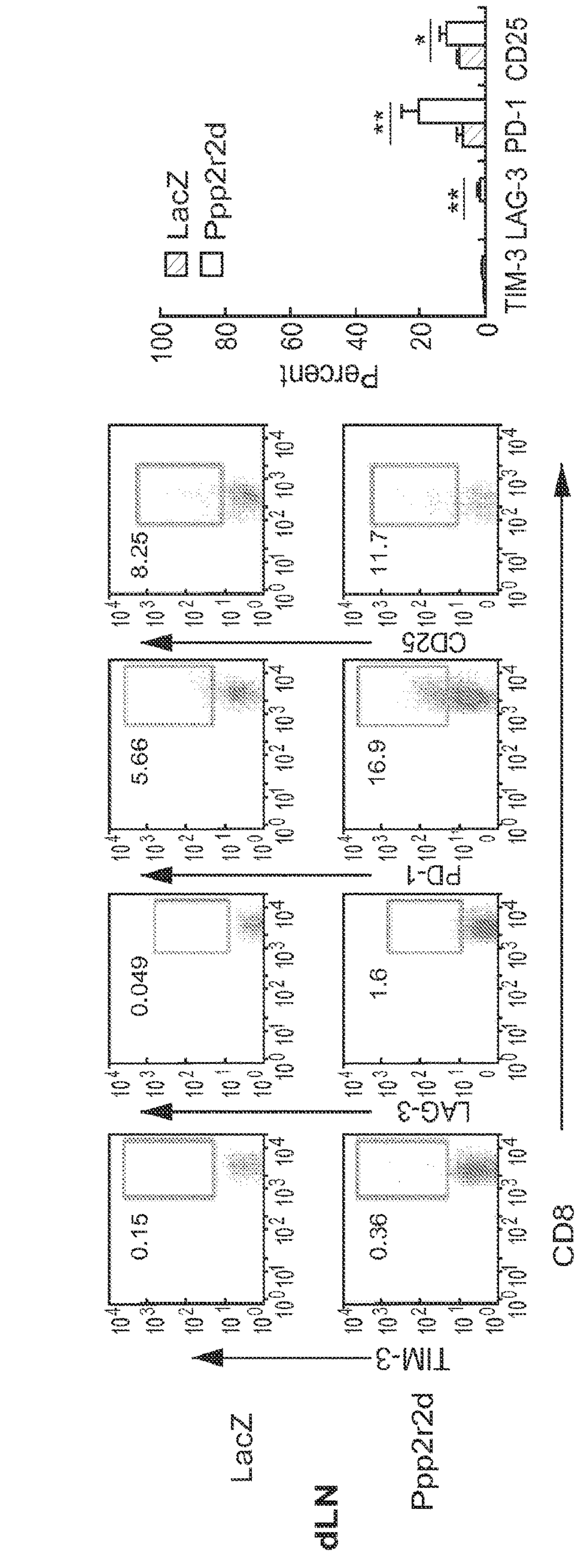
Figure 22B:
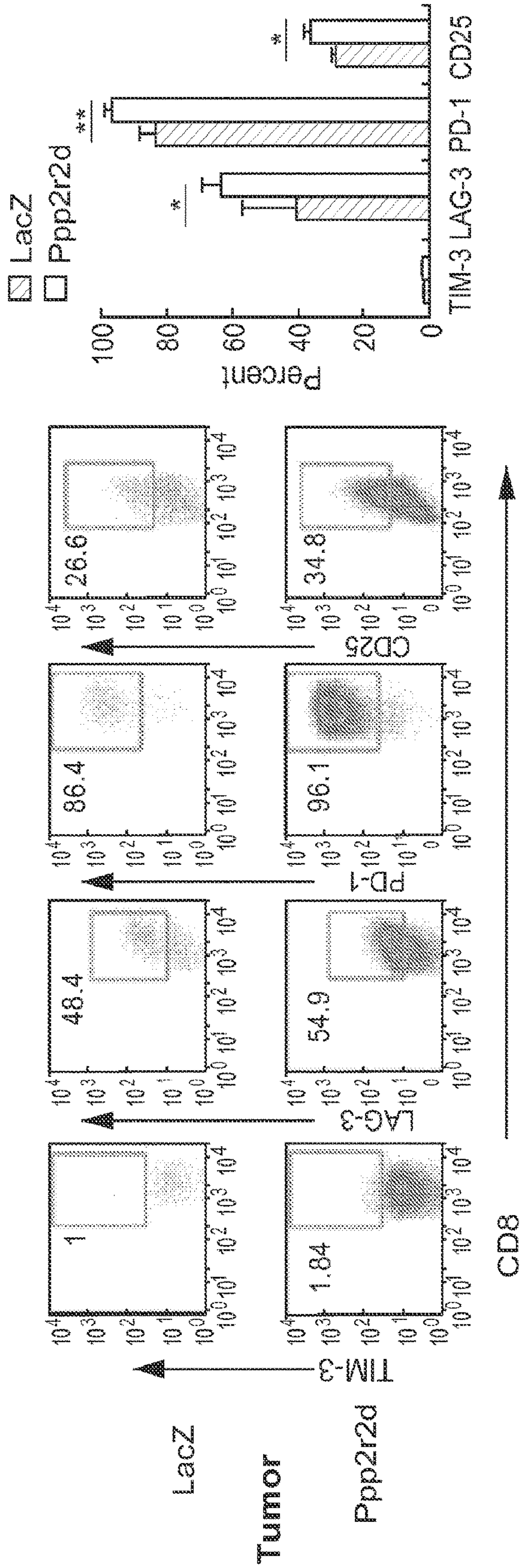

FIG. 22*b* is a set of graphs showing representative flow cytometry plots demonstrating analysis of exhaustion markers. OT-I cells were harvested from draining lymph nodes and tumors of mice and stained with antibodies specific for TIM-3, LAG-3, PD-1 and CD25. For all experiments (n=3 biological replicates; * P<0.05, ** P<0.01, Two-sided Student's t-test); each value represents mean+/−s.d.

Figure 23A:
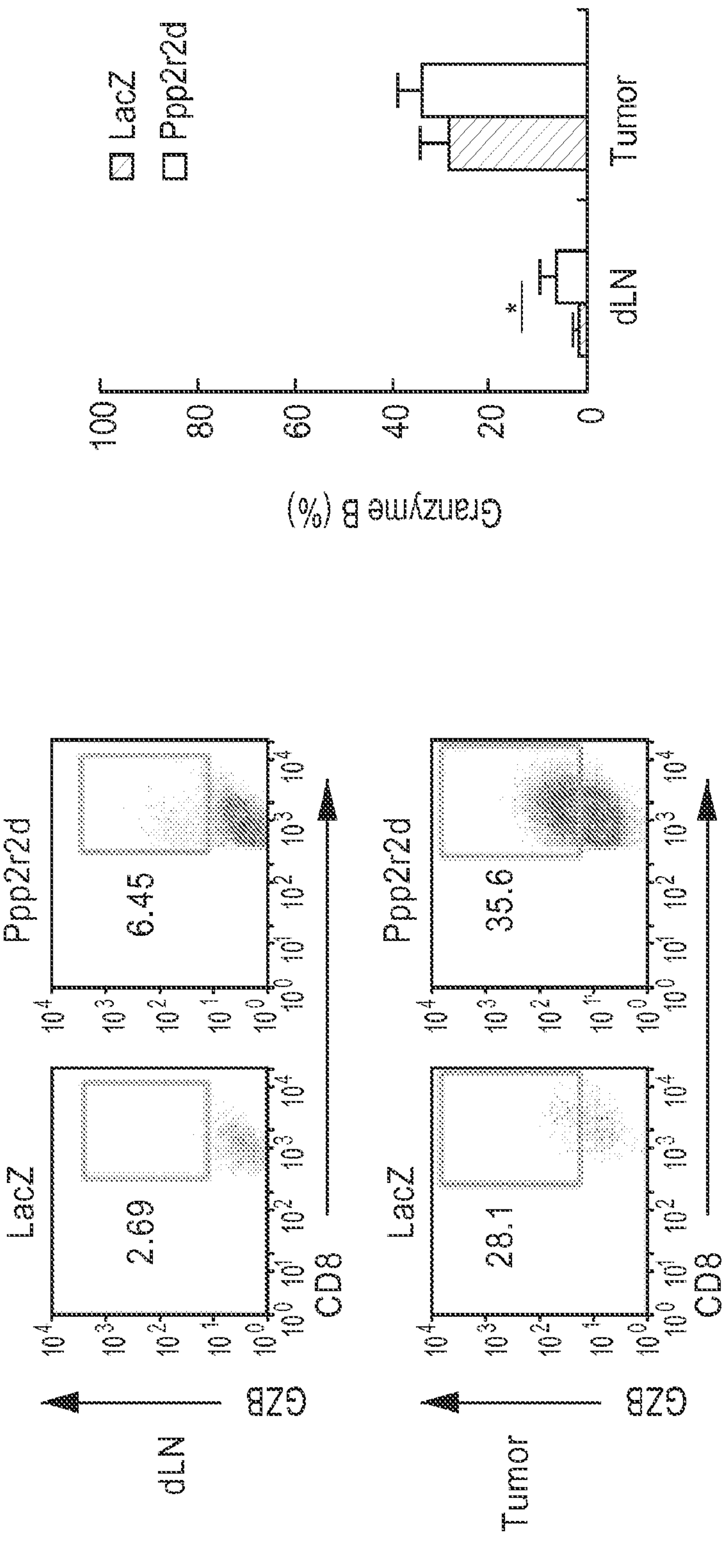

FIG. 23*a* is a set of graphs showing demonstrating intracellular staining for granzyme B by OT-I T cells in tumor-draining lymph nodes and tumors.

Figure 23B:
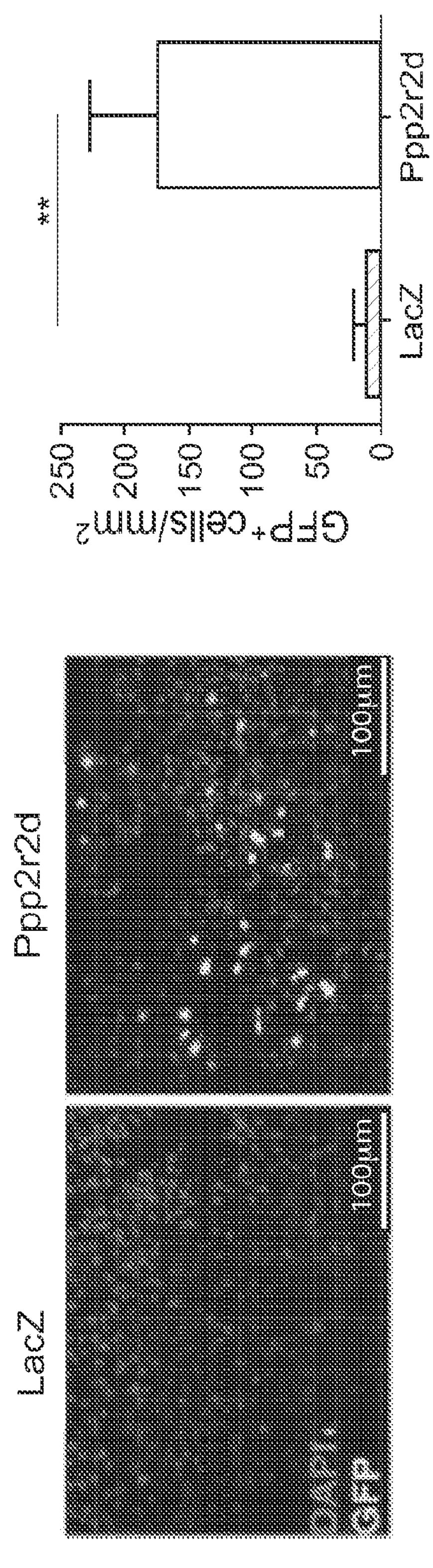

FIG. 23*b* is a pair of images and a graph demonstrating infiltration of shRNA-expressing T cells into tumors. OT-I T cells were transduced with LacZ or Ppp2r2d shRNA vectors encoding a GFP reporter and injected into B16-Ova tumor-bearing mice. After 7 days, tumors were excised and frozen sections stained with anti-GFP and DAPI to enumerate shRNAexpressing OT-I T cells in tumors.

Figure 23C:
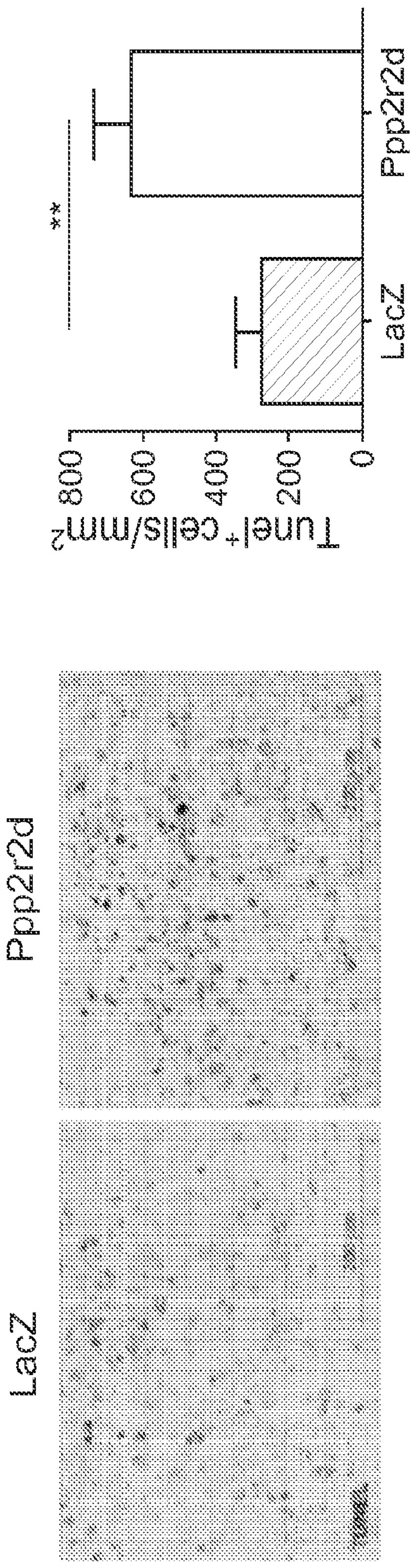

FIG. 23*c* is a pair of images and a graph demonstrating TUNEL immunohistochemistry performed on tissue sections and apoptotic cells were quantified.

Figure 23D:
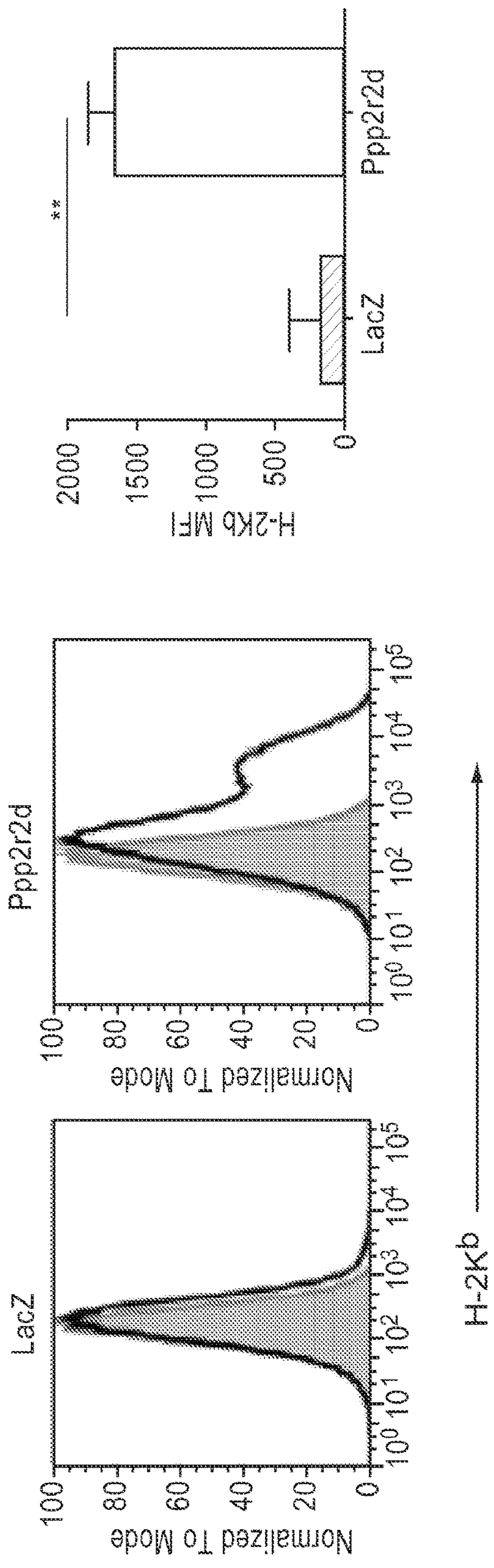

FIG. 23*d* is a set of graphs demonstrating MHC class I expression by tumor cells. Tumors were digested with collagenase and stained with CD45.2 and H-2Kb antibodies. FACS analysis for H-2Kb expression was performed by gating on CD45.2-negative melanoma cells. Datarepresent biological replicates (n=3), each value represents mean+/−s.d.

DETAILED DESCRIPTION

The present disclosure is based, in part, on the observation that the regulatory mechanisms that result in loss of T cell function within immunosuppressive tumors can be systematically discovered in vivo using a pooled small hairpin RNA (shRNA) screening approach aimed at identifying genes that block the function of tumor infiltrating T-cells. As described in the background section above, tumor associated immunosuppressive mechanisms actively block the activity of T cells in the tumor microenvironment. The methods described herein identify shRNAs that enable robust T cell infiltration and accumulation in tumors, despite the multiple inhibitory signals. As described below, the methods identify shRNA that silence expression of genes responsible for immunosuppression by tumors, allowing for enhanced T cell infiltration and accumulation in tumors and resistance to apoptosis.

In some instances, the disclosure provides methods for specifically identifying regulatory mechanisms that result in the loss of T cell function within the tumor microenvironment. These methods can include: providing a population of T cells harboring vectors expressing a shRNA; contacting the population of T cells with an immunosuppressive tumor; determining whether a shRNA restores T cell function (e.g., restores ability of T cell to infiltrate and proliferate within the tumor microenvironment) within the immunosuppressive tumor; identifying a gene associated with a shRNA that restores T cell function within the tumor as a gene that inhibits T cell function within the tumor microenvironment.

The disclosure provides target genes for reducing the immunosuppressive effect of tumors. The expression of the target genes can be reduced in immune cells, e.g., T cells that recognize tumor associated antigens, and the reduction in expression of the target genes can increase the ability of the cells to evade tumor associated immunosuppressive mechanisms.

The disclosure provides shRNAs that reduce (e.g., silence, eliminate, knock down, knock out, or decrease) expression of genes that impair the function of tumor infiltrating T-cells. These shRNA were identified from the transfer of shRNA transduced T cells into tumors, followed by deep sequencing to quantify the representation of all shRNAs in the tumor and lymphoid organs. Representative shRNA disclosed herein include shRNA that reduce the activity of genes including, for example, Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

In some instances, the disclosure provides therapeutic compositions (e.g., including isolated nucleic acid molecules, vectors expressing nucleic acid molecules encoding the shRNA) related to the shRNAs that silence expression of genes that block the function of tumor infiltrating T-cells. In other aspects, the disclosure provides modified immunoresponsive cells (e.g., T cells, including Natural Killer T cells (NKT), a cytotoxic T lymphocytes (CTL), and a regulatory T cells) that harbor vectors capable of expressing the shRNA described herein. In another aspect, the modified immunoresponsive cells further harbor a vector capable of expressing a CAR having an antigen binding domain that targets a tumor specific antigen.

RNA Interference

One of the most important recent discoveries in biomedical research is the RNA interference (RNAi) pathway, which is used by cells to regulate the activity of many genes. The principles of RNAi have opened many new possibilities for the identification of therapeutic targets. RNA interference (RNAi) is an effective tool for genome-scale, high throughput analysis of gene function. The term "RNA interference" (RNAi), also called post transcriptional gene silencing (PTGS), refers to the biological process in which RNA molecules inhibit gene expression. An "RNA interfering agent" as used herein, is defined as any agent that interferes with or inhibits expression of a target gene, e.g., a target gene of the invention, by RNA interference (RNAi). Such RNA interfering agents include, but are not limited to, nucleic acid molecules including RNA molecules which are homologous to the target gene, e.g., a target gene of the invention, or a fragment thereof, short interfering RNA (siRNA), short hairpin RNA (shRNA), and small molecules which interfere with or inhibit expression of a target gene by RNA interference (RNAi).

"RNA interference (RNAi)" is a process whereby the expression or introduction of RNA of a sequence that is identical or highly similar to a target gene results in the sequence specific degradation or PTGS of messenger RNA (mRNA) transcribed from that targeted gene, thereby inhibiting expression of the target gene. This process has been described in plants, invertebrates, and mammalian cells. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene. These are the effector molecules for inducing RNAi, leading to posttranscriptional gene silencing with RNA-induced silencing complex (RISC). In addition to siRNA, which can be chemically synthesized, various other systems in the form of potential effector molecules for posttranscriptional gene silencing are available, including short hairpin RNAs (shRNAs), long dsRNAs, short temporal RNAs, and micro RNAs (miRNAs). These effector molecules either are processed into siRNA, such as in the case of shRNA, or directly aid gene silencing, as in the case of miRNA. The present invention thus encompasses the use of shRNA as well as any other suitable form of RNA to effect posttranscriptional gene silencing by RNAi. Use of shRNA has the advantage over use of chemically synthesized siRNA in that the suppression of the target gene is typically long-term and stable. An siRNA may be chemically synthesized, may be produced by in vitro by transcription, or may be produced within a host cell from expressed shRNA.

In one embodiment, a siRNA is a small hairpin (also called stem loop) RNA (shRNA). These shRNAs are composed of a short (e.g., 19-25 nucleotides) antisense strand, followed by a 5-9 nucleotide loop, and the complementary sense strand. Alternatively, the sense strand may precede the nucleotide loop structure and the antisense strand may follow. These shRNAs may be contained in plasmids, retroviruses, and lentiviruses.

As used herein, "gene silencing" induced by RNA interference refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without introduction of RNA interference. In one preferred embodiment, the mRNA levels are decreased by at least about 70%, about 80%, about 90%, about 95%, about 99%, about 100%.

The term "reduced" or "reduce" as used herein generally means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease, or any integer decrease between 10-100% as compared to a reference level.

The term "increased" or "increase" as used herein generally means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any integer increase between 10-100% as compared to a reference level, or about a 2-fold, or about a 3-fold, or about a 4-fold, or about a 5-fold or about a 10-fold increase, or any increase between 2-fold and 10-fold or greater as compared to a reference level.

Immunoresponsive Cells

In some embodiments, the disclosure provides immunoresponsive cells, including T cells, cytotoxic T cells, tumor-infiltrating lymphocytes (TIL), regulatory (CD4) T cells, and Natural Killer (NKT) cells, expressing at least one of an antigen-recognizing receptor. In any aspect, the immunoresponsive cells express at least one tumor specific antigen-recognizing receptor. In some aspects, tumor cell antigen specific T cells, NKT cells, TIL, CTL cells or other immunoresponsive cells are used. Non-limiting examples of immunoresponsive cells include T cells, such as, for example, αβ-TCR+ T cells (e.g., CD8+ T cells or CD4+ T cells) γδ-TCR+ T cells, tumor-infiltrating lymphocytes (TIL), Natural Killer T cells (NKT), a cytotoxic T lymphocytes (CTL), and a CD4 T cells.

Nucleic Acid Compositions

In some embodiments, the disclosure provides isolated nucleic acids encoding shRNA sequences comprising a sequence at least 12, 15, 20 or 25 contiguous nucleotides complementary to a nucleic acid sequence selected from the group consisting of SEQ ID NOs: 604-620 and 653-678. The shRNA also includes the reverse complement of the contiguous nucleotide sequence and a short sequence located between the two sequences so that the two sequences form a stem loop shRNA that can be processed within a cell provide an siRNA that inhibits the expression of the protein encoded by one of SEQ ID NOs: 604-620 and 653-678, and compositions thereof.

Table 1 provides a list of genes identified here as being involved with tumor immunosuppression of T cells.

TABLE 1

| Gene | Human Gene Sequence | Human Sequence Accession No. | Murine Sequence Accession No. |
|---|---|---|---|
| Ppp2r2d | gtgtccggccaagcggcgccctgaaggcgtgtccggccgcagcttaggctctccgggagtccccggagagtaggggcggccggcggc<br>gctagtcttctggggagcgccgggtgcacaccggaccactgcgggaggcctagggccgagggccgaggagctggcctgcgcccggc<br>gaccccggcttccctccgcagtcgcccaggcgtcccttccccctacagccgagcggcgccgggcgcaggcgcattgggcgcccccg<br>gcagcccccgcggcccgccccgtccgctgcccgtccgaggaggcggagggcgatgacgtcatcgagcggggcgacgggcattgggc<br>gccattttgaaaagggaaaaaaatccctccccggcggcggcggcggcggcggcggcgccggcggtggtggcggccccggggctgag<br>cgctcggctgcagcggcgcggaggccgtctccctggtctgccgcggtccccgcccgtcccgccgccggctgccatggcaggagccgg<br>aggcggcggctgccccgcgggcggcaacgacttccagtggtgcttctcgcaggtcaaggggccatcgacgaggacgtggccgaagc<br>ggacatcatttccaccgttgagtttaattactctggagatcttcttgcaacaggagacaagggcggcagagttgttatttttcagcgtgaacaag<br>agaataaaagccgccctcattctaggggagaatataatgtttacagcacctttcaaagtcatgaaccggagtttgactatttgaaaagtctaga<br>aattgaggaaaaaattaataaaattaggtggttaccacaacagaatgctgctcattttctactgtctacaaatgataaaactataaaattatggaa<br>aataagtgaacgggataaaagagcagaaggttataacctgaaagacgaagatggaagacttcgagacccatttaggatcacggcgctacg<br>ggtcccaatattgaagcccatggatcttatggtagaagcgagtccacggcgaatttttgcaaatgctcacacatatcatataaattccatttcag<br>taaatagtgatcatgaaacatatctttctgcagatgacctgagaattaatttatggcacttagaaatcacagatagaagctttaacatcgtggaca<br>tcaagcctgctaacatggaggagctgaccgaagtcatcactgcagccgagttccacccgcaccagtgcaacgtgttcgtctacagcagtag<br>caaagggaccatccgcctgtgtgacatgcgctcctcggccctgtgcgacagacactccaagtttttgaagagcctgaagatcccagcagt<br>aggtccttcttctcagaaataatttcatccatatccgatgtaaaattcagtcatagtgggcggtacatgatgaccagagactacctgtcggtgaa<br>ggtgtgggacctcaacatggagagcaggccggtggagacccaccaggtccacgagtacctgcgcagcaagctctgctctctctatgaga<br>acgactgcatctttgacaagtttgagtgttgctggaacggttcggatagcgccatcatgaccgggtcctataacaacttcttcaggatgtttgat<br>agagacacgcggagggatgtgaccctggaggcctcgagagagagcagcaaaccgcgcgccagcctcaaaccccggaaggtgtgtac<br>ggggggtaagcggaggaaagacgagatcagtgtggacagtctggacttcaacaagaagatcctgcacacagcctggcaccccgtggac<br>aatgtcattgccgtggctgccaccaataacttgtacatattccaggacaaaatcaactagagacgcgaacgtgaggaccaagtcttgtcttgc<br>atagttaagccggacatttttctgtcagagaaaaggcatcattgtccgctccattaagaacagtgacgcacctgctacttcccttcacagacac<br>aggagaaagccgcctccgctggaggcccggtgtggttccgcctcggcgaggcgcgagacaggcgctgctgctcacgtggagacgctct<br>cgaagcagagttgacggacactgctcccaaaaggtcattactcagaataaatgtatttatttcagtccgagccttcctttccaatttatagacca<br>aaaaattaacatccaagagaaaagttattgtcagataccgctctttctccaactttccctctttctctgccatcacacttgggccttcactgcagcg<br>tggtgtggccaccgtccgtgtcctctcggccttcctccgagtccaggtggactctgtggatgtgtggatgtggcccgagcaggctcaggcg<br>gccccactcacccacagcatccgccgccaccccttcgggtgtgagcgctcaataaaaacaacacactataaagtgtttttaaatccaaaaaa<br>aaaaaaaaa (SEQ ID NO: 604) | NM_018461 | NM_026391 |
| Eif2ak3 | ggaaagtccaccttccccaacaaggccagcctgggaacatggagtggcagcggccgcagccaatgagagagcaaacgcgcggaaagt<br>ttgctcaatgggcgatgtccgagataggctgtcactcaggtggcagcggcagaggccgggctgagacgtggccaggggaacacggctg<br>gctgtccaggccgtcggggcggcagtagggtccctagcacgtccttgccttcttgggagctccaagcggcgggagaggcaggcgtcagt<br>ggctgcgcctccatgcctgcgcgcggggcgggacgctgatggagcgcgccatcagcccggggctgctggtacgggcgctgctgctgct<br>gctgctgctgctggggctcgcggcaaggacggtggccgcggggcgcgcccgtggcctcccagcgccgacggcggaggcggcgttcg<br>gcctcggggcggccgctgctcccacctcagcgacgcgagtaccggcggcgggcgccgtggctgcggccgaggtgactgtggaggac<br>gctgaggcgctgccggcagccgcgggagagcaggagcctcggggtccggaaccagacgatgagacagagttgcgaccgcgcggca<br>ggtcattagtaattatcagcactttagatgggagaattgctgccttggatcctgaaaatcatggtaaaaagcagtgggatttggatgtgggatc<br>cggttccttggtgtcatccagccttagcaaaccagaggtatttgggaataagatgatcattccttccctggatggagccctcttccagtgggac<br>caagaccgtgaaagcatggaaacagttcctttcacagttgaatcacttcttgaatcttcttataaatttggagatgatgttgttttggttggaggaa<br>aatctctgactacatatggactcagtgcatatagtggaaaggtgaggtatatctgttcagctctgggttgtcgccaatgggatagtgacgaaat<br>ggaacaagaggaagacatcctgcttctacagcgtacccaaaaaactgttagagctgtcggacctcgcagtggcaatgagaagtggaatttc<br>agtgttggccactttgaacttcggtatattccagacatggaaacgagagccggatttattgaaagcacctttaagcccaatgagaacacagaa<br>gagtctaaaattatttcagatgtggaagaacaggaagctgccataatggacatagtgataaaggtttcggttgctgactggaaagttatggcat<br>tcagtaagaagggaggacatctggaatgggagtaccagttttgtactccaattgcatctgcctggttacttaaggatgggaaagtcattcccat<br>cagtctttttgatgatacaagttatacatctaatgatgatgttttagaagatgaagaagacattgtagaagctgccagaggagccacagaaaac<br>agtgtttacttgggaatgtatagaggccagctgtatctgcagtcatcagtcagaatttcagaaaagtttccttcaagtcccaaggctttggaatct<br>gtcactaatgaaaacgcaattattcctttaccaacaatcaaatggaaacccttaattcattctccttccagaactcctgtcttggtaggatctgatg<br>aatttgacaaatgtctcagtaatgataagttttctcatgaagaatatagtaatggtgcactttcaatcttgcagtatccatatgataatggttattatc | NM_004836.5 | NM_010121.2 |

TABLE 1-continued

| Gene | Human Gene Sequence | Human Sequence Accession No. | Murine Sequence Accession No. |
|---|---|---|---|
| | taccatactacaagagggagaggaacaaacgaagcacacagattacagtcagattcctcgacaacccacattacaacaagaatatccgca<br>aaaaggatcctgttcttcttttacactggtggaaagaaatagttgcaacgattttgttttgtatcatagcaacaacgtttattgtgcgcaggcttttc<br>catcctcatcctcacaggcaaaggaaggagtctgaaactcagtgtcaaactgaaaataaatatgattctgtaagtggtgaagccaatgacagt<br>agctggaatgacataaaaaactctggatatatatcacgatatctaactgattttgagccaattcaatgcctgggacgtggtggctttggagttgtt<br>tttgaagctaaaaacaaagtagatgactgcaattatgctatcaagaggatccgtctccccaatagggaattggctcgggaaaaggtaatgcg<br>agaagttaaagccttagccaagcttgaacacccgggcattgttagatatttcaatgcctggctcgaagcaccaccagagaagtggcaagaa<br>aagatggatgaaatttggctgaaagatgaaagcacagactggccactcagctctcctagcccaatggatgcaccatcagttaaaatacgca<br>gaatggatcctttcgctacaaaagaacatattgaaatcatagctccttcaccacaaagaagcaggtctttttcagtagggatttcctgtgaccag<br>acaagttcatctgagagccagttctcaccactggaattctcaggaatggaccatgaggacatcagtgagtcagtggatgcagcatacaacct<br>ccaggacagttgccttacagactgtgatgtggaagatgggactatggatggcaatgatgaggggcactcctttgaactttgtccttctgaagc<br>ttctccttatgtaaggtcaagggagagaacctcctcttcaatagtatttgaagattctggctgtgataatgcttccagtaaagaagagccgaaaa<br>ctaatcgattgcatattggcaaccattgtgctaataaactaactgctttcaagcccaccagtagcaaatcttcttctgaagctacattgtctatttct<br>cctccaagaccaaccactttaagtttagatctcactaaaaacaccacagaaaaactccagcccagttcaccaaaggtgtatctttacattcaaa<br>tgcagctgtgcagaaaagaaaacctcaaagactggatgaatggacgatgtaccatagaggagagagagaggagcgtgtgtctgcacatct<br>tcctgcagatcgcagaggcagtggagtttcttcacagtaaaggactgatgcacagggacctcaagccatccaacatattctttacaatggatg<br>atgtggtcaaggttggagactttgggttagtgactgcaatggaccaggatgaggaagagcagacggttctgaccccaatgccagcttatgc<br>cagacacacaggacaagtagggaccaaactgtatatgagcccagagcagattcatggaaacagctattctcataaagtggacatcttttcttt<br>aggcctgattctatttgaattgctgtatccattcagcactcagatggagagagtcaggaccttaactgatgtaagaaatctcaaatttccaccatt<br>atttactcagaaatatccttgtgagtacgtgatggttcaagacatgctctctccatcccccatggaacgacctgaagctataaacatcattgaaa<br>atgctgtatttgaggacttggactttccaggaaaaacagtgctcagacagaggtctcgctccttgagttcatcgggaacaaaacattcaagac<br>agtccaacaactcccatagccctttgccaagcaattagccttaagttgtgctagcaaccctaataggtgatgcagataatagcctacttcttaga<br>atatgcctgtccaaaattgcagacttgaaaagtttgttcttcgctcaatttttttgtggactactttttttatatcaaatttaagctggatttgggggcat<br>aacctaatttgagccaactcctgagttttgctatacttaaggaaagggctatctttgttctttgttagtctcttgaaactggctgctggccaagcttt<br>atagccctcaccatttgcctaaggaggtagcagcaatccctaatatatatatatagtgagaactaaaatggatatatttttataatgcagaagaa<br>ggaaagtcccccctgtgtggtaactgtattgttctagaaatatgctttctagagatatgatgattttgaaactgatttctagaaaaagctgactccat<br>ttttgtccctggcgggtaaattaggaatctgcactattttggaggacaagtagcacaaactgtataacggtttatgtccgtagttttatagtcctatt<br>tgtagcattcaatagctttattccttagatggttctagggtgggtttacagctttttgtactttacctccaataaagggaaaatgaagctttttatgta<br>aattggttgaaaggtctagttttgggaggaaaaaagccgtagtaagaaatggatcatatatattacaactaacttcttcaactatggactttttaa<br>gcctaatgaaatcttaagtgtcttatatgtaatcctgtaggttggtacttcccccaaactgattataggtaacagtttaatcatctcacttgctaaca<br>tgtttttatttttcactgtaaatatgtttgttttatttataaaaattctgaaatcaatccatttgggttggtggtgtacagaacacacttaagtgtgtta<br>acttgtgacttctttcaagtctaaatgatttaataaaactttttttaaattaaaaaaaaaaaaaaaaaaa (SEQ ID NO: 605) | | |
| Arhgap5 | ctcggtgagcgcgccgaggaagagaggcgagcggagagtggaggaggaggcggcggcggcgggagcggtccccaggaatgtcgc<br>tgccgccgccaccgccggggccgctgccgttgaggaggagacggaggagaccgacgttgttaggaagatgatccctatgatcttgaaga<br>tgtttctgcacagaaatgagggaaatacaaagaaccaaatacagttctgaaatttgggatctgtattttgagatgattttattttcagaatgagaa<br>gcatatctggttacctttatgaatgtagagacatgagaagagagttatgatggcaaaaaacaaagagcctcgtcccccatcctataccatcag<br>tatagttggactctctgggactgaaaaagacaaaggtaactgtggagttggaaagtcttgtttgtgcaatagatttgtacgctcaaaagcagat<br>gaatattatccagagcatacttctgtgcttagcaccattgactttggaggacgagtagtaaacaatgatcactttttgtactggggtgacataata<br>caaaatagtgaagatggagtagaatgcaaaattcatgtcattgaacaaacagagttcattgatgaccagactttcttgcctcatcggagtacga<br>atttgcaaccatatataaaacgtgcagctgcatctaaattgcagtcagcagaaaaactaatgtacatttgcactgatcagctaggcttagaaca<br>agactttgaacagaagcaaatgcctgaagggaagctcaacgtagatggattttattatgcattgatgtaagtcaaggatgcaataggaagttt<br>gatgatcaacttaaatttgtgaataacctttttgtccagttatcaaaatcaaaaaaacctgtaataatagcagcaactaaatgtgatgaatgcgtg<br>gatcattatcttagagaagttcaggcatttgcttcaaataaaaagaaccttcttgtagtggaaacatcagcacgatttaatgtcaacattgaaaca<br>tgttttactgcactggtacaaatgttggataaaactcgtagcaagcctaaaattattccctatttggatgcttataaaacacagagacaacttgttg<br>tcacagcaacagataagtttgaaaaacttgtgcagactgtgagagattatcatgcaacttggaaaactgttagtaataaattaaaaaatcatcct<br>gattatgaagaatacatcaacttagagggaacaagaaaggccagaaatacattctcaaaacatatagaacaacttaaacaggaacatataag<br>aaaaaggagagaagagtatataaatactttaccaagagcttttaacactcttttgccaaatctagaagagattgaacatttgaattggtcagaag<br>ctttgaagttaatggaaaagagagcagatttccagttatgttttgtggtgctagaaaaaactccttgggatgaaactgaccatatagacaaaatt<br>aatgataggcggattccatttgacctcctgagcactttagaagctgaaaaagtctatcagaaccatgtacagcatctgatatccgagaagagg<br>agggtggaaatgaaggaaaaattcaaaaagactttggaaaaaattcaattcatttcaccagggcagccatgggaggaagttatgtgctttgtt | NM_001030055.1 | NM_009706.2 |

TABLE 1-continued

| Gene | Human Gene Sequence | Human Sequence Accession No. | Murine Sequence Accession No. |
|---|---|---|---|
| | atggaggatgaagcctacaaatatatcactgaggctgatagcaaagaggtatatggtaggcatcagcgagaaatagttgaaaaagccaaa | | |
| | gaagagtttcaagaaatgcttttttgagcattctgaactttttatgatttagatcttaatgcaacacctagttcagataaaatgagtgaaattcatac | | |
| | agttctgagtgaagaacctagatataaagctttacagaaacttgcacctgatagggaatcccttctacttaagcatataggatttgtttatcatcc | | |
| | cactaaagaaacatgtcttagtggccaaaattgtacagacattaaagtggagcagttacttgctagtagtcttttacagttggatcatggccgct | | |
| | taagattatatcacgatagtaccaatatagataaagttaaccttttttattttagggaaggatggccttgcccaagaactagcaaatgagataagg | | |
| | acacaatccactgatgatgagtatgccttagatggaaaaatttatgaacttgatcttcggccggttgatgccaaatcgccttactttttgagtcag | | |
| | ttatggactgccgcctttaaaccacatgggtgcttctgtgtatttaattccattgagtcattgagttttattggggaatttattgggaaaataagaac | | |
| | tgaagcttctcagatcagaaaagataaatacatggctaatcttccatttacattaattctggctaatcagagagattccattagtaagaatctacc | | |
| | aattctcaggcaccaagggcagcagttggcaaacaagttgcaatgtccttttgtagatgtacctgctggtacatatcctcgtaaatttaatgaaa | | |
| | cccaaataaagcaagctctcagaggagtattggaatcagttaaacacaatttggatgtggtgagcccaattcctgccaataaggacttatcag | | |
| | aagctgacttgagaattgtcatgtgcgccatgtgtggagatccatttagtgtggatcttattctttcacccttccttgattctcattcttgcagtgctg | | |
| | ctcaagctggacagaataattccctaatgcttgataaaatcattggtgaaaaaaggaggcgaatacagatcacaatattatcataccactcttc | | |
| | aattggagtaagaaaagatgaactagttcatgggtatatattagtttactctgcaaaacggaaagcttcgatgggaatgcttcgagcatttctat | | |
| | cagaagttcaagacaccattcctgtacagctggtggcagttactgacagccaagcagatttttttgaaaatgaggctatcaaagagttaatgac | | |
| | tgaaggagaacacattgcaactgagatcactgctaaatttacagcactgtattctttatctcagtatcatcggcaaactgaggtctttactctgttt | | |
| | tttagtgatgttctagagaaaaaaaatatgatagaaaattcttatttgtctgataatacaagggaatcaacccatcaaagtgaagatgtttttctac | | |
| | catctcccagagactgttttccctataataactaccctgattcagatgatgacacagaagcaccacctccttatagtccaattggggatgatgta | | |
| | cagttgcttccaacacctagtgaccgttccagatatagattagatttggaaggaaatgagtatcctattcatagtaccccaaactgtcatgacca | | |
| | tgaacgcaaccataaagtgcctccacctattaaacctaaaccagttgtacctaagacaaatgtgaaaaaactcgatccaaaccttttaaaaaca | | |
| | attgaagctggtattggtaaaaatccaagaaagcagacttcccgggtgcctttggcacatcctgaagatatggatccttcagataactatgcg | | |
| | gaacccattgatacaattttcaaacagaagggctattctgatgagatttatgttgtcccagatgatagtcaaaatcgtattaaaattcgaaactca | | |
| | tttgtaaataacacccaaggagatgaagaaaatgggttttctgatagaacctcaaaaagtcatggggaacggaggccttcaaaatacaaatat | | |
| | aaatctaaaaccttgtttagtaaagccaagtcatactatagaagaacacattcagatgccagtgatgatgaggctttcaccacttctaaaacaaa | | |
| | aagaaaaggaagacatcgtggaagtgaagaagatccacttctttctcctgttgaaacttggaaaggtggtattgataatcctgcaatcacttct | | |
| | gaccaggagttagatgataagaagatgaagaagaaaacccacaaagtgaaagaagataaaaagcagaaaaagaaaactaagaacttcaa | | |
| | tccaccaacacgtagaaattgggaaagtaattactttgggatgcccctccaggatctggttacagctgagaagcccataccactatttgttgag | | |
| | aaatgtgtggaatttattgaagatacagggttatgtaccgaaggactctaccgtgtcagcgggaataaaactgaccaagacaatattcaaaag | | |
| | cagtttgatcaagatcataatatcaatctagtgtcaatggaagtaacagtaaatgctgtagctggagcccttaaagctttctttgcagatctgcca | | |
| | gatcctttaattccatattctcttcatccagaactattggaagcagcaaaaatcccggataaaacagaacgtcttcatgccttgaaagaaattgtt | | |
| | aagaaatttcatcctgtaaactatgatgtattcagatacgtgataacacatctaaacagggttagtcagcaacataaaatcaacctaatgacagc | | |
| | agacaacttatccatctgtttttggccaaccttgatgagacctgattttgaaaatcgagagtttctgtctactactaagattcatcaatctgttgttga | | |
| | aacattcattcagcagtgtcagttttctttacaatggagaaattgtagaaacgacaaacattgtggctcctccaccaccttcaaacccaggac | | |
| | agttggtggaaccaatggtgccacttcagttgccgccaccattgcaacctcagctgatacaaccacaattacaaacggatcctcttggtattat | | |
| | atgagtaggaagtgattgcaaacaggctggatttggacaaaaagcaaatctagacatgcatgtttcagggttcagtagtatacttcatgtttcat | | |
| | acagataattcacattcaaaattacattttctctttgaactagatggtattccttattcacttacattacaaatctaagaccatgtgataagcatgact | | |
| | ggagaggtttaatttttataaacaaaaatagctataaagtacaaagctgctgctgcatgcaaccttattgcaatcagtatatcattcctgtggcaa | | |
| | tttctgtcaccttatattgtgaataaaatttttctatagaaattaaatgatttaaaaactcacctatatgaaacatttaatgcttttcagcctgctttctgg | | |
| | ctgattttgttatttgatgtgctaatttgggcaacttaatttacattctggcagtcggtgtagataactaaaagcccagttaagtattttataatttcag | | |
| | gctactgaggccatgcttgggatgttgtttgaaagaaagaaaaaatacacttgacatatttcacatttctgtaccttcatctttacttccaagtaaa | | |
| | cccgtggatgatttgatgagggataaatgaacctatttcttttacacacataccaaggacatgcttgtggctaaagtgagttgataatgttgtgca | | |
| | aaggatagttgtcaccaactcatttctttatggtccataatgaaataaaaattttgtatactgttaattctgtaaacagatgcatgttcaaaagatcta | | |
| | tgatggtcttgtaatcttaatctaatatatttagatattttaatttttttccctcttggggaacacatttagtatagtgtagaaaatacttccatgacatttt | | |
| | catataaggttatataacttttcatacataaacatgaaatttgttgtagaaaattctttaaaccaaacatttaaatctaggacttcaatttaatttgttcc | | |
| | ttgaatctattttttatgtggcccttaaaaaatatccaaaaaacccattgctaatatagcaataaaaatactttgggtactgacagactctttggagt | | |
| | gtttatattacaaatttgtattcatattcttttctgtgatgtgttgtactaaaatccaaaatggcttttgcaccattttttaagccaatttttttcctttgatgtt | | |
| | ggtaccagaattactataagtgactgctgcttttgggggtaaacatttttgttagtgaagataaaaccagaacactaaattatggataaaattttca | | |
| | gaataggtggcacaggtaaatttcactaggttatattttgtgtagtaaagaaaaaaaattatttggtcaatgttatcttaattcatactacaatttaaga | | |
| | ttatcttatgtgtattatagtaaatagatgattttcagattcaaggctcctaagagtttgatttgctctgtttttttcctaaaataaatattgtctctcccaa | | |
| | ctgttaagttctaggtattgtacttccaattttaacttcagaaccaagatgttggcatgaaccaggctgctgttgaagtacatgtatattataaatta | | |
| | tcttatttgtgttatactcttacatgttatcttttctaagaaaacaaagtccctattattcctattgcaaagcacacaggaattaagaaagtacagtaa | | |

TABLE 1-continued

| Gene | Human Gene Sequence | Human Sequence Accession No. | Murine Sequence Accession No. |
|---|---|---|---|
| | tttttaaaaaaaaatccggtaaatgtagtattcttaacctgttctatattacttatacctattgtctatatagctttaatttatagttgtcagtttaactatt ggcatgtctggcaaagaaaattaaactttaagagttttataaactgtttctaggttgctaaagaatttatttttctactatatatggtatagacaaagc atcaaactatgtacaggaaaaaagcctgactatttctatttggaagtaggctgaaaagagaattttcaaaactgttcgtgtcttcagttcattctgt cataactttgctattgtaatatgtgaataccagtttatttaagctgttctcttttatactgtattaatttaatgttcatctgcgtttagtaccatttttgttatt aaaactggcatttaccgttttcacattaacccaccttgcaccttcccccaaacttatctccacttttctatgcattctatcattgatttgacacacttc atagtgagtcatttaaatactctacgtttggttcaattaaccagtaggttacagttattgaaaattaaagtacagtttaaagctcagtctgttacact gaattgattgtgtttgtttttgccaagggtttagatatgcttttaaatattagaaacatctaagaacagaataacataattaaactttttctggtaagt tactggaaggtttcactgtttagggacctatcatatgagacttcttaaaggattaaaagaataggatagtctcataattgtgagtaaacatcaag gcattatattttacaatactgaataaaatttcatctacacacatgttgccattgtttcatttaaggttcagtgcttatagttaactacaatattggacct aacaggatctagattagcaatataaagaagcatagtggtactctgtttcacactttcagtagatttattagaagtcaaattctattcaacagacact tattaggatatacaactaatttaagaataaaattccaggcacaatatattttttttaaatggtatttgttagtagtgcttcttccccttaacatttacagt gtaaatactgcaggtaaccgcaatctaagttagccaaaaagcagcttttttttcccatactgtatgtaaataatgtagacctgggttttttttgtttattt gggtttgttttttttttttgaggtactggaatctaattaatatctcttaggtatcaacaaaagggaacaattggaatgagaatttaggccttagcttcc atggtgattttttagtttttttatacagtaataattgtgatgctatttgtcaactggatataaatacacatataattttaaaaagtcaaaagtgcttttgtttc tttgtttaatgtaatttttgtgcttcacctacaggatgctgcagtaaattaaatatcagtgaagcttctgatgtataaagaatgctatgaataaaacat taagaagctgtgtaattttaagttatagttgcctctatttttaccatttcattggtaaaaattagctaatttttttcaagtgaaatgaaaaataaaaatat aaatttatcaatatgatggaaatcttattaaggagatgtattattgaattttcactgtacctgaaaaggagattcaaaattttttctggggatgtatat aggtgaaaatttgatttttttaaattatcaggaaaacaagataatgcacagatttctaagactaagatcttacctggatgtgattttttgagctgtggc tagacattctttagagccactggaaatattttgaaaactattctagttatagcagagctgctaatattaacgaatatatttgtgtcttcatggtttgtg actattaggccaaattttgtggtatatgttgtcagtctggatctggtgaggtctgttcaacatgaatctttgtgttatcttgaatttagtagtttcaagg tacttaaattcttaacagtttctaatttgtttcaatacatatgggacatggttgattttttttactgtattagaactcttggaagttcttagccttttcaggtt atgaaatacctgaaagtaaaattttctaagatttaataagggaagatactattcaaatcattttcttaggatagcatctttacatacaatgagagga ttgtacaagcattaatctcatattccaacatccagttacttgatgtgatccaagtaccctggtctttttgaagcagttaaaatctaattaattaacttt gggagtcttcactattcaattgatcctcatcattgtcctatttgcatgactccatttttttcctccactatatgagttttctttgtcaggggggagaggag tgggaagagtcacagaatctcatattcacatcttaattaaattgtgtgaaattagtcttttgtggaaattctgtaggcagtatgattttgaaaagcta accaatgataattagcattttagttaatactaaatgcataaaattataacccttgaaattaatttggtgctggcagttctggtttagtcatttttaccag tagttagtagtattaagacctgcagtatatgcacttttttgagtagctgtcaaataattgtagttgagaaacaacttgtttattctcacaattcagatttt ctattcagttttgtctcaaatagtaagttattgtgaacaatttaataacggccctcctgttctagtttgcctaatatttagttaagctttagtgttttaac ctatttttttaagtttatttttttgtattagatttatttgaataagttatgtgggtttagtaattgacctatttattcattgcttcactaattcatccagcttagt tttaagtgtgtatatgtatttgctcaccagatcattttcttgggaccttgaactgtgaatgttttgtcctaaccatttaatattttctaggtacttgctgc aagttcttgaactattttaccagctttaactttggggctcttagtttcttttctccagattcttgttattttattttatccaaataaatatttaggtgttctaa gaa (SEQ ID NO: 606) | | |
| Smad2 | cggccgggaggcggggcgggccgtaggcaaagggaggtggggaggcggtggccggcgactccccgcgccccgctcgccccccgg cccttcccgcggtgctcggcctcgttcctttcctcctccgctccctccgtcttccatacccgccccgcgcggctttcggccggcgtgcctcgc gccctaacgggcggctggaggcgccaatcagcgggcggcagggtgccagccccggggctgcgccggcgaatcggcggggcccgcg gcccagggtggcaggcgggtctacccgcgcggccgcggcggcggagaagcagctcgccagccagcagcccgccagccgccggga ggttcgatacaagaggctgttttcctagcgtggcttgctgcctttggtaagaacatgtcgtccatcttgccattcacgccgccagttgtgaaga gactgctgggatggaagaagtcagctggtgggtctggaggagcaggcggaggagagcagaatgggcaggaagaaaagtggtgtgaga aagcagtgaaaagtctggtgaagaagctaaagaaaacaggacgattagatgagcttgagaaagccatcaccactcaaaactgtaatactaa atgtgttaccataccaagcacttgctctgaaatttggggactgagtacaccaaatacgatagatcagtgggatacaacaggcctttacagcttc tctgaacaaaccaggtctcttgatggtcgtctccaggtatcccatcgaaaaggattgccacatgttatatattgccgattatggcgctggcctga tcttcacagtcatcatgaactcaaggcaattgaaaactgcgaatatgcttttaatcttaaaaaggatgaagtatgtgtaaacccttaccactatca gagagttgagacaccagttttgcctccagtattagtgccccgacacaccgagatcctaacagaacttccgcctctggatgactatactcactc cattccagaaaacactaacttcccagcaggaattgagccacagagtaattatattccagaaacgccacctcctggatatatcagtgaagatgg agaaacaagtgaccaacagttgaatcaaagtatggacacaggctctccagcagaactatctcctactactctttcccctgttaatcatagcttg gatttacagccagttacttactcagaacctgcattttggtgttcgatagcatattatgaattaaatcagagggttggagaaaccttccatgcatca cagccctcactcactgtagatggctttacagacccatcaaattcagagaggttctgcttaggtttactctccaatgttaaccgaaatgccacggt agaaatgacaagaaggcatataggaagaggagtgcgcttatactacataggtggggaagtttttgctgagtgcctaagtgatagtgcaatctt tgtgcagagccccaattgtaatcagagatatggctggcaccctgcaacagtgtgtaaaattccaccaggctgtaatctgaagatcttcaacaa | NM_001003652 | NM_001252481 |

TABLE 1-continued

| Gene | Human Gene Sequence | Human Sequence Accession No. | Murine Sequence Accession No. |
|---|---|---|---|
| | ccaggaatttgctgctcttctggctcagtctgttaatcagggttttgaagccgtctatcagctaactagaatgtgcaccataagaatgagttttgt | | |
| | gaaagggtggggagcagaataccgaaggcagacggtaacaagtactccttgctggattgaacttcatctgaatggacctctacagtggttg | | |
| | gacaaagtattaactcagatgggatccccttcagtgcgttgctcaagcatgtcataaagcttcaccaatcaagtcccatgaaaagacttaatgt | | |
| | aacaactcttctgtcatagcattgtgtgtggtccctatggactgtttactatccaaaagttcaagagagaaaacagcacttgaggtctcatcaatt | | |
| | aaagcaccttgtggaatctgtttcctatatttgaatattagatgggaaaattagtgtctagaaatactctcccattaaagaggaagagaagatttt | | |
| | aaagacttaatgatgtcttattgggcataaaactgagtgtcccaaaggtttattaataacagtagtagttatgtgtacaggtaatgtatcatgatcc | | |
| | agtatcacagtattgtgctgtttatatacattttagtttgcatagatgaggtgtgtgtgtgcgctgcttcttgatctaggcaaacctttataaagttg | | |
| | cagtacctaatctgttattcccacttctctgttattttgtgtgtctttttaatatataatatatatcaagcttttcaaattatttagaagcagcttttcctgt | | |
| | agaaaaactaattttctgccttttaccaaaataaactcttggggaagaaaagtggattaactttgaaatccttgaccttaatgtgttcagtgg | | |
| | ggcttaaacagtcattctttttgtggtttttgtttttttttgttttttttttaactgctaaatcttattataaggaaaccatactgaaaacctttccaagcct | | |
| | ctttttccattcccattttgtcctcataatcaaaacagcataacatgacatcatcaccagtaatagttgcattgatactgctggcaccagttaattc | | |
| | tgggatacagtaagaattcatatggagaaagtccctttgtcttatgcccaaatttcaacaggaataattggcttgtataatctagcagtctgttgat | | |
| | ttatccttccacctcataaaaaatgcataggtggcagtataattattttcagggatatgctagaattacttccacatatttatccctttttaaaaaagc | | |
| | taatctataaataccgtttttccaaaggtattttacaatatttcaacagcagaccttctgctcttcgagtagtttgatttggtttagtaaccagattgca | | |
| | ttatgaaatgggccttttgtaaatgtaattgtttctgcaaaatacctagaaaagtgatgctgaggtaggatcagcagatatgggccatctgtttta | | |
| | aagtatgttgtattcagtttataaattgattgttattctacacataattatgaattcagaattttaaaaattgggggaaaagccatttatttagcaagttt | | |
| | tttagcttataagttacctgcagtctgagctgttcttaactgatcctggttttgtgattgacaatatttcatgctctgtagtgagaggagatttccgaa | | |
| | actctgttgctagttcattctgcagcaaataattattatgtctgatgttgactcattgcagtttaaacatttcttcttgtttgcatcttagtagaaatgga | | |
| | aaataaccactcctggtcgtcttttcataaatttcatattttgaagctgtctttggtacttgttctttgaaatcatatccacctgtctctataggtatca | | |
| | ttttcaatactttcaacatttggtggttttctattgggtactccccatttcctatatttgtgtgtatatgtatgtgttcatgtaaatttggtatagtaatttttt | | |
| | tattcattcaacaaatatttattgttcacctgtttgtaccaggaacttttcttagtctttgggtaaaggtgaacaagacaactacagttcctgcctttg | | |
| | ctgagacagcagttacactaacccttaattatcttacttgtctatgaaggagataaacagggtactgtactggagaataacagatgggatgctt | | |
| | caggtaggacatcaaggaaagcctctaaggaaaggatgcatgagctaacacctgacattaaagaagcaagccaagtgaggagccaggg | | |
| | gagataagcattcctggcaaagagaatagcatcaaatgcaaaaaggttcacactaaaggaaactcctgattaggtattaatgctttatacaga | | |
| | aacctctatacaaatccaaacttgaagatcagaatggttctacagttcataacattttgaaggtggccttattttgtgatagtctgcttcatgtgatt | | |
| | ctcactaacatatctccttcctcaacctttgctgtaaaaatttcatttgcaccacatcagtactacttaatttaacaagcttttgttgtgtaagctctca | | |
| | ctgttttagtgccctgctgcttgcttccagactttgtgctgtccagtaattatgtcttccactacccatcttgtgagcagagtaaatgtcctaggtaa | | |
| | taccactatcaggcctgtaggagatactcagtggagcctctgcccttctttttcttacttgagaacttgtaatggtgttagggaacagttgtaggg | | |
| | gcagaaaacaactctgaaagtggtagaaggtcctgatcttggtggttactcttgcattactgtgttaggtcaagcagtgcctactatgctgtttc | | |
| | agtagtggagcgcatctctacagttctgatgcgattttctgtacagtatgaaattgggactcaactctttgaaaacacctattgagcagttatac | | |
| | ctgttgagcagtttacttcctggttgtaattacatttgtgtgaatgtgtttgatgctttttaacgagatgatgtttttttgtattttatctactgtggcctgat | | |
| | tttttttttgttttctgcccctccccccatttataggtgtggttttcatttttctaagtgatagaatcccctctttgttgaatttttgtctttatttaaattagca | | |
| | acattacttaggatttattcttcacaatactgttaattttctaggaatgatgacctgagaaccgaatggccatgctttctatcacatttctaagatga | | |
| | gtaatatttttttccagtaggttccacagagacaccttgggggctggcttaggggaggctgttggagttctcactgacttagtggcatatttattct | | |
| | gtactgaagaactgcatggggtttcttttggaaagagtttcattgctttaaaaagaagctcagaaagtctttataaccactggtcaacgattaga | | |
| | aaaatataactggatttaggcctaccttctggaataccgctgattgtgctctttttatcctactttaaagaagctttcatgattagatttgagctatat | | |
| | cagttataccgattataccttataatacacattcagttagtaaacatttattgatgcctgttgtttgcccagccactgtgatggatattgaataataa | | |
| | aaagatgactaggacggggccctgacccttgagctgtgcttggtcttgtagaggttgtgtttttttttcctcaggacctgtcactttggcagaagg | | |
| | aaatctgcctaatttttcttgaaagctaaatttctttgtaagtttttacaaattgtttaatacctagttgtatttttttaccttaagccacattgagttttgct | | |
| | tgatttgtctgtcttttaaacactgtcaaatgctttcccttttgttaaaattattttaatttcactttttttgtgcccttgtcaatttaagactaagactttga | | |
| | aggtaaaacaaacaaacaaacatcagtcttagtctcttgctagttgaaatcaaataaaagaaaatatatacccagttggtttctctacctcttaaa | | |
| | agcttcccatatataccttttaagatccttctcttttttctttaactactaaataggttcagcatttattcagtgttagataccctcttcgtctgagggtgg | | |
| | cgtaggtttatgttgggatataaagtaacacaagacaatcttcactgtacataaaatatgtcttcatgtacagtctttactttaaaagctgaacattc | | |
| | caatttgcgccttccctcccaagcccctgcccaccaagtatctctttagatatctagtctgtggacatgaacaatgaatactttttttcttactctgat | | |
| | cgaaggcattgatacttagacatatcaaacatttcttcctttcatatgctttactttgctaaatctattatattcattgcctgaattttattcttcctttcta | | |
| | cctgacaacacacatccaggtggtacttgctggttatcctctttcttgttagccttgtttttttgttttttttttttttttttgagagggagtctcgctctgtt | | |
| | gcccaacctggagtgcagtggtgcgatcttggttcactgcaagctccgcctcccgggttcacgccatgcttctgcctcagcctcccaagtag | | |
| | ctgggactacaggcgcccaccaccacactcggctaatttttttgtatttttagtagagacggggtttcaccgtgttggccaggatggtctcgatct | | |
| | cctgacctcgtgatctgtccacctcggcttcccaaagtgctgggattacaggcatgagccaccgcgcccagcctagccatattttttatctgcat | | |
| | atatcagaatgtttctctcctttgaacttattaacaaaaaaggaacatgcttttcatacctagagtcctaatttcttcatcatgaaggttgctattcaa | | |

TABLE 1-continued

| Gene | Human Gene Sequence | Human Sequence Accession No. | Murine Sequence Accession No. |
|---|---|---|---|
| | attgatcaatcattttaattttacaaatggctcaaaaattctgttcagtaaatgtctttgtgactggcaaatggcataaattatgtttaagattatgaac | | |
| | ttttctgacagttgcagccaatgttttccctacgataccagatttccatcttggggcatattggattgttgtatttaagacagtcagaataatgatag | | |
| | tgtgtggtctccagaggtagtcagaatcctgctattgagttctttttatatcttccttttcaatttttttattaccatttttgtttgtttagactacactttgtag | | |
| | ggattgaggggcaaattatctcttggagtggaattcctgtgttttgagccttacaaccaggaaatatgagctatactagatagcctcatgatagc | | |
| | atttacgataagaacttatctcgtgtgttcatgtaatttttttgagtaggaactgttttatcttgaatattgtagctaactatatatagcagaactgcctc | | |
| | agtcttttttaagaaggaaataaataatatatgtgtatgaatttatatatacatatacactcatagacaaacttaacagttggggtcattctaacagtt | | |
| | aaaacaattgttccattgtttaaatctcagatcctggtaaaatgttcttaatttgtctgtgtacattttcctttcatggacagaccattggagtacatta | | |
| | attttcttaatctgccatttggcagttcatttaatataccattttttggcaacttggtaactaagaatcacagccaaaatttgttaacatcaaagaaag | | |
| | ctctgccatataccccgttactaaattattatacatccagcagattctgggatgtactaacttagggttaactttgttgttgttgataatactagattg | | |
| | ctccctctttaattcttcttctggtgcaaggttgctgcttaagttaccctgggaaatactactacaaggtcaaattttctagtatcttacagcctgatt | | |
| | gaaggtgattcagatctttgctcaatataaatggattttccaagattctctgggccatccttgacccacaggtgatctcgctggagtatattaactt | | |
| | aacttcagtgccagttggtttggtgccatgagatccataatgaatccagaacttcaccattgcttagatataagagtcccttggaagaataatgc | | |
| | cactgatgatgggggtcagaaggtgtattaactcaacatagagggcttttagatttttcttcaaaaaaatttcgagaaaagtattcttttaccctcc | | |
| | aaacagttaacagctcttagtttctccaaatatgctctttgatttacttatttttaattaaagatggtaatttattgaacaatgaaatccgtaatatattg | | |
| | atttaaggacaaaagtgaagttttagaattataaaagtacttaaatattatatattttccatttcataattgttttcctttctctgtggctttaaagtttttg | | |
| | actattttacaatgttaatcactaggtaacttgccatatttctggttctatattaagttctatcctttataatgctgttattataaagctggtttttagcattt | | |
| | gtctgtagcaatagaaattttactaagtctctgttctcccagtaagtttttttcttttctcagtaagtccctaagaaaacatttgtttgccactcttactat | | |
| | tcccaatcttggattgttcgagctgaaaaaaaaatttgatgagaaacaggaggatccttttctggtgaatataggttcctgctttaagaatgtggaa | | |
| | atccattgctttatataactaatatacacacagattaattaaaattgtgagaaataattcacacatgacaagtaggtaacatgcatgagttttgaatt | | |
| | tttttaaaaacccaactgtttgacaaaatatagaacccaaattggtactttcttagaccagtgtaacctcacacctcagttttgcttttccaaccctg | | |
| | acttgaaaggcatatttgtatctttttattagtgatagtgaagctgtgacactaaccttttatacaaaagagtaaagaaagaaaaactacagcgat | | |
| | taagatgagaacagttctgcagttgttgaactagatcacagcattgtaggcagaataaaaaatgttcatatctgagaatattcctttcgccatcttt | | |
| | tcccaaggccagacctcctggtggagcacagttaaaagtaacattctgggcctttgtaatcggagggctgtgtctccagctggcagcctttgt | | |
| | tttaatatataatgcaggactgtggaaaacagttggcatagaatattttcacctaaaaaagaaagaaaagacatacaaaactggattaattgca | | |
| | aaaagagaatacagtaaaataccatataactggacaaagctagaagaacctttagaagatttgtctgaaaacagatttcaagagtgagctttta | | |
| | tacactgctcactaatttgcttgattactaccaactcttcttaaagttaacacgtttaaggtatttctggacttcctagccttttagcaagcttagagg | | |
| | aactagccattagctagtgatgtaaaaatattttggggactgatgcccttaaaggttatgcccttgaaagttcttaccttttctctagtgatattaag | | |
| | gaacgagtgggtagtgttctcagggtgaccagctgccctaaagtgcctgggattgagggtttccctggatgcgggactttccctggatacaa | | |
| | aacttttagcagagttttgtatatatgtggatttttctgataagtagcacatcagaggccttaaccactgcccaaaagcgattctccattgagagt | | |
| | acatatcttgaacttaagaaattcatttgctctgattttaatcttgtaaagtttttgctaaactcaaaacaagtcccaggcacaccagaaggagct | | |
| | gaccaccttaggtgttcttgtgatttatccttacttccctatgttgtcatagttgcttctaaactcagctgcactatggctgtcaacatttctgatactt | | |
| | attgggatatgtgccatccagtcatttagtactttgaatggaacatgagatttataacacaggtaatagctgaaggtaccagtatggtggtgaga | | |
| | ctcacacttagtgatccagctaaggtaactgatgttataatggaacagagaagaggccaactagatagctaagttcttctgaacctatgtgtat | | |
| | atgtaagtacaaatcatgcgtccttatggggttaaacttaatctgaaatttacattttcatagtaaaaggaaaccaattgttgcagatttcttttctt | | |
| | gtgaggaaatacatggcctttgatgctctggcgtctactgcatttcccagtctgttctgctcgagaagccagaatgtgttgttaacatttttccgtg | | |
| | aatgttgtgttaaaatgattaaatgcatcagccaatggcaagtgaaggaattgggtgtcctgatgcagactgagcagtttctctcaattgtagcc | | |
| | tcatactcataaggtgcttaccagctagaacattgagcacgtgaggtgagatttttttctctgatggcattaactttgtaatgcaatatgatggat | | |
| | gcagaccctgttcttgtttccctctggaagtccttagtggctgcatccttggtgcactgtgatggagatattaaatgtgttctttgtgagctttcgtt | | |
| | ctatgattgtcaaaagtacgatgtggttcctttttttattttttattaaacaatgagctgaggctttattacagctggttttcaagttaaaattgttgaatac | | |
| | tgatgtctttctcccacctacaccaaatattttagtctatttaaagtacaaaaaaaagttctgcttaagaaaacattgcttacatgtcctgtgatttctg | | |
| | gtcaatttttatatatatttgtgtgcatcatctgtatgtgctttcactttttaccttgtttgctcttacctgtgttaacagccctgtcaccgttgaaaggtg | | |
| | gacagttttcctagcattaaaagaaagccatttgagttgtttaccatgttaaaaaaaaaaaaaaaa (SEQ ID NO: 607) | | |
| Akap81 | gtgtgtggaggggaccctgtggttagcagcagctatcgcagcgtcggatgttcagagcagcagaagccggcgtcgtcggatgttgtgttgc | NM_014371 | NM_017476 |
| | ccgccaccatgagctacacaggctttgtccagggatctgaaaccactttgcagtcgacatactcggataccagcgctcagcccacctgtgat | | |
| | tatggatatggaacttggaactctgggacaaatagaggctacgagggctatggctatggctatggctatggccaggataacaccaccaact | | |
| | atgggtatggtatggccacttcacactcttgggaaatgcctagctctgacacaaatgcaaacactagtgcctcgggtagcgccagtgccgat | | |
| | tccgttttatccagaattaaccagcgcttagatatggtgccgcatttggagacagacatgatgcaaggaggcgtgtacggctcaggtggaga | | |
| | aaggtatgactcttatgagtcctgcgactcgagggccgtcctgagtgagcgcgacctgtaccggtcaggctatgactacagcgagcttgac | | |
| | cctgagatggaaatggcctatgagggccaatacgatgcctaccgcgaccagttccgcatgcgtggcaacgacaccttcggtcccagggca | | |

TABLE 1-continued

| Gene | Human Gene Sequence | Human Sequence Accession No. | Murine Sequence Accession No. |
|---|---|---|---|
| | cagggctgggcccgggatgcccggagcggccggccaatggcctcaggctatgggcgcatgtgggaagaccccatgggggcccgggg ccagtgcatgtctggtgcctctcggctgccctccctcttctcccagaacatcatccccgagtacggcatgttccagggcatgcgaggtgggg gcgccttcccgggcggctcccgctttggtttcgggtttggcaatggcatgaagcagatgaggcggacctggaagacctggaccacagccg acttccgaaccaagaagaagaagagaaagcagggcggcagtcctgatgagccagatagcaaagccacccgcacggactgctcggaca acagcgactcagacaatgatgagggcaccgagggggaagccacagagggccttgaaggcaccgaggctgtggagaagggctccaga gtggacggagaggatgaggagggaaaagaggatgggagagaagaaggcaaagaggatccagagaagggggccctaaccacccag gatgaaaatggccagaccaagcgcaagttgcaggcaggcaagaagagtcaggacaagcagaaaaagcggcagcgagaccgcatggt ggaaaggatccagtttgtgtgttctctgtgcaaataccggaccttctatgaggacgagatggccagccatcttgacagcaagttccacaagg aacactttaagtacgtaggcaccaagctccctaagcagacggctgactttctgcaggagtacgtcactaacaagaccaagaagacagagg agctccgaaaaaccgtggaggaccttgatggcctcatccaccaaatctacagagaccaggatctgacccaggaaattgccatggagcattt tgtgaagaaggtggaggcagcccattgtgcagcctgcgacctcttcattcccatgcagtttgggatcatccagaagcatctgaagaccatgg atcacaaccggaaccgcaggctcatgatggagcagtccaagaagtcctccctcatggtggcccgcagtattctcaacaacaagctcatcag caagaagctggagcgctacctgaagggcgagaaccctttcaccgacagccccgaggaggagaaggagcaggaggaggctgagggcg gtgccctggacgagggggcgcagggcgaagcggcagggatctcggagggcgcagagggcgtgccggcgcagcctcccgtgccccc agagccagcccccggggccgtgtcgccgccaccgccgccgcccccagaggaggaggaggagggcgccgtgcccttgctgggaggg gcgctgcaacgccagatccgcggcatcccgggcctcgacgtggaggacgacgaggagggcggcgggggcgccccgtgacccgagc tcggggcgggcggagcccgcgtggccgaagctggaaaccaaacctaataaagttttcccatcccaccaaaaaaaaaaaaaaaaaaaaaa (SEQ ID NO: 608) | | |
| Rbks | acctttgagcgatggcggcgtctggggaaccccagaggcagtggcaagaggaggtggcggcggtggtagtggtgggctcctgcatgac cgacctggtcagtcttacttctcgtttgccaaaaactggagaaaccatccatggacataagtttttttattggctttggagggaaaggtgccaacc agtgtgtccaagctgctcggcttggagcaatgacgtccatggtgtgtaaggttggcaaagattcttttggcaatgattatatagaaaacttaaaa cagaatgatatttctacagaatttacatatcagactaaagatgctgctacaggaactgcttctataattgtcaataatgaaggccagaatatcatt gtcatagtggctggagcaaatttacttttgaatacggaggatctgagggcagcagccaatgtcattagcagagccaaagtcatggtctgcca gctcgaaataactccagcaacttctttggaagccctaacaatggcccgcaggagtggagtgaaaaccttgttcaatccagcccctgccattg ctgacctggatccccagttctacaccctctcagatgtgttctgctgcaatgaaagtgaggctgagattttaactggcctcacggtgggcagcg ctgcagatgctggggaggctgcattagtgctcttgaaaaggggctgccaggtggtaatcattaccttaggggctgaaggatgtgtggtgctg tcacagacagaacctgagccaaagcacattcccacagagaaagtcaaggctgtggataccacgggtgctggtgacagctttgtgggagct ctggccttctacctggcttactatccaaatctgtccttggaagacatgctcaacagatccaatttcattgcagcagtcagtgtccaggctgcag gaacacagtcatcttacccttacaaaaaagaccttccgcttactctgttttgattgctattagtcccaaaataaatatacctgggaataaaatgtac ttgggggtggctgctcctggctaatgcttattagaaaatgtcctcgtcccctttctttgcaaatattagttcttttacgaagtcatcctcaagcttca atttatttataacgatgattcttttgctttccatgcatttgcacaaaacaaccagaattaaagattccacaacc (SEQ ID NO: 609) | NM_022128 | NM_153196 |
| Egr2 | aactgagcgaggagcaattgattaatagctcggcgaggggactcactgactgttataataacactacaccagcaactcctggcttcccagca gccggaacacagacaggagagagtcagtggcaaatagacatttttcttatttcttaaaaaacagcaacttgtttgctacttttatttctgttgatttt tttttcttggtgtgtgtggtggttgtttttaagtgtggagggcaaaaggagataccatcccaggctcagtccaacccctctccaaaacggcttttc tgacactccaggtagcgagggagttgggtctccaggttgtgcgaggagcaaatgatgaccgccaaggccgtagacaaaatcccagtaact ctcagtggttttgtgcaccagctgtctgacaacatctacccggtggaggacctcgccgccacgtcggtgaccatctttcccaatgccgaactg ggaggcccctttgaccagatgaacggagtggccggagatggcatgatcaacattgacatgactggagagaagaggtcgttggatctccca tatcccagcagctttgctcccgtctctgcacctagaaaccagaccttcacttacatgggcaagttctccattgaccctcagtaccctggtgcca gctgctacccagaaggcataatcaatattgtgagtgcaggcatcttgcaaggggtcacttccccagcttcaaccacagcctcatccagcgtc acctctgcctcccccaacccactggccacaggacccctgggtgtgtgcaccatgtcccagacccagcctgacctggaccacctgtactctc cgccaccgcctcctcctccttattctggctgtgcaggagacctctaccaggacccttctgcgttcctgtcagcagccaccacctccacctcttc ctctctggcctacccaccacctccttcctatccatcccccaagccagccacggacccaggtctcttcccaatgatcccagactatcctggattc tttccatctcagtgccagagagacctacatggtacagctggcccagaccgtaagccctttccctgcccactggacaccctgcgggtgcccc ctccactcactccactctctacaatccgtaactttaccctgggggccccagtgctggggtgaccggaccaggggccagtggaggcagcg agggaccccggctgcctggtagcagctcagcagcagcagcagccgccgccgccgccgcctataacccacaccacctgccactgcggc ccattctgaggcctcgcaagtaccccaacagacccagcaagacgccggtgcacgagaggccctacccgtgcccagcagaaggctgcga ccggcggttctcccgctctgacgagctgacacggcacatccgaatccacactgggcataagcccttccagtgtcggatctgcatgcgcaac ttcagccgcagtgaccacctcaccacccatatccgcacccacaccggtgagaagcccttcgcctgtgactactgtggccgaaagtttgccc | NM_000399 | NM_010118 |

TABLE 1-continued

| Gene | Human Gene Sequence | Human Sequence Accession No. | Murine Sequence Accession No. |
|---|---|---|---|
| | ggagtgatgagaggaagcgccacaccaagatccacctgagacagaaagagcggaaaagcagtgccccctctgcatcggtgccagccc cctctacagcctcctgctctgggggcgtgcagcctgggggtaccctgtgcagcagtaacagcagcagtcttggcggagggccgctcgcc ccttgctcctctcggacccggacaccttgagatgagactcaggctgatacaccagctcccaaaggtcccggaggccctttgtccactggag ctgcacaacaaacactaccaccctttcctgtccctctctccctttgttgggcaaagggctttggtggagctagcactgccccctttccacctaga agcaggttcttcctaaaacttagcccattctagtctctcttaggtgagttgactatcaacccaaggcaaaggggaggctcagaaggaggtggt gtggggacccctggccaagagggctgaggtctgaccctgctttaaagggttgtttgactaggttttgctaccccacttccccttattttgaccca tcacaggtttttgaccctggatgtcagagttgatctaagacgttttctacaataggttgggagatgctgatcccttcaagtggggacagcaaaa agacaagcaaaactgatgtgcactttatggcttgggactgatttgggggacattgtacagtgagtgaagtatagcctttatgccacactctgtg gccctaaaatggtgaatcagagcatatctagttgtctcaacccttgaagcaatatgtattataaactcagagaacagaagtgcaatgtgatggg aggaacatagcaatatctgctccttttcgagttgtttgagaaatgtaggctatttttcagtgtatatccactcagattttgtgtatttttgatgtacact gttctctaaattctgaatctttgggaaaaaatgtaaagcatttatgatctcagaggttaacttatttaaggggatgtacatatattctctgaaacta ggatgcatgcaattgtgttggaagtgtccttggtgccttgtgtgatgtagacaatgttacaaggtctgcatgtaaatgggttgccttattatggag aaaaaaatcactccctgagtttagtatggctgtatatttctgcctattaatatttggaatttttttagaaagtatatttttgtatgctttgttttgtgactta aaagtgttacctttgtagtcaaatttcagataagaatgtacataatgttaccggagctgatttgtttggtcattagctcttaatagttgtgaaaaaat aaatctattctaacgcaaaaccactaactgaagttcagataatggatggtttgtgactatagtgtaaataaatacttttcaacaataaaaaaaaaa aaaaa (SEQ ID NO: 610) | | |
| Dgka | agttcctgccagtgagtccctaggcctccatctctctcccttgctgtaccaccttcaccaccatccatgcgaccccaagagccttaatgactcta gaagagactccaggcaggggaagctgaaaggacctttcactccctacttttggccagggccttctgtgccacctgccaagaccagcaggc ctaccctctgaagaggtccaagcaacggaagtactactacgaagctgcctttctggccatccttgagaaaaatagacagatggccaaggag aggggcctaataagccccagtgatttgcccagctgcaaaaatacatggaatactccaccaaaaaggtcagtgatgtcctaaagctcttcga ggatggcgagatggctaaatatgtccaaggagatgccattgggtacgagggattccagcaattcctgaaaatctatctcgaagtggataatg ttcccagacacctaagcctggcactgtttcaatcctttgagactggtcactgcttaaatgagacaaatgtgacaaaagatgtggtgtgtctcaat gatgtttcctgctacttttcccttctggagggtggtcggccagaagacaagttagaattcaccttcaagctgtacgacacggacagaaatggg atcctggacagctcagaagtggacaaaattatcctacagatgatgcgagtggctgaatacctggattgggatgtgtctgagctgaggccgat tcttcaggagatgatgaaagagattgactatgatggcagtggctctgtctctcaagctgagtgggtccgggctggggccaccaccgtgcca ctgctagtgctgctgggtctggagatgactctgaaggacgacggacagcacatgtggaggcccaagaggttccccagaccagtctactgc aatctgtgcgagtcaagcattggtcttggcaaacagggactgagctgtaacctctgtaagtacactgttcacgaccagtgtgccatgaaagc cctgccttgtgaagtcagcacctatgccaagtctcggaaggacattggtgtccaatcacatgtgtgggtgcgaggaggctgtgagtccggg cgctgcgaccgctgtcagaaaaagatccggatctaccacagtctgaccgggctgcattgtgtatggtgccacctagagatccacgatgact gcctgcaagcggtgggccatgagtgtgactgtgggctgctccgggatcacatcctgcctccatcttccatctatcccagtgtcctggcctctg gaccggatcgtaaaaatagcaaaacaagccagaagaccatggatgatttaaatttgagcacctctgaggctctgcggattgaccctgttcct aacacccacccacttctcgtctttgtcaatcctaagagtggcgggaagcaggggcaaagggtgctctggaagttccagtatatattaaaccct cgacaggtgttcaacctcctaaaggatggtcctgagatagggctccgattattcaaggatgttcctgatagccggattttggtgtgtggtggag acggcacagtaggctggattctagagaccattgacaaagctaacttgccagttttgcctcctgttgctgtgttgcccctgggtactggaaatga tctggctcgatgcctaagatggggaggaggttatgaaggacagaatctggcaaagatcctcaaggatttagagatgagtaaagtggtacat atggatcgatggtctgtggaggtgatacctcaacaaactgaagaaaaaagtgacccagtcccctttcaaatcatcaataactacttctctattg gcgtggatgcctctattgctcatcgattccacatcatgcgagagaaatatccggagaagttcaacagcagaatgaagaacaagctatggtac ttcgaatttgccacatctgaatccatcttctcaacatgcaaaaagctggaggagtctttgacagttgagatctgtgggaaaccgctggatctga gcaacctgtccctagaaggcatcgcagtgctaaacatccctagcatgcatggtggctccaacctctggggtgataccaggagaccccatgg ggatatctatgggatcaaccaggccttaggtgctacagctaaagtcatcaccgaccctgatatcctgaaaacctgtgtaccagacctaagtga caagagactggaagtggttgggctggagggtgcaattgagatgggccaaatctataccaagctcaagaatgctggacgtcggctggccaa gtgctctgagatcaccttccacaccacaaaaacccttcccatgcaaattgacggagaaccctggatgcagacgccctgtacaatcaagatca cccacaagaaccagatgcccatgctcatgggcccacccccccgctccaccaatttctttggcttcttgagctaaggggacacccttggcct ccaagccagccttgaacccacctccctgtccctggactctactcccgaggctctgtacattgctgccacatactcctgccagcttgggggagt gttccttcaccctcacagtatttattatcctgcaccacctcactgttccccatgcgcacacacatacacacaccccaaaacacatacattgaaag tgcctcatctgaataaaatgacttgtgtttcccctttgggatctgctaaaaaaaaaaaaaaaaaaaaaaaaaaaaaa (SEQ ID NO: 611) | NM_001345 | NM_016811 |

TABLE 1-continued

| Gene | Human Gene Sequence | Human Sequence Accession No. | Murine Sequence Accession No. |
|---|---|---|---|
| Cblb | ctgggtcctgtgtgtgccacaggggtggggtgtccagcgagcggtctcctcctcctgctagtgctgctgcggcgtcccgcggcctccccga<br>gtcgggcgggaggggagagcgggtgtggatttgtcttgacggtaattgttgcgtttccacgtctcggaggcctgcgcgctgggttgctcctt<br>cttcgggagcgagctgttctcagcgatcccactcccagccggggctccccacacacactgggctgcgtgcgtgtggagtgggacccgcg<br>cacacgcgtgtctctggacagctacggcgccgaaagaactaaaattccagatggcaaactcaatgaatggcagaaaccctggtggtcgag<br>gaggaaatccccgaaaaggtcgaattttgggtattattgatgctattcaggatgcagttggacccccctaagcaagctgccgcagatcgcagg<br>accgtggagaagacttggaagctcatggacaaagtggtaagactgtgccaaaatcccaaacttcagttgaaaaatagcccaccatatatact<br>tgatattttgcctgatacatatcagcatttacgacttatattgagtaaatatgatgacaaccagaaacttgcccaactcagtgagaatgagtacttt<br>aaaatctacattgatagccttatgaaaaagtcaaaacgggcaataagactctttaaagaaggcaaggagagaatgtatgaagaacagtcaca<br>ggacagacgaaatctcacaaaactgtcccttatcttcagtcacatgctggcagaaatcaaagcaatctttcccaatggtcaattccagggaga<br>taactttcgtatcacaaaagcagatgctgctgaattctggagaaagtttttggagacaaaactatcgtaccatggaaagtattcagacagtgc<br>cttcatgaggtccaccagattagctctggcctggaagcaatggctctaaaatcaacaattgatttaacttgcaatgattacatttcagtttttgaat<br>ttgatatttttaccaggctgtttcagccttggggctctatttgcggaattggaatttcttagctgtgacacatccaggttacatggcatttctcacat<br>atgatgaagttaaagcacgactacagaaatatagcaccaaacccggaagctatattttccggttaagttgcactcgattgggacagtgggcc<br>attggctatgtgactggggatgggaatatcttacagaccatacctcataacaagcccttatttcaagccctgattgatggcagcagggaagga<br>ttttatctttatcctgatgggaggagttataatcctgatttaactggattatgtgaacctacacctcatgaccatataaaagttacacaggaacaat<br>atgaattatattgtgaaatgggctccacttttcagctctgtaagatttgtgcagagaatgacaaagatgtcaagattgagccttgtgggcatttga<br>tgtgcacctcttgccttacggcatggcaggagtcggatggtcagggctgccctttctgtcgttgtgaaataaaaggaactgagcccataatcg<br>tggacccctttgatccaagagatgaaggctccaggtgttgcagcatcattgacccctttggcatgccgatgctagacttggacgacgatgatg<br>atcgtgaggagtccttgatgatgaatcggttggcaaacgtccgaaagtgcactgacaggcagaactcaccagtcacatcaccaggatcctc<br>tccccttgcccagagaagaaagccacagcctgacccactccagatcccacatctaagcctgccacccgtgcctcctcgcctggatctaattc<br>agaaaggcatagttagatctccctgtggcagcccaacgggttcaccaaagtcttctccttgcatggtgagaaaacaagataaaccactccca<br>gcaccacctcctcccttaagagatcctcctccaccgccacctgaaagacctccaccaatcccaccagacaatagactgagtagacacatcc<br>atcatgtggaaagcgtgccttccagagacccgccaatgcctcttgaagcatggtgccctcgggatgtgtttgggactaatcagcttgtgggat<br>gtcgactcctaggggagggctctccaaaacctggaatcacagcgagttcaaatgtcaatggaaggcacagtagagtgggctctgacccag<br>tgcttatgcggaaacacagacgccatgatttgcctttagaaggagctaaggtcttttccaatggtcaccttggaagtgaagaatatgatgttcct<br>ccccggctttctcctcctcctccagttaccaccctcctccctagcataaagtgtactggtccgttagcaaattctctttcagagaaaacaagaga<br>cccagtagaggaagatgatgatgaatacaagattccttcatcccaccctgtttccctgaattcacaaccatctcattgtcataatgtaaaacctc<br>ctgttcggtcttgtgataatggtcactgtatgctgaatggaacacatggtccatcttcagagaagaaatcaaacatccctgacttaagcatatatt<br>taaagggagatgtttttgattcagcctctgatcccgtgccattaccacctgccaggcctccaactcgggacaatccaaagcatggttcttcact<br>caacaggacgccctctgattatgatcttctcatccctccattaggtgaagatgcttttgatgccctccctccatctctcccacctcccccacctcc<br>tgcaaggcatagtctcattgaacattcaaaacctcctggctccagtagccggccatcctcaggacaggatctttttcttcttccttcagatccctt<br>tgttgatctagcaagtggccaagttcctttgcctcctgctagaaggttaccaggtgaaaatgtcaaaactaacagaacatcacaggactatgat<br>cagcttccttcatgttcagatggttcacaggcaccagccagacccccctaaaccacgaccgcgcaggactgcaccagaaattcaccacaga<br>aaaccccatgggcctgaggcggcattggaaaatgtcgatgcaaaaattgcaaaactcatgggagagggttatgcctttgaagaggtgaag<br>agagccttagagatagcccagaataatgtcgaagttgcccggagcatcctccgagaatttgccttccctcctccagtatccccacgtctaaat<br>ctatagcagccagaactgtagacaccaaaatggaaagcaatcgatgtattccaagagtgtggaaataaagagaactgagatggaattcaag<br>agagaagtgtctcctcctcgtgtagcagcttgagaagaggcttgggagtgcagcttctcaaaggagaccgatgcttgctcaggatgtcgac<br>agctgtggcttccttgtttttgctagccatatttttaaatcagggttgaactgacaaaaataatttaaagacgtttacttcccttgaactttgaacctg<br>tgaaatgctttaccttgtttacagtttggcaaagttgcagtttgttcttgtttttagtttagttttgttttggtgttttgatacctgtactgtgttcttcacag<br>accctttgtagcgtggtcaggtctgctgtaacatttcccaccaactctcttgctgtccacatcaacagctaaatcatttattcatatggatctctac<br>catccccatgccttgcccaggtccagttccatttctctcattcacaagatgctttgaaggttctgattttcaactgatcaaactaatgcaaaaaaaa<br>aaaagtatgtattcttcactactgagtttcttctttggaaaccatcactattgagagatgggaaaaacctgaatgtataaagcatttatttgtcaata<br>aactgccttttgtaaggggttttcacataacata (SEQ ID NO: 612) | NM_170662 | NM_001033238 |
| Mdfic | cccaggccggctctggcctcctgacccagacagcgcagggcgcgagggatcgcgcggccgagcccgggtcgcgccgctcccagcat<br>cggggccgctagccaagagttcgaggccttcccgatccggatgtgatgaaaaagagcaacagagggagaagtgtttcaggattgtagga<br>gtggaagaggggaaagagaggcagagagggggaaggcccccctcgcaggggagccggctggagtgagctggctggaaagaggggg<br>cggagtgcgcggagtcagagccgccaccgctgccgcagttgccgccactgcggcgtctgggctgagccggagggaggcgggaggac<br>gcgcaggggcggccgccgccgtcgtcaggccaccggggcgaaaatgcggccgctgccggaggctcgctaactttccggggcggaag | NM_001166345 | NM_175088 |

TABLE 1-continued

| Gene | Human Gene Sequence | Human Sequence Accession No. | Murine Sequence Accession No. |
|---|---|---|---|
| | aggaggaggaggaggaggaaggggcttggagcgactacggggggatgcggagaagcagtcagttccctgcacccagcacctcacag<br>cccttcctccgtgcgccctgccgggcggcgagctaggcggcagcggcgcggcgcgggctcggcggagcggcccatgtccggcgcgg<br>gcgaagccctcgctcccgggcccgtggggccgcagcgcgtggccgaggcgggcggcggccagctgggctccacagcccagggaaa<br>atgtgataaagacaatactgagaaagatataactcaagctaccaatagccacttcacacatggagagatgcaagaccagtccatttggggaa<br>atccttcggatggtgaactcattagaacccaacctcagcgcttgcctcagcttcagacttcagcccaggtgccaagtggtgaggaaataggc<br>aagataaagaacggccacacaggtctgagcaatggaaatggaattcaccacggggccaaacacggatccgcagataatcgcaaactttca<br>gcacctgtttctcaaaaaatgcatagaaaaattcagtccagcttgtctgtaaacagcgatatcagtaagaagagcaaagtaaatgctgtcttttc<br>ccaaaagacaggctcttcacctgaagattgttgtgtccactgtatcctggcttgcttgttctgcgaattcctgaccctttgcaacattgtcctggg<br>acaagcgtcatgtggcatctgcacctcagaagcctgctgctgttgctgtggtgacgagatgggggatgattgtaactgcccttgtgatatgga<br>ctgtggcatcatggatgcctgttgtgaatcatcagactgcttggaaatctgtatggaatgctgtggaatttgttttccttcataaatatttatcttttgt<br>ttgtgttaaaactggagagtgtttaaaaatttccttttgggggggaagaaaagcacattgtaagattctcatgaaacaacatggaatttgcactgtt<br>aactcattattgtaagtaatctctgaaagcctttttactttaaccaaatctacatggtttaatatgtgaaattttaactactttaactagttttataaatttc<br>ttaatatgttacaataacttagggacattttgacacccccttcccaaatgttaaatgccttctcctttttaccgatatttctgtttcttttaaccgttctc<br>aggagcactttgctccaaatatattatttttcagtgtgtatttaaacgaggcagtttattttgatatgtatctattcatgattgaaaggaagcagtctt<br>ggccaggcacggtggcttacacctgtaaccctggcattttgggaggccaaggtgggcagattgcctgagctcaggagttcgagaccagcc<br>agggcaacatggtgaaaccccatctctactaaaatacaaaaagttagctgggcttggcggtgtgcgcctgtagtcccagctactcaggagg<br>ctgaggcaggagaattgcttgaacccgagaggcggaagttgcagtgagccgagattgtgccactgaactccaacctgcactccagcctgg<br>gcaacagagcgagactccatctctaaataaataaataaataaataaataaataaataaataaacaaaccagtctttattttaaaagaaact<br>ttaggaaacaaacccacataatagttgggaaccagtgttgatctctctcccttaccttctccacttgttcaacagactctgaatgccgactgtgtg<br>gactctcttcctcagactgtggggacagatacaattccactcctgtccacaggaacatgagatttagcagactaaggagatctgtaaagaatg<br>aaccataccacaaggcatactgaagtgaggattataagagaaataaactcaaaatgctgttggaatatgcagagaattgctaccagaatattc<br>agtaaggtttcagggagaatgtggcatttgaggactctcttagaatgagtgattcacctgctatttaaatgaattatttagatttttgacaaagattt<br>aggtggacaccctaaactgtgtgtgcctttaaccagttaaaagaacagtgccttcagcatactttttttattagttgtaggaatacagcttttttgaaa<br>aagctataaagtttaaattaactaaaaatatgcattttcttacacataatttaaatgttatcatactttttttgatgaaaacataatgccttagtaaaata<br>gctctatttaataaagaagattgagtactctgacacatttcatttaaattaggaaatttttaatattaaaatcccagtgttctgagttattgaaaggctt<br>tcttttattttgagagctttaggtctttttgggatgagaacattttagttgtttagtttgtttcttaagcagtgctatttttttgtaaacacagataaatgga<br>aaccattcttttcaatgcagaagaaatctagatatcccctactgtgaccaaatttctgtattacgattttatgttaaattaaactaatatggcaggtta<br>taatgatccttaagtgtaaagaaatcagtcaattacaagagtaattgtatagttattgagacctatagtgtgtggcttagatgaaagggagagta<br>aattttcataccatgctctctcctactcagtttgatctctctaaaattgtagtttggtttgatttaatataattcttagtagaaattttgaaagtatgctttg<br>ggattaataattattttttaatttttctggctgaatatcaaattgatagtaacaacagaagcataattttaggaaggctttcgcaaacctagccttttaa<br>gagaggtttttaacctgaagcatgagaatatatcacctgtggtttttcctttgagatgaaacgtagtttctagttatatcattacttaaagggcttaa<br>aaagaaaaaacttagcaaactttgaatctttcttttattgctatttacacatacatacacacatacaaaacctttaaattttgggatctgaatataatt<br>ctggtaaacagctgtcttcatttttctcctctaaagaacttaattcatttgttacataaaatataaggaaatctttatactattttacagtaaccacaat<br>ctaaatatttacatatacccaaaattaacttatgctcatatattaggatgtgagaatatcatctgtttatggacacatgaaacctcctaatgacctgg<br>aattgttagaatatttgactttttatatgcaaagtttttcaaccaagtggtttgtctaatatttaaacatgtactggcacaatttgtgatgaaaatattag<br>cacatttgcaataatgtttctccataacagagaatgttaatggataccagaattttatttttgtatttatgttcatagtacttttcctcttgtctactccag<br>acagttattccataaagcatttgtataattaaaaggaaaacagaaaaaggaaaagtaggcaaatgtgaaaatagtttcaatatatcttatgatttc<br>ttaatgtaaaatgttttgttgaagtatatggctatcatgactaagtgctagaatttatagttacaggcggtgtccttttaaatgtggaaaggcttttaa<br>aatattttaaaactggacctgtattatcctgaatacactattttgaaaatttttaaaaatgacttctttattttgctttaccgtatgtttatatctaattgac<br>atattgactaatgtttgaaagaattcaaccataagttaaaatctgaaggttatctttatcatgtttcatccctgtctgaagatttcctagtcttcttatgt<br>aaatcacatgactcatgtccgtaaatgaactatgaaagatatcgatcagtttatgatcattgacatgtgatttcaaaacacagtgttcttttaaaaa<br>tctataatatgtcaaaatacaagtttttttttttacatcgttttagtaagttaatttcatttatttactttggagctatatttccacttagaaaaactaaggt<br>aattttacaatatatgctgagattaaaaaccaaggtaaaaatgatcaaacatatatgaaattgagtcttagatttaatgaatttcactcgaaaataa<br>atgatcagaagaattttcatctaaggcatagagtggcgaaatttttgtaaatgctcgcagttagcatctaactaaaacaatacagtatgactttatt<br>taggagaaggcttttttatttagaaaattatttttttcatttttacagtgtatcaactgtatccattttcctcacctggatagtcaatgttatctgagcagtt<br>caaggagtaaccaaggcaaccttatgtaataactttccattctttatccatacaaactctttcagtgccctagattctaatgttataaacgtcaaac<br>atcactgcccaacataaataagactcgagacttattaacataaataagtatcttgccttcttgaatgctagttaaatgcttagatttacctaactgc<br>ctaatgaatcaggttatttgttaataagattatttttcaaattatttaagacctttatgccccttccaattacttgtgatttgtaggcctgtaggattgttg | | |

TABLE 1-continued

| Gene | Human Gene Sequence | Human Sequence Accession No. | Murine Sequence Accession No. |
|---|---|---|---|
| | catctaatctgactggcaacagaaaatgtcatcaaatactataatatccattttgttttcttttgcactaatacaacagaacatatcatttttgttttaa<br>acaatggttaatatattaatagggtttgttccacacttactatttatagtttttataatcaagcattgggtattaaaagagaatcctttcaacccttcat<br>cttcgtatgcttatacaataaattgcagtgagtgt (SEQ ID NO: 613) | | |
| Entpdl | agggaagaagggagaaagagagagagatttgaatatacattgcttcaaggatgcaaaaaattacaacctggaaaaggcttcgagtaacttt<br>aggaaaatgagctgctggactcctcagtcaatctgtcctttctagtcaatgaaaaagacagggtttgaggttccttccgaaacggggccggct<br>aatttagcccctcccacgagcccaagggtctgttatatctctgtttccttgaggacctctctcacggagacggaccacagcaagcagaggct<br>gggggggggaaagacgaggaaagaggaggaaaacaaaagctgctacttatggaagatacaaaggagtctaacgtgaagacattttgctc<br>caagaatatcctagccatccttggcttctcctctatcatagctgtgatagctttgcttgctgtggggttgacccagaacaaagcattgccagaaa<br>acgttaagtatgggattgtgctggatgcgggttcttctcacacaagtttatacatctataagtggccagcagaaaaggagaatgacacaggcg<br>tggtgcatcaagtagaagaatgcagggttaaaggtcctggaatctcaaaatttgttcagaaagtaaatgaaataggcatttacctgactgattg<br>catggaaagagctagggaagtgattccaaggtcccagcaccaagagacacccgtttacctgggagccacggcaggcatgcggttgctca<br>ggatggaaagtgaagagttggcagacagggttctggatgtggtggagaggagcctcagcaactacccctttgacttccagggtgccagga<br>tcattactggccaagaggaaggtgcctatggctggattactatcaactatctgctgggcaaattcagtcagaaaacaaggtggttcagcatag<br>tcccatatgaaaccaataatcaggaaacctttggagctttggaccttgggggagcctctacacaagtcacttttgtaccccaaaaccagactat<br>cgagtccccagataatgctctgcaatttcgcctctatggcaaggactacaatgtctacacacatagcttcttgtgctatgggaaggatcaggca<br>ctctggcagaaactggccaaggacattcaggttgcaagtaatgaaattctcagggacccatgctttcatcctggatataagaaggtagtgaac<br>gtaagtgacctttacaagacccccctgcaccaagagatttgagatgactcttccattccagcagtttgaaatccagggtattggaaactatcaac<br>aatgccatcaaagcatcctggagctcttcaacaccagttactgcccttactcccagtgtgccttcaatgggatttcttgccaccactccaggg<br>ggattttggggcattttcagctttttactttgtgatgaagtttttaaacttgacatcgagaaagtctctcaggaaaaggtgactgagatgatgaaaa<br>agttctgtgctcagccttgggaggagataaaaacatcttacgctggagtaaaggagaagtacctgagtgaatactgcttttctggtacctacat<br>tctctccctccttctgcaaggctatcatttcacagctgattcctgggagcacatccatttcattggcaagatccagggcagcgacgccggctg<br>gactttgggctacatgctgaacctgaccaacatgatcccagctgagcaaccattgtccacacctctctcccactccacctatgtcttcctcatg<br>gttctattctccctggtccttttcacagtggccatcataggcttgcttatctttcacaagccttcatatttctggaaagatatggtatagcaaaagca<br>gctgaaatatgctggctggagtgaggaaaaaaatcgtccagggagcattttcctccatcgcagtgttcaaggccatccttccctgtctgccag<br>ggccagtcttgacgagtgtgaagcttccttggcttttactgaagcctttcttttggaggtattcaatatcctttgcctcaaggacttcggcagatac<br>tgtctctttcatgagtttttcccagctacacctttctcctttgtactttgtgcttgtataggttttaaagacctgacacctttcataatctttgctttataaa<br>agaacaatattgactttgtctagaagaactgagagtcttgagtcctgtgataggaggctgagctggctgaaagaagaatctcaggaactggtt<br>cagttgtactctttaagaacccctttctctctcctgtttgccatccattaagaaagccatatgatgcctttggagaaggcagacacacattccattc<br>ccagcctgctctgtgggtaggagaattttctacagtaggcaaatatgtgctaaagccaaagagttttataaggaaatatatgtgctcatgcagt<br>caatacagttctcaatcccacccaaagcaggtatgtcaataaatcacatattcctaggtgatacccaaatgctacagagtggaacactcagac<br>ctgagatttgcaaaaagcagatgtaaatatatgcattcaaacatcagggcttactatgaggtaggtggtatatacatgtcacaaataaaaatac<br>agttacaactcagggtcacaaaaaatgcatcttccaatgcatatttttattatggtaaaatatacataaatataattcaccattttaacatttaattcat<br>attaaatacgtacaaatcagtgacatttagtacattcacagtgttgtgccaccatcaccactatttagttccagaacatttgcatcatcaatacatt<br>gtctagagacaagactatcctgggtaggcagaaaccatagatcttttgtgtttacagctatggaaaccaactgtaccataaagatagttcactg<br>agttttaaagccaagccacatcttatttttccaaggtttaatttagtgagagggcagcattagtgtggagtggcatgcttttgccctatcgtggaat<br>ttacacatcagaatgtgcaggatccaagtctgaaagtgttgccacccgtcacacaacatgggctttgtttgcttattccatgaagcagcagcta<br>tagaccttaccatggaaacatgaagagaccctgcacccctttccttaaggattgctgcaagagttacctgttgagcaggattgactggtgatgt<br>ttcattctgaccttgtcccaagctctccatctctagatctggggactgactgttgagctgatggggaaagaaaagctctcacacaaaccggaa<br>gccaaatgtcccctatctcttgaatgatcaagtcacttttgacaacatccaggtgaatataaaaacttaataaagctgtggaaaggaactcttaat<br>cttcttttctgctacttaggttaaattcactagatcttgattaggaatcaaaattcgaattgggacatgttcaaattctttcttgtggtagttgcctata<br>ctgtcatcgctgctgttggttgagcatttgtggtgtaccacgctgtgtgctcaagggtattacattcatcttctcatttaatcctcacaacaatctga<br>agaaggtaggtattacaattcccacttcatagaaacagaaactgaggttcagagaggttaagtcatttgcccaaatggctgagccaaagcct<br>accatgtacctaacctttattttctttcccgaacataccaggctgtctcctcataacttccaagcatgcacttaaaactccacatgaatacaaggtt<br>catgggacttggtattcatagaaagggaggcagaaagctggtctgttcctgataggcttgtaatttaatatcattctgttcatgtgctttggatgg<br>aagcacatctggcatatgatgctaatcagtggttcccatacccctggcttcctaattttaatgtttgctcacagcatagtagattgacatcaaata<br>gtggccgatgatgatgaaaataaaggtcaaataagttgagccaataacagccgctttttccttctgtctgcgtatacaaagcactgtcatgca<br>cacaatctattctgaccctcacaacaacccataagggtgtaaatagtatttccattttacaaatgaggatcacacaaactactacatggcagag<br>cagatactccaactcatgtcttctggttgaagcctattgctttttcttttctaaacactttccctcagcaagttggaattagacttcacaagtctcctt<br>cagagaacacaaatcttttcttattccattcctgtttggttgcctacgtccaatctcccctccccagagatgccaaaaaaaaaatcctttaaggt | NM_001776 | NM_009848 |

TABLE 1-continued

| Gene | Human Gene Sequence | Human Sequence Accession No. | Murine Sequence Accession No. |
|---|---|---|---|
| | atttgggagccaaactcaacttgttaaaatctcaaattatggagacaatcagcagacacaacctaaccccaattattttggcaggaaggttggt | | |
| | ttagaggcagatccagcaatctgctttgggccactctgggtggggtaggtgaaataagattggtcactgttaactaattttaatattggattggc | | |
| | cattggttatcactgattaccattctcccctggattttcacccaggactcaaaacttggttctgctaaccctgttcctttatgaggaaccttttaaag | | |
| | attcctttataaggtgggagtttttttctatgaacctatagggagaaaaaagatcagcagaagtcattacttttttttttttttttttttttgagag | | |
| | agagtctcactccattgcccaggctggagtgcagtggtgctatctcggctcactgcaacctccgcctcctgggttcaagcaattctcctgcct | | |
| | cagcctcccgagtagctgggattgcaggtgcccaccaccacacccggctaattttgtatttttagtaaagacagggtttcaccatgttggcca | | |
| | ggctggtctccaactcccaatctcaggtgatcctattgcctcgggctcccaaagtgctgggattacaggagtgagccaccatgcctggccag | | |
| | aagtggttacttctgtagacaaaagaataatgctacttaatcaggctttctgtgtgacaagaaagagaaagaaaataaagaagtttcaattcatc | | |
| | caattcttaataagaaatatgtaaataaaatttttaaaattacacttcattttaatgttgtatcagtcaaggtccctgcaagagatggatggtatggt | | |
| | acactcaaactgggtaacacaggagagttttcagaaagcaactaaatccaaaatactatcaaggaatcaatataaaaattgttaatatttttctca | | |
| | tactaaattttcaaaatatttgtgtctattacatttacagcacatcttaattaggactagctgtgtgttcacctcacatgtggcttgtagctaccatac | | |
| | tggacagcacatgtccaaaaaaatacacgtaaagttaaagtttaaaagacacaggaactaagccctcattgtctttcccttgggaggtagttta | | |
| | aagagctatagatgctgtaacattcttgctattatttattatatatgacattattcctaaaaaagcttttgagatcctaggttgtattcctcaggttttgt | | |
| | tgccttcccatgaagatgtgaaggcagggatgcctgttattcagtccaagatgcatgacaagagaccttgggaaagtttcatctggatttaaa | | |
| | gattaattcttgatgcttacattccatactcaaaatgtaaatttgaatattaaaataaagatgattttttttttggagctagtcttgctctgttgcccagg | | |
| | ctggaatgcagtggcatgatcatggctcactgcagcctcgacctcccaagctcaagcaaggctacaggtgtgcacctaagtagctaggact | | |
| | acaggtgtgcaccaccatgtctagctatttttttttctgtagagacagggttttcctatgttgtccaggctggtctcgaactcctgccctcaagcaa | | |
| | tcctcctgccttggcctcccaaagtgttgagattacaggcgtaagccactgcacctggccaagatgaatattttaatagctcacagaacaaag | | |
| | tttgccacataatgataaaattactatgaaaatatattccctttattgtcagtttaaaagatgaactgagtttcacccaaactggtctggcccctctc | | |
| | tgattcaaataccaatagttgctctgattcaaattccaactgttagaacatgacagctgctcataactagctttgcttactaaccatgtttctttccat | | |
| | ttgtattaggtcctttactttttataacagcctcaaagtttcatgaattgctgcagtaaacattgattttcatgtttgtgagtctgcaagccagctggg | | |
| | cagctctacttcaggtggtaagggtggatcagacctattccatatacctcttgttctccttgtccagtggtttctagggatatgttctcatgatgaa | | |
| | ccccgcagaggctcgtgaaagtgagaggaaactaggatgcctcttaaggtcttggtcaggatggggtctcctgtcacttctgtcacaggcta | | |
| | ttgtaagtcatatgagcaagctcaataaaatataaacaagtcagataaacagtgggaggaatggcaaagtcatatggccaaggccatgagt | | |
| | gattaattttaacacaggaaaaaagtaaagcattaaatgcgattatttaatatacaatgtcttattaactgaaatataaaatgtgtttactgtaaaat | | |
| | ataatctgtttatctcaccaaagaaatattatctttaaaaaatgtcattacttctaagacatcatcagtctgcaacttctttccatagccttaatcagg | | |
| | atgctgtggcagctcccacattagcctcgcattctaaactggtagatgtcctaggaaaccatacatctatgtattttttcttattttatacgtttagga | | |
| | caatgtatagctaattacccaactttttatttgcatacaaatctaatacaactgaacacaatcagttttatcacaggtataatggatttttcaatagtg | | |
| | aggaggtgcctccatgagccttctctttagaaaagtggcattcaagactcttcatttgaagtgaagattgctatgtcttttgcattgctctattttac | | |
| | ataaattaagttataaattgacactataatcaactgacaccatgatcagtgatgatgatcaccctcatcagcactagagttgacttgtttttataac | | |
| | ccctttgcatgtatgttgaatagcaaagttcatcagagaacatgtattagtcaatggtaagtaagatactctcatctaagaaataacatcacctctt | | |
| | ctaatgaagttctaagaagagagggaagaaaaagtcttgggagctagtcagggaatagtgtgtatttgcaattacctaaactgaactctacca | | |
| | ttactcctaacccagttcctcctcctgtgttttacatgattaatgccacccctgcctcaatgaaccaagatcagctccatcactgggacctcccca | | |
| | ttctgcctgtgcaatatttttctttttatttctccttctaatattactgttattgctccagtaaagagctgtaatatattttacctggactgataccagga | | |
| | atggtggtgttgcttccaatctgttgctgctagattaatctttgcaaagcacaggcttaatttcattgctgctcaactaaaaccactggtggctttc | | |
| | cattgcctacaaaataaagtcaacctccccatcagacattcaaggctttcaatgatccatggccgccagctctctccaggctcatatcccactc | | |
| | cactcctctgatgtttcctacactacactacactatactacactacagccaggtagaatgactgttcacccaacaccactcaggttgtcttctcaa | | |
| | cttggaatactcttgcaccttcaaagctcatttcaaatgccccttcatttgtgaagccttctccaaatttccaagtcagaatgtctcttccttgtgcta | | |
| | ccacaaccctttaactgagcctccattagtgcactgagaccattctgttcagtgtctgggtgaagcttcctggtgaaaaatatgttacctatttctt | | |
| | tctgaaaagttggattcagggatattatcacggacctaaggtaatagttctagccaacctccctgtccactgccaggccgactacaaacccttc | | |
| | tgttgctggcgagctggtccgcaccactagttctgcttcactctatttatctcttgatgtaaccatcttctttctccaggttttaagaaccagcccaa | | |
| | ctcctggttccctgatgaagcttttattcccctagccacatggaacttttcctttttggaacatgcctttagtttctgtgtagtttgccatgcagcactt | | |
| | cattgtacacattattaaaacagaattttaaggattagaatgaaccttaaaagatcatgcatctcaaaatttaatgtacatacaaattacccaggg | | |
| | atttgttgaaataaaaattatttaattttaattaatataaataattcagtaggtctggggtgaggcctgaggttttacatttccaacaagctgccag | | |
| | gtaaagccaatacatctgtccaggaatcacactttgcgtatcaaaggtctagatgacattatcattccaaagagtttcttttacaggctctcagat | | |
| | cagtgttcatccactacctgactactgtcattcacaggcattctgttccacagcaggccagctaacgtggtatttacaaagctcactcctcttata | | |
| | caacaatccaagtgtttcttttgtcagttgtctgtgccccaggagatccctctctgccttgccttgccctctgcctttggagaccagcacctcata | | |
| | ctcagtgaaggcctggagtgcttaagagggatttcttccagctctcttgccctggtcttcagtgtattagatgtattacctccatgctctcagtag | | |
| | aggcccataggaaagagtaggtaggttatgccagctcacacgcatcctttaaaaatggtttagaagtttagctggtttcttattactcctgtctat | | |
| | ggatgtttccttctgtcactctactagggatgaaacagctaatcatgttcaatagttacatttagattggtttttaaaaactatgattgtattagttcgt | | |

TABLE 1-continued

| Gene | Human Gene Sequence | Human Sequence Accession No. | Murine Sequence Accession No. |
|---|---|---|---|
| | ttccatgctgctgataaagacatatctgagactggaaacaaaaagggtttaattggacttacagttccacatggctggggaggcctcaaaatc<br>aggtgggaggcaaaaggtacttcttacgtggtggcatcaagagcaaaatgaggaagaagcaaaagcagaaactcttcataaacccaccag<br>atcttgtgggacttattatcacgagaatagcacagaaaagactggcctccatgattcaattacctcccactgcgtccctcccacaacatgtggg<br>aattctgggagatacaattcaagttgagatttgggtggggacacagccaaaccatatcattcctccctgggctcctccaaatttcataatcctca<br>catttcaaaaccaatcattccttcccaacagttccccaaagtcttaactcatttcagcattaacccaaaagtccacagtccaaagtctcatctgag<br>acaaggcaagtcccttccacttacaagcctgtaaaagcaagctagttacctcctagatacaatggggggtacaggtattgggtaaatacagc<br>tgttccaaatgagagaaattggccaaaacaaaggggttacagggtccatgcaagtctgaaatccagtggggcagtcaaattttaaagctcca<br>taatgatctcctttgactccatgtctcacattcaggtcatgctgatgcaagagataggttcccatggtcttgtgcagctccgcccctgtggctttg<br>cagagtacagcctccctcctggctgctttctcaggctgatgttgagtgtctgtagcttttccaggcacaagatgcaagttggtggttgatctacc<br>attctggggtctaccattctggggtctaccgttctgggactgtggccttcttctcacagctccactaggcagtgccccaacagggactctgtgt<br>gggggctctgccccacatttcccttccacactgccctaggagaggttccccatgagggctctgcccctgcagcaaacttttgcctggacatc<br>caggtgtttccatatatattctgaaatctaggcagaggttcccaaatctcaattcttgacatctctgcacccacaggctcaacatcacatggaag<br>ctgccaatgcttggggcctctaccctctgaagccacagcccaagctctatgttggctcctttcagccatggctggagcagctgggacacagg<br>gcaccaagtccctaggctgcacacagcacagagaccctgggcccagcccacaaaaccactttttcctcctgggcctctgggcctgtgatgg<br>gaggggctgccatgaaggtctctgacatgacctggagacattttccccatggtcttggggattaacattaggctccttgctgcttatgcaaattt<br>ctgcagccagcttgaatttctccttaaaaaaaatgggtttttcttttctactgcatcatcaggctgcagattttccacatttatgctcttgtttccctttt<br>aaaacagaatgtttttaacagcacccaagtcaccttttgaatgctttgctgcttagaaatttattccaccagataccctaagtcatctctctcaagc<br>tctaagttccacaaatctctagggcaagggtgaaatgctgccagtctccttgctaaaacataacaagggtcacctttacttcagttcccaacaa<br>ggtcttcatctccatctgagaccacctcagcctggaccttattgttcatatcactatcagtatttttgtcaatgccattcacagtctctaggaggttc<br>caaactttcctacattttcctatcttcttctgagccctccagattatttcaacacccagttccaaagttgcttccacattttcgggtatcttttcagcaa<br>tgccccactctactggtactattagtccattttcatgctgctgataaagacatacctgagactgggaacaaaaagaggtttaattggacttatagt<br>tccacctggctggggaggcctcagaatcatggcaggaggtgaaaggcatttcttacacggcagcagcaagagaaaaatgaagaagcagc<br>aaaagcagaaacccctgataaaaccatcagatctcgtgagacttattcactatcacaagaatagcatgggaaagaccagccccccttgattca<br>attacctcccccctgggtcctgtgggaattctggaaggtacaattcaagttgagatttgggtggggacacagccaaaccatatcaatgattttgt<br>actttaaccagctgaatggaagtacaatctcttgctatatgacacaataattatttgcaaaatgagtaaacatatcataaggaaattatttttacaa<br>ggtttgaaacctgaaatgcagtctattatcatacataactaaaaatagagcctcaataaacagattcccagttttgaaaatgcaacatttgtactc<br>cacattgtcagttttcttaggtatatttataaatactcctataaaaatgtaaagaaacacataatgtagattgctaattttataataacacaagttgatt<br>ttgacatccaacttattaattatgaaatgacttttggcctagtaacaatgaaaatgggggcaaatacagataaatggtaattcttagaatgaacta<br>ctcagcaccaattctaagtttttcttgatggtaaatcataatgttccctttctcctcggttctgcaatctataggcataccataattgtaatcaatagc<br>ttaaaaatatgtctctctgtcctattctgtatctgtatctcttggattttttacctttgcaatagtcaactgaaccatcttcttggagtactcatgaagatg<br>gaagtctacatggagaatacaggatgaatccactctgtctcctgcagtgaagtctgtttgaaggatgtatttggctgtcttctggacaggccatt<br>ctaataacagaaacaaacaagttattttaaaacttattggaatattcaaatattaaccaaagtagaaaaatataatacacatccatgtgcccatca<br>cagaacttcactgattatcatcatttagccagtcttgaagaagcaagtgctaattacaatcacaaatgaaacaagattcagacttcatgaagag<br>cactgcgctataataaaagaagaaatgagcacatacattcttttactgacagtcaaatggtgaaggtgggcagaatcattatgtgatgcaacat<br>ggcaaaagtatacagacagtgcatccagaggaaggcaccttgctgaatgactagaatggaagtaggagacattttgcaggccccccttcatc<br>ctgcagggagaaccagaaccacagcagctctatttgcctattcctctttaaattacaaagttaaaatttgggagtagtagaaaatcaattggtta<br>tcttatagagtctcctagaatatttcattggcattgagaaggtggaaaatgcaaattatatactttaaaatgtaatttttgcttttcacatatgcttaaa<br>gcctaaaacctcttaataaacttcttctgaaatata (SEQ ID NO: 614) | | |
| Dgkz | ggagagtgtctctaaggtgacactcgggtgcgcggcagcagcggcggttgcaggagctcgctctccgcccgggctccggctccgctcca<br>gccgtccggggggcgccgcggcgcgcagagcgcagcaccccgactccagccaggagcccccgcccccccggagcgcaggaggac<br>cccggcccgcctctcccaggcgcagcgcccagcatctcgctgctcctgtcgtctaagcgtcggcgtcgctagggacctgcggaacccgg<br>cgctcccctccctccccgcctcgcgtccccggcccgggcggactggagactcgaacttgagcgggtgcccgaaaggccgcaggagcc<br>gcgggcggaaggcggccgcacgatggccgagggggcagggcggcggagggcagcgctgggactgggctggcggcggccgggcag<br>ccgaggaggaggtggtgcggcggcgatgccggcgcggggaggaggcccaggtcgcgcagccctggcccgagggttcccggggcac<br>ggccgctgggcccccggtggaggagcgtttccgccagctgcacctacgaaagcaggtgtcttacaggaaagccatcaccaagtcgggc<br>ctccagcacctggccccccctccgcccacccctggggccccgtgcagcgagtcagagcggcagatccggagtacagtggactggagc<br>gagtcagcgacatatggggagcacatctggttcgagaccaacgtgtccggggacttctgctacgttggggagcagtactgtgtagccagg<br>atgctgaagtcagtgtctcgaagaaagtgcgcagcctgcaagattgtggtgcacacgccctgcatcgagcagctggagaagataaatttcc<br>gctgtaagccgtccttccgtgaatcaggctccaggaatgtccgcgagccaacctttgtacggcaccactgggtacacagacgacgccagg | NM_201532 | NM_138306 |

TABLE 1-continued

| Gene | Human Gene Sequence | Human Sequence Accession No. | Murine Sequence Accession No. |
|---|---|---|---|
| | acggcaagtgtcggcactgtgggaagggattccagcagaagttcaccttccacagcaaggagattgtggccatcagctgctcgtggtgca agcaggcataccacagcaaggtgtcctgcttcatgctgcagcagatcgaggagccgtgctcgctgggggtccacgcagccgtggtcatcc cgcccacctggatcctccgcgcccggaggccccagaatactctgaaagcaagcaagaagaagaagagggcatccttcaagaggaagtc cagcaagaaagggcctgaggagggccgctggagacccttcatcatcaggcccacccccctccccgctcatgaagcccctgctggtgtttgt gaaccccaagagtgggggcaaccagggtgcaaagatcatccagtctttcctctggtatctcaatccccgacaagtcttcgacctgagccag ggagggcccaaggaggcgctggagatgtaccgcaaagtgcacaacctgcggatcctggcgtgcgggggcgacggcacggtgggctg gatcctctccaccctggaccagctacgcctgaagccgccacccccctgttgccatcctgcccctgggtactggcaacgacttggcccgaacc ctcaactggggtgggggctacacagatgagcctgtgtccaagatcctctcccacgtggaggaggggaacgtggtacagctggaccgctg ggacctccacgctgagcccaaccccgaggcagggcctgaggaccgagatgaaggcgccaccgaccggttgcccctggatgtcttcaac aactacttcagcctgggctttgacgcccacgtcaccctggagttccacgagtctcgagaggccaacccagagaaattcaacagccgctttc ggaataagatgttctacgccgggacagctttctctgacttcctgatgggcagctccaaggacctggccaagcacatccgagtggtgtgtgat ggaatggacttgactcccaagatccaggacctgaaaccccagtgtgttgttttcctgaacatccccaggtactgtgcgggcaccatgccctg gggccaccctggggagcaccacgactttgagccccagcggcatgacgacggctacctcgaggtcattggcttcaccatgacgtcgttggc cgcgctgcaggtgggcggacacggcgagcggctgacgcagtgtcgcgaggtggtgctcaccacatccaaggccatcccggtgcaggt ggatggcgagccctgcaagcttgcagcctcacgcatccgcatcgccctgcgcaaccaggccaccatggtgcagaaggccaagcggcg gagcgccgccccctgcacagcgaccagcagccggtgccagagcagttgcgcatccaggtgagtcgcgtcagcatgcacgactatgag gccctgcactacgacaaggagcagctcaaggaggcctctgtgccgctgggcactgtggtggtcccaggagacagtgacctagagctctg ccgtgcccacattgagagactccagcaggagcccgatggtgctggagccaagtccccgacatgccagaaactgtcccccaagtggtgctt cctggacgccaccactgccagccgcttctacaggatcgaccgagcccaggagcacctcaactatgtgactgagatcgcacaggatgagat ttatatcctggaccctgagctgctgggggcatcggcccggcctgacctcccaaccccacttcccctctccccacctcaccctgctcaccca cgccccggtcactgcaaggggatgctgcacccccctcaaggtgaagagctgattgaggctgccaagaggaacgacttctgtaagctccag gagctgcaccgagctgggggcgacctcatgcaccgagacgagcagagtcgcacgctcctgcaccacgcagtcagcactggcagcaag gatgtggtccgctacctgctggaccacgcccccccagagatccttgatgcggtggaggaaaacggggagacctgtttgcaccaagcagc ggccctgggccagcgcaccatctgccactacatcgtggaggccggggcctcgctcatgaagacagaccagcagggcgacactccccg gcagcgggctgagaaggctcaggacaccgagctggccgcctacctggagaaccggcagcactaccagatgatccagcgggaggacc aggagacggctgtgtagcgggccgcccacgggcagcaggagggacaatgcggccaggggacgagcgccttccttgcccacctcactg ccacattccagtgggacggccacgggggggacctaggccccagggaaagagccccatgccgcccccctaaggagccgcccagacctag ggctggactcaggagctggggggcctcacctgttcccctgaggaccccgccggacccggaggctcacagggaacaagacacggctg ggttggatatgcctttgccggggttctggggcagggcgctccctggccgcagcagatgccctcccaggagtggaggggctggagaggg ggaggccttcgggaagaggcttcctgggccccctggtcttcggccgggtccccagccccccgctcctgccccaccccacctcctccgggct tcctcccggaaactcagcgcctgctgcacttgcctgccctgccttgcttggcacccgctccggcgaccctccccgctcccctgtcatttcatc gcggactgtgcggcctgggggtgggggcgggactctcacggtgacatgtttacagctgggtgtgactcagtaaagtggattttttttttcttta aaaaaaa (SEQ ID NO: 615) | | |
| Vamp7 | attggaggagcgctcccactcccaagaggccacgcgtagacggggcgcttcatgcggaagtcagcggcgtccggtcccagcctcctctg ggagcgggcagttggcgaccctgcactgacccgcgtccctccgtcccgagcccgcgcgccctcagagggtgcccggacagactgaag ccatggcgattctttttgctgttgttgccaggggaccactatccttgccaaacatgcttggtgtggaggaaacttcctggaggtgacagagc agattctggctaagataccttctgaaaataacaaactaacgtactcacatggcaattatttgtttcattacatctgccaagacaggattgtatatct ttgtatcactgatgatgattttgaacgttcccgagcctttaattttctgaatgagataaagaagaggttccagactacttacggttcaagagcaca gacagcacttccatatgccatgaatagcgagttctcaagtgtcttagctgcacagctgaagcatcactctgagaataagggcctagacaaag tgatggagactcaagcccaagtggatgaactgaaaggaatcatggtcagaaacatagatctggtagctcagcgaggagaaagattggaatt attgattgacaaaacagaaaatcttgtggattcttctgtcaccttcaaaactaccagcagaaatcttgctcgagccatgtgtatgaagaacctca agctcactattatcatcatcatcgtatcaattgtgttcatctatatcattgtttcacctctctgtggtggatttacatggccaagctgtgtgaagaaat aggaaagaagaagttaccattaaccaaggatatgagagaacaaggagttaaaagcaatccatgtgactcaagcctttcacatactgacagat ggtatctgccagtctcttcaaccctcttctcacttttttaaaatcttgttccatgcctccaggtttatctttgtcttatctaccagtttattcctgtgaactt cagattgaaccattcattgcagcagtagccttaaaaaggcttttgtttatttctttggtttgttaactagtgtcatctatttagagaaacatttttgttttt aattgctcaaagctgtcgccgctagtcttatgagctatctactaaaactatggagaaactttgtatgtgcacacaaaagtattcaagagacagta ttgctaacatctcatcttaatgtcttttgttattgagaagttttaggtgcttcaaaacaatataaatggataatagttgttatttggggaattgtaatgat gttggtgctgcttccttctaagagctcagacaagtaaagtatgaaacattcttatttcagttagatggggaacattttgctagcccattagaagca cacagaattatccttgtcctcctaatattgactttcaggaataaagttcagtgtgctgatcattcacaatacagtggatagcttgatatcttctgtttt | NM_005638 | NM_011515 |

TABLE 1-continued

| Gene | Human Gene Sequence | Human Sequence Accession No. | Murine Sequence Accession No. |
|---|---|---|---|
| | cccattgcagttgatttgagaagatgaaggtttaaatattgttgaaagttgcagtttttaaatgtgttccttttcttctgtgaatatttagggcaatc<br>gtgtcgctaatagaatatgtagtagagggggtggggaggtaaattcctctgacttgccaaagaaaaagaagggaaccacagtggatatgct<br>agcattttagctgtgcaaagggaggtagtgtgggaaaagtgtttccattctgggaaaagcccaaaccgaatacggtcagcagtcaactcca<br>gggtttgggcttgattcctgttgaataatagttttgagcattctttgtggttaaataaattcttaaatctgcctagttttgatgaattcttttgtgaaactt<br>gaaagagaatagacagtatgacatatagaattaatacaaaacagtttaacaaccatttaactgcagtgtaagaaaattggactgtaatcatatc<br>gctactggcatctgttatctagtatgcatttctggtgtgtatctgaaaggaagacattttctaccctagatccaattgcatttatttatcaataagtgc<br>cattaaattgaaattatattacattttacactttctcaatgaatgaacaaattagtctgtagaatctagccacctgtttagcctagtcatgtgccttga<br>acatatatgtgtcccataatctggctcatggtacctgttcttctatccaaacctttcaattcatgctacctgattcatttatttgacatagatcttaggc<br>ccacttgaactcttttcttgtttatctagcatagcacaaacgtttttccagtcttctttatcaacactaatgcctcttaattgcatcagtatttcctattgg<br>aaaatacatctgttccagaaaaacatttggcattcctgaataatttccaaatgtttttaatccaaagaaaaaggtttaaagcttatttccctttcttata<br>cacacctgaataaaattgatgtgcatgttttagggatcaattacctaactgttccttggtctatttatgtataagaatgctttttaaagcacatgtctc<br>attttaaatgacgcacaaactgaagatgttaataaaatttaagagtaatacaatgaaaaaa (SEQ ID NO: 616) | | |
| Hipk1 | gcagagtctgcagtgcggagggggcgggaagtccaggccccgcactcgatccacgctggctccctacggaggcccacctactcgagg<br>cccaccgactcctactgcaatcagtactatgcgatcgtcctagagagtccattcagctgcacttccgcctcagtatggcatcacagctgcaag<br>tgttttcgcccccatcagtgtcgtcgagtgccttctgcagtgcgaagaaactgaaaatagagccctctggctgggatgtttcaggacagagta<br>gcaacgacaaatattatacccacagcaaaaccctcccagccacacaagggcaagccaactcctctcaccaggtagcaaatttcaacatccc<br>tgcttacgaccagggcctcctcctcccagctcctgcagtggagcatattgttgtaacagccgctgatagctcgggcagtgctgctacatcaac<br>cttccaaagcagccagaccctgactcacagaagcaacgtttctttgcttgagccatatcaaaaatgtggattgaaacgaaaaagtgaggaag<br>ttgacagcaacggtagtgtgcagatcatagaagaacatcccccctctcatgctgcaaaacaggactgtggtgggtgctgctgccacaaccac<br>cactgtgaccacaaagagtagcagttccagcggagaaggggattaccagctggtccagcatgagatcctttgctctatgaccaatagctatg<br>aagtcttggagttcctaggccgggggacatttggacaggtggctaagtgctggaagaggagcaccaaggaaattgtggctattaaaatcttg<br>aagaaccacccctcctatgccagacaaggacagattgaagtgagcatcctttcccgcctaagcagtgaaaatgctgatgagtataattttgtc<br>cgttcatacgagtgctttcagcataagaatcacacctgccttgtttttgaaatgttggagcagaacttatatgattttctaaagcaaaacaaattta<br>gcccactgccactcaagtacatcagaccaatcttgcagcaggtggccacagccttgatgaagctcaagagtcttggtctgatccacgctgac<br>cttaagcctgaaaacatcatgctggttgatccagttcgccagccctaccgagtgaaggtcattgactttggttctgctagtcacgtttccaaagc<br>tgtgtgctcaacctacttacagtcacgttactacagagctcctgaaattattcttgggttaccattttgtgaagctattgatatgtggtcactgggct<br>gtgtgatagctgagctgttcctgggatggcctctttatcctggtgcttcagaatatgatcagattcgttatatttcacaaacacaaggcttgccag<br>ctgaatatcttctcagtgccggaacaaaaacaaccaggtttttcaacagagatcctaatttggggtacccactgtggaggcttaagacacctg<br>aagaacatgaactggagactggaataaaatcaaaagaagctcggaagtacattttttaattgcttagatgacatggctcaggtgaatatgtctac<br>agacctggagggaacagacatgttggcagagaaggcagaccgaagagaatacattgatctgttaaagaaaatgctcacaattgatgcaga<br>taagagaattacccctctaaaaactcttaaccatcagtttgtgacaatgactcaccttttggattttccacatagcaatcatgttaagtcttgttttca<br>gaacatggagatctgcaagcggagggttcacatgtatgatacagtgagtcagatcaagagtcccttcactacacatgttgccccaaatacaa<br>gcacaaatctaaccatgagcttcagcaatcagctcaatacagtgcacaatcaggccagtgttctagcttccagttctactgcagcagctgcta<br>ctctttctctggctaattcagatgtctcactactaaactaccagtcagctttgtacccatcatctgctgcaccagttcctggagttgcccagcagg<br>gtgtttccttgcagcctggaaccacccagatttgcactcagacagatccattccaacagacatttatagtatgtccacctgcgtttcaaactgga<br>ctacaagcaacaacaaagcattctggattccctgtgaggatggataatgctgtaccgattgtaccccaggcaccagctgctcagccactaca<br>gattcagtcaggagttctcacgcagggaagctgtacaccactaatggtagcaactctccaccctcaagtagccaccatcacaccgcagtatg<br>cggtgccctttactctgagctgcgcagccggccggccggcgctggttgaacagactgccgctgtactgcaggcgtggcctggagggact<br>cagcaaattctcctgccttcaacttggcaacagttgcctggggtagctctacacaactctgtccagcccacagcaatgattccagaggccatg<br>gggagtggacagcagctagctgactggaggaatgcccactctcatggcaaccagtacagcactatcatgcagcagccatccttgctgacta<br>accatgtgacattggccactgctcagcctctgaatgttggtgttgcccatgttgtcagacaacaacaatccagttccctcccttcgaagaagaa<br>taagcagtcagctccagtctcttccaagtcctctctagatgttctgccttcccaagtctattctctggttgggagcagtcccctccgcaccacatc<br>ttcttataattccttggtccctgtccaagatcagcatcagcccatcatcattccagatactcccagccctcctgtgagtgtcatcactatccgaag<br>tgacactgatgaggaagaggacaacaaatacaagcccagtagctctggactgaagccaaggtctaatgtcatcagttatgtcactgtcaatg<br>attctccagactctgactcttctttgagcagcccttattccactgataccctgagtgctctccgaggcaatagtggatccgttttggagggcct<br>ggcagagttgtggcagatggcactggcacccgcactatcattgtgcctccactgaaaactcagcttggtgactgcactgtagcaacccagg<br>cctcaggtctcctgagcaataagactaagccagtcgcttcagtgagtgggcagtcatctggatgctgtatcacccccacagggtatcgagct<br>caacgcggggggaccagtgcagcacaaccactcaatcttagccagaaccagcagtcatcggcggctccaacctcacaggagagaagca<br>gcaacccagcccccgcaggcagcaggcgtttgtggcccctctctcccaagcccccctacaccttccagcatggcagcccgctacactcga | NM_198268 | NM_010432 |

TABLE 1-continued

| Gene | Human Gene Sequence | Human Sequence Accession No. | Murine Sequence Accession No. |
|---|---|---|---|
| | cagggcacccacaccttgccccggcccctgctcacctgccaagccaggctcatctgtatacgtatgctgccccgacttctgctgctgcactg | | |
| | ggctcaaccagctccattgctcatcttttctccccacagggttcctcaaggcatgctgcagcctataccactcaccctagcactttggtgcacc | | |
| | aggtccctgtcagtgttgggcccagcctcctcacttctgccagcgtggcccctgctcagtaccaacaccagtttgccacccaatcctacattg | | |
| | ggtcttcccgaggctcaacaatttacactggatacccgctgagtcctaccaagatcagccagtattcctacttatagttggtgagcatgaggg | | |
| | aggaggaatcatggctaccttctcctggccctgcgttcttaatattgggctatggagagatcctcctttaccctcttgaaatttcttagccagcaa | | |
| | cttgttctgcaggggcccactgaagcagaaggttttctctggggaacctgtctcagtgttgactgcattgttgtagtcttcccaaagtttgccc | | |
| | tatttttaaattcattattttgtgacagtaattttggtacttggaagagttcagatgcccatcttctgcagttaccaaggaagagagattgttctgaa | | |
| | gttaccctctgaaaaatatttgtctctctgacttgatttctataaatgcttttaaaaacaagtgaagcccctctttatttcattttgtgttattgtgattg | | |
| | ctggtcaggaaaaatgctgatagaaggagttgaaatctgatgacaaaaaaagaaaaattacttttgtttgtttataaactcagacttgcctatttt | | |
| | attttaaaagcggcttacacaatctccctttgtttattggacatttaaacttacagagtttcagttttgttttaatgtcatattatacttaatgggcaatt | | |
| | gttatttttgcaaaactggttacgtattactctgtgttactattgagattctctcaattgctcctgtgtttgttataaagtagtgtttaaaaggcagctca | | |
| | ccatttgctggtaacttaatgtgagagaatccatatctgcgtgaaaacaccaagtattctttttaaatgaagcaccatgaattctttttttaaattatttt | | |
| | ttaaaagtctttctctctctgattcagcttaaattttttttatcgaaaaagccattaaggtggttattattacatggtggtggtggttttattatatgcaaa | | |
| | atctctgtctattatgagatactggcattgatgagctttgcctaaagattagtatgaattttcagtaatacacctctgttttgctcatctctcccttctgt | | |
| | tttatgtgatttgtttggggagaaagctaaaaaaacctgaaaccagataagaacatttcttgtgtatagcttttatacttcaaagtagcttcctttgt | | |
| | atgccagcagcaaattgaatgctctcttattaagacttatataataagtgcatgtaggaattgcaaaaaatattttaaaaatttattactgaatttaa | | |
| | aaatattttagaagttttgtaatggtggtgttttaatattttacataattaaatatgtacatattgattagaaaaatataacaagcaattttttcctgctaa | | |
| | cccaaaatgttatttgtaatcaaatgtgtagtgattacacttgaattgtgtacttagtgtgtatgtgatcctccagtgttatcccggagatggattga | | |
| | tgtctccattgtatttaaaccaaaatgaactgatacttgttggaatgtatgtgaactaattgcaattatattagagcatattactgtagtgctgaatg | | |
| | agcaggggcattgcctgcaaggagaggagacccttggaattgttttgcacaggtgtgtctggtgaggagttttttcagtgtgtgtctcttccttcc | | |
| | ctttcttcctccttcccttattgtagtgccttatatgataatgtagtggttaatagagtttacagtgagcttgccttaggatggaccagcaagcccc | | |
| | cgtggaccctaagttgttcaccgggatttatcagaacaggattagtagctgtattgtgtaatgcattgttctcagtttccctgccaacattgaaaa | | |
| | ataaaaacagcagcttttctcctttaccaccacctctacccctttccattttggattctcggctgagttctcacagaagcattttccccatgtggctc | | |
| | tctcactgtgcgttgctaccttgcttctgtgagaattcaggaagcaggtgagaggagtcaagccaatattaaatatgcattcttttaaagtatgtg | | |
| | caatcacttttagaatgaattttttttttcctttttcccatgtggcagtccttcctgcacatagttgacattcctagtaaaatatttgcttgttgaaaaaaac | | |
| | atgttaacagatgtgtttataccaaagagcctgttgtattgcttaccatgtccccatactatgaggagaagttttgtggtgccgctggtgacaag | | |
| | gaactcacagaaaggtttcttagctggtgaagaatatagagaaggaaccaaagcctgttgagtcattgaggcttttgaggtttctttttttaacag | | |
| | cttgtatagtcttggggcccttcaagctgtgaaattgtccttgtactctcagctcctgcatggatctgggtcaagtagaaggtactggggatgg | | |
| | ggacattcctgcccataaaggatttggggaaagaagattaatcctaaaatacaggtgtgttccatctgaattgaaaatgatatatttgagatata | | |
| | attttaggactggttctgtgtagatagagatggtgtcaaggaggtgcaggatggagatgggagatttcatggagcctggtcagccagctctgt | | |
| | accaggttgaacaccgaggagctgtcaaagtatttggagtttcttcattgtaaggagtaagggcttccaagatggggcaggtagtccgtaca | | |
| | gcctaccaggaacatgttgtgttttctttatttttttaaaatcattatattgagttgtgttttcagcactatattggtcaagatagccaagcagtttgtata | | |
| | atttctgtcactagtgtcatacagttttctggtcaacatgtgtgatctttgtgtctccttttttgccaagcacattctgattttcttgttggaacacaggtc | | |
| | tagtttctaaaggacaaatttttttgttccttgtctttttttctgtaagggacaagatttgttgtttttgtaagaaatgagatgcaggaaagaaaaccaaa | | |
| | tcccattcctgcaccccagtccaataagcagataccacttaagataggagtctaaactccacagaaaaggataataccaagagcttgtattgtt | | |
| | accttagtcacttgcctagcagtgtgtggctttaaaaactagagatttttcagtcttagtctgcaaactggcatttccgattttccagcataaaaat | | |
| | ccacctgtgtctgctgaatgtgtatgtatgtgctcactgtggctttagattctgtccctggggttagccctgttggccctgacaggaagggagg | | |
| | aagcctggtgaatttagtgagcagctggcctgggtcacagtgacctgacctcaaaccagcttaaggctttaagtcctctctcagaacttggca | | |
| | tttccaacttcttcctttccgggtgagagaagaagcggagaagggttcagtgtagccactctgggctcatagggacacttggtcactccaga | | |
| | gtttttaatagctcccaggaggtgatattattttcagtgctcagctgaaataccaaccccaggaataagaactccatttcaaacagttctggccat | | |
| | tctgagcctgcttttgtgattgctcatccattgtcctccactagaggggctaagcttgactgcccttagccaggcaagcacagtaatgtgtgtttt | | |
| | gttcagcattattatgcaaaaattcactagttgagatggtttgttttaggataggaaatgaaattgcctctcagtgacaggagtggcccgagcct | | |
| | gcttcctattttgatttttttttttttttaactgatagatggtgcagcatgtctacatggttgtttgttgctaaactttatataatgtgtggtttcaattcagct | | |
| | tgaaaaataatctcactacatgtagcagtacattatatgtacattatatgtaatgttagtatttctgctttgaatccttgatattgcaatggaattccta | | |
| | ctttattaaatgtatttgatatgctagttattgtgtgcgatttaaactttttttgctttctcccttttttttggttgtgcgctttcttttacaacaagcctctaga | | |
| | aacagatagtttctgagaattactgagctatgtttgtaatgcagatgtacttagggagtatgtaaaataatcattttaacaaaagaaatagatattt | | |
| | aaaatttaatactaactatgggaaaagggtccattgtgtaaaacatagtttatctttggattcaatgtttgtctttggttttacaaagtagcttgtatttt | | |
| | cagtattttctacataatatggtaaaatgtagagcaattgcaatgcatcaataaaatgggtaaattttctgacttatgtggctgtttttgacttctgtta | | |
| | taggatataaaggggatcaataaatgacatctttgaaagtgaaaa (SEQ ID NO: 617) | | |

TABLE 1-continued

| Gene | Human Gene Sequence | Human Sequence Accession No. | Murine Sequence Accession No. |
|---|---|---|---|
| Nuak2 | gtgctttactgcgcgctctggtactgctgtggctccccgtcctggtgcgggacctgtgccccgcgcttcagccctccccgcacagcctactg<br>attcccctgccgcccttgctcacctcctgctcgccatggagtcgctggttttcgcgcggcgctccggccccactccctcggccgcagagcta<br>gcccggccgctggcggaagggctgatcaagtcgcccaagcccctaatgaagaagcaggcggtgaagcggcaccaccacaagcacaac<br>ctgcggcaccgctacgagttcctggagaccctgggcaaaggcacctacgggaaggtgaagaaggcgcgggagagctcggggcgcctg<br>gtggccatcaagtcaatccggaaggacaaaatcaaagatgagcaagatctgatgcacatacggagggagattgagatcatgtcatcactca<br>accaccctcacatcattgccatccatgaagtgtttgagaacagcagcaagatcgtgatcgtcatggagtatgccagccggggcgacctttat<br>gactacatcagcgagcggcagcagctcagtgagcgcgaagctaggcatttcttccggcagatcgtctctgccgtgcactattgccatcaga<br>acagagttgtccaccgagatctcaagctggagaacatcctcttggatgccaatgggaatatcaagattgctgacttcggcctctccaacctct<br>accatcaaggcaagttcctgcagacattctgtgggagcccctctatgcctcgccagagattgtcaatgggaagccctacacaggcccaga<br>ggtggacagctggtccctgggtgttctcctctacatcctggtgcatggcaccatgccctttgatgggcatgaccataagatcctagtgaaaca<br>gatcagcaacggggcctaccgggagccacctaaaccctctgatgcctgtggcctgatccggtggctgttgatggtgaaccccacccgccg<br>ggccaccctggaggatgtggccagtcactggtgggtcaactggggctacgccacccgagtgggagagcaggaggctccgcatgagggt<br>gggcaccctggcagtgactctgcccgcgcctccatggctgactggctccggcgttcctcccgcccccctcctggagaatggggccaaggtg<br>tgcagcttcttcaagcagcatgcacctggtgggggaagcaccacccctggcctggagcgccagcattcgctcaagaagtcccgcaagga<br>gaatgacatggcccagtctctccacagtgacacggctgatgacactgcccatcgccctggcaagagcaacctcaagctgccaaagggcat<br>tctcaagaagaaggtgtcagcctctgcagaaggggtacaggaggaccctccggagctcagcccaatccctgcgagcccagggcaggct<br>gccccgctgctccccaagaagggcattctcaagaagccccgacagcgcgagtctggctactactcctctcccgagcccagtgaatctggg<br>gagctcttggacgcaggcgacgtgtttgtgagtggggatcccaaggagcagaagcctccgcaagcttcagggctgctcctccatcgcaaa<br>ggcatcctcaaactcaatggcaagttctcccagacagccttggagctcgcggccccccaccaccttcggctccctggatgaactcgccccac<br>ctcgcccccctggcccgggccagccgaccctcaggggctgtgagcgaggacagcatcctgtcctctgagtcctttgaccagctggacttgc<br>ctgaacggctcccagagccccccactgcggggctgtgtgtctgtggacaacctcacggggcttgaggagccccccctcagagggccctgga<br>agctgcctgaggcgctggcggcaggatcctttgggggacagctgcttttccctgacagactgccaggaggtgacagcgacctaccgaca<br>ggcactgagggtctgctcaaagctcacctgagtggagtaggcattgccccagcccggtcaggctctcagatgcagctggttgcaccccga<br>ggggagatgccttctccccccacctcccaggacctgcatcccagctcagaaggctgagagggtttgcagtggagccctgagcagggctgg<br>atatgggaagtaggcaaatgaaatgcgccaagggttcagtgtctgtcttcagccctgctgaacgaagaggatactaaagagaggggaacg<br>ggaatgcccgcgacagagtccacattgcctgtttcttgtgtacatggggggccacagagacctggaaagagaactctcccagggcccat<br>ctcctgcatcccatgaatactctgtacacatggtgccttctaaggacagctccttccctactcattccctgcccaagtggggccagacctcttta<br>cacacacattcccgttcctaccaaccaccagaactggatggtggcacccctaatgtgcatgaggcatcctgggaatggtctggagtaacgct<br>tcgttattttattttattttatttatttatttatttttttgagacggagtttcgctcttggtgcccaggctagagtgcaatggcgcgatctcagctcac<br>ctcaacctccgcctcccgggttcaagcgattctcctgcctcagcctccctagtagctgggattacaggcgcccgccaccatgcccggctaat<br>tttgtatttttagtagagacagggtttctccatgttggtcaggctggtctcaaactcccgacctcaggtgatccacccacctcggcctcccaaag<br>tgctgggattacaggcgtgagccaccgcgccccacctaacccttccttatttagcctaggagtaagagaacacaatctctgtttcttcaatggt<br>tctcttcccttttccatcctccaaacctggcctgagcctcctgaagttgctgctgtgaatctgaaagacttgaaaagcctccgcctgctgtgtgg<br>acttcatctcaaggggcccagcctcctctggactccaccttggacctcagtgactcagaacttctgcctctaagctgctctaaagtccagacta<br>tggatgtgttctctaggccttcaggactctagaatgtccatatttatttttatgttcttggctttgtgttttaggaaaagtgaatcttgctgttttcaata<br>atgtgaatgctatgttctgggaaaatccactatgacatctaagttttgtgtacagagagatatttttgcaactatttccacctcctcccacaacccc<br>ccacactccactccacactcttgagtctctttacctaatggtctctacctaatggacctccgtggccaaaaagtaccattaaaaccagaaaggt<br>gattggaaaaaaaaaaaaaaaaaaaaaaaaaaaaaaaaaaaaaaaaa (SEQ ID NO: 618) | NM_030952 | NM_001195025 |
| Alk | agctgcaagtggcgggcgcccaggcagatgcgatccagcggctctgggggcggcagcggtggtagcagctggtacctcccgccgcct<br>ctgttcggagggtcgcggggcaccgaggtgctttccggccgccctctggtcggccacccaaagccgcgggcgctgatgatgggtgagg<br>agggggcggcaagatttcgggcgcccctgccctgaacgccctcagctgctgccgccggggccgctccagtgcctgcgaactctgagga<br>gccgaggcgccggtgagagcaaggacgctgcaaacttgcgcagcgcgggggctgggattcacgcccagaagttcagcaggcagaca<br>gtccgaagccttcccgcagcggagagatagcttgagggtgcgcaagacggcagcctccgccctcggttcccgcccagaccgggcagaa<br>gagcttggaggagccaaaaggaacgcaaaaggcggccaggacagcgtgcagcagctgggagccgccgttctcagccttaaaagttgca<br>gagattggaggctgccccgagaggggacagaccccagctccgactgcgggggcaggagaggacggtacccaactgccacctccctt<br>caaccatagtagttcctctgtaccgagcgcagcgagctacagacgggggcgcggcactcggcgcggagagcgggaggctcaaggtcc<br>cagccagtgagcccagtgtgcttgagtgtctctggactcgcccctgagcttccaggtctgtttcatttagactcctgctcgcctccgtgcagttg<br>ggggaaagcaagagacttgcgcgcacgcacagtcctctggagatcaggtggaaggagccgctgggtaccaaggactgttcagagcctct<br>tcccatctcggggagagcgaagggtgaggctgggcccggagagcagtgtaaacggcctcctccggcgggatgggagccatcgggctc | NM_004304 | NM_007439 |

TABLE 1-continued

| Gene | Human Gene Sequence | Human Sequence Accession No. | Murine Sequence Accession No. |
|---|---|---|---|
| | ctgtggctcctgccgctgctgctttccacggcagctgtgggctccgggatggggaccggccagcgcgcgggctccccagctgcggggc<br>cgccgctgcagccccgggagccactcagctactcgcgcctgcagaggaagagtctggcagttgacttcgtggtgccctcgctcttccgtgt<br>ctacgcccgggacctactgctgccaccatcctcctcggagctgaaggctggcaggcccgaggcccgcggctcgctagctctggactgcg<br>ccccgctgctcaggttgctggggccggcgccgggggtctcctggaccgccggttcaccagccccggcagaggcccggacgctgtccag<br>ggtgctgaagggcggctccgtgcgcaagctccggcgtgccaagcagttggtgctggagctgggcgaggaggcgatcttggagggttgc<br>gtcgggcccccggggaggcggctgtggggctgctccagttcaatctcagcgagctgttcagttggtggattcgccaaggcgaagggcg<br>actgaggatccgcctgatgcccgagaagaaggcgtcggaagtgggcagagagggaaggctgtccgcggcaattcgcgcctcccagcc<br>ccgccttctcttccagatcttcgggactggtcatagctccttggaatcaccaacaaacatgccttctccttctcctgattattttacatggaatctc<br>acctggataatgaaagactccttccctttcctgtctcatcgcagccgatatggtctggagtgcagctttgacttcccctgtgagctggagtattc<br>ccctccactgcatgacctcaggaaccagagctggtcctggcgccgcatcccctccgaggaggcctcccagatggacttgctggatgggcc<br>tggggcagagcgttctaaggagatgcccagaggctcctttctccttctcaacacctcagctgactccaagcacaccatcctgagtccgtgga<br>tgaggagcagcagtgagcactgcacactggccgtctcggtgcacaggcacctgcagccctctggaaggtacattgcccagctgctgccc<br>cacaacgaggctgcaagagagatcctcctgatgcccactccagggaagcatggttggacagtgctccagggaagaatcgggcgtccaga<br>caacccatttcgagtggccctggaatacatctccagtggaaaccgcagcttgtctgcagtggacttctttgccctgaagaactgcagtgaag<br>gaacatccccaggctccaagatggccctgcagagctccttcacttgttggaatgggacagtcctccagcttgggcaggcctgtgacttccac<br>caggactgtgcccagggagaagatgagagccagatgtgccggaaactgcctgtgggtttttactgcaactttgaagatggcttctgtggctg<br>gacccaaggcacactgtcaccccacactcctcaatggcaggtcaggaccctaaaggatgcccggttccaggaccaccaagaccatgctct<br>attgctcagtaccactgatgtccccgcttctgaaagtgctacagtgaccagtgctacgtttcctgcaccgatcaagagctctccatgtgagctc<br>cgaatgtcctggctcattcgtggagtcttgaggggaaacgtgtccttggtgctagtggagaacaaaaccgggaaggagcaaggcaggatg<br>gtctggcatgtcgccgcctatgaaggcttgagcctgtggcagtggatggtgttgcctctcctcgatgtgtctgacaggttctggctgcagatg<br>gtcgcatggtggggacaaggatccagagccatcgtggcttttgacaatatctccatcagcctggactgctacctcaccattagcggagagg<br>acaagatcctgcagaatacagcacccaaatcaagaaacctgtttgagagaaacccaaacaaggagctgaaacccggggaaaattcacca<br>agacagacccccatctttgaccctacagttcattggctgttcaccacatgtggggccagcgggccccatggccccacccaggcacagtgca<br>acaacgcctaccagaactccaacctgagcgtggaggtggggagcgagggcccccctgaaaggcatccagatctggaaggtgccagcca<br>ccgacacctacagcatctcgggctacggagctgctggcgggaaaggcgggaagaacaccatgatgcggtcccacggcgtgtctgtgctg<br>ggcatcttcaacctggagaaggatgacatgctgtacatcctggttgggcagcagggagaggacgcctgccccagtacaaaccagttaatc<br>cagaaagtctgcattggagagaacaatgtgatagaagaagaaatccgtgtgaacagaagcgtgcatgagtgggcaggaggcggaggag<br>gaggggggtggagccacctacgtatttaagatgaaggatggagtgccggtgcccctgatcattgcagccggaggtggtggcagggcctac<br>ggggccaagacagacacgttccacccagagagactggagaataactcctcggttctagggctaaacggcaattccggagccgcaggtgg<br>tggaggtggctggaatgataacacttccttgctctgggccggaaaatctttgcaggagggtgccaccggaggacattcctgcccccaggcc<br>atgaagaagtgggggtgggagacaagagggggtttcggagggggtggagggggggtgctcctcaggtggaggaggcggaggatatata<br>ggcggcaatgcagcctcaaacaatgaccccgaaatggatggggaagatggggtttccttcatcagtccactgggcatcctgtacacccca<br>gctttaaaagtgatggaaggccacggggaagtgaatattaagcattatctaaactgcagtcactgtgaggtagacgaatgtcacatggaccc<br>tgaaagccacaaggtcatctgcttctgtgaccacgggacggtgctggctgaggatggcgtctcctgcattgtgtcacccaccccggagcca<br>cacctgccactctcgctgatcctctctgtggtgacctctgccctcgtggccgccctggtcctggctttctccggcatcatgattgtgtaccgcc<br>ggaagcaccaggagctgcaagccatgcagatggagctgcagagccctgagtacaagctgagcaagctccgcacctcgaccatcatgac<br>cgactacaaccccaactactgctttgctggcaagacctcctccatcagtgacctgaaggaggtgccgcggaaaaacatcaccctcattcgg<br>ggtctgggccatggcgcctttggggaggtgtatgaaggccaggtgtccggaatgcccaacgacccaagcccccctgcaagtggctgtgaa<br>gacgctgcctgaagtgtgctctgaacaggacgaactggatttcctcatggaagccctgatcatcagcaaattcaaccaccagaacattgttc<br>gctgcattggggtgagcctgcaatccctgccccggttcatcctgctggagctcatggcgggggagacctcaagtccttcctccgagagac<br>ccgccctcgcccgagccagccctcctccctggccatgctggaccttctgcacgtggctcgggacattgcctgtggctgtcagtatttggagg<br>aaaaccacttcatccaccgagacattgctgccagaaactgcctcttgacctgtccaggccctggaagagtggccaagattggagacttcgg<br>gatggcccgagacatctacagggcgagctactatagaaagggaggctgtgccatgctgccagttaagtggatgcccccagaggccttcat<br>ggaaggaatattcacttctaaaacagacacatggtcctttggagtgctgctatgggaaatcttttctcttggatatatgccataccccagcaaaa<br>gcaaccaggaagttctggagtttgtcaccagtggaggccggatggacccacccaagaactgccctgggcctgtataccggataatgactc<br>agtgctggcaacatcagcctgaagacaggcccaactttgccatcattttggagaggattgaatactgcacccaggacccggatgtaatcaac<br>accgctttgccgatagaatatggtccacttgtggaagaggaagagaaagtgcctgtgaggcccaaggaccctgaggggggttcctcctctcc<br>tggtctctcaacaggcaaaacgggaggaggagcgcagcccagctgccccaccacctctgcctaccacctcctctggcaaggctgcaaag<br>aaacccacagctgcagagatctctgttcgagtccctagagggccggccgtggaaggggacacgtgaatatggcattctctcagtccaac<br>cctccttcggagttgcacaaggtccacggatccagaaacaagcccaccagcttgtggaacccaacgtacggctcctggtttacagagaaac | | |

TABLE 1-continued

| Gene | Human Gene Sequence | Human Sequence Accession No. | Murine Sequence Accession No. |
|---|---|---|---|
| | ccaccaaaaagaataatcctatagcaaagaaggagccacacgacaggggtaacctggggctggagggaagctgtactgtcccacctaac gttgcaactgggagacttccgggggcctcactgctcctagagccctcttcgctgactgccaatatgaaggaggtacctctgttcaggctacgt cacttcccttgtgggaatgtcaattacggctaccagcaacagggcttgcccttagaagccgctactgcccctggagctggtcattacgagga taccattctgaaaagcaagaatagcatgaaccagcctgggccctgagctcggtcgcacactcacttctcttccttgggatccctaagaccgtg gaggagagagaggcaatggctccttcacaaaccagagaccaaatgtcacgttttgttttgtgccaacctattttgaagtaccaccaaaaaagc tgtattttgaaaatgctttagaaaggttttgagcatgggttcatcctattctttcgaaagaagaaaatatcataaaaatgagtgataaatacaagg cccagatgtggttgcataaggtttttatgcatgtttgttgtatacttccttatgcttctttcaaattgtgtgtgctctgcttcaatgtagtcagaattagc tgcttctatgtttcatagttggggtcatagatgtttccttgccttgttgatgtggacatgagccatttgaggggagagggaacggaaataaagga gttatttgtaatgactaaaa (SEQ ID NO: 619) | | |
| Pdzklip1 | gcccgtcttcgtgtctcctccctccctcgccttcctccttcctagctcctctcctccagggccagactgagcccaggttgatttcaggcggaca ccaatagactccacagcagctccaggagcccagacaccggcggccagaagcaaggctaggagctgctgcagccatgtcggccctcagc ctcctcattctgggcctgctcacggcagtgccacctgccagctgtcagcaaggcctggggaaccttcagccctggatgcagggccttatcg cggtggccgtgttcctggtcctcgttgcaatcgcctttgcagtcaaccacttctggtgccaggaggagccggagcctgcacacatgatcctg accgtcggaaacaaggcagatggagtcctggtgggaacagatggaaggtactcttcgatggcggccagtttcaggtccagtgagcatgag aatgcctatgagaatgtgcccgaggaggaaggcaaggtccgcagcaccccgatgtaaccttctctgtggctccaaccccaagactcccag gcacatgggatggatgtccagtgctaccacccaagcccccctccttctttgtgtggaatctgcaatagtgggctgactccctccagccccatgc cggccctacccgcccttgaagtatagccagccaaggttggagctcagaccgtgtctaggttggggctcggctgtggccctggggtctcctg ctcagctcagaagagccttctggagaggacagtcagctgagcacctcccatcctgctcacacgtccttccccataactatggaaatggccct aatttctgtgaaataaagactttttgtatttctggggctgaggctcagcaacagcccctcaggcttccagtga (SEQ ID NO: 620) | NM_005764 | NM_001164557 |
| Inpp5b | aaatgtagtcactgtcccggaacctggggcagcggagtcccgtgcgccctgtggtgacagctcaggagggtgtgtgcgctcagcagggg ccagcatggaccagtctgtggcaatccaggagacgctggctgaggggaatactgcgtcatcgcggtgcaaggtgtgctgtgtgagggg gacagccggcagagccgcctcctgggactcgtgcgctaccgcctggagcacggcggccaggaacacgctctcttcctctatacgcaccg gaggatggccattaccggggacgatgtctctctggaccagatagtgccagtctcgcgggattttacgctggaagaagtgtccccagatggt gaactctacatccttggctcagatgtgaccgtccagctggacacagcagagcttagcctcgtattccaactgccctttggttcacaaaccagg atgttcctccacgaagttgccagggcctgtccaggcttcgattctgcgacccgggatcctgaattcctgtggctgtctcggtataggtgcgca gagctggagctggagatgccaacgccgcgcggttgtaactcggccctagttacctggccagggtacgcgacaattggcggaggtggttct aactttgatggtttgagaccaaatgggaagggagtgcctatggaccaaagctccaggggtcaagataaaccagaaagcttgcaaccaaga cagaataaatccaagtccgaaattactgacatggttcgctcctccactatcacagtgtcggacaaggctcatattttatccatgcagaagtttgg actgcgagatacaattgtgaaatcacatctactacagaaagaagaggattacacctatatccagaacttcaggtttttttgcgggaacatacaat gtaaatgggcagtcccccaaagaatgcctccggctgtggctgagcaatggtatccaggccccagatgtctattgtgtagggttccaggagct tgatctgagtaaggaagctttttttctttcacgataccccaaaggaggaagagtggttcaaagctgtgtcagagggtcttcatccagatgccaaa tatgcaaaggtgaagcttatccgactggttgggattatgctgctgttatatgtcaaacaggagcatgcagcttatatctcagaagtggaagccg agactgtggggacaggaatcatggggaggatgggcaacaagggaggcgtggcgatcaggttccagttccacaacaccagcatctgcgtt gtgaattctcacttggcagcccacattgaagagtatgagaggaggaaccaggactataaggacatttgttctcgaatgcagttttgtcagcct gacccaagccttcccccctctcaccatcagcaaccatgatgtgatcttgtggctgggggacctcaactacaggatagaagagctggatgtgg aaaaagtgaaaaagctcatcgaagagaaggactttcaaatgctgtatgcatatgatcagctgaaaattcaggtggccgcaaagactgtctttg aaggcttcacagagggtgagctcacattccagcctacttacaagtatgatacgggctctgacgactgggataccagtgagaagtgccgtgc tcctgcctggtgtgatcggattctctggaaagggaagaacatcactcagctgagttaccagagccacatggccctgaagaccagtgaccac aagcctgtcagctcagtgtttgacatcggggtgagggtcgtaaatgacgagctttaccggaagacactggaggaaattgttcgctccctgga taagatggaaaatgccaacattccttctgtgtccctgtccaagcgagagttctgttttcagaatgtgaagtacatgcaattgaaagtagaatcctt tacaattcataatggacaagtaccctgtcattttgaattcatcaacaagcctgatgaagagtcttactgtaagcagtggctgaatgccaacccca gcagaggcttcctcctgccagattctgatgttgagattgacttggagctcttcgtaaataagatgacagctacaaagctcaactcgggtgaag acaaaattgaggacattctggttctgcacttggacaggggaaaggattactttttgtctgtgtctgggaactacctgcccagctgttttgggtctc ccattcatacactgtgttacatgagagagccaatcttggacctaccacttgaaaccattagtgagctgactctgatgccagtatggactggaga tgatgggagccagttggatagccccatggaaatccccaaagagctctggatgatggttgattacctgtaccgaaatgctgtccagcaggaa gatctgtttcagcaaccaggcctgaggtcagaatttgaacatatcagggactgcttggatactggaatgattgataacctctctgccagcaatc attctgtagccgaagccctgctgcttttcctggagagccttccagagcctgtcatctgttacagcacctaccataactgcttggagtgttctggc aactacacagcaagcaaacaggtcatttctactctccccatattccacaaaaatgtcttccactacttgatggcgtttttgcgagaactgctgaa | NM_005540 | NM_008385 |

TABLE 1-continued

| Gene | Human Gene Sequence | Human Sequence Accession No. | Murine Sequence Accession No. |
|---|---|---|---|
| | aaattcagcaaaaaatcatttggatgagaatattctagctagcatatttggcagcttattgcttcgaaacccagctggtcaccaaaagcttgatat gacagagaagaagaaggctcaagaatttattcaccagttcctctgcaacccactctgagcctctctctcctcctattttacttgaggctgccaat taccagccccacctgtttcagctcaagagatgccttaagataattatgtgaggccacttggtagcaagaatggcagctatttcctgagcctagt accccaattaagcccaccattggttagcacactcagcgctgtgagtcgtgaagacacgggagaaaatccaccataataaaactgacattcaa ttttcaactttagttatttaacacagatttttttatttttttatttttttttatttttgagacggagttttgctctgtcgcgcagggtggagtgcggtggcacg atctcggctcactgcaacctctgcctcctgggtgcaagcaattatcctgcctcagcctcccgagtagctgggactgcaggcacacactgcca cgcccagctaattttttgcattttagtagagacggggtttcaccgtgttgcccaggctgttctaaaactcctgaactcaggtaatctgcctgcctc ggcctccccaagtgctaggattacagatgtgagccaccacgcccggcctttttttttttttttttctttttgagatggagtttcactcttgttgcccag gctggagtgcgttggcgtggtcttggctcactgcaacctctgcctccttggttcaagcaattctcctgcctcagcctctcgagtagctgggatt ataggcgtccgccaccatgcctggctaatttttttgtgtgtttttagtatagacacggtttcaccatgttggccaggctggtctcgaatgcctggc ctcaggtgatccacctgccttggcctcccaaagtgctgggattacaggcatgaaccaccacgcctggcctaaaatgtttttaaataactgtact tgtactcactcaccctacctccagggcatagtcagtctgggctgagatccccatgatcagatatttgatggaaagtcctgaaaggccaatgag ttggatggcaagaatgcaggcagaagctgctggataaaataggctacagccacctcagatgctttcagtgctctgtctgaggatgtgtatatg catatgcaaactcgaccccccgttcctgcccagataatggctcaataactctgaggctggttgctcagcctctgagggcaatacaggcatttaa aaaattaaaatgaccaggcacagtggctcacgcctgtaatctcggcactttgggagactgaggtgggagcatcacttgagaccaggagttt gggaccaggctgggcaacacagggagacccccctctctacaaaaacatttttaaaaaattagctgggtgtggtgatgcatgcctgtggtccca gttacttgggaggctgacgtgggtggctcacttgagcacaggagtttgaggctgcagtgacctatgaccacatcactgtacgccagcccgg gtgagagagggagaccccgtctctaaaaataaaatgtaaaatcactgaaaaaatgagtgttcggtgaaacaagtgggattttctgggccagc aagtcttccaaactgtatatgatgcatcctgtctccatgtgtaatatattttaatgataaatgtatttttaacagtgaaaaaaaaaaaaaaa (SEQ ID NO: 653) | | |
| Socs1 | ggcagctgcacggctcctggccccggagcatgcgcgagagccgccccggagcgccccggagccccccgccgtcccgcccgcggcgt cccgcgccccgccgccagcgcaccccggacgctatggcccacccctccggctggccccttctgtaggatggtagcacacaaccaggt ggcagccgacaatgcagtctccacagcagcagagccccgacggcggccagaaccttcctcctcttcctcctcctcgcccgcggccccg cgcgcccgcggccgtgccccgcggtcccggccccggcccccggcgacacgcacttccgcacattccgttcgcacgccgattaccggcg catcacgcgcgccagcgcgctcctggacgcctgcggattctactgggggcccctgagcgtgcacggggcgcacgagcggctgcgcgc cgagcccgtgggcaccttcctggtgcgcgacagccgccagcggaactgctttttcgcccttagcgtgaagatggcctcgggacccacgag catccgcgtgcactttcaggccggccgctttcacctggatggcagccgcgagagcttcgactgcctcttcgagctgctggagcactacgtg gcggcgccgcgccgcatgctgggggccccgctgcgccagcgccgcgtgcggccgctgcaggagctgtgccgccagcgcatcgtggc caccgtgggccgcgagaacctggctcgcatcccccctcaaccccgtcctccgcgactacctgagctccttccccttccagatttgaccggca gcgcccgccgtgcacgcagcattaactgggatgccgtgttattttgttattacttgcctggaaccatgtgggtaccctccccggcctgggttg gaggggagcggatgggtgtaggggcgaggcgcctcccgccctcggctggagacgaggccgcagaccccttctcacctcttgagggggtc ctcccccctcctggtgctccctctgggtcccccctggttgttgtagcagcttaactgtatctggagccaggacctgaactcgcacctcctacctctt catgtttacatatacccagtatctttgcacaaaccaggggttgggggagggtctctggctttatttttctgctgtgcagaatcctattttatattttta aagtcagtttaggtaataaactttattatgaaagttttttttt (SEQ ID NO: 654) | NM_003745 | NM_001271603 |
| Jun | gacatcatgggctatttttaggggttgactggtagcagataagtgttgagctcgggctggataagggctcagagttgcactgagtgtggctga agcagcgaggcgggagtggaggtgcgcggagtcaggcagacagacagacacagccagccagccaggtcggcagtatagtccgaact gcaaatcttattttcttttcaccttctctctaactgcccagagctagcgcctgtggctcccgggctggtgtttcgggagtgtccagagagcctgg tctccagccgcccccgggaggagagccctgctgcccaggcgctgttgacagcggcggaaagcagcggtacccacgcgcccgccggg ggaagtcggcgagcggctgcagcagcaaagaactttcccggctgggaggaccggagacaagtggcagagtcccggagcgaacttttgc aagcctttcctgcgtcttaggcttctccacggcggtaaagaccagaaggcggcggagagccacgcaagagaagaaggacgtgcgctca gcttcgctcgcaccggttgttgaacttgggcgagcgcgagccgcggctgccgggcgcccctcccccctagcagcggaggaggggacaa gtcgtcggagtccgggcggccaagacccgccgccggccggccactgcagggtccgcactgatccgctccgcggggagagccgctgct ctgggaagtgagttcgcctgcggactccgaggaaccgctgcgcccgaagagcgctcagtgagtgaccgcgacttttcaaagccgggtag cgcgcgcgagtcgacaagtaagagtgcgggaggcatcttaattaaccctgcgctccctggagcgagctggtgaggagggcgcagcggg gacgacagccagcgggtgcgtgcgctcttagagaaactttccctgtcaaaggctccgggggggcgcgggtgtcccccgcttgccagagcc ctgttgcggccccgaaacttgtgcgcgcagcccaaactaacctcacgtgaagtgacggactgttctatgactgcaaagatggaaacgacct tctatgacgatgccctcaacgcctcgttcctcccgtccgagagcggaccttatggctacagtaaccccaagatcctgaaacagagcatgacc ctgaacctggccgacccagtgggagcctgaagccgcacctccgcgccaagaactcggacctcctcacctcgcccgacgtggggctgctc | NM_002228 | NM_010591 |

TABLE 1-continued

| Gene | Human Gene Sequence | Human Sequence Accession No. | Murine Sequence Accession No. |
|---|---|---|---|
| | aagctggcgtcgcccgagctggagcgcctgataatccagtccagcaacgggcacatcaccaccacgccgacccccacccagttcctgtg ccccaagaacgtgacagatgagcaggagggcttcgccgagggcttcgtgcgcgccctggccgaactgcacagccagaacacgctgcc cagcgtcacgtcggcggcgcagccggtcaacggggcaggcatggtggctcccgcggtagcctcggtggcagggggcagcggcagcg gcggcttcagcgccagcctgcacagcgagccgccggtctacgcaaacctcagcaacttcaacccaggcgcgctgagcagcggcggcg gggcgccctcctacggcgcggccggcctggcctttcccgcgcaaccccagcagcagcagcagccgccgcaccacctgccccagcaga tgcccgtgcagcacccgcggctgcaggccctgaaggaggagcctcagacagtgcccgagatgcccggcgagacaccgcccctgtccc ccatcgacatggagtcccaggagcggatcaaggcggagaggaagcgcatgaggaaccgcatcgctgcctccaagtgccgaaaaagga agctggagagaatcgcccggctggaggaaaaagtgaaaaccttgaaagctcagaactcggagctggcgtccacggccaacatgctcag ggaacaggtggcacagcttaaacagaaagtcatgaaccacgttaacagtgggtgccaactcatgctaacgcagcagttgcaaacattttga agagagaccgtcgggggctgaggggcaacgaagaaaaaaaataacacagagagacagacttgagaacttgacaagttgcgacggaga gaaaaaagaagtgtccgagaactaaagccaagggtatccaagttggactgggttgcgtcctgacggcgcccccagtgtgcacgagtggg aaggacttggcgcgccctcccttggcgtggagccagggagcggccgcctgcgggctgccccgctttgcggacgggctgtccccgcgcg aacggaacgttggacttttcgttaacattgaccaagaactgcatggacctaacattcgatctcattcagtattaaagggggagggggaggg ggttacaaactgcaatagagactgtagattgcttctgtagtactccttaagaacacaaagcgggggagggttggggagggggcggcagga gggaggtttgtgagagcgaggctgagcctacagatgaactctttctggcctgccttcgttaactgtgtatgtacatatatatatttttttaatttgatg aaagctgattactgtcaataaacagcttcatgcctttgtaagttatttcttgtttgtttgtttgggtatcctgcccagtgttgtttgtaaataagagattt ggagcactctgagtttaccatttgtaataaagtatataattttttttatgttttgtttctgaaaattccagaaaggatatttaagaaaatacaataaacta ttggaaagtactcccctaacctcttttctgcatcatctgtagatactagctatctaggtggagttgaaagagttaagaatgtcgattaaaatcactc tcagtgcttcttactattaagcagtaaaaactgttctctattagactttagaaataaatgtacctgatgtacctgatgctatggtcaggttatactcct cctcccccagctatctatatggaattgcttaccaaaggatagtgcgatgtttcaggaggctggaggaagggggggttgcagtggagagggac agcccactgagaagtcaaacatttcaaagtttggattgtatcaagtggcatgtgctgtgaccatttataatgttagtagaaattttacaataggtg cttattctcaaagcaggaattggtggcagattttacaaaagatgtatccttccaatttggaatcttctctttgacaattcctagataaaaagatggc ctttgcttatgaatatttataacagcattcttgtcacaataaatgtattcaaataccaaaaaaaaaaaaaaaaaa (SEQ ID NO: 655) | | |
| Nptxr | cggccgcggcgacagctccagctccggctccggctccggctccggctccggctcccgcgcctgccccgctcggcccagcgcgcccgg gctccgcgccccgaccccgccgccgcgcctgccgggggcctcgggcgccccgccgcccgcctcacgctgaagttcctggccgtgct gctggccgcgggcatgctggcgttcctcggtgccgtcatctgcatcatcgccagcgtgcccctggcggccagcccggcgcgggcgctgc ccggcggcgccgacaatgcttcggtcgcctcgggcgccgccgcgtccccgggcccgcagcggagcctgagcgcgctgcacggcgcg ggcggttcagccgggcccccgcgctgcccggggcacccgcggccagcgcgcacccgctgccgcccgggcccctgttcagccgcttc ctgtgcacgccgctggctgctgcctgcccgtcgggggcccagcagggggacgcggcgggcgctgcgccgggcgagcgcgaagagct gctgctgctgcagagcacggccgagcagctgcgccagacggcgctgcagcaggaggcgcgcatccgcgccgaccaggacaccatcc gtgagctcaccggcaagctgggccgctgcgagagcggcctgccgcgcggcctccagggcgccgggccccgccgcgacaccatggcc gacgggccctgggactcgcctgcgctcattctggagctggaggacgccgtgcgcgccctgcgggaccgcatcgaccgcctggagcag gagcttccagcccgtgtgaacctctcagctgccccagccccagtctctgctgtgcccaccggcctacactccaagatggaccagctggag gggcagctgctggcccaggtgctggcactggagaaggagcgtgtggccctcagccacagcagccgccggcagaggcaggaagtgga aaaggagttggacgtcctgcagggtcgtgtggctgagctggagcacgggtcctcagcctacagtcctccagatgccttcaagatcagcatc cccatccgtaacaactacatgtacgcccgcgtgcggaaggctctgcccgagctctacgcattcaccgcctgcatgtggctgcggtccaggt ccagcggcaccggccagggcacccccttctcctactcagtgcccgggcaggccaacgagattgtactgctagaggcgggccatgagcc catggagctgctgatcaacgacaaggtggcccagctgcccctgagcctgaaggacaatggctggcaccacatctgcatcgcctggacca caagggatggcctatggtctgcctaccaggacggggagctgcagggctccggtgagaacctggctgcctggcaccccatcaagcctcat gggatccttatcttgggccaggagcaggataccctgggtggccggtttgatgccacccaggcctttgtcggtgacattgcccagtttaacctg tgggaccacgccctgacaccagcccaggtcctgggcattgccaactgcactgcgccactgctgggcaacgtccttccctgggaagacaa gttggtggaggcctttgggggtgcaacaaaggctgccttcgatgtctgcaaggggagggccaaggcatgaggggccacctcatccaggg cccctcccttgcctgccactttggggacttgaggggggtcatattccctcctcagcctgcccacgcactggccttccctcctgccccactcct ggctgtgcctcccatttcccctcacctgtacccacacctccagaatgccctgccctgcgagtgtgtcccctgtccccacctgagtggggagg agcgtctcaagtgaacagtgggagcctgcccacctggcactgcactggagttgtctcttaccccaccctccctgcccatcaactgtatctgat ttcactaattttgacagcacccccagtagggtaggattgtgtatgaggggggaccccactatctcagtggtgggggtggccgcccgcccccctt gtcccccatgcaacaggcccagtggcttccccttcagggccacaacaggctgtagaaggggatgacgaggacatcagaggttagacttac cctcctccctctttccaccagctgccagtcaagggcagtgggatctcgatggagcctcccccccccccacccatgcctccctcttcctcctc tttcctcctctctttgtgtgtagcggtttgaatgttggttccatgcctggcccagccccacctcagtctccaggacattcctttcccagctccagc | NM_014293 | NM_030689 |

TABLE 1-continued

| Gene | Human Gene Sequence | Human Sequence Accession No. | Murine Sequence Accession No. |
|---|---|---|---|
| | ctggagggaaggggacaaagaccccaggaggccaaagggctgcagtcaccccttgtgctcacccatagtgatggccactggtatagtca<br>tcgctctccctccatgccaaggacaggacttggaccgcttcagcctgggctgggagcagccctaaggtagaggcctcatggcccaggag<br>accccacctctggcagagccacattacctaccctgtgcatggtcctggggcagcaaggaagaagctcagagggtggggagaagcatgaa<br>gcagtgagcagagcactgggtgagagggagaagaccttggttcctagccagccctgctaatgtgctgtgtggccttctgtaagtccctgcc<br>ctctctgggcctggccttcctcattcgtgagctgaggccctcgctttggtcatttgctctccagattgggtgtgagcttctctgtgattccaggtg<br>gatatgtggggaaagctctggtgaccctgggcttcgcaggggtagatcccaggactcggcagtggatgggatgcagccagtcatgggtta<br>gggtcagcagagactcagagtccagggcaaggttcaaggcagactaacctcatgcatggattgtaaaaaaccagctccctttggatcaacc<br>cagcctggcacccttgcctgtctgagagtgtctcaaagggctgatggcttcctggtccccttgagtcatcaccagcttccccaagagagtgtc<br>agaatcttaagagctgagaggccgggcacggtggctcacgcctgtaatcccagcactttgggaggctgagacaggcagatcacttgaggt<br>caggagttcgaagtcagcctggccaacgtggtgaaaccccatcttcactaaaaatacaaaacttagctggttaggtggtgcatgcctgtagtc<br>ccagctactcgggaggccgaggcagaagaatctcttgaactgaggaggtggaggttgcagtgagccgagatcacgccattgcactccag<br>cctgggcaacagagcaagactccatctcaaaaaaataataataatcttaaagatgagaaaagccaccccatctggcaccacagctgcatctt<br>gcttgtgagaaatggggaagagttcagggaggacacgtgacctgcacaggatcacagagcatggggcagagccaggactagagctcag<br>ggcatctgactccctcttcagtgttcttcccccctccatgttgcctgcccctgaagacctttgagttcagtctacacctaagcaggtagacatccg<br>cgaggtcagatgctttccaacatgacacctgaacatcttcctttatgcaacacccaaacatcttggcatccccaccccaggaagtgcgggga<br>ggaggttatgatccctgggcgcttcggcagaatggagagctgaggtgtccctcccctgctagtcacctaccaggtgtctgagcagctgcat<br>gctccctggctcaagtgggcactgtaccttttgcctgcctttttgttccctatctccactccctgaggccacttagcctgagacatgatgcaaga<br>gctgcaggccggggggctcagtgccatggaagctactccaagttgcattgcctcccgcgcccagatcctgctttccatttcgagaacataaa<br>tagattgcccagcccctccagtacaatcccactggaagaaaaggcaatggcgggcttcagccagacctgctgagacctaggttgccacgg<br>taacagccaaagacatcaacccaagtgctgggtcaagtgtctcatcatactggcactgttgctggggtgacggcagaattcagaacttcaatt<br>tcagtgacgccaagcttgatgtgtttctgttattgttttgaagaaggtagctcttgtggaggacttgggagaaggatggggtcttaggaaggag<br>gtgacagcacttgcatggtcacttgagcccacacacacgctcaaccccaagtcctttatgctttgtcacagtgaagatgagacctctgacgtc<br>caagccttgttcctgtgctgcatcacccactcagccttccaaagggaacaggaacaaatttccccagcaccactgtttgggtcccgcttttcct<br>atcttctgctgcccctgagcacatccaagcagacagggaaagaggagtcagacatggcccagtcacatcctgagctgctcctggctgataa<br>ccacgatggagcccgtgtttgtcctgccatctggcactgcactgagtgtggcacaggcaccgtcctgttgatctcacaacacagttctaagtt<br>aggacgttcttggctccgttagacaggtgaggaaactggggcacagagaggtgatgtcatctgcctggtgtcaatcagctagcaagtgatg<br>gagcccagatttcaaaccaaagggggttacgtccaggggctgagttcccactcacctgtgtagagtgccatctgggcaccattgctccaga<br>cgtgttccgacccctttcccagcccacagggcttgaagtgaaggaacagaggcagggggtgggccagccccagggccagggtcccctt<br>ggtgaagccgtgccaggggggctcagctgcttcagggaatgtgtccctcccaccatgggccagagcttcagcccttctttagctcagctaga<br>gttcacaggagagccaaaaaagaaaaggaagctgagcatctcccgagtcctgggcagggaaggggagggaaattgctgcttctccaact<br>cttgcttggggccaagccctgcaccagttgcttcccagctgttatctgccagatcttcccatcttgtggcatgtggtgcccccaccaacatccc<br>aaggggaccaatccccttgccaccactttgcatcacctgggaccacagatttggacaggaagggctctgagaagaggccaaagccctcat<br>tttacagatgaggaagctgaagcccggggaggggagcgaccctcaaggccacccagctggacacgggagacttgagcccagccttctg<br>actgcattcagccctctctaggacgcagcagcctctccccagcactgagtccccccctcctttgtgtgtcccagcacccttggcctgagtaaac<br>ttggaaaggggctccctcccagagaagggactactctcttcacccctttattccagctgcctgccaccccagacccccacctcccaccctga<br>cccccgacccctgggtggggaaggggctcacatgggcccaggctgagtgtgagtgagcatgtcaagttgtctgacactgtgacattagtg<br>caccctactgacaacccctccccagccttgcccctttctcctctccctgttttgtacataaattgacatgagctgcaacatgtgtgcgtgtgtgtg<br>cgtgtgtgtgtgtgtgtatgtgtgtgtgatctgtgtcatggttttgttacctttttgtttttgtaaacttgaatgttcaaaataaacatgctgtttactctg<br>agaaaaaaaaaaaaaaaa (SEQ ID NO: 656) | | |
| Socs3 | gcggctccgacttggactccctgctccgctgctgccgcttcggccccgcacgcagccagccgccagccgcccgcccggcccagctccc<br>gccgcggccccttgccgcggtccctctcctggtcccctcccggttggtccgggggtgcgcagggggcagggcgggcgcccaggggaa<br>gctcgagggacgcgcgcgcgaaggctcctttgtggacttcacggccgccaacatctgggcgcagcgcgggccaccgctggccgtctcg<br>ccgccgcgtcgccttggggacccgagggggctcagccccaaggacggagacttcgattcgggaccagcccccccgggatgcggtagcg<br>gccgctgtgcggaggccgcgaagcagctgcagccgccgccgcgcagatccacgctggctccgtgcgccatggtcacccacagcaagtt<br>tcccgccgccgggatgagccgcccccctggacaccagcctgcgcctcaagaccttcagctccaagagcgagtaccagctggtggtgaac<br>gcagtgcgcaagctgcaggagagcggcttctactggagcgcagtgaccggcggcgaggcgaacctgctgctcagtgccgagcccgcc<br>ggcacctttctgatccgcgacagctcggaccagcgccacttcttcacgctcagcgtcaagacccagtctgggaccaagaacctgcgcatcc<br>agtgtgagggggggcagcttctctctgcagagcgatccccggagcacgcagcccgtgccccgcttcgactgcgtgctcaagctggtgcac<br>cactacatgccgcccccctggagccccctccttcccctcgccacctactgaaccctcctccgaggtgcccgagcagccgtctgcccagcca | NM_003955 | NM_007707 |

TABLE 1-continued

| Gene | Human Gene Sequence | Human Sequence Accession No. | Murine Sequence Accession No. |
|---|---|---|---|
| | ctccctgggagtcccccagaagagcctattacatctactccgggggcgagaagatcccctggtgttgagccggcccctctcctccaacg<br>tggccactcttcagcatctctgtcggaagaccgtcaacggccacctggactcctatgagaaagtcacccagctgccggggcccattcggga<br>gttcctggaccagtacgatgccccgctttaaggggtaaagggcgcaaagggcatgggtcgggagaggggacgcaggcccctctcctcc<br>gtggcacatggcacaagcacaagaagccaaccaggagagagtcctgtagctctgggggaaagagggcggacaggcccctccctctg<br>ccctctccctgcagaatgtggcaggcggacctggaatgtgttggagggaagggggagtaccacctgagtctccagcttctccggaggagc<br>cagctgtcctggtgggacgatagcaaccacaagtggattctccttcaattcctcagcttcccctctgcctccaaacaggggacacttcggga<br>atgctgaactaatgagaactgccagggaatcttcaaactttccaacggaacttgtttgctctttgatttggtttaaacctgagctggttgtggagc<br>ctgggaaaggtggaagagagagaggtcctgagggccccagggctgcgggctggcgaaggaaatggtcacacccccgcccacccca<br>ggcgaggatcctggtgacatgctcctctccctggctccggggagaagggcttggggtgacctgaagggaaccatcctggtaccccacatc<br>ctctcctccgggacagtcaccgaaaacacaggttccaaagtctacctggtgcctgagagcccagggcccttcctccgttttaagggggaag<br>caacatttggaggggatggatgggctggtcagctggtctccttttcctactcatactataccttcctgtacctgggtggatggagcgggaggat<br>ggaggagacgggacatctttcacctcaggctcctggtagagaagacaggggattctactctgtgcctcctgactatgtctggctaagagatt<br>cgccttaaatgctccctgtcccatggagagggacccagcataggaaagccacatactcagcctggatgggtggagaggctgagggactc<br>actggagggcaccaagccagcccacagccagggaagtggggagggggggcggaaacccatgcctcccagctgagcactgggaatgt<br>cagcccagtaagtattggccagtcaggcgcctcgtggtcagagcagagccaccaggtcccactgccccgagccctgcacagccctccct<br>cctgcctgggtgggggaggctggaggtcattggagaggctggactgctgccaccccgggtgctcccgctctgccatagcactgatcagtg<br>acaatttacaggaatgtagcagcgatggaattacctggaacagtttttgtttttgtttttgtttttgtttttgtgggggggggcaactaaacaaaca<br>caaagtattctgtgtcaggtattgggctggacagggcagttgtgtgttggggtggtttttttctctatttttttgtttgtttcttgtttttaataatgttta<br>caatctgcctcaatcactctgtcttttataaagattccacctccagtcctctctcctccccccctactcaggcccttgaggctattaggagatgcttg<br>aagaactcaacaaaatcccaatccaagtcaaactttgcacatatttatatttatattcagaaaagaaacatttcagtaatttataataaagagcact<br>attttttaatgaaaaac (SEQ ID NO: 657) | | |
| F11r | gaggcagctcctgtggggaaaggcgccagtgcgccgaggcggggagtggcggcggggtaacacctggccgaggtgactcgttctgaa<br>gagcagcggttccttacaccaatcggaacgtgcaggggtggggagctggccaatcaggcgcggagggcggggccgggcggggttcc<br>acctggcggctggctctcagtcccctcgctgtagtcgcggagctgtgtctgttcccaggagtccttcggcggctgttgtgtcgggagcctgat<br>cgcgatggggacaaaggcgcaagtcgagaggaaactgttgtgcctcttcatattggcgatcctgttgtgctccctggcattgggcagtgtta<br>cagtgcactcttctgaacctgaagtcagaattcctgagaataatcctgtgaagttgtcctgtgcctactcgggcttttcttctccccgtgtggagt<br>ggaagtttgaccaaggagacaccaccagactcgtttgctataataacaagatcacagcttcctatgaggaccgggtgaccttcttgccaact<br>ggtatcaccttcaagtccgtgacacgggaagacactgggacatacacttgtatggtctctgaggaaggcggcaacagctatggggaggtc<br>aaggtcaagctcatcgtgcttgtgcctccatccaagcctacagttaacatcccctcctctgccaccattgggaaccgggcagtgctgacatgc<br>tcagaacaagatggttccccaccttctgaatacacctggttcaaagatgggatagtgatgcctacgaatcccaaaagcacccgtgccttcag<br>caactcttcctatgtcctgaatcccacaacaggagagctggtctttgatcccctgtcagcctctgatactggagaatacagctgtgaggcacg<br>gaatgggtatgggacacccatgacttcaaatgctgtgcgcatggaagctgtggagcggaatgtggggtcatcgtggcagccgtccttgta<br>accctgattctcctgggaatcttggtttttggcatctggtttgcctatagccgaggccactttgacagaacaaagaaagggacttcgagtaaga<br>aggtgatttacagccagcctagtgcccgaagtgaaggagaattcaaacagacctcgtcattcctggtgtgagcctggtcggctcaccgccta<br>tcatctgcatttgccttactcaggtgctaccggactctggcccctgatgtctgtagtttcacaggatgccttatttgtcttctacaccccacaggg<br>ccccctacttcttcggatgtgtttttaataatgtcagctatgtgccccatcctccttcatgccctccctccctttcctaccactgctgagtggcctgg<br>aacttgtttaaagtgtttattccccatttctttgagggatcaggaaggaatcctgggtatgccattgacttcccttctaagtagacagcaaaaatg<br>gcgggggtcgcaggaatctgcactcaactgcccacctggctggcagggatctttgaataggtatcttgagcttggttctgggctctttccttgt<br>gtactgacgaccagggccagctgttctagagcgggaattagaggctagagcggctgaaatggttgtttggtgatgacactggggtccttcc<br>atctctggggcccactctcttctgtcttcccatgggaagtgccactgggatccctctgccctgtcctcctgaatacaagctgactgacattgact<br>gtgtctgtggaaaatgggagctcttgttgtggagagcatagtaaattttcagagaacttgaagccaaaaggatttaaaaccgctgctctaaag<br>aaaagaaaactggaggctgggcgcagtggctcacgcctataatcccagaggctgaggcaggcggatcacctgaggtcaggagttcaag<br>atcagcctgaccaacatggagaaaccctactaaaaatacaaagttagccaggcatagtggtgcatgcctgtaatcccagctgctcaggagc<br>ctggcaacaagagcaaaactccagctcaaaaaaaaaaagaaagaaaagaaagctggagctggtggcttaggccatcacccttcccttggc<br>tggaactactggacagacccttttgagatgtgcctgtggtgctgtggagatgtgtgtagtggtcttagctctttgttgagcttgtgtgtgtgttgtg<br>tagtcttagctgtatgctgaaattgggcgtgtgttggagggcttcttagctctttggtgagcttgtatttctatgtgtttgtatcagctgaatgttgct<br>ggaaataaaaccttggtttgtcaaggctctttttttgtgggaagtaagtaggggaaaaggtctttgagggttcctaggctcctttgtacaacagga<br>aaatgcctcaaagccttgcttcccagcaacctggggctggttcccagtgcctggtcctgccccttcctggttcttatctcaaggcagagcttct<br>gaatttcaggccttcattccagagccctcttgtggccaggccttcctttgctggaggaaggtacacagggtgaagctgatgctgtacttgggg | NM_016946 | NM_172647 |

TABLE 1-continued

| Gene | Human Gene Sequence | Human Sequence Accession No. | Murine Sequence Accession No. |
|---|---|---|---|
| | gatctccttggcctgttccaccaagtgagagaaggtacttactcttgtacctcctgttcagccaggtgcattaacagacctccctacagctgta ggaactactgtcccagagctgaggcaaggggatttctcaggtcatttggagaacaagtgctttagtagtagtttaaagtagtaactgctactgt atttagtggggtggaattcagaagaaatttgaagaccagatcatgggtggtctgcatgtgaatgaacaggaatgagccggacagcctggct gtcattgctttcttcctccccatttggacccttctctgcccttacattttgtttctccatctaccaccatccaccagtctatttattaacttagcaagag gacaagtaaagggccctcttggcttgattttgcttctttctttctgtggaggatatactaagtgcgactttgccctatcctatttggaaatccctaac agaattgagttttctattaaggatccaaaaagaaaaacaaaatgctaatgaagccatcagtcaagggtcacatgccaataaacaataaattttc cagaagaaatgaaatccaactagacaaataaagtagagcttatgaaatggttcagtaaagatgagtttgttgtttttgttttgttttgttttgttttttt aaagacggagtctcgctctgtcacccaggctggagtgcagtggtatgatcttggctcactgtaacctccgcctcccgggttcaagccattctc ctgcctcagtctcctgagtagctgggattacgggtgcgtgccaccatgcctggctaatttttgtgtttttagtagagacagggtttcaccatgttg gtcgggctggtctcaaactcctgacctcttgatccgcctgccttggcctcccaaagtgatgggattacagatgtgagccaccgtgcctagcc aaggatgagattttaaagtatgtttcagttctgtgtcatggttggaagacagagtaggaaggatatggaaaaggtcatggggaagcagaggt gattcatggctctgtgaatttgaggtgaatggttccttattgtctaggccacttgtgaagaatatgagtcagttattgccagccttggaatttacttc tctagcttacaatggaccttttgaactggaaaacaccttgtctgcattcactttaaaatgtcaaaactaatttttataataaatgtttattttcacattg agtttgtttaaatcctgaagttcttaccttaagagaattgggactcctagagtgattggacattcaaaatattcctgatagtcttgttaattaagaga ttaggatatctttccattaccttgataattacgttttaatttagctttttttcattggcctgtgtttaaatgcaaataaccccacaatggacatttcctatgt taaagtgacatttaggggataaaaaatgagagcagttccatggattttggtgtttcccctgagacatgaactcagcataatctgggataaaatg attgagtgttaaggatgtgtttgttgttcctgtcgttttttttattttcttcaaagtatacaacatggtttgatatgcacatacatttgtgtaatgcttgcca tggtcaattaacacatcaccatttttgtgtgtgtgtgtgtgtgtgtgtgtgtgagggagtcttgctccgttgccaggctggagtgcaatggtacaac cttggctcactgcaacctccacctcctgggttcaagcaattctcttgcctcagcctcctaagtagctgggactataggcgtgtgccaccatgcc cagctaattttgtatttttagtagagacggggtttcaccatgttggccaggatgatctcgatcccttgacctcatgatccgcccacctcggcctc ccaaagtgctgggattacaggcgtgagtcactgcacccggccacatcacctcccatgttctatcttacgtattcagaacttgttcatcttgtaac tgaaagcgtgtaccctttgaccaacactgtttttcctgtcttaacaggatctacagatcaaggacaggggaggggatagtggaggaaaacgg agttagtctgtttctaaatgaggggacagtatgtttcttggggcctgaggacagcttaataaagtagacaaatgaagaaaaacaacaatttgca ttaaaaaatatccaattcttta (SEQ ID NO: 658) | | |
| Fyn | agagcatcagcaagagtagcagcgagcagccgcgctggtggcggcggcgcgtcgttgcagttgcgccatctgtcaggagcggagccg gcgaggagggggctgccgcgggcgaggaggaggggtcgccgcgagccgaaggccttcgagacccgcccgccgcccggcggcgag agtagaggcgaggttgttgtgcgagcggcgcgtcctctcccgcccgggcgcgccgcgcttctcccagcgcaccgaggaccgcccgggc gcacacaaagccgccgcccgcgccgcaccgcccggcggccgccgcccgcgccagggagggattcggccgccgggccggggacac cccggcgccgcccccctcggtgctctcggaaggcccaccggctcccgggcccgccggggacccccggagccgcctcggccgcgccg gaggagggcggggagaggaccatgtgagtgggctccggagcctcagcgccgcgcagtttttttgaagaagcaggatgctgatctaaacg tggaaaaagaccagtcctgcctctgttgtagaagacatgtggtgtatataaagtttgtgatcgttggcggacattttggaatttagataatgggc tgtgtgcaatgtaaggataaagaagcaacaaaactgacggaggagagggacggcagcctgaaccagagctctgggtaccgctatggca cagaccccacccctcagcactaccccagcttcggtgtgacctccatccccaactacaacaacttccacgcagccgggggccaaggactca ccgtctttggaggtgtgaactcttcgtctcatacggggaccttgcgtacgagaggaggaacaggagtgacactctttgtggccctttatgact atgaagcacggacagaagatgacctgagttttcacaaaggagaaaaatttcaaatattgaacagctcggaaggagattggtgggaagccc gctccttgacaactggagagacaggttacattcccagcaattatgtggctccagttgactctatccaggcagaagagtggtactttggaaaac ttggccgaaaagatgctgagcgacagctattgtcctttggaaacccaagaggtacctttcttatccgcgagagtgaaaccaccaaaggtgcc tattcactttctatccgtgattgggatgatatgaaaggagaccatgtcaaacattataaaattcgcaaacttgacaatggtggatactacattacc acccgggcccagtttgaaacacttcagcagcttgtacaacattactcagagagagctgcaggtctctgctgccgcctagtagttccctgtcac aaagggatgccaaggcttaccgatctgtctgtcaaaaccaaagatgtctgggaaatccctcgagaatccctgcagttgatcaagagactgg gaaatgggcagtttggggaagtatggatgggtacctggaatggaaacacaaaagtagccataaagactcttaaaccaggcacaatgtccc ccgaatcattccttgaggaagcgcagatcatgaagaagctgaagcacgacaagctggtccagctctatgcagtggtgtctgaggagcccat ctacatcgtcaccgagtatatgaacaaaggaagtttactggatttcttaaaagatggagaaggaagagctctgaaattaccaaatcttgtggac atggcagcacaggtggctgcaggaatggcttacatcgagcgcatgaattatatccatagagatctgcgatcagcaaacattctagtgggga atggactcatatgcaagattgctgacttcggattggcccgattgatagaagacaatgagtacacagcaagacaaggtgcaaagttccccatc aagtggacggcccccgaggcagccctgtacgggaggttcacaatcaagtctgacgtgtggtcttttggaatcttactcacagagctggtcac caaaggaagagtgccatacccaggcatgaacaaccgggaggtgctggagcaggtggagcgaggctacaggatgccctgcccgcagga ctgccccatctctctgcatgagctcatgatccactgctggaaaaaggaccctgaagaacgccccacttttgagtacttgcagagcttcctgga agactactttaccgcgacagagccccagtaccaacctggtgaaaacctgtaaggcccgggtctgcggagagaggccttgtcccagaggct | NM_002037 | NM_001122892 |

TABLE 1-continued

| Gene | Human Gene Sequence | Human Sequence Accession No. | Murine Sequence Accession No. |
|---|---|---|---|
| | gccccacccctccccattagctttcaattccgtagccagctgctccccagcagcggaaccgcccaggatcagattgcatgtgactctgaagc<br>tgacgaacttccatggccctcattaatgacacttgtccccaaatccgaacctcctctgtgaagcattcgagacagaaccttgttatttctcagact<br>ttggaaaatgcattgtatcgatgttatgtaaaaggccaaacctctgttcagtgtaaatagttactccagtgccaacaatcctagtgctttcctttttt<br>aaaaatgcaaatcctatgtgattttaactctgtcttcacctgattcaactaaaaaaaaaaaagtattattttccaaaagtggcctctttgtctaaaac<br>aataaaatttttttcatgttttaacaaaaaccaatcaggacaggtgtttgtttttgttttctttttttataaatatgaatatatataatatatatgtccctgta<br>catatacaatgtgggtgctaatgtggagactgtggccggcctgagccaccaagctgcgggacccagagggaggattttactgcaagtcag<br>catcaaagcaccggtgttattctgaaaacaccagtggcctcattttttggcttttgcaaagcatgaatttttttcatttggattgcactttcctggttcat<br>gactgtacctgtaggtggttgttactttgactcttttcaggaaccacccccccaagctgaatttacaagttctgttagcactatttgcttcaacttact<br>gcgatttgttctcaaaacttaaaaataagcaagcaaatggctgatactaccaagagaactggaagatggataccacacaaacttcttgtataaa<br>aatatgaatgctgaaatgtttcagacatttttaatttaataaacctgtaaccacatttaagtgatctaaaacccatagcattgtagtcatggcaacc<br>cgctaaactttctcatgcaactaaaatttctgggggaaatgagggtgggggttgtacatttcccattgtaaaataagtgttttaaatgtcctgtact<br>gctaacgaatgactttctatatgtccaggagttctccagtggaataactatgcactactttacatttcatggggatgcacaaaaacaaaaaagta<br>ttacatttttagttgctgtttgtaccaaccttaaattacatatgtttaacaacaacaaatcaaaaatcctatttctattgagtttttaatactgactagca<br>actctgaagtcttaattcctttttgttatgatttatttgtgagtttacatttttaaattgtttaactttcttaatttagtaattaaaaagagagcattttacatt<br>tgaa (SEQ ID NO: 659) | | |
| Ypel2 | gccgcggcggtggcggagactgtggctttaagagcgtgccgggagcccgagccccagccgggccgcgcttcgccgctgcgcacccca<br>gcggagccaagccccacgctggccggacagggccgcctgtcgccgggctgctgagaactagccctagacctctgcgtgagggttcttct<br>gccgaagacatcaccagtgtgtggagcctgccacacccacccgctgccaaaccacggcctttacctgtgtcttccggtgtttcccgtgcgac<br>ccatcctgtgggagtgcctcgtgggctgccccagagttcaccccacactcagcagcaccaatggtgaagatgacaagatcgaagactttcc<br>aggcatatctgccctcctgccaccggacctacagctgcattcactgcagagctcacttggccaatcatgatgaactaatttccaagtcattcca<br>aggaagtcaaggacgagcatacctctttaactcagtagttaatgtgggctgtgggcctgcagaagagcgagtgttgctaacaggactgcat<br>gcagtcgcagacatttactgtgaaaactgcaaaaccactctgggctggaaatacgaacatgcttttgaaagcagccagaaatataaagaag<br>gcaaatacatcattgaactagcacacatgatcaaggacaatggctgggactgattggacagcatctacccaacccagtgtccacgtgaacg<br>ccattcaaccgaacattcttcccaagcgtgagagagtgactgacacttggttccatccatttaggggccttgccatccggggcatcctcccac<br>cctgacgccatctttctggtgaccggcctctaaatcgctgtctctctgtctctttgctttgtatctgtttgtgagttgatcctggcttctctctctgttct<br>agttttggctgaaaacaaaacaacaaaaggaacagatccttgaccgcatggcggcagcccaccttggtaagggccccagggcccatgcg<br>agagctgcctgatggcctcttgtcaggagagcagtggcacgggggcgtgaggaagagggaaaggggaaactctaagggtcctggcgc<br>ggggaaggggtggaagggtggaggtaggaacaaaattgcgccgctcctggagacctgataacttaggcttgaaataattgacttgtctaaa<br>aggacaaagagaaaaaaaaaatacctcatgactgcattctctctgactagaagcttctgttcctgacaccaaatgtgccaggttagcaaatga<br>gcacaagatgtggccctgattctagttggtggggcaagggcctggttctcctgggctgagtgggggagtgtcctggcagcagcgagtgac<br>ctgggcagtggccaggtgggtgcgatgactctgatgcctcactcagtctctgggcaatcatcatctttgcctctagccaccgtagataaggtg<br>tgaagggactgctgtttgcaatgggcttaccatccaaatatcccaaaggctttgaccagcaaccaagtaaaatcagtaattgaggagagcag<br>ggcacaaaggggctgcagtttgggagctcctgaagaaatggctcagatattgagtcagagaaataaaaagtaggatcagttagcaattcta<br>actgcccttccttctgacccctcataagaggagtgtggtgagggaggggactgggtaggggtcatcccaggaggaggggtttacattgga<br>accagttcaggttcggtgcatctttcctcttcggttttacagtggcttccgtgggatcgtcaatttcttgttcttagagtttcgggtgtttttctccagt<br>cttgttactgtagactgtagaaagcacgggccccaggctctgagcttagtaataacctggctggtagattcctcatgcccctaattgtcccactt<br>aggcctgaatgtcttgcatggagagaaatctcctgtcagtgtggtccagcagcagggaggagttctgcccaaattccgatatcaccccttcc<br>cccatccaagcatccttcgattagggaagtggagagcacatccctgtaaggcccataagagaaagaggagtttgttacatttaatcaacact<br>gtgaagtctgttctacagcaattcagccattacacagtatatgactgaaactcatttaactgggttaatttcatttcttagactgaatatattattgtta<br>agatacgtgtgcgtgttaggtaattctcagcatctcctccaagtaggccgaccttctcggaaaattcaccctaaaagtctcacaaaagaatga<br>gttcatggggagattctgtaaagtgatgaactgagatgaaagcagccaacagcccaggagcttttcagaatagcgtctgcagcagaaccag<br>tttccattcagagcgcgtccttggtggaaatgctttttttgtgtgtctccacgcgctgatggtggaatgggagccccaagacgtgtgggcttaga<br>aatcaacttttgttccccaaggcttcttgtccagatctttccagtgctttcatagccctgggagatcaagttgttctccccactttactgcaaggta<br>gactgaagttcagaagaaatactgaatttctgctcccagaagaatagtttctctggctcacaggcccaagttctcaatgaaatcgtttttttaacttt<br>cacattcctaagctggcttcccggcacagaagccatggatttcccctctctcccttccccctcctcaaggaaatagtcttcctttatggattttcat<br>tggactctttcctcagcgattgtcctggctgtttattgatagtccttcccataagaaaatggggttaaacatggggtaggtattttgtctttcaaact<br>acaaatggaatgtggtgacataaactagacatggggtgccctcaagtttccaaggggaccaatgtgccactgttcttccttggggatgaggc<br>ctttgactgttggatggatcagagcaggctccagtcagaccctggttctgaatgtttttttttcggtgactatccagtgagccttcagtgggtgc<br>aaggcgccatacttgctgtgagagagctgagtagagtgttggtttttccataactacaggggggaaaaaaagtcattaggctttccctttgtgtc | NM_001005404 | NM_001005341 |

TABLE 1-continued

| Gene | Human Gene Sequence | Human Sequence Accession No. | Murine Sequence Accession No. |
|---|---|---|---|
| | agtgaaaccaaaagtgcttcttacaacgttcgctctgttcatgggttgtctatctaacattgagcagcattggagaggccacagctgagctatg<br>gagatgctaaattaactcatggcctcagtcagttcattctttaatttcctcaccaaattattgacttagagcataaccaaagacctcattcattcacc<br>ccaggtgggttggggtaattggagtttgttggtgaagtttgggggcggggtgttgggagtagagacagggtaaggggacgtgagaaagg<br>aaaaggcatgaagttctatacctcagccagcagctgccttcgtttggaactgaagtccagccagcagactctctagctccatctcccctgtgc<br>caccctaggtcatatgaccttggccaccttggagtagacccagacccctcgggacccgggacattagtctcaggctgctgatggattgattt<br>gacatgaaccaaacacagccaaactcgatacccacaagctgtcagctgaacctgactgagtgttcttcctgagttcacgaggataggctaga<br>gtgcatttttactggtggatcagtgtgtgcgaaagagatgaccctttataaagagattttcaagtggatatatataaaagaaacagttgcttgtaa<br>aatatacttttgtaaataatatttaatttttaaataatatatttggtgctgttttctcagatcccctgagagcactttttattttccttttaaattctatggttt<br>cctttgcatttcttgaagtatatttaagggaaacagtgatcaccaatacatgttttcagtttttttttttttttaaggtctctatcactttaatctggatcaa<br>ggctttgaagcaatgcctctctgcatttttttccccagtggaacagactctgcagtacattaatcaggttgagaattgaaatattttcttgcatcagt<br>attggctagaaaagaaaataaataaaaccaagttaatttagtagtaacaacttacagtgattcttcctgttggaagaatttccaacaaatcagaat<br>cacgtttttagttgtgcgtgtgcgcgcacacgtgtgtaaaaagcactttcgcttgtgcctcctgttttctcgagtggggacactttaactacagttt<br>acacctcgggcgcataaagtttttcttctctttctctctggttgtttctgtttctgagtggaccaacagcagaacccacgaggatttgttttgagtat<br>ggagctgttgcgggtttgctcctttttcttgctttgcgtgctcagtttttacagactgtaaaggagatgtgttgtttgtgaagatggagcagagtca<br>aatctgtgcttctaactgagatgagagtgtattaatcacgtatcgcagggctccagctgttttagaagccacatcatgttaaacattaactggttt<br>ggattaaaagaacattaatattataatacacatatcttagtggtaaacagcttttttttttttaaggtcagattgcctcaggtttagaaagaggctgag<br>aaatcaaatcttgaacacaatcaacttacatattttaaaggaatctgcctcaaatgagaaaatatgctagttatctagatagaggaaagagatatt<br>tactttttttaaaaattaaaatagttatgaaatctggcagaaaaggtaaagcctagaagaaactatgaaagctattctcatgttaccaaattctatct<br>gcgcatatgtttttgtataacatttcggtgacagtgggagtcggttccctttcccaacctgcagagactatcttccaatacagaatctgtctatttat<br>gcttgtgtttacaaactgtatttgttgggtttgggtttttgttttctttggtggcatttttcaggtcactttgcttctataacaaaggtaattgttttcaaat<br>aatttgtcttcacctttttcctgtatttgtacatagtgattcagtattagagaaaagtgcattgtttctgtcatatttccaatctgtgttggtgctcatttga<br>gaaaataaaagttttcaaatattaactcttaaaaaaaaaa (SEQ ID NO: 660) | | |
| Pkd1 | ccctcccctcccgatcctcatccccttgccctcccccagcccagggacttttccggaaagtttttattttccgtctgggctctcggagaaagaa<br>gctcctggctcagcggctgcaaaactttcctgctgccgcgccgccagccccccgccctccgctgcccggccctgcgccccgccgagcgat<br>gagcgcccctccggtcctgcggccgcccagtccgctgctgcccgtggcggcggcagctgccgcagcggccgccgcactggtcccagg<br>gtccgggcccgggcccgcgccgttcttggctcctgtcgcggccccggtcgggggcatctcgttccatctgcagatcggcctgagccgtga<br>gccggtgctgctgctgcaggactcgtccggggactacagcctggcgcacgtccgcgagatggcttgctccattgtcgaccagaagttccct<br>gaatgtggtttctacggaatgtatgataagatcctgctttttcgccatgaccctacctctgaaaacatccttcagctggtgaaagcggccagtga<br>tatccaggaaggcgatcttattgaagtggtcttgtcagcttccgccacctttgaagactttcagattcgtccccacgctctctttgttcattcatac<br>agagctccagctttctgtgatcactgtggagaaatgctgtgggggctggtacgtcaaggtcttaaatgtgaagggtgtggtctgaattaccata<br>agagatgtgcatttaaaatacccaacaattgcagcggtgtgaggcggagaaggctctcaaacgtttccctcactggggtcagcaccatccg<br>cacatcatctgctgaactctctacaagtgcccctgatgagccccttctgcaaaaatcaccatcagagtcgtttattggtcgagagaagaggtc<br>aaattctcaatcatacattggacgaccaattcaccttgacaagattttgatgtctaaagttaaagtgccgcacacatttgtcatccactcctacac<br>ccggcccacagtgtgccagtactgcaagaagcttctgaaggggcttttcaggcagggcttgcagtgcaaagattgcagattcaactgccat<br>aaacgttgtgcaccgaaagtaccaaacaactgccttggcgaagtgaccattaatggagatttgcttagccctggggcagagtctgatgtggt<br>catggaagaagggagtgatgacaatgatagtgaaaggaacagtgggctcatggatgatatggaagaagcaatggtccaagatgcagaga<br>tggcaatggcagagtgccagaacgacagtggcgagatgcaagatccagacccagaccacgaggacgccaacagaaccatcagtccatc<br>aacaagcaacaatatcccactcatgagggtagtgcagtctgtcaaacacacgaagaggaaaagcagcacagtcatgaaagaaggatgga<br>tggtccactacaccagcaaggacacgctgcggaaacggcactattggagattggatagcaaatgtattaccctctttcagaatgacacagga<br>agcaggtactacaaggaaattcctttatctgaaattttgtctctggaaccagtaaaaacttcagctttaattcctaatggggccaatcctcattgttt<br>cgaaatcactacggcaaatgtagtgtattatgtgggagaaaatgtggtcaatccttccagcccatcaccaaataacagtgttctcaccagtgg<br>cgttggtgcagatgtggccaggatgtgggagatagccatccagcatgcccttatgcccgtcattcccaagggctcctccgtgggtacagga<br>accaacttgcacagagatatctctgtgagtatttcagtatcaaattgccagattcaagaaaatgtggacatcagcacagtatatcagatttttcct<br>gatgaagtactgggttctggacagtttggaattgtttatggaggaaaacatcgtaaaacaggaagagatgtagctattaaaatcattgacaaat<br>tacgatttccaacaaaacaagaaagccagcttcgtaatgaggttgcaattctacagaaccttcatcaccctggtgttgtaaatttggagtgtatg<br>tttgagacgcctgaaagagtgtttgttgttatggaaaaactccatggagacatgctggaaatgatcttgtcaagtgaaaagggcaggttgcca<br>gagcacataacgaagtttttaattactcagatactcgtggctttgcggcaccttcattttaaaaatatcgttcactgtgacctcaaaccagaaaat<br>gtgttgctagcctcagctgatccttttcctcaggtgaaactttgtgattttggttttgcccggatcattggagagaagtctttccggaggtcagtg<br>gtgggtacccccgcttacctggctcctgaggtcctaaggaacaagggctacaatcgctctctagacatgtggtctgttggggtcatcatctat | NM_002742 | NM_008858 |

TABLE 1-continued

| Gene | Human Gene Sequence | Human Sequence Accession No. | Murine Sequence Accession No. |
|---|---|---|---|
| | gtaagcctaagcggcacattcccatttaatgaagatgaagacatacacgaccaaattcagaatgcagctttcatgtatccaccaaatccctgg<br>aaggaaatatctcatgaagccattgatcttatcaacaatttgctgcaagtaaaaatgagaaagcgctacagtgtggataagaccttgagccac<br>ccttggctacaggactatcagacctggttagatttgcgagagctggaatgcaaaatcggggagcgctacatcacccatgaaagtgatgacct<br>gaggtgggagaagtatgcaggcgagcaggggctgcagtaccccacacacctgatcaatccaagtgctagccacagtgacactcctgaga<br>ctgaagaaacagaaatgaaagccctcggtgagcgtgtcagcatcctctgagttccatctcctataatctgtcaaaacactgtggaactaataa<br>atacatacggtcaggtttaacatttgccttgcagaactgccattattttctgtcagatgagaacaaagctgttaaactgttagcactgttgatgtat<br>ctgagttgccaagacaaatcaacagaagcatttgtattttgtgtgaccaactgtgttgtattaacaaaagttccctgaaacacgaaacttgttatt<br>gtgaatgattcatgttatatttaatgcattaaacctgtctccactgtgcctttgcaaatcagtgtttttcttactggagcttcattttggtaagagaca<br>gaatgtatctgtgaagtagttctgtttggtgtgtcccattggtgttgtcattgtaaacaaactcttgaagagtcgcttatttccagtgttctatgaaca<br>actccaaaacccatgtgggaaaaaaatgaatgaggagggtagggaataaaatcctaagacacaaatgcatgaacaagttttaatgtatagttt<br>tgaatcctttgcctgcctggtgtgcctcagtatatttaaactcaagacaatgcacctagctgtgcaagacctagtgctcttaagcctaaatgcctt<br>agaaatgtaaactgccatatataacagatacatttccctctttcttataatactctgttgtactatggaaaatcagctgctcagcaacctttcaccttt<br>gtgtatttttcaataataaaaaatattcttgtcaaaa (SEQ ID NO: 661) | | |
| Ptpn2 | gctcgggcgccgagtctgcgcgctgacgtccgacgctccaggtactttccccacggccgacagggcttggcgtgggggcggggcgcg<br>gcgcgcagcgcgcatgcgccgcagcgccagcgctctccccggatcgtgcggggcctgagcctctccgccggcgcaggctctgctcgc<br>gccagctcgctcccgcagccatgcccaccaccatcgagcgggagttcgaagagttggatactcagcgtcgctggcagccgctgtacttgg<br>aaattcgaaatgagtcccatgactatcctcatagagtggccaagtttccagaaaacagaaatcgaaacagatacagagatgtaagcccatat<br>gatcacagtcgtgttaaactgcaaaatgctgagaatgattatattaatgccagtttagttgacatagaagaggcacaaaggagttacatcttaa<br>cacagggtccacttcctaacacatgctgccatttctggcttatggtttggcagcagaagaccaaagcagttgtcatgctgaaccgcattgtgg<br>agaaagaatcggttaaatgtgcacagtactggccaacagatgaccaagagatgctgtttaaagaaacaggattcagtgtgaagctcttgtca<br>gaagatgtgaagtcgtattatacagtacatctactacaattagaaaatatcaatagtggtgaaaccagaacaatatctcactttcattatactacct<br>ggccagattttggagtccctgaatcaccagcttcatttctcaatttcttgtttaaagtgagagaatctggctccttgaaccctgaccatgggcctg<br>cggtgatccactgtagtgcaggcattgggcgctctggcaccttctctctggtagacacttgtcttgttttgatggaaaaaggagatgatattaac<br>ataaaacaagtgttactgaacatgagaaaataccgaatgggtcttattcagaccccagatcaactgagattctcatacatggctataatagaag<br>gagcaaaatgtataaagggagattctagtatacagaaacgatggaaagaactttctaaggaagacttatctcctgcctttgatcattcaccaaa<br>caaaataatgactgaaaaatacaatgggaacagaataggtctagaagaagaaaaactgacaggtgaccgatgtacaggactttcctctaaa<br>atgcaagatacaatggaggagaacagtgagagtgctctacggaaacgtattcgagaggacagaaaggccaccacagctcagaaggtgc<br>agcagatgaaacagaggctaaatgagaatgaacgaaaaagaaaaaggtggttatattggcaacctattctcactaagatggggtttatgtca<br>gtcattttggttggcgcttttgttggctggacactgtttttcagcaaaatgccctataaacaattaattttgcccagcaagcttctgcactagtaac<br>tgacagtgctacattaatcataggggtttgtctgcagcaaacgcctcatatcccaaaaacggtgcagtagaatagacatcaaccagataagtg<br>atatttacagtcacaagcccaacatctcaggactcttgactgcaggttcctctgaaccccaaactgtaaatggctgtctaaaataaagacattca<br>tgtttgttaaaaactggtaaattttgcaactgtattcatacatgtcaaacacagtatttcacctgaccaacattgagatatcctttatcacaggctttg<br>tttttggaggctatctggattttaacctgcacttgatataagcaataaatattgtggttttatctacgttattggaaagaaaatgacatttaaataatgt<br>gtgtaatgtataatgtactattgacatgggcatcaacacttttattcttaagcatttcagggtaaatatattttataagtatctatttaatcttttgtagtt<br>aactgtactttttaagagctcaatttgaaaaatctgttactaaaaaaataaattgtatgtcgattgaattgtactggatacattttccatttttctaaag<br>agaagtttgatatgagcagttagaagttggaataagcaatttctactatatattgcatttcttttatgttttacagttttccccattttaaaaagaaaag<br>caaacaaagaaacaaaagtttttcctaaaaatatctttgaaggaaaattctccttactgggatagtcaggtaaacagttggtcaagactttgtaa<br>agaaattggtttctgtaaatcccattattgatatgtttatttttcatgaaaatttcaatgtagttggggtagattatgatttaggaagcaaaagtaaga<br>agcagcattttatgattcataatttcagtttactagactgaagttttgaagtaaacacttttcagtttctttctacttcaataaatagtatgcttatatgc<br>aaaccttacattgtcattttaacttaatgaatatttttaaagcaaactgtttaatgaatttaactgctcatttgaatgctagctttcctcagctttcaac<br>attccattcagtgtttaatttgtcttacttaaacttgaaattgttgttacaaatttaattgctaggaggcatggatagcatacattattatggatagcat<br>accttatttcagtggttttcaaactatgctcattggatgtccaggtgggtcaagaggttactttcaaccacagcatctctgccttgtctctttatatg<br>ccacataagatttctgcataaggcttaagtattttaaagggggcagttatcatttaaaaacagtttggtcgggcgcggtggctcatgcctgtaat<br>cccagcactttgggaggctgaagtgggcagatcacctgaggtcaggagttcaagaccagcctggccaacgtggtgaaacaccatctctac<br>taaaaatgcaaaaattagctgggcatggtggagggcacctgtaatctcagctactcaggaggctgaggtaggagaattgcttgaacccagg<br>agatggaggttgcagtgagctgagatcacgtcactgcactccagccagggcgacagagcgagactccatctcaaaagaaacaaacaaaa<br>aaaacagtttgggccgggtgtggtggctcacgcttgtaatcccagcacttcggaaggccaaggcgggcggatcacgaggtcaagagatg | NM_002828 | NM_008977 |

TABLE 1-continued

| Gene | Human Gene Sequence | Human Sequence Accession No. | Murine Sequence Accession No. |
|---|---|---|---|
| | gagactgtcctggccaacatggtgaaatcccttctttactaaaaatacaaaaattatctgggcgtggtggtgcatgcctgtagtcccagctcctt<br>gggaggctaaggcaggagaatcacttgaacccgggaggcagaggttgcagtgagccgagattgcaccactgcactccagcctggcaac<br>agagcaagacttcgtctc (SEQ ID NO: 662) | | |
| Grk6 | cggctggctgcggcggccggggaggccggggaggccgcggcgcggtcactgcgagccgagccgagccgcgccgagccgcgccga<br>tcgccatccggcctcggcactcgcgcgcgatcccggccggcggcgcggcccggcgggccaggcggcgccacagcccatggagctcg<br>agaacatcgtagcgaacacggtgctactcaaggcccgggaaggtggcggtggaaatcgcaaaggcaaaagcaagaaatggcggcaga<br>tgctccagttccctcacatcagccagtgcgaagagctgcggctcagcctcgagcgtgactatcacagcctgtgcgagcggcagcccattg<br>ggcgcctgctgttccgagagttctgtgccacgaggccggagctgagccgctgcgtcgccttcctggatggggtggccgagtatgaagtga<br>ccccggatgacaagcggaaggcatgtgggcggcagctaacgcagaattttctgagccacacgggtcctgacctcatccctgaggtccccc<br>ggcagctggtgacgaactgcacccagcggctggagcagggtccctgcaaagaccttttccaggaactcacccggctgacccacgagtac<br>ctgagcgtggccccttttgccgactacctcgacagcatctacttcaaccgtttcctgcagtggaagtggctggaaaggcagccagtgaccaa<br>aaacaccttcaggcaataccgagtcctgggcaaaggtggctttggggaggtgtgcgcctgccaggtgcgggccacaggtaagatgtatgc<br>ctgcaagaagctagagaaaaagcggatcaagaagcggaaaggggaggccatggcgctgaacgagaagcagatcctggagaaagtga<br>acagtaggtttgtagtgagcttggcctacgcctatgagaccaaggacgcgctgtgcctggtgctgacactgatgaacgggggcgacctcaa<br>gttccacatctaccacatgggccaggctggcttccccgaagcgcgggccgtcttctacgccgccgagatctgctgtggcctggaggacct<br>gcaccgggagcgcatcgtgtacagggacctgaagcccgagaacatcttgctggatgaccacggccacatccgcatctctgacctgggact<br>agctgtgcatgtgcccgagggccagaccatcaaagggcgtgtgggcaccgtgggttacatggctccggaggtggtgaagaatgaacggt<br>acacgttcagccctgactggtgggcgctcggctgcctcctgtacgagatgatcgcaggccagtcgcccttccagcagaggaagaagaag<br>atcaagcgggaggaggtggagcggctggtgaaggaggtccccgaggagtattccgagcgcttttccccgcaggcccgctcactttgctca<br>cagctcctctgcaaggaccctgccgaacgcctggggtgtcgtgggggcagtgcccgcgaggtgaaggagcacccccctctttaagaagct<br>gaacttcaagcggctgggagctggcatgctggagccgccgttcaagcctgacccccaggccatttactgcaaggatgttctggacattgaa<br>cagttctctacggtcaagggcgtggagctggagcctaccgaccaggacttctaccagaagtttgccacaggcagtgtgcccatcccctggc<br>agaacgagatggtggagaccgagtgcttccaagagctgaatgtctttgggctggatggctcagttcccccagacctggactggaagggcc<br>agccacctgcacctcctaaaaagggactgctgcagagactcttcagtcgccaagattgctgtggaaactgcagcgacagcgaggaagag<br>ctccccacccgcctctagccccagcccgaggcccccaccagcagttggcggtagcagctactccgagcgccgtttacagttttgcacagt<br>gatcttccccattgtccactcaagtcgtggcctggggaacacagacggagctgtccccagtgtcctccgtccctcagcccctggcctggctg<br>agtttggcagggcctgggccatccctgggacaaaggtgcgtcccttcagctcttctccgtggagctcggggctttctgtatttatgtatttgtac<br>gaatgtatatagcgaccagagcattcttaattcccgccgcagacctggcgcccccgccttggctcctgggggcagccagccctggctggg<br>agagcgggagctggcagaggagccactgccaaactcaaggctcctctggcccagcttggatggctgagggtggtcacacccctgagcct<br>tcagcactgtgctggccaccccggcctctgagtaagactcgtgcctcccctgctgccctgggctcaggctgctaccctctggggcccaaa<br>gctgtcccttctcagtgcttgtcagcgctgggtctggggcctctgtatgccctaggcctgtgccaaagtggccagagattgggctgcctgtga<br>tacccatcagcccactgccccggccggcccagataggtctgcctctgccttccagctcccacagcctggtccctgatactgggctctgtcct<br>gcagacacctctttcagaaacgcccaagcccagcccctaggaggggtggggcatccctggtcaaccctcaaacattccggactcccctc<br>ataacaatagacacatgtgcccagcaataatccgccccttcctgtgtgcgcctgtggggtgcgtgcgcgcgcgtgtgtacctgtgtgggtga<br>aggggatagggcgaggctgtgcctgtgccccaggtcccagccctggcccttcccagactgtgatggccatcctggtcccagtgttagggt<br>agcatgggattacagggccctgtttttccatatttaaagccaatttttattactcgttttgtccaacgtaa (SEQ ID NO: 663) | NM_001004106 | NM_001038018 |
| Cdkn2a | cgagggctgcttccggctggtgcccccggggagacccaacctggggcgacttcaggggtgccacattcgctaagtgctcggagttaata<br>gcacctcctccgagcactcgctcacggcgtccccttgcctggaaagataccgcggtccctccagaggatttgagggacagggtcggagg<br>gggctcttccgccagcaccggaggaagaaagaggaggggctggctggtcaccagagggtggggcggaccgcgtgcgctcggcggct<br>gcggagaggggggagagcaggcagcgggcggcggggagcagcatggagccggcggcggggagcagcatggagccttcggctgact<br>ggctggccacggccgcggcccggggtcgggtagaggaggtgcgggcgctgctggaggcgggggcgctgcccaacgcaccgaatag<br>ttacggtcggaggccgatccaggtcatgatgatgggcagcgcccgagtggcggagctgctgctgctccacggcgcggagcccaactgc<br>gccgaccccgccactctcacccgacccgtgcacgacgctgcccgggagggcttcctggacacgctggtggtgctgcaccgggccggg<br>gcgcggctggacgtgcgcgatgcctggggccgtctgcccgtggacctggctgaggagctgggccatcgcgatgtcgcacggtacctgc<br>gcgcggctgcgggggcaccagaggcagtaaccatgcccgcatagatgccgcggaaggtccctcagacatccccgattgaaagaacc<br>agagaggctctgagaaacctcgggaaacttagatcatcagtcaccgaaggtcctacagggccacaactgcccccgccacaacccacccc<br>gctttcgtagttttcatttagaaaatagagcttttaaaaatgtcctgccttttaacgtagatatatgccttcccccactaccgtaaatgtccatttatat<br>catttttatatattcttataaaaatgtaaaaaagaaaaacaccgcttctgccttttcactgtgttggagttttctggagtgagcactcacgccctaa | NM_000077 | NM_001040654 |

TABLE 1-continued

| Gene | Human Gene Sequence | Human Sequence Accession No. | Murine Sequence Accession No. |
|---|---|---|---|
| | gcgcacattcatgtgggcatttcttgcgagcctcgcagcctccggaagctgtcgacttcatgacaagcattttgtgaactagggaagctcagg<br>ggggttactggcttctcttgagtcacactgctagcaaatggcagaaccaaagctcaaataaaaataaaataattttcattcattcactcaaaaaa<br>aaaaaaaa (SEQ ID NO: 664) | | |
| Sbf1 | gggcgggccggctggctgggaagatggcggcgggaacctgggccgccgccgccgccgccgccgcggagcgaaccaggg<br>gtgtccggggtgcgcggtccagggccggggccgggccatgagcgcgccgtcctcgagtccccgagccgcggagcccgcccgcgccc<br>ctcgggccgccccgcgtccctcgccatggcgcggctcgcggactacttcgtgctggtggcgttcgggccgcacccgcgcgggagtggg<br>gaaggccagggccagattctgcagcgcttcccagagaaggactgggaggacaacccattcccccagggcatcgagctgttttgccagcc<br>cagcgggtggcagctgtgtcccgagaggaatccaccgaccttctttgttgctgtcctcaccgacatcaactccgagcgccactactgcgcct<br>gcttgaccttctgggagccagcggagccttcacaggaaacgacgcgcgtggaggatgccacagagagggaggaagaggggggatgag<br>ggaggccagacccacctgtctcccacagcacctgccccatctgcccagctgtttgcaccgaagacgctggtactggtgtcgcgactcgac<br>cacacggaggtgttcaggaacagccttggcctcatctatgccatccacgtggagggcctgaatgtgtgcctggagaacgtgattgggaacc<br>tgctgacgtgcactgtgccccctggctgggggctcgcagaggacgatctctttggggggctggtgaccggcaggtcatccagactccactgg<br>ccgactcgctgcccgtcagccgctgcagcgtggccctgctcttccgccagctaggcatcaccaacgtgctgtctttgttctgtgccgccctca<br>cggagcacaaggttctcttcctgtcccggagctaccagcggctcgccgatgcctgtaggggcctcctggcactgctgtttcctctcagatac<br>agcttcacctatgtgcccatcctgccggctcagctgctggaggtcctcagcacacccacgcccttcatcattggggtcaacgcggccttcca<br>ggcagagacccaggagctgctcgatgtgattgttgctgatctggatggagggacggtcaccattcctgagtgtgtgcacattccacccttgc<br>cagagccactgcagagtcagacgcacagtgtgctgagcatggtcctggacccggagctggagttggctgacctcgccttccctccgccca<br>cgacatccacctcctccctgaagatgcaggacaaggagctgcgcgcggtcttcctgcggctgttcgctcagctgctgcagggctatcgctg<br>gtgcctgcacgtcgtgcgcatccacccggagcctgtcatccgcttccataaggcagccttcctgggccagcgtgggctggtagaggacga<br>tttcctgatgaaggtgctggagggcatggcctttgctggctttgtgtcagagcgtggggtcccataccgccctacggacctgttcgatgagct<br>ggtggcccacgaggtggcaaggatgcgggcggatgagaaccacccccagcgtgtcctgcgtcacgtccaggaactggcagagcagct<br>ctacaagaacgagaacccgtacccagccgtggcgatgcacaaggtacagaggcccggtgagagcagccacctgcgacgggtgccccg<br>acccttcccccggctggatgagggcaccgtgcagtggatcgtggaccaggctgcagccaagatgcagggtgcacccccagctgtgaag<br>gccgagaggaggaccaccgtgccctcagggcccccatgactgccatactggagcggtgcagtgggctgcatgtcaacagcgcccggc<br>ggctggaggttgtgcgcaactgcatctcctacgtgtttgaggggaaaatgcttgaggccaagaagctgctcccagccgtgttgagggccct<br>gaaggggcgagctgcccgccgctgcctcgcccaggagctgcacctgcatgtgcagcagaaccgtgcggtcctggaccaccagcagttt<br>gactttgtcgtccgtatgatgaactgctgcctgcaggactgcacttctctggacgagcatggcattgcggcggctctgctgcctctggtcaca<br>gccttctgccggaagctgagcccgggggtgacgcagtttgcatacagctgtgtgcaggagcacgtggtgtggagcacgccacagttctgg<br>gaggccatgttctatggggatgtgcagactcacatccgggccctctacctggagcccacggaggacctggcccccgcccaggaggttgg<br>ggaggcaccttcccaggaggacgagcgctctgccctagacgtggcttctgagcagcggcgcttgtggccaactctgagtcgtgagaagc<br>agcaggagctggtgcagaaggaggagagcacggtgttcagccaggccatccactatgccaaccgcatgagctacctcctcctgcccctg<br>gacagcagcaagagccgcctacttcgggagcgtgccgggctgggcgacctggagagcgccagcaacagcctggtcaccaacagcatg<br>gctggcagtgtggccgagagctatgacacggagagcggcttcgaggatgcagagacctgcgacgtagctggggctgtggtccgcttcat<br>caaccgctttgtggacaaggtctgcacggagagtggggtcaccagcgaccacctcaaggggctgcatgtcatggtgccagacattgtcca<br>gatgcacatcgagaccctggaggccgtgcagcgggagagccggaggctgccgcccatccagaagcccaagctgctgcggccgcgcct<br>gctgccgggtgaggagtgtgtgctggacggcctgcgcgtctacctgctgccggatgggcgtgaggagggcgcgggggggcagtgctgg<br>gggaccagcattgctcccagctgagggcgccgtcttcctcaccacgtaccgggtcatcttcacggggatgcccacggacccccctggttgg<br>ggagcaggtggtggtccgctccttcccggtggctgcgctgaccaaggagaagcgcatcagcgtccagacccctgtggaccagctcctgc<br>aggacgggctccagctgcgctcctgcacattccagctgctgaaaatggcctttgacgaggaggtggggtctgacagcgccgagctcttcc<br>gtaagcagctgcataagctgcggtacccgccggacatcagggccacctttgcgttcaccttgggctctgcccacacacctggccggccac<br>cgcgagtcaccaaggacaagggtccttccctcagaaccctgtcccggaacctggtcaagaacgccaagaagaccatcgggcggcagca<br>tgtcactcgcaagaagtacaacccccccagctgggagcaccggggccagccgccccctgaggaccaggaggacgagatctcagtgtcg<br>gaggagctggagcccagcacgctgaccccgtcctcagccctgaagccctccgaccgcatgaccatgagcagcctggtggaaagggctt<br>gctgtcgcgactaccagcgcctcggtctgggcaccctgagcagcagcctgagccgggccaagtctgagcccttccgcatttctccggtca<br>accgcatgtatgccatctgccgcagctacccagggctgctgatcgtgccccagagtgtccaggacaacgccctgcagcgcgtgtcccgct<br>gctaccgccagaaccgcttccccgtggtctgctggcgcagcgggcggtccaaggcggtgctgctgcgctctggaggcctgcatggcaaa<br>ggtgtcgtcggcctcttcaaggcccagaacgcaccttctccaggccagtcccaggcggactcgagtagcctggagcaggagaagtacct<br>gcaggctgtggtcagctccatgccccgctacgccgacgcgtcgggacgcaacacgcttagcggcttctcctcagcccacatgggcagtca<br>cgttcccagccccagagccagggtcaccacgctgtccaaccccatggcggcctcggcctccagacggaccgcaccccgaggtaagtgg | NM_002972 | NM_001170561 |

TABLE 1-continued

| Gene | Human Gene Sequence | Human Sequence Accession No. | Murine Sequence Accession No. |
|---|---|---|---|
| | ggcagtgtccggaccagtggacgcagcagtggccttggcaccgatgtgggctcccggctagctggcagagacgcgctggccccacccc<br>aggccaacgggggccctcccgacccgggcttcctgcgtccgcagcgagcagccctctatatccttggggacaaagcccagctcaagggt<br>gtgcggtcagacccccctgcagcagtgggagctggtgcccattgaggtattcgaggcacggcaggtgaaggctagcttcaagaagctgct<br>gaaagcatgtgtcccaggctgccccgctgctgagcccagcccagcctccttcctgcgctcactggaggactcagagtggctgatccagat<br>ccacaagctgctgcaggtgtctgtgctggtggtggagctcctggattcaggctcctccgtgctggtgggcctggaggatggctgggacatc<br>accacccaggtggtatccttggtgcagctgctctcagaccccttctaccgcacgctggagggctttcgcctgctggtggagaaggagtggc<br>tgtccttcggccatcgcttcagccaccgtggagctcacaccctggccgggcagagcagcggcttcacacccgtcttcctgcagttcctgga<br>ctgcgtacaccaggtccacctgcagttccccatggagtttgagttcagccagttctacctcaagttcctcggctaccaccatgtgtcccgccgt<br>ttccggaccttcctgctcgactctgactatgagcgcattgagctggggctgctgtatgaggagaagggggaacgcaggggccaggtgccg<br>tgcaggtctgtgtgggagtatgtggaccggctgagcaagaggacgcctgtgttccacaattacatgtatgcgcccgaggacgcagaggtc<br>ctgcggccctacagcaacgtgtccaacctgaaggtgtgggacttctacactgaggagacgctggccgagggccctccctatgactgggaa<br>ctggcccaggggcccccctgaacccccagaggaagaacggtctgatggaggcgctccccagagcaggcgccgcgtggtgtggccctgtt<br>acgacagctgcccgcgggcccagcctgacgccatctcacgcctgctggaggagctgcagaggctggagacagagttgggccaacccg<br>ctgagcgctggaaggacacctgggaccgggtgaaggctgcacagcgcctcgagggccggccagacggccgtggcacccctagctccc<br>tccttgtgtccaccgcaccccaccaccgtcgctcgctgggtgtgtacctgcaggaggggcccgtgggctccaccctgagcctcagcctgg<br>acagcgaccagagtagtggctcaaccacatccggctcccgtcaggctgcccgccgcagcaccagcaccctgtacagccagttccagaca<br>gcagagagtgagaacaggtcctacgagggcactctgtacaagaagggggccttcatgaagccttggaaggcccgctggttcgtgctgga<br>caagaccaagcaccagctgcgctactacgaccaccgtgtggacacagagtgcaagggtgtcatcgacttggcggaggtggaggctgtgg<br>cacctggcacgcccactatgggtgcccctaagactgtggacgagaaggccttctttgacgtgaagacaacgcgtcgcgtttacaacttctgt<br>gcccaggacgtgccctcggcccagcagtgggtggaccggatccagagctgcctgtcggacgcctgagcctcccagccctgcccggctg<br>ctctgcttccggtcgttaccgaccactaggggtgggcagggccgccccggccatgtttacagccccggccctcgacagtattgaggcccc<br>gagcccccagcacttgtgtgtacagccccgtccccgccccgccccgcccggccggccctaacttattttggcgtcacagctgagcaccgt<br>gccgggaggtggccaaggtacagcccgcaatgggcctgtaaatagtccggccccgtcagcgtgtgctggtccagccagcggctgcagg<br>cgagtttctagaaccagagtctatataaagagagaactaacgccacgctcctgtgcctgccttccccactccccggctgcctgctctcggcct<br>acccagagggtcccatctgcccctatccaggcccacctggcgggaggttggcatctttctcgtgagcctctcctggtgcctgggtccaccca<br>gctcggcctgcatgtccctgggagtgactttgctctgggggcggatcgagcaggaggcttcactggggacttgcttgattccctccacgcct<br>cagggctggtctaggggccggcacggctggagaggaagcccccatccctacccaggggatgcagaagctgacctcacagaggcttgg<br>gggtgaaagggtgggtggtcatttgaccccagaaggctgttgcaggtccagaggacacttgaggtggacgtcagtttctggctagacccg<br>agctgaagggatggaggccggaggcgggggggggggggggacagtgggctcccaggggaatgcaggttgaccacatctggctcctg<br>ccaggcaacgagcagcatctggcagagtaaggggccaacgcccatggggggatggaccctctcagttcttgggaattctgccccaaaagt<br>cctttccctggggtctcagagggcccccgtccttcccttcttggtgtcactgtggcccctcactgctcttttcctattcaaacctgagtcccacca<br>ggcccagggcttcacctgctgagctgttgtgtccttgcctgtgacgaggcctggccaggggtgcaggagcagaaggtggggagggttata<br>gacgctgcaaaggccaagagaacatctgagagtggcagctggtgacctggccagaggggctggtgaggggcagagaacctggctaga<br>ggctgggtccctcaggtggtcctctcaggtgggaggcgagcagcaggtgtgggtgaggggaaggttctgatgacagctgcagaggcag<br>ggcccagtgctggcaggtggggggccaagaccctcccctggtgggacgttgaagccaaggatggccttggaccctgtcaggcccagca<br>tggtcccgccacctcccccaccccacaggtggtgttgggacacctgggcgagatgtgagggtgggctcacttgagccactgaaaccagc<br>caggtcttccctcaggccggacagatggcgcctgaccgaagttcctggcacctggaaaacccacaggtcagagtaaggggagaaagga<br>ccctgccctccctgttccacgtctgtgggggggagaggacaaatgccaggcacagggtaggcggcgagaacaaggcactcaatgtgtagc<br>tggggcagagactcggcctctggggagctgagcgggttccctccaccccccaaccgtggtggaaagacaagctcgctggggcggggtgg<br>gggtctggtctccacctgcccctcccactcagccactgaggacaaggtggggcccaggcttctgggaggggggagctggcacaaaagga<br>agtcctggggttgatgtgtttgagcgttaggcgaagtggttccccccatcccccaaacggaaaaatgtcagtatttgctaagctgtagagacc<br>tgatgccgtgatgtggcctgttccgcctccacccattacacggggataacgctggggggtggcgggcccacaaaagaggtgctggagga<br>gactctcccacccctggccgggccggggctttggggccggaaggttcacagtacgcggtttgtccgaacgtcacggcttttattgggagtt<br>gggggtttggggtgccctgtcaggtgatcagaacattaaaaatggactcaacgtaaaaaaaaaaaaaaaaaa (SEQ ID NO: 665) | | |
| Lpmk | gccgtcagggccccagggagcgcggggcgccgctgctgctgttcttcggctcggttctgtctaccgggcagcgccggggccggcggct<br>gcggcggcagaggaacaggagccgggagccgcgttccgccgagagttgggcagaggagcgcccgcgccccggcggcgtcatgggc<br>cccctccccgcgcttcagagggcaccagccgcgggaacccccgggcctcctcgcgcccgagcctgagcgaccctcgggttctccggcg<br>ccccctccctcgccctattttttttcctactctcgctgccgttaccgcttctgctctccgttatggcaacagagccaccatccccccctccgggtcg<br>aggcgccgggcccccccagaaatgcggacctcaccggcgatcgagtccaccccctgagggcaccccgcagccggcgggcggcagactc | NM_152230 | NM_027184 |

TABLE 1-continued

| Gene | Human Gene Sequence | Human Sequence Accession No. | Murine Sequence Accession No. |
|---|---|---|---|
| | cgcttcctcaacggctgcgtgcccctctcgcatcaggtggccgggcacatgtacgggaaggacaaagtgggtatactgcaacatccagat | | |
| | ggcacagttttgaaacagttacaaccacctccaaggggcccaagagagctggaattctataatatggtttatgctgctgactgttttgatggtgt | | |
| | tcttctagagctacgaaaatatttgccaaaatattatggcatctggtcacctcccactgcaccaaacgatttatacctaaaactggaagatgtga | | |
| | cccataaatttaataagccctgtataatggatgtaaagatagggcaaaaaagctatgatccttttgcctcatctgagaagattcagcaacaggt | | |
| | cagcaagtacccattaatggaagagattgggttcttggtgcttggcatgagggtttatcatgttcattccgatagctatgagacagaaaaccag | | |
| | cattacggaagaagcttaacaaaagaaactataaaggatggagtctccagatttttcataatgggtactgcttaagaaaagatgctgttgctg | | |
| | ccagtattcagaagattgagaaaattctgcagtggtttgaaaaccagaagcagcttaatttttacgcaagttcattactctttgtttatgaaggttc | | |
| | atctcagccaaccactacaaaattgaatgacagaactttggcagaaaagtttttgtccaaaggacaactgtcagacacagaagtactagagta | | |
| | caataataactttcatgtgttaagttccacagctaatggaaaaatagagtcttcagtgggcaaaagcttgtccaagatgtatgcgcgtcacagg | | |
| | aaaatatatacaaaaaagcatcacagtcagacttcattgaaagttgaaaatctggagcaagacaatgggtggaaaagcatgtcacaggaac | | |
| | atttaaatggaaatgtactttcccaactggaaaaagttttctaccatcttcccactggttgccaagagattgctgaagtagaagtgcgaatgata | | |
| | gattttgctcatgtgttccctagcaacacaatagatgagggatatgtttatgggctaaagcatttaatttctgtacttcgaagtattttagacaattg | | |
| | aatcctctgttgcagtctttttaaggggtgggccaatcataatgaagaggggcagtcaatatctgcacctttaatgctatgtaaaaaatttgtatta | | |
| | tgagtcgacattttatttgtctttatactttggaagaatggttaactttttataatcttactcaggaaaactaactatttgttcattagaaaactatgaa | | |
| | gaataaagaaacttaggaatgttaagcagggaatgtggtggtacatggcttaaacatctttttggctcaagcaaaatgcaaaccattattcagt | | |
| | cattaagagtttagttagctttctgtagccaattcatgaaatctctgtccacccagccttgacaatgagccatatctaaaatattacattattagaac | | |
| | acctaccaaaatctcgaaagcacaggttgatgtccttagtattgctatgtatgaagttactaaaactggagaaaattctacttcagaaataagta | | |
| | ctgtttaggttttatattaaaagttcagaccagcatatcaaagggtgctccttagtgaaatgatttagaattgttgcattccaaaagcaggttttctc | | |
| | tttaatttttacatctctctctcaaaatattatacttcatgaaaaagacaattgatgtggatgacaacaacaaagtcttgaaattaagggcacacta | | |
| | attgtccttactggggttaggggaagagagatattattttcaaggaacaaaatatttcctttacaatctttcattcatgagaaaattggaatataaa | | |
| | tttattacattgtgaaagtatcataaaccatatacctttgtatctaaatgcagcttcaaaaaagtaaataattgaagttttatttctcctctaaataactt | | |
| | gaatttttttctttaaaaatttatgtatttatatgtccccatttagttaagtggtagtgtaaatgtatgttgttaaaaacagtttctcagaattatagtaag | | |
| | caatgaaagacaatatctaattaggttgttatcaaaaatactgtgtgtaaattagtccgtaatatagggtttggtgcgtatctatattcatgcttctat | | |
| | ttcactcttcctcaaaacagttttatattatgttgaccagtgaaattgtaacttaatttcatggggacaggggcagtgctacagttcctggaaaaat | | |
| | tagatttgtattatctttgtttcacacccaccaccttaaaaaaaaatcaactagttatttgtcatttaaaacatttaaaactttgagtcttcaaatacatt | | |
| | tgatgttaatgctgccattacttgcacttccattcactaataacatttctaggtagttatcagttttgtcatattcctggaaaatattttggggttgtaa | | |
| | attctttctcctctttttcttctggagttacaaattgaatttttaaatccgagcacctttattgtggtgtggagaaaattatcacaattttatgtttattta | | |
| | ccttctcagccttctctgagggcactttgcaaatacctgagtccaaacagaagtaccaactaaatgctctatgaactctatccttagtaaatctatt | | |
| | aaacctgaataatttaaaagatcatgttcattttgtaatagcaaaatttgattttaatttttttatttagaattggtgtatttatcatagggacttccaatttt | | |
| | tcttcacttttttgaatggatattggctatagttttatgttttaacgggaatgaatttcaagtcataataatcagaattttttagttttactttttttcttttacaat | | |
| | atggattttgttgttatttggatagtggttcaataaatcttaagctcagataattaaacactattttgaatcttaacaagatactgaggctttttttgtat | | |
| | gggatgatatcaacctatgtacaatgaatttaataaacttaagtattgtcagatttttttgcacattttagctcaataaaatcttaatgttcaagatttttt | | |
| | tatctgcatttggaaatacaattttgtaaaatcaatgtcttacctttttgatacaatagatcatgttttgtttttaataaagcaagaagccctttttatctgt | | |
| | tgtttttcagggaagggattaacatttaattctgtttgtttacatttgttatcattgttatccaatgctcattttatgttgctttataagtaggcttaggtat | | |
| | aacagaataagtatctgtttatctaatctacatgtgactatcttagtctctctcggtcacttaatattatgctgaaatttaccactgtggggatgaatg | | |
| | atcgctattcaccaagtatatttgaacatgtaaatgcttaagaaataagcataatgcggatatagtttgggttaataggattctcatagtttttttttcc | | |
| | cctatgaaacataagtaatgattttagtgtatttcttatggaatacactcatttaaaaaggactttaagaaattgtggatgtgaataatacctttctct | | |
| | aataaaaatttaaattgtataatagttttataatatttacattaattgatattttaatatggatagacattgcatagattcaaataaattaaaatcaatga | | |
| | taaatgctaaatatttttatctaaatagtttttcaagaaacagttatggaaatgtgtatattaaatggctctaatgtggagcttgtggtatttcaactca | | |
| | gtattcattattagttgtgtgtctggaaagattgtacttacttttcctctttacactacagtttgctcttatggggctctaaactgtttaactgaagaac | | |
| | cttcgtctgtattttgattgagcataatttagtattttatgatttccaagatgatgttcttatgtctatcaagtctatgtatcaaatttataacatcatttaa | | |
| | gaaaaaggaatttccacagatacttcagttgcaatttttttgtttcatgctactgaaaatacatttgtttctaggggttggaatattatagaagatgta | | |
| | ggatgaaagaaaacgatagaacaacgaaagaattctgtttatgaaattacaggaattgtgtccactatggtaaagcattgtcattttagtacattt | | |
| | tctcttagtagtttggcattttatactttaaaacttgttttgctttaaaaattgtttataatgcttaccttctttctccagtgcctttagtcttgatttgatatg | | |
| | tttgtaccctcagttaccctttctattacatgtttttgatgttttcatagcctaggaaacatcgattccttttttaataattgtcaatctgattatttaaaga | | |
| | ggtaacaattatctgttaatgctttggaaaaacaagtagggttgcctttggaggccaggcttcttagttcattcaaaaatattccttggatttatgc | | |
| | catgtattaagcatttttagcccccagtattacaactgtgaaccaaacggataaggccctaaccattttcagcattctctttggatggggtgggat | | |
| | tggggacttaattaaaatagagatatagaaaaataggcatctaaataagataataagtgtggggttgaaatgaagcatctaacaatagttgaa | | |
| | gttagaagtaatattttacagtattgtaacctctatttaagtttgggtattagttacagatagcataaaaaagccttaatttttcactttccttgctggc | | |
| | aaaggtacatttatttagactgtccatttaaagtaatgtttaacataaacattactgtgaaaaacattccattacatattcccaagcaaatgagctg | | |

TABLE 1-continued

| Gene | Human Gene Sequence | Human Sequence Accession No. | Murine Sequence Accession No. |
|---|---|---|---|
| | catcttctttactgtattttacaatttagtacaacagttttaggcctcaatcttaacatcactggtattttaaatttggcaatgaatatgaaattacttttg | | |
| | acttacagattgattatattattactttgaaaatgcattaatttcttagaaaagtttggagcctctatctttttttgagttaatacttaaattctcattactt | | |
| | atattaatagcctgtactaagtgaaaatattatttatgcaagtaaacaagtcactataggcttttaagacttttctttaattttagattttgtcatcaaag | | |
| | tttaaatttttacctactgtccacttaaatataatttaacagtttgtaaagtgaaatagttttaagtatgatgtatgatgcacctgcatataaatgaaa | | |
| | atggcgtgcacaaagacactttactatgggaactgtactggaagatttatgaaagcatgtgaaattgcacctaaaattgtgttattagtgactat | | |
| | aagcagcaatgctaaatttattgtacttgatgaatgaatgtatttagtcacagttactttggtttaaatgtataaatgtctttagggtttttrnaaatgt | | |
| | gtttgtaatttgtactattgtgggggtatacttggactgcaggggttattgtcaatgtgtgctttgtgtttttattttatagaatcatctaatgtgatata | | |
| | ccaatttttataagtgatatttacataattctaataactgtatatttgacaacctattaaaatgttttgcattggaa (SEQ ID NO: 666) | | |
| Rock1 | gctggttccccttccgagcgtccgcgccccgcatgcgcagtctgccccggcggtctccgtttgtttgaacaggaaggcggacatattagtcc | NM_005406 | NM_009071 |
| | ctctcagccccctcgccccacccccaggcattcgccgccgcgactcgccctttccccggctgggaccgcagcccctcccagaagctcc | | |
| | cccatcagcagccgccgggacccaactatcgtcttcctcttcgcccgctctccagcctttcctctgctaagtctccatcgggcatcgacctcg | | |
| | ccctgccccaccggacaccgtagcagcagccccagcagcgacgggacaaaatgggagagtgaggctgtcctgcgtggaccagctcgt | | |
| | ggccgagactgatcggtgcgtcgggccgggccgagtagagccggggacgcggggctagaccgtctacagcgcctctgagcggagcg | | |
| | ggcccggcccgtggcccgagcggcggccgcagctggcacagctcctcacccgccctttgctttcgcctttcctcttctccctcccttgttgcc | | |
| | cggagggagtctccaccctgcttctctttctctacccgctcctgcccatctcgggacggggacccctccatggcgacggcggccggggcc | | |
| | cgctagactgaagcacctcgccggagcgacgaggctggtggcgacggcgctgtcggctgtcgtgaggggctgccgggtgggatgcga | | |
| | ctttgggcgtccgagcggctgtgggtcgctgttgcccccggcccggggtctggagagcggaggtcccctcagtgaggggaagacgggg | | |
| | gaaccgggcgcacctggtgaccctgaggttccggctcctccgccccgcggctgcgaacccaccgcggaggaagttggttgaaattgcttt | | |
| | ccgctgctggtgctggtaagagggcattgtcacagcagcagcaacatgtcgactggggacagttttgagactcgatttgaaaaaatggaca | | |
| | acctgctgcgggatcccaaatcggaagtgaattcggattgtttgctggatggattggatgctttggtatatgatttggattttcctgccttaagaa | | |
| | aaaacaaaaatattgacaacttttaagcagatataaagacacaataaataaaatcagagatttacgaatgaaagctgaagattatgaagtagt | | |
| | gaaggtgattggtagaggtgcatttggagaagttcaattggtaaggcataaatccaccaggaaggtatatgctatgaagcttctcagcaaattt | | |
| | gaaatgataaagagatctgattctgctttttttctgggaagaaagggacatcatggcttttgccaacagtccttgggttgttcagctttttttatgcatt | | |
| | ccaagatgatcgttatctctacatggtgatggaatacatgcctggtggagatcttgtaaacttaatgagcaactatgatgtgcctgaaaaatgg | | |
| | gcacgattctatactgcagaagtagttcttgcattggatgcaatccattccatgggttttattcacagagatgtgaagcctgataacatgctgctg | | |
| | gataaatctggacatttgaagttagcagattttggtacttgtatgaagatgaataaggaaggcatggtacgatgtgatacagcggttggaacac | | |
| | ctgattatatttcccctgaagtattaaaatcccaaggtggtgatggttattatggaagagaatgtgactggtggtcggttggggtatttttatacga | | |
| | aatgcttgtaggtgatacaccttttttatgcagattctttggttggaacttacagtaaaattatgaaccataaaaattcacttacctttcctgatgataa | | |
| | tgacatatcaaaagaagcaaaaaaccttatttgtgccttccttactgacagggaagtgaggttagggcgaaatggtgtagaagaaatcaaac | | |
| | gacatctcttcttcaaaaatgaccagtgggcttgggaaacgctccgagacactgtagcaccagttgtacccgatttaagtagtgacattgatac | | |
| | tagtaattttgatgacttggaagaagataaaggagaggaagaaacattccctattcctaaagctttcgttggcaatcaactaccttttgtaggatt | | |
| | tacatattatagcaatcgtagatacttatcttcagcaaatcctaatgataacagaactagctccaatgcagataaaagcttgcaggaaagtttgc | | |
| | aaaaaacaatctataagctggaagaacagctgcataatgaaatgcagttaaaagatgaaatggagcagaagtgcagaacctcaaacataaa | | |
| | actagacaagataatgaaagaattggatgaagagggaaatcaaagaagaaatctagaatctacagtgtctcagattgagaaggagaaaatg | | |
| | ttgctacagcatagaattaatgagtaccaaagaaaagctgaacaggaaaatgagaagagaagaaatgtagaaaatgaagtttctacattaaa | | |
| | ggatcagttggaagacttaaagaaagtcagtcagaattcacagcttgctaatgagaagctgtcccagttacaaaagcagctagaagaagcc | | |
| | aatgacttacttaggacagaatcggacacagctgtaagattgaggaagagtcacacagagatgagcaagtcaattagtcagttagagtccct | | |
| | gaacagagagttgcaagagagaaatcgaattttagagaattctaagtcacaaacagacaaagattattaccagctgcaagctatattagaag | | |
| | ctgaacgaagagacagaggtcatgattctgagatgattggagaccttcaagctcgaattacatctttacaagaggaggtgaagcatctcaaa | | |
| | cataatctcgaaaaagtggaaggagaaagaaaagaggctcaagacatgcttaatcactcagaaaaggaaaagaataatttagagatagattt | | |
| | aaactacaaacttaaatcattacaacaacggttagaacaagaggtaaatgaacacaaagtaaccaaagctcgtttaactgacaaacatcaatc | | |
| | tattgaagaggcaaagtctgtggcaatgtgtgagatggaaaaaaagctgaaagaagaaagagaagctcgagagaaggctgaaaatcggg | | |
| | ttgttcagattgagaaacagtgttccatgctagacgttgatctgaagcaatctcagcagaaactagaacatttgactggaaataaagaaaggat | | |
| | ggaggatgaagttaagaatctaaccctgcaactggagcaggaatcaaataagcggctgttgttacaaaatgaattgaagactcaagcatttg | | |
| | aggcagacaatttaaaaggtttagaaaagcagatgaaacaggaaataaatactttattggaagcaaagagattattagaatttgagttagctca | | |
| | gcttacgaaacagtatagaggaaatgaaggacagatgcgggagctacaagatcagcttgaagctgagcaatatttctcgacactttataaaa | | |
| | cccaggtaaaggaacttaaagaagaaattgaagaaaaaaacagagaaaatttaaagaaaatacaggaactacaaaatgaaaaagaaactc | | |
| | ttgctactcagttggatctagcagaaacaaaagctgagtctgagcagttggcgcgaggccttctggaagaacagtattttgaattgacgcaag | | |
| | aaagcaagaaagctgcttcaagaaatagacaagagattacagataaagatcacactgttagtcggcttgaagaagcaaacagcatgctaac | | | |

TABLE 1-continued

| Gene | Human Gene Sequence | Human Sequence Accession No. | Murine Sequence Accession No. |
|---|---|---|---|
| | caaagatattgaaatattaagaagagagaatgaagagctaacagagaaaatgaagaaggcagaggaagaatataaactggagaaggag<br>gaggagatcagtaatcttaaggctgcctttgaaaagaatatcaacactgaacgaacccttaaaacacaggctgttaacaaattggcagaaata<br>atgaatcgaaaagattttaaaattgatagaaagaaagctaatacacaagatttgagaaagaaagaaaaggaaaatcgaaagctgcaactgg<br>aactcaaccaagaaagagagaaattcaaccagatggtagtgaaacatcagaaggaactgaatgacatgcaagcgcaattggtagaagaat<br>gtgcacataggaatgagcttcagatgcagttggccagcaaagagagtgatattgagcaattgcgtgctaaacttttggacctctcggattcta<br>caagtgttgctagttttcctagtgctgatgaaactgatggtaacctcccagagtcaagaattgaaggttggctttcagtaccaaatagaggaaa<br>tatcaaacgatatggctggaagaaacagtatgttgtggtaagcagcaaaaaaattttgttctataatgacgaacaagataaggagcaatccaa<br>tccatctatggtattggacatagataaactgtttcacgttagacctgtaacccaaggagatgtgtatagagctgaaactgaagaaattcctaaaa<br>tattccagatactatatgcaaatgaaggtgaatgtagaaaagatgtagagatggaaccagtacaacaagctgaaaaaactaatttccaaaatc<br>acaaaggccatgagtttattcctacactctaccactttcctgccaattgtgatgcctgtgccaaacctctctggcatgtttttaagccacccctg<br>ccctagagtgtcgaagatgccatgttaagtgccacagagatcacttagataagaaagaggacttaatttgtccatgtaaagtaagttatgatgt<br>aacatcagcaagagatatgctgctgttagcatgttctcaggatgaacaaaaaaaatgggtaactcatttagtaaagaaaatccctaagaatcc<br>accatctggttttgttcgtgcttcccctcgaacgctttctacaagatccactgcaaatcagtctttccggaaagtggtcaaaaatacatctggaaa<br>aactagttaaccatgtgactgagtgccctgtggaatcgtgtgggatgctacctgataaaccaggcttctttaaccatgcagagcagacaggct<br>gtttctttgacacaaatatcacaggcttcagggttaagattgctgtttttctgtccttgctttggcacaacacactgagggtttttttattgcgggttt<br>gcctacaggtagattagattaattattactatgtaatgcaagtacagttgggggaaagcttaggtagatatatttttttaaaaggtgctgcctttttt<br>ggatttataagaaaatgcctgtcagtcgtgatagaacagagttttcctcatatgagtaagaggaagggactttcactttcaagtggaacagcca<br>tcactatcaagatcagctcatggaaggagtaaagaaaatatctcaaaatgagacaaactgaagttttgttttttttttaatgacttaagtttttgtgct<br>cttgcaagactatacaaaactattttaagaaagcagtgatatcacttgaacttcagtgccctcactgtagaatttaaaagccttactgttgattgcc<br>catgttggacttgatggagaaattaaatatctttcattatgctttacaaaatactgtatatgtttcagcaagtttggggaatgggagaggacaaaa<br>aaaagttacatttaatctatgcatttttgccaagccatattgagttattttactactagagacattaggaaactaactgtacaaaagaaccaagttta<br>aaagcattttgtggggtacatcatttctataattgtataatgtatttctttgtggttttaaatgataaagacattaagttaacaaacatataagaaatgt<br>atgcactgtttgaaatgtaaattattcttagaacactttcaatggggggttgcattgtcctttttagtgccttaatttgagataattattttactgccatga<br>gtaagtatagaaatttcaaaaaatgtattttcaaaaaattatgtgtgtcagtgagtttttcattgataattggtttaatttaaaatatttagaggtttgtt<br>ggactttcataaattgagtacaatctttgcatcaaactacctgctacaataatgactttataaaactgcaaaaaatgtagaaggttgcaccaacat<br>aaaaaggaaatatggcaatacatccatgatgttttccagttaacataggaattaccagataaatactgttaaactcttgtccagtaacaagagtt<br>gattcatatggacagtatgatttattgtttatttttttaaccaaatacctcctcagtaatttataatggctttgcagtaatgtgtatcagataagaagca<br>ctggaaaaccgatcgtctctaggatgatatgcatgtttcaagtggtattgaaagccgcactgatggatatgtaataataaacatatctgttattaa<br>tatactaatgactctgtgctcatttaatgagaaataaaagtaatttatggatgggtatctttaatttttactgcaatgtgttttctcatggctgaaatga<br>atggaaaacatacttcaaattagtctctgattgtatataaatgtttgtgaaattccatggttagcttaaagtgtatttttaaaagataaaa (SEQ<br>ID NO: 667) | | |
| Stk17b | gaacggcgatgccccagacgcggctgcagttttcaaaccgcgactgcaagcttcggtagtcctctccgctgctgtcgccaggagtcacttc<br>acgagaagccaggtcacaaccgtcggcccttgtctggaaaagtaaaagtggatcctgccacgttcggagctccctggcgcctcgcccggc<br>tggagctagagaactcgtcctgtggcggcccccggcgtggggcgggacagcggcccccctggagggggcagtcccgggagaacctgc<br>ggcggccggagcggtaaaaataagtgactaaagaagcagacctgggaatcacctaacatgtcgaggaggagatttgattgccgaagtatt<br>tcaggcctactaactacaactcctcaaattccaataaaaatggaaaactttaataatttctatatacttacatctaaagagctagggagaggaaa<br>atttgctgtggttagacaatgtatatcaaaatctactggccaagaatatgctgcaaaatttctaaaaaagagaagaagaggacaggattgtcga<br>gcagaaattttacacgagattgctgtgcttgaattggcaaagtcttgtccccgtgttattaatcttcatgaggtctatgaaaatacaagtgaaatc<br>attttgatattggaatatgctgcaggtggagaaattttcagcctgtgtttacctgagttggctgaaatggtttctgaaaatgatgttatcagactcat<br>taaacaaatacttgaaggagtttattatctacatcagaataacattgtacaccttgatttaaagccacagaatatattactgagcagcatataccct<br>ctcggggacattaaaatagtagattttggaatgtctcgaaaaatagggcatgcgtgtgaacttcgggaaatcatgggaacaccagaatattta<br>gctccagaaatcctgaactatgatcccattaccacagcaacagatatgtggaatattggtataatagcatatatgttgttaactcacacatcacc<br>atttgtgggagaagataatcaagaaacatacctcaatatttctcaagttaatgtagattattcggaagaaactttttcatcagtttcacagctggcc<br>acagactttattcagagccttttagtaaaaaatccagagaaaagaccaacagcagagatatgcctttctcattcttggctacagcagtgggact<br>ttgaaaacttgtttcaccctgaagaaacttccagttcctctcaaactcaggatcattctgtaaggtcctctgaagacaagacttctaaatcctcct<br>gtaatggaacctgtggtgatagagaagacaaagagaatatcccagaggatagcagcatggtttccaaaagatttcgtttcgatgactcattac<br>ccaatccccatgaacttgtttcagatttgctctgttagcactttttctttgactcatttggactgaatttgaaattttatatccactccagtgagcttat<br>gatttgtagcttcatatatgacatgtttatattgtaaatgcacttttccatggaataatttagggaagtgttttaatgttaaattactagttgctagcatg<br>ttatgatttcatatcctgagatagctctgcagataagaaaatatttaaatatatgacaaaaagtaaaattgtacatgtgagtttacatgttaatgaaa | NM_004226 | NM_133810 |

TABLE 1-continued

| Gene | Human Gene Sequence | Human Sequence Accession No. | Murine Sequence Accession No. |
|---|---|---|---|
| | taattcaacttcaaatgaacttaccagaatgttttgcatatcaacaaaaaaagtggcttgagttttattatagttggtgtaaactgaacacagtgaa gacattggaatttaataggttctctctctaaggtgactcttataccatgcctctatcaacataatttgtttaggaaagcagtatgaagtttaagcca aaataatttctactttatagatgctcaagagacattttacaattgaaaatgtattcaattacaaatattttgaaacttcgtaagcttttcattctctgtg gtctgttatatgagagagatcctttaactagagcaaagagggagttagaaacctgatcagggatattctttacaagttggagcagaggaaaga gtagcatgccttcgtattttaacgcaaatgtctttttcctcctcccaacctacttgagatctgataaggtctggaagatggagatatttggtatgca agtgtagagtttttaatcctccagaatttctagagtagaagatacttaggtatagttaaatattctgtatttttagtcaaacatatttattaattgaata tagaagaaaatgttgacacactcagacagcttactgaattttagatgtcttctgcatcttagaatacaagccagtcattcagagttctaaaagtat gcataaaaaattacagcaccggtaggtctattaacacagtgcccgagtcagcggtagcaagactgatgtgatcataaaacatgacatcagg ctcgtctgaagttcttgtgtgaaattcctagtgagtgaggaggctcagcttaaagccatctgcagagtggcccctcattgtggtcttttgctggg accaatgcaagagactagggagagcaaaatgtttgcttatggctagagactatatccagccctaatgatggggaaagttagtccttttcgggt aatcttttatgaattttcacctgatgaccgttatattggtctgttatcatgttacgataactgtgatctcatgaccatgttgctgtatcagaagaaata gtttgacaaatggtaacaacaacctgatgttcccccttttagacctttaacttctcaaaatttggtaagtttccaaattctttaataataacttaaaact ttttgaataactatcaggtcactttatttgaccacatggtgaattcctttaatgtcttcagcatttgttaaggaaaagttttctctacttgtgtgtgtatg tgtgcacatgtgtgtatgtacaggtgtatgtatatatctatagatagatacaatacattctttagacacttttcaagattctttgctgtggtatattgtg ctcaactcaggtgccaaaggagcttttttttttttttttttttgagatggagttttgctctgtctctcaggctggagtgcagtggcatgatctcagc tcacggcaacctctgcctcccgggttcaagcaattctcctgtctcagcctcctgagtagttgggattacaggcgcatgccaccgtgcccagct aatttttgtatttttagtagagacggggtttcaccatgttggccaggctggtcacaaactcctgacttcaagtgatccacccgcctcggcctccc aaagtgctgggattacaggcgtgagccactgcgcccccgcccaggagctcttttcttatgacatataaattatgacatttatattctttatatgac tttatgttctcttcttatgacatttaaattctttaagtagtttgttggtccaataaactagacgttgtataatctaaattgagcccttgtatatctaaaact gatgagttgtttctaaattgttgattgtccatttacttgccttggtattaagataatgcaagtaaagtttagtaagtcattggataatgaaatgcttat gtttctgaagaccatattatatttttaatttttagaggaatcatgccatcccccaaaaaatcaagaaatatttgaattttaaattataagttcatttgtta aaagacattttacaaatgtctgaaaatcttaaaatactttacatctacctttaagtagtagaatacagagctgtaaatttccatgcatttttcctgat attaagttttatagtaaaaaagcaactagtgattgcacaaagaatataaaaatccactctttttacaaaggtgtgaatttaaataacgttattgattg gaatatgaaaatagaccaatcatttaagagctttttagcaaatgattcaattcttactctttttctcccaagattgaaaagcataatgtatttctctaa agtaggaatctagagagcccctgtgagtggacaaatgtcagtaacacttgaacacatgagaagataagtgttatgttgtgataatttaaagtta aatttgctttttgggtaggatccctaaatagatgggatttttaaatagatgatatatagatgacaattgcaattgtcattttaattattttccctacagt aaagaacctagctctgagcagtgaaattgtaatggcactttaaaggaagtaagccgttaactgttctctagtggagcgatctccaactgttttg gcactagggacgggttttgtggaagaaaatttttccacaggactgggggtttagggggatggtttcaggatgattcaagtacattacatttatc attagattctcataaggagcatgcaacctagatctcttgcacgtgtggttcacagcaggattcgagctcctttgagaatctaatgccatggctga tctaacaggaaactgagctcaggcagtaatgcttggcaccgcccccccaccttctatgcagcccggtcgtggcctggggactggggacccc tgctctagtcagtaataaggtacttgtgccagaatataaatcaacacattgcttcctttatcaaagaagtcttgttatttaaaaaaagtcaactgag ccagtatgattagtgatgtaattgattttcattctggcacaagcctctttcattctggacagctcacaaatagttaatggaccatgctttgaatagc cttcctctaagcaacatttataaatactgatattttagaactgtttacatttcttctgtttatttttgaattttcagtttgatatcttgtccttattcattgttgt ataaacaactgtactttaatttcaagtagtattaaaagtatttcacttcagtttggggggattattatcaatttataattttataaaagtattttaaagaa taattgtaaattttccataaattacaacttcctgccatatttattaaataataatcttgcttaaggcatatagacagacattattatgagtattccagta aaaaaaatctacatcaacttgaccattctggctaaaaattaaaaagcactttttttatatctgtggttgtcatttgtttcaaagcatttctaaatttattgt tcttaaaagtatgtctgcatgttctagcctttgacctaggtcatctatgaaccctctttgtgtctaataaacatatctgtaaaggcaaaaaaaaaaa aaaaaaa (SEQ ID NO: 668) | | |
| Mast2 | taggcaggcggctgagccggcggcgggtggcctgcccaacgtgtgctgggtgggagaaggcgaggcgtcagcgatgctgtctcttccg tgaggagcgcagaggaggtcgcggcgccggaggccccagaaggctcgaaggcgccgcgggctggggtcggtggcttagggagccc gtccggccatggtggccgcgggtggtggttggcgcggctgcgctgcggcccggggcagtgcggagccgggacagtcgcggcgctga cgcccgcgggccccagctgcagatatgaagcggagccgctgccgcgaccgaccgcagccgccgccgcccgaccgccgggaggatg gagttcagcgggcagcggagctgtctcagtctttgccgccgcgccggcgagcgccgcccgggaggcagcggctggaggagcggacg ggccccgcggggcccgagggcaaggagcaggatgtagtaactggagttagtcccctgctcttcaggaaactcagtaatcctgacatatttt catccactggaaaagttaaacttcagcgacaactgagtcaggatgattgtaagttatggagaggaaacctggccagctctctatcgggtaag cagctgctccctttgtccagcagtgtacatagcagtgtgggacaggtgacttggcagtcgtcaggagaagcatcaaacctggttcgaatgag aaaccagtcccttggacagtctgcaccttctcttactgctggcctgaaggagttgagccttccaagaagaggcagcttttgtcggacaagtaa ccgcaagagcttgattgtgacctctagcacatcacctacactaccacggccacactcaccactccatggccacacaggtaacagtcctttgg acagcccccggaatttctctccaaatgcacctgctcacttttcttttgttcctgcccgtaggactgatgggcggcgctggtctttggcctctttgc | NM_015112 | NM_001042743 |

TABLE 1-continued

| Gene | Human Gene Sequence | Human Sequence Accession No. | Murine Sequence Accession No. |
|---|---|---|---|
| | cctcttcaggatatggaactaacactcctagctccactgtctcatcatcatgctcctcacaggaaaagctgcatcagttgcctttccagcctaca | | |
| | gctgatgagctgcacttttgacgaagcatttcagcacagagagcgtaccagatgaggaaggacggcagtccccagccatgcggcctcgc | | |
| | tcccggagcctcagtcccggacgatccccagtatcctttgacagtgaaataataatgatgaatcatgtttacaaagaaagattcccaaaggcc | | |
| | accgcacaaatggaagagcgactagcagagtttatttcctccaacactccagacagcgtgctgcccttggcagatggagccctgagctttat | | |
| | tcatcatcaggtgattgagatggcccgagactgcctggataaatctcggagtggcctcattacatcacaatacttctacgaacttcaagataatt | | |
| | tggagaaacttttacaagatgctcatgagcgctcagagagctcagaagtggcttttgtgatgcagctggtgaaaaagctgatgattatcattgc | | |
| | ccgcccagcacgtctcctggaatgcctggagtttgaccctgaagagttctaccaccttttagaagcagctgagggccacgccaaagaggg | | |
| | acaagggattaaatgtgacattccccgctacatcgttagccagctgggcctcacccgggatcccctagaagaaatggcccagttgagcagc | | |
| | tgtgacagtcctgacactccagagacagatgattctattgagggccatggggcatctctgccatctaaaaagacaccctctgaagaggactt | | |
| | cgagaccattaagctcatcagcaatggcgcctatggggctgtatttctggtgcggcacaagtccacccggcagcgctttgccatgaagaag | | |
| | atcaacaagcagaacctgatcctacggaaccagatccagcaggccttcgtggagcgtgacatactgactttcgctgagaacccctttgtggt | | |
| | cagcatgttctgctcctttgataccaagcgccacttgtgcatggtgatggagtacgttgaagggggagactgtgccactctgctgaagaatatt | | |
| | ggggccctgcctgtggacatggtgcgtctatactttgcggaaactgtgctggccctggagtacttacacaactatggcatcgtgcaccgtga | | |
| | cctcaagcctgacaacctcctaattacatccatggggcacatcaagctcacggactttggactgtccaaaattggcctcatgagtctgacaac | | |
| | gaacttgtatgagggtcatattgaaaaggatgcccgggaattcctggacaagcaggtatgcgggaccccagaatacattgcgcctgaggtg | | |
| | atcctgcgccagggctatgggaagccagtggactggtgggccatgggcattatcctgtatgagttcctggtgggctgcgtcccttttttttgga | | |
| | gatactccggaggagctctttgggcaggtgatcagtgatgagattgtgtggcctgagggtgatgaggcactgcccccagacgcccaggac | | |
| | ctcacctccaaactgctccaccagaaccctctggagagacttggcacaggcagtgcctatgaggtgaagcagcacccattctttactggtct | | |
| | ggactggacaggacttctccgccagaaggctgaatttattcctcagttggagtcagaggatgatactagctattttgacacccgctcagagcg | | |
| | ataccaccacatggactcggaggatgaggaagaagtgagtgaggatggctgccttgagatccgccagttctcttcctgctctccaaggttca | | |
| | acaaggtgtacagcagcatggagcggctctcactgctcgaggagcgccggacaccacccccgaccaagcgcagcctgagtgaggaga | | |
| | aggaggaccattcagatggcctggcagggctcaaaggccgagaccggagctgggtgattggctcccctgagatattacggaagcggctg | | |
| | tcggtgtctgagtcatcccacacagagagtgactcaagccctccaatgacagtgcgacgccgctgctcaggcctcctggatgcgcctcggt | | |
| | tcccggagggccctgaggaggccagcagcaccctcaggaggcaaccacaggagggtatatgggtcctgacacccccatctggagagg | | |
| | gggtatctgggcctgtcactgaacactcaggggagcagcggccaaagctggatgaggaagctgttggccggagcagtggttccagtcca | | |
| | gctatggagacccgaggccgtgggacctcacagctggctgagggagccacagccaaggccatcagtgacctggctgtgcgtagggccc | | |
| | gccaccggctgctctctggggactcaacagagaagcgcactgctcgccctgtcaacaaagtgatcaagtccgcctcagccacagccctct | | |
| | cactcctcattccttcggaacaccacacctgctccccgttggccagccccatgtccccacattctcagtcgtccaacccatcatcccgggact | | |
| | cttctccaagcagggacttcttgccagcccttggcagcatgaggcctcccatcatcatccaccgagctggcaagaagtatggcttcaccctg | | |
| | cgggccattcgcgtctacatgggtgactccgatgtctacaccgtgcaccatatggtgtggcacgtggaggatggaggtccggccagtgag | | |
| | gcagggcttcgtcaaggtgacctcatcacccatgtcaatggggaacctgtgcatggcctggtgcacacggaggtggtagagctgatcctga | | |
| | agagtggaaacaaggtggccatttcaacaactcccctggagaacacatccattaaagtggggccagctcggaagggcagctacaaggcc | | |
| | aagatggcccgaaggagcaagaggagccgcggcaaggatgggcaagaaagcagaaaaaggagctccctgttccgcaagatcaccaa | | |
| | gcaagcatccctgctccacaccagccgcagcctttcttcccttaaccgctccttgtcatcaggggagagtgggccaggctctcccacacaca | | |
| | gccacagcctttcccccgatctcccactcaaggctaccgggtgacccccgatgctgtgcattcagtgggagggaattcatcacagagcag | | |
| | ctcccccagctccagcgtgcccagttccccagccggctctgggcacacacggcccagctccctccacggtctggcacccaagctccaac | | |
| | gccagtaccgctctccacggcgcaagtcagcaggcagcatcccactgtcaccactggcccacaccccttctcccccacccccaacagctt | | |
| | cacctcagcggtccccatcgcccctgtctggccatgtagcccaggcctttcccacaaagcttcacttgtcacctcccctgggcaggcaactct | | |
| | cacggcccaagagtgcggagccaccccgttcaccactactcaagagggtgcagtcggctgagaaactggcagcagcacttgccgcctct | | |
| | gagaagaagctagccacttctcgcaagcacagccttgacctgccccactctgaactaaagaaggaactgccgcccagggaagtgagccc | | |
| | tctggaggtagttggagccaggagtgtgctgtctggcaaggggccctgccagggaagggggtgctgcagcctgctccctcacgggccc | | |
| | taggcaccctccggcaggaccgagccgaacgacgggagtcgctgcagaagcaagaagccattcgtgaggtggactcctcagaggacg | | |
| | acaccgaggaagggcctgagaacagccagggtgcacaggagctgagcttggcacctcacccagaagtgagccagagtgtggcccta | | |
| | aaggagcaggagagagtggggaagaggatcctttcccgtccagagaccctaggagcctgggcccaatggtcccaagcctattgacagg | | |
| | gatcacactggggcctcccagaatggaaagtcccagtggtccccacaggaggctcgggagcccacaagccattgaggaggctgccagc | | |
| | tcctcctcagcaggccccaacctaggtcagtctggagccacagaccccatccctcctgaaggttgctggaaggcccagcacctccacacc | | |
| | caggcactaacagcactttctcccagcacttcgggactcacccccaccagcagttgctctcctcccagctccacctctgggaagctgagcat | | |
| | gtggtcctggaaatcccttattgagggcccagacagggcatccccaagcagaaaggcaaccatggcaggtgggctagccaacctccagg | | |
| | atttggaaaacacaactccagcccagcctaagaacctgtctcccagggagcaggggaagacacagccacctagtgcccccagactggcc | | |
| | catccatcttatgaggatcccagccagggctggctatgggagtctgagtgtgcacaagcagtgaaagaggatccagccctgagcatcacc | | |

TABLE 1-continued

| Gene | Human Gene Sequence | Human Sequence Accession No. | Murine Sequence Accession No. |
|---|---|---|---|
| | caagtgcctgatgcctcaggtgacagaaggcaggacgttccatgccgaggctgccccctcacccagaagtctgagcccagcctcaggag gggccaagaaccagggggccatcaaaagcatcgggatttggcattggttccagatgagcttttaaagcaaacatagcagttgtttgccatttc ttgcactcagacctgtgtaatatatgctcctggaaaccatcaaaaaaaaaaaaaaaaaa (SEQ ID NO: 669) | | |
| Pdp1 | agagtgggcaggccgggggtgagggctcgcgctccgggagctgcacggggctgcgtggaaagagcgccgagcggtggcgtcgttgt cgccccctcctcgtcgggaagaatcgtttggtctcctgccgtgcccggttcgtattccctactccctgccacgagccgccccgtccgggatc ctccacccgtccaaagttgtgagggggcgccgggcgtgctcgcggatcggcggccgcgggcgtgcggagggctggacgagccctgg agcgccaggagaatgtgtgtgtgtcccgggcccagacgaattggaatcccagtcagaagttccagcctgccactgttctctgatgccatgc cagcaccaactcaactgtttttcctctcatccgtaactgtgaactgagcaggatctatggcactgcatgttactgccaccacaaacatctctgtt gttcctcatcgtacattcctcagagtcgactgagatacacacctcatccagcatatgctaccttttgcaggccaaaggagaactggtggcagt acacccaaggaaggagatatgcttccacaccacagaaattttacctcacacctccacaagtcaatagcatccttaaagctaatgaatacagttt caaagtgccagaatttgacggcaaaaatgtcagttctatccttggatttgacagcaatcagctgcctgcaaatgcacccattgaggaccgga gaagtgcagcaacctgcttgcagaccagagggatgcttttgggggtttttgatggccatgcaggttgtgcttgttcccaggcagtcagtgaaa gactcttttattatattgctgtctctttgttaccccatgagactttgctagagattgaaaatgcagtggagagcggccgggcactgctacccattc tccagtggcacaagcaccccaatgattactttagtaaggaggcatccaaattgtactttaacagcttgaggacttactggcaagagcttataga cctcaacactggtgagtcgactgatattgatgttaaggaggctctaattaatgccttcaagaggcttgataatgacatctccttggaggcgcaa gttggtgatcctaattcttttctcaactacctggtgcttcgagtggcattttctggagccactgcttgtgtggcccatgtggatggtgttgaccttc atgtggccaatactggcgatagcagagccatgctgggtgtgcaggaagaggacggctcatggtcagcagtcacgctgtctaatgaccaca atgctcaaaatgaaagagaactagaacggctgaaattggaacatccaaagagtgaggccaagagtgtcgtgaaacaggatcggctgcttg gcttgctgatgccatttagggcatttggagatgtaaagttcaaatggagcattgaccttcaaaagagagtgatagaatctggcccagaccagt tgaatgacaatgaatataccaagtttattcctcctaattatcacacacctccttatctcactgctgagccagaggtaacttaccaccgattaaggc cacaggataagtttctggtgttggctactgatgggttgtgggagactatgcataggcaggatgtggttaggattgtgggtgagtacctaactg gcatgcatcaccaacagccaatagctgttggtggctacaaggtgactctgggacagatgcatggccttttaacagaaaggagaaccaaaat gtcctcggtatttgaggatcagaacgcagcaacccatctcattcgccacgctgtgggcaacaacgagtttgggactgttgatcatgagcgcc tctctaaaatgcttagtcttcctgaagagcttgctcgaatgtacagagatgacattacaatcattgtagttcagttcaattctcatgttgtaggggc gtatcaaaaccaagaatagtgagtggctctttcactggcaattctcaaatgatatacatttaaagggcagatttttttaaaaagatactactataata aacatttccagttggtcattctaagcatttacccttttgatactctagctagtcaggtactccaaattgactttgcagcagggtggcagggtcagg agagtctggtcctgcctagctcagatttcatggcacctgcacttgaagcaagtcacttctttatcacaggtgtcttgaaacattagcttcttttacc aacctgagaaaattaggatgacctggcaaataagatcttgaataggccaaaagcaagtatcttgctgtgtgtagtctcttggttaaagtgaaga aacagtactgttcacacctttcttcactgagattccagtgtacatgagaacatatatttattgcatgattttctagatacacagtctatgcattattca tatacatttattttagcctaaagtggttttcaaatccagttcttcaagccataaatgaccaagatccaagcaatctgaatttgtttttgtgcttatttga ctggaatgcttcttaagtggaataactatactccgttatccacccgatttcctaatgtaattgaaagattttctattttgccacacacttggagacaa taagggtttttagttttatctactcttctattgaagttaaagaaagaaaaaaagctttttttatttgtattaatgaaaagctttagtttaaaataaggaga tccagaataaaaagaagagactgatctcttcaattattgtcatctgtagccaccagcacatcactcttatgtaatccccaaaggcttggcatgcc gtaagtgtgtggtgggtagactgctgccggggaatcgtacttcttatttagtaatgataagacttttcattattttggaattttaaagatgacataa ataagtttaaatatcaatttggggagtaaggtttaatattgccatcgggtattgagacaggaggaagtttctgtttttctccatttagacataggtc aattaaaatatttgggtttaaaatgactaaatgctttaaacatattgtagcttaagatatatgtgttaagatatatacatgagaaactttaaaaggta actactgtgcatgcctgatgcttaatagaatacttagtggcatcaaatgtttgcagcagtctccataattatattcagtcccttctaatactgtatca atgtaaatgaaataaatatattcaaattggcttttttgatatgcatcaagtggcattttgttcctgtgtttaatagtgatctgtatacagctgtgcacata ttgtcatcacttattctagcatcactgttaaggctgtgattatgtttgatattcacctggattttaatacaagccaatatcagcttcccattgtgtaata acttgggtgtttaggagtcttttcacatttttttggggatatgaactagatgttcaagaactccttctggactgtggatactgaatcagtgtactattg gctgcagaatttgtttcaattgaaaatagactcaggaagattgctgctcagaatatcatataatgtttatttttttgaggtgtttttgtttttatttgtgtgt tttttttttttaagtcagcttggaactttttttcctgggtagtatttgggagagggaaaggctgtactatatatttatttctaaatgttttgactgggcatt tttcttttaatgaaatatgtggactgctctagcaaaccctattttcagctactatttgaatattcttgaacaccaccactgaagagtttcatatacacc aaataatgtctcatctctatagtacagggaatataaaattggtttcctgtggtcatgatcaagatagtagtattattacacaagaaacttggtctgc agtctggaagcttgtctgctctatagaaatgaaaatgcagcatgaagttgacattgtggaaatgaaagtaattgggtattagaaatctgaaagt actgtcatctaaaagcaattgtgattttattgtaattggttgtcactgttgtacggtgtctagaattaaagaatacatgtaaactttcatggtatttag cctttcttaaatttttttaaaatttaaactttctaacctatgtattcaacttctgtatttatatttaatcagtggttcatgttatataatacacccttaactagt taaatggaatgttggtatggtacagagtaccatattgctaagaaaactgtcttataaaagatgtatatgtgtgaagacatgaaagtttaatgtaca gaatggttggagaaatgcctatggtgaattaaagcttcatatctgctttctgaaaaaaaaaaaaaaaa (SEQ ID NO: 670) | NM_001161779 | NM_001098231 |

TABLE 1-continued

| Gene | Human Gene Sequence | Human Sequence Accession No. | Murine Sequence Accession No. |
|---|---|---|---|
| Yes1 | ggaggaggtggagagtgaggccgaggcgtggggagcccgggaactccctcctcctgaagtaacgcgtcccgggccggctctgccgtc gttgctgccgccgggcgccccgggacgaggaggtggaggagggagagggcccgcgggcctcgcctccgccctccgccacctcgagc tgcggtagcagcgactcatgagagcgcggccggaggacagatttgataatgggctgcattaaaagtaaagaaaacaaaagtccagccatt aaatacagacctgaaaatactccagagcctgtcagtacaagtgtgagccattatggagcagaacccactacagtgtcaccatgtccgtcatct tcagcaaagggaacagcagttaatttcagcagtctttccatgacaccatttggaggatcctcaggggtaacgccttttggaggtgcatcttcct cattttcagtggtgccaagttcatatcctgctggtttaacaggtggtgttactatatttgtggccttatatgattatgaagctagaactacagaaga cctttcatttaagaagggtgaaagatttcaaataattaacaatacggaaggagattggtgggaagcaagatcaatcgctacaggaaagaatg gttatatcccgagcaattatgtagcgcctgcagattccattcaggcagaagaatggtattttggcaaaatggggagaaaagatgctgaaagat tacttttgaatcctggaaatcaacgaggtattttcttagtaagagagagtgaaacaactaaaggtgcttattccctttctattcgtgattgggatga gataaggggtgacaatgtgaaacactacaaaattaggaaacttgacaatggtggatactatatcacaaccagagcacaatttgatactctgca gaaattggtgaaacactacacagaacatgctgatggtttatgccacaagttgacaactgtgtgtccaactgtgaaacctcagactcaaggtct agcaaaagatgcttgggaaatccctcgagaatctttgcgactagaggttaaactaggacaaggatgtttcggcgaagtgtggatgggaacat ggaatggaaccacgaaagtagcaatcaaaacactaaaaccaggtacaatgatgccagaagctttccttcaagaagctcagataatgaaaaa attaagacatgataaacttgttccactatatgctgttgtttctgaagaaccaatttacattgtcactgaatttatgtcaaaaggaagcttattagattt ccttaaggaaggagatggaaagtatttgaagcttccacagctggttgatatggctgctcagattgctgatggtatggcatatattgaaagaatg aactatattcaccgagatcttcgggctgctaatattcttgtaggagaaaatcttgtgtgcaaaatagcagactttggtttagcaaggttaattgaa gacaatgaatacacagcaagacaaggtgcaaaatttccaatcaaatggacagctcctgaagctgcactgtatggtcggtttacaataaagtct gatgtctggtcatttggaattctgcaaacagaactagtaacaaagggccgagtgccatatccaggtatggtgaaccgtgaagtactagaaca agtggagcgaggatacaggatgccgtgccctcagggctgtccagaatccctccatgaattgatgaatctgtgttggaagaaggaccctgat gaaagaccaacatttgaatatattcagtccttcttggaagactacttcactgctacagagccacagtaccagccaggagaaaatttataattca agtagcctattttatatgcacaaatctgccaaaatataaagaacttgtgtagattttctacaggaatcaaaagaagaaaatcttctttactctgcat gtttttaatggtaaactggaatcccagatatggttgcacaaaaccactttttttccccaagtattaaactctaatgtaccaatgatgaatttatcag cgtatttcagggtccaaacaaaatagagctaagatactgatgacagtgtgggtgacagcatggtaatgaaggacagtgaggctcctgcttatt tataaatcatttcctttcttttttccccaaagtcagaattgctcaaagaaaattatttattgttacagataaaacttgagagataaaaagctataccat aataaaatctaaaattaaggaatatcatgggaccaaataattccattccagtttttaaagtttcttgcatttattattctcaaaagtttttctaagtta aacagtcagtatgcaatcttaatatatgctttcttttgcatggacatgggccaggtttttcaaaaggaatataaacaggatctcaaacttgattaaa tgttagaccacagaagtggaatttgaaagtataatgcagtacattaatattcatgttcatggaactgaaagaataagaactttttcacttcagtcct tttctgaagagtttgacttagaataatgaaggtaactagaaagtgagttaatcttgtatgaggttgcattgatttttaaggcaatatataattgaaa ctactgtccaatcaaaggggaaatgttttgatctttagatagcatgcaaagtaagacccagcattttaaaagccctttttaaaaactagacttcgt actgtgagtattgcttatatgtccttatggggatgggtgccacaaatagaaaatatgaccagatcagggacttgaatgcacttttgctcatggtg aatatagatgaacagagaggaaaatgtatttaaaagaaatacgagaaaagaaagtgaaagttttacaagttagagggatggaaggtaatgtt taatgttgatgtcatggagtgacagaatggctttgctggcactcagagctcctcacttagctatattctgagactttgaagagttataaagtataa ctataaaactaattttcttacacactaaatgggtatttgttcaaaataatgaagttatggcttcacattcattgcagtgggatatggttttatgtaaa acatttttagaactccagttttcaaatcatgtttgaatctacattcactttttttttgtttttctttttttgagacggagtctcgctctgtcgcccaggctgga gtgcagtggcgcgatctcggctcactgcaagctctgcctcccaggttcacaccattctcctgcctcagcctcccgagtagctgggactacag gtgcccaccaccacgcctggctagtttttttgtatttttagtagagacgcagtttcaccgtgttagccaggatggtctcgatctcctgaccttgtga tctgcccgcctcggcctcccaaagtgctgggattacaggcgtgagccaccgcgcccagcctacattcacttctaaagtctatgtaatggtggt catttttttccctttttagaatacattaaatggttgatttggggaggaaaacttattctgaatattaacggtggtgaaaaggggacagtttttaccctaa agtgcaaaagtgaaacatacaaaataagactaatttttaagagtaactcagtaatttcaaaatacagatttgaatagcagcattagtggtttgagt gtctagcaaaggaaaaattgatgaataaaatgaaggtctggtgtatatgttttaaaatactctcatatagtcacactttaaattaagccttatattag gcccctctatttcaggatataattcttaactatcattatttacctgattttaatcatcagattcgaaattctgtgccatggcatatatgttcaaattcaa accatttttaaaatgtgaagatggacttcatgcaagttggcagtggactggtactaaaaattgtggagcttactgtttacgtaacctgcttagta ttgacactctctaccaagagggtcttcctaagaagagtgctgtcattatttcctcttatcaacaacttgtgacatgagatttttttaagggctttatgt gaactatgatattgtaatttttctaagcatattcaaaagggtgacaaaattacgtttatgtactaaatctaatcaggaaagtaaggcaggaaaagt tgatggtattcattaggttttaactgaatggagcagttccttatataataacaattgtatagtagggataaaacactaacttaatgtgtattcattta aattgttctgtatttttaaattgccaagaaaaacaactttgtaaatttggagatattttccaacagcttttcgtcttcagtgtcttaatgtggaagttaa cccttaccaaaaaaggaagttggcaaaaacagccttctagcacactttttttaaatgaataatggtagcctaaacttaatatttttataaagtattgt aatattgttttgtggataattgaaataaaaagttctcattgaatgcacctattaatcgttttagttgctattcatattctcattcgtttttttaaaaactgat atattctgaatttattcttccattgagaaaaaaaatgttcagttacttgtaactactgagcagaatttaatcaatcctttattaaattcagaacattattg aa (SEQ ID NO: 671) | NM_005433 | NM_009535 |

TABLE 1-continued

| Gene | Human Gene Sequence | Human Sequence Accession No. | Murine Sequence Accession No. |
|---|---|---|---|
| Met | gccctcgccgcccgcggcgccccgagcgctttgtgagcagatgcggagccgagtggagggcgcgagccagatgcggggcgacagct<br>gacttgctgagaggaggcggggaggcgcggagcgcgcgtgtggtccttgcgccgctgacttctccactggttcctgggcaccgaaagat<br>aaacctctcataatgaaggcccccgctgtgcttgcacctggcatcctcgtgctcctgtttaccttggtgcagaggagcaatggggagtgtaaa<br>gaggcactagcaaagtccgagatgaatgtgaatatgaagtatcagcttcccaacttcaccgcggaaacacccatccagaatgtcattctacat<br>gagcatcacattttccttggtgccactaactacatttatgttttaaatgaggaagaccttcagaaggttgctgagtacaagactgggcctgtgct<br>ggaacacccagattgtttcccatgtcaggactgcagcagcaaagccaatttatcaggaggtgtttggaaagataacatcaacatggctctagt<br>tgtcgacacctactatgatgatcaactcattagctgtggcagcgtcaacagagggacctgccagcgacatgtctttccccacaatcatactgc<br>tgacatacagtcggaggttcactgcatattctccccacagatagaagagcccagccagtgtcctgactgtgtggtgagcgccctgggagcc<br>aaagtcctttcatctgtaaaggaccggttcatcaacttctttgtaggcaataccataaattcttcttatttcccagatcatccattgcattcgatatca<br>gtgagaaggctaaaggaaacgaaagatggttttatgtttttgacggaccagtcctacattgatgttttacctgagttcagagattcttaccccatt<br>aagtatgtccatgcctttgaaagcaacaattttatttacttcttgacggtccaaagggaaactctagatgctcagacttttcacacaagaataatc<br>aggttctgttccataaactctggattgcattcctacatggaaatgcctctggagtgtattctcacagaaaagagaaaaaagagatccacaaag<br>aaggaagtgtttaatatacttcaggctgcgtatgtcagcaagcctggggcccagcttgctagacaaataggagccagcctgaatgatgacat<br>tcttttcggggtgttcgcacaaagcaagccagattctgccgaaccaatggatcgatctgccatgtgtgcattccctatcaaatatgtcaacgac<br>ttcttcaacaagatcgtcaacaaaaacaatgtgagatgtctccagcattttacggacccaatcatgagcactgctttaataggacacttctgag<br>aaattcatcaggctgtgaagcgcgccgtgatgaatatcgaacagagtttaccacagctttgcagcgcgttgacttattcatgggtcaattcagc<br>gaagtcctcttaacatctatatccaccttcattaaaggagacctcaccatagctaatcttgggacatcagagggtcgcttcatgcaggttgtggt<br>ttctcgatcaggaccatcaacccctcatgtgaattttctcctggactcccatccagtgtctccagaagtgattgtggagcatacattaaaccaaa<br>atggctacacactggttatcactgggaagaagatcacgaagatcccattgaatggcttgggctgcagacatttccagtcctgcagtcaatgcc<br>tctctgccccaccctttgttcagtgtggctggtgccacgacaaatgtgtgcgatcggaggaatgcctgagcgggacatggactcaacagatc<br>tgtctgcctgcaatctacaaggttttcccaaatagtgcaccccttgaaggagggacaaggctgaccatatgtggctgggactttggatttcgg<br>aggaataataaatttgatttaaagaaaactagagttctccttggaaatgagagctgcaccttgactttaagtgagagcacgatgaatacattga<br>aatgcacagttggtcctgccatgaataagcatttcaatatgtccataattatttcaaatggccacgggacaacacaatacagtacattctcctatg<br>tggatcctgtaataacaagtatttcgccgaaatacggtcctatggctggtggcactttacttactttaactggaaattacctaaacagtgggaatt<br>ctagacacatttcaattggtggaaaaacatgtactttaaaaagtgtgtcaaacagtattcttgaatgttataccccagcccaaaccatttcaactg<br>agtttgctgttaaattgaaaattgacttagccaaccgagagacaagcatcttcagttaccgtgaagatcccattgtctatgaaattcatccaacc<br>aaatcttttattagtacttggtggaaagaacctctcaacattgtcagttttctattttgctttgccagtggtgggagcacaataacaggtgttggga<br>aaaacctgaattcagttagtgtcccgagaatggtcataaatgtgcatgaagcaggaaggaactttacagtggcatgtcaacatcgctctaattc<br>agagataatctgttgtaccactccttccctgcaacagctgaatctgcaactccccctgaaaaccaaagcctttttcatgttagatgggatcctttc<br>caaatactttgatctcatttatgtacataatcctgtgtttaagccttttgaaaagccagtgatgatctcaatgggcaatgaaaatgtactggaaatt<br>aagggaaatgatattgaccctgaagcagttaaaggtgaagtgttaaaagttggaaataagagctgtgagaatatacacttacattctgaagcc<br>gttttatgcacggtccccaatgacctgctgaaattgaacagcgagctaaatatagagtggaagcaagcaatttcttcaaccgtccttggaaaa<br>gtaatagttcaaccagatcagaatttcacaggattgattgctggtgttgtctcaatatcaacagcactgttattactacttgggtttttcctgtggct<br>gaaaaagagaaagcaaattaaagatctgggcagtgaattagttcgctacgatgcaagagtacacactcctcatttggataggcttgtaagtgc<br>ccgaagtgtaagcccaactacagaaatggtttcaaatgaatctgtagactaccgagctacttttccagaagatcagtttcctaattcatctcaga<br>acggttcatgccgacaagtgcagtatcctctgacagacatgtcccccatcctaactagtggggactctgatatatccagtccattactgcaaaa<br>tactgtccacattgacctcagtgctctaaatccagagctggtccaggcagtgcagcatgtagtgattgggcccagtagcctgattgtgcatttc<br>aatgaagtcataggaagagggcattttggttgtgtatatcatgggactttgttggacaatgatggcaagaaaattcactgtgctgtgaaatcctt<br>gaacagaatcactgacataggagaagtttcccaatttctgaccgagggaatcatcatgaaagattttagtcatcccaatgtcctctcgctcctg<br>ggaatctgcctgcgaagtgaagggtctccgctggtggtcctaccatacatgaaacatggagatcttcgaaatttcattcgaaatgagactcat<br>aatccaactgtaaaagatcttattggctttggtcttcaagtagccaaaggcatgaaatatcttgcaagcaaaaagtttgtccacagagacttggc<br>tgcaagaaactgtatgctggatgaaaaattcacagtcaaggttgctgattttggtcttgccagagacatgtatgataaagaatactatagtgtac<br>acaacaaaacaggtgcaaagctgccagtgaagtggatggctttggaaagtctgcaaactcaaaagtttaccaccaagtcagatgtgtggtc<br>ctttggcgtgctcctctgggagctgatgacaagaggagccccaccttatcctgacgtaaacacctttgatataactgtttacttgttgcaaggg<br>agaagactcctacaacccgaatactgcccagaccccttatatgaagtaatgctaaaatgctggcaccctaaagccgaaatgcgcccatccttt<br>tctgaactggtgtcccggatatcagcgatcttctctactttcattggggagcactatgtccatgtgaacgctacttatgtgaacgtaaaatgtgtc<br>gctccgtatccttctctgttgtcatcagaagataacgctgatgatgaggtggacacacgaccagcctccttctgggagacatcatagtgctagt<br>actatgtcaaagcaacagtccacactttgtccaatggtttttcactgcctgacctttaaaaggccatcgatattctttgctcttgccaaaattgca<br>ctattataggacttgtattgttatttaaattactggattctaaggaatttcttatctgacagagcatcagaaccagaggcttggtcccacaggcca | NM_001127500 | NM_008591 |

TABLE 1-continued

| Gene | Human Gene Sequence | Human Sequence Accession No. | Murine Sequence Accession No. |
|---|---|---|---|
| | cggaccaatggcctgcagccgtgacaacactcctgtcatattggagtccaaaacttgaattctgggttgaatttttaaaaatcaggtaccactt gatttcatatgggaaattgaagcaggaaatattgagggcttcttgatcacagaaaactcagaagagatagtaatgctcaggacaggagcgg cagccccagaacaggccactcatttagaattctagtgtttcaaaacacttttgtgtgttgtatggtcaataacatttttcattactgatggtgtcattc acccattaggtaaacattcccttttaaatgtttgtttgtttttttgagacaggatctcactctgttgccagggctgtagtgcagtggtgtgatcatagc tcactgcaacctccacctcccaggctcaagcctcccgaatagctgggactacaggcgcacaccaccatccccggctaatttttgtatttttttgt agagacggggttttgccatgttgccaaggctggtttcaaactcctggactcaagaaatccacccacctcagcctcccaaagtgctaggatta caggcatgagccactgcgcccagcccttataaatttttgtatagacattcctttggttggaagaatatttataggcaatacagtcaaagtttcaaa atagcatcacacaaaacatgtttataaatgaacaggatgtaatgtacatagatgacattaagaaaatttgtatgaaataatttagtcatcatgaaa tatttagttgtcatataaaaacccactgtttgagaatgatgctactctgatctaatgaatgtgaacatgtagatgttttgtgtgtattttttttaaatgaa aactcaaaataagacaagtaatttgttgataaatatttttaaagataactcagcatgtttgtaaagcaggatacattttactaaaaggttcattggtt ccaatcacagctcataggtagagcaaagaaagggtggatggattgaaaagattagcctctgtctcggtggcaggttcccacctcgcaagca attggaaacaaaacttttggggagttttattttgcattagggtgtgttttatgttaagcaaaacatactttagaaacaaatgaaaaaggcaattgaa aatcccagctatttcacctagatggaatagccaccctgagcagaactttgtgatgcttcattctgtggaattttgtgcttgctactgtatagtgcat gtggtgtaggttactctaactggttttgtcgacgtaaacatttaaagtgttatatttttttataaaaatgtttattttttaatgatatgagaaaaattttgtta ggccacaaaaacactgcactgtgaacattttagaaaaggtatgtcagactgggattaatgacagcatgattttcaatgactgtaaattgcgata aggaaatgtactgattgccaatacaccccaccctcattacatcatcaggacttgaagccaagggttaacccagcaagctacaaagagggtgt gtcacactgaaactcaatagttgagtttggctgttgttgcaggaaaatgattataactaaaagctctctgatagtgcagagacttaccagaaga cacaaggaattgtactgaagagctattacaatccaaatattgccgtttcataaatgtaataagtaatactaattcacagagtattgtaaatggtgg atgacaaaagaaaatctgctctgtggaaagaaagaactgtctctaccagggtcaagagcatgaacgcatcaatagaaagaactcggggaa acatcccatcaacaggactacacacttgtatatacattcttgagaacactgcaatgtgaaaatcacgtttgctatttataaacttgtccttagatta atgtgtctggacagattgtgggagtaagtgattcttctaagaattagatacttgtcactgcctatacctgcagctgaactgaatggtacttcgtat gttaatagttgttctgataaatcatgcaattaaagtaaagtgatgcaacatcttgtaaaaaaaaaaaaaaaaaaaaa (SEQ ID NO: 672) | | |
| Ppm1g | agttgctaaggaaatgactgcccgcagcgcctggccccgccgcgcaggccgggcggggtctggagcggcgccgtttccgcttccgctc cctcacagctcccgtcccgttaccgcctcctggccggcctcgcgcctttcaccggcaccttgcgtcggtcgcgccgcggggcctgctcctg ccgcgcgcaccccccggggcttcggctccggcacgggtcgcgcccagctttcctgcacctgaggccgccggccagccgccgccatgggt gcctacctctcccagcccaacacggtgaagtgctccggggacggggtcggcgccccgcgcctgccgctgccctacggcttctccgccat gcaaggctggcgcgtctccatggaggatgctcacaactgtattcctgagctggacagtgagacagccatgttttctgtctacgatggacatg gaggggaggaagttgccttgtactgtgccaaatatcttcctgatatcatcaaagatcagaaggcctacaaggaaggcaagctacagaaggc tttagaagatgccttcttggctattgacgccaaattgaccactgaagaagtcattaaagagctggcacagattgcagggcgacccactgagg atgaagatgaaaaagaaaaagtagctgatgaagatgatgtggacaatgaggaggctgcactgctgcatgaagaggctaccatgactattga agagctgctgacacgctacgggcagaactgtcacaagggccctccccacagcaaatctggaggtgggacaggcgaggaaccagggtc ccagggcctcaatggggaggcaggacctgaggactcaactagggaaactccttcacaagaaaatggccccacagccaaggcctacaca ggcttttcctccaactcggaacgtgggactgaggcaggccaagttggtgagcctggcattcccactggtgaggctgggccttcctgctcttc agcctctgacaagctgcctcgagttgctaagtccaagttctttgaggacagtgaggatgagtcagatgaggcggaggaagaagaggaaga cagtgaggaatgcagcgaggaagaggatggctacagcagtgaggaggcagagaatgaggaagatgaggatgacaccgaggaggctg aagaggacgatgaagaagaagaagaagagatgatggtgccagggatggaaggcaaagaggagcctggctctgacagtggtacaacag cggtggtggccctgatacgagggaagcagttgattgtagccaacgcaggagactctcgctgtgtggtatctgaggctggcaaagctttaga catgtcctatgatcacaaaccagaggatgaagtagaactagcacgcatcaagaatgctggtggcaaggtcaccatggatgggcgagtcaa cgggggcctcaacctctccagagccattggggaccacttctataagagaaacaagaacctgccacctgaggaacagatgatttcagccctt cctgacatcaaggtgctgactctcactgacgaccatgaattcatggtcattgcctgtgatggcatctggaatgtgatgagcagccaggaagtt gtagatttcattcaatcaaagatcagccagcgtgatgaaaatggggagcttcggttattgtcatccattgtggaagagctgctggatcagtgcc tggcaccagacacttctggggatggtacagggtgtgacaacatgacctgcatcatcatttgcttcaagccccgaaacacagcagagctcca gccagagagtggcaagcgaaaactagaggaggtgctctctactgaggggggctgaagaaaatggcaacagcgacaagaagaagaaggc caagcgagactagcagtcatccagacccctgcccacctagactgttttctgagccctccggacctgagactgagttttgtctttttcctttagcc ttagcagtgggtatgaggtgtgcaggggggagctgggtggcttcactccgcccattccaaagagggctctccctccacactgcagccggga gcctctgctgtccttcccagccgcctctgctcctcgggctcatcaccggttctgtgcctgtgctctgttgtgttggagggaaggactggcggtt ctggtttttactctgtgaactttatttaaggacattctttttttattggcggctccatggccctcggccgcttgcacccgctctctgttgtacactttca atcaacactttttcagactaaaggccaaaacctaa (SEQ ID NO: 673) | NM_177983 | NM_008014 |

TABLE 1-continued

| Gene | Human Gene Sequence | Human Sequence Accession No. | Murine Sequence Accession No. |
|---|---|---|---|
| Blvrb | Ggcgtggcccttcgagccagctccgccccgttgttcctggcttgagtagggcagagagcaccgcccagcagccagtgggttcccgcgc<br>gtgccgagactctgaggccttgcacccccacgatcccgtacgatggccgtcaagaagatcgcgatcttcggcgccactggccagaccgg<br>gctcaccaccctggcgcaggcggtgcaagcaggttacgaagtgacagtgctggtgcgggactcctccaggctgccatcagaggggccc<br>cggccggcccacgtggtagtgggagatgttctgcaggcagccgatgtggacaagaccgtggctgggcaggacgctgtcatcgtgctgct<br>gggcacccgcaatgacctcagtcccacgacagtgatgtccgagggcgcccggaacattgtggcagccatgaaggctcatggtgtggaca<br>aggtcgtggcctgcacctcggctttcctgctctgggaccctaccaaggtgcccccacgactgcaggctgtgactgatgaccacatccggat<br>gcacaaggtgctgcgggaatcaggcctgaagtacgtggctgtgatgccgccacacataggagaccagccactaactggggcgtacaca<br>gtgaccctggatggacgagggccctcaagggtcatctccaaacatgacctgggccatttcatgctgcgctgcctcaccaccgatgagtacg<br>acggacacagcacctacccctcccaccagtaccagtagcactctgtccccatctgggagggtggcattctgggacatgaggagcaaagga<br>agggggcaataaatgttgagccaagagcttcaaattactctagagaaaccgacaaaaaaaaaaaaaaaaaa (SEQ ID NO: 674) | NM_000713 | NM_144923 |
| Tnk1 | ggaactcggggtgcggccctcgccggccccgggccagcggccaggtccccgccctccgcgggatttactcctgtcccgcctcctcggat<br>ttagcccaggcagcctgggaggttccgcagtcgccgcttccgccttgaccaggtggagctggagacctggtctctctagggcctaccctga<br>gctcaccatctgaaggagagtgccatcatccttaggaactccttctccagacatgcttcctgaggctggctccctgtggctactgaagctgct<br>ccgggacatccagttggcccagttttactggcccatccttgaggagcttaatgtcactcggccagagcacttcgactttgtaaagcctgagga<br>cctggacggcattggcatgggccggcctgcccagcgcagactgtccgaagctctgaaaaggctacgttctgggcctaagtctaagaactg<br>ggtctacaagatccttggaggttttgcccctgagcacaaggagcccaccctgccctcggacagcccacggcacctccctgagccagagg<br>ggggcctcaagtgtctgatcccagagggtgctgtttgcagaggggagctgctgggttcaggctgcttcggtgtggtgcaccgagggctgtg<br>gacgctgcccagtggcaagagtgtcccagtggctgtcaagtccctccgggtaggtcccgaaggcccgatgggcacagaactgggggac<br>ttcctgcgagaggtatcggtcatgatgaacttggagcacccacacgtgctgcgtctgcacggccttgtactgggccagcctctgcagatggt<br>gatggagctggcgccactgggctccctgcacgcgcgcctaacggccccggccccgacacccccgctgctcgtggccctgctctgcctctt<br>cctgcggcagctggcgggagccatggcgtacctgggggcccgcgggctggtgcaccgagacctcgctacgcgcaacctactgctggc<br>gtcgccgcgcaccatcaaggtggctgacttcgggctggtgcggcctctgggcggtgcccggggccgctacgtcatgggcgggccccgc<br>cctatcccctacgcctggtgtgccccagagagcctgcgccacggagccttctcgtctgcctcggacgtgtggatgtttggggtgacgctgtg<br>ggagatgttctccgggggcgaggaaccctgggccggggtcccaccgtacctcatcctgcagcggctggaggacagagcccggctgcct<br>aggcctcccctctgctccagggccctctactccctcgccttgcgctgctgggcccccaccctgccgaccggcctagcttttcccacctgga<br>ggggctgctgcaagaggccgggccttcggaagcatgttgtgtgagggatgtcacagaaccaggcgccctgaggatggagactggtgac<br>cccatcacagtcatcgagggcagctcctctttccacagccccgactccacaatctggaagggccagaatggtcgcaccttcaaagtgggca<br>gcttcccagcctcggcagtgacgctggcagatgcggggggcttgccagccacccgtccagtccacagaggcacccctgcccggggaga<br>tcaacacccaggaagcatagatggagacagaaagaaggcaaatctttgggatgcgcccccagcacggggccagaggaggaacatgcc<br>cctggagaggatgaaaggcatttccaggagtctggagtcagttctgtccctcggtcctcgtcccacaggggggtggttcaagccccccctgaa<br>attcgacaagccagagctgtgccccagggacctccaggcctgcctccacgcccacctttatcctctagctctcctcagcccagccagccctc<br>tagggagaggcttccctggcccaaaagaaaacccccacacaatcaccccatgggaatgcctggagcccgtaaagccgctgccctctctg<br>gaggcctcttgtccgatcctgagttgcagaggaagattatggaggtggagctgagtgtgcatggggtcacccaccaggagtgccagacag<br>cactaggagccactgggggagatgtggtttctgccatccggaacctcaaggtagatcagctcttccacctgagtagccggtccagagctga<br>ctgctggcgcatcctggagcattaccagtgggacctctcagctgccagccgctatgtcctggccaggccctgagctcagcttctgcgggca<br>cagacaccagcatgaaaagcctaggcccctgagggcctggccacatgggaccaagcggaaccagaacaaggtcccgacaggggtaga<br>cgttccacctggggagatcccacctgccgtaggcacatggaggaggagcccagagttgggcactggcaaatgtctcctccctcccatgct<br>ccttggcttctgaaggctgaagctcctttggctgggccaagaaggatctagtctgcccactacattctcaaacaagaggacttggaggaaaa<br>gagctgctatacatcatatgcagaggaagcttctacgcgctagagaggatcaaggggccacactggaccatgtgaacagccatcctgaact<br>gccatcagctaccacactggactctgcagggcagccatcctggatgatggaagccaccatattgacttggggtataggcccaaactgcctt<br>cgtttggtccagggccatcgtgggtgatgacgattgctctcttgcactcaaggacatttgatgctggtagtatggattatgagatggactagcc<br>cctgccccagcccagctctcacattcccctttgtttttcccataccaactgcttctaccctcccctattacatacatctttcaatgtccaaaaagtt<br>acaaagtttatatgaatgtaacatataaaaaaa (SEQ ID NO: 675) | NM_001251902 | NM_031880 |
| Prkab2 | actgggcggactccgcgccgccggccttgtagccattttaggaggaatcgctggtcgccagcgaggggtgcggcttcaatttcaataacttt<br>attggtggcctgatctgcagaacagccatcacatcagtggcccttggaggagggagcgcatcgcccgaggtggtccccgacgagctgca<br>gccatgggaaacaccaccagcgaccgggtgtccggggagcgccacggcgccaaggctgcacgctccgagggcgcaggcggccatg<br>ccccggggaaggagcacaagatcatggtggggagtacggacgaccccagcgtgttcagcctccctgactccaagctccctggggacaa<br>agagtttgtatcatggcagcaggatttggaggactccgtaaagcccacacagcaggcccggcccactgttatccgctggtctgaaggagg | NM_005399 | NM_182997 |

TABLE 1-continued

| Gene | Human Gene Sequence | Human Sequence Accession No. | Murine Sequence Accession No. |
|---|---|---|---|
| | caaggaggtcttcatctctgggtccttcaacaattggagcaccaagattccactgattaagagccataatgactttgttgccatcctggacctcc | | |
| | ctgagggagagcaccaatacaagttctttgtggatggacagtgggttcatgatccatcagagcctgtggttaccagtcagcttggcacaatta | | |
| | acaatttgatccatgtcaagaaatctgattttgaggtgttcgatgctttaaagttagattctatggaaagttctgagacatcttgtagagacctttcc | | |
| | agctcaccccccagggccttatggtcaagaaatgtatgcgtttcgatctgaggaaagattcaaatccccacccatccttcctcctcatctacttca | | |
| | agttattcttaacaaagacactaatatttcttgtgacccagccttactccctgagcccaaccatgttatgctgaaccatctctatgcattgtccatta | | |
| | aggacagtgtgatggtccttagcgcaacccatcgctacaagaagaagtatgttactactctgctatacaagcccatttgaagggatcccttctt | | |
| | gcctctaaggattcaggagaagcatctcccttgcatttctggactgaaccagtcttacctgagactggaaggctgatttgctttgaggctgatat | | |
| | gtgtgtttcagagcctctgagtaggatgctctgctttgcatttgattgcagatgagagctttatgagttcacggaatttattttaagaaaaaaaaa | | |
| | tatacatatgagaagaaggtaaatggaagcctcctagccccagctagaagtattgtttctgcctgtgggttttcaccaagacctgtttgggggc | | |
| | gctgcaggaataactatataggaagattttttcctaaaatgaaagaacagcaaactcttaggatccttgttgggtggagattctatcactgctacc | | |
| | ttggctctccaaggaatgggcttgtgctagaccgctgccctacttaacagctgcctcattgcaagggcagtttttcttgcatgggttctctatatt | | |
| | cccagagtatgtggcacaatctgtgttgtttatatgataccagatgccccacaagaacccttattcctctcatttcacattcttcctttaatagcctc | | |
| | cttcagatcccatacctgacccctctctaacacaaaacttattgggtaagtgactttgaaaagttttgtggcacctgacccaccccagacacta | | |
| | gggctatcagaaggtctcctttttagcccagcacaggcccaggccactttgtcgtgtttgttttaacttctaaagaaaatatgtttcagcattataa | | |
| | gaaaggcagaatgcagaacacctacattttgttttagtttggtgccaaggctcaggctgtattggcaaattcccgaaagttttcccactttgcct | | |
| | ggccctgcttctgtcttttctttctcagtaaacagttctgaaggcaggagtggaacccgggagtattttcatgtctttcatccttgaaagatttttat | | |
| | gtgcctgcatttttttttaattaaaaaatgccttttcattggtcttaagagaccgcattggagaatttcaggcttttgataaatgcttcttcaaagaga | | |
| | ttttcttctctagtctagccttccacattcttagattaatatggccaaccctgtacacatcactacactaaacactgctctagataaactgctcaagt | | |
| | tcatttaactcatttgatgcacctaaaggggttcctcattttaaagatttgttaggccaagaagcaagagagtattcctagtattcccaaccatga | | |
| | aaagtatcattctttgcaccaaatgttaacaaaatcatttgttctcctgcctcttctttttaaaggtgtttgatgcttaagtggggtcactgaattcca | | |
| | tttgtggactgaaaagtattcaatccacttttggggttcagagataaaacatttttttcccaagtagctggggctcttccattttgcagataagtcaa | | |
| | ataatcaacactaaaggaggctaaactgttgatgaatgagagactccctgactgctcagatgaccctagccacactgaaagggcacctaca | | |
| | ggtcagtttagctacctcctgtctttcccatgcaaagctgataacacagttgtctttggacttgtagacctcttggattccaggtgtgatggagta | | |
| | aagtgtgggattgttgttttgctgggatgcaaataactaaatgctttggtggttaattgctaagagtaaatactactttagccatccaaggccacc | | |
| | ttctgcagcaaaaggcttttgtggagaaccttttatgttcccaaccactttttgaatggtgtgccatttaaaaatccaggccagatcctattataac | | |
| | caactctcaggatttacagccttcagttgtactagaattttgtttttatccaatactcattaaataagtgggccacttaggaagattcaaaatcttgg | | |
| | ttattacatgaagtttgttatatttcttgtcaacagtattgaaatgtaatatgtatgtgttcatgtatgaaaatttttactccacacaggtgtttcagtag | | |
| | agtggggcaggaaaagagatctcttcgatttctttcaggcctgaggcttttgtgaaatgcgtcagccccctgtgacagtaggttttgatgctagt | | |
| | gatcttcagatctttctctctggaaatgtgcagagagtgtcagtttcccaagttctgaggtaactctcagcccagatgtgaaatgggagcctac | | |
| | cagctggtatagaagggaatgggtaggaggcactgggtgctgactcattcagcactgtccctttttctatactgctgatacatcccatggttctg | | |
| | agaagccttatctcagtctatttggaagagagggaggaagagaaggaagtaacccaaagtactactcatttatcattgtatattgattagttaaa | | |
| | gggataattaatttaatgctgaggagagtttgacagattttgaaaatgagtaaaggcaaaaaaaatttttttagcctttattttgcttttgggaatttt | | |
| | acagagtcaaagtaggcagaataagaaaatagttcttcaggagggccgacctttaaagaacttcaacatagtttcggaattgtggggaagag | | |
| | aagagtgactgagctgagaagtaataatagaataaagggttgagtaacttacaactgaaaatgatctcttttaaaaagaaattaaatcagacac | | |
| | cacatggtggtgtccttggatctcactgtacagaattagcagtgtataaccatcttctcttttcatcttgttccaattctctcctctttcctttccattct | | |
| | gctttaagctcatgtgtcaggcagactttaccagagtgtcagacattacctaaaacacatacgttagccatgctgctggtatggagaaattcca | | |
| | caccatgattattagcctcctttaagctgaatgggatttaaccattctaggcaacaccccctgaagggcatacctaacctcaatagtgttggctttt | | |
| | aaaacgtatgtttgtatggtagagaaactttgtaaaagaagaatccaagagaagtttgtgaggatcctacaaacccaggcccactcactttgct | | |
| | ctaattctttctagtatcttgtagatctaatgggtctgggataaaaactttgaaaagtgtcaatattccatgtatgctgctgaaatgaagttaagtttg | | |
| | gaaagaagtgatacctctagactgggtttatattaatctgggatataaatgaagaagacatactaatagaactccttgcttttaattggggaaata | | |
| | gggctttaataatttgacctcaactaaaaatgatatgcaatagtctctgtgtgtgtttgaaatacattgtgttctcagagatttctacattctcacgtt | | |
| | ctagtgatttggggcatgggcttaatagcagatgtacagtgtattcctgcattattgtgcttccccttaaagcccagttcttgctgtcttctaccag | | |
| | gggctgctgactccagttacccatggaatgcaggacctgggaggggtagccattagggtctttcaaaactctttggatctaagcatttgtctct | | |
| | ccttaagtgccaatcacaattggatatggaaggactgtgatttctgcaatgaacccaaacttttagagtaaaaagccaaatttaaattataagaa | | |
| | agaagggaaaaaagagaaaaactcaagtctattacttgtagagtccaattcttagcaatggaatcgctctaggattctagtttgggctttgtctg | | |
| | gatttgcttttctcagttgtgctttgaagtgaataagctttgttacaaattaatttttttattagttccaatattagttggagttaacttgaattgcttgtatg | | |
| | tagcacagcacttttgcagtaagattggtgtgaaatactaaacactatggattttgtaggtgtcaggttaaatggtcaagggatacctacattaa | | |
| | gtcatatattaggtattgatgatcttacttcttttctgttcccctgtacaaaacacttacctaacccagcttgtggttttaggacagccaaagctcac | | |
| | tgttgttggttagtcctaatcactacacgggtctcataaatgagacttgtttgaattttggtacattggagcatgttggttggtattacacggcagc | | |
| | atttcgaatgagtgcagctctgtgtctgtcagaaaggagagataagactactttgaagggaattaaatatgtgagtcctcttttaatggtgcttttt | | |

TABLE 1-continued

| Gene | Human Gene Sequence | Human Sequence Accession No. | Murine Sequence Accession No. |
|---|---|---|---|
| | tgtaacctttaatgctgaggtacagagctgcttttcaatatttcataaaggagtggcagacaagagtggattttaaagctgttcttcaaacgtaatt tgtcactggactctgacacacctggaaattatatgatatgatacatacagaaatgttgtgggtttttccataaaactttaataaaagtattatacag caataaaaaaaaaaaaaaa (SEQ ID NO: 676) | | |
| Trpm7 | gcgccgctcacgtggtccgtccccagccccgtcgccggcggaggcgggcgcgggcgcgtccctgtggccagtcacccggaggagttg gtcgcacaattatgaaagactcggcttctgctgctagcgccggagctgagttagttctgagaaggtttccctgggcgttccttgtccggcggc ctctgctgccgcctccggagacgcttcccgatagatggctacaggccgcggaggaggaggaggtggagttgctgcccttccggagtccg ccccgtgaggagaatgtcccagaaatcctggatagaaagcactttgaccaagagggaatgtgtatatattataccaagttccaaggaccctc acagatgccttccaggatgtcaaatttgtcagcaactcgtcaggtgtttttgtggtcgcttggtcaagcaacatgcttgttttactgcaagtcttgc catgaaatactcagatgtgaaattgggtgaccattttaatcaggcaatagaagaatggtctgtggaaaagcatacagaacagagcccaacg gatgcttatggagtcataaattttcaaggggggttctcattcctacagagctaagtatgtgaggctatcatatgacaccaaacctgaagtcattct gcaacttctgcttaaagaatggcaaatggagttacccaaacttgttatctctgtacatgggggcatgcagaaatttgagcttcacccacgaatc aagcagttgcttggaaaaggtcttattaaagctgcagttacaactggagcctggattttaactggaggagtaaacacaggtgtggcaaaacat gttggagatgccctcaaagaacatgcttccagatcatctcgaaagatttgcactatcggaatagctccatggggagtgattgaaaacagaaat gatcttgttgggagagatgtggttgctccttatcaaaccttattgaacccccctgagcaaattgaatgttttgaataatctgcattcccatttcatatt ggtggatgatggcactgttggaaagtatggggcggaagtcagactgagaagagaacttgaaaaaactattaatcagcaaagaattcatgct aggattggccagggtgtccctgtggtggcacttatatttgagggtgggccaaatgttatcctcacagttcttgaataccttcaggaaagccccc ctgttccagtagttgtgtgtgaaggaacaggcagagctgcagatctgctagcgtatattcataaacaaacagaagaaggagggaatcttcct gatgcagcagagcccgatattatttccactatcaaaaaaacatttaactttggccagaatgaagcacttcatttatttcaaacactgatggagtg catgaaaagaaaggagcttatcactgttttccatattgggtcagatgaacatcaagatatagatgtagcaatacttactgcactgctaaaaggta ctaatgcatctgcatttgaccagcttatccttacattggcatgggatagagttgacattgccaaaaatcatgtatttgtttatggacagcagtggct ggttggatccttggaacaagctatgcttgatgctcttgtaatggatagagttgcatttgtaaaacttcttattgaaaatggagtaagcatgcataa attccttaccattccgagactggaagaactttacaacactaaacaaggtccaactaatccaatgctgtttcatcttgttcgagacgtcaaacagg gaaatcttcctccaggatataagatcactctgattgatataggacttgttattgaatatctcatgggaggaacctacagatgcacctatactagg aaacgttttcgattaatatataatagtcttggtggaaataatcggaggtctggccgaaatacctccagcagcactcctcagttgcgaaagagtc atgaatcttttggcaatagggcagataaaaaggaaaaaatgaggcataaccatttcattaagacagcacagccctaccgaccaaagattgat acagttatggaagaaggaaagaagaaaagaaccaaagatgaaattgtagacattgatgatccagaaaccaagcgctttccttatccacttaat gaacttttaatttgggcttgccttatgaagaggcaggtcatggcccgtttttatggcaacatggtgaagaatcaatggctaaagcattagttgc ctgtaagatctatcgttcaatggcatatgaagcaaagcagagtgacctggtagatgatacttcagaagaactaaaacagtattccaatgatttt ggtcagttggccgttgaattattagaacagtccttcagacaagatgaaaccatggctatgaaattgctcacttatgaactgaagaactggagta attcaacctgccttaagttagcagtttcttcaagacttagaccttttgtagctcacacctgtacacaaatgttgttatctgatatgtggatgggaag gctgaatatgaggaaaaattcctggtacaaggtcatactaagcattttagttccacctgccatattgctgttagagtataaaactaaggctgaaa tgtcccatatcccacaatctcaagatgctcatcagatgacaatggatgacagcgaaaacaactttcagaacataacagaagagatccccatg gaagtgtttaaagaagtacggattttggatagtaatgaaggaaagaatgagatggagatacaaatgaaatcaaaaaagcttccaattacgcg aaagttttatgccttttatcatgcaccaattgtaaaattctggtttaacacgttggcatatttaggctttctgatgctttatacatttgtggttcttgtaca aatggaacagttaccttcagttcaagaatggattgttattgcttatatttttacttatgccattgagaaagtccgtgagatctttatgtctgaagctg ggaaagtaaaccagaagattaaagtatggtttagtgattacttcaacatcagtgatacaattgccataatttctttcttcattggctttggactaag atttggagcaaaatggaactttgcaaatgcatatgataatcatgtttttgtggctggaagattaatttactgtcttaacataatattttggtatgtgcg tttgctagattttctagctgtaaatcaacaggcaggaccttatgtaatgatgcttggaaaaatggtggccaatatgttctacattgtagtgcttatg gctcttgtattacttagttttggtgttcccagaaaggcaatactttatcctcatgaagcaccatcttggactcttgctaaagatatagtttttcaccca tactggatgattttggtgaagtttatgcatacgaaattgatgtgtgtgcaaatgattctgttatccctcaaatctgtggtcctgggacgtggttga ctccatttcttcaagcagtctacctctttgtacagtatatcattatggttaatcttcttattgcatttttcaacaatgtgtatttacaagtgaaggcaattt ccaatattgtatggaagtaccagcgttatcattttattatggcttatcatgagaaaccagttctgcctcctccacttatcattcttagccatatagttt ctctgttttgctgcatatgtaagagaagaaagaaagataagacttccgatggaccaaaacttttcttaacagaagaagatcaaaagaaacttca tgattttgaagagcagtgtgttgaaatgtatttcaatgaaaaagatgacaaatttcattctgggagtgaagagagaattcgtgtcacttttgaaag agtggaacagatgtgcattcagattaaagaagttggagatcgtgtcaactacataaaaagatcattacaatcattagattctcaaattggccatt tgcaagatctttcagccctgacggtagatacattaaaaacactcactgcccagaaagcgtcggaagctagcaaagttcataatgaaatcaca cgagaactgagcatttccaaacacttggctcaaaaccttattgatgatggtcctgtaagaccttctgtatggaaaaagcatggtgttgtaaatac acttagctcctctcttcctcaaggtgatcttgaaagtaataatccttttcattgtaatattttaatgaaagatgacaaagatccccagtgtaatatatt tggtcaagacttacctgcagtaccccagagaaaagaatttaattttccagaggctggttcctcttctggtgccttattcccaagtgctgtttcccc | NM_017672 | NM_021450 |

TABLE 1-continued

| Gene | Human Gene Sequence | Human Sequence Accession No. | Murine Sequence Accession No. |
|---|---|---|---|
| | tccagaactgcgacagagactacatggggtagaactcttaaaaatatttaataaaaatcaaaaattaggcagttcatctactagcataccacat | | |
| | ctgtcatccccaccaaccaaatttttttgttagtacaccatctcagccaagttgcaaaagccacttggaaactggaaccaaagatcaagaaact | | |
| | gtttgctctaaagctacagaaggagataatacagaatttggagcatttgtaggacacagagatagcatggatttacagaggtttaaagaaaca | | |
| | tcaaacaagataaaaatactatccaataacaatacttctgaaaacactttgaaacgagtgagttctcttgctggatttactgactgtcacagaact | | |
| | tccattcctgttcattcaaaacaagcagaaaaaatcagtagaaggccatctaccgaagacactcatgaagtagattccaaagcagctttaata | | |
| | ccggattggttacaagatagaccatcaaacagagaaatgccatctgaagaaggaacattaaatggtctcacttctccatttaagccagctatg | | |
| | gatacaaattactattattcagctgtggaaagaaataacttgatgaggttatcacagagcattccatttacacctgtgcctccaagaggggagc | | |
| | ctgtcacagtgtatcgtttggaagagagttcacccaacatactaaataacagcatgtcttcttggtcacaactaggcctctgtgccaaaataga | | |
| | gtttttaagcaaagaggagatgggaggaggtttacgaagagctgtcaaagtacagtgtacctggtcagaacatgatatcctcaaatcagggc | | |
| | atctttatattatcaaatcttttcttccagaggtggttaatacatggtcaagtatttacaaagaagatacagttctgcatctctgtctgagagaaattc | | |
| | aacaacagagagcagcacaaaagcttacgtttgcctttaatcaaatgaaacccaaatccataccatattctccaaggttccttgaagttttcctg | | |
| | ctgtattgccattcagcaggacagtggtttgctgtggaagaatgtatgactggagaatttagaaaatacaacaataataatggagatgagatta | | |
| | ttccaactaatactctggaagagatcatgctagcctttagccactggacttacgaatatacaagaggggagttactggtacttgatttgcaaggt | | |
| | gttggtgaaaatttgactgacccatctgtgataaaagcagaagaaaagagatcctgtgatatggtttttggcccagcaaatctaggagaagat | | |
| | gcaattaaaaacttcagagcaaaacatcactgtaattcttgctgtagaaagcttaaacttccagatctgaagaggaatgattatacgcctgataa | | |
| | aattatatttcctcaggatgagccttcagatttgaatcttcagcctggaaattccaccaaagaatcagaatcaactaattctgttcgtctgatgttat | | |
| | aatattaatattactgaatcattggttttgcctgcacctcacagaaatgttactgtgtcacttttccctcgggaggaaattgtttggtaatatagaaa | | |
| | ggtgtatgcaagttgaatttgctgactccagcacagttaaaaggtcaatattcttttgacctgattaatcagtcagaaagtccctataggataga | | |
| | gctggcagctgagaaattttaaaggtaattgataattagtatttataactttttaaagggctctttgtatagcagaggatctcatttgactttgttttga | | |
| | tgagggtgatgctctctcttatgtggtacaataccattaaccaaaggtaggtgtccatgcagattttattggcagctgttttattgccattcaacta | | |
| | gggaaatgaagaaatcacgcagccttttggttaaatggcagtcaaaattttcctcagtgtatttagtgtgttcagtgatgatatcactggttccca | | |
| | actagatgcttgttggccacgggaagggaaatgacttgttctaattctaggttcacagaggtatgagaagcctgaactgaagaccattttcaa | | |
| | gagggacggtatttatgaatcagggttaggctccatatttaaagatagagccagtttttttttttaaatagaacccaaattgtgtaaaaatgttaatt | | |
| | gggtttttttaaacattgttttatcaagtcactgttaagtagaagaaagccatggtaaactgatacataacctaaattataaaagcagaaacctaac | | |
| | tcactcgtcaagggaagttacctttttgaggaaagttaaagtactttttttccctatctgtatctatagcaacaacccagaacttacaaacttctccaa | | |
| | agattttattgattgttatatcaaatcagaatgtaaacatgaactcttgcatatatttaaaattgtgttggaacatttgaacatgaatgctgtttgtggt | | |
| | acttaagaaattaattcagttggattatcattatgtgatactggcagattgcagtgcaaccttatgccaataaaatgtaatttaacagccccagat | | |
| | attgttgaatattcaacaataacaagaaaagcttttcatctaagttttatgctttaatttttttttcttttttttttctttttctttttgtttccttggtactaattttaat | | |
| | ttttatttggaagggagcagtataaagcttatttgtatttagtagtgtatctcatagatacagacaaggcaagagatgataagctgtttaaatagtg | | |
| | tttaatattgattgggggtggggagaaagaaaaaagtgtattacttaaagatactatatacgttttgtatatcattaaatctttaaaagaaatgaaata | | |
| | aatttattgtttacagatgtttagtgagtttaatcattctgaaaaattatctgacattttcagggtgtcaatttgagtatcagtttttttaaatgaaccatt | | |
| | tgtatacctgtgctttgatctcctgtcctgtacaatgtttaaattaatactgatttcttactgtcttcttagaaatctgtttttttgttaggccaaaaaagg | | |
| | gcaatatgggctgtctgttgatttttaattttatattgattattttcacaggcttataatagtagctatactttttttttttttttttttttttgagacggagtctc | | |
| | gctctgttgcttgggctggagtgcagtggtgcgatctcagctcaccacaaccgccgccttccgggtttaagtgattctcctgcctcagcctcc | | |
| | cgagtagctgggactacaggcacacgccaccatgcccagctaattttttatatttttagtagagacagggtttcactatgttggccagtgtggtc | | |
| | acaaactcctgaccttgtgagccaccgcacctggctgctaacacttatttagtgcctactgtgtaccagacattactctaagtatttcacatatatt | | |
| | aacctacttaatccttataacaatgttataaagaaataggtgttattatcctgttttgcagatttgaaagtcaaggtgctagagaggtaaagtaac | | |
| | gtccataagattcttacgtttatttaataataagtagcaacggtaggatttgaacccaggctggctgcctttcatctatactgtttttgttttgttttgtt | | |
| | ttgttttgttttgttttgtttgtcttggtggggcatggtggctcatgcctgtaatcccagcacttcgggaggccaaggcaggtggatcacttgggc | | |
| | tcaggagtttgagaccagcctgggcaacatggcaaaatcctatctctgctaaaaaaaaaaaatacaaaaattaggccaggtgcagtggctcat | | |
| | gcctgtaatcccagcactttgggaggccaaggtgggcggatcacaaggtcaggagttcgagaccagcctgaccaacatagtgaaacccc | | |
| | gtctctactaaaaatacaaaaaattagctgggcatggcggtgagtgcctgtaatcccagctactcaggagtctgaggcaggagaattgcttg | | |
| | aacctgggaggtggaggttgcagtgagctgagatcgtgccattgcgctccagcctgggcaacagtgcgagactccgtcaaaaaaaaaaa | | |
| | aataactggatgtgatggtgtgcacctgtagttccagctacttgggagactgaggtgggaggatcacttgagcctgggagactgaggcagc | | |
| | agtgagctgagatcatgccactgctttccaacctgggcaacagagtgagatcctgtctcagaaagaaaaaaaaaaaaaagacaacctcttg | | |
| | ctctgttgcccaggctggagtgtagtagcgtgatcatagctcactgcagccgtaaactcctgggctcaagcaatcctcctgccactgcctctt | | |
| | gattaggtggaaccacaggcatgcaccaccacacgtacctaattttatatatatattttttttattttttcatttttatttatttttgtttttttgagttgaagtc | | |
| | tcactctgttgcccaggccggagtacagtggcacaatcttggctcactgcaacctctgcctcccaagatcaagcaattctcgtgcttcagcct | | |
| | ccaaagtagctgagattacaggtacccaccataatgcctggctgctttttgtatttttcgtagagacaaggtttcaccttgttggccaggctgatc | | |
| | tcaaactcctgacctcaagtgatccacctcccccggctacccaaagtactgggattataggtgtgagccaccatgcctgggtaacacccaac | | |

TABLE 1-continued

| Gene | Human Gene Sequence | Human Sequence Accession No. | Murine Sequence Accession No. |
|---|---|---|---|
| | taattttaaatatatattttgtagagatggggtctagccttgttgcccacgctggtctcaaattcctgggctcaagtgatcctctcgcctgagcttc ccaaagtggtagaattgcaggcatgaattgctgcacccagcctcatctgtgctgtgaattatgtgctgtattgactctcaagcatgatgaccatt ggtggtttctgtaccatttcctgttactttactgaaacacacctactccattaacttcttgggttaagtctagaaagtaacagtttacttgtaaacca catttcttatccccaataagtattttttaagcttattaaagttcattattactaccctatgatgtgaaagtgtcatttgcttaatctttttaatttttttattctc aacctcatcttactgaagagaataaaactcttttaccatattcttaaaatgtggaattctcggccaggtgcagtggctcacgcctgtaattccatc actttgggaggccaaggtgggtggatcatctgaggtcaggagttcaagaccagcctggccaacatggtgaaaccccgtctctactaaaaat acaaaaattatctgggtgtggtggcgcgtgcctgtaggcccagctactcaggaggctgaggcaggagaattgcttgaacccaagaggtgg aggttgcagtgagcctagattgctgccactgcactccagcctgggtgacagcagaactctgtctcaaaaaaaagatgtggaattcttttctgc aaatgttctctaatagtataccttcttcagtctgtcgatatatgtatgctattattttacaagtaatacatgttgcttgtattggaaattatagaaaagat tatattggattgtttagaaaatatttttaaatgtgaagaaaaatataaaaattactcccttgttccactttccccactctcaagtcagactatgttgtttt catagttagtagctagcagtctaccccactagattatatgcttcacagagggaagggaccctcaagacttcactggattgagtagcacccaat accttgcttgctgcctggtttgtgatgggcatactgtaagaaaaaaaaatctgaatgacaaaatgtttttccataataccagacttcctcttgaag agatgggtcgtaatgttgtagtcttacatgcttacgtagacaatcaaagcaagaatactcaataaatggctatttaccacttgaaagaaa (SEQ ID NO: 677) | | |
| Ppp3cc | aaggcggaagggtggggagggcggcgctcggggcgggaggcccggccgggtccgctaggacagcggggccgctgggaagttgtg agagcggcgctcgggggcgcgcttgcgtgcacgagggcccgggccgcgagcagccgcggccgtcccggtcgccacccttagcagcg gtcgcggtcggtgccgaagcggtgttccccgccttagccgctggcgcctcccaagagagcggccggtgggccctcgtcctgtcagtggc gtcggaggccggcgctgcggtggccgcgcccttctggtgctcggacaccgctgaggagccggggccgggcacggctggctgacggct ccgggcagctaaggctgcccgaggagaaggcggcggccgcggcgtaggcgcacgtccggcgggctcctggagcctggaggaggcc gaggggaccatgtccgggaggcgcttccacctctccaccaccgaccgcgtcatcaaagctgtcccctttcctccaacccaacggcttacttt caaggaagtatttgagaatgggaaacctaaagttgatgttttaaaaaaccatttggtaaaggaaggacgactggaagaggaagtagccttaa agataatcaatgatggggctgccatcctgaggcaagagaagactatgatagaagtagatgctccaatcacagtatgtggtgatattcatgga caattctttgacctaatgaagttatttgaagttggaggatcacctagtaacacacgctacctctttctgggtgactatgtggacagaggctatttc agtatagagtgtgtgctgtatttatggagtttaaagattaatcatcccaaaacattgtttctgcttcggggaaatcatgaatgcaggcatcttaca gactatttcaccttcaaacaggaatgtcgaatcaaatattcggaacaggtgtatgatgcctgtatggagacatttgactgtcttcctcttgctgcc ctcttaaaccagcagtttctctgtgtacatggaggaatgtcacctgaaattacttctttagatgacattaggaaattagacaggtttacggaacct cccgcctttggacctgtgtgtgacctgctttggtctgatccctcagaggattatggcaatgagaagaccttggagcactatacccacaacact gtccgagggtgctcttatttctacagttaccctgcagtttgtgaatttttgcagaacaataatttactatcaattatcagagcccatgaagcccaag atgctgggtatcgaatgtacaggaagagccaagccacaggctttccatcacttattacaattttctctgcccccaattacctagatgtctataac aataaagctgctgtgttgaaatatgaaaacaatgtcatgaatatcaggcagtttaactgttctccacacccctactggcttccaaactttatggat gttttcacatggtctttgccttttgttggggaaaaagtcacagagatgctggtaaatgtgctcaacatatgctctgatgacgaactgatttctgatg atgaagcagaagatcactacattccaagctatcagaaaggaagcactacagttcgtaaggagatcatcaggaataagatcagagccattgg gaagatggcacgggtcttttcaattcttcggcaagaaagtgagagtgtgctgactctcaagggcctgactcccacaggcacactccctctgg gcgtcctctcaggaggcaagcagactatcgagacagccacagtagaagcggtagaggcccgggaagccatcagagggttctcgcttca gcacaagatccggagttttgaagaagcgcgaggtctggaccgaattaatgagcgaatgccaccccgaaaggatagcatacacgctggtg ggccaatgaaatctgtaacctcagcacactcacatgctgcgcacaggagcgaccaagggaagaaagcccattcatgacttagagtcctgc cgtggctcaggtggatctaaaactcaagaacaaattctatttatttattattggaaaatgaaaagcaactcaaaacaacttcaacgtggaggtg catttataattcagtctgcatttattctgtaaaaaggtggctgttttataaattcttttaatttatgttcaatatatataaaaagtgcatctgttttgtttttc cctttttttctccataattttaagaaatgaatctgattgttgtcaacacatttgtgaagtcttgtgctataaaggggaacttcccctaataaaagggcc ttggaaacctcaaacctgggtttctgacttgaaaaaaaaaaaaaaa (SEQ ID NO: 678) | NM_001243974 | NM_008915 |

In some aspects, the nucleic acids of the compositions encode the shRNA sequences targeting the sequences provided in Table 2. Table 2 further demonstrates enrichment in tumor versus spleen for the selected shRNA based on deep sequencing analysis ("Enrich Fold")

TABLE 2

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Akap8l | 54194 | ND000290 | CGAAACCGCAGGCTTATGATG | 1 | 0.5 | AKAP8L | 26993 |
| Akap8l | 54194 | ND000285 | CAGACTGCTCAGACAACAGTG | 2 | 0.7 | AKAP8L | 26993 |
| Akap8l | 54194 | TRCN0000288034 | CCACAAGGAACACTTCAAATA | 3 | 1.0 | AKAP8L | 26993 |
| Akap8l | 54194 | ND000291 | AGACCTCTACCGGTCAAGCTA | 4 | 1.1 | AKAP8L | 26993 |
| Akap8l | 54194 | ND000286 | ATAGAGGCTACGAGAACTATG | 5 | 1.4 | AKAP8L | 26993 |
| Akap8l | 54194 | TRCN0000288033 | CCAGAACATCATACCCGAGTA | 6 | 1.6 | AKAP8L | 26993 |
| Akap8l | 54194 | ND000289 | TTAGATATGATGCCGCACTTG | 7 | 1.7 | AKAP8L | 26993 |
| Akap8l | 54194 | TRCN0000088483 | CCCACCTGTGATTATGGATAT | 8 | 1.8 | AKAP8L | 26993 |
| Akap8l | 54194 | ND000288 | GGCGAGAATCCTTTCACTGAC | 9 | 1.9 | AKAP8L | 26993 |
| Akap8l | 54194 | TRCN0000088486 | CGAGAACTATGGTTATGGCTA | 10 | 2.1 | AKAP8L | 26993 |
| Akap8l | 54194 | ND000292 | CAAATACCGGACCTTCTATGA | 11 | 2.8 | AKAP8L | 26993 |
| Akap8l | 54194 | TRCN0000307538 | GATATCTGAAGGGCGAGAATC | 12 | 3.8 | AKAP8L | 26993 |
| Akap8l | 54194 | TRCN0000307539 | ACCGGTCAAGCTATGACTATG | 13 | 4.4 | AKAP8L | 26993 |
| Akap8l | 54194 | ND000287 | TTGGATTTGGCAATGGCATGA | 14 | 7.1 | AKAP8L | 26993 |
| Akap8l | 54194 | TRCN0000088487 | CCGAAACCACTTTGCAGTCTA | 15 | 11.8 | AKAP8L | 26993 |
| Alk | 11682 | TRCN0000361004 | ACCTAGAGGAGAATCACTTTA | 16 | 0.2 | ALK | 238 |
| Alk | 11682 | TRCN0000023725 | GCCTTCATGGAAGGGATATTT | 17 | 0.4 | ALK | 238 |
| Alk | 11682 | TRCN0000361067 | CGGGCCTGTATACCGGATAAT | 18 | 0.7 | ALK | 238 |
| Alk | 11682 | TRCN0000361003 | GTGGAGCCACCTACGTGTTTA | 19 | 0.9 | ALK | 238 |
| Alk | 11682 | ND000299 | GGAATCTGACCTGGACGATGA | 20 | 1.0 | ALK | 238 |
| Alk | 11682 | ND000293 | CTTCGTTGTACCCTCGCTCTT | 21 | 1.1 | ALK | 238 |
| Alk | 11682 | ND000298 | GAAGGGATATTTACCTCTAAA | 22 | 1.3 | ALK | 238 |
| Alk | 11682 | TRCN0000023728 | CCGGGATATTGCTGCTAGAAA | 23 | 1.7 | ALK | 238 |
| Alk | 11682 | TRCN0000023724 | GCATCGCATTGGAGGCTATAA | 24 | 2.1 | ALK | 238 |
| Alk | 11682 | ND000297 | GGGCCTGTATACCGGATAATG | 25 | 2.4 | ALK | 238 |
| Alk | 11682 | TRCN0000023726 | CGGAGGATATATAGGTGGCAA | 26 | 2.9 | ALK | 238 |
| Alk | 11682 | ND000300 | ATCGAATACGGTCCAGTAGTA | 27 | 3.4 | ALK | 238 |
| Alk | 11682 | ND000296 | TGCTTCCGCGTAGTCAGAAAT | 28 | 3.8 | ALK | 238 |
| Alk | 11682 | ND000294 | CCTGCGGCAATGTCAACTATG | 29 | 9.4 | ALK | 238 |
| Alk | 11682 | TRCN0000023727 | CCCGAACGTCAACTATGGTTA | 30 | 9.5 | ALK | 238 |
| Alk | 11682 | ND000295 | GGCGAGGAGACGATTCTTGAA | 31 | 13.5 | ALK | 238 |
| Arhgap5 | 11855 | TRCN0000321111 | TGGTACATATCCTCGTAAATT | 32 | 0.5 | ARHGAP5 | 394 |
| Arhgap5 | 11855 | TRCN0000360350 | ATTGCAATCAGTATATCATTC | 33 | 0.8 | ARHGAP5 | 394 |
| Arhgap5 | 11855 | TRCN0000360421 | GATCATGAACGTAACCATAAA | 34 | 1.2 | ARHGAP5 | 394 |
| Arhgap5 | 11855 | TRCN0000360349 | TGATAATAGCAGCAACTAAAT | 35 | 1.3 | ARHGAP5 | 394 |
| Arhgap5 | 11855 | TRCN0000321112 | AGCATGACTGGAGAGGTTTAA | 36 | 1.4 | ARHGAP5 | 394 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Arhgap5 | 11855 | TRCN0000321110 | TGATAGTCAGAATCGAATTAT | 37 | 1.4 | ARHGAP5 | 394 |
| Arhgap5 | 11855 | TRCN0000321109 | GAACTGGTTCATGGGTATATA | 38 | 1.5 | ARHGAP5 | 394 |
| Arhgap5 | 11855 | TRCN0000012706 | GCAAGCTCTAAGAGGAGTATT | 39 | 3.6 | ARHGAP5 | 394 |
| Arhgap5 | 11855 | TRCN0000012707 | CCTGATCCTTTGATTCCATAT | 40 | 6.0 | ARHGAP5 | 394 |
| Arhgap5 | 11855 | TRCN0000321181 | ACAGATCCTCTTGGTATTATA | 41 | 8.3 | ARHGAP5 | 394 |
| Arhgap5 | 11855 | TRCN0000012703 | GCACGATTTAATGTCAACATT | 42 | 15.7 | ARHGAP5 | 394 |
| Blvrb | 233016 | ND000310 | CTCAGTCCCACTACAGTAATG | 43 | 0.8 | BLVRB | 645 |
| Blvrb | 233016 | ND000308 | TGACCACATCCGGATGCATAA | 44 | 1.0 | BLVRB | 645 |
| Blvrb | 233016 | ND000306 | GCCTCACCACCAATGAGTATG | 45 | 1.2 | BLVRB | 645 |
| Blvrb | 233016 | ND000309 | TGAGAAATGACACAAATAGAG | 46 | 1.2 | BLVRB | 645 |
| Blvrb | 233016 | ND000303 | TGCAAGAGTCAGGGCTGAAAT | 47 | 1.3 | BLVRB | 645 |
| Blvrb | 233016 | ND000301 | GGAAGCTGTCATCGTGCTACT | 48 | 1.5 | BLVRB | 645 |
| Blvrb | 233016 | ND000304 | GCATAAGATTCTGCAAGAGTC | 49 | 1.9 | BLVRB | 645 |
| Blvrb | 233016 | TRCN0000042385 | CCTCAGTCCCACTACAGTAAT | 50 | 2.2 | BLVRB | 645 |
| Blvrb | 233016 | ND000302 | TCGAGGGTCATATCCAAGCAT | 51 | 2.4 | BLVRB | 645 |
| Blvrb | 233016 | TRCN0000324726 | GAACATCGTGACAGCCATGAA | 52 | 3.0 | BLVRB | 645 |
| Blvrb | 233016 | TRCN0000042384 | CCAATGAGTATGACGGACACA | 53 | 3.1 | BLVRB | 645 |
| Blvrb | 233016 | ND000307 | GAGGGTCATGCATCCTGAGAA | 54 | 3.1 | BLVRB | 645 |
| Blvrb | 233016 | ND000305 | TAGGAGACCAACCACTAACTG | 55 | 5.3 | BLVRB | 645 |
| Blvrb | 233016 | TRCN0000324662 | GCTGAAATACGTGGCAGTGAT | 56 | 5.3 | BLVRB | 645 |
| Blvrb | 233016 | TRCN0000042386 | CGGATGCATAAGATTCTGCAA | 57 | 8.0 | BLVRB | 645 |
| Cblb | 208650 | ND000027 | TCTACATCGATAGTCTCATGA | 58 | 0.7 | CBLB | 868 |
| Cblb | 208650 | TRCN0000244603 | CTACACCTCACGATCATATAA | 59 | 0.9 | CBLB | 868 |
| Cblb | 208650 | TRCN0000244605 | TGAGCGAGAATGAGTACTTTA | 60 | 0.9 | CBLB | 868 |
| Cblb | 208650 | ND000026 | ATCGAACATCCCAGATTTAGG | 61 | 1.0 | CBLB | 868 |
| Cblb | 208650 | ND000029 | TAAAGTGTACTGGTCCATTAG | 62 | 1.4 | CBLB | 868 |
| Cblb | 208650 | TRCN0000244607 | CTTGTACTCCAGTACCATAAT | 63 | 1.5 | CBLB | 868 |
| Cblb | 208650 | ND000028 | GTATGAGACAGAAGGACTGAG | 64 | 1.5 | CBLB | 868 |
| Cblb | 208650 | TRCN0000244604 | CCAGATTTAGGCATCTATTTG | 65 | 1.6 | CBLB | 868 |
| Cblb | 208650 | ND000031 | TCAGCACTTGAGACTTATATT | 66 | 1.7 | CBLB | 868 |
| Cblb | 208650 | ND000024 | TACACCTCACGATCATATAAA | 67 | 2.1 | CBLB | 868 |
| Cblb | 208650 | ND000033 | AACACAGACGCCATGATTTGC | 68 | 5.1 | CBLB | 868 |
| Cblb | 208650 | ND000032 | AAGATGTCAAGATTGAGCCTT | 69 | 5.3 | CBLB | 868 |
| Cblb | 208650 | TRCN0000244606 | CCCTGATTTAACCGGATTATG | 70 | 6.1 | CBLB | 868 |
| Cblb | 208650 | ND000030 | AGCCAGGTCCAATTCCATTTC | 71 | 10.0 | CBLB | 868 |
| Cblb | 208650 | ND000025 | CGAGCGATCCGGCTCTTTAAA | 72 | 10.8 | CBLB | 868 |
| Cdkn2a | 12578 | ND000317 | CTTGGTGAAGTTCGTGCGATC | 73 | 0.6 | CDKN2A | 1029 |
| Cdkn2a | 12578 | TRCN0000257162 | CGCTCTGGCTTTCGTGAACAT | 74 | 0.8 | CDKN2A | 1029 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Cdkn2a | 12578 | TRCN0000362594 | GATGATGATGGGCAACGTTCA | 75 | 0.9 | CDKN2A | 1029 |
| Cdkn2a | 12578 | TRCN0000231228 | TCCCAAGAGCAGAGCTAAATC | 76 | 0.9 | CDKN2A | 1029 |
| Cdkn2a | 12578 | TRCN0000362666 | TCTTGGTGAAGTTCGTGCGAT | 77 | 1.0 | CDKN2A | 1029 |
| Cdkn2a | 12578 | TRCN0000362596 | ACGGGCATAGCTTCAGCTCAA | 78 | 1.1 | CDKN2A | 1029 |
| Cdkn2a | 12578 | TRCN0000222730 | GCTCGGCTGGATGTGCGCGAT | 79 | 1.1 | CDKN2A | 1029 |
| Cdkn2a | 12578 | TRCN0000231225 | TTGAGGCTAGAGAGGATCTTG | 80 | 1.2 | CDKN2A | 1029 |
| Cdkn2a | 12578 | TRCN0000222731 | CATCAAGACATCGTGCGATAT | 81 | 2.1 | CDKN2A | 1029 |
| Cdkn2a | 12578 | TRCN0000077815 | GTGAACATGTTGTTGAGGCTA | 82 | 2.3 | CDKN2A | 1029 |
| Cdkn2a | 12578 | TRCN0000077816 | GTCTTTGTGTACCGCTGGGAA | 83 | 3.3 | CDKN2A | 1029 |
| Cdkn2a | 12578 | TRCN0000362595 | CTAGCGATGCTAGCGTGTCTA | 84 | 4.1 | CDKN2A | 1029 |
| Cdkn2a | 12578 | TRCN0000222729 | GTGATGATGATGGGCAACGTT | 85 | 5.6 | CDKN2A | 1029 |
| Cdkn2a | 12578 | TRCN0000231226 | GCTCAACTACGGTGCAGATTC | 86 | 6.9 | CDKN2A | 1029 |
| Cdkn2a | 12578 | TRCN0000231227 | TCAAGACATCGTGCGATATTT | 87 | 7.2 | CDKN2A | 1029 |
| Dgka | 13139 | TRCN0000024825 | GAGCTAAGTAAGGTGGTATAT | 88 | 0.7 | DGKA | 1606 |
| Dgka | 13139 | TRCN0000368765 | GCGATGTACTGAAGGTCTTTG | 89 | 0.7 | DGKA | 1606 |
| Dgka | 13139 | ND000059 | TCAGTGATGTGTACTGCTACT | 90 | 0.8 | DGKA | 1606 |
| Dgka | 13139 | ND000054 | GTATATCTCGACCGATGGTTC | 91 | 1.0 | DGKA | 1606 |
| Dgka | 13139 | TRCN0000378505 | TGATGCGAGTGGCCGAATATC | 92 | 1.1 | DGKA | 1606 |
| Dgka | 13139 | TRCN0000024828 | CCTAGGATTTGAACAATTCAT | 93 | 1.2 | DGKA | 1606 |
| Dgka | 13139 | ND000058 | AAAGATTCTCAAGGATATAGA | 94 | 1.6 | DGKA | 1606 |
| Dgka | 13139 | ND000056 | GAGGGATGTTCCATCACCTTC | 95 | 1.9 | DGKA | 1606 |
| Dgka | 13139 | ND000053 | TACAGACATCCTTACACAACC | 96 | 2.0 | DGKA | 1606 |
| Dgka | 13139 | TRCN0000024824 | GCCGAATATCTAGACTGGGAT | 97 | 3.4 | DGKA | 1606 |
| Dgka | 13139 | TRCN0000024827 | CGGCTGGAAGTGGTAGGAATA | 98 | 3.5 | DGKA | 1606 |
| Dgka | 13139 | ND000055 | GTTCCTCAGTTCCGGATATTG | 99 | 5.0 | DGKA | 1606 |
| Dgka | 13139 | TRCN0000024826 | CCTGAGCTGTAACTTCTGTAA | 100 | 6.8 | DGKA | 1606 |
| Dgka | 13139 | ND000057 | TGCGAACAGAGCATTAGCCTT | 101 | 7.8 | DGKA | 1606 |
| Dgka | 13139 | TRCN0000361167 | TGTTCCTCAGTTCCGGATATT | 102 | 10.2 | DGKA | 1606 |
| Dgkz | 104418 | ND000063 | CACCTTCCACAGCAAGGAGAT | 103 | 0.4 | DGKZ | 8525 |
| Dgkz | 104418 | ND000061 | ATCGTGGTGCATACCCAATGC | 104 | 0.4 | DGKZ | 8525 |
| Dgkz | 104418 | TRCN0000278613 | CCTGGATGTCTTTAACAACTA | 105 | 0.7 | DGKZ | 8525 |
| Dgkz | 104418 | ND000060 | CGAGTAGTGTGTGACGGAATG | 106 | 0.9 | DGKZ | 8525 |
| Dgkz | 104418 | ND000065 | CACATCTGGTTTGAGACCAAC | 107 | 1.4 | DGKZ | 8525 |
| Dgkz | 104418 | TRCN0000278690 | GAGAAGTTCAACAGCCGCTTT | 108 | 1.6 | DGKZ | 8525 |
| Dgkz | 104418 | ND000069 | ACTGTGCAGGCACCATGCCCT | 109 | 2.0 | DGKZ | 8525 |
| Dgkz | 104418 | ND000068 | AGAAGCTGTTCAGATCTAGGG | 110 | 2.8 | DGKZ | 8525 |
| Dgkz | 104418 | TRCN0000297512 | GTGGACTTCAAAGAATTCATT | 111 | 3.6 | DGKZ | 8525 |
| Dgkz | 104418 | ND000064 | ACTACGAGGCTCTACATTATG | 112 | 5.2 | DGKZ | 8525 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Dgkz | 104418 | ND000067 | AGTACATAATTTGAGGATTCT | 113 | 5.5 | DGKZ | 8525 |
| Dgkz | 104418 | TRCN0000278682 | CGAGGCTCTACATTATGACAA | 114 | 6.0 | DGKZ | 8525 |
| Dgkz | 104418 | TRCN0000278614 | CCTGTAAGATCGTGGTGCATA | 115 | 6.4 | DGKZ | 8525 |
| Dgkz | 104418 | ND000062 | GAAACCGCAGTGCATCGTCTT | 116 | 7.7 | DGKZ | 8525 |
| Dgkz | 104418 | ND000066 | CAGCATCACGGATTCGAATTG | 117 | 14.0 | DGKZ | 8525 |
| Egr2 | 13654 | TRCN0000218224 | AGGATCCTTCAGCATTCTTAT | 118 | 0.4 | EGR2 | 1959 |
| Egr2 | 13654 | ND000075 | AGCTCTGGCTGACACACCAG | 119 | 0.6 | EGR2 | 1959 |
| Egr2 | 13654 | TRCN0000081682 | CCAGGATCCTTCAGCATTCTT | 120 | 0.6 | EGR2 | 1959 |
| Egr2 | 13654 | TRCN0000081678 | GCTGTATATTTCTGCCTATTA | 121 | 1.3 | EGR2 | 1959 |
| Egr2 | 13654 | TRCN0000235777 | ACTATTGTGGCCGCAAGTTTG | 122 | 1.3 | EGR2 | 1959 |
| Egr2 | 13654 | TRCN0000235775 | AGCGGGTACTACCGTTTATTT | 123 | 1.6 | EGR2 | 1959 |
| Egr2 | 13654 | TRCN0000235778 | CTGTATATTTCTGCCTATTAA | 124 | 2.4 | EGR2 | 1959 |
| Egr2 | 13654 | ND000073 | GTGACCACCTTACTACTCACA | 125 | 3.2 | EGR2 | 1959 |
| Egr2 | 13654 | ND000074 | GTTTGCCAGGAGTGACGAAAG | 126 | 3.9 | EGR2 | 1959 |
| Egr2 | 13654 | TRCN0000081681 | CCTTCACCTACATGGGCAAAT | 127 | 4.0 | EGR2 | 1959 |
| Egr2 | 13654 | TRCN0000081680 | CCAGAAGGTATCATCAATATT | 128 | 5.1 | EGR2 | 1959 |
| Egr2 | 13654 | TRCN0000081679 | CCACTCTCTACCATCCGTAAT | 129 | 5.2 | EGR2 | 1959 |
| Egr2 | 13654 | ND000072 | CCGTGCCAGAGAGATCCACAC | 130 | 5.6 | EGR2 | 1959 |
| Egr2 | 13654 | ND000071 | CAATAGGTTGGGAGTTGCTGA | 131 | 8.6 | EGR2 | 1959 |
| Egr2 | 13654 | TRCN0000235776 | ACTCTCTACCATCCGTAATTT | 132 | 10.2 | EGR2 | 1959 |
| Eif2ak3 | 13666 | TRCN0000321872 | CCATGAGTTCATCTGGAACAA | 133 | 0.4 | EIF2AK3 | 9451 |
| Eif2ak3 | 13666 | ND000328 | CATAGCTCCTTCTCCTGAAAG | 134 | 0.9 | EIF2AK3 | 9451 |
| Eif2ak3 | 13666 | ND000332 | GATGACTGCAATTACGCTATC | 135 | 1.1 | EIF2AK3 | 9451 |
| Eif2ak3 | 13666 | ND000325 | GTCGCCATTTATGTCGGTAGT | 136 | 1.1 | EIF2AK3 | 9451 |
| Eif2ak3 | 13666 | ND000326 | TGGAAACAACTACTCCCATAA | 137 | 1.1 | EIF2AK3 | 9451 |
| Eif2ak3 | 13666 | TRCN0000321873 | GTGACCCATCTGCACTAATTT | 138 | 1.3 | EIF2AK3 | 9451 |
| Eif2ak3 | 13666 | ND000329 | GCATGATGGCAACCATTATGT | 139 | 1.3 | EIF2AK3 | 9451 |
| Eif2ak3 | 13666 | ND000330 | ATCCCGATATCTAACAGATTT | 140 | 1.6 | EIF2AK3 | 9451 |
| Eif2ak3 | 13666 | ND000333 | TGTCGCCGATGGGATAGTGAT | 141 | 1.9 | EIF2AK3 | 9451 |
| Eif2ak3 | 13666 | TRCN0000321805 | GCCACTTTGAACTTCGGTATA | 142 | 2.0 | EIF2AK3 | 9451 |
| Eif2ak3 | 13666 | TRCN0000028759 | CCATACGATAACGGTTACTAT | 143 | 4.8 | EIF2AK3 | 9451 |
| Eif2ak3 | 13666 | TRCN0000321806 | CCTCTACTGTTCACTCAGAAA | 144 | 5.8 | EIF2AK3 | 9451 |
| Eif2ak3 | 13666 | ND000327 | CATACGATAACGGTTACTATC | 145 | 5.9 | EIF2AK3 | 9451 |
| Eif2ak3 | 13666 | ND000331 | CGTGACCCATCTGCACTAATT | 146 | 7.3 | EIF2AK3 | 9451 |
| Eif2ak3 | 13666 | TRCN0000028799 | GCCTGTTTGATGATACAAGTT | 147 | 13.4 | EIF2AK3 | 9451 |
| Entpd1 | 12495 | ND000082 | GAATGTAAGTGAGCTCTATGG | 148 | 0.3 | ENTPD1 | 953 |
| Entpd1 | 12495 | TRCN0000222348 | CCGAACTGATACCAACATCCA | 149 | 0.4 | ENTPD1 | 953 |
| Entpd1 | 12495 | TRCN0000222346 | CCCATGCTTTAACCCAGGATA | 150 | 0.4 | ENTPD1 | 953 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Entpd1 | 12495 | TRCN0000222345 | CCTTGGTTTCACCTCTATCTT | 151 | 0.8 | ENTPD1 | 953 |
| Entpd1 | 12495 | TRCN0000222344 | CCAAGGACATTCAGGTTTCAA | 152 | 0.9 | ENTPD1 | 953 |
| Entpd1 | 12495 | ND000085 | CAGGAACAGAGTTGGCTAAGC | 153 | 1.0 | ENTPD1 | 953 |
| Entpd1 | 12495 | ND000078 | TTAACCCAGGATACGAGAAGG | 154 | 1.1 | ENTPD1 | 953 |
| Entpd1 | 12495 | ND000081 | ACTATCTCAGCCATGGCTTTG | 155 | 1.2 | ENTPD1 | 953 |
| Entpd1 | 12495 | ND000077 | TTCAAGTGGTGGCGTCCTTAA | 156 | 1.3 | ENTPD1 | 953 |
| Entpd1 | 12495 | ND000076 | GACTTTGGGCTACATGCTGAA | 157 | 1.4 | ENTPD1 | 953 |
| Entpd1 | 12495 | ND000080 | GGCATGCGCTTGCTTAGAATG | 158 | 1.9 | ENTPD1 | 953 |
| Entpd1 | 12495 | ND000084 | GCACTGGAGACTACGAACAGT | 159 | 1.9 | ENTPD1 | 953 |
| Entpd1 | 12495 | ND000083 | GTGGATTACTATTAACTATCT | 160 | 6.5 | ENTPD1 | 953 |
| Entpd1 | 12495 | TRCN0000222347 | GCTCCTGGGAACAGATTCATT | 161 | 7.3 | ENTPD1 | 953 |
| Entpd1 | 12495 | ND000079 | ACCATTTGATCAGTTTCGAAT | 162 | 13.3 | ENTPD1 | 953 |
| F11r | 16456 | TRCN0000284518 | GCTGATTCCCAGGACTATATT | 163 | 0.6 | F11R | 50848 |
| F11r | 16456 | TRCN0000124868 | GTATCGCTGTATAACTATGTA | 164 | 0.6 | F11R | 50848 |
| F11r | 16456 | ND000093 | ATTGACCTGCACCTACTCT | 165 | 0.6 | F11R | 50848 |
| F11r | 16456 | ND000094 | GCCGGGAGGAAACTGTTGT | 166 | 0.6 | F11R | 50848 |
| F11r | 16456 | TRCN0000271840 | CCTGGTTCAAGGACGGGATAT | 167 | 0.7 | F11R | 50848 |
| F11r | 16456 | TRCN0000271841 | TTCGGTGTACACTGCTCAATC | 168 | 0.7 | F11R | 50848 |
| F11r | 16456 | TRCN0000271792 | CACCGGGTAAGAAGGTCATTT | 169 | 0.9 | F11R | 50848 |
| F11r | 16456 | ND000088 | ACTTGCATGGTCTCCGAGGAA | 170 | 0.9 | F11R | 50848 |
| F11r | 16456 | ND000086 | GTAACACTGATTCTCCTTGGA | 171 | 1.0 | F11R | 50848 |
| F11r | 16456 | ND000090 | GTTATAACAGCCAGATCACAG | 172 | 1.1 | F11R | 50848 |
| F11r | 16456 | ND000092 | TAGCTGCACAGGATGCCTTCA | 173 | 1.3 | F11R | 50848 |
| F11r | 16456 | ND000087 | GGTTTGCCTATAGCCGTGGAT | 174 | 1.9 | F11R | 50848 |
| F11r | 16456 | TRCN0000271794 | CCTATAGCCGTGGATACTTTG | 175 | 4.3 | F11R | 50848 |
| F11r | 16456 | ND000091 | CTCCGTTGTCCATTTGCCTTA | 176 | 4.6 | F11R | 50848 |
| F11r | 16456 | ND000089 | CCACCCTCTGAATATTCCTGG | 177 | 6.8 | F11R | 50849 |
| Fyn | 14360 | TRCN0000023383 | CATCCCGAACTACAACAACTT | 178 | 0.7 | FYN | 2534 |
| Fyn | 14360 | TRCN0000023381 | CCTTTGGAAACCCAAGAGGTA | 179 | 0.9 | FYN | 2534 |
| Fyn | 14360 | TRCN0000361148 | TCTGAGACAGAAGCGTGTTAT | 180 | 1.4 | FYN | 2534 |
| Fyn | 14360 | TRCN0000023379 | GCTCGGTTGATTGAAGACAAT | 181 | 1.4 | FYN | 2534 |
| Fyn | 14360 | TRCN0000361213 | TTGACAATGGTGGATACTATA | 182 | 1.9 | FYN | 2534 |
| Fyn | 14360 | TRCN0000361149 | TCTTCACCTGATTCAACTAAA | 183 | 1.9 | FYN | 2534 |
| Fyn | 14360 | TRCN0000023382 | GCTCTGAAGTTGCCAAACCTT | 184 | 2.0 | FYN | 2534 |
| Fyn | 14360 | TRCN0000361212 | CACTGTTTGTGGCGCTTTATG | 185 | 2.3 | FYN | 2534 |
| Fyn | 14360 | TRCN0000361152 | CATCGAGCGCATGAATTATAT | 186 | 2.9 | FYN | 2534 |
| Fyn | 14360 | TRCN0000023380 | CCTGTATGGAAGGTTCACAAT | 187 | 6.5 | FYN | 2534 |
| Fyn | 14360 | ND000111 | TCGATGTTATGTCAAAGGCC | 188 | 0.5 | FYN | 2534 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Fyn | 14360 | ND000112 | ACCACACAAACTTCCTGTAT | 189 | 0.7 | FYN | 2534 |
| Fyn | 14360 | ND000115 | ACAGCTCCTGTCCTTTGGAAA | 190 | 1.0 | FYN | 2534 |
| Fyn | 14360 | ND000113 | GCAGCGAAACTGACAGAGGAG | 191 | 4.1 | FYN | 2534 |
| Fyn | 14360 | ND000114 | ACACTGTTTGTGGCGCTTTAT | 192 | 4.4 | FYN | 2534 |
| Grk6 | 26385 | ND000356 | TGACTACCACAGCCTATGTGA | 193 | 0.5 | GRK6 | 2870 |
| Grk6 | 26385 | TRCN0000022851 | CGAGAAACAGATCTTGGAGAA | 194 | 0.6 | GRK6 | 2870 |
| Grk6 | 26385 | ND000355 | CTAACCTTGCTTAGCAACTGT | 195 | 0.6 | GRK6 | 2870 |
| Grk6 | 26385 | ND000359 | AGGAATGAGCGCTACACGTTC | 196 | 1.0 | GRK6 | 2870 |
| Grk6 | 26385 | TRCN0000022853 | TCTTGGAGAAAGTGAACAGTA | 197 | 1.1 | GRK6 | 2870 |
| Grk6 | 26385 | TRCN0000022850 | GCGCCTGTTATTTCGTGAGTT | 198 | 1.1 | GRK6 | 2870 |
| Grk6 | 26385 | TRCN0000361581 | GAACAGTTCTCTACAGTTAAA | 199 | 1.1 | GRK6 | 2870 |
| Grk6 | 26385 | ND000354 | CAGGCTATTTATTGCAAGGAT | 200 | 1.2 | GRK6 | 2870 |
| Grk6 | 26385 | ND000357 | GAGCTTAGCCTACGCCTATGA | 201 | 1.3 | GRK6 | 2870 |
| Grk6 | 26385 | TRCN0000022852 | GCAAAGGCAAGAGCAAGAAAT | 202 | 1.3 | GRK6 | 2870 |
| Grk6 | 26385 | TRCN0000361580 | CCATGGCTCTCAACGAGAAAC | 203 | 2.7 | GRK6 | 2870 |
| Grk6 | 26385 | ND000358 | TCTATGCTGCTGAGATCTGCT | 204 | 4.2 | GRK6 | 2870 |
| Grk6 | 26385 | TRCN0000361508 | GCCGACTAATGCAGAACTTTC | 205 | 4.5 | GRK6 | 2870 |
| Grk6 | 26385 | ND000360 | CGCCTGTTATTTCGTGAGTTC | 206 | 5.8 | GRK6 | 2870 |
| Grk6 | 26385 | TRCN0000022849 | CGCCGACTAATGCAGAACTTT | 207 | 11.0 | GRK6 | 2870 |
| Hipk1 | 15257 | ND000371 | CTACCTGCAATCACGCTACTA | 208 | 0.3 | HIPK1 | 204851 |
| Hipk1 | 15257 | ND000374 | AGCGGAGGGTTCACATGTATG | 209 | 0.4 | HIPK1 | 204851 |
| Hipk1 | 15257 | TRCN0000361231 | CAACCAGTACAGCACTATTAT | 210 | 0.4 | HIPK1 | 204851 |
| Hipk1 | 15257 | TRCN0000361237 | TACCCTTTCTCTGGCTAATTC | 211 | 0.7 | HIPK1 | 204851 |
| Hipk1 | 15257 | TRCN0000368011 | AGCCTGAAGGCGAGGTCTAAT | 212 | 1.1 | HIPK1 | 204851 |
| Hipk1 | 15257 | ND000376 | CATTGGCACCCGTACTATCAT | 213 | 1.1 | HIPK1 | 204851 |
| Hipk1 | 15257 | TRCN0000023157 | GCTTCAGAATACGATCAGATT | 214 | 1.2 | HIPK1 | 204851 |
| Hipk1 | 15257 | ND000375 | GAAGACTCTTAACCACCAATT | 215 | 1.8 | HIPK1 | 204851 |
| Hipk1 | 15257 | TRCN0000361233 | ATACGATCAGATTCGCTATAT | 216 | 1.9 | HIPK1 | 204851 |
| Hipk1 | 15257 | ND000372 | CTGTCATACATTTGGTCTCTT | 217 | 2.7 | HIPK1 | 204851 |
| Hipk1 | 15257 | ND000377 | GCTACTAGCCCTGAGTTCTTA | 218 | 3.4 | HIPK1 | 204851 |
| Hipk1 | 15257 | TRCN0000361232 | TATAACTTTGTCCGTTCTTAT | 219 | 4.5 | HIPK1 | 204851 |
| Hipk1 | 15257 | ND000373 | CTCGCTGCTAAACTACCAATC | 220 | 6.3 | HIPK1 | 204851 |
| Hipk1 | 15257 | ND000378 | GCCAATCATCATTCCAGATAC | 221 | 6.7 | HIPK1 | 204851 |
| Hipk1 | 15257 | TRCN0000023154 | CGCTCCAAATACAAGCACAAA | 222 | 12.3 | HIPK1 | 204851 |
| Inpp5b | 16330 | TRCN0000080903 | GCTTAGAGGTTCCTGGATAAA | 223 | 0.5 | INPP5B | 3633 |
| Inpp5b | 16330 | TRCN0000080906 | CCTTTGGTTCACACACCAGAA | 224 | 0.7 | INPP5B | 3633 |
| Inpp5b | 16330 | ND000130 | CTGTTAGTGACCTGACGTTGA | 225 | 0.8 | INPP5B | 3633 |
| Inpp5b | 16330 | TRCN0000305895 | ATATTCTAGCTAGCATATTTG | 226 | 0.8 | INPP5B | 3633 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Inpp5b | 16330 | TRCN0000311434 | GGCCAGAGTTTGACCATATAA | 227 | 1.4 | INPP5B | 3633 |
| Inpp5b | 16330 | ND000131 | GAGTCCTTCACGATTCATAAT | 228 | 1.4 | INPP5B | 3633 |
| Inpp5b | 16330 | TRCN0000080905 | CGGATCTCCTATCCATACATT | 229 | 1.5 | INPP5B | 3633 |
| Inpp5b | 16330 | ND000128 | GTATCGGACAAGGCTCACATT | 230 | 1.6 | INPP5B | 3633 |
| Inpp5b | 16330 | ND000129 | TTCGAGACACAATCGTGAGAT | 231 | 1.9 | INPP5B | 3633 |
| Inpp5b | 16330 | ND000127 | CTGTCCAAGCCGCAAACATGT | 232 | 3.1 | INPP5B | 3633 |
| Inpp5b | 16330 | ND000133 | CTCAAGCTTGTATTCCAACTT | 233 | 4.3 | INPP5B | 3633 |
| Inpp5b | 16330 | ND000132 | ATATAAGGGACTGTCTAGATA | 234 | 4.6 | INPP5B | 3633 |
| Inpp5b | 16330 | TRCN0000080904 | CGAGTCCTTCACGATTCATAA | 235 | 6.2 | INPP5B | 3633 |
| Inpp5b | 16330 | TRCN0000080907 | CCGAGTCCTTCACGATTCATA | 236 | 8.1 | INPP5B | 3633 |
| Inpp5b | 16330 | ND000134 | CGTCCGACTGGTTGGGATTAT | 237 | 9.5 | INPP5B | 3633 |
| Ipmk | 69718 | TRCN0000024840 | CCCAGATGGTACAGTTCTGAA | 238 | 0.5 | IPMK | 253430 |
| Ipmk | 69718 | ND000384 | CGAGGCTCTGTGGGTTCTATA | 239 | 0.5 | IPMK | 253430 |
| Ipmk | 69718 | TRCN0000360733 | TTGCCGTGCTTCGGAGTATTT | 240 | 0.6 | IPMK | 253430 |
| Ipmk | 69718 | TRCN0000360808 | GATGCGATTGCCGCCAGTATT | 241 | 0.7 | IPMK | 253430 |
| Ipmk | 69718 | TRCN0000024839 | CCTAACGAAAGAGACCCTGAA | 242 | 0.8 | IPMK | 253430 |
| Ipmk | 69718 | ND000383 | ATTGCCGTGCTTCGGAGTATT | 243 | 1.1 | IPMK | 253430 |
| Ipmk | 69718 | ND000380 | AGCGGAAGTACGGATGATAGA | 244 | 1.3 | IPMK | 253430 |
| Ipmk | 69718 | TRCN0000360807 | GAGGCTCTGTGGGTTCTATAT | 245 | 1.4 | IPMK | 253430 |
| Ipmk | 69718 | ND000379 | TGCCCAAATACTACGGCGTCT | 246 | 1.7 | IPMK | 253430 |
| Ipmk | 69718 | TRCN0000024843 | CGGCAAGGACAAAGTGGGCAT | 247 | 2.9 | IPMK | 253430 |
| Ipmk | 69718 | ND000381 | CTAGCAACACAGTCGATGAGG | 248 | 3.2 | IPMK | 253430 |
| Ipmk | 69718 | TRCN0000360732 | ACCAAACGATGTGTACCTAAA | 249 | 4.0 | IPMK | 253430 |
| Ipmk | 69718 | TRCN0000024841 | ACCCTGTATAATGGACGTGAA | 250 | 4.1 | IPMK | 253430 |
| Ipmk | 69718 | ND000382 | CCTGTATAATGGACGTGAAGA | 251 | 4.7 | IPMK | 253430 |
| Ipmk | 69718 | TRCN0000024842 | CACCAAACGATGTGTACCTAA | 252 | 6.9 | IPMK | 253430 |
| Jun | 16476 | TRCN0000229526 | GAACAGGTGGCACAGCTTAAG | 253 | 0.5 | JUN | 3725 |
| Jun | 16476 | TRCN0000042693 | CGGCTACAGTAACCCTAAGAT | 254 | 0.5 | JUN | 3725 |
| Jun | 16476 | TRCN0000055205 | CTACGCCAACCTCAGCAACTT | 255 | 0.7 | JUN | 3725 |
| Jun | 16476 | TRCN0000055206 | CGGTGCCTACGGCTACAGTAA | 256 | 0.8 | JUN | 3725 |
| Jun | 16476 | TRCN0000042695 | GCTTAAGCAGAAAGTCATGAA | 257 | 0.9 | JUN | 3725 |
| Jun | 16476 | TRCN0000360499 | AGCGCATGAGGAACCGCATTG | 258 | 0.9 | JUN | 3725 |
| Jun | 16476 | TRCN0000360498 | CCTATCGACATGGAGTCTCAG | 259 | 0.9 | JUN | 3725 |
| Jun | 16476 | TRCN0000042697 | GAAGCGCATGAGGAACCGCAT | 260 | 1.0 | JUN | 3725 |
| Jun | 16476 | TRCN0000360511 | ATTCGATCTCATTCAGTATTA | 261 | 1.1 | JUN | 3725 |
| Jun | 16476 | TRCN0000360572 | GGATCGCTCGGCTAGAGGAAA | 262 | 1.2 | JUN | 3725 |
| Jun | 16476 | TRCN0000055207 | GCGGATCAAGGCAGAGAGGAA | 263 | 3.1 | JUN | 3725 |
| Jun | 16476 | TRCN0000229528 | GGCATGTGCTGTGATCATTTA | 264 | 3.2 | JUN | 3725 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Jun | 16476 | TRCN0000042694 | ACGCAGCAGTTGCAAACGTTT | 265 | 3.3 | JUN | 3725 |
| Jun | 16476 | TRCN0000055203 | GCGGGCTAACTGCAATAAGAT | 266 | 5.2 | JUN | 3725 |
| Jun | 16476 | TRCN0000229525 | CAGTAACCCTAAGATCCTAAA | 267 | 5.5 | JUN | 3725 |
| Jun | 16476 | TRCN0000229527 | GCTAACGCAGCAGTTGCAAAC | 268 | 5.8 | JUN | 3725 |
| Jun | 16476 | TRCN0000218856 | GAAAGTCATGAACCACGTTAA | 269 | 6.4 | JUN | 3725 |
| Mast2 | 17776 | TRCN0000225743 | AGCAACAACAGGAAGGTATAT | 270 | 0.4 | MAST2 | 23139 |
| Mast2 | 17776 | TRCN0000022896 | GCATCCACGAACAAGACCATA | 271 | 0.7 | MAST2 | 23139 |
| Mast2 | 17776 | TRCN0000225741 | TTGAGACCAAGCGTCACTTAT | 272 | 1.0 | MAST2 | 23139 |
| Mast2 | 17776 | ND000396 | CCGCAAGAGCTTGATTGTAAC | 273 | 1.2 | MAST2 | 23139 |
| Mast2 | 17776 | TRCN0000022898 | GCTGGTTCTGAAGAGTGGAAA | 274 | 1.2 | MAST2 | 23139 |
| Mast2 | 17776 | ND000392 | GATATTACGGAAGCGGTTATC | 275 | 1.3 | MAST2 | 23139 |
| Mast2 | 17776 | ND000393 | ACGAATACCACGGTCCCAAAT | 276 | 1.4 | MAST2 | 23139 |
| Mast2 | 17776 | TRCN0000218393 | GTGGAAACAAGGTATCAATTT | 277 | 1.5 | MAST2 | 23139 |
| Mast2 | 17776 | ND000397 | GAAGTGTGCTATCCGGGAAAG | 278 | 1.6 | MAST2 | 23139 |
| Mast2 | 17776 | ND000395 | GCCTCATTACGTCACACTATT | 279 | 1.6 | MAST2 | 23139 |
| Mast2 | 17776 | TRCN0000022895 | CCTCATTACGTCACACTATTT | 280 | 1.9 | MAST2 | 23139 |
| Mast2 | 17776 | TRCN0000225742 | ACTTGTATGAGGGTCATATTG | 281 | 4.1 | MAST2 | 23139 |
| Mast2 | 17776 | TRCN0000022897 | CGAATGAGAAACCAATCCCTT | 282 | 4.2 | MAST2 | 23139 |
| Mast2 | 17776 | ND000394 | GCATCAAACCTGGTTCGAATG | 283 | 4.3 | MAST2 | 23139 |
| Mast2 | 17776 | TRCN0000022894 | CCCTGTCAACAAAGTAATCAA | 284 | 5.1 | MAST2 | 23139 |
| Mdfic | 16543 | TRCN0000237997 | GGAGGAAACAGGCAAGATAAA | 285 | 0.2 | MDFIC | 29969 |
| Mdfic | 16543 | TRCN0000237994 | TGATGCGGGACCAGTCCATTT | 286 | 0.4 | MDFIC | 29969 |
| Mdfic | 16543 | ND000148 | TGTAATGAGGACAATACGGAG | 287 | 0.4 | MDFIC | 29969 |
| Mdfic | 16543 | TRCN0000362432 | TCCTGACCCTCTGCAACATTG | 288 | 0.6 | MDFIC | 29969 |
| Mdfic | 16543 | TRCN0000237996 | TGACATGGACTGCGGCATCAT | 289 | 0.8 | MDFIC | 29969 |
| Mdfic | 16543 | TRCN0000095981 | CGAAGCATGTAATGAGGACAA | 290 | 1.0 | MDFIC | 29969 |
| Mdfic | 16543 | TRCN0000095982 | GACATCAGTAAGAAGAGTAAA | 291 | 1.1 | MDFIC | 29969 |
| Mdfic | 16543 | TRCN0000237998 | TGCCAAGTGACAGGTTATAAA | 292 | 1.1 | MDFIC | 29969 |
| Mdfic | 16543 | TRCN0000095983 | TGCAACATTGTCCTGGGACAA | 293 | 1.5 | MDFIC | 29969 |
| Mdfic | 16543 | TRCN0000237995 | ATCGTCAGACTGTCTAGAAAT | 294 | 1.6 | MDFIC | 29969 |
| Mdfic | 16543 | TRCN0000095980 | CCGTGGAGAATCACAAGATAT | 295 | 2.6 | MDFIC | 29969 |
| Mdfic | 16543 | TRCN0000362509 | GTTTATCTATTGGAGGTTAAA | 296 | 4.4 | MDFIC | 29969 |
| Mdfic | 16543 | ND000147 | GAAGAGTAAAGTAAATGCTGT | 297 | 5.1 | MDFIC | 29969 |
| Mdfic | 16543 | TRCN0000095979 | CGCCGGATGTATGTGGTTTAA | 298 | 7.2 | MDFIC | 29969 |
| Mdfic | 16543 | TRCN0000362431 | GCCGGATGTATGTGGTTTAAT | 299 | 10.0 | MDFIC | 29969 |
| Nptxr | 73340 | TRCN0000219475 | CTTGGTCTCTCCCATCATATA | 300 | 0.5 | NPTXR | 23467 |
| Nptxr | 73340 | ND000150 | ACAGCAACTGGCACCATATCT | 301 | 0.8 | NPTXR | 23467 |
| Nptxr | 73340 | TRCN0000219474 | GATACCTTGGGAGGCCGATTT | 302 | 0.8 | NPTXR | 23467 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Nptxr | 73340 | ND000155 | GGCCAATGAGATCGTGCTTCT | 303 | 1.0 | NPTXR | 23467 |
| Nptxr | 73340 | ND000154 | GTAGCCTTTGACCCTCAAATC | 304 | 1.0 | NPTXR | 23467 |
| Nptxr | 73340 | ND000152 | CAATGGAGCTGCTGATCAACG | 305 | 1.0 | NPTXR | 23467 |
| Nptxr | 73340 | TRCN0000219472 | GACAGCAACTGGCACCATATC | 306 | 1.1 | NPTXR | 23467 |
| Nptxr | 73340 | ND000158 | TTGGTCTCTCCCATCATATAC | 307 | 1.3 | NPTXR | 23467 |
| Nptxr | 73340 | ND000159 | ATACCTTGGGAGGCCGATTTG | 308 | 1.3 | NPTXR | 23467 |
| Nptxr | 73340 | ND000153 | CCTGTCAGTTTCAGGACTTTG | 309 | 2.0 | NPTXR | 23467 |
| Nptxr | 73340 | ND000156 | TCCGCAACAACTACATGTACG | 310 | 2.1 | NPTXR | 23467 |
| Nptxr | 73340 | ND000157 | ATAAGCTGGTAGAGGCCTTTG | 311 | 3.9 | NPTXR | 23467 |
| Nptxr | 73340 | ND000149 | CGGTGCCGTCATCTGCATCAT | 312 | 6.6 | NPTXR | 23467 |
| Nptxr | 73340 | TRCN0000219473 | CAAGCCACACGGCATCCTTAT | 313 | 7.0 | NPTXR | 23467 |
| Nptxr | 73340 | ND000151 | TCAAGCCACACGGCATCCTTA | 314 | 7.2 | NPTXR | 23467 |
| Nuak2 | 74137 | ND000434 | TTGGACTTGCCTGAACGTCTT | 315 | 0.2 | NUAK2 | 81788 |
| Nuak2 | 74137 | TRCN0000361872 | TTTGACGGGCAGGATCATAAA | 316 | 0.4 | NUAK2 | 81788 |
| Nuak2 | 74137 | TRCN0000024271 | GCCAATGGAAACATCAAGATT | 317 | 0.7 | NUAK2 | 81788 |
| Nuak2 | 74137 | TRCN0000361873 | GTGTAGTGACTGCCATTATTT | 318 | 0.7 | NUAK2 | 81788 |
| Nuak2 | 74137 | ND000436 | CCAAGGTGTGCAGCTTCTTCA | 319 | 1.6 | NUAK2 | 81788 |
| Nuak2 | 74137 | ND000431 | CCTGATCCGGTGGCTGTTAAT | 320 | 1.7 | NUAK2 | 81788 |
| Nuak2 | 74137 | TRCN0000378457 | GGGCTCATCAAGTCGCCTAAA | 321 | 1.8 | NUAK2 | 81788 |
| Nuak2 | 74137 | TRCN0000024270 | CCGAAAGGCATTCTCAAGAAA | 322 | 2.1 | NUAK2 | 81788 |
| Nuak2 | 74137 | TRCN0000024273 | GTCGCCTAAACCTCTGATGAA | 323 | 2.1 | NUAK2 | 81788 |
| Nuak2 | 74137 | TRCN0000024272 | CCGAGGCGATCTGTATGATTA | 324 | 2.1 | NUAK2 | 81788 |
| Nuak2 | 74137 | TRCN0000378409 | GAAGTCTCGACAGCGTGAATC | 325 | 2.8 | NUAK2 | 81788 |
| Nuak2 | 74137 | ND000435 | TCGGACCGCTGTTTGACTTCA | 326 | 2.8 | NUAK2 | 81788 |
| Nuak2 | 74137 | ND000433 | TAGCAGCAAGATTGTGATTGT | 327 | 4.5 | NUAK2 | 81788 |
| Nuak2 | 74137 | ND000432 | AGTCTCGACAGCGTGAATCTG | 328 | 5.4 | NUAK2 | 81788 |
| Nuak2 | 74137 | TRCN0000024269 | CCCAAGGAAAGGCATCCTTAA | 329 | 13.1 | NUAK2 | 81788 |
| Pdzk1ip1 | 67182 | TRCN0000244507 | GATGGCAGATACTCCTCAATG | 330 | 0.4 | PDZK1IP1 | 10158 |
| Pdzk1ip1 | 67182 | ND000172 | GGGAATGGATGGCAGATACTC | 331 | 0.5 | PDZK1IP1 | 10158 |
| Pdzk1ip1 | 67182 | ND000176 | CTCCCTCACCTCTCTAGAATC | 332 | 0.6 | PDZK1IP1 | 10158 |
| Pdzk1ip1 | 67182 | ND000170 | TGCAATCGTCTTCGCCGTCAA | 333 | 0.8 | PDZK1IP1 | 10158 |
| Pdzk1ip1 | 67182 | ND000173 | CATTGCTGTCGCTGTGTTCTT | 334 | 1.2 | PDZK1IP1 | 10158 |
| Pdzk1ip1 | 67182 | TRCN0000244505 | ACAAGAATGCCTACGAGAATG | 335 | 1.7 | PDZK1IP1 | 10158 |
| Pdzk1ip1 | 67182 | ND000174 | TTCTTGGTCCTTGTTGCAATC | 336 | 2.0 | PDZK1IP1 | 10158 |
| Pdzk1ip1 | 67182 | TRCN0000244509 | GGAGCACAGTGATGATCATTG | 337 | 2.5 | PDZK1IP1 | 10158 |
| Pdzk1ip1 | 67182 | ND000171 | ACTGCTCTACAGGAATCTACT | 338 | 2.5 | PDZK1IP1 | 10158 |
| Pdzk1ip1 | 67182 | ND000175 | CTGTCAACAAGGTCTAGGAAA | 339 | 4.8 | PDZK1IP1 | 10158 |
| Pdzk1ip1 | 67182 | TRCN0000244508 | CCTCATTGCTGTCGCTGTGTT | 340 | 6.3 | PDZK1IP1 | 10158 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| PdzK1ip1 | 67182 | TRCN0000244506 | TCTACAGGAATCTACTGAAAC | 341 | 12.9 | PDZK1IP1 | 10158 |
| Pkd1 | 18763 | ND000445 | CAAGTCCTATGACCCTAATTT | 342 | 0.5 | PKD1 | 5310 |
| Pkd1 | 18763 | TRCN0000304664 | GGTGGACACCACTCAGTATTA | 343 | 0.8 | PKD1 | 5310 |
| Pkd1 | 18763 | TRCN0000072086 | CCAACTCAACATCACCGTAAA | 344 | 0.8 | PKD1 | 5310 |
| Pkd1 | 18763 | TRCN0000304612 | ACACAATACCACGCATATTTA | 345 | 0.9 | PKD1 | 5310 |
| Pkd1 | 18763 | ND000447 | GGCCGCTTCAAATATGAAATA | 346 | 1.2 | PKD1 | 5310 |
| Pkd1 | 18763 | ND000444 | TTCACTAGGAGTGGCATATTC | 347 | 1.3 | PKD1 | 5310 |
| Pkd1 | 18763 | ND000442 | CATCTATAAGGGTAGTCTTTC | 348 | 1.4 | PKD1 | 5310 |
| Pkd1 | 18763 | ND000441 | GTTATTACCTCTCTTGTTTCT | 349 | 1.8 | PKD1 | 5310 |
| Pkd1 | 18763 | ND000446 | GTAGTCTACCCTGTCTATTTG | 350 | 2.9 | PKD1 | 5310 |
| Pkd1 | 18763 | TRCN0000072084 | GCCCTGTACCTTTCAACCAAT | 351 | 4.9 | PKD1 | 5310 |
| Pkd1 | 18763 | ND000443 | CATGTCATCGAGTACTCTTTA | 352 | 6.2 | PKD1 | 5310 |
| Pkd1 | 18763 | TRCN0000304611 | CAACTGATGGTGTCCTATATA | 353 | 7.7 | PKD1 | 5310 |
| Pkd1 | 18763 | TRCN0000072085 | CCATCATTGAAGGTGGCTCAT | 354 | 8.9 | PKD1 | 5310 |
| Pkd1 | 18763 | TRCN0000072087 | GCTTCACTACTCTTCCTGCTT | 355 | 9.9 | PKD1 | 5310 |
| Pkd1 | 18763 | TRCN0000331808 | CGCTCGCACTTTCAGCAATAA | 356 | 47.6 | PKD1 | 5310 |
| Ppm1g | 14208 | TRCN0000326875 | GAGGATGATAAAGACAAAGTA | 357 | 0.3 | PPM1G | 5496 |
| Ppm1g | 14208 | TRCN0000326874 | GCTTTCCTCAGCCCATTACAA | 358 | 0.5 | PPM1G | 5496 |
| Ppm1g | 14208 | ND000458 | GAGATGATGGTCCCTGGAATG | 359 | 0.8 | PPM1G | 5496 |
| Ppm1g | 14208 | TRCN0000375841 | TGACCACAGAGGAAGTCATTA | 360 | 1.1 | PPM1G | 5496 |
| Ppm1g | 14208 | TRCN0000081212 | GATGCCTTCTTGGCTATTGAT | 361 | 1.1 | PPM1G | 5496 |
| Ppm1g | 14208 | TRCN0000306418 | CCATGGATGGACGAGTCAATG | 362 | 1.2 | PPM1G | 5496 |
| Ppm1g | 14208 | ND000460 | TGACGCGATATGGGCAGAACT | 363 | 1.2 | PPM1G | 5496 |
| Ppm1g | 14208 | ND000464 | GCTACCATGACTATTGAAGAG | 364 | 1.3 | PPM1G | 5496 |
| Ppm1g | 14208 | ND000462 | TGGCAAAGCTTTAGATATGTC | 365 | 2.1 | PPM1G | 5496 |
| Ppm1g | 14208 | ND000465 | CATGGATGGACGAGTCAATGG | 366 | 2.9 | PPM1G | 5496 |
| Ppm1g | 14208 | TRCN0000081210 | CTTCGGTTATTGTCATCCATT | 367 | 3.0 | PPM1G | 5496 |
| Ppm1g | 14208 | ND000459 | TGCCTGTGCTCTGTTGTGTTG | 368 | 3.6 | PPM1G | 5496 |
| Ppm1g | 14208 | ND000461 | CAAATTAGTGAGCCCGGTACT | 369 | 6.2 | PPM1G | 5496 |
| Ppm1g | 14208 | TRCN0000081209 | GCCTTGTACTGTGCCAAATAT | 370 | 7.1 | PPM1G | 5496 |
| Ppm1g | 14208 | ND000463 | CATGACGTGCATCATCATTTG | 371 | 8.5 | PPM1G | 5496 |
| Ppp2r2d | 52432 | ND000490 | ACTTCGAGACCCATTTAGAAT | 372 | 0.7 | PPP2R2D | 55844 |
| Ppp2r2d | 52432 | ND000488 | CAGAAGATCCCAGCAGTAGAT | 373 | 0.9 | PPP2R2D | 55844 |
| Ppp2r2d | 52432 | TRCN0000080899 | GCCACCAATAACTTGTATATA | 374 | 1.0 | PPP2R2D | 55844 |
| Ppp2r2d | 52432 | TRCN0000430828 | ATAGTGATCATGAAACATATC | 375 | 1.3 | PPP2R2D | 55844 |
| Ppp2r2d | 52432 | ND000487 | ATATGTACGCCGGTCAATTAG | 376 | 1.4 | PPP2R2D | 55844 |
| Ppp2r2d | 52432 | TRCN0000425449 | ATGCTCATACATATCACATAA | 377 | 1.5 | PPP2R2D | 55844 |
| Ppp2r2d | 52432 | TRCN0000427220 | TCATCTCCACCGTTGAGTTTA | 378 | 1.6 | PPP2R2D | 55844 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Ppp2r2d | 52432 | ND000491 | GATCTGAGAATTAACCTATGG | 379 | 1.7 | PPP2R2D | 55844 |
| Ppp2r2d | 52432 | TRCN0000080901 | CCATTTAGAATTACGGCACTA | 380 | 1.9 | PPP2R2D | 55844 |
| Ppp2r2d | 52432 | TRCN0000080902 | CGGTTCAGACAGTGCCATTAT | 381 | 2.0 | PPP2R2D | 55844 |
| Ppp2r2d | 52432 | ND000489 | CACCGTTGAGTTTAACTACTC | 382 | 4.0 | PPP2R2D | 55844 |
| Ppp2r2d | 52432 | ND000486 | GCTCAATAAAGGCCATTACTC | 383 | 4.9 | PPP2R2D | 55844 |
| Ppp2r2d | 52432 | TRCN0000431278 | GAGAATTAACCTATGGCATTT | 384 | 8.3 | PPP2R2D | 55844 |
| Ppp2r2d | 52432 | ND000492 | CCACAGTGGTCGATACATGAT | 385 | 16.3 | PPP2R2D | 55844 |
| Ppp2r2d | 52432 | TRCN0000080900 | CCCACATCAGTGCAATGTATT | 386 | 17.2 | PPP2R2D | 55844 |
| Ppp3cc | 19057 | ND000512 | CCCGAGGTCTAGACCGAATTA | 387 | 0.1 | PPP3CC | 5533 |
| Ppp3cc | 19057 | ND000510 | TCACAGTGTGTGGTGATGTTC | 388 | 0.4 | PPP3CC | 5533 |
| Ppp3cc | 19057 | TRCN0000012695 | GCTGTATCTATGGAGCTTAAA | 389 | 0.4 | PPP3CC | 5533 |
| Ppp3cc | 19057 | TRCN0000012693 | CCTATGAGCAAATCACATTTA | 390 | 0.4 | PPP3CC | 5533 |
| Ppp3cc | 19057 | ND000511 | AGGAATGTCGGATCAAGTATT | 391 | 0.7 | PPP3CC | 5533 |
| Ppp3cc | 19057 | TRCN0000012694 | CGGCTAACTTTGAAGGAAGTT | 392 | 0.9 | PPP3CC | 5533 |
| Ppp3cc | 19057 | TRCN0000012696 | CGGATGAAGAAATGAACGTAA | 393 | 1.2 | PPP3CC | 5533 |
| Ppp3cc | 19057 | ND000508 | ACCTAGTAATACTCGCTACCT | 394 | 1.4 | PPP3CC | 5533 |
| Ppp3cc | 19057 | ND000513 | CTGTATCTATGGAGCTTAAAG | 395 | 1.6 | PPP3CC | 5533 |
| Ppp3cc | 19057 | ND000515 | AGAAATGAACGTAACCGATGA | 396 | 1.8 | PPP3CC | 5533 |
| Ppp3cc | 19057 | ND000514 | CAAACAACTTAAACTTGGAGG | 397 | 2.4 | PPP3CC | 5533 |
| Ppp3cc | 19057 | ND000507 | TGTAATTCAGTCGCATTTATT | 398 | 2.6 | PPP3CC | 5533 |
| Ppp3cc | 19057 | ND000506 | GGACAATTCTTTGACCTGATG | 399 | 4.2 | PPP3CC | 5533 |
| Ppp3cc | 19057 | TRCN0000012697 | CGAGGTCTAGACCGAATTAAT | 400 | 4.3 | PPP3CC | 5533 |
| Ppp3cc | 19057 | ND000509 | TTCCGTCACTTATTACGATTT | 401 | 4.4 | PPP3CC | 5533 |
| Prkab2 | 108097 | ND000529 | CTGTGGTTACCAGTCAGCTTG | 402 | 0.2 | PRKAB2 | 5565 |
| Prkab2 | 108097 | TRCN0000025112 | GTATGTCACCACGCTGCTGTA | 403 | 0.4 | PRKAB2 | 5565 |
| Prkab2 | 108097 | ND000527 | CCCTCACCTACTCCAAGTTAT | 404 | 0.7 | PRKAB2 | 5565 |
| Prkab2 | 108097 | TRCN0000361908 | TATGAGTTCACGGAGTTTATT | 405 | 0.7 | PRKAB2 | 5565 |
| Prkab2 | 108097 | TRCN0000025111 | CGCAACCCATCGCTACAAGAA | 406 | 0.8 | PRKAB2 | 5565 |
| Prkab2 | 108097 | TRCN0000025109 | CATCGCTACAAGAAGAAGTAT | 407 | 0.9 | PRKAB2 | 5565 |
| Prkab2 | 108097 | ND000528 | CAATTGGAGCACCAAGATCCC | 408 | 1.1 | PRKAB2 | 5565 |
| Prkab2 | 108097 | ND000530 | AGTGGGTTCATGATCCGTCAG | 409 | 1.1 | PRKAB2 | 5565 |
| Prkab2 | 108097 | ND000526 | ACCGTTATCCGCTGGTCTGAA | 410 | 1.8 | PRKAB2 | 5565 |
| Prkab2 | 108097 | TRCN0000361952 | GATCTGAGGAGAGATTCAAAT | 411 | 2.0 | PRKAB2 | 5565 |
| Prkab2 | 108097 | TRCN0000361953 | CTTAACAAGGACACGAATATT | 412 | 2.3 | PRKAB2 | 5565 |
| Prkab2 | 108097 | TRCN0000361910 | CTCTGATAAAGAGTCATAATG | 413 | 2.6 | PRKAB2 | 5565 |
| Prkab2 | 108097 | TRCN0000025110 | CGCTGCTGTATAAGCCCATCT | 414 | 4.1 | PRKAB2 | 5565 |
| Prkab2 | 108097 | ND000525 | CTTACGGTCAAGAAATGTATG | 415 | 4.8 | PRKAB2 | 5565 |
| Prkab2 | 108097 | TRCN0000025113 | CATTAAGGACAGTGTGATGGT | 416 | 7.0 | PRKAB2 | 5565 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Ptpn2 | 19255 | ND000532 | TCCGAACACATGCTGCCATTT | 417 | 0.5 | PTPN2 | 5771 |
| Ptpn2 | 19255 | TRCN0000029891 | GCCAAGATTGACAGACACCTA | 418 | 1.0 | PTPN2 | 5771 |
| Ptpn2 | 19255 | TRCN0000279253 | AGACTATTCTGCAGCTATAAA | 419 | 1.0 | PTPN2 | 5771 |
| Ptpn2 | 19255 | TRCN0000029893 | CCGTTATACTTGGAAATTCGA | 420 | 1.0 | PTPN2 | 5771 |
| Ptpn2 | 19255 | TRCN0000279254 | AGTATCGAATGGGACTTATTC | 421 | 1.2 | PTPN2 | 5771 |
| Ptpn2 | 19255 | ND000534 | TTATATTAATGCCAGCTTAGT | 422 | 1.4 | PTPN2 | 5771 |
| Ptpn2 | 19255 | ND000531 | ATGTTCATGACTTGAGACTAT | 423 | 1.7 | PTPN2 | 5771 |
| Ptpn2 | 19255 | TRCN0000279329 | ATATGATCACAGTCGTGTTAA | 424 | 2.2 | PTPN2 | 5771 |
| Ptpn2 | 19255 | TRCN0000279252 | CGGTGGAAAGAACTTTCTAAA | 425 | 2.2 | PTPN2 | 5771 |
| Ptpn2 | 19255 | ND000533 | CCATATCTCACTTCCATTATA | 426 | 4.7 | PTPN2 | 5771 |
| Ptpn2 | 19255 | TRCN0000279330 | TCTCCTACATGGCCATAATAG | 427 | 5.0 | PTPN2 | 5771 |
| Ptpn2 | 19255 | TRCN0000029890 | CGGTGGAAAGAACTTTCTAAA | 428 | 5.1 | PTPN2 | 5771 |
| Ptpn2 | 19255 | ND000535 | TATCGAATGGGACTTATTCAG | 429 | 5.5 | PTPN2 | 5771 |
| Ptpn2 | 19255 | TRCN0000029892 | CCTGTCTTGTTCTGATGGAAA | 430 | 7.4 | PTPN2 | 5771 |
| Rbks | 71336 | ND000536 | TCGCTGCAGTCAGTGTACAGG | 431 | 0.4 | RBKS | 611132 |
| Rbks | 71336 | ND000543 | GGCCTTCTACCTGGCTTACTA | 432 | 0.6 | RBKS | 611132 |
| Rbks | 71336 | ND000537 | CTGCAATGATTCTCCTAGAAC | 433 | 0.9 | RBKS | 611132 |
| Rbks | 71336 | ND000544 | AGTGGTGGGTTCCTGCATGAC | 434 | 0.9 | RBKS | 611132 |
| Rbks | 71336 | ND000539 | ATATGCCAGCTAGAAATAAGC | 435 | 1.1 | RBKS | 611132 |
| Rbks | 71336 | TRCN0000078936 | GTGATGATATGCCAGCTAGAA | 436 | 1.2 | RBKS | 611132 |
| Rbks | 71336 | ND000538 | CATATTTCTACAGAGTTTACA | 437 | 1.7 | RBKS | 611132 |
| Rbks | 71336 | TRCN0000078934 | TCAATAATGAAGGCCAGAATA | 438 | 1.9 | RBKS | 611132 |
| Rbks | 71336 | ND000545 | GCTGCCAGGTTGTGGTCATCA | 439 | 2.7 | RBKS | 611132 |
| Rbks | 71336 | TRCN0000078937 | TGATGATATGCCAGCTAGAAA | 440 | 4.0 | RBKS | 611132 |
| Rbks | 71336 | ND000541 | CAAGGTTGGCAACGATTCTTT | 441 | 4.1 | RBKS | 611132 |
| Rbks | 71336 | ND000542 | GAGCCTGTTCCAAAGCACATT | 442 | 5.0 | RBKS | 611132 |
| Rbks | 71336 | TRCN0000078935 | CCAAAGCACATTCCCACTGAA | 443 | 5.7 | RBKS | 611132 |
| Rbks | 71336 | ND000540 | CATTAGCCGAGCCAAAGTGAT | 444 | 12.8 | RBKS | 611132 |
| Rbks | 71336 | TRCN0000078933 | GCCTCCATAATTGTCAATAAT | 445 | 13.9 | RBKS | 611132 |
| Rock1 | 19877 | ND000568 | CATACTGTTAGTCGGCTTGAA | 446 | 0.6 | ROCK1 | 6093 |
| Rock1 | 19877 | ND000567 | ATGACATGCAAGCGCAATTGG | 447 | 0.7 | ROCK1 | 6093 |
| Rock1 | 19877 | ND000565 | GCCTACAGGTAGATTAGATTA | 448 | 0.9 | ROCK1 | 6093 |
| Rock1 | 19877 | ND000569 | AGTTCAATTGGTGAGGCATAA | 449 | 1.0 | ROCK1 | 6093 |
| Rock1 | 19877 | TRCN0000361452 | CTAGCAAAGAGAGTGATATTG | 450 | 1.2 | ROCK1 | 6093 |
| Rock1 | 19877 | TRCN0000022901 | CCTGGTTTATGATTTGGATTT | 451 | 1.6 | ROCK1 | 6093 |
| Rock1 | 19877 | TRCN0000022900 | CGGGAGTTACAAGATCAACTT | 452 | 1.7 | ROCK1 | 6093 |
| Rock1 | 19877 | TRCN0000022902 | CCGTGCAAAGTAAGTTACGAT | 453 | 1.8 | ROCK1 | 6093 |
| Rock1 | 19877 | TRCN0000022899 | GCAGAAATAATGAATCGCAAA | 454 | 2.0 | ROCK1 | 6093 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Rock1 | 19877 | ND000566 | ATCAAGATCAGATCGTGGAAG | 455 | 2.2 | ROCK1 | 6093 |
| Rock1 | 19877 | TRCN0000361453 | TTCAATTGGTGAGGCATAAAT | 456 | 2.3 | ROCK1 | 6093 |
| Rock1 | 19877 | TRCN0000022903 | GCAGTGTCTCAAATTGAGAAA | 457 | 4.1 | ROCK1 | 6093 |
| Rock1 | 19877 | TRCN0000361455 | TGTGGGATGCTACCTGATAAA | 458 | 4.4 | ROCK1 | 6093 |
| Rock1 | 19877 | TRCN0000361522 | CTACAGGTAGATTAGATTAAT | 459 | 5.6 | ROCK1 | 6093 |
| Rock1 | 19877 | TRCN0000361521 | CAACTTTCTAAGCAGATATAA | 460 | 6.5 | ROCK1 | 6093 |
| Sbf1 | 77980 | ND000571 | CAGTATGTTACTCGTAAGAAG | 461 | 0.2 | SBF1 | 6305 |
| Sbf1 | 77980 | TRCN0000081099 | GCAGTATGTTACTCGTAAGAA | 462 | 0.4 | SBF1 | 6305 |
| Sbf1 | 77980 | ND000575 | TGCTAAGTTGTTTCTAGAACC | 463 | 0.8 | SBF1 | 6305 |
| Sbf1 | 77980 | ND000570 | CGATACTATGACCACCGAATG | 464 | 0.8 | SBF1 | 6305 |
| Sbf1 | 77980 | TRCN0000081101 | CGAGAGGAATCCACCAACTTT | 465 | 0.9 | SBF1 | 6305 |
| Sbf1 | 77980 | TRCN0000081102 | GCGATACTATGACCACCGAAT | 466 | 1.5 | SBF1 | 6305 |
| Sbf1 | 77980 | ND000578 | CTAACTTATTGTGGTGTCATG | 467 | 1.5 | SBF1 | 6305 |
| Sbf1 | 77980 | ND000574 | TCTTGCTGGACTCTGATTATG | 468 | 1.6 | SBF1 | 6305 |
| Sbf1 | 77980 | ND000572 | GGCTAGATGAGGGCACAATTC | 469 | 2.2 | SBF1 | 6305 |
| Sbf1 | 77980 | ND000573 | GAAGACAACACGTCGCGTTTA | 470 | 3.1 | SBF1 | 6305 |
| Sbf1 | 77980 | ND000577 | TACGGAATTGCATCTCCTATG | 471 | 3.2 | SBF1 | 6305 |
| Sbf1 | 77980 | TRCN0000081098 | CACGCGGACATCTATGACAAA | 472 | 4.8 | SBF1 | 6305 |
| Sbf1 | 77980 | ND000579 | TTACCACATACCGCGTCATCT | 473 | 5.6 | SBF1 | 6305 |
| Sbf1 | 77980 | TRCN0000081100 | CCCTACAGCAATGTGTCCAAT | 474 | 6.0 | SBF1 | 6305 |
| Sbf1 | 77980 | ND000576 | GACTTTGTCGTCCGCATGATG | 475 | 6.9 | SBF1 | 6305 |
| Smad2 | 17126 | ND000208 | AGATCAGTGGGACACAACAGG | 476 | 0.4 | SMAD2 | 4087 |
| Smad2 | 17126 | TRCN0000089336 | TGGTGTTCAATCGCATACTAT | 477 | 1.0 | SMAD2 | 4087 |
| Smad2 | 17126 | ND000205 | GTAATTACATCCCAGAAACAC | 478 | 1.1 | SMAD2 | 4087 |
| Smad2 | 17126 | TRCN0000089334 | CGGTTAGATGAGCTTGAGAAA | 479 | 1.2 | SMAD2 | 4087 |
| Smad2 | 17126 | TRCN0000089333 | CCAGTAGTAGTGCCTGAAGTA | 480 | 1.2 | SMAD2 | 4087 |
| Smad2 | 17126 | ND000207 | TAACCCGAATGTGCACCATAA | 481 | 1.2 | SMAD2 | 4087 |
| Smad2 | 17126 | ND000199 | CCCAACTGTAACCAGAGATAC | 482 | 1.4 | SMAD2 | 4087 |
| Smad2 | 17126 | TRCN0000089335 | CCACTGTAGAAATGACAAGAA | 483 | 1.5 | SMAD2 | 4087 |
| Smad2 | 17126 | ND000200 | CCTCCGTCGTAGTATTCATGT | 484 | 1.9 | SMAD2 | 4087 |
| Smad2 | 17126 | ND000201 | GCCAGTGGTGAAGAGACTTCT | 485 | 1.9 | SMAD2 | 4087 |
| Smad2 | 17126 | ND000203 | CTCGGCACACGGAGATTCTAA | 486 | 6.7 | SMAD2 | 4087 |
| Smad2 | 17126 | ND000204 | GACAGTATCCCAAAGGTTATT | 487 | 7.1 | SMAD2 | 4087 |
| Smad2 | 17126 | ND000202 | GAGTGCGCTTGTATTACATAG | 488 | 7.1 | SMAD2 | 4087 |
| Smad2 | 17126 | TRCN0000089337 | CTAAGTGATAGTGCAATCTTT | 489 | 19.3 | SMAD2 | 4087 |
| Smad2 | 17126 | ND000206 | TGCCTAAGTGATAGTGCAATC | 490 | 30.3 | SMAD2 | 4087 |
| Socs1 | 12703 | ND000214 | TTTCGAGCTGCTGGAGCACTA | 491 | 0.6 | SOCS1 | 8651 |
| Socs1 | 12703 | ND000219 | TCGAGCTGCTGGAGCACTACG | 492 | 1.2 | SOCS1 | 8651 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Socs1 | 12703 | TRCN0000231240 | TCGCCAACGGAACTGCTTCTT | 493 | 1.4 | SOCS1 | 8651 |
| Socs1 | 12703 | ND000218 | ACTTCTGGCTGGAGACCTCAT | 494 | 1.5 | SOCS1 | 8651 |
| Socs1 | 12703 | TRCN0000067420 | GCGAGACCTTCGACTGCCTTT | 495 | 1.7 | SOCS1 | 8651 |
| Socs1 | 12703 | TRCN0000067418 | CGACACTCACTTCCGCACCTT | 496 | 1.8 | SOCS1 | 8651 |
| Socs1 | 12703 | ND000220 | CTACCTGAGTTCCTTCCCCTT | 497 | 1.8 | SOCS1 | 8651 |
| Socs1 | 12703 | TRCN0000231238 | TTCCGCTCCCACTCCGATTAC | 498 | 1.8 | SOCS1 | 8651 |
| Socs1 | 12703 | TRCN0000231241 | TAACCCGGTACTCCGTGACTA | 499 | 1.9 | SOCS1 | 8651 |
| Socs1 | 12703 | ND000216 | TACTCCGTGACTACCTGAGTT | 500 | 2.4 | SOCS1 | 8651 |
| Socs1 | 12703 | ND000211 | CTTCCGCTCCCACTCCGATTA | 501 | 2.6 | SOCS1 | 8651 |
| Socs1 | 12703 | TRCN0000067422 | GCGCGACAGTCGCCAACGGAA | 502 | 2.7 | SOCS1 | 8651 |
| Socs1 | 12703 | TRCN0000231239 | TGGACGCCTGCGGCTTCTATT | 503 | 2.9 | SOCS1 | 8651 |
| Socs1 | 12703 | TRCN0000067419 | CGCATCCCTCTTAACCCGGTA | 504 | 3.4 | SOCS1 | 8651 |
| Socs1 | 12703 | ND000212 | TACATATTCCCAGTATCTTTG | 505 | 3.6 | SOCS1 | 8651 |
| Socs1 | 12703 | TRCN0000231242 | GCGCCTTATTATTTCTTATTA | 506 | 4.1 | SOCS1 | 8651 |
| Socs1 | 12703 | TRCN0000067421 | CCGTGACTACCTGAGTTCCTT | 507 | 5.8 | SOCS1 | 8651 |
| Socs1 | 12703 | ND000215 | GGAGGGTCTCTGGCTTCATTT | 508 | 7.8 | SOCS1 | 8651 |
| Socs1 | 12703 | ND000213 | TTCGCGCTCAGCGTGAAGATG | 509 | 8.4 | SOCS1 | 8651 |
| Socs1 | 12703 | ND000217 | ATCCCTCTTAACCCGGTACTC | 510 | 8.5 | SOCS1 | 8651 |
| Socs3 | 12702 | ND000222 | CGAGAAGATTCCGCTGGTACT | 511 | 0.3 | SOCS3 | 9021 |
| Socs3 | 12702 | TRCN0000067472 | GCTGCAGGAGAGCGGATTCTA | 512 | 0.4 | SOCS3 | 9021 |
| Socs3 | 12702 | TRCN0000231180 | GGCTAGGAGACTCGCCTTAAA | 513 | 0.7 | SOCS3 | 9021 |
| Socs3 | 12702 | TRCN0000067468 | GCTAGGAGACTCGCCTTAAAT | 514 | 0.8 | SOCS3 | 9021 |
| Socs3 | 12702 | ND000227 | GAGAGCTTACTACATCTATTC | 515 | 0.9 | SOCS3 | 9021 |
| Socs3 | 12702 | ND000221 | GGGAGTTCCTGGATCAGTATG | 516 | 1.0 | SOCS3 | 9021 |
| Socs3 | 12702 | TRCN0000067470 | CAAGAGAGCTTACTACATCTA | 517 | 1.1 | SOCS3 | 9021 |
| Socs3 | 12702 | TRCN0000231179 | CAGTATGATGCTCCACTTTAA | 518 | 1.2 | SOCS3 | 9021 |
| Socs3 | 12702 | ND000223 | CAAGCTGGTGCACCACTACAT | 519 | 1.3 | SOCS3 | 9021 |
| Socs3 | 12702 | ND000224 | ACCTGGACTCCTATGAGAAAG | 520 | 1.4 | SOCS3 | 9021 |
| Socs3 | 12702 | TRCN0000067471 | CTTCTTCACGTTGAGCGTCAA | 521 | 1.6 | SOCS3 | 9021 |
| Socs3 | 12702 | ND000228 | TCGGGAGTTCCTGGATCAGTA | 522 | 1.7 | SOCS3 | 9021 |
| Socs3 | 12702 | ND000226 | TGCAGGAGAGCGGATTCTACT | 523 | 1.9 | SOCS3 | 9021 |
| Socs3 | 12702 | ND000225 | CCTGGTGGGACAATACCTTTG | 524 | 3.3 | SOCS3 | 9021 |
| Socs3 | 12702 | TRCN0000067469 | GATCAGTATGATGCTCCACTT | 525 | 4.6 | SOCS3 | 9021 |
| Socs3 | 12702 | TRCN0000231176 | TCTTCACGTTGAGCGTCAAGA | 526 | 4.7 | SOCS3 | 9021 |
| Socs3 | 12702 | TRCN0000231177 | CGCTTCGACTGTGTACTCAAG | 527 | 4.9 | SOCS3 | 9021 |
| Socs3 | 12702 | ND000229 | GGAGCAAAAGGGTCAGAGGGG | 528 | 5.3 | SOCS3 | 9021 |
| Stk17b | 98267 | ND000590 | AGTGGGACTTTGGAAGCTTGT | 529 | 0.3 | STK17B | 9262 |
| Stk17b | 98267 | ND000597 | CATCTGGACTGACTCGGAAAT | 530 | 0.5 | STK17B | 9262 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Stk17b | 98267 | ND000596 | ATGCTGCGGGTGGAGAAATTT | 531 | 0.6 | STK17B | 9262 |
| Stk17b | 98267 | ND000588 | TATCTGAATATTTCTCAAGTG | 532 | 0.6 | STK17B | 9262 |
| Stk17b | 98267 | ND000593 | TTTACCTGAGTTAGCCGAAAT | 533 | 0.7 | STK17B | 9262 |
| Stk17b | 98267 | ND000589 | GTTAACTCATACATCACCATT | 534 | 1.1 | STK17B | 9262 |
| Stk17b | 98267 | ND000594 | CCTATACCATAACTCTATTAC | 535 | 1.3 | STK17B | 9262 |
| Stk17b | 98267 | ND000592 | CTCAACTATGATCCCATTACC | 536 | 1.3 | STK17B | 9262 |
| Stk17b | 98267 | ND000591 | AGACCTCCAAGTCCTCCTGTA | 537 | 1.4 | STK17B | 9262 |
| Stk17b | 98267 | TRCN0000024255 | GCTGTGGTTAGACAATGTATA | 538 | 1.6 | STK17B | 9262 |
| Stk17b | 98267 | ND000595 | TATTGGCATAATAGCGTATAT | 539 | 3.6 | STK17B | 9262 |
| Stk17b | 98267 | TRCN0000024256 | GCTTGTTTCATCCTGAGGAAA | 540 | 4.0 | STK17B | 9262 |
| Stk17b | 98267 | TRCN0000024258 | TCCTCAACTATGATCCCATTA | 541 | 4.2 | STK17B | 9262 |
| Stk17b | 98267 | TRCN0000024254 | GCAGAAGCTAAGGACGAATTT | 542 | 4.4 | STK17B | 9262 |
| Stk17b | 98267 | TRCN0000024257 | CAGAATAACATTGTTCACCTT | 543 | 6.4 | STK17B | 9262 |
| Tnk1 | 83813 | ND000599 | TGCCCAGCGCAGACTTAATGA | 544 | 0.3 | TNK1 | 8711 |
| Tnk1 | 83813 | TRCN0000023704 | CGTGACACTCTGGGAAATGTT | 545 | 0.6 | TNK1 | 8711 |
| Tnk1 | 83813 | ND000602 | GTGTCCCACCATATCTCATCC | 546 | 0.7 | TNK1 | 8711 |
| Tnk1 | 83813 | ND000600 | AGTAGCAATACCGGATCACTG | 547 | 0.7 | TNK1 | 8711 |
| Tnk1 | 83813 | TRCN0000023706 | GCGGGAAGTATCTGTCATGAT | 548 | 0.8 | TNK1 | 8711 |
| Tnk1 | 83813 | ND000603 | AGAGGATGCGAGGCATTTCCA | 549 | 1.1 | TNK1 | 8711 |
| Tnk1 | 83813 | ND000601 | GGACAGAGAGAAGGCAACGTT | 550 | 1.1 | TNK1 | 8711 |
| Tnk1 | 83813 | TRCN0000361891 | AGAATTGGGTGTACAAGATAC | 551 | 1.3 | TNK1 | 8711 |
| Tnk1 | 83813 | TRCN0000023707 | CCACCTATTATCTGCAACTCT | 552 | 1.6 | TNK1 | 8711 |
| Tnk1 | 83813 | TRCN0000023705 | GCCTCTGATGTGTGGATGTTT | 553 | 1.7 | TNK1 | 8711 |
| Tnk1 | 83813 | TRCN0000361890 | TGCAGAGGATGCGAGGCATTT | 554 | 1.8 | TNK1 | 8711 |
| Tnk1 | 83813 | TRCN0000361889 | TGGCGTGACACTCTGGGAAAT | 555 | 2.0 | TNK1 | 8711 |
| Tnk1 | 83813 | TRCN0000023708 | CAGACTTAATGAAGCCCTGAA | 556 | 5.2 | TNK1 | 8711 |
| Tnk1 | 83813 | TRCN0000361892 | GTGTTGTACATCGAGGGTTAT | 557 | 5.2 | TNK1 | 8711 |
| Tnk1 | 83813 | ND000598 | CCAGAACTTCGGCGTACAAGA | 558 | 7.6 | TNK1 | 8711 |
| Trpm7 | 58800 | ND000607 | GAAGTATCAGCGGTATCATTT | 559 | 0.4 | TRPM7 | 54822 |
| Trpm7 | 58800 | TRCN0000274774 | ATGGATTGTTATCGCTTATAT | 560 | 0.7 | TRPM7 | 54822 |
| Trpm7 | 58800 | ND000606 | GCTTGGAAAGGGTCTTATTAA | 561 | 0.9 | TRPM7 | 54822 |
| Trpm7 | 58800 | ND000608 | ATTGAATCCCTTGAGCAAATT | 562 | 0.9 | TRPM7 | 54822 |
| Trpm7 | 58800 | TRCN0000274712 | CCTTATCAAACCCTATTGAAT | 563 | 1.1 | TRPM7 | 54822 |
| Trpm7 | 58800 | TRCN0000274773 | CCAAAGATCAAGAACCCATTT | 564 | 1.2 | TRPM7 | 54822 |
| Trpm7 | 58800 | ND000604 | TAGAGGTAATGTTCTCATTGA | 565 | 1.2 | TRPM7 | 54822 |
| Trpm7 | 58800 | ND000610 | ACCGGATTGGTTACGAGATAG | 566 | 1.5 | TRPM7 | 54822 |
| Trpm7 | 58800 | TRCN0000274772 | ACCTGGTGCAGGACCATTAAC | 567 | 1.7 | TRPM7 | 54822 |
| Trpm7 | 58800 | ND000605 | TAGACTTTCTAGCCGTAAATC | 568 | 2.9 | TRPM7 | 54822 |

TABLE 2-continued

| Mouse Gene Symbol | Mouse Gene ID | shRNA Clone ID | shRNA Target Sequence | SEQ ID NO: | Enrich Fold | Human Gene Symbol | Human Gene ID |
|---|---|---|---|---|---|---|---|
| Trpm7 | 58800 | TRCN0000274711 | CTAGACTTTCTAGCCGTAAAT | 569 | 3.1 | TRPM7 | 54822 |
| Trpm7 | 58800 | TRCN0000023957 | CCTCAGGATGAGTCATCAGAT | 570 | 3.5 | TRPM7 | 54822 |
| Trpm7 | 58800 | TRCN0000023956 | CCTGGTATAAGGTCATATTAA | 571 | 4.9 | TRPM7 | 54822 |
| Trpm7 | 58800 | TRCN0000023955 | GCTCAGAATCTTATTGATGAT | 572 | 5.3 | TRPM7 | 54822 |
| Trpm7 | 58800 | ND000609 | GCCCTAACAGTAGATACATTG | 573 | 5.9 | TRPM7 | 54822 |
| Vamp7 | 20955 | TRCN0000115068 | CTTACTCACATGGCAATTATT | 574 | 0.6 | VAMP7 | 6845 |
| Vamp7 | 20955 | TRCN0000380436 | GCACAACTGAAGCATCACTCT | 575 | 0.8 | VAMP7 | 6845 |
| Vamp7 | 20955 | TRCN0000336075 | GCACAAGTGGATGAACTGAAA | 576 | 0.9 | VAMP7 | 6845 |
| Vamp7 | 20955 | TRCN0000336077 | TTACGGTTCAAGAGCACAAAC | 577 | 1.0 | VAMP7 | 6845 |
| Vamp7 | 20955 | TRCN0000380733 | TAAGAGCCTAGACAAAGTGAT | 578 | 1.0 | VAMP7 | 6845 |
| Vamp7 | 20955 | ND000255 | AGCCATGTGTATGAAGAATAT | 579 | 1.2 | VAMP7 | 6845 |
| Vamp7 | 20955 | ND000258 | TCCAGGAGCCCATACAAGTAA | 580 | 1.4 | VAMP7 | 6845 |
| Vamp7 | 20955 | ND000256 | ATAAACTAACTTACTCACATG | 581 | 1.5 | VAMP7 | 6845 |
| Vamp7 | 20955 | TRCN0000336014 | GCCGCCACATTTCGTTGTAAA | 582 | 1.8 | VAMP7 | 6845 |
| Vamp7 | 20955 | TRCN0000353419 | GCACTTCCTTATGCTATGAAT | 583 | 1.9 | VAMP7 | 6845 |
| Vamp7 | 20955 | TRCN0000115066 | GCCTTAAGATATGCAATGTTA | 584 | 2.2 | VAMP7 | 6845 |
| Vamp7 | 20955 | ND000257 | CTGAAAGGAATAATGGTCAGA | 585 | 4.0 | VAMP7 | 6845 |
| Vamp7 | 20955 | ND000259 | CTCCTTGTAAATGATACACAA | 586 | 9.8 | VAMP7 | 6845 |
| Vamp7 | 20955 | TRCN0000353291 | CTTTGCCTGTCATATAGTTTG | 587 | 10.5 | VAMP7 | 6845 |
| Vamp7 | 20955 | TRCN0000115069 | TCGAGCCATGTGTATGAAGAA | 588 | 11.3 | VAMP7 | 6845 |
| Yes1 | 22612 | ND000617 | ATCCCTAGCAATTACGTAGTG | 589 | 0.5 | YES1 | 7525 |
| Yes1 | 22612 | TRCN0000339152 | TGGTTATATCCCTAGCAATTA | 590 | 0.5 | YES1 | 7525 |
| Yes1 | 22612 | ND000614 | TATGCTTCACTCGGCATGTTT | 591 | 0.6 | YES1 | 7525 |
| Yes1 | 22612 | ND000616 | ATTCCAGATACGGTTACTCAA | 592 | 0.6 | YES1 | 7525 |
| Yes1 | 22612 | ND000613 | TTTAAGAAGGGTGAACGATTT | 593 | 0.7 | YES1 | 7525 |
| Yes1 | 22612 | ND000612 | CACGACCAGAGCTCAGTTTGA | 594 | 0.8 | YES1 | 7525 |
| Yes1 | 22612 | ND000615 | CAGGTATGGTAAACCGTGAAG | 595 | 0.8 | YES1 | 7525 |
| Yes1 | 22612 | ND000611 | GGAGTGGAACATGCTACAGTT | 596 | 1.0 | YES1 | 7525 |
| Yes1 | 22612 | ND000618 | CCTCATTCTCAGTGGTGTCAA | 597 | 2.6 | YES1 | 7525 |
| Yes1 | 22612 | ND000619 | TCGAGAATCATTGCGACTAGA | 598 | 2.8 | YES1 | 7525 |
| Yes1 | 22612 | TRCN0000339083 | CCAGGTACAATGATGCCAGAA | 599 | 2.8 | YES1 | 7525 |
| Yes1 | 22612 | TRCN0000339150 | GCGGAAAGATTACTTCTGAAT | 600 | 3.9 | YES1 | 7525 |
| Yes1 | 22612 | TRCN0000023616 | GCTGCTCTGTATGGTCGATTT | 601 | 4.1 | YES1 | 7525 |
| Yes1 | 22612 | TRCN0000023618 | CCTTGTATGATTATGAAGCTA | 602 | 5.4 | YES1 | 7525 |
| Yes1 | 22612 | TRCN0000023617 | GCCAGTCATTATGGAGTGGAA | 603 | 9.7 | YES1 | 7525 |

shRNAs demonstrating an at least ≥3 shRNAs fold enrichment in tumor relative to spleen indicate a more active target sequence region.

In some aspects, the nucleic acids of the compositions encode the shRNA sequences targeting the human Ppp2r2d and Cblb sequences provided in Table 2a.

TABLE 2a

| # | Gene | Human shRNA Target Sequence |
|---|---|---|
| 1 | Ppp2r2d | CCCGCACCAGTGCAACGTGTT (SEQ ID NO: 636) |
| 2 | Ppp2r2d | TCATAGTGGGCGGTACATGAT (SEQ ID NO: 637) |
| 3 | Ppp2r2d | GAGAATTAATTTATGGCACTT (SEQ ID NO: 638) |
| 4 | Ppp2r2d | CCATTTAGGATCACGGCGCTA (SEQ ID NO: 639) |
| 5 | Ppp2r2d | ATAGTGATCATGAAACATATC (SEQ ID NO: 375) |
| 6 | Ppp2r2d | GCCACCAATAACTTGTACATA (SEQ ID NO: 640) |
| 7 | Ppp2r2d | CGGTTCGGATAGCGCCATCAT (SEQ ID NO: 641) |
| 8 | Ppp2r2d | TCATTTCCACCGTTGAGTTTA (SEQ ID NO: 642) |
| 9 | Ppp2r2d | ATGCTCACACATATCATATAA (SEQ ID NO: 643) |
| 1 | Cblb | CGGGCAATAAGACTCTTTAA (SEQ ID NO: 644) |
| 2 | Cblb | TGCCCAGGTCCAGTTCCATTTC (SEQ ID NO: 645) |
| 3 | Cblb | TCCTGATTTAACTGGATTATG (SEQ ID NO: 646) |
| 4 | Cblb | ATCAAACATCCCTGACTTAAG (SEQ ID NO: 647) |
| 5 | Cblb | CTACACCTCATGACCATATAA (SEQ ID NO: 648) |
| 6 | Cblb | TACACCTCATGACCATATAAA (SEQ ID NO: 649) |
| 7 | Cblb | TCAGTGAGAATGAGTACTTTA (SEQ ID NO: 650) |
| 8 | Cblb | CCTGACTTAAGCATATATTTA (SEQ ID NO: 651) |
| 9 | Cblb | TCTACATTGATAGCCTTATGA (SEQ ID NO: 652) |

In other embodiments, the disclosure provides isolated nucleic acids encoding shRNA sequences complementary to a Ppp2r2d target sequence identical to at least 12, at least 15, at least 20, or at least 25 contiguous nucleotides set forth in SEQ ID NO: 372, 373, 374, 375, 376, 377, 378, 378, 379, 380, 381, 382, 383, 384, 385, or 386.

In other embodiments, the disclosure provides isolated nucleic acids encoding a shRNA comprising a sequence complementary to a human Pp2r2d sequence that corresponds to a murine target sequence set forth in SEQ ID NO: 372, 373, 374, 375, 376, 377, 378, 378, 379, 380, 381, 382, 383, 384, 385, or 386.

In other embodiments, the disclosure provides isolated nucleic acids encoding shRNA sequences complementary to a Eif2ak3 target sequence identical to at least 12, at least 15, at least 20, or at least 25 contiguous nucleotides set forth in SEQ ID NO: 133, 134, 135, 136, 137, 138, 139, 140, 141, 142, 143, 144, 145, 146 or 147.

In other embodiments, the disclosure provides isolated nucleic acids encoding a shRNA comprising a sequence complementary to a human Eif2ak3 sequence that corresponds to a murine target sequence set forth in SEQ ID NO: 133, 134, 135, 136, 137, 138, 139, 140, 141, 142, 143, 144, 145, 146 or 147.

In other embodiments, the disclosure provides isolated nucleic acids encoding shRNA sequences complementary to an Arhgap5 target sequence identical to at least 12, at least 15, at least 20, or at least 25 contiguous nucleotides set forth in SEQ ID NO: 32, 33, 34, 35, 36, 37, 38, 39, 40, 41, or 42.

In other embodiments, the disclosure provides isolated nucleic acids encoding a shRNA comprising a sequence complementary to a human Arhgap5 sequence that corresponds to a murine target sequence set forth in SEQ ID NO: 32, 33, 34, 35, 36, 37, 38, 39, 40, 41, or 42.

In other embodiments, the disclosure provides isolated nucleic acids encoding shRNA sequences complementary to a Smad2 target sequence identical to at least 12, at least 15, at least 20, or at least 25 contiguous nucleotides set forth in SEQ ID NO: 476, 477, 478, 479, 480, 481, 482, 483, 484, 485, 486, 487, 488, 489, or 490.

In other embodiments, the disclosure provides isolated nucleic acids encoding a shRNA comprising a sequence complementary to a human Smad2 sequence that corresponds to a murine target sequence set forth in SEQ ID NO: 476, 477, 478, 479, 480, 481, 482, 483, 484, 485, 486, 487, 488, 489, or 490.

In other embodiments, the disclosure provides isolated nucleic acids encoding shRNA sequences complementary to an Akap81 target sequence identical to at least 12, at least 15, at least 20, or at least 25 contiguous nucleotides set forth in SEQ ID NO: 1, 2, 3, 4, 5, 6, 7, 8, 9, 10, 11, 12, 13, 14, or 15.

In other embodiments, the disclosure provides isolated nucleic acids encoding a shRNA comprising a sequence complementary to a human Akap81 sequence that corresponds to a murine target sequence set forth in SEQ ID NO: 1, 2, 3, 4, 5, 6, 7, 8, 9, 10, 11, 12, 13, 14, or 15.

In other embodiments, the disclosure provides isolated nucleic acids encoding shRNA sequences complementary to a Rbks target sequence identical to at least 12, at least 15, at least 20, or at least 25 contiguous nucleotides set forth in SEQ ID NO: 431, 432, 433, 434, 435, 436, 437, 438, 439, 440, 441, 442, 443, 444, or 445.

In other embodiments, the disclosure provides isolated nucleic acids encoding a shRNA comprising a sequence complementary to a human Rbks sequence that corresponds to a murine target sequence set forth in SEQ ID NO: 431, 432, 433, 434, 435, 436, 437, 438, 439, 440, 441, 442, 443, 444, or 445.

In other embodiments, the disclosure provides isolated nucleic acids encoding shRNA sequences complementary to an Egr2 target sequence identical to at least 12, at least 15, at least 20, or at least 25 contiguous nucleotides set forth in SEQ ID NO: 118, 119, 120, 121, 122, 123, 124, 125, 126, 127, 128, 129, 130, 131, or 132.

In other embodiments, the disclosure provides isolated nucleic acids encoding a shRNA comprising a sequence complementary to a human Egr2 sequence that corresponds to a murine target sequence set forth in SEQ ID NO: 118, 119, 120, 121, 122, 123, 124, 125, 126, 127, 128, 129, 130, 131, or 132.

In other embodiments, the disclosure provides isolated nucleic acids encoding shRNA sequences complementary to a Dgka target sequence identical to at least 12, at least 15, at least 20, or at least 25 contiguous nucleotides set forth in SEQ ID NO: 88, 89, 90, 91, 92, 93, 94, 95, 96, 97, 98, 99, 100, 101, 102, 103, 104, 105, 106, 107, 108, 109, 110, 111, 112, 113, 114, 115, 116 or 117.

In other embodiments, the disclosure provides isolated nucleic acids encoding a shRNA comprising a sequence complementary to a human Dgka sequence that corresponds to a murine target sequence set forth in SEQ ID NO: 88, 89, 90, 91, 92, 93, 94, 95, 96, 97, 98, 99, 100, 101, 102, 103, 104, 105, 106, 107, 108, 109, 110, 111, 112, 113, 114, 115, 116 or 117.

In other embodiments, the disclosure provides isolated nucleic acids encoding shRNA sequences complementary to a Cblb target sequence identical to at least 12, at least 15, at least 20, or at least 25 contiguous nucleotides set forth in SEQ ID NO: 58, 59, 60, 61, 62, 63, 64, 65, 66, 67, 68, 69, 70, 71, or 72.

In other embodiments, the disclosure provides isolated nucleic acids encoding a shRNA comprising a sequence complementary to a human Cblb sequence that corresponds to a murine target sequence set forth in SEQ ID NO: 58, 59, 60, 61, 62, 63, 64, 65, 66, 67, 68, 69, 70, 71, or 72.

In other embodiments, the disclosure provides isolated nucleic acids encoding shRNA sequences complementary to a Mdfic target sequence identical to at least 12, at least 15, at least 20, or at least 25 contiguous nucleotides set forth in SEQ ID NO: 285, 286, 287, 288, 289, 290, 291, 292, 293, 294, 295, 296, 297, 298, or 299.

In other embodiments, the disclosure provides isolated nucleic acids encoding a shRNA comprising a sequence complementary to a human Mdfic sequence that corresponds to a murine target sequence set forth in SEQ ID NO: 285, 286, 287, 288, 289, 290, 291, 292, 293, 294, 295, 296, 297, 298, or 299.

In other embodiments, the disclosure provides isolated nucleic acids encoding shRNA sequences complementary to an Entpd1 target sequence identical to at least 12, at least 15, at least 20, or at least 25 contiguous nucleotides set forth in SEQ ID NO: 148, 149, 150, 151, 152, 153, 154, 155, 156, 157, 158, 159, 160, 161, or 162.

In other embodiments, the disclosure provides isolated nucleic acids encoding a shRNA comprising a sequence complementary to a human Entpd1 sequence that corresponds to a murine target sequence set forth in SEQ ID NO: 148, 149, 150, 151, 152, 153, 154, 155, 156, 157, 158, 159, 160, 161, or 162.

In other embodiments, the disclosure provides isolated nucleic acids encoding shRNA sequences complementary to a Vamp7 target sequence identical to at least 12, at least 15, at least 20, or at least 25 contiguous nucleotides set forth in SEQ ID NO: 574, 575, 576, 577, 578, 579, 580, 581, 582, 583, 584, 585, 586, or 587.

In other embodiments, the disclosure provides isolated nucleic acids encoding a shRNA comprising a sequence complementary to a human Vamp7 sequence that corresponds to a murine target sequence set forth in SEQ ID NO: 574, 575, 576, 577, 578, 579, 580, 581, 582, 583, 584, 585, 586, or 587.

In other embodiments, the disclosure provides isolated nucleic acids encoding shRNA sequences complementary to a Hipk1 target sequence identical to at least 12, at least 15, at least 20, or at least 25 contiguous nucleotides set forth in SEQ ID NO: 208, 209, 210, 211, 212, 213, 214, 215, 216, 217, 218, 219, 220, 221, or 222.

In other embodiments, the disclosure provides isolated nucleic acids encoding a shRNA comprising a sequence complementary to a human Hipk1 sequence that corresponds to a murine target sequence set forth in SEQ ID NO: 208, 209, 210, 211, 212, 213, 214, 215, 216, 217, 218, 219, 220, 221, or 222.

In other embodiments, the disclosure provides isolated nucleic acids encoding shRNA sequences complementary to a Nuak2 target sequence identical to at least 12, at least 15, at least 20, or at least 25 contiguous nucleotides set forth in SEQ ID NO: 315, 316, 317, 318, 319, 320, 321, 322, 323, 324, 325, 326, 327, 328, or 329.

In other embodiments, the disclosure provides isolated nucleic acids encoding a shRNA comprising a sequence complementary to a human Nuak2 sequence that corresponds to a murine target sequence set forth in SEQ ID NO: 315, 316, 317, 318, 319, 320, 321, 322, 323, 324, 325, 326, 327, 328, or 329.

In other embodiments, the disclosure provides isolated nucleic acids encoding shRNA sequences complementary to an Alk target sequence identical to at least 12, at least 15, at least 20, or at least 25 contiguous nucleotides set forth in SEQ ID NO: 16, 17, 18, 19, 20, 21, 22, 23, 24, 25, 26, 27, 28, 29, 30, or 31.

In other embodiments, the disclosure provides isolated nucleic acids encoding a shRNA comprising a sequence complementary to a human Alk sequence that corresponds to a murine target sequence set forth in SEQ ID NO: 16, 17, 18, 19, 20, 21, 22, 23, 24, 25, 26, 27, 28, 29, 30, or 31.

In other embodiments, the disclosure provides isolated nucleic acids encoding shRNA sequences complementary to a Pdzk1ip1 target sequence identical to at least 12, at least 15, at least 20, or at least 25 contiguous nucleotides set forth in SEQ ID NO: 330, 331, 332, 333, 334, 335, 336, 337, 338, 339, 340, or 341.

In other embodiments, the disclosure provides isolated nucleic acids encoding a shRNA comprising a sequence complementary to a human Pdzk1ip1 sequence that corresponds to a murine target sequence set forth in SEQ ID NO: 330, 331, 332, 333, 334, 335, 336, 337, 338, 339, 340, or 341.

In other embodiments, the disclosure provides isolated nucleic acids encoding shRNA sequences complementary to a Blvrb target sequence identical to at least 12, at least 15, at least 20, or at least 25 contiguous nucleotides set forth in SEQ ID NO: 52, 53, 54, 55, 56 or 57.

In other embodiments, the disclosure provides isolated nucleic acids encoding a shRNA comprising a sequence complementary to a human Blvrb that corresponds to a murine target sequence set forth in SEQ ID NO: 52, 53, 54, 55, 56 or 57.

In other embodiments, the disclosure provides isolated nucleic acids encoding shRNA sequences complementary to a Cdkn2a target sequence identical to at least 12, at least 15, at least 20, or at least 25 contiguous nucleotides set forth in SEQ ID NO: 83, 84, 85, 86 or 87.

In other embodiments, the disclosure provides isolated nucleic acids encoding a shRNA comprising a sequence complementary to a human Cdkn2a that corresponds to a murine target sequence set forth in SEQ ID NO: 83, 84, 85, 86 or 87.

In other embodiments, the disclosure provides isolated nucleic acids encoding shRNA sequences complementary to a F11r target sequence identical to at least 12, at least 15, at least 20, or at least 25 contiguous nucleotides set forth in SEQ ID NO: 175, 176 or 177.

In other embodiments, the disclosure provides isolated nucleic acids encoding a shRNA comprising a sequence complementary to a human F11r that corresponds to a murine target sequence set forth in SEQ ID NO: 175, 176 or 177.

In other embodiments, the disclosure provides isolated nucleic acids encoding shRNA sequences complementary to a Fyn target sequence identical to at least 12, at least 15, at least 20, or at least 25 contiguous nucleotides set forth in SEQ ID NO: 187, 191 or 192.

In other embodiments, the disclosure provides isolated nucleic acids encoding a shRNA comprising a sequence complementary to a human Fyn that corresponds to a murine target sequence set forth in SEQ ID NO: 187, 191 or 192.

In other embodiments, the disclosure provides isolated nucleic acids encoding shRNA sequences complementary to a Grk6 target sequence identical to at least 12, at least 15, at least 20, or at least 25 contiguous nucleotides set forth in SEQ ID NO: 204, 205, 206 or 207.

In other embodiments, the disclosure provides isolated nucleic acids encoding a shRNA comprising a sequence complementary to a human Grk6 that corresponds to a murine target sequence set forth in SEQ ID NO: 204, 205, 206 or 207.

In other embodiments, the disclosure provides isolated nucleic acids encoding shRNA sequences complementary to an Inpp5b target sequence identical to at least 12, at least 15, at least 20, or at least 25 contiguous nucleotides set forth in SEQ ID NO: 232, 234, 235, 236 or 237.

In other embodiments, the disclosure provides isolated nucleic acids encoding a shRNA comprising a sequence complementary to a human Inpp5b that corresponds to a murine target sequence set forth in SEQ ID NO: 232, 234, 235, 236 or 237.

In other embodiments, the disclosure provides isolated nucleic acids encoding shRNA sequences complementary to an Impk target sequence identical to at least 12, at least 15, at least 20, or at least 25 contiguous nucleotides set forth in SEQ ID NO: 248, 249, 250, 251 or 252.

In other embodiments, the disclosure provides isolated nucleic acids encoding a shRNA comprising a sequence complementary to a human Impk that corresponds to a murine target sequence set forth in SEQ ID NO: 248, 249, 250, 251 or 252.

In other embodiments, the disclosure provides isolated nucleic acids encoding shRNA sequences complementary to a Jun target sequence identical to at least 12, at least 15, at least 20, or at least 25 contiguous nucleotides set forth in SEQ ID NO: 263, 264, 265, 266, 267, 268 or 269.

In other embodiments, the disclosure provides isolated nucleic acids encoding a shRNA comprising a sequence complementary to a human Jun that corresponds to a murine target sequence set forth in SEQ ID NO: 263, 264, 265, 266, 267, 268 or 269.

In other embodiments, the disclosure provides isolated nucleic acids encoding shRNA sequences complementary to a Mast2 target sequence identical to at least 12, at least 15, at least 20, or at least 25 contiguous nucleotides set forth in SEQ ID NO: 281, 282, 283 or 284.

In other embodiments, the disclosure provides isolated nucleic acids encoding a shRNA comprising a sequence complementary to a human Mast2 that corresponds to a murine target sequence set forth in SEQ ID NO: 281, 282, 283 or 284.

In other embodiments, the disclosure provides isolated nucleic acids encoding shRNA sequences complementary to a Nptxr target sequence identical to at least 12, at least 15, at least 20, or at least 25 contiguous nucleotides set forth in SEQ ID NO: 311, 312, 313 or 314.

In other embodiments, the disclosure provides isolated nucleic acids encoding a shRNA comprising a sequence complementary to a human Nptxr that corresponds to a murine target sequence set forth in SEQ ID NO: 311, 312, 313 or 314.

In other embodiments, the disclosure provides isolated nucleic acids encoding shRNA sequences complementary to a Pkd1 target sequence identical to at least 12, at least 15, at least 20, or at least 25 contiguous nucleotides set forth in SEQ ID NO: 351, 352, 353, 354, 355 or 356.

In other embodiments, the disclosure provides isolated nucleic acids encoding a shRNA comprising a sequence complementary to a human Pkd1 that corresponds to a murine target sequence set forth in SEQ ID NO: 351, 352, 353, 354, 355 or 356.

In other embodiments, the disclosure provides isolated nucleic acids encoding shRNA sequences complementary to a Ppm1g target sequence identical to at least 12, at least 15, at least 20, or at least 25 contiguous nucleotides set forth in SEQ ID NO: 367, 368, 369, 370 or 371.

In other embodiments, the disclosure provides isolated nucleic acids encoding a shRNA comprising a sequence complementary to a human Ppm1g that corresponds to a murine target sequence set forth in SEQ ID NO: 367, 368, 369, 370 or 371.

In other embodiments, the disclosure provides isolated nucleic acids encoding shRNA sequences complementary to a Ppp3cc target sequence identical to at least 12, at least 15, at least 20, or at least 25 contiguous nucleotides set forth in SEQ ID NO: 399, 400 or 401.

In other embodiments, the disclosure provides isolated nucleic acids encoding a shRNA comprising a sequence complementary to a human Ppp3cc that corresponds to a murine target sequence set forth in SEQ ID NO: 399, 400 or 401.

In other embodiments, the disclosure provides isolated nucleic acids encoding shRNA sequences complementary to a Prkab2 target sequence identical to at least 12, at least 15, at least 20, or at least 25 contiguous nucleotides set forth in SEQ ID NO: 414, 415 or 416.

In other embodiments, the disclosure provides isolated nucleic acids encoding a shRNA comprising a sequence complementary to a human Prkab2 that corresponds to a murine target sequence set forth in SEQ ID NO: 414, 415 or 416.

In other embodiments, the disclosure provides isolated nucleic acids encoding shRNA sequences complementary to a Ptpn2 target sequence identical to at least 12, at least 15, at least 20, or at least 25 contiguous nucleotides set forth in SEQ ID NO: 426, 427, 428, 429 or 430.

In other embodiments, the disclosure provides isolated nucleic acids encoding a shRNA comprising a sequence complementary to a human Ptpn2 that corresponds to a murine target sequence set forth in SEQ ID NO: 426, 427, 428, 429 or 430.

In other embodiments, the disclosure provides isolated nucleic acids encoding shRNA sequences complementary to a Rock1 target sequence identical to at least 12, at least 15, at least 20, or at least 25 contiguous nucleotides set forth in SEQ ID NO: 457, 458, 459 or 460.

In other embodiments, the disclosure provides isolated nucleic acids encoding a shRNA comprising a sequence complementary to a human Rock1 that corresponds to a murine target sequence set forth in SEQ ID NO: 457, 458, 459 or 460.

In other embodiments, the disclosure provides isolated nucleic acids encoding shRNA sequences complementary to a Sbf1 target sequence identical to at least 12, at least 15, at least 20, or at least 25 contiguous nucleotides set forth in SEQ ID NO: 470, 471, 472, 473, 474 or 475.

In other embodiments, the disclosure provides isolated nucleic acids encoding a shRNA comprising a sequence complementary to a human Sbf1 that corresponds to a murine target sequence set forth in SEQ ID NO: 470, 471, 472, 473, 474 or 475.

In other embodiments, the disclosure provides isolated nucleic acids encoding shRNA sequences complementary to a Socs1 target sequence identical to at least 12, at least 15, at least 20, or at least 25 contiguous nucleotides set forth in SEQ ID NO: 504, 505, 506, 507, 508, 509 or 510.

In other embodiments, the disclosure provides isolated nucleic acids encoding a shRNA comprising a sequence complementary to a human Socs1 that corresponds to a murine target sequence set forth in SEQ ID NO: 504, 505, 506, 507, 508, 509 or 510.

In other embodiments, the disclosure provides isolated nucleic acids encoding shRNA sequences complementary to a Socs3 target sequence identical to at least 12, at least 15, at least 20, or at least 25 contiguous nucleotides set forth in SEQ ID NO: 524, 525, 526, 527 or 528.

In other embodiments, the disclosure provides isolated nucleic acids encoding a shRNA comprising a sequence complementary to a human Socs3 that corresponds to a murine target sequence set forth in SEQ ID NO: 524, 525, 526, 527 or 528.

In other embodiments, the disclosure provides isolated nucleic acids encoding shRNA sequences complementary to a Stk17b target sequence identical to at least 12, at least 15, at least 20, or at least 25 contiguous nucleotides set forth in SEQ ID NO: 539, 540, 541, 542 or 543.

In other embodiments, the disclosure provides isolated nucleic acids encoding a shRNA comprising a sequence complementary to a human Stk17b that corresponds to a murine target sequence set forth in SEQ ID NO: 539, 540, 541, 542 or 543.

In other embodiments, the disclosure provides isolated nucleic acids encoding shRNA sequences complementary to a Tnk1 target sequence identical to at least 12, at least 15, at least 20, or at least 25 contiguous nucleotides set forth in SEQ ID NO: 556, 557 or 558.

In other embodiments, the disclosure provides isolated nucleic acids encoding a shRNA comprising a sequence complementary to a human Tnk1 that corresponds to a murine target sequence set forth in SEQ ID NO: 556, 557 or 558.

In other embodiments, the disclosure provides isolated nucleic acids encoding shRNA sequences complementary to a Trpm7 target sequence identical to at least 12, at least 15, at least 20, or at least 25 contiguous nucleotides set forth in SEQ ID NO: 569, 570, 571, 572 or 573.

In other embodiments, the disclosure provides isolated nucleic acids encoding a shRNA comprising a sequence complementary to a human Trpm7 that corresponds to a murine target sequence set forth in SEQ ID NO: 569, 570, 571, 572 or 573.

In other embodiments, the disclosure provides isolated nucleic acids encoding shRNA sequences complementary to a Yes1 target sequence identical to at least 12, at least 15, at least 20, or at least 25 contiguous nucleotides set forth in SEQ ID NO: 600, 601, 602 or 603.

In other embodiments, the disclosure provides isolated nucleic acids encoding a shRNA comprising a sequence complementary to a human Yes1 that corresponds to a murine target sequence set forth in SEQ ID NO: 600, 601, 602 or 603.

In any embodiment, a human sequence that corresponds to a murine target sequence is a sequence which perfectly corresponds to the human gene sequence, and for example, can have none, 1, 2, 3 or 4 nucleotide mismatches with the at least 12, at least 15, at least 20, or at least 25 contiguous nucleotides of the selected murine target sequence.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, cDNA, or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, adeno-associated virus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

As used herein, the term "percent sequence identity" refers to the degree of identity between any given query sequence and a subject sequence. A percent identity for any query nucleic acid or amino acid sequence, e.g., a transcription factor, relative to another subject nucleic acid or amino acid sequence can be determined as follows.

As used herein, the term "complementary nucleotide sequence," also known as an "antisense sequence," refers to a sequence of a nucleic acid that is completely complementary to the sequence of a "sense" nucleic acid encoding a protein (e.g., complementary to the coding strand of a double-stranded cDNA molecule or complementary to an mRNA sequence). Herein, nucleic acid molecules are provided that comprise a sequence complementary to at least about 15, 16, 17, 18, 19, 20, 21, 22, 23, 24, or 25 nucleotides or an entire gene coding strand, or to only a portion thereof.

As used herein, the term "correspond to a nucleotide sequence" refers to a nucleotide sequence of a nucleic acid encoding an identical sequence. In some instances, when antisense nucleotides (nucleic acids) or siRNA's (small inhibitory RNA) hybridize to a target sequence a particular antisense or small inhibitory RNA (siRNA) sequence is substantially complementary to the target sequence, and thus will specifically bind to a portion of an mRNA encoding polypeptide. As such, typically the sequences of those nucleic acids will be highly complementary to the mRNA target sequence, and will have no more than 1, 2, 3, 4, 5, 6, 7, 8, 9, or 10 base mismatches throughout the sequence. In many instances, it may be desirable for the sequences of the nucleic acids to be exact matches, i.e. be completely complementary to the sequence to which the oligonucleotide specifically binds, and therefore have zero mismatches along the complementary stretch. Highly complementary sequences will typically bind quite specifically to the target sequence region of the mRNA and will therefore be highly efficient in reducing, and/or even inhibiting the translation of the target mRNA sequence into polypeptide product.

As used herein, the term "vector" refers to any viral or non-viral vector, as well as any plasmid, cosmid, phage or binary vector in double or single stranded linear or circular form that may or may not be self transmissible or mobilizable, and that can transform prokaryotic or eukaryotic host cells either by integration into the cellular genome or which can exist extrachromosomally (e.g., autonomous replicating plasmid with an origin of replication). Any vector known in the art is envisioned for use in the practice of this invention.

Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom, Thus, a gene encodes a protein if transcription and translation of mRNA corresponding to that gene produces the protein in a cell or other biological system, Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" as used herein is defined as the transcription and/or translation of a particular nucleotide sequence driven by its promoter.

Vectors capable of directing the expression of genes to which they are operatively linked are referred to herein as "expression vectors". Thus, an "Expression vector" is a specialized vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

In some aspects, the disclosure provides modified cells that harbor vectors capable of expressing the shRNA described herein and further modified to express a CAR. In one aspect the shRNA and the CAR are expressed on the same vector. In another aspect, the shRNA and the CAR are expressed on separate vectors.

In some embodiments, the modified cells described herein are immunoresponsive cells. In some aspects, the immunoresponsive cells express at least one of an antigen-recognizing receptor. In any aspect, the immunoresponsive cells express at least one of an tumor specific antigen-recognizing receptor. In some aspects, tumor cell antigen specific T cells, NKT cells, TIL, CTL cells or other immunoresponsive cells are used. Non-limiting examples of immunoresponsive cells include T cells, such as, for example, αβ-TCR+ T cells (e.g., CD8+ T cells or CD4+ T cells) γδ-TCR+ T cells, tumor-infiltrating lymphocytes (TIL), Natural Killer T cells (NKT), a cytotoxic T lymphocytes (CTL), and a CD4 T cells.

Compositions comprising the immunoresponsive cells of the invention (e.g., T cells, NKT cells, TILs, CTL cells, or their progenitors) can be provided systemically or directly to a subject for the treatment of a cancer. In one embodiment, cells of the invention are directly injected into an organ of interest (e.g., an organ affected by a cancer). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, NKT cells, TILs, CTL cells in vitro or in vivo.

The modified immunoresponsive cells can be administered in any physiologically acceptable vehicle, normally intravascularly, although they may also be introduced into bone or other convenient site where the cells may find an appropriate site for regeneration and differentiation (e.g., thymus). Usually, at least $1\times10^5$ cells will be administered, eventually reaching $1\times10^{10}$, or more. Immunoresponsive cells of the invention can comprise a purified population of cells. Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage).

The cells can be introduced by injection, catheter, or the like. If desired, factors can also be included, including, but not limited to, interleukins, e.g. IL-2, IL-3, IL-6, and IL-11, as well as the other interleukins, the colony stimulating factors, such as G-, M- and GM-CSF, interferons, e.g. .gamma.-interferon and erythropoietin.

Compositions of the invention include pharmaceutical compositions comprising the immunoresponsive cells of the invention or their progenitors and a pharmaceutically acceptable carrier. Administration can be autologous or heterologous. For example, immunoresponsive cells, or progenitors can be obtained from one subject, and administered to the same subject or a different, compatible subject.

Chimeric Antigen Receptors

In some instances, the invention provides chimeric antigen receptors (CARs) comprising an antigen binding domain directed to a tumor cell antigen. A CAR is an artificially constructed hybrid protein or polypeptide containing an extracellular portion that recognizes a tumor cell antigen (e.g., the antigen binding domains of an antibody (scFv) and a cytoplasmic signaling domain derived from the T cell receptor and costimulatory domain. (Kalos M, et al., Sci Transl Med. 2011 Aug. 10; 3(95)) Kalos et al. describes the generation of CAR T cells that target CD19 and demonstrates the CAR modified T-cells mediated potent antitumor effect in chronic lymphocytic leukemia patients. Characteristics of CARs include their ability to redirect T-cell specificity and reactivity toward a selected target in a non-MHC-restricted manner, exploiting the antigen-binding properties of monoclonal antibodies. The CAR-modified T-cells have the potential to replicate in vivo and long term persistence allows for sustained tumor control and obviate the need for repeated infusions of antibody. (Kalos M, et al., Sci Transl Med. 2011 Aug. 10; 3(95)) The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains. CAR-modified T cells are described in detail in WO2012/079000 and WO2012/09999 and in Milone et al. 2009 Mol. Ther. 17:1453.

A CAR combines the binding site of a molecule that recognizes an antigen being targeted (i.e., an "antigen binding domain") with one or more domains of conventional immune receptors responsible for initiating signal transduction that leads to lymphocyte activation (e.g., the "stimulatory domain" or "signaling domain").

In some embodiments, the binding portion used is derived from the structure of the Fab (antigen binding) fragment of a monoclonal antibody (mAb) that has high affinity for the tumor antigen being targeted. Because the Fab is the product of two genes, the corresponding sequences are usually combined via a short linker fragment that allows the heavy-chain to fold over the light-chain derived peptides into their native configuration, creating a single-chain fragment variable (scFv) region.

Fv or (scFv) antibody fragments comprise the VH and VL domains of antibody, wherein these domains are present in a single polypeptide chain. Generally the Fv polypeptide further comprises a polypeptide linker between the VH and VL domains, which enables the scFv to form the desired structure for antigen binding.

In some embodiments, the binding portion used is derived from a cytoplasmic signaling domain derived from T cell receptor and costimulatory molecules.

In some embodiments, the signaling portion of CARs contains usually the intracellular domains of the zeta (ζ) chain of the TCR/CD3 complex[25] or, less commonly, of the gamma (γ) chain of the immunoglobulin receptor FcεRI[26,27] or the CD3-epsilon (ε) chain,[28] with the transmembrane region being derived from the same molecule.

In some aspects, the CARs comprise an antigen binding domain, a transmembrane domain, a stimulatory domain, and a co-stimulatory domain. Further embodiments of the invention provide related nucleic acids, recombinant expression vectors, host cells, populations of cells, antibodies, or antigen binding portions thereof, and pharmaceutical compositions relating to the CARs of the invention.

In one aspect, the antigen binding domain binds to a tumor cell antigen. The term "tumor cell antigen" or "tumor antigen" as used herein refers to any polypeptide expressed by a tumor that is capable of inducing an immune response. Non-limiting examples of tumor antigens include, for example, prostate-specific membrane antigen (PSMA), Carcinoembryonic Antigen (CEA), CD19, CD20, CD22, ROR1, mesothelin, CD333/IL3Ra, c-Met, Glycolipid F77, EGFRvIII, GD-2, NY-ESO-1 TCR, ERBB2, BIRC5, CEACAM5, WDR46, BAGE, CSAG2, DCT, MAGED4, GAGE1, GAGE2, GAGE3, GAGE4, GAGE5, GAGE6, GAGE7, GAGE5, IL13RA2, MAGEA1, MAGEA2, MAGEA3, MAGEA4, MAGEA6, MAGEA9, MAGEA10, MAGEA12, MAGEB1, MAGEB2, MAGEC2, TP53, TYR, TYRP1, SAGE1, SYCP1, SSX2, SSX4, KRAS, PRAME, NRAS, ACTN4, CTNNB1, CASP8, CDC27, CDK4, EEF2, FN1, HSPA1B, LPGAT1, ME1, HHAT, TRAPPC1, MUM3, MYO1B, PAPOLG, OS9, PTPRK, TPI1, ADFP, AFP, AIM2, ANXA2, ART4, CLCA2, CPSF1, PPIB, EPHA2, EPHA3, FGF5, CA9, TERT, MGAT5, CEL, F4.2, CAN, ETV6, BIRC7, CSF1, OGT, MUC1, MUC2, MUM1, CTAG1A, CTAG2, CTAG, MRPL28, FOLH1, RAGE, SFMBT1, KAAG1, SART1, TSPYL1, SART3, SOX10, TRG, WT1, TACSTD1, SILV, SCGB2A2, MC1R, MLANA, GPR143, OCA2, KLK3, SUPT7L, ARTC1, BRAF, CASP5, CDKN2A, UBXD5, EFTUD2, GPNMB, NFYC, PRDX5, ZUBR1, SIRT2, SNRPD1, HERV-K-MEL, CXorf61, CCDC110, VENTXP1, SPA17, KLK4, ANKRD30A, RAB38, CCND1, CYP1B1, MDM2, MMP2, ZNF395, RNF43, SCRN1, STEAP1, 707-AP, TGFBR2, PXDNL, AKAP13, PRTN3, PSCA, RHAMM, ACPP, ACRBP, LCK, RCVRN, RPS2, RPL10A, SLC45A3, BCL2L1, DKK1, ENAH, CSPG4, RGS5, BCR, BCR-ABL, ABL-BCR, DEK, DEK-CAN, ETV6-AML1, LDLR-FUT, NPM1-ALK1, PML-RARA, SYT-SSX1, SYT-SSX2, FLT3, ABL1, AML1, LDLR, FUT1, NPM1, ALK, PML1, RARA, SYT, SSX1, MSLN, UBE2V1, HNRPL, WHSC2, EIF4EBP1, WNK2, OAS3, BCL-2, MCL1, CTSH, ABCC3, BST2, MFGE8, TPBG, FMOD, XAGE1, RPSA, COTL1, CALR3, PA2G4, EZH2, FMNL1, HPSE, APC, UBE2A, BCAP31, TOP2A, TOP2B, ITGB8, RPA1, ABI2, CCNI, CDC2, SEPT2, STAT1, LRP1, ADAM17, JUP, DDR1, ITPR2, HMOX1, TPM4, BAAT, DNAJC8, TAPBP, LGALS3BP, PAGE4, PAK2, CDKN1A, PTHLH, SOX2, SOX11, TRPM8, TYMS, ATIC, PGK1, SOX4, TOR3A, TRGC2, BTBD2, SLBP, EGFR, IER3, TTK, LY6K, IGF2BP3, GPC3, SLC35A4, HSMD, H3F3A, ALDH1A1, MFI2, MMP14, SDCBP, PARP12, MET, CCNB1, PAX3-FKHR, PAX3, FOXO1, XBP1, SYND1, ETV5, HSPA1A, HMHA1, TRIM68 and any combination thereof.

The present invention relates generally to the use of T cells genetically modified to stably express a shRNA of the invention and a desired CAR. T cells expressing a CAR are generally referred to as CAR T cells. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular stimulatory domain (e.g., signaling domain). Thus, in addition to an antigen binding domain the CAR can include the intracellular domains of the zeta (ζ) chain of the TCR/CD3 complex, the gamma (γ) chain of the immunoglobulin receptor FcεRI26, 27 or the CD3-epsilon (ε) chain. The CAR can also include a transmembrane region being from the same molecules or other type I transmembrane proteins such as CD4, CD8 and CD28.

In one embodiment, the CAR of the invention comprises an extracellular domain having an antigen recognition domain, a transmembrane domain, and a cytoplasmic domain.

In one embodiment, the transmembrane domain that naturally is associated with one of the domains in the CAR is used. In another embodiment, the cytoplasmic domain can be designed to comprise a stimulatory domain and a costimulatory domain.

A CAR can include intracytoplasmatic portion of co-stimulatory molecules, such as CD28, CD134/OX40, CD137/4-1BB, Lck, ICOS or DAP10.

The disclosure also relates to a strategy of Adoptive cell therapy (ACT). ACT is a procedure in which therapeutic lymphocytes are administered to patients in order to treat cancer. This approach entails the ex vivo generation of tumor specific T cell lymphocytes and infusing them to patients. In addition to the lymphocyte infusion the host may be manipulated in other ways which support the take of the T cells and their immune response, for example, preconditioning the host (with radiation or chemotherapy) and administration of lymphocyte growth factors (such as IL-2). One method for generating such tumor specific lymphocytes involves the expansion of antigen specific T cells.

In one embodiment, the invention provides generating T cells expressing a shRNA of the invention and a desired CAR directed to a tumor antigen. The modified T cells can be generated by introducing a vector (e.g., plasmid, lentiviral vector, retroviral vector, adenoviral vector, adeno-associated viral vector) encoding both 1) an shRNA capable of reducing expression of a target gene described herein and 2) a desired CAR into the cells. The modified T cells of the invention are able to replicate in vivo resulting in long term persistence that can lead to tumor control.

In one aspect, the disclosure provides methods of treating cancer comprising administering a composition capable of silencing genes that inhibit T cell function. In one embodiment, the methods relate to administering T cell expressing a shRNA of the invention and a desired CAR directed to a tumor antigen. In one aspect the T cell to be administered comprises a vector encoding a shRNA of the invention and a desired CAR directed to a tumor antigen.

Pharmaceutical Formulations

In some instances, therapeutic compositions disclosed herein can include, in addition to the tumor targeting T cells, compounds, drugs, and/or agents used for the treatment of cancer. Such compounds, drugs, and/or agents can include, for example, chemotherapy drugs, small molecule drugs or antibodies that stimulate the immune response to a given cancer. In other instances, therapeutic compositions can include, for example, one or more small molecule inhibitors that silence, reduces, eliminates, knocks down, knocks out, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc. Accordingly, the invention provides one or more inhibitors of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 or Ppp3cc.

In one aspect, the invention provides one or more inhibitors of Ppp2r2d.

In another aspect, the invention provides one or more inhibitors of Eif2ak3.

In another aspect, the invention provides one or more inhibitors of Arhgap5.

In another aspect, the invention provides one or more inhibitors of Smad2.

In another aspect, the invention provides one or more inhibitors of Akap81.

In another aspect, the invention provides one or more inhibitors of Rbks.

In another aspect, the invention provides one or more inhibitors of Egr2.

In another aspect, the invention provides one or more inhibitors of Dgka.

In another aspect, the invention provides one or more inhibitors of Cblb.

In another aspect, the invention provides one or more inhibitors of Map3k3.

In another aspect, the invention provides one or more inhibitors vMdfic.

In another aspect, the invention provides one or more inhibitors of Entpd1.

In another aspect, the invention provides one or more inhibitors of Dgkz.

In another aspect, the invention provides one or more inhibitors of Vamp7.

In another aspect, the invention provides one or more inhibitors of Nuak2.

In another aspect, the invention provides one or more inhibitors of Hipk1.

In another aspect, the invention provides one or more inhibitors of Alk. In one embodiment, the inhibitor of Alk includes, for example, for example CH5424802 (Hoffmann-La Roche), LDK378 (Novartis), Crizotinib and PF-02341066 (Pfizer) or AP26113 (Ariad Pharmaceuticals).

In another aspect, the invention provides one or more inhibitors of Pdzk1ip1.

In some instances, therapeutic compositions can include, for example, cytokines, chemokines and other biologic signaling molecules, tumor specific vaccines, cellular cancer vaccines (e.g., GM-CSF transduced cancer cells), tumor specific monoclonal antibodies, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria) and gene therapy.

In some instances, therapeutic compositions disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm).

In some instances, pharmaceutical compositions can include an effective amount of one or more peptides. The terms "effective amount" and "effective to treat," as used herein, refer to an amount or a concentration of one or more peptides for a period of time (including acute or chronic administration and periodic or continuous administration) that is effective within the context of its administration for causing an intended effect or physiological outcome.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

Methods

In some instances, methods can include selection of a human subject who has or had a condition or disease (e.g., cancer). In some instances, suitable subjects include, for example, subjects who have or had a condition or disease but that resolved the disease or an aspect thereof, present reduced symptoms of disease (e.g., relative to other subjects (e.g., the majority of subjects) with the same condition or disease), and/or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease).

The term "subject," as used herein, refers to any animal. In some instances, the subject is a mammal. In some instances, the term "subject", as used herein, refers to a human (e.g., a man, a woman, or a child). Samples for use in the methods can include serum samples, e.g., obtained from the selected subject.

In some instances, subject selection can include obtaining a sample from a subject (e.g., a candidate subject) and testing the sample for an indication that the subject is suitable for selection. In some instances, the subject can be confirmed or identified, e.g. by a health care professional, as having had or having a condition or disease. In some instances, exhibition of a positive immune response towards a condition or disease can be made from patient records, family history, and/or detecting an indication of a positive immune response. In some instances multiple parties can be included in subject selection. For example, a first party can obtain a sample from a candidate subject and a second party can test the sample. In some instances, subjects can be selected and/or referred by a medical practitioner (e.g., a general practitioner). In some instances, subject selection can include obtaining a sample from a selected subject and storing the sample and/or using the in the methods disclosed herein. Samples can include, for example, cells or populations of cells.

Methods of Use

In some embodiments, the disclosure provides methods for increasing the immune response in a subject in need thereof. The disclosure provides therapies that are particularly useful for the treatment of subjects having cancer. In some instances, the disclosure provides methods of treatment that include administering to a subject a composition disclosed herein.

Provided herein are methods for treating and/or preventing cancer or symptoms of cancer in a subject comprising administering to the subject a therapeutically effective amount of a composition capable of silencing genes that inhibit T cell function (e.g., an immunoresponsive T cell expressing a shRNA of the invention and a desired CAR directed to a tumor antigen). In some cases the T cell is derived from the patient to be treated and has been modified to express the CAR and an shRNA that reduces expression of a target gene described herein.

In some embodiments, the cancer is a carcinoma, sarcomas, adenocarcinoma, lymphoma, leukemia, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), and multiple myeloma. In some embodiments, the cancer is melanoma. In some embodiments, the cancer is a plasma cell malignancy, for example, multiple myeloma (MM) or pre-malignant condition of plasma cells. In some embodiments the subject has been diagnosed as having a cancer or as being predisposed to cancer.

As used herein, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), and multiple myeloma.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The terms "treat" or "treating," as used herein, refers to partially or completely alleviating, inhibiting, ameliorating, and/or relieving the disease or condition from which the subject is suffering. In some instances, treatment can result in the continued absence of the disease or condition from which the subject is suffering.

In general, methods include selecting a subject at risk for or with a condition or disease. In some instances, the subject's condition or disease can be treated with a pharmaceutical composition disclosed herein. For example, in some instances, methods include selecting a subject with cancer, e.g., wherein the subject's cancer can be treated by increasing T cell accumulation and infiltration within the tumor.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

It is also within the scope of the present invention to combine any of the methods and any of the compositions disclosed herein with one or more therapeutic agents. A therapeutic agent includes, but is not limited to, small molecules, peptides, antibodies, ribozymes, antisense oligonucleotides, chemotherapeutic agents and radiation.

It is also within the scope of the present invention to combine any of the methods and any of the compositions disclosed herein with conventional cancer therapies and various drugs in order to enhance the efficacy of such therapies through either reducing the doses/toxicity of conventional therapies and/or to increase the sensitivity of conventional therapies. One conventional therapy is the use of radiation therapy. Another conventional therapy is the use of chemotherapeutic drugs that can be divided into: alkylating agents, antimetabolites, anthracyclines, plant alkaloids, topoisomerase inhibitors, and antitumour agents. All of these drugs affect cell division or DNA synthesis and function in some way. Other conventional cancer therapies are agents that do not directly interfere with DNA. Examples of such agents for which to combine with the present invention may include for example "small-molecule" drugs that block specific enzymes involved in cancer cell growth. Monoclonal antibodies, cancer vaccines, angiogenesis inhibitors, and gene therapy are targeted therapies that can also be combined with the compositions and methods disclosed herein because they also interfere with the growth of cancer cells.

Methods of Screening Test Compounds

Included herein are methods for screening test compounds, e.g., polypeptides, polynucleotides, inorganic or organic large or small molecule test compounds, to identify agents useful in the treatment of cancer e.g., test compounds that silence, reduces, eliminates, knocks down, knocks out, modulates, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to silence, reduces, eliminates, knocks down, knocks out, modulates, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc.

In some embodiments, the test sample is, or is derived from (e.g., a sample taken from) an in vivo model of a disorder as described herein. For example, an animal model, e.g., a rodent such as a rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc activity or gene expression.

A test compound that has been screened by a method described herein and determined to silence, reduces, eliminates, knocks down, knocks out, or decreases the expression and/or activity of genes selected from the group consisting of Ppp2r2d, Eif2ak3, Arhgap5, Smad2, Akap81, Rbks, Egr2, Dgka, Cblb, Mdfic, Entpd1, Dgkz, Vamp7, Hipk1, Nuak2, Alk, Pdzk1ip1, Inpp5b, Socs1, Jun, Nptxr, Socs3, F11r, Fyn, Ypel2, Pkd1, Grk6, Cdkn2a, Sbf1, Ipmk, Rock1, Stk17b, Mast2, Pdp1, Yes1, Met, Ppm1g, Blvrb, Tnk1, Prkab2, Trpm7 and Ppp3cc, can be considered a candidate compound. A candidate compound that has been screened, e.g., in an in vivo model of a disorder, e.g., cancer, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that inhibiting immunosuppressive pathways used by tumor cells to inactivate and/or suppress immune cells) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

EXAMPLES

The invention is further described in the following examples, which do not limit the scope of the invention described in the claims.

Recent work has shown that cytotoxic T cells play a central role in immune-mediated control of cancers[1-3], and monoclonal antibodies that target inhibitory receptors on T cells can induce significant clinical benefit in patients with advanced disease[4-6]. However, many of the regulatory mechanisms that result in loss of T cell function within immunosuppressive tumors remain unknown. In the following examples, the inventors demonstrate that such regulatory mechanisms can be systematically discovered in vivo in the tumor microenvironment. The inventors postulated that shRNAs targeting key inhibitors would enable robust T cell infiltration and accumulation in tumors, despite multiple inhibitory signals. Using a pool shRNA screening approach aimed at identifying genes that block the function of tumor-infiltrating CD8 T cells, candidate shRNA were discovered by transfer of shRNA-transduced T cells into tumor-bearing mice, followed by deep sequencing to quantify the representation of all hairpins in tumors and lymphoid organs. The majority of shRNAs induced T cell accumulation in tumors but not the spleen, demonstrating feasibility of discovering shRNAs with differential action across tissues. One of the targets was Ppp2r2d, a regulatory subunit of the PP2A phosphatase[7]. Control shRNA-transduced T cells underwent apoptosis upon recognition of melanoma cells, while Ppp2r2d shRNA-transduced T cells accumulated in tumors due to enhanced proliferation and resistance to apoptosis. Ppp2r2d shRNA-expressing T cells also significantly delayed tumor growth. This in vivo approach has widespread applications to dissect complex immune functions in relevant tissue micro environments.

Immune cells perform complex surveillance functions throughout the body and interact with many different types of cells in distinct tissue microenvironments. Therapeutic targets for modulating immune responses are typically identified in vitro and tested in animal models at a late stage of the process. Here the inventors have addressed the challenge of how targets for immune modulation can be systematically discovered in vivo. This is a central issue in oncology because strong infiltration by CD8 T cells—which have cytotoxic function against tumor cells—is associated with a favorable prognosis in multiple types of human cancer[1,3,8]. Unfortunately, this natural defense mechanism is severely blunted in the majority of patients by multiple inhibitory signals emanating from the tumor, its stroma, regulatory T cells and myeloid cell populations.[9-11]

Figure 1:
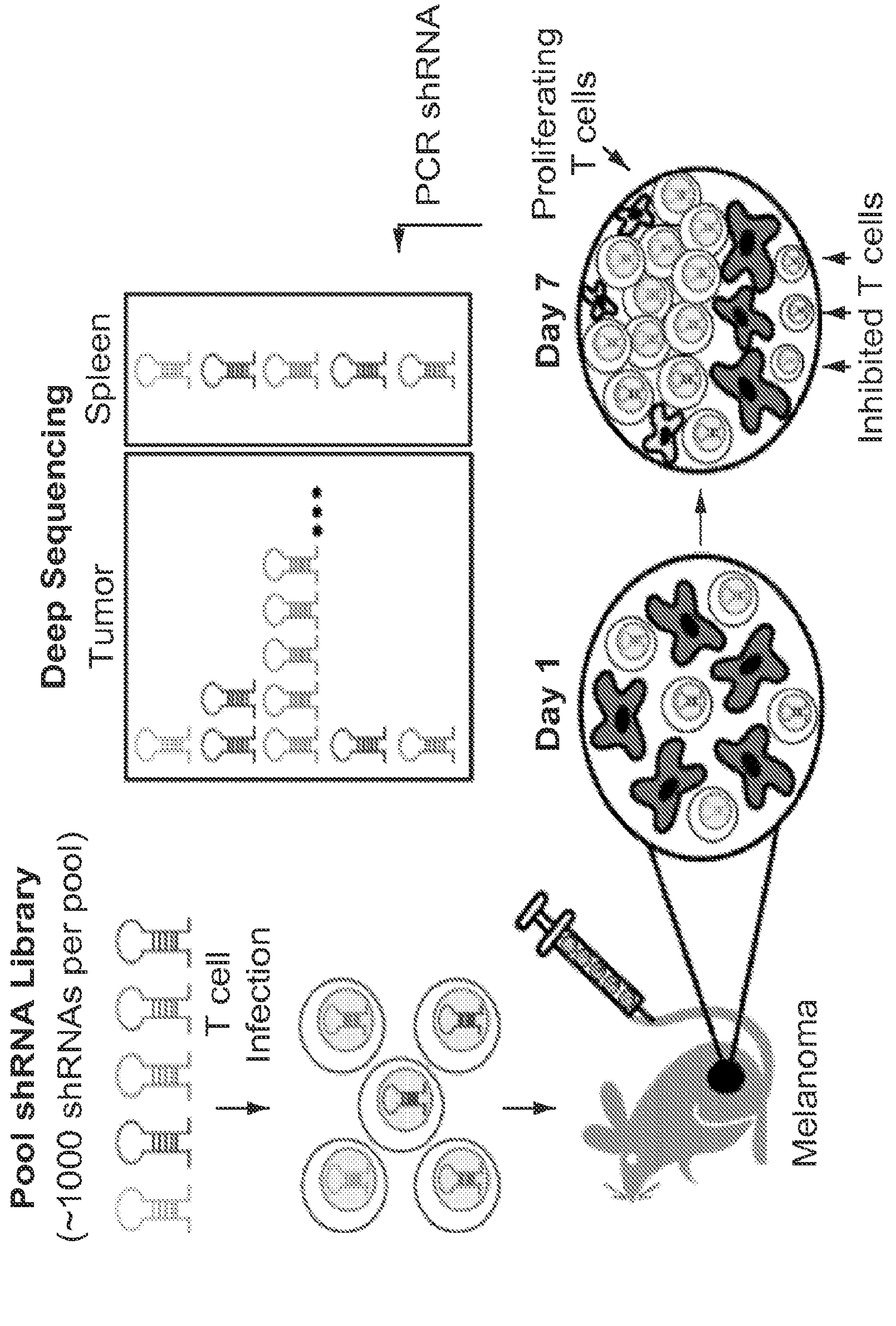
FIG. 1 is a schematic diagram demonstrating an exemplary approach for in vivo discovery of shRNAs that enhance T cell infiltration and accumulation within the tumor microenvironment.

Pooled shRNA libraries have been shown to be powerful discovery tools[12-14]. The inventors reasoned that shRNAs capable of restoring CD8 T cell function can be systematically discovered in vivo by taking advantage of the extensive proliferative capacity of T cells following triggering of the T cell receptor by a tumor-associated antigen. When introduced into T cells, only a small subset of shRNAs from a pool will restore T cell proliferation resulting in their enrichment within tumors. Over-representation of active shRNAs within each pool can be quantified by deep sequencing of the shRNA cassette from tumors and secondary lymphoid organs (FIG. 1).

Experimental Animals.

C57BL/6 mice, TRP-1 mice (transgenic mice expressing T-cell receptor (TCR) specific for tyrosinase-related protein 1)[23], pmel-1 mice (transgenic mice expressing TCR specific for gp100)[18], and b2m−/− mice[24] were purchased from The Jackson Laboratory. The Rag1−/− OT-I mice[16] were purchased from Taconic Farms, Inc. Mice were bred at the Dana-Farber Cancer Institute animal facility. All experimental procedures were approved by the Dana-Farber Cancer Institute Animal Care and Use Committee.

Cell Lines.

B16 melanomas, an aggressive tumor that is difficult to treat, express the surrogate tumor antigen Ovalbumin (Ova), which is recognized by CD8 T cells from OT-I T cell receptor transgenic mice[16,17]. EL4 thymoma[38] and B16-F10 melanoma[15] cells were maintained in RPMI 1640 supplemented with 10% FBS, 2 mM L-glutamine, 100 μg/ml streptomycin and 100 μg/ml penicillin. Ovalbumin-expressing B16 tumor cells (B16-Ova) were maintained in the same media with addition of 600 μg/mL G418 (Invitrogen).

Vectors and shRNA Sequences.

shRNAs were selected for 255 genes over-expressed in dysfunctional T cells (anergic or exhausted state). pLKO.3G vector was obtained from The RNAi Consortium. pLKO-Thy1.1, pLKO-Ametrine, pLKO-RFP, pLKO-TFP vectors were modified from pLKO.3G vector by replacing GFP with the corresponding reporter gene. Murine Ppp2r2d and Cblb sequences targeted by 10 selected shRNAs are provided in Table 3 (listed in order of shRNA activity (highest to lowest)). The LacZ target sequence targeted by a control shRNA is also listed. All other target sequences can be found in Table 2.

TABLE 3

| # | Gene | Clone ID | Murine shRNA Target Sequence |
|---|---|---|---|
| | LacZ | TRCN0000072227 | GCGCTAATCACGACGCGCTGT (SEQ ID NO: 621) |
| 1 | Ppp2r2d | TRCN0000080900 | CCCACATCAGTGCAATGTATT (SEQ ID NO: 386) |
| 2 | Ppp2r2d | ND000492 | CCACAGTGGTCGATACATGAT (SEQ ID NO: 385) |
| 3 | Ppp2r2d | TRCN0000431278 | GAGAATTAACCTATGGCATTT (SEQ ID NO: 384) |
| 4 | Ppp2r2d | ND000486 | GCTCAATAAAGGCCATTACTC (SEQ ID NO: 383) |
| 5 | Ppp2r2d | TRCN0000080901 | CCATTTAGAATTACGGCACTA (SEQ ID NO: 380) |
| 6 | Ppp2r2d | TRCN0000430828 | ATAGTGATCATGAAACATATC (SEQ ID NO: 375) |
| 7 | Ppp2r2d | TRCN0000080899 | GCCACCAATAACTTGTATATA (SEQ ID NO: 374) |
| 8 | Ppp2r2d | TRCN0000080902 | CGGTTCAGACAGTGCCATTAT (SEQ ID NO: 381) |
| 9 | Ppp2r2d | TRCN0000427220 | TCATCTCCACCGTTGAGTTTA (SEQ ID NO: 378) |
| 10 | Ppp2r2d | TRCN0000425449 | ATGCTCATACATATCACATAA (SEQ ID NO: 377) |
| 1 | Cblb | ND000025 | CGAGCGATCCGGCTCTTTAAA (SEQ ID NO: 72) |
| 2 | Cblb | ND000030 | AGCCAGGTCCAATTCCATTTC (SEQ ID NO: 71) |
| 3 | Cblb | TRCN0000244606 | CCCTGATTTAACCGGATTATG (SEQ ID NO: 70) |
| 4 | Cblb | ND000026 | ATCGAACATCCCAGATTTAGG (SEQ ID NO: 61) |
| 5 | Cblb | TRCN0000244603 | CTACACCTCACGATCATATAA (SEQ ID NO: 59) |
| 6 | Cblb | ND000024 | TACACCTCACGATCATATAAA (SEQ ID NO: 67) |
| 7 | Cblb | TRCN0000244605 | TGAGCGAGAATGAGTACTTTA (SEQ ID NO: 60) |
| 8 | Cblb | TRCN0000244604 | CCAGATTTAGGCATCTATTTG (SEQ ID NO: 65) |
| 9 | Cblb | TRCN0000244607 | CTTGTACTCCAGTACCATAAT (SEQ ID NO: 63) |
| 10 | Cblb | ND000027 | TCTACATCGATAGTCTCATGA (SEQ ID NO: 58) |

Antibodies and Flow Cytometry.

Single-cell suspensions were stained in PBS, 2% FBS with labeled antibodies at 4° C. for 20 minutes, followed by two washes with ice-cold PBS, 2% FBS. Cells were analyzed/sorted using a FACSAria (BD Biosciences) and FlowJo software (TriStar). Antibodies used were specific for CD4, CD8, Vα2, Vβ5.1/5.2, Thy1.1, CD25, CD44, CD62L, CD69, CD122, CD127, IFNγ, TNFα (BioLegend), PD-1, TIM-3, LAG-3, granzyme B, and H-2Kb (BioLegend), Vα3.2 (eBioscience), Vβ13, Vβ14 (BD Biosciences), phospho-Akt (Ser473) and phospho-Bad (Ser112) (Cell Signaling). Apoptotic cells were detected by labeling with annexin V (BioLegend) or activated caspase-3 antibody (Cell Signaling). Mouse anti-CD3/CD28 beads were purchased from Invitrogen.

T Cell Isolation from Tumors.

B16-Ova melanomas were cut into small pieces in petri dishes containing 5 mL of PBS, 2% FBS and washed with PBS. Tumors were resuspended in 15 mL RPMI supplemented with 2% FBS, 50 U/mL Collagenase Type IV (Invitrogen), 20 U/mL DNase (Roche), samples incubated at 37° C. for 2 hours and tissue further dissociated using a gentleMACS Dissociator (Miltenyi Biotech). Suspensions were washed three times with PBS and passed through a 70 μM strainer. Lymphocytes were isolated by density gradient centrifugation and then either analyzed or sorted by flow cytometry using a FACSAria (BD Biosciences).

T Cell Apoptosis.

Cytokine pre-treated OT-I cells were transduced with LacZ or Ppp2r2d shRNAs and injected into mice bearing day 14 B16-Ova tumors. After 7 days, intracellular staining was performed using an activated caspase-3 antibody (Cell Signaling) and CD8/Thy1.1 double-positive T cells were gated in the FACS analysis.

Immunofluorescence and Immunohistochemistry.

B16-Ova tumors from mice treated with OT-I T cells expressing LacZ or Ppp2r2d shRNAs (GFP-expressing vector) were cryopreserved in optimal cutting temperature (O.C.T.) compound (Tissue-Tek). 10 μm-sections from cryopreserved tumors were permeabilized with 0.2% Triton X-100, fixed in 4% paraformaldehyde and stained with a GFP antibody (Molecular Probes) in combination with DAPI. For TUNEL detection, sections were stained with TACS 2 TdT Blue Label (Trevigen) based on manufacturer's directions. Samples were visualized using a laser-scanning confocal microscope (Leica SP5X) and analyzed with ImageJ software (NIH).

qRT-PCR Assay.

Total RNA was extracted using TRIzol reagent (Invitrogen). RNA was reverse transcribed with the High Capacity cDNA Reverse Transcription kit (Applied Biosystems). Real time quantitative PCR reactions were performed as triplicates using an ABI 7900HT instrument with SYBR green (ABI). Rpl23 levels were used for normalization. The following primers were used:

```
Ppp2r2d forward
                                  (SEQ ID NO: 622)
GGAAGCCGACATCATCTCCAC,

Ppp2r2d reverse
                                  (SEQ ID NO: 623)
GTGAGCGCGGCCTTTATTCT;

Cblb forward
                                  (SEQ ID NO: 624)
GGTCGCATTTTGGGGATTATTGA,

Cblb reverse
                                  (SEQ ID NO: 625)
TTTGGCACAGTCTTACCACTTT;

Rpl23 forward
                                  (SEQ ID NO: 626)
CTGTGAAGGGAATCAAGGGA
and
```

-continued

```
Rpl23 reverse
                                  (SEQ ID NO: 627)
TGTCGAATTACCACTGCTGG.
```

Microarray Analysis.

IL-7/IL-15 cultured OT-I T cells were transduced with one of five experimental shRNAs (Ppp2r2d, Arhgap5, Alk, Egr2, Ptpn2) or a LacZ control shRNA. Infected cells were sorted to purity using GFP encoded by the vector as a reporter. T cells ($5\times10^6$) were injected i.v. into mice bearing day 14 B16-Ova tumors. Seven days later, shRNA-expressing OT-I T cells (CD8+GFP+) were isolated from tumors and spleens. Cells were sorted twice to high purity and total RNA was extracted using TRIzol reagent (Invitrogen) for Affymetrix gene expression profiling (Mouse Genome 430 2.0 Arrays). Arrays for each shRNA were done in triplicate (6 mice per group).

Nanowell Analysis of Cytokine Production at a Single Cell Level

Materials.

Antibodies used for T cell activation were anti-mouse CD3 and anti-mouse CD28 (Biolegend). Antibodies used to capture secreted cytokines were anti-mouse IFNγ (Biolegend), anti-mouse IL-2 (Biolegend), anti-mouse TNFα (Biolegend) and anti-mouse GM-CSF (Biolegend). Detection antibodies were anti-mouse IFNγ (Biolegend), anti-mouse IL-2 (Biolegend), anti-mouse TNFα (Biolegend) and anti-mouse GM-CSF (Biolegend), and they were fluorescently labeled with appropriate Alexa Fluor dyes (Invitrogen) following manufacturer's instructions. The lipids used to prepare supported bilayers were: 1,2-dioleoyl-sn-glycero-3-phosphocholine (DOPC) and 1,2-dioleoyl-sn-glycero-3-phosphoethanolamine-N-(cap biotinyl) (Biotinyl Cap PE) (Avanti Polar Lipids).

Fabrication of PDMS Arrays of Nanowells and Preparation of Supported Lipid Bilayers.

The array of nanowells was manufactured by injecting polydimethylsiloxane (PDMS, Dow Corning) prepared at a 10:1 base/catalyst weight ratio into a custom-built mold encasing a micropatterned silicon master. Arrays of nanowells were cured at 70° C. for 4-16 h. Each array comprised 72×24 blocks, each containing a 7×7 (50 μm×50 μm×50 μm) subarray of nanowells (total of 84,672 wells). The PDMS arrays adhered directly to a 3"×1" glass slide forming a 1 mm thick layer. Supported lipid bilayers were prepared as described previously 14. Bilayers were generated by applying DOPC liposomes containing 2 mol % biotin-Cap-PE lipids on the PDMS array of nanowells. The surfaces were rinsed with deionized water to remove excess liposomes. Before use, the lipid bilayer was blocked with BSA in PBS (100 μg/mL) for 45 minutes. The bilayer was then incubated with 1 μg/mL of streptavidin in a solution of 100 μg/mL BSA in PBS, followed by incubation with biotinylated CD3 and CD28 antibodies. The device was rinsed extensively with PBS before adding the cells.

Microengraving.

Capture antibodies were diluted in borate buffer (50 mM sodium borate, 8 mM sucrose, and 50 mM NaCl, pH 9.0) to a final concentration of 10 μg/mL and deposited on the surface of epoxy-modified slides for 1 h at room temperature. Slides were blocked with 3% non-fat milk in PBST (PBS with 0.05% (v/v) Tween 20) for 30 min at room temperature and washed with PBS before placing them into contact with the PDMS array of nanowells. A suspension of T cells was dispensed onto the surface of the nanowells, modified with a supported lipid bilayer in media and allowed to settle into the wells. The density of suspended cells applied to the array was optimized empirically to maximize well occupancy by single cells (typically ~30% of wells). After incubation of the cell-loaded wells, a glass slide coated with capture antibodies was then placed onto the loaded array for cytokine capture. The microarray and glass slide were held together by compression in a hybridization chamber (Agilent Technologies, G2534A) and incubated for 1 h at 37° C. with 5% $CO_2$. The glass slide was then separated from the array and placed in PBS. After microengraving, slides were incubated for 30 min with blocking buffer (PBS, 10 mg/mL BSA, 0.05% (v/v) Tween-20, 2% mouse serum and 2 mM sodium azide), washed with PBST (PBS+ 0.05% v/v Tween-20), and then incubated with fluorescence detection antibodies at 1 μg/mL for 45 min at 25° C. The slides were washed with PBST and PBS, rinsed briefly with water, and dried with a $N_2$ stream. Reference slides were generated at the end of each experiment with the same detection antibodies used on the printed slides. For reference slides, antibodies were diluted in water, spotted onto blank poly-L-lysine slides (1 μL/spot), and the reference slides were dried under vacuum. Slides were scanned using a Genepix 4200AL microarray scanner (Molecular Devices). The median fluorescence intensity of each spot was extracted using Genepix Pro.

On-Chip Image-Based Cytometry.

Before imaging, T cells were stained with CellMask™ Plasma Membrane Stain (Invitrogen, Life Technologies) and SYTOX green (for detection of dead cells, Life Technologies). The cell-loaded arrays of nanowells were mounted face-up on the microscope with a coverslip placed on top of the array. Images were acquired on an automated inverted epifluorescence microscope (Carl Zeiss). Transmitted light and epifluoresence micrographs were collected block-by-block (7×7 microwells per block). The resulting collection of images was analyzed using a custom program to determine the number of cells present in each well and the mean fluorescence intensity of each label. Only viable T cells were considered for the analysis. Although the cells expressed GFP, the fluorescence intensity of GFP was negligible under the utilized microscope acquisition setting compared to SYTOX green, enabling identification of dead cells.

Data Analysis.

Data extracted from both on-chip cytometry and printed cytokines were matched in Microsoft Excel using unique identifiers assigned to each well within the array. The dataset was filtered to include wells containing only single cells. To compensate from signal bleed-through and convert the measured fluorescence intensity for the captured cytokines from a given cell into a rate of secretion, the data from standard calibration curves (from reference slides) prepared with known amounts of detection antibodies was used to convert measured intensities to a number of molecules, as described previously (Han, Q., et. al., Multidimensional analysis of the frequencies and rates of cytokine secretion from single cells by quantitative microengraving. Lab Chip 10, 1391-1400, doi:10.1039/b926849a (2010).

Example 1: In Vivo RNAi Discovery of Immunotherapy Targets

Two large primary screens were performed, with the first focusing on genes over-expressed in dysfunctional T cells (T cell anergy or exhaustion; 255 genes, 1,275 shRNAs divided into two pools), and the second on kinases/phosphatases (1,307 genes, 6,535 shRNAs divided into seven pools) (Table 4). In these primary screens, each gene was represented by ~5 shRNAs.

TABLE 4

| | | T cell Dysfunction | Kinase/ Phosphatase | shRNA Enrichment |
|---|---|---|---|---|
| $1^{st}$ Screen | Genes | 255 | 1307 | 4-10x: 123 |
| | shRNAs | 1275 | 6535 | 10-20x: 17 |
| | Candidate Genes | 32 | 82 | >20x: 1 |
| $2^{nd}$ Screen | Genes | 32 | 43 | 4-10x: 191 |
| | shRNAs | 480 | 645 | 10-20x: 27 |
| | Candidate Genes | 17 | 26 | >20x: 1 |

shRNAs targeting 255 genes over-expressed in dysfunctional T cells (anergic or exhausted state)[31-37] and 1,307 kinase/phosphatase genes (~5 shRNAs per gene) were obtained from The RNAi Consortium (TRC; Broad Institute, Cambridge, Mass., USA). Nine pools were created and shRNAs subcloned into the pLKO-Thy1.1 lentiviral vector. Each pool also contained 85 negative-control shRNAs (number of shRNAs: GFP, 24; LacZ, 20; luciferase 25; RFP 16). OT-I T cells isolated by negative selection (Stemcell Technologies) were cultured with IL-7 (5 ng/mL, Peprotech) and IL-15 (100 ng/mL, Peprotech) in complete RPMI media (RPMI 1640, 10% FBS, 20 mM HEPES, 1 mM sodium pyruvate, 0.05 mM 2-mercaptoethonal, 2 mM L-glutamine, 100 μg/ml streptomycin and 100 μg/ml penicillin). On day 2, OT-I T cells were spin-infected with lentiviral pools (nine lentiviral shRNA pools and a LacZ control shRNA lentiviral vector control) supplemented with protamine sulfate (5 μg/mL) in 24-well plates coated with retronectin (5 μg/mL) at a multiplicity of infection (MOI) of 15. Typically, ~$5\times10^6$ OT-1 T cells were infected for each pool.

Figure 2:
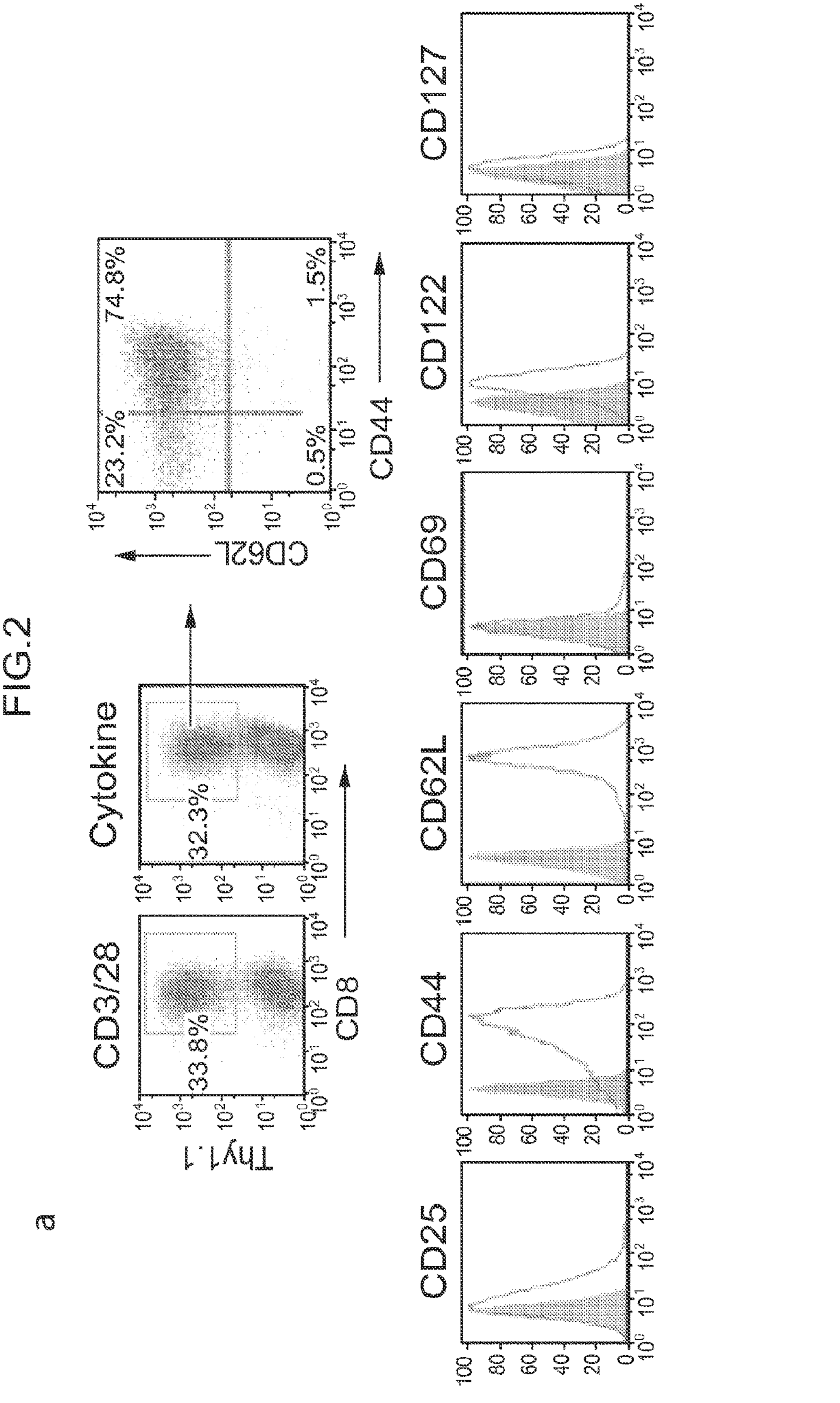
FIG. 2 is a set of graphs showing representative flow cytometry plots of $CD8^+$ T cells from Rag1−/−/OT-I TCR transgenic mice following infection with an shRNA vector. Transduction efficiency was determined based on expression of the Thy1.1 reporter encoded by the lentiviral vector. Cytokine-cultured T cells expressing the LacZ control shRNA were then stained with a panel of activation markers (black lines; isotype control, shaded). The majority of infected T cells exhibited a central memory phenotype ($CD62L^+CD44^+$).
Figure 3:
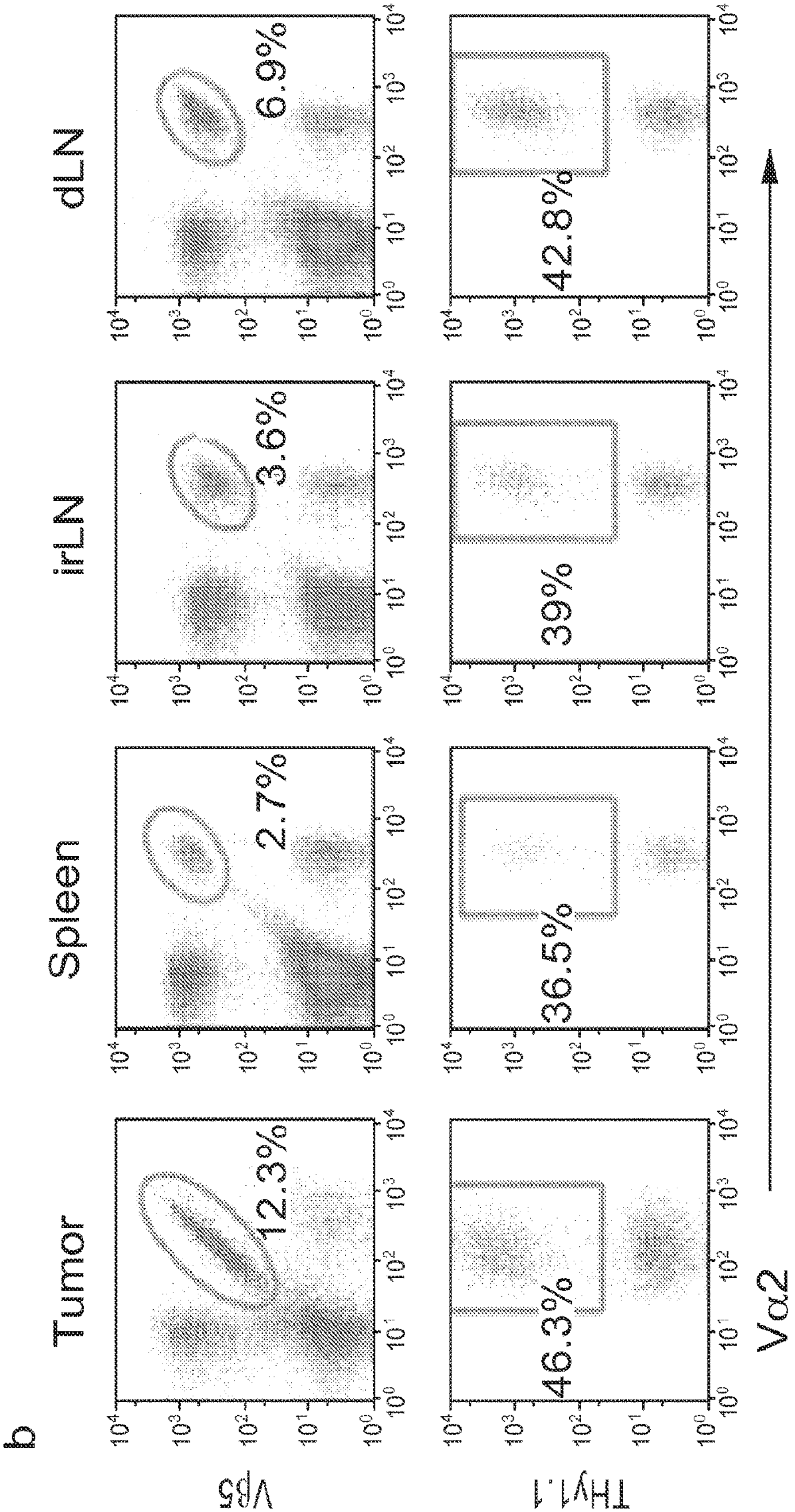
FIG. 3 is a set of graphs showing representative flow cytometry plots of OT-I T cells sorted from tumors and secondary lymphoid organs for deep sequencing analysis (dLN, tumor-draining lymph node; irLN, irrelevant lymph node). $CD8^+V\alpha2^+V\beta5^+Thy1.1^+$ cells were sorted and genomic DNA was extracted for PCR amplification of the shRNA cassette.

Following infection, OT-I cells were cultured with IL-7 (2.5 ng/mL), IL-15 (50 ng/mL) and IL-2 (2 ng/mL) in complete RPMI media. On day 5, live shRNA-transduced T were enriched using a dead cell removal kit (Miltenyi), and infected cells were positively selected based on Thy1.1 marker (Stemcell Technologies) to 50-60% Thy1.1 positivity. Successful transduction was monitored by surface expression of the Thy1.1 reporter (FIG. 2). T cells ($5\times10^6$) were injected i.v. into C57BL/6 mice bearing day 14 B16-Ova tumors (15 mice per shRNA pool)(number of animals chosen to provide sufficient cells for T cell isolation and PCR). Genomic DNA was isolated from $5\times10^6$ enriched OT-I cells as the start population for deep sequencing. Seven days later, shRNA-expressing T cells ($CD8^+V\alpha2^+V\beta5^+$ $Thy1.1^+$) were isolated by flow cytometry from tumors, spleens, tumor-draining lymph nodes and irrelevant lymph nodes for isolation of genomic DNA, followed by PCR amplification of the shRNA cassette. (FIG. 3) Genomic DNA was isolated (Qiagen) and deep-sequencing templates were generated by PCR of the shRNA cassette. Representation of shRNAs in each pool was analyzed by deep sequencing using an Illumina Genome Analyzer[30]. Data were normalized using the average reads of control shRNAs in each pool. Kinase/phosphatase genes were selected for the secondary screen based on expression levels in T cells.

For certain genes, shRNAs were over-represented in all tested tissues compared to the starting T cell population (e.g. SHP-1), indicative of enhanced proliferation independent of TCR recognition of a tumor antigen. For other genes, there was a selective loss of shRNAs within tumors (e.g. ZAP-70, a critical kinase in the T cell activation pathway). We focused our analysis on genes whose shRNAs showed substantial over-representation in tumor but not spleen, a secondary lymphoid organ. Substantial T cell accumulation in tumors was observed for a number of shRNAs, despite the immunosuppressive environment. For secondary screens, we created focused pools in which each candidate gene was represented by ~15 shRNAs.

Figure 4:
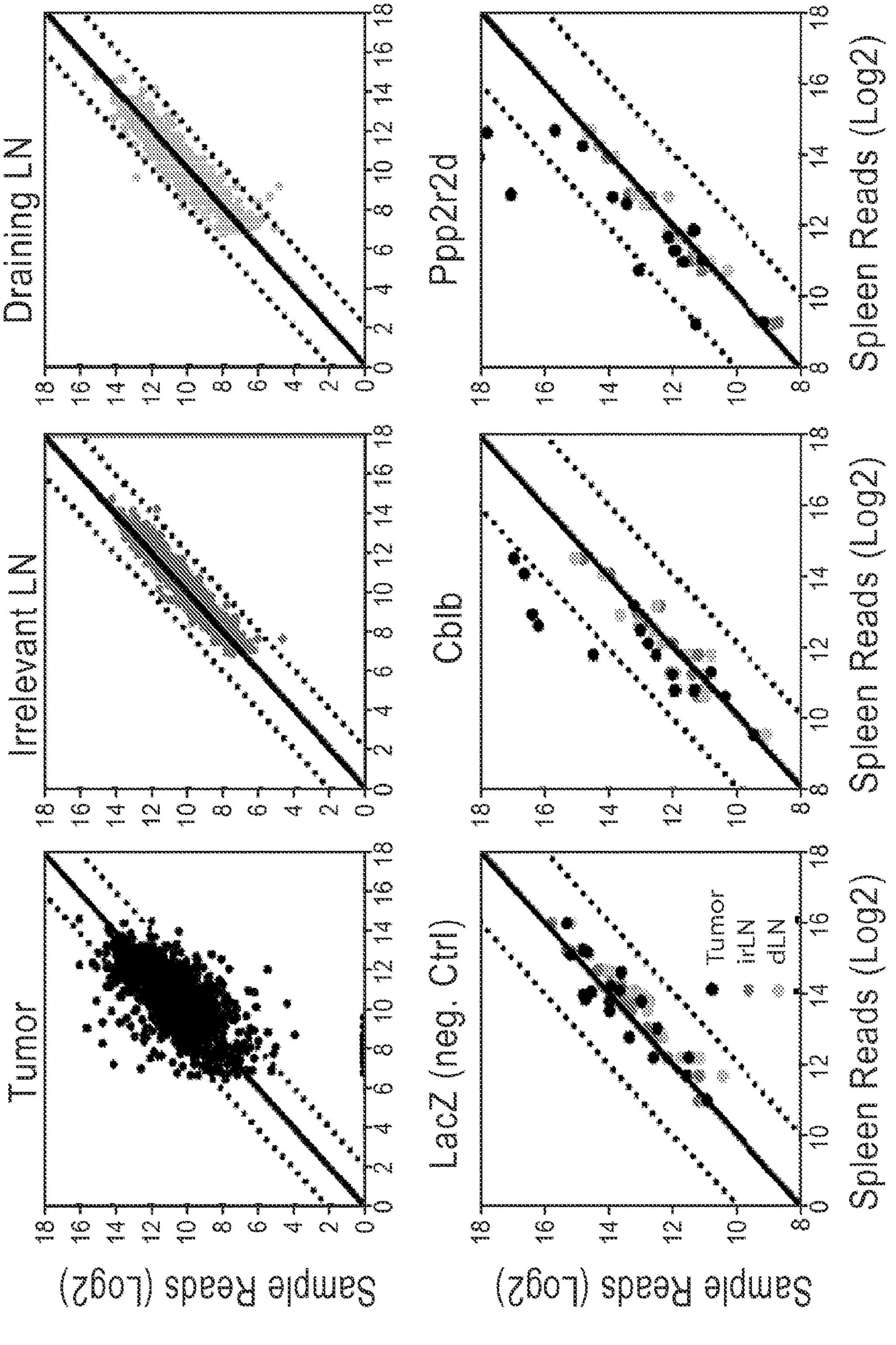
FIG. 4 is a set of graphs showing deep sequencing data from in vivo shRNA pool screen. Upper row, sequence reads for all genes in a pool in tumor, irrelevant (irLN) and draining lymph node (dLN); lower row, three individual genes (LacZ, negative control) are plotted in comparison to spleen for tumors, irrelevant lymph nodes (irLN) and tumor-draining lymph nodes (dLN). Sequence reads are plotted for these tissues versus spleen. Dashed lines indicate a deviation by log 2 from diagonal.
Figure 5:
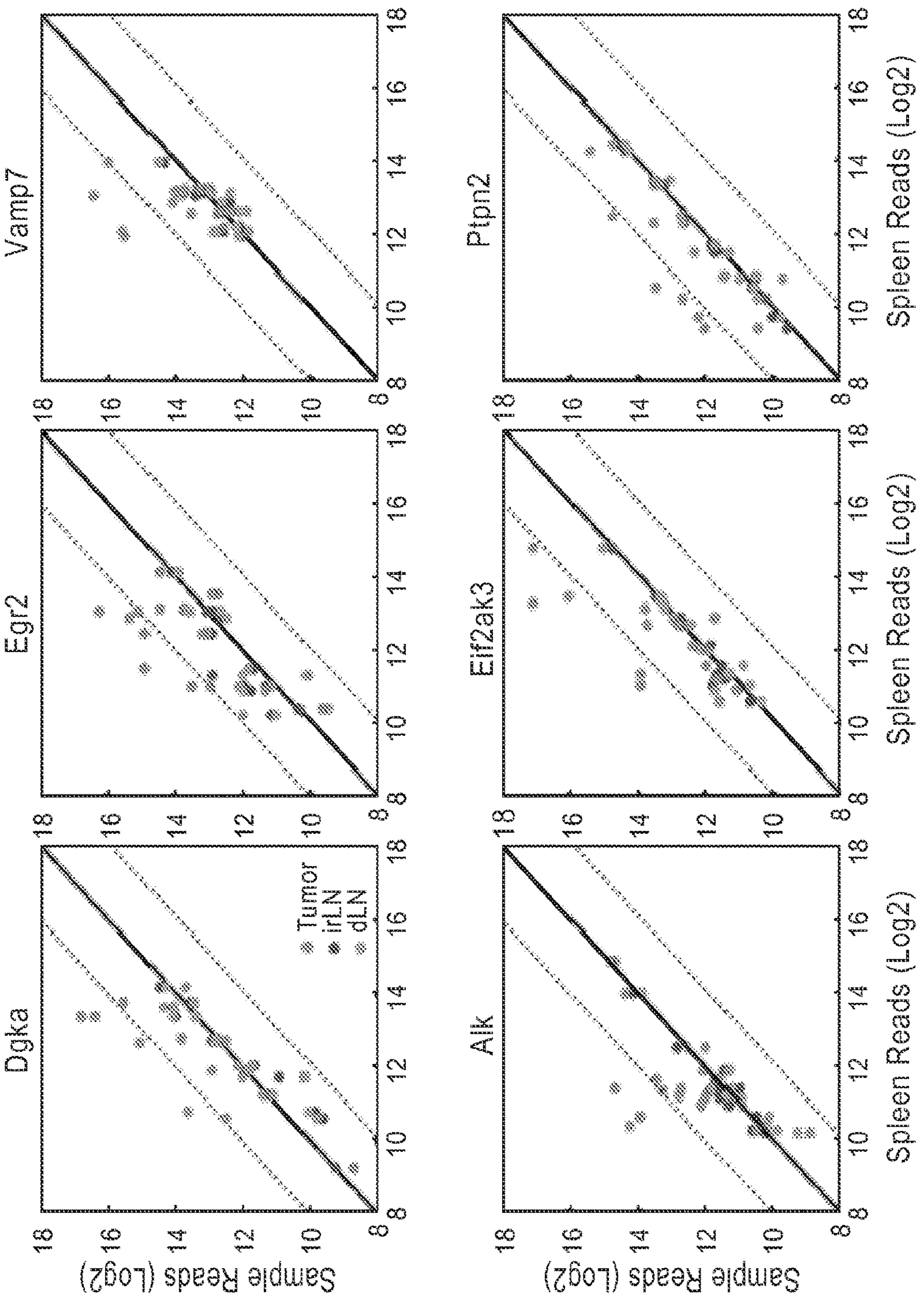
FIG. 5 is a set of graphs showing deep sequencing data from T cell dysfunction screen. shRNA sequencing reads for genes positive in secondary screen are plotted in comparison to spleen for tumors, irrelevant lymph nodes (irLN) and tumor-draining lymph nodes (dLN, with dashed lines indicating a deviation of log 2 from the diagonal. Data show enrichment of particular shRNAs representing these genes in tumors compared to spleens or lymph nodes.

Primary data from this analysis are shown for three genes in FIG. 4: LacZ (negative control), Cblb (an E3 ubiquitin ligase that induces T cell receptor internalization)[19] and Ppp2r2d (not previously studied in T cells). For both Ppp2r2d and Cblb, five shRNAs were substantially increased in tumors (red) compared to spleen, while no enrichment was observed for LacZ shRNAs. Overall, 43 genes met the following criteria: ≥4-fold enrichment for 3 or more shRNAs in tumors compared to spleen (Table 5, FIG. 4, FIG. 5). The set included gene products previously identified as inhibitors of T cell receptor signaling (including Cblb, Dgka, Dgkz, Ptpn2) as well as other well-known inhibitors of T cell function (e.g. Smad2, Socs1, Socs3, Egr2), validating our approach (Table 5, Table 6).[20-22] Table 5 describes the functional classification of candidate genes from the secondary screen.

TABLE 5

| Function | Genes |
|---|---|
| Inhibition of TCR signaling | Cbib, Dgka, Dgkz, Fyn, Inpp5b, Ppp3cc, Ptpn2, Stk17b, Tnk1 |
| Phosphoinositol metabolism | Dgka, Dgkz, Impk, Inpp5b, Sbf1 |
| Inhibitory cytokine signaling pathways | Smad2, Socs1, Socs 3 |
| AMP signaling, inhibition of mTOR | Entpd1, Prkab2, Nuak |
| Cell cycle | Cdkn2a, Pkd1, Ppp2r2d |
| Actin and microtubules | Arhgap5, Mast2, Rock 1 |
| Potential nuclear functions | Blvrb, Egr2, Impk, Jun, Ppm1g |
| Role in cancel cells | Alk, Arhgap5, Eif2ak3, Hipk1, Met, Nuak, Pdzk1ip, Rock1, Yes1 |

Secondary screens were performed focusing on genes whose shRNAs showed substantial over-representation in tumor but not spleen, a secondary lymphoid organ. Substantial T cell accumulation in tumors was observed for a number of shRNAs, despite the immunosuppressive environment. For these secondary screens, ~10 additional shRNAs were synthesized for each gene (IDT) for a total of ~15 shRNAs per gene. These focused pools contained 85 negative-control shRNAs. Two control shRNAs (one for RFP, one for luciferase) showed some enrichment in tumors relative to spleen (4.0 and 5.1-fold, respectively). Cut-off in the secondary screen was defined as ≥3 shRNAs with ≥4 fold enrichment in tumor relative to spleen. Screening results were validated at a cellular level by introducing individual shRNAs into T cells, along with a reporter protein (GFP, TFP, RFP or Ametrine fluorescent proteins, Thy1.1). This approach enabled simultaneous testing of five shRNAs in an animal (three mice per group). Proliferation of shRNA-transduced T cells was visualized based on CFSE dilution after 24 hours as well as 3, 5 and 7 days. In addition, intracellular staining was performed on days 3, 5 and 7 for IFNγ, TNFα and isotype controls. Results from the primary and secondary screen of T cell dysfunction pool shRNA library are provided in Table 6. Genes for which at least 3 shRNAs showed >4 fold enrichment in tumors are listed, along with a brief description of their function. Results from secondary screen of kinase and phosphatase shRNA libraries are shown in Table 7.

TABLE 6

| Symbol | Total # shRNAs | Enrichment (fold) | Function |
|---|---|---|---|
| Dgkz | 6 | 5.2-14.0 | Phosphorylates and thereby inactivates DAG |
| Egr2 | 6 | 4.0-10.2 | Transcription factor involved in T cell unresponsiveness, expression of Cblb |
| Smad2 | 5 | 6.7-30.3 | TGF beta signaling pathway |
| Cblb | 5 | 4.1-10.8 | E3 ubiquitin ligase (degradation of TCR and signaling molecules; ko mice reject tumors) |
| Inpp5b | 5 | 4.3-9.5 | Inositol polyphosphate-5-phosphatase, hydrolyzes PIP2 |
| Socs1 | 5 | 4.1-8.5 | Inhibitor of cytokine signaling |
| Jun | 5 | 5.2-6.4 | Persistent AP-1 activation in tumor-infiltrating T cells leads to upregulated PD-1 |
| Entpd1 | 4 | 6.5-13.3 | Extracellular degradation of ATP to AMP (an inhibitory signal through AMP kinase) |
| Vamp7 | 4 | 4.0-11.3 | Vesicle associated transmembrane protein |
| Dgka | 4 | 5.0-10.2 | Phosphorylates and thereby inactivates DAG |
| Mdfic | 4 | 4.4-10.0 | Inhibits viral gene expression, interacts with cyclin T1 and T2 |
| Nptxr | 4 | 4.0-7.2 | Pentraxin Receptor |
| F11r | 4 | 4.6-6.8 | Cell migration |
| Socs3 | 4 | 4.6-6.3 | Inhibitor of cytokine signaling |
| Pdzk1ip1 | 3 | 4.8-12.9 | Pdzkl interacting protein, expression correlates with tumor progression |
| Fyn | 3 | 4.1-6.5 | Inhibits activation of resting T cells (through Csk) |
| Ypel2 | 3 | 4.6-5.1 | Function unknown |

TABLE 7

| Symbol | Total # shRNAs | Enrichment (fold) | Function |
|---|---|---|---|
| Rbks | 6 | 4.0-12.8 | Ribokinase carbohydrate metabolism |
| Pkd1 | 6 | 4.9-9.9 | Cell cycle arrest (activates JAK/STAT pathway) |
| Ppp2r2d | 5 | 4.0-17.2 | Regulatory subunit of PP2A phosphatase |
| Eif2ak3 | 5 | 4.8-13.4 | ER stress sensor, resistance of cancer cells to chemotherapy |
| Ptpn2 | 5 | 4.7-7.4 | Inhibitor of T cell and cytokine signaling |
| Hipk1 | 4 | 4.5-12.3 | Interacts with p53 and c-myb, knockout mice develop fewer carcinogen-induced tumors |
| Grk6 | 4 | 4.2-11 | Regulator of particular G-protein coupled receptors |
| Cdkn2a | 4 | 4.1-7.2 | G1 cell cycle arrest and apoptosis in T cells |
| Sbf1 | 4 | 4.8-6.9 | Activates MTMR2, which dephosphorylates PI(3)P and PI(3,5)P2 |
| Ipmk | 4 | 4.0-6.9 | Inositol polyphosphate kinase, nuclear functions such a schromatin remodeling |
| Rock1 | 4 | 4 4.1-6.5 | Rho kinase, inhibitors have shown activity in mouse models of cancer |
| Stk17b | 4 | 4.0-6.4 | Inhibitor of T cell signaling forms complex with protein kinase D |
| Mast2 | 4 | 4.1-5.1 | Microtubule-associated serine/threonine kinase |
| Arhgap5 | 3 | 6.0-15.7 | Negative regulator of Rho GTPases, inhibition can reduce cancer cell invasion |
| Alk | 3 | 9.6-13.5 | Anaplastic lymphoma kinase (translocation of nucleophosmin and ALK in ALCL) |
| Nuak | 3 | 4.5-13.1 | Member of AMP-activated protein kinase-related kinase family, oncogene in melanoma |
| Akap8l | 3 | 4.4-11.8 | A-kinase anchoring protein, recruits cAMP-dependent protein kinase (PKA) to chromatin |
| Pdp1 | 3 | 4.1-9.8 | Pyruvate dehydrogenase phosphatase 1, regulation of glucose metabolism |
| Yes1 | 3 | 5.4-9.7 | Src family kinase, oncogene in several tumors |

TABLE 7-continued

| Symbol | Total # shRNAs | Enrichment (fold) | Function |
|---|---|---|---|
| Met | 3 | 4.1-8.9 | Receptor tyrosine kinase, involved in hepatocellular and other cancers |
| Ppm1g | 3 | 6.2-8.2 | Dephosphorylates spliceosome substrates and histones H2A-H2B |
| Blvrb | 3 | 5.3-8.0 | Biliverdin reductase, also transcription factor, arrest of cell cycle |
| Tnk1 | 3 | 5.2-7.6 | Downregulates Ras pathway (phosphorylation of Grb2), inhibition of NF-kB pathway |
| Prkab2 | 3 | 4.1-7.0 | Subunit of AMP kinase, inhibits fatty acid synthesis and mTOR pathway |
| Trpm7 | 3 | 4.9-5.9 | Ion channel and serine-threonine kinase |
| Ppp3cc | 3 | 4.2-4.4 | Regulatory subunit of calcineurin (phosphatase in T cell receptor signaling) |

Example 2: shRNA-Driven Expansion of CD4 and CD8 T Cells in B16 Melanomas

Figure 6:
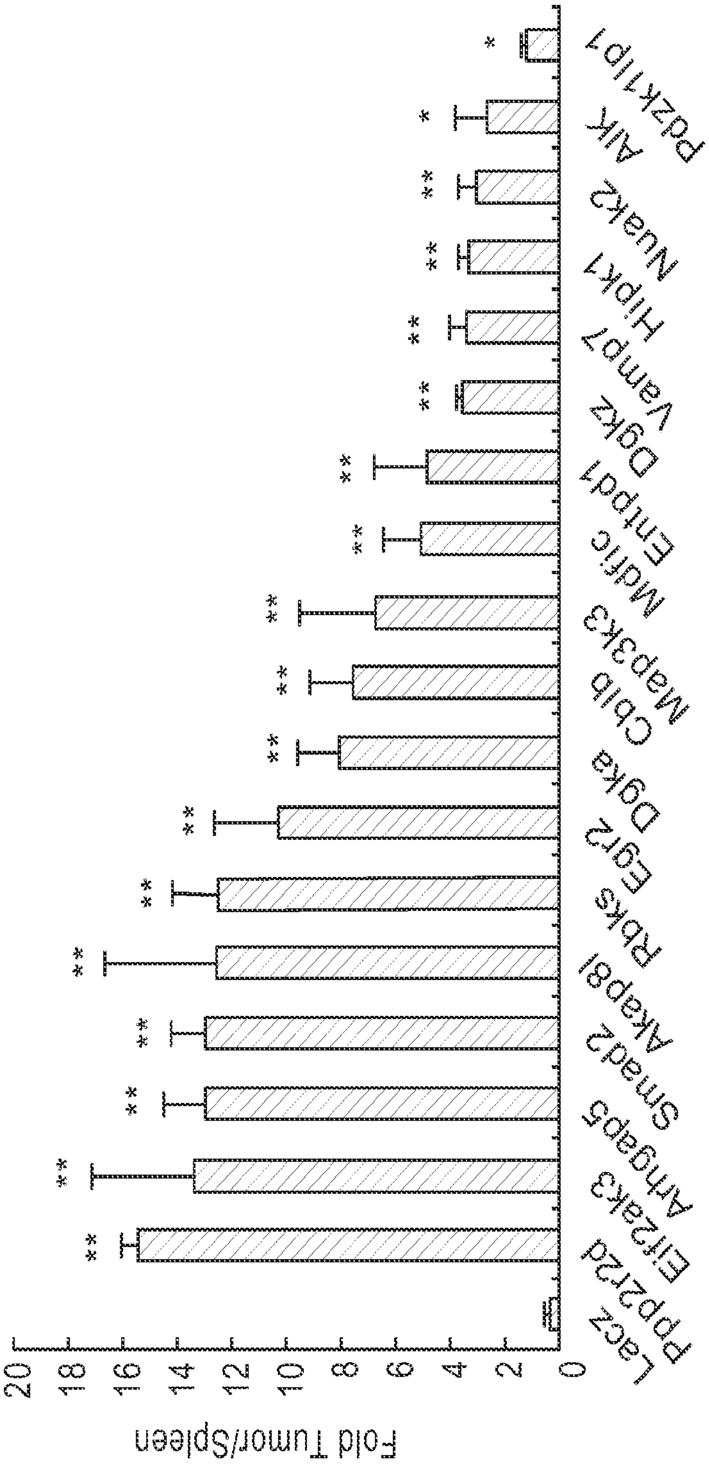
FIG. 6 is a graph showing flow cytometry based quantification of OT-I $CD8^+$ T cell enrichment in tumors relative to spleen. The percentage of shRNA-expressing OT-I T cells was determined by flow cytometry in tumors/spleens by gating on reporter proteins in $CD8^+V\alpha2^+V\beta5^+$ T cells. Statistical significance was determined for each experimental shRNA against LacZ shRNA (fold enrichment tumor/spleen) (n=3; * $p<0.05$, ** $p<0.01$, Student's t-test).
Figure 7:
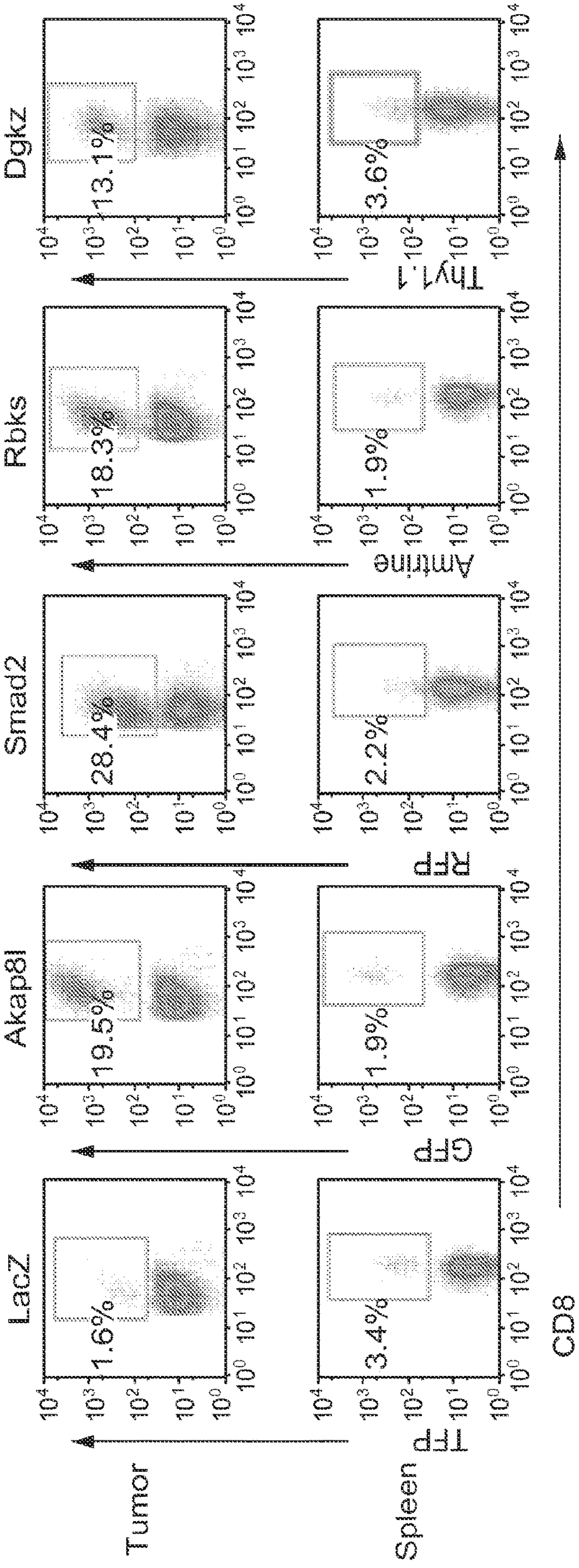
FIG. 7 is a set of graphs showing representative flow cytometry plots of cell enrichment in tumor transduced with shRNA vectors (LacZ, Akap8I, Smad2, Rbks, Dgkz). The percentage of shRNA-expressing OT-I T cells was determined by flow cytometry in tumors/spleens by gating on reporter proteins in $CD8^+V\alpha2^+V\beta5^+$ T cells.

Positive shRNAs from deep sequencing analysis were cloned into lentiviral vectors encoding five different reporter proteins (GFP, TFP, RFP or Ametrine fluorescent proteins, Thy1.1). Cytokine-pretreated OT-I T cells were transduced with lentiviral vectors driving expression of a single shRNA and a reporter protein; $1\times10^6$ T cells of each population were mixed and co-injected i.v. into C57BL/6 mice bearing day 14 B16-Ova tumors. After seven days T cells were isolated from tumors, spleens and lymph nodes, and the percentage of reporter-positive $CD8^+V\alpha2^+V\beta5^+$ T cells was determined by flow cytometry based on co-introduced reporters. Fold-enrichment in tumors compared to spleen was calculated based on the percentage of OT-I T cells in each organ expressing a particular reporter. When the control LacZ shRNA was expressed in CD8 OT-I T cells, the frequency of shRNA-expressing CD8 OT-I T cells was lower in tumors compared to spleen (~2-fold). In contrast, experimental shRNAs induced accumulation of CD8 OT-I T cells in tumors but not the spleen (FIG. 6, FIG. 7). For seven of these shRNAs (e.g., Ppp2r2D, Eif2ak3, Arhgap5, Smad2, Akap8I, Rbks and Egr2), T cell accumulation in tumors was >10-fold relative to spleen. The strongest phenotype was observed with shRNAs targeting Ppp2r2d, a regulatory subunit of the PP2A phosphatase7.

Figure 8A:
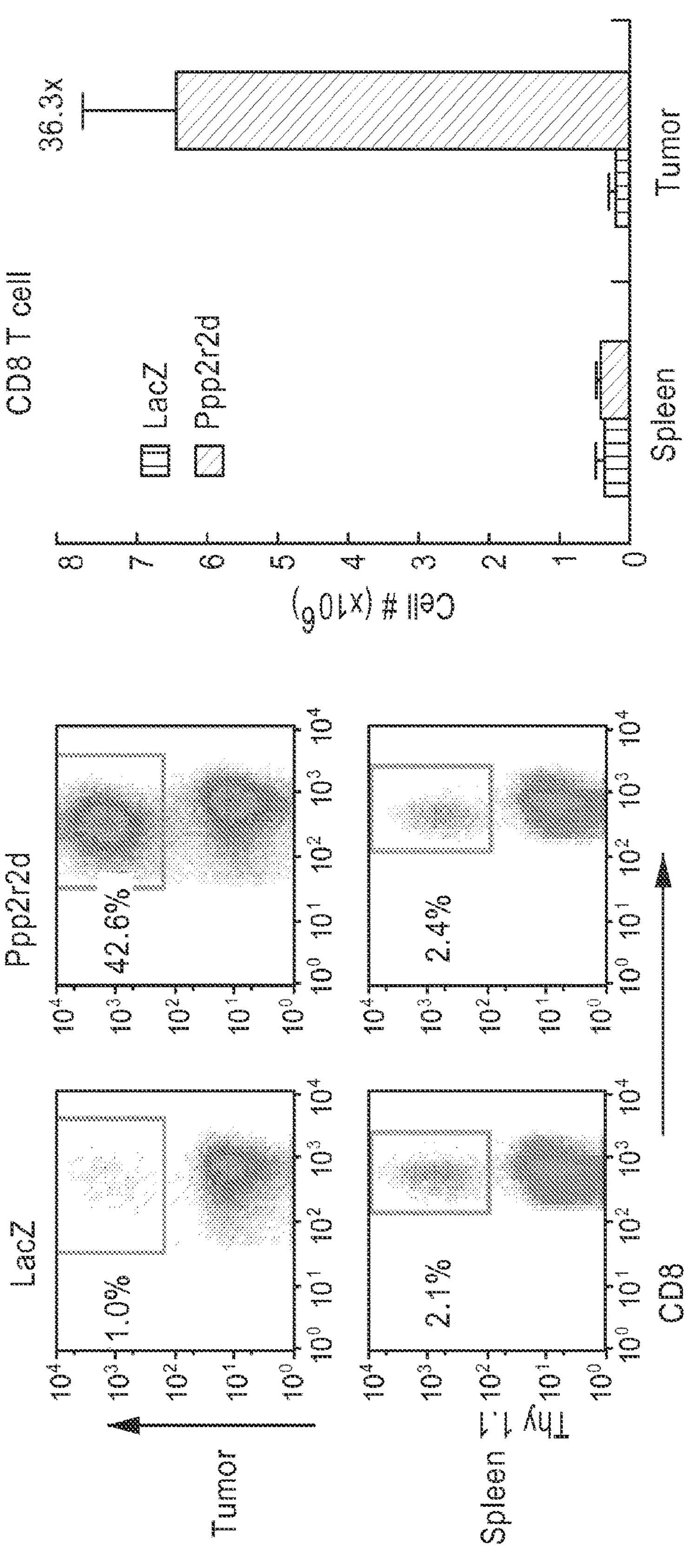
FIG. 8 is a set of graphs showing flow cytometry-based quantification of CD4+ and CD8+ T cell enrichment in tumors. shRNA-expressing T cells were identified in tumors and spleens using Thy1.1 reporter (% Thy1.1+ CD8 T cells or CD4+ T cells, top and bottom panels). Total numbers of LacZ or Ppp2r2d shRNA-expressing T cells were determined in tumors and spleens 7 days following transfer of 2×106 shRNA-expressing cells (right panels). Fold-enrichment of Ppp2r2d versus LacZ shRNA-expressing T cells in tumors is indicated.
Figure 8B:
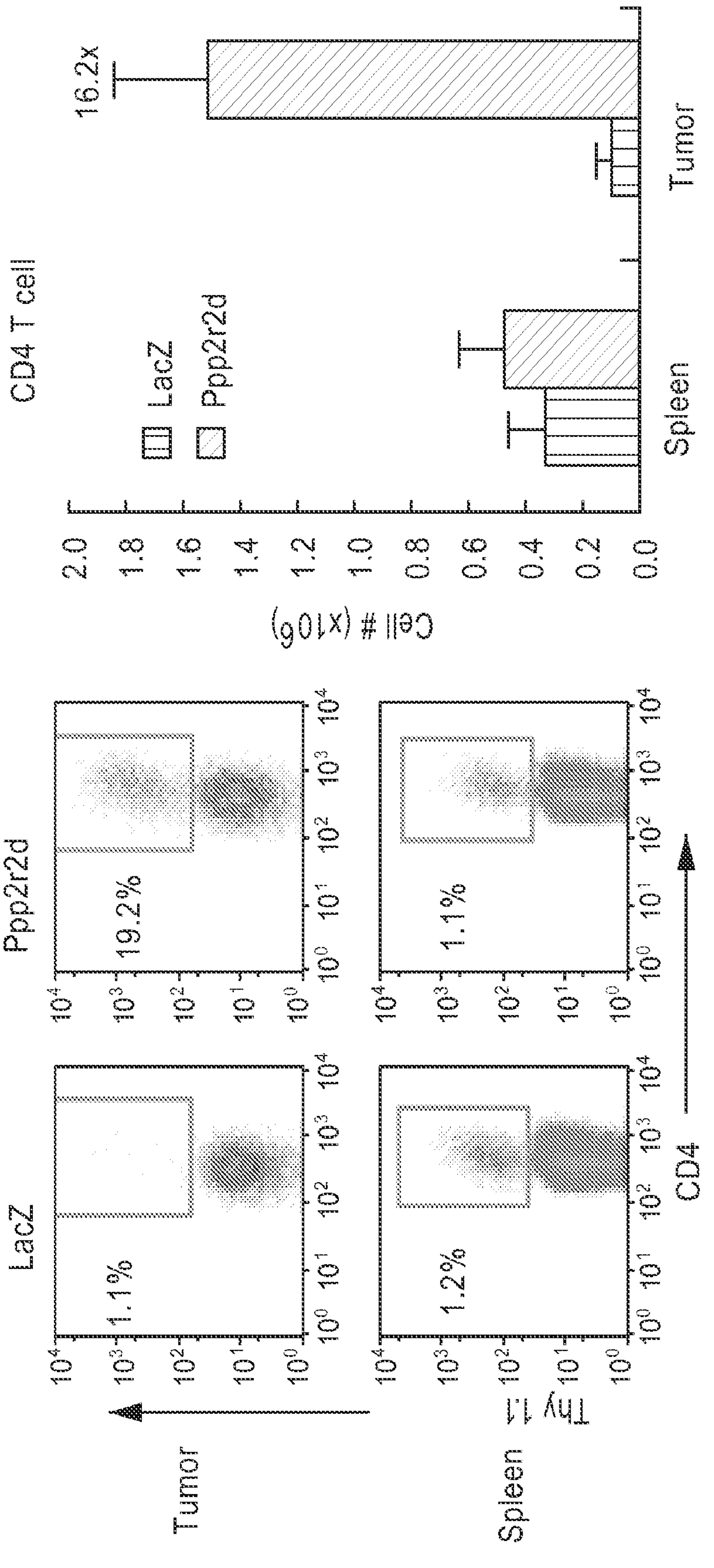
Figure 9:
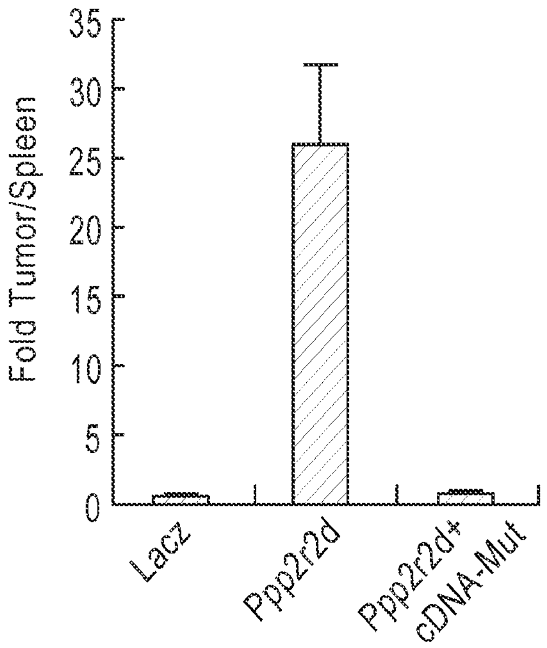
FIG. 9 is a graph showing reversal of Ppp2r2d shRNA-mediated T cell expansion in tumors by Ppp2r2d cDNA with a mutated shRNA binding site but preserved protein sequence. The three cell populations were identified based on co-expressed reporters; fold-enrichment was calculated based on percentage of reporter-positive cells in tumors versus spleens.

$CD8^+$ OT-I or $CD4^+$ TRP-1 T cells expressing Ppp2r2d or LacZ shRNAs were injected into mice bearing day 14 B16-Ova tumors. shRNA-expressing T cells were identified in tumors and spleens using Thy1.1 reporter (FIG. 8, % $Thy1.1^+$ CD8 T cells, left panels). Total numbers of LacZ or Ppp2r2d shRNA-expressing T cells were determined in tumors and spleens 7 days following transfer of 2×106 shRNA-expressing cells (FIG. 8, right panels). Fold-enrichment of Ppp2r2d versus LacZ shRNA-expressing T cells in tumors is indicated. Ppp2r2d shRNA not only induced accumulation of OT-I CD8 T cells, but also CD4 T cells (from TRP-1 TCR transgenic mice)[23], with T cell numbers in tumors being significantly higher when Ppp2r2d rather than LacZ shRNA was expressed (36.3-fold for CD8; 16.2-fold for CD4 T cells) (FIG. 8).

T cell enrichment in tumors compared to spleen for cells expressing a panel of Ppp2r2d or Cblb shRNAs (FIG. 17, upper panels) Ppp2r2d and Cblb mRNA levels were also measured by qPCR prior to T cell transfer (FIG. 17, lower panels). The strongest T cell enrichment in tumors was observed for shRNAs with >80% knock-down efficiency at the mRNA level (shRNAs #1 and 2 for both Ppp2r2d and Cblb). CD8 T cell accumulation correlated with the degree of Ppp2r2d knock-down, and two Ppp2r2d shRNAs with the highest in vivo activity induced the lowest levels of Ppp2r2d mRNA (FIG. 17).

Ppp2r2d knockdown was also confirmed at the protein level using a quantitative mass spectrometry approach (FIG. 18). A previously reported approach for absolute quantification (AQUA) of proteins from cell lysates by mass spectrometry was used to measure the effect of Ppp2r2d shRNA expression at the protein level (Gerber, S. A., Rush, J., Stemman, O., Kirschner, M. W. & Gygi, S. P. Absolute quantification of proteins and phosphoproteins from cell lysates by tandem MS. PNAS, 100, 6940-6945 (2003). This strategy is based on a 'selective reaction monitoring' approach in which a synthetic peptide with incorporated stable isotopes is used as an internal standard for mass spectrometry analysis. OT-I cells expressing LacZ or Ppp2r2d shRNAs were sorted to purity using FACS. Cells ($1\times10^6$) were lysed in 1 ml of MPER extraction reagent (Pierce) containing a Protease Inhibitor Cocktail (Sigma), 1 mM EDTA and 1 mM PMSF for 15 minutes on ice with occasional vortexing. Cell debris was removed by centrifugation and the protein supernatant was filtered (0.2 μm SpinX centrifuge filter, Costar). Protein concentration was determined by Bradford assay (Biorad) and UV280 nm analysis (Nanodrop instrument); 0.1 mg of cellular protein was separated by SDS-PAGE and stained with Coomassie blue reagent (Pierce). Gel bands corresponding to a MW range of 45-60 kDa were excised followed by in-gel digestion of proteins with trypsin. Eluted peptides were spiked with 300 fmol of isotopically labeled Ppp2r2d (FFEEPEDPSS[13C-15N-R]—OH)(SEQ ID NO: 628) and Actin B (GYSFTTTAE[13C-15N-R]—OH) (SEQ ID NO: 629) peptides (21st Century Biochemicals) for quantification by LC MS/MS (LTQ XL Orbitrap, Thermo Scientific). The Ppp2r2d peptide was chosen from a region of the protein that differs from other regulatory subunits of PP2A. Initially, a LC-MS/MS run of a LacZ shRNA sample was analyzed to localize the Ppp2r2d and Actin B peptides that were being monitored. The absolute quantification AQUA peptides co-eluted with the corresponding endogenous peptides from the reverse-phase column, yet their higher MW (10 Da) enabled the ratio of peak intensity for endogenous and AQUA peptides to be determined using abundant peptide fragment ions. Triplicate samples were analyzed by SDS-PAGE-LC-MS/MS and statistical significance was determined using Graphpad Prism 6.0 software using a two-sided Student t-test (F test, * p=0.0062).

The specificity of Ppp2r2d shRNA was determined. Ppp2r2d shRNA activity was specific because the phenotype was reversed when a mutated Ppp2r2d cDNA (with wild-type protein sequence, but mutated DNA sequence at the shRNA binding site) was co-introduced with the Ppp2r2d shRNA (FIG. 9, 10*a*-*c*). Furthermore, OT-I CD8 T cells over-expressed Ppp2r2d in tumors compared to spleen (in the absence of any shRNA expression), suggesting that it is an intrinsic component of the signaling network inhibiting T cell function in tumors (FIG. 19).

OT-I T cells transduced with lentiviral vectors driving expression of LacZ shRNA, Ppp2r2d shRNA, Ppp2r2d shRNA. Mutant Ppp2r2d cDNA with preserved protein sequence but disrupted shRNA binding site were generated. Wild-type Ppp2r2d cDNA was isolated by RT-PCR using forward primer GGATCCATGGCAGGAGCTGGAGGC (SEQ ID NO: 630) and reverse primer: GCTAGCATTAATTTTGTCCTGGAATATATACAAGTTATTGGTGG (SEQ ID NO: 631). The target sequence of Ppp2r2d shRNA, CCCACATCAGTGCAATGTATT (SEQ ID NO: 632) was mutated to TCCCCACCAATGTAACGTGTT (SEQ ID NO: 633) by overlapping PCR (which conserves protein coding sequence) using forward primer: TCCATCCCCACCAATGTAACGTGTTTGTTTACAGCAGCAGCAAGG (SEQ ID NO: 634) and reverse primer: AAACAAACACGTTACATTGGTGGGGATGGAACTCTGCGGCAGTGA (SEQ ID NO: 635). (FIG. 10*a*) Both wild-type and mutant Ppp2r2d cDNAs were cloned into a modified pLKO.3 vector with a 2A ribosomal skip peptide-GFP sequence (resulting in stoichiometric Ppp2r2d and GFP expression in cells). Constructs were introduced into EL4 thymoma cells. GFP-expressing EL4 cells were sorted to purity and then transduced with LacZ or Ppp2r2d shRNA lentiviral vectors driving expression of a Thy1.1 reporter. shRNA-transduced ($Thy1.1^+$) cells were analyzed by flow cytometry for GFP expression. The Ppp2r2d shRNA reduced GFP levels when wild-type Ppp2r2d. The Ppp2r2d shRNA was not able to reduce expression of the GFP reporter in cells expressing the mutant Ppp2r2d cDNA, demonstrating that the shRNA binding site had been successfully mutated. (FIG. 10*a*)

Expression of Ppp2r2d mutant cDNA also prevents phenotype induced by Ppp2r2d shRNA. (FIG. 10*b*) Ppp2r2d shRNA was cloned into the mutant Ppp2r2d cDNA-2A-GFP construct which resulted in co-expression of Ppp2r2d shRNA and mutated Ppp2r2d cDNA in one vector. OT-I T cells were separately infected with lentiviruses encoding LacZ shRNA (Thy1.1), Ppp2r2d shRNA (Ametrine) or Ppp2r2d shRNA plus mutant Ppp2r2d cDNA (GFP). (FIG. 10*b*) These three populations there then mixed at the same ratio and injected into mice bearing day 14 B16-Ova tumors. On day 7, each T cell population was quantified in tumors and spleens by gating on OT-I ($CD8^+V\alpha2^+V\beta5^+$)-T cells followed by analysis of populations marked by Thy1.1, Ametrine or GFP expression. The percentage of each T cell population in tumors and spleens was quantified by gating on $V\alpha2^+V\beta5^+$ T cells; transduced cells were detected based on expression of Thy1.1 or Ametrine/GFP fluorescent reporters and the results are shown in FIG. 10*b*. (representative data from 2 independent experiments, n=3 mice per experiment).

Figure 10C:
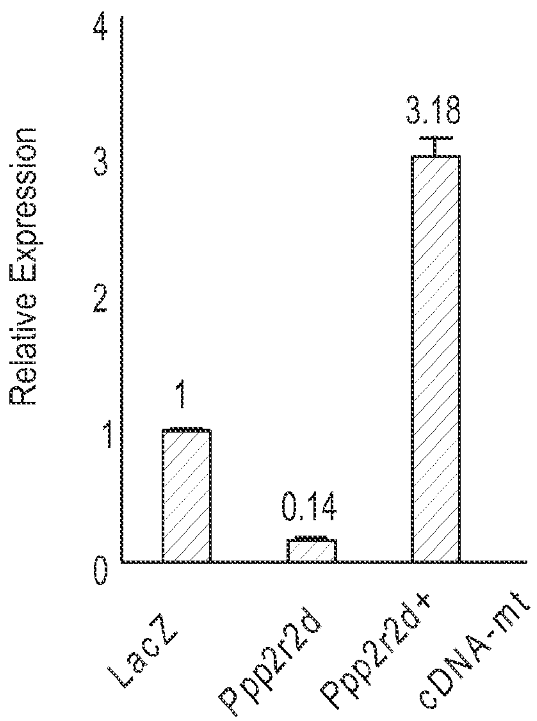

FIG. 10*c* provides real-time PCR analysis for Ppp2r2d expression in OT-I T cells transduced with LacZ shRNA, Ppp2r2d shRNA, and Ppp2r2d shRNA plus Ppp2r2d mutant cDNA. Also, the Ppp2r2d shRNA with the highest in vivo activity was associated with the lowest levels of Ppp2r2d mRNA (FIG. 11).

Microarray analysis of tumor-infiltrating T cells expressing experimental or control shRNAs showed that each shRNA induced a distinct set of gene expression changes, with some overlap between particular shRNAs (FIG. 12*a*-*c*). Two genes (Egr2 and Ptpn2) have known functions in T cells. Enrichment in tumor versus spleen was calculated based on deep sequencing results from the secondary screen. (FIG. 12*a*) Clustering of mean expression levels for mRNAs found to be significantly regulated by T cells in spleens or tumors expressing the LacZ control shRNA or one of five experimental shRNAs. (FIG. 12*b*) Significant expression differences were defined as an Anova p value<0.01 between T cells expressing LacZ control shRNA or one of five experimental shRNAs (Alk, Arhgap5, Egr2, Ptpn2 or Ppp2r2d) (JMP-Genomics 6.0, SAS Institute Inc.). mRNAs significantly regulated in one or more treatment groups are shown after clustering (Fast Ward). FIG. 12*c* is a Venn diagram showing overlaps between expression signatures by tumor-infiltrating T cells transduced with one of the five experimental shRNAs (signatures defined as an Anova p<0.01 as described above). Indicated are the numbers of overlapping probe IDs for any combination of the 5 signatures, as indicated by the overlapping ovals. The significance of the overlaps versus that expected by random chance (Fishers Exact Test) is shown in the accompanying table.

Example 3: Changes in T Cell Function Induced by Ppp2r2d

For this example, the cellular mechanisms driving T cell accumulation by a Ppp2r2d shRNA in tumors—specifically T cell infiltration, accumulation and apoptosis were examined. T cell infiltration into tumors was assessed by transfer of OT-I CD8 T cells labeled with a cytosolic dye, CFSE. OT-I T cells expressing Ppp2r2d or LacZ shRNAs were labeled with CFSE and injected into B16-Ova tumor-bearing mice. Twenty-four hours later transduced T cells were isolated from tumors and spleens and quantified by flow cytometry. OT-I T cells expressing LacZ or Ppp2r2d shRNAs were purified using the Thy1.1 reporter and cultured in complete RPMI media without added cytokines for 24 hours. Live cells isolated by Ficoll density gradient centrifugation (Sigma) were labeled with CFSE (carboxyfluorescein diacetate, succinimidyl ester, Invitrogen), and 2×106 labeled cells were injected into mice bearing day 14 B16-Ova tumors. CFSE dilution was quantified by flow cytometry at 24 hours and days 3, 5 and 7 following transfer. In addition, intracellular staining was performed on days 3, 5 and 7 for IFNγ, TNFα and isotype controls (BD). No differences were observed in the frequency of Ppp2r2d or LacZ shRNA-transduced CD8 T cells in tumors on day 1, arguing against a substantial effect on T cell infiltration (FIG. 13*a*). However, analysis of later time points (days 3 and 5) demonstrated a higher degree of proliferation (based on CFSE dilution) by Ppp2r2d compared to LacZ shRNA-transduced T cells (FIG. 13*b*, FIG. 20*a*). Ppp2r2d shRNA-transduced T cells also produced higher levels of interferon-γ, a cytokine critical for anti-tumor immunity (FIG. 13*e*). The action of Ppp2r2d was downstream of T cell receptor activation because T cell accumulation was enhanced in tumors and to a lesser extent in tumor-draining lymph nodes. In contrast, no accumulation was observed in irrelevant lymph nodes or the spleen where the relevant antigen is not presented to T cells (FIG. 15). A substantial degree of T cell accumulation was even observed for LacZ shRNA-transduced T cells (complete dilution of CFSE dye by day 7), despite the presence of small numbers of such cells in tumors. This suggested that LacZ shRNA-transduced T cells were lost by apoptosis. Indeed, a larger percentage of tumor-infiltrating T cells were labeled with an antibody specific for active caspase-3 when the LacZ control shRNA (rather than Ppp2r2d shRNA) was expressed (FIG. 13*g*, FIG. 20*b*). Furthermore, co-culture of CD8 T cells with B16-Ova tumor cells showed that the majority of LacZ shRNA expressing T cells became apoptotic (65.7%) while most Ppp2r2d shRNA-transduced T cells were viable (89.5%, FIG. 13*c*).

OT-I T cells expressing LacZ or Ppp2r2d shRNAs were purified based on Thy1.1 expression and labeled with CFSE, as described above. CFSE labeled OT-I T cells ($1\times10^5$) were co-cultured with $5\times10^4$ B16-Ova cells per well in a 96-well plate for 72 h. Prior to the assay, B16-Ova cells were exposed to 1 ng/mL IFNγ for 48 hours (to induce MHC class I, which is not expressed in vitro) and washed three times. Apoptosis of OT-I T cells was detected by annexin V labeling of $CD8^+$ cells. (FIG. 13*c*) Intracellular staining of phospho-AKT (Ser473), phopsho-Bad (Ser 112), Bcl-2 and isotype control was performed at 48 hours using a BD intracellular staining kit. Co-culture of CD8 T cells with B16-Ova tumor cells indeed showed that the majority of LacZ shRNA expressing T cells were apoptotic (65.7%) while the majority of Ppp2r2d shRNA-transduced T cells were viable (89.5%, FIG. 13*c*). A similar phenotype was observed when Ppp2r2d and LacZ shRNA-expressing T cells were stimulated with immobilized CD3 antibody in the absence of CD28 costimulation (FIG. 14). Specifically, B16-Ova cells ($2\times10^5$) were injected s.c. into female C57BL/6 mice (10 weeks of age). On day 12, mice bearing tumors of similar size were divided into 7 groups (7-8 mice/group). Anti-CD3/CD28 bead activated CD4 TRP-1 or/and CD8 OT-I T cells infected with Ppp2r2d or LacZ shRNA vectors ($2\times10^6$ T cells each) were injected i.v. on days 12 and day 17. For the treatment of B16 tumors, mice were treated at day 10 with anti-CD3/CD28 bead activated CD4 TRP-1 and CD8 pmel-1 T cells expressing Ppp2r2d or LacZ shRNAs ($3\times10^6$ T cells each). Tumor size was measured every three days following transfer and calculated as length×width. Mice with tumors≥20 mm on the longest axis were sacrificed.

These results suggested the possibility that Ppp2r2d shRNA-transduced CD8 T cells may be able to proliferate and survive even when they recognize their antigen directly presented by B16-Ova tumor cells. This idea was tested by implantation of tumor cells into b2m−/− mice which are deficient in expression of MHC class I proteins[24]. In such mice, only tumor cells but not professional antigen presenting cells of the host could present tumor antigens to T cells. Indeed, Ppp2r2d shRNA-transduced OT-I CD8 T cells showed massive accumulation within B16-Ova tumors in b2m−/− mice (FIG. 12*f*) while there were very small numbers of T cells in contralateral B16 tumors that lacked expression of the Ova antigen. T cells expressing a Ppp2r2d shRNA could thus effectively proliferate and survive in response to tumor cells, despite a lack of suitable co-stimulatory signals and an inhibitory microenvironment.

Ex vivo analysis of tumor-infiltrating T cells at a single-cell level using a nanowell device also demonstrated that Ppp2r2d silencing increased cytokine production by T cells (FIG. 21*a-c*). T cells were activated for 3 hours by CD3/CD28 antibodies on lipid bilayers, followed by 1 hour cytokine capture on antibody-coated slides. CD8 T cells showed a higher secretion rate for IFNγ, IL-2 and GM-CSF, and a larger fraction of T cells more than one cytokine (FIG. 21*b, c*). The presence of larger numbers of IFNγ-producing T cells was confirmed by intracellular cytokine staining (FIG. 21*d*, FIG. 20).

PP2A phosphatase is composed of a catalytic and scaffolding subunit, and its substrate specificity is determined by one of many regulatory subunits[7]. Ppp2r2d directs PP2A to Cdk1 substrates during interphase and anaphase; it thereby inhibits entry into mitosis and induces exit from mitosis[25]. PP2A plays a gatekeeper role for BAD-mediated apoptosis. Phosphorylated BAD is sequestered in its inactive form in the cytosol by 14-3-3, while dephosphorylated BAD is targeted to mitochondria where it causes cell death by binding Bcl-$X_L$ and Bcl-2[26]. PP2A phosphatases have also been shown to interact with the cytoplasmic domains of CD28 and CTLA-4 as well as Carma1 (upstream of the NF-κB pathway), but it is not known which regulatory subunits are required for these activities; Ppp2r2d antibodies suitable for the required biochemical studies are currently not available.

Example 4: Silencing of Ppp2r2d Enhances Anti-Tumor Activity of CD4 and CD8 T Cells The ability of a Ppp2r2d shRNA to enhance the efficacy of adoptive T cell therapy was assessed. B16-Ova tumor cells ($2\times10^5$) were injected subcutaneously into female C57BL/6 mice (10 weeks of age). On day 12, mice bearing tumors of similar size were divided into seven groups (7-8 mice/group), either receiving no T cells, $2\times10^6$ shRNA-transduced TRP-1 CD4 T cells, $2\times10^6$ shRNA infected OT-I CD8 T cells, or both CD4 and CD8 T cells (days 12 and day 17). According to group, anti-CD3/CD28 bead activated CD4 TRP-1 or/and CD8 OT-I T cells infected with Ppp2r2d or LacZ shRNA vectors ($2\times10^6$ T cells each) were injected i.v. on days 12 and day 17. For the treatment of B16 tumors, mice were treated at day 10 with anti-CD3/CD28 bead activated CD4 TRP-1 and CD8 pmel-1 T cells expressing Ppp2r2d or LacZ shRNAs (3×106 T cells each). Tumor size was measured every three days following transfer and calculated as length×width. Mice with tumors≥20 mm on the longest axis were sacrificed. Ppp2r2d-silencing improved the therapeutic activity of CD4 and CD8 T cells, and a synergistic effect was observed when Ppp2r2d shRNA-transduced CD4 and CD8 T cells were co-administered (FIG. 16*a, b*). A Ppp2r2d shRNA also enhanced anti-tumor responses when introduced into T cells specific for endogenous tumor antigens (pmel-1 CD8 T cells and TRP-1 CD4 T cells) (FIG. 16*c*).

Ppp2r2d-silenced T cells acquired an effector phenotype in tumors (FIG. 22*a*) and >30% of the cells expressed granzyme B (FIG. 23*a*). Consistent with greatly increased numbers of such effector T cells in tumors (FIG. 23*b*), TUNEL staining demonstrated increased apoptosis in tumors when Ppp2r2d rather than LacZ shRNA expressing T cells were present (FIG. 23*c*). B16 melanomas are highly aggressive tumors in part because MHC class I expression is very low. Interestingly, Ppp2r2d but not LacZ shRNA-expressing T cells significantly increased MHC class I expression (H-2Kb) by tumor cells (FIG. 23*d*), possibly due to the observed increase in IFNγ secretion by T cells (FIG. 21*a-c*, FIG. 13*e*). A Ppp2r2d shRNA did not reduce expression of inhibitory PD-1 or LAG-3 receptors on tumor-infiltrating T cells, demonstrating that its mechanism of action is distinct from these known negative regulators of T cell function (FIG. 22*b*). This finding suggests combination approaches targeting these intracellular and cell surface molecules.

These results establish the feasibility of in vivo discovery of novel targets for immunotherapy in complex tissue microenvironments. The inventors have shown that it is possible to discover genes with differential action across tissues, as exemplified by T cell accumulation in tumors compared to secondary lymphoid organs. For genes with tissue-selective action, T cell accumulation and survival are likely to be under the control of the T cell receptor and therefore do not occur in tissues lacking presentation of a relevant antigen. Many variations of the approach presented here can be envisioned to investigate control of particular immune cell functions in vivo. For example, fluorescent reporters for expression of cytokines or cytotoxic molecules (granzyme B, perforin) could be integrated into our approach to discover genes that control critical T cell effector functions in tumors.

Targeting of key regulatory switches may offer new approaches to modify the activity of T cells in cancer and other pathologies. The efficacy of such T cell-based therapies could be enhanced by shRNA-mediated silencing of genes that inhibit T cell function in the tumor microenvironment.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Galon, J., et al. Type, density, and location of immune cells within human colorectal tumors predict clinical outcome. *Science* 313, 1960-1964 (2006).
2. Hamanishi, J., et al. Programmed cell death 1 ligand 1 and tumor-infiltrating CD8+ T lymphocytes are prognostic factors of human ovarian cancer. *Proceedings of the National Academy of Sciences of the United States of America* 104, 3360-3365 (2007).
3. Mahmoud, S. M., et al. Tumor-Infiltrating CD8+ Lymphocytes Predict Clinical Outcome in Breast Cancer. *J Clin Oncol* 29, 1949-1955 (2011).
4. Topalian, S. L., et al. Safety, activity, and immune correlates of anti-PD-1 antibody in cancer. *The New England journal of medicine* 366, 2443-2454 (2012).
5. Brahmer, J. R., et al. Safety and activity of anti-PD-L1 antibody in patients with advanced cancer. *The New England journal of medicine* 366, 2455-2465 (2012).
6. Hodi, F. S., et al. Improved Survival with Ipilimumab in Patients with Metastatic Melanoma. *N Engl J Med* (2011).
7. Barr, F. A., Elliott, P. R. & Gruneberg, U. Protein phosphatases and the regulation of mitosis. *J Cell Sci* 124, 2323-2334 (2011).
8. Pages, F., et al. In situ cytotoxic and memory T cells predict outcome in patients with early-stage colorectal cancer. *J Clin Oncol* 27, 5944-5951 (2009).
9. Shiao, S. L., Ganesan, A. P., Rugo, H. S. & Coussens, L. M. Immune microenvironments in solid tumors: new targets for therapy. *Genes Dev* 25, 2559-2572 (2011).
10. Gabrilovich, D. I. & Nagaraj, S. Myeloid-derived suppressor cells as regulators of the immune system. *Nat Rev Immunol* 9, 162-174 (2009).
11. Topalian, S. L., Drake, C. G. & Pardoll, D. M. Targeting the PD-1/B7-H1(PD-L1) pathway to activate anti-tumor immunity. *Current opinion in immunology* 24, 207-212 (2012).
12. Westbrook, T. F., et al. A genetic screen for candidate tumor suppressors identifies REST. *Cell* 121, 837-848 (2005).
13. Luo, B., et al. Highly parallel identification of essential genes in cancer cells. *Proceedings of the National Academy of Sciences of the United States of America* 105, 20380-20385 (2008).
14. Zender, L., et al. An oncogenomics-based in vivo RNAi screen identifies tumor suppressors in liver cancer. *Cell* 135, 852-864 (2008).
15. Fidler, I. J. Biological behavior of malignant melanoma cells correlated to their survival in vivo. *Cancer research* 35, 218-224 (1975).
16. Hogquist, K. A., et al. T cell receptor antagonist peptides induce positive selection. *Cell* 76, 17-27 (1994).

17. Bellone, M., et al. Relevance of the tumor antigen in the validation of three vaccination strategies for melanoma. *Journal of immunology* 165, 2651-2656 (2000).

18. Overwijk, W. W., et al. Tumor regression and autoimmunity after reversal of a functionally tolerant state of self-reactive CD8+ T cells. *The Journal of experimental medicine* 198, 569-580 (2003).

19. Paolino, M. & Penninger, J. M. Cbl-b in T-cell activation. *Semin Immunopathol* 32, 137-148 (2010).

20. Zheng, Y., Zha, Y. & Gajewski, T. F. Molecular regulation of T-cell anergy. *EMBO Rep* 9, 50-55 (2008).

21. Doody, K. M., Bourdeau, A. & Tremblay, M. L. T-cell protein tyrosine phosphatase is a key regulator in immune cell signaling: lessons from the knockout mouse model and implications in human disease. *Immunological reviews* 228, 325-341 (2009).

22. Tamiya, T., Kashiwagi, I., Takahashi, R., Yasukawa, H. & Yoshimura, A. Suppressors of cytokine signaling (SOCS) proteins and JAK/STAT pathways: regulation of T-cell inflammation by SOCS1 and SOCS3. *Arterioscler Thromb Vasc Blot* 31, 980-985 (2011).

23. Muranski, P., et al. Tumor-specific Th17-polarized cells eradicate large established melanoma. *Blood* 112, 362-373 (2008).

24. Koller, B. H., Marrack, P., Kappler, J. W. & Smithies, O. Normal development of mice deficient in beta 2M, MHC class I proteins, and CD8+ T cells. *Science* 248, 1227-1230 (1990).

25. Mochida, S., Maslen, S. L., Skehel, M. & Hunt, T. Greatwall phosphorylates an inhibitor of protein phosphatase 2A that is essential for mitosis. *Science* 330, 1670-1673 (2010).

26. Chiang, C. W., et al. Protein phosphatase 2A dephosphorylation of phosphoserine 112 plays the gatekeeper role for BAD-mediated apoptosis. *Mol Cell Biol* 23, 6350-6362 (2003).

27. Turtle, C. J., Hudecek, M., Jensen, M. C. & Riddell, S. R. Engineered T cells for anti-cancer therapy. *Current opinion in immunology* 24, 633-639 (2012).

28. Restifo, N. P., Dudley, M. E. & Rosenberg, S. A. Adoptive immunotherapy for cancer: harnessing the T cell response. Nature reviews. *Immunology* 12, 269-281 (2012).

29. Bollard, C. M., Rooney, C. M. & Heslop, H. E. T-cell therapy in the treatment of post-transplant lymphoproliferative disease. *Nat Rev Clin Oncol* 9, 510-519 (2012).

30. Ashton, J. M., et al. Gene sets identified with oncogene cooperativity analysis regulate in vivo growth and survival of leukemia stem cells. *Cell Stem Cell* 11, 359-372 (2012).

31. Wherry, E. J., et al. Molecular signature of CD8+ T cell exhaustion during chronic viral infection. *Immunity* 27, 670-684 (2007).

32. Parish, I. A., et al. The molecular signature of CD8+ T cells undergoing deletional tolerance. *Blood* 113, 4575-4585 (2009).

33. Macian, F., et al. Transcriptional mechanisms underlying lymphocyte tolerance. *Cell* 109, 719-731 (2002).

34. Zha, Y., et al. T cell anergy is reversed by active Ras and is regulated by diacylglycerol kinase-alpha. *Nat Immunol* 7, 1166-1173 (2006).

35. Lopes, A. R., et al. Bim-mediated deletion of antigen-specific CD8 T cells in patients unable to control HBV infection. *The Journal of clinical investigation* 118, 1835-1845 (2008).

36. Kurella, S., et al. Transcriptional modulation of TCR, Notch and Wnt signaling pathways in SEB-anergized CD4+ T cells. *Genes Immun* 6, 596-608 (2005).

37. Xu, T., et al. Microarray analysis reveals differences in gene expression of circulating CD8(+) T cells in melanoma patients and healthy donors. *Cancer research* 64, 3661-3667 (2004).

38. Gorer, P. A. Studies in antibody response of mice to tumour inoculation. *Br J Cancer* 4, 372-379 (1950).

What is claimed is:

1. An immunoresponsive cell having tumor specificity comprising a vector, the vector comprising a sequence encoding a shRNA, wherein the shRNA comprises 15 contiguous nucleotides complementary to a nucleic acid sequence of SEQ ID NO: 604.

2. The immunoresponsive cell of claim 1, wherein the immunoresponsive cell is selected from the group consisting of a tumor-infiltrating lymphocyte (TIL), a Natural Killer T cell (NKT), a cytotoxic T lymphocyte (CTL), and a CD4T cell.

3. The immunoresponsive cell of claim 1, wherein the immunoresponsive cell expresses a tumor-specific T-cell receptor.

4. The immunoresponsive cell of claim 1, wherein the immunoresponsive cell further comprises a vector encoding a chimeric antigen receptor (CAR), wherein the CAR comprises an antigen binding domain, a transmembrane domain, and a stimulatory domain.

5. The immunoresponsive cell of claim 1, wherein the shRNA sequence reduces expression of Ppp2r2d.

6. The immunoresponsive cell of claim 4, wherein the CAR is directed to a tumor antigen comprising prostate-specific membrane antigen (PSMA).

7. The immunoresponsive cell of claim 4, wherein the CAR further comprises a costimulatory domain.

8. A composition comprising the immunoresponsive cell of claim 1 and a pharmaceutically acceptable carrier.

9. The composition of claim 8, further comprising an inhibitor of Ppp2r2d.

10. The immunoresponsive cell of claim 1 wherein the sequence encoding the shRNA comprises a first sequence comprising 15-25 nucleotides complementary to SEQ ID NO: 604 and a second sequence that is the reverse complement of the first sequence with one or no mismatches, and a third sequence of 5-9 nucleotides positioned between the first and second sequences.

11. The immunoresponsive cell of claim 10 wherein the first sequence comprises 19-25 nucleotides complementary to SEQ ID NO: 604.

* * * * *

SEQUENCE LISTING

<160> NUMBER OF SEQ ID NOS: 681

<210> SEQ ID NO 1
<211> LENGTH: 21
<212> TYPE: DNA
<213> ORGANISM: Homo sapiens

<400> SEQUENCE: 1
cgaaaccgca ggcttatgat g 21

<210> SEQ ID NO 2
<211> LENGTH: 21
<212> TYPE: DNA
<213> ORGANISM: Homo sapiens

<400> SEQUENCE: 2
cagactgctc agacaacagt g 21

<210> SEQ ID NO 3
<211> LENGTH: 21
<212> TYPE: DNA
<213> ORGANISM: Homo sapiens

<400> SEQUENCE: 3
ccacaaggaa cacttcaaat a 21

<210> SEQ ID NO 4
<211> LENGTH: 21
<212> TYPE: DNA
<213> ORGANISM: Homo sapiens

<400> SEQUENCE: 4
agacctctac cggtcaagct a 21

<210> SEQ ID NO 5
<211> LENGTH: 21
<212> TYPE: DNA
<213> ORGANISM: Homo sapiens

<400> SEQUENCE: 5
atagaggcta cgagaactat g 21

<210> SEQ ID NO 6
<211> LENGTH: 21
<212> TYPE: DNA
<213> ORGANISM: Homo sapiens

<400> SEQUENCE: 6
ccagaacatc atacccgagt a 21

<210> SEQ ID NO 7
<211> LENGTH: 21
<212> TYPE: DNA
<213> ORGANISM: Homo sapiens

<400> SEQUENCE: 7
ttagatatga tgccgcactt g 21

<210> SEQ ID NO 8
<211> LENGTH: 21
<212> TYPE: DNA
<213> ORGANISM: Homo sapiens

<400> SEQUENCE: 8
cccacctgtg attatggata t 21

<210> SEQ ID NO 9
<211> LENGTH: 21
<212> TYPE: DNA
<213> ORGANISM: Homo sapiens

<400> SEQUENCE: 9
ggcgagaatc ctttcactga c 21

<210> SEQ ID NO 10
<211> LENGTH: 21
<212> TYPE: DNA
<213> ORGANISM: Homo sapiens

<400> SEQUENCE: 10
cgagaactat ggttatggct a 21

<210> SEQ ID NO 11
<211> LENGTH: 21
<212> TYPE: DNA
<213> ORGANISM: Homo sapiens

<400> SEQUENCE: 11
caaataccgg accttctatg a 21

<210> SEQ ID NO 12
<211> LENGTH: 21
<212> TYPE: DNA
<213> ORGANISM: Homo sapiens

<400> SEQUENCE: 12
gatatctgaa gggcgagaat c 21

<210> SEQ ID NO 13
<211> LENGTH: 21
<212> TYPE: DNA
<213> ORGANISM: Homo sapiens

<400> SEQUENCE: 13
accggtcaag ctatgactat g 21

<210> SEQ ID NO 14
<211> LENGTH: 21
<212> TYPE: DNA
<213> ORGANISM: Homo sapiens

<400> SEQUENCE: 14
ttggatttgg caatggcatg a 21

<210> SEQ ID NO 15
<211> LENGTH: 21
<212> TYPE: DNA
<213> ORGANISM: Homo sapiens

<400> SEQUENCE: 15
ccgaaaccac tttgcagtct a 21

<210> SEQ ID NO 16
<211> LENGTH: 21
<212> TYPE: DNA
<213> ORGANISM: Homo sapiens

<400> SEQUENCE: 16
acctagagga gaatcacttt a 21

<210> SEQ ID NO 17
<211> LENGTH: 21
<212> TYPE: DNA
<213> ORGANISM: Homo sapiens

<400> SEQUENCE: 17
gccttcatgg aagggatatt t 21

<210> SEQ ID NO 18
<211> LENGTH: 21
<212> TYPE: DNA
<213> ORGANISM: Homo sapiens

<400> SEQUENCE: 18
cgggcctgta taccggataa t 21

<210> SEQ ID NO 19
<211> LENGTH: 21
<212> TYPE: DNA
<213> ORGANISM: Homo sapiens

<400> SEQUENCE: 19
gtggagccac ctacgtgttt a 21

<210> SEQ ID NO 20
<211> LENGTH: 21
<212> TYPE: DNA
<213> ORGANISM: Homo sapiens

<400> SEQUENCE: 20
ggaatctgac ctggacgatg a 21

<210> SEQ ID NO 21
<211> LENGTH: 21
<212> TYPE: DNA
<213> ORGANISM: Homo sapiens

<400> SEQUENCE: 21
cttcgttgta ccctcgctct t 21

<210> SEQ ID NO 22
<211> LENGTH: 21
<212> TYPE: DNA
<213> ORGANISM: Homo sapiens

<400> SEQUENCE: 22
gaagggatat ttacctctaa a 21

<210> SEQ ID NO 23
<211> LENGTH: 21
<212> TYPE: DNA
<213> ORGANISM: Homo sapiens

<400> SEQUENCE: 23
ccgggatatt gctgctagaa a 21

<210> SEQ ID NO 24
<211> LENGTH: 21
<212> TYPE: DNA
<213> ORGANISM: Homo sapiens

<400> SEQUENCE: 24
gcatcgcatt ggaggctata a 21

<210> SEQ ID NO 25
<211> LENGTH: 21
<212> TYPE: DNA
<213> ORGANISM: Homo sapiens

<400> SEQUENCE: 25
gggcctgtat accggataat g 21

<210> SEQ ID NO 26
<211> LENGTH: 21
<212> TYPE: DNA
<213> ORGANISM: Homo sapiens

<400> SEQUENCE: 26
cggaggatat ataggtggca a 21

<210> SEQ ID NO 27
<211> LENGTH: 21
<212> TYPE: DNA
<213> ORGANISM: Homo sapiens

<400> SEQUENCE: 27

-continued atcgaatacg gtccagtagt a 21

<210> SEQ ID NO 28
<211> LENGTH: 21
<212> TYPE: DNA
<213> ORGANISM: Homo sapiens

<400> SEQUENCE: 28
tgcttccgcg tagtcagaaa t 21

<210> SEQ ID NO 29
<211> LENGTH: 21
<212> TYPE: DNA
<213> ORGANISM: Homo sapiens

<400> SEQUENCE: 29
cctgcggcaa tgtcaactat g 21

<210> SEQ ID NO 30
<211> LENGTH: 21
<212> TYPE: DNA
<213> ORGANISM: Homo sapiens

<400> SEQUENCE: 30
cccgaacgtc aactatggtt a 21

<210> SEQ ID NO 31
<211> LENGTH: 21
<212> TYPE: DNA
<213> ORGANISM: Homo sapiens

<400> SEQUENCE: 31
ggcgaggaga cgattcttga a 21

<210> SEQ ID NO 32
<211> LENGTH: 21
<212> TYPE: DNA
<213> ORGANISM: Homo sapiens

<400> SEQUENCE: 32
tggtacatat cctcgtaaat t 21

<210> SEQ ID NO 33
<211> LENGTH: 21
<212> TYPE: DNA
<213> ORGANISM: Homo sapiens

<400> SEQUENCE: 33
attgcaatca gtatatcatt c 21

<210> SEQ ID NO 34
<211> LENGTH: 21
<212> TYPE: DNA
<213> ORGANISM: Homo sapiens

<400> SEQUENCE: 34
gatcatgaac gtaaccataa a 21

<210> SEQ ID NO 35
<211> LENGTH: 21
<212> TYPE: DNA
<213> ORGANISM: Homo sapiens

<400> SEQUENCE: 35
tgataatagc agcaactaaa t 21

<210> SEQ ID NO 36
<211> LENGTH: 21
<212> TYPE: DNA
<213> ORGANISM: Homo sapiens

<400> SEQUENCE: 36
agcatgactg gagaggttta a 21

<210> SEQ ID NO 37
<211> LENGTH: 21
<212> TYPE: DNA
<213> ORGANISM: Homo sapiens

<400> SEQUENCE: 37
tgatagtcag aatcgaatta t 21

<210> SEQ ID NO 38
<211> LENGTH: 21
<212> TYPE: DNA
<213> ORGANISM: Homo sapiens

<400> SEQUENCE: 38
gaactggttc atgggtatat a 21

<210> SEQ ID NO 39
<211> LENGTH: 21
<212> TYPE: DNA
<213> ORGANISM: Homo sapiens

<400> SEQUENCE: 39
gcaagctcta agaggagtat t 21

<210> SEQ ID NO 40
<211> LENGTH: 21
<212> TYPE: DNA
<213> ORGANISM: Homo sapiens

<400> SEQUENCE: 40
cctgatcctt tgattccata t 21

<210> SEQ ID NO 41
<211> LENGTH: 21
<212> TYPE: DNA
<213> ORGANISM: Homo sapiens

<400> SEQUENCE: 41
acagatcctc ttggtattat a 21

<210> SEQ ID NO 42
<211> LENGTH: 21
<212> TYPE: DNA
<213> ORGANISM: Homo sapiens

<400> SEQUENCE: 42
gcacgattta atgtcaacat t 21

<210> SEQ ID NO 43
<211> LENGTH: 21
<212> TYPE: DNA
<213> ORGANISM: Homo sapiens

<400> SEQUENCE: 43
ctcagtccca ctacagtaat g 21

<210> SEQ ID NO 44
<211> LENGTH: 21
<212> TYPE: DNA
<213> ORGANISM: Homo sapiens

<400> SEQUENCE: 44
tgaccacatc cggatgcata a 21

<210> SEQ ID NO 45
<211> LENGTH: 21
<212> TYPE: DNA
<213> ORGANISM: Homo sapiens

<400> SEQUENCE: 45
gcctcaccac caatgagtat g 21

<210> SEQ ID NO 46
<211> LENGTH: 21
<212> TYPE: DNA
<213> ORGANISM: Homo sapiens

<400> SEQUENCE: 46
tgagaaatga cacaaataga g 21

<210> SEQ ID NO 47
<211> LENGTH: 21
<212> TYPE: DNA
<213> ORGANISM: Homo sapiens

<400> SEQUENCE: 47
tgcaagagtc agggctgaaa t 21

<210> SEQ ID NO 48
<211> LENGTH: 21
<212> TYPE: DNA
<213> ORGANISM: Homo sapiens

<400> SEQUENCE: 48
ggaagctgtc atcgtgctac t 21

<210> SEQ ID NO 49
<211> LENGTH: 21
<212> TYPE: DNA
<213> ORGANISM: Homo sapiens

<400> SEQUENCE: 49
gcataagatt ctgcaagagt c 21

<210> SEQ ID NO 50
<211> LENGTH: 21
<212> TYPE: DNA
<213> ORGANISM: Homo sapiens

<400> SEQUENCE: 50
cctcagtccc actacagtaa t 21

<210> SEQ ID NO 51
<211> LENGTH: 21
<212> TYPE: DNA

<213> ORGANISM: Homo sapiens

<400> SEQUENCE: 51
tcgagggtca tatccaagca t 21

<210> SEQ ID NO 52
<211> LENGTH: 21
<212> TYPE: DNA
<213> ORGANISM: Homo sapiens

<400> SEQUENCE: 52
gaacatcgtg acagccatga a 21

<210> SEQ ID NO 53
<211> LENGTH: 21
<212> TYPE: DNA
<213> ORGANISM: Homo sapiens

<400> SEQUENCE: 53
ccaatgagta tgacggacac a 21

<210> SEQ ID NO 54
<211> LENGTH: 21
<212> TYPE: DNA
<213> ORGANISM: Homo sapiens

<400> SEQUENCE: 54
gagggtcatg catcctgaga a 21

<210> SEQ ID NO 55
<211> LENGTH: 21
<212> TYPE: DNA
<213> ORGANISM: Homo sapiens

<400> SEQUENCE: 55
taggagacca accactaact g 21

<210> SEQ ID NO 56
<211> LENGTH: 21
<212> TYPE: DNA
<213> ORGANISM: Homo sapiens

<400> SEQUENCE: 56
gctgaaatac gtggcagtga t 21

<210> SEQ ID NO 57
<211> LENGTH: 21
<212> TYPE: DNA
<213> ORGANISM: Homo sapiens

<400> SEQUENCE: 57
cggatgcata agattctgca a 21

<210> SEQ ID NO 58
<211> LENGTH: 21
<212> TYPE: DNA
<213> ORGANISM: Homo sapiens

<400> SEQUENCE: 58
tctacatcga tagtctcatg a 21

<210> SEQ ID NO 59
<211> LENGTH: 21

-continued

<212> TYPE: DNA
<213> ORGANISM: Homo sapiens

<400> SEQUENCE: 59
ctacacctca cgatcatata a 21

<210> SEQ ID NO 60
<211> LENGTH: 21
<212> TYPE: DNA
<213> ORGANISM: Homo sapiens

<400> SEQUENCE: 60
tgagcgagaa tgagtacttt a 21

<210> SEQ ID NO 61
<211> LENGTH: 21
<212> TYPE: DNA
<213> ORGANISM: Homo sapiens

<400> SEQUENCE: 61
atcgaacatc ccagatttag g 21

<210> SEQ ID NO 62
<211> LENGTH: 21
<212> TYPE: DNA
<213> ORGANISM: Homo sapiens

<400> SEQUENCE: 62
taaagtgtac tggtccatta g 21

<210> SEQ ID NO 63
<211> LENGTH: 21
<212> TYPE: DNA
<213> ORGANISM: Homo sapiens

<400> SEQUENCE: 63
cttgtactcc agtaccataa t 21

<210> SEQ ID NO 64
<211> LENGTH: 21
<212> TYPE: DNA
<213> ORGANISM: Homo sapiens

<400> SEQUENCE: 64
gtatgagaca gaaggactga g 21

<210> SEQ ID NO 65
<211> LENGTH: 21
<212> TYPE: DNA
<213> ORGANISM: Homo sapiens

<400> SEQUENCE: 65
ccagatttag gcatctattt g 21

<210> SEQ ID NO 66
<211> LENGTH: 21
<212> TYPE: DNA
<213> ORGANISM: Homo sapiens

<400> SEQUENCE: 66
tcagcacttg agacttatat t 21

<210> SEQ ID NO 67

<211> LENGTH: 21
<212> TYPE: DNA
<213> ORGANISM: Homo sapiens

<400> SEQUENCE: 67
tacacctcac gatcatataa a 21

<210> SEQ ID NO 68
<211> LENGTH: 21
<212> TYPE: DNA
<213> ORGANISM: Homo sapiens

<400> SEQUENCE: 68
aacacagacg ccatgatttg c 21

<210> SEQ ID NO 69
<211> LENGTH: 21
<212> TYPE: DNA
<213> ORGANISM: Homo sapiens

<400> SEQUENCE: 69
aagatgtcaa gattgagcct t 21

<210> SEQ ID NO 70
<211> LENGTH: 21
<212> TYPE: DNA
<213> ORGANISM: Homo sapiens

<400> SEQUENCE: 70
ccctgattta accggattat g 21

<210> SEQ ID NO 71
<211> LENGTH: 21
<212> TYPE: DNA
<213> ORGANISM: Homo sapiens

<400> SEQUENCE: 71
agccaggtcc aattccattt c 21

<210> SEQ ID NO 72
<211> LENGTH: 21
<212> TYPE: DNA
<213> ORGANISM: Homo sapiens

<400> SEQUENCE: 72
cgagcgatcc ggctctttaa a 21

<210> SEQ ID NO 73
<211> LENGTH: 21
<212> TYPE: DNA
<213> ORGANISM: Homo sapiens

<400> SEQUENCE: 73
cttggtgaag ttcgtgcgat c 21

<210> SEQ ID NO 74
<211> LENGTH: 21
<212> TYPE: DNA
<213> ORGANISM: Homo sapiens

<400> SEQUENCE: 74
cgctctggct ttcgtgaaca t 21

<210> SEQ ID NO 75
<211> LENGTH: 21
<212> TYPE: DNA
<213> ORGANISM: Homo sapiens

<400> SEQUENCE: 75
gatgatgatg ggcaacgttc a 21

<210> SEQ ID NO 76
<211> LENGTH: 21
<212> TYPE: DNA
<213> ORGANISM: Homo sapiens

<400> SEQUENCE: 76
tcccaagagc agagctaaat c 21

<210> SEQ ID NO 77
<211> LENGTH: 21
<212> TYPE: DNA
<213> ORGANISM: Homo sapiens

<400> SEQUENCE: 77
tcttggtgaa gttcgtgcga t 21

<210> SEQ ID NO 78
<211> LENGTH: 21
<212> TYPE: DNA
<213> ORGANISM: Homo sapiens

<400> SEQUENCE: 78
acgggcatag cttcagctca a 21

<210> SEQ ID NO 79
<211> LENGTH: 21
<212> TYPE: DNA
<213> ORGANISM: Homo sapiens

<400> SEQUENCE: 79
gctcggctgg atgtgcgcga t 21

<210> SEQ ID NO 80
<211> LENGTH: 21
<212> TYPE: DNA
<213> ORGANISM: Homo sapiens

<400> SEQUENCE: 80
ttgaggctag agaggatctt g 21

<210> SEQ ID NO 81
<211> LENGTH: 21
<212> TYPE: DNA
<213> ORGANISM: Homo sapiens

<400> SEQUENCE: 81
catcaagaca tcgtgcgata t 21

<210> SEQ ID NO 82
<211> LENGTH: 21
<212> TYPE: DNA
<213> ORGANISM: Homo sapiens

<400> SEQUENCE: 82
gtgaacatgt tgttgaggct a 21

<210> SEQ ID NO 83
<211> LENGTH: 21
<212> TYPE: DNA
<213> ORGANISM: Homo sapiens

<400> SEQUENCE: 83
gtctttgtgt accgctggga a 21

<210> SEQ ID NO 84
<211> LENGTH: 21
<212> TYPE: DNA
<213> ORGANISM: Homo sapiens

<400> SEQUENCE: 84
ctagcgatgc tagcgtgtct a 21

<210> SEQ ID NO 85
<211> LENGTH: 21
<212> TYPE: DNA
<213> ORGANISM: Homo sapiens

<400> SEQUENCE: 85
gtgatgatga tgggcaacgt t 21

<210> SEQ ID NO 86
<211> LENGTH: 21
<212> TYPE: DNA
<213> ORGANISM: Homo sapiens

<400> SEQUENCE: 86
gctcaactac ggtgcagatt c 21

<210> SEQ ID NO 87
<211> LENGTH: 21
<212> TYPE: DNA
<213> ORGANISM: Homo sapiens

<400> SEQUENCE: 87
tcaagacatc gtgcgatatt t 21

<210> SEQ ID NO 88
<211> LENGTH: 21
<212> TYPE: DNA
<213> ORGANISM: Homo sapiens

<400> SEQUENCE: 88
gagctaagta aggtggtata t 21

<210> SEQ ID NO 89
<211> LENGTH: 21
<212> TYPE: DNA
<213> ORGANISM: Homo sapiens

<400> SEQUENCE: 89
gcgatgtact gaaggtcttt g 21

<210> SEQ ID NO 90
<211> LENGTH: 21
<212> TYPE: DNA
<213> ORGANISM: Homo sapiens

<400> SEQUENCE: 90
tcagtgatgt gtactgctac t 21

<210> SEQ ID NO 91
<211> LENGTH: 21
<212> TYPE: DNA
<213> ORGANISM: Homo sapiens

<400> SEQUENCE: 91
gtatatctcg accgatggtt c 21

<210> SEQ ID NO 92
<211> LENGTH: 21
<212> TYPE: DNA
<213> ORGANISM: Homo sapiens

<400> SEQUENCE: 92
tgatgcgagt ggccgaatat c 21

<210> SEQ ID NO 93
<211> LENGTH: 21
<212> TYPE: DNA
<213> ORGANISM: Homo sapiens

<400> SEQUENCE: 93
cctaggattt gaacaattca t 21

<210> SEQ ID NO 94
<211> LENGTH: 21
<212> TYPE: DNA
<213> ORGANISM: Homo sapiens

<400> SEQUENCE: 94
aaagattctc aaggatatag a 21

<210> SEQ ID NO 95
<211> LENGTH: 21
<212> TYPE: DNA
<213> ORGANISM: Homo sapiens

<400> SEQUENCE: 95
gagggatgtt ccatcacctt c 21

<210> SEQ ID NO 96
<211> LENGTH: 21
<212> TYPE: DNA
<213> ORGANISM: Homo sapiens

<400> SEQUENCE: 96
tacagacatc cttacacaac c 21

<210> SEQ ID NO 97
<211> LENGTH: 21
<212> TYPE: DNA
<213> ORGANISM: Homo sapiens

<400> SEQUENCE: 97
gccgaatatc tagactggga t 21

<210> SEQ ID NO 98
<211> LENGTH: 21
<212> TYPE: DNA
<213> ORGANISM: Homo sapiens

<400> SEQUENCE: 98
cggctggaag tggtaggaat a 21

<210> SEQ ID NO 99
<211> LENGTH: 21
<212> TYPE: DNA
<213> ORGANISM: Homo sapiens

<400> SEQUENCE: 99
gttcctcagt tccggatatt g 21

<210> SEQ ID NO 100
<211> LENGTH: 21
<212> TYPE: DNA
<213> ORGANISM: Homo sapiens

<400> SEQUENCE: 100
cctgagctgt aacttctgta a 21

<210> SEQ ID NO 101
<211> LENGTH: 21
<212> TYPE: DNA
<213> ORGANISM: Homo sapiens

<400> SEQUENCE: 101
tgcgaacaga gcattagcct t 21

<210> SEQ ID NO 102
<211> LENGTH: 21
<212> TYPE: DNA
<213> ORGANISM: Homo sapiens

<400> SEQUENCE: 102
tgttcctcag ttccggatat t 21

<210> SEQ ID NO 103
<211> LENGTH: 21
<212> TYPE: DNA
<213> ORGANISM: Homo sapiens

<400> SEQUENCE: 103
caccttccac agcaaggaga t 21

<210> SEQ ID NO 104
<211> LENGTH: 21
<212> TYPE: DNA
<213> ORGANISM: Homo sapiens

<400> SEQUENCE: 104
atcgtggtgc atacccaatg c 21

<210> SEQ ID NO 105
<211> LENGTH: 21
<212> TYPE: DNA
<213> ORGANISM: Homo sapiens

<400> SEQUENCE: 105
cctggatgtc tttaacaact a 21

<210> SEQ ID NO 106
<211> LENGTH: 21
<212> TYPE: DNA
<213> ORGANISM: Homo sapiens

<400> SEQUENCE: 106
cgagtagtgt gtgacggaat g 21

<210> SEQ ID NO 107
<211> LENGTH: 21
<212> TYPE: DNA
<213> ORGANISM: Homo sapiens

<400> SEQUENCE: 107
cacatctggt ttgagaccaa c 21

<210> SEQ ID NO 108
<211> LENGTH: 21
<212> TYPE: DNA
<213> ORGANISM: Homo sapiens

<400> SEQUENCE: 108
gagaagttca acagccgctt t 21

<210> SEQ ID NO 109
<211> LENGTH: 21
<212> TYPE: DNA
<213> ORGANISM: Homo sapiens

<400> SEQUENCE: 109
actgtgcagg caccatgccc t 21

<210> SEQ ID NO 110
<211> LENGTH: 21
<212> TYPE: DNA
<213> ORGANISM: Homo sapiens

<400> SEQUENCE: 110
agaagctgtt cagatctagg g 21

<210> SEQ ID NO 111
<211> LENGTH: 21
<212> TYPE: DNA
<213> ORGANISM: Homo sapiens

<400> SEQUENCE: 111
gtggacttca aagaattcat t 21

<210> SEQ ID NO 112
<211> LENGTH: 21
<212> TYPE: DNA
<213> ORGANISM: Homo sapiens

<400> SEQUENCE: 112
actacgaggc tctacattat g 21

<210> SEQ ID NO 113
<211> LENGTH: 21
<212> TYPE: DNA
<213> ORGANISM: Homo sapiens

<400> SEQUENCE: 113
agtacataat ttgaggattc t 21

<210> SEQ ID NO 114
<211> LENGTH: 21
<212> TYPE: DNA
<213> ORGANISM: Homo sapiens

<400> SEQUENCE: 114
cgaggctcta cattatgaca a 21

<210> SEQ ID NO 115
<211> LENGTH: 21
<212> TYPE: DNA
<213> ORGANISM: Homo sapiens

<400> SEQUENCE: 115
cctgtaagat cgtggtgcat a 21

<210> SEQ ID NO 116
<211> LENGTH: 21
<212> TYPE: DNA
<213> ORGANISM: Homo sapiens

<400> SEQUENCE: 116
gaaaccgcag tgcatcgtct t 21

<210> SEQ ID NO 117
<211> LENGTH: 21
<212> TYPE: DNA
<213> ORGANISM: Homo sapiens

<400> SEQUENCE: 117
cagcatcacg gattcgaatt g 21

<210> SEQ ID NO 118
<211> LENGTH: 21
<212> TYPE: DNA
<213> ORGANISM: Homo sapiens

<400> SEQUENCE: 118
aggatccttc agcattctta t 21

<210> SEQ ID NO 119
<211> LENGTH: 20
<212> TYPE: DNA
<213> ORGANISM: Homo sapiens

<400> SEQUENCE: 119
agctctggct gacacaccag 20

<210> SEQ ID NO 120
<211> LENGTH: 21
<212> TYPE: DNA
<213> ORGANISM: Homo sapiens

<400> SEQUENCE: 120
ccaggatcct tcagcattct t 21

<210> SEQ ID NO 121
<211> LENGTH: 21
<212> TYPE: DNA
<213> ORGANISM: Homo sapiens

<400> SEQUENCE: 121
gctgtatatt tctgcctatt a 21

<210> SEQ ID NO 122
<211> LENGTH: 21
<212> TYPE: DNA
<213> ORGANISM: Homo sapiens

<400> SEQUENCE: 122
actattgtgg ccgcaagttt g 21

<210> SEQ ID NO 123
<211> LENGTH: 21
<212> TYPE: DNA
<213> ORGANISM: Homo sapiens

<400> SEQUENCE: 123
agcgggtact accgtttatt t 21

<210> SEQ ID NO 124
<211> LENGTH: 21
<212> TYPE: DNA
<213> ORGANISM: Homo sapiens

<400> SEQUENCE: 124
ctgtatattt ctgcctatta a 21

<210> SEQ ID NO 125
<211> LENGTH: 21
<212> TYPE: DNA
<213> ORGANISM: Homo sapiens

<400> SEQUENCE: 125
gtgaccacct tactactcac a 21

<210> SEQ ID NO 126
<211> LENGTH: 21
<212> TYPE: DNA
<213> ORGANISM: Homo sapiens

<400> SEQUENCE: 126
gtttgccagg agtgacgaaa g 21

<210> SEQ ID NO 127
<211> LENGTH: 21
<212> TYPE: DNA
<213> ORGANISM: Homo sapiens

<400> SEQUENCE: 127
ccttcaccta catgggcaaa t 21

<210> SEQ ID NO 128
<211> LENGTH: 21
<212> TYPE: DNA
<213> ORGANISM: Homo sapiens

<400> SEQUENCE: 128
ccagaaggta tcatcaatat t 21

<210> SEQ ID NO 129
<211> LENGTH: 21
<212> TYPE: DNA
<213> ORGANISM: Homo sapiens

<400> SEQUENCE: 129
ccactctcta ccatccgtaa t 21

<210> SEQ ID NO 130
<211> LENGTH: 21
<212> TYPE: DNA

<213> ORGANISM: Homo sapiens

<400> SEQUENCE: 130
ccgtgccaga gagatccaca c 21

<210> SEQ ID NO 131
<211> LENGTH: 21
<212> TYPE: DNA
<213> ORGANISM: Homo sapiens

<400> SEQUENCE: 131
caataggttg ggagttgctg a 21

<210> SEQ ID NO 132
<211> LENGTH: 21
<212> TYPE: DNA
<213> ORGANISM: Homo sapiens

<400> SEQUENCE: 132
actctctacc atccgtaatt t 21

<210> SEQ ID NO 133
<211> LENGTH: 21
<212> TYPE: DNA
<213> ORGANISM: Homo sapiens

<400> SEQUENCE: 133
ccatgagttc atctggaaca a 21

<210> SEQ ID NO 134
<211> LENGTH: 21
<212> TYPE: DNA
<213> ORGANISM: Homo sapiens

<400> SEQUENCE: 134
catagctcct tctcctgaaa g 21

<210> SEQ ID NO 135
<211> LENGTH: 21
<212> TYPE: DNA
<213> ORGANISM: Homo sapiens

<400> SEQUENCE: 135
gatgactgca attacgctat c 21

<210> SEQ ID NO 136
<211> LENGTH: 21
<212> TYPE: DNA
<213> ORGANISM: Homo sapiens

<400> SEQUENCE: 136
gtcgccattt atgtcggtag t 21

<210> SEQ ID NO 137
<211> LENGTH: 21
<212> TYPE: DNA
<213> ORGANISM: Homo sapiens

<400> SEQUENCE: 137
tggaaacaac tactcccata a 21

<210> SEQ ID NO 138
<211> LENGTH: 21

<212> TYPE: DNA
<213> ORGANISM: Homo sapiens

<400> SEQUENCE: 138
gtgacccatc tgcactaatt t 21

<210> SEQ ID NO 139
<211> LENGTH: 21
<212> TYPE: DNA
<213> ORGANISM: Homo sapiens

<400> SEQUENCE: 139
gcatgatggc aaccattatg t 21

<210> SEQ ID NO 140
<211> LENGTH: 21
<212> TYPE: DNA
<213> ORGANISM: Homo sapiens

<400> SEQUENCE: 140
atcccgatat ctaacagatt t 21

<210> SEQ ID NO 141
<211> LENGTH: 21
<212> TYPE: DNA
<213> ORGANISM: Homo sapiens

<400> SEQUENCE: 141
tgtcgccgat gggatagtga t 21

<210> SEQ ID NO 142
<211> LENGTH: 21
<212> TYPE: DNA
<213> ORGANISM: Homo sapiens

<400> SEQUENCE: 142
gccactttga acttcggtat a 21

<210> SEQ ID NO 143
<211> LENGTH: 21
<212> TYPE: DNA
<213> ORGANISM: Homo sapiens

<400> SEQUENCE: 143
ccatacgata acggttacta t 21

<210> SEQ ID NO 144
<211> LENGTH: 21
<212> TYPE: DNA
<213> ORGANISM: Homo sapiens

<400> SEQUENCE: 144
cctctactgt tcactcagaa a 21

<210> SEQ ID NO 145
<211> LENGTH: 21
<212> TYPE: DNA
<213> ORGANISM: Homo sapiens

<400> SEQUENCE: 145
catacgataa cggttactat c 21

<210> SEQ ID NO 146

<211> LENGTH: 21
<212> TYPE: DNA
<213> ORGANISM: Homo sapiens

<400> SEQUENCE: 146
cgtgacccat ctgcactaat t 21

<210> SEQ ID NO 147
<211> LENGTH: 21
<212> TYPE: DNA
<213> ORGANISM: Homo sapiens

<400> SEQUENCE: 147
gcctgtttga tgatacaagt t 21

<210> SEQ ID NO 148
<211> LENGTH: 21
<212> TYPE: DNA
<213> ORGANISM: Homo sapiens

<400> SEQUENCE: 148
gaatgtaagt gagctctatg g 21

<210> SEQ ID NO 149
<211> LENGTH: 21
<212> TYPE: DNA
<213> ORGANISM: Homo sapiens

<400> SEQUENCE: 149
ccgaactgat accaacatcc a 21

<210> SEQ ID NO 150
<211> LENGTH: 21
<212> TYPE: DNA
<213> ORGANISM: Homo sapiens

<400> SEQUENCE: 150
cccatgcttt aacccaggat a 21

<210> SEQ ID NO 151
<211> LENGTH: 21
<212> TYPE: DNA
<213> ORGANISM: Homo sapiens

<400> SEQUENCE: 151
ccttggtttc acctctatct t 21

<210> SEQ ID NO 152
<211> LENGTH: 21
<212> TYPE: DNA
<213> ORGANISM: Homo sapiens

<400> SEQUENCE: 152
ccaaggacat tcaggtttca a 21

<210> SEQ ID NO 153
<211> LENGTH: 21
<212> TYPE: DNA
<213> ORGANISM: Homo sapiens

<400> SEQUENCE: 153
caggaacaga gttggctaag c 21

<210> SEQ ID NO 154
<211> LENGTH: 21
<212> TYPE: DNA
<213> ORGANISM: Homo sapiens

<400> SEQUENCE: 154
ttaacccagg atacgagaag g 21

<210> SEQ ID NO 155
<211> LENGTH: 21
<212> TYPE: DNA
<213> ORGANISM: Homo sapiens

<400> SEQUENCE: 155
actatctcag ccatggcttt g 21

<210> SEQ ID NO 156
<211> LENGTH: 21
<212> TYPE: DNA
<213> ORGANISM: Homo sapiens

<400> SEQUENCE: 156
ttcaagtggt ggcgtcctta a 21

<210> SEQ ID NO 157
<211> LENGTH: 21
<212> TYPE: DNA
<213> ORGANISM: Homo sapiens

<400> SEQUENCE: 157
gactttgggc tacatgctga a 21

<210> SEQ ID NO 158
<211> LENGTH: 21
<212> TYPE: DNA
<213> ORGANISM: Homo sapiens

<400> SEQUENCE: 158
ggcatgcgct tgcttagaat g 21

<210> SEQ ID NO 159
<211> LENGTH: 21
<212> TYPE: DNA
<213> ORGANISM: Homo sapiens

<400> SEQUENCE: 159
gcactggaga ctacgaacag t 21

<210> SEQ ID NO 160
<211> LENGTH: 21
<212> TYPE: DNA
<213> ORGANISM: Homo sapiens

<400> SEQUENCE: 160
gtggattact attaactatc t 21

<210> SEQ ID NO 161
<211> LENGTH: 21
<212> TYPE: DNA
<213> ORGANISM: Homo sapiens

<400> SEQUENCE: 161
gctcctggga acagattcat t 21

<210> SEQ ID NO 162
<211> LENGTH: 21
<212> TYPE: DNA
<213> ORGANISM: Homo sapiens

<400> SEQUENCE: 162
accatttgat cagtttcgaa t 21

<210> SEQ ID NO 163
<211> LENGTH: 21
<212> TYPE: DNA
<213> ORGANISM: Homo sapiens

<400> SEQUENCE: 163
gctgattccc aggactatat t 21

<210> SEQ ID NO 164
<211> LENGTH: 21
<212> TYPE: DNA
<213> ORGANISM: Homo sapiens

<400> SEQUENCE: 164
gtatcgctgt ataactatgt a 21

<210> SEQ ID NO 165
<211> LENGTH: 19
<212> TYPE: DNA
<213> ORGANISM: Homo sapiens

<400> SEQUENCE: 165
attgacctgc acctactct 19

<210> SEQ ID NO 166
<211> LENGTH: 19
<212> TYPE: DNA
<213> ORGANISM: Homo sapiens

<400> SEQUENCE: 166
gccgggagga aactgttgt 19

<210> SEQ ID NO 167
<211> LENGTH: 21
<212> TYPE: DNA
<213> ORGANISM: Homo sapiens

<400> SEQUENCE: 167
cctggttcaa ggacgggata t 21

<210> SEQ ID NO 168
<211> LENGTH: 21
<212> TYPE: DNA
<213> ORGANISM: Homo sapiens

<400> SEQUENCE: 168
ttcggtgtac actgctcaat c 21

<210> SEQ ID NO 169
<211> LENGTH: 21
<212> TYPE: DNA
<213> ORGANISM: Homo sapiens

<400> SEQUENCE: 169
caccgggtaa gaaggtcatt t 21

<210> SEQ ID NO 170
<211> LENGTH: 21
<212> TYPE: DNA
<213> ORGANISM: Homo sapiens

<400> SEQUENCE: 170
acttgcatgg tctccgagga a 21

<210> SEQ ID NO 171
<211> LENGTH: 21
<212> TYPE: DNA
<213> ORGANISM: Homo sapiens

<400> SEQUENCE: 171
gtaacactga ttctccttgg a 21

<210> SEQ ID NO 172
<211> LENGTH: 21
<212> TYPE: DNA
<213> ORGANISM: Homo sapiens

<400> SEQUENCE: 172
gttataacag ccagatcaca g 21

<210> SEQ ID NO 173
<211> LENGTH: 21
<212> TYPE: DNA
<213> ORGANISM: Homo sapiens

<400> SEQUENCE: 173
tagctgcaca ggatgccttc a 21

<210> SEQ ID NO 174
<211> LENGTH: 21
<212> TYPE: DNA
<213> ORGANISM: Homo sapiens

<400> SEQUENCE: 174
ggtttgccta tagccgtgga t 21

<210> SEQ ID NO 175
<211> LENGTH: 21
<212> TYPE: DNA
<213> ORGANISM: Homo sapiens

<400> SEQUENCE: 175
cctatagccg tggatacttt g 21

<210> SEQ ID NO 176
<211> LENGTH: 21
<212> TYPE: DNA
<213> ORGANISM: Homo sapiens

<400> SEQUENCE: 176
ctccgttgtc catttgcctt a 21

<210> SEQ ID NO 177
<211> LENGTH: 21
<212> TYPE: DNA
<213> ORGANISM: Homo sapiens

<400> SEQUENCE: 177
ccaccctctg aatattcctg g 21

<210> SEQ ID NO 178
<211> LENGTH: 21
<212> TYPE: DNA
<213> ORGANISM: Homo sapiens

<400> SEQUENCE: 178
catcccgaac tacaacaact t 21

<210> SEQ ID NO 179
<211> LENGTH: 21
<212> TYPE: DNA
<213> ORGANISM: Homo sapiens

<400> SEQUENCE: 179
cctttggaaa cccaagaggt a 21

<210> SEQ ID NO 180
<211> LENGTH: 21
<212> TYPE: DNA
<213> ORGANISM: Homo sapiens

<400> SEQUENCE: 180
tctgagacag aagcgtgtta t 21

<210> SEQ ID NO 181
<211> LENGTH: 21
<212> TYPE: DNA
<213> ORGANISM: Homo sapiens

<400> SEQUENCE: 181
gctcggttga ttgaagacaa t 21

<210> SEQ ID NO 182
<211> LENGTH: 21
<212> TYPE: DNA
<213> ORGANISM: Homo sapiens

<400> SEQUENCE: 182
ttgacaatgg tggatactat a 21

<210> SEQ ID NO 183
<211> LENGTH: 21
<212> TYPE: DNA
<213> ORGANISM: Homo sapiens

<400> SEQUENCE: 183
tcttcacctg attcaactaa a 21

<210> SEQ ID NO 184
<211> LENGTH: 21
<212> TYPE: DNA
<213> ORGANISM: Homo sapiens

<400> SEQUENCE: 184
gctctgaagt tgccaaacct t 21

<210> SEQ ID NO 185
<211> LENGTH: 21
<212> TYPE: DNA
<213> ORGANISM: Homo sapiens

<400> SEQUENCE: 185
cactgtttgt ggcgctttat g 21

<210> SEQ ID NO 186
<211> LENGTH: 21
<212> TYPE: DNA
<213> ORGANISM: Homo sapiens

<400> SEQUENCE: 186
catcgagcgc atgaattata t 21

<210> SEQ ID NO 187
<211> LENGTH: 21
<212> TYPE: DNA
<213> ORGANISM: Homo sapiens

<400> SEQUENCE: 187
cctgtatgga aggttcacaa t 21

<210> SEQ ID NO 188
<211> LENGTH: 20
<212> TYPE: DNA
<213> ORGANISM: Homo sapiens

<400> SEQUENCE: 188
tcgatgttat gtcaaaggcc 20

<210> SEQ ID NO 189
<211> LENGTH: 20
<212> TYPE: DNA
<213> ORGANISM: Homo sapiens

<400> SEQUENCE: 189
accacacaaa cttcctgtat 20

<210> SEQ ID NO 190
<211> LENGTH: 21
<212> TYPE: DNA
<213> ORGANISM: Homo sapiens

<400> SEQUENCE: 190
acagctcctg tcctttggaa a 21

<210> SEQ ID NO 191
<211> LENGTH: 21
<212> TYPE: DNA
<213> ORGANISM: Homo sapiens

<400> SEQUENCE: 191
gcagcgaaac tgacagagga g 21

<210> SEQ ID NO 192
<211> LENGTH: 21
<212> TYPE: DNA
<213> ORGANISM: Homo sapiens

<400> SEQUENCE: 192
acactgtttg tggcgcttta t 21

<210> SEQ ID NO 193
<211> LENGTH: 21
<212> TYPE: DNA
<213> ORGANISM: Homo sapiens

<400> SEQUENCE: 193
tgactaccac agcctatgtg a 21

<210> SEQ ID NO 194
<211> LENGTH: 21
<212> TYPE: DNA
<213> ORGANISM: Homo sapiens

<400> SEQUENCE: 194
cgagaaacag atcttggaga a 21

<210> SEQ ID NO 195
<211> LENGTH: 21
<212> TYPE: DNA
<213> ORGANISM: Homo sapiens

<400> SEQUENCE: 195
ctaaccttgc ttagcaactg t 21

<210> SEQ ID NO 196
<211> LENGTH: 21
<212> TYPE: DNA
<213> ORGANISM: Homo sapiens

<400> SEQUENCE: 196
aggaatgagc gctacacgtt c 21

<210> SEQ ID NO 197
<211> LENGTH: 21
<212> TYPE: DNA
<213> ORGANISM: Homo sapiens

<400> SEQUENCE: 197
tcttggagaa agtgaacagt a 21

<210> SEQ ID NO 198
<211> LENGTH: 21
<212> TYPE: DNA
<213> ORGANISM: Homo sapiens

<400> SEQUENCE: 198
gcgcctgtta tttcgtgagt t 21

<210> SEQ ID NO 199
<211> LENGTH: 21
<212> TYPE: DNA
<213> ORGANISM: Homo sapiens

<400> SEQUENCE: 199
gaacagttct ctacagttaa a 21

<210> SEQ ID NO 200
<211> LENGTH: 21
<212> TYPE: DNA
<213> ORGANISM: Homo sapiens

<400> SEQUENCE: 200
caggctattt attgcaagga t 21

<210> SEQ ID NO 201
<211> LENGTH: 21
<212> TYPE: DNA
<213> ORGANISM: Homo sapiens

<400> SEQUENCE: 201
gagcttagcc tacgcctatg a 21

<210> SEQ ID NO 202
<211> LENGTH: 21
<212> TYPE: DNA
<213> ORGANISM: Homo sapiens

<400> SEQUENCE: 202
gcaaaggcaa gagcaagaaa t 21

<210> SEQ ID NO 203
<211> LENGTH: 21
<212> TYPE: DNA
<213> ORGANISM: Homo sapiens

<400> SEQUENCE: 203
ccatggctct caacgagaaa c 21

<210> SEQ ID NO 204
<211> LENGTH: 21
<212> TYPE: DNA
<213> ORGANISM: Homo sapiens

<400> SEQUENCE: 204
tctatgctgc tgagatctgc t 21

<210> SEQ ID NO 205
<211> LENGTH: 21
<212> TYPE: DNA
<213> ORGANISM: Homo sapiens

<400> SEQUENCE: 205
gccgactaat gcagaacttt c 21

<210> SEQ ID NO 206
<211> LENGTH: 21
<212> TYPE: DNA
<213> ORGANISM: Homo sapiens

<400> SEQUENCE: 206
cgcctgttat ttcgtgagtt c 21

<210> SEQ ID NO 207
<211> LENGTH: 21
<212> TYPE: DNA
<213> ORGANISM: Homo sapiens

<400> SEQUENCE: 207
cgccgactaa tgcagaactt t 21

<210> SEQ ID NO 208
<211> LENGTH: 21
<212> TYPE: DNA
<213> ORGANISM: Homo sapiens

<400> SEQUENCE: 208
ctacctgcaa tcacgctact a 21

<210> SEQ ID NO 209
<211> LENGTH: 21
<212> TYPE: DNA

-continued

<213> ORGANISM: Homo sapiens

<400> SEQUENCE: 209
agcggagggt tcacatgtat g 21

<210> SEQ ID NO 210
<211> LENGTH: 21
<212> TYPE: DNA
<213> ORGANISM: Homo sapiens

<400> SEQUENCE: 210
caaccagtac agcactatta t 21

<210> SEQ ID NO 211
<211> LENGTH: 21
<212> TYPE: DNA
<213> ORGANISM: Homo sapiens

<400> SEQUENCE: 211
taccctttct ctggctaatt c 21

<210> SEQ ID NO 212
<211> LENGTH: 21
<212> TYPE: DNA
<213> ORGANISM: Homo sapiens

<400> SEQUENCE: 212
agcctgaagg cgaggtctaa t 21

<210> SEQ ID NO 213
<211> LENGTH: 21
<212> TYPE: DNA
<213> ORGANISM: Homo sapiens

<400> SEQUENCE: 213
cattggcacc cgtactatca t 21

<210> SEQ ID NO 214
<211> LENGTH: 21
<212> TYPE: DNA
<213> ORGANISM: Homo sapiens

<400> SEQUENCE: 214
gcttcagaat acgatcagat t 21

<210> SEQ ID NO 215
<211> LENGTH: 21
<212> TYPE: DNA
<213> ORGANISM: Homo sapiens

<400> SEQUENCE: 215
gaagactctt aaccaccaat t 21

<210> SEQ ID NO 216
<211> LENGTH: 21
<212> TYPE: DNA
<213> ORGANISM: Homo sapiens

<400> SEQUENCE: 216
atacgatcag attcgctata t 21

<210> SEQ ID NO 217
<211> LENGTH: 21

<212> TYPE: DNA
<213> ORGANISM: Homo sapiens

<400> SEQUENCE: 217
ctgtcataca tttggtctct t 21

<210> SEQ ID NO 218
<211> LENGTH: 21
<212> TYPE: DNA
<213> ORGANISM: Homo sapiens

<400> SEQUENCE: 218
gctactagcc ctgagttctt a 21

<210> SEQ ID NO 219
<211> LENGTH: 21
<212> TYPE: DNA
<213> ORGANISM: Homo sapiens

<400> SEQUENCE: 219
tataactttg tccgttctta t 21

<210> SEQ ID NO 220
<211> LENGTH: 21
<212> TYPE: DNA
<213> ORGANISM: Homo sapiens

<400> SEQUENCE: 220
ctcgctgcta aactaccaat c 21

<210> SEQ ID NO 221
<211> LENGTH: 21
<212> TYPE: DNA
<213> ORGANISM: Homo sapiens

<400> SEQUENCE: 221
gccaatcatc attccagata c 21

<210> SEQ ID NO 222
<211> LENGTH: 21
<212> TYPE: DNA
<213> ORGANISM: Homo sapiens

<400> SEQUENCE: 222
cgctccaaat acaagcacaa a 21

<210> SEQ ID NO 223
<211> LENGTH: 21
<212> TYPE: DNA
<213> ORGANISM: Homo sapiens

<400> SEQUENCE: 223
gcttagaggt tcctggataa a 21

<210> SEQ ID NO 224
<211> LENGTH: 21
<212> TYPE: DNA
<213> ORGANISM: Homo sapiens

<400> SEQUENCE: 224
cctttggttc acacaccaga a 21

<210> SEQ ID NO 225

<211> LENGTH: 21
<212> TYPE: DNA
<213> ORGANISM: Homo sapiens

<400> SEQUENCE: 225
ctgttagtga cctgacgttg a 21

<210> SEQ ID NO 226
<211> LENGTH: 21
<212> TYPE: DNA
<213> ORGANISM: Homo sapiens

<400> SEQUENCE: 226
cggatctcct atccatacat t 21

<210> SEQ ID NO 227
<211> LENGTH: 21
<212> TYPE: DNA
<213> ORGANISM: Homo sapiens

<400> SEQUENCE: 227
gtatcggaca aggctcacat t 21

<210> SEQ ID NO 228
<211> LENGTH: 21
<212> TYPE: DNA
<213> ORGANISM: Homo sapiens

<400> SEQUENCE: 228
ttcgagacac aatcgtgaga t 21

<210> SEQ ID NO 229
<211> LENGTH: 21
<212> TYPE: DNA
<213> ORGANISM: Homo sapiens

<400> SEQUENCE: 229
cggatctcct atccatacat t 21

<210> SEQ ID NO 230
<211> LENGTH: 21
<212> TYPE: DNA
<213> ORGANISM: Homo sapiens

<400> SEQUENCE: 230
ctcaagcttg tattccaact t 21

<210> SEQ ID NO 231
<211> LENGTH: 21
<212> TYPE: DNA
<213> ORGANISM: Homo sapiens

<400> SEQUENCE: 231
atataaggga ctgtctagat a 21

<210> SEQ ID NO 232
<211> LENGTH: 21
<212> TYPE: DNA
<213> ORGANISM: Homo sapiens

<400> SEQUENCE: 232
cgagtccttc acgattcata a 21

<210> SEQ ID NO 233
<211> LENGTH: 21
<212> TYPE: DNA
<213> ORGANISM: Homo sapiens

<400> SEQUENCE: 233
ccgagtcctt cacgattcat a 21

<210> SEQ ID NO 234
<211> LENGTH: 21
<212> TYPE: DNA
<213> ORGANISM: Homo sapiens

<400> SEQUENCE: 234
cgtccgactg gttgggatta t 21

<210> SEQ ID NO 235
<211> LENGTH: 21
<212> TYPE: DNA
<213> ORGANISM: Homo sapiens

<400> SEQUENCE: 235
cccagatggt acagttctga a 21

<210> SEQ ID NO 236
<211> LENGTH: 21
<212> TYPE: DNA
<213> ORGANISM: Homo sapiens

<400> SEQUENCE: 236
cgaggctctg tgggttctat a 21

<210> SEQ ID NO 237
<211> LENGTH: 21
<212> TYPE: DNA
<213> ORGANISM: Homo sapiens

<400> SEQUENCE: 237
ttgccgtgct tcggagtatt t 21

<210> SEQ ID NO 238
<211> LENGTH: 21
<212> TYPE: DNA
<213> ORGANISM: Homo sapiens

<400> SEQUENCE: 238
gatgcgattg ccgccagtat t 21

<210> SEQ ID NO 239
<211> LENGTH: 21
<212> TYPE: DNA
<213> ORGANISM: Homo sapiens

<400> SEQUENCE: 239
cctaacgaaa gagaccctga a 21

<210> SEQ ID NO 240
<211> LENGTH: 21
<212> TYPE: DNA
<213> ORGANISM: Homo sapiens

<400> SEQUENCE: 240
atattctagc tagcatattt g 21

<210> SEQ ID NO 241
<211> LENGTH: 21
<212> TYPE: DNA
<213> ORGANISM: Homo sapiens

<400> SEQUENCE: 241
ggccagagtt tgaccatata a 21

<210> SEQ ID NO 242
<211> LENGTH: 21
<212> TYPE: DNA
<213> ORGANISM: Homo sapiens

<400> SEQUENCE: 242
gagtccttca cgattcataa t 21

<210> SEQ ID NO 243
<211> LENGTH: 21
<212> TYPE: DNA
<213> ORGANISM: Homo sapiens

<400> SEQUENCE: 243
attgccgtgc ttcggagtat t 21

<210> SEQ ID NO 244
<211> LENGTH: 21
<212> TYPE: DNA
<213> ORGANISM: Homo sapiens

<400> SEQUENCE: 244
agcggaagta cggatgatag a 21

<210> SEQ ID NO 245
<211> LENGTH: 21
<212> TYPE: DNA
<213> ORGANISM: Homo sapiens

<400> SEQUENCE: 245
gaggctctgt gggttctata t 21

<210> SEQ ID NO 246
<211> LENGTH: 21
<212> TYPE: DNA
<213> ORGANISM: Homo sapiens

<400> SEQUENCE: 246
tgcccaaata ctacggcgtc t 21

<210> SEQ ID NO 247
<211> LENGTH: 21
<212> TYPE: DNA
<213> ORGANISM: Homo sapiens

<400> SEQUENCE: 247
cggcaaggac aaagtgggca t 21

<210> SEQ ID NO 248
<211> LENGTH: 21
<212> TYPE: DNA
<213> ORGANISM: Homo sapiens

<400> SEQUENCE: 248
ctagcaacac agtcgatgag g 21

-continued

<210> SEQ ID NO 249
<211> LENGTH: 21
<212> TYPE: DNA
<213> ORGANISM: Homo sapiens

<400> SEQUENCE: 249
accaaacgat gtgtacctaa a 21

<210> SEQ ID NO 250
<211> LENGTH: 21
<212> TYPE: DNA
<213> ORGANISM: Homo sapiens

<400> SEQUENCE: 250
accctgtata atggacgtga a 21

<210> SEQ ID NO 251
<211> LENGTH: 21
<212> TYPE: DNA
<213> ORGANISM: Homo sapiens

<400> SEQUENCE: 251
cctgtataat ggacgtgaag a 21

<210> SEQ ID NO 252
<211> LENGTH: 21
<212> TYPE: DNA
<213> ORGANISM: Homo sapiens

<400> SEQUENCE: 252
caccaaacga tgtgtaccta a 21

<210> SEQ ID NO 253
<211> LENGTH: 21
<212> TYPE: DNA
<213> ORGANISM: Homo sapiens

<400> SEQUENCE: 253
gaacaggtgg cacagcttaa g 21

<210> SEQ ID NO 254
<211> LENGTH: 21
<212> TYPE: DNA
<213> ORGANISM: Homo sapiens

<400> SEQUENCE: 254
cggctacagt aaccctaaga t 21

<210> SEQ ID NO 255
<211> LENGTH: 21
<212> TYPE: DNA
<213> ORGANISM: Homo sapiens

<400> SEQUENCE: 255
ctacgccaac ctcagcaact t 21

<210> SEQ ID NO 256
<211> LENGTH: 21
<212> TYPE: DNA
<213> ORGANISM: Homo sapiens

<400> SEQUENCE: 256
cggtgcctac ggctacagta a 21

<210> SEQ ID NO 257
<211> LENGTH: 21
<212> TYPE: DNA
<213> ORGANISM: Homo sapiens

<400> SEQUENCE: 257
gcttaagcag aaagtcatga a 21

<210> SEQ ID NO 258
<211> LENGTH: 21
<212> TYPE: DNA
<213> ORGANISM: Homo sapiens

<400> SEQUENCE: 258
agcgcatgag gaaccgcatt g 21

<210> SEQ ID NO 259
<211> LENGTH: 21
<212> TYPE: DNA
<213> ORGANISM: Homo sapiens

<400> SEQUENCE: 259
cctatcgaca tggagtctca g 21

<210> SEQ ID NO 260
<211> LENGTH: 21
<212> TYPE: DNA
<213> ORGANISM: Homo sapiens

<400> SEQUENCE: 260
gaagcgcatg aggaaccgca t 21

<210> SEQ ID NO 261
<211> LENGTH: 21
<212> TYPE: DNA
<213> ORGANISM: Homo sapiens

<400> SEQUENCE: 261
attcgatctc attcagtatt a 21

<210> SEQ ID NO 262
<211> LENGTH: 21
<212> TYPE: DNA
<213> ORGANISM: Homo sapiens

<400> SEQUENCE: 262
ggatcgctcg gctagaggaa a 21

<210> SEQ ID NO 263
<211> LENGTH: 21
<212> TYPE: DNA
<213> ORGANISM: Homo sapiens

<400> SEQUENCE: 263
gcggatcaag gcagagagga a 21

<210> SEQ ID NO 264
<211> LENGTH: 21
<212> TYPE: DNA
<213> ORGANISM: Homo sapiens

<400> SEQUENCE: 264
ggcatgtgct gtgatcattt a 21

<210> SEQ ID NO 265
<211> LENGTH: 21
<212> TYPE: DNA
<213> ORGANISM: Homo sapiens

<400> SEQUENCE: 265
acgcagcagt tgcaaacgtt t 21

<210> SEQ ID NO 266
<211> LENGTH: 21
<212> TYPE: DNA
<213> ORGANISM: Homo sapiens

<400> SEQUENCE: 266
gcgggctaac tgcaataaga t 21

<210> SEQ ID NO 267
<211> LENGTH: 21
<212> TYPE: DNA
<213> ORGANISM: Homo sapiens

<400> SEQUENCE: 267
cagtaaccct aagatcctaa a 21

<210> SEQ ID NO 268
<211> LENGTH: 21
<212> TYPE: DNA
<213> ORGANISM: Homo sapiens

<400> SEQUENCE: 268
gctaacgcag cagttgcaaa c 21

<210> SEQ ID NO 269
<211> LENGTH: 21
<212> TYPE: DNA
<213> ORGANISM: Homo sapiens

<400> SEQUENCE: 269
gaaagtcatg aaccacgtta a 21

<210> SEQ ID NO 270
<211> LENGTH: 21
<212> TYPE: DNA
<213> ORGANISM: Homo sapiens

<400> SEQUENCE: 270
agcaacaaca ggaaggtata t 21

<210> SEQ ID NO 271
<211> LENGTH: 21
<212> TYPE: DNA
<213> ORGANISM: Homo sapiens

<400> SEQUENCE: 271
gcatccacga acaagaccat a 21

<210> SEQ ID NO 272
<211> LENGTH: 21
<212> TYPE: DNA
<213> ORGANISM: Homo sapiens

<400> SEQUENCE: 272
ttgagaccaa gcgtcactta t 21

<210> SEQ ID NO 273
<211> LENGTH: 21
<212> TYPE: DNA
<213> ORGANISM: Homo sapiens

<400> SEQUENCE: 273
ccgcaagagc ttgattgtaa c 21

<210> SEQ ID NO 274
<211> LENGTH: 21
<212> TYPE: DNA
<213> ORGANISM: Homo sapiens

<400> SEQUENCE: 274
gctggttctg aagagtggaa a 21

<210> SEQ ID NO 275
<211> LENGTH: 21
<212> TYPE: DNA
<213> ORGANISM: Homo sapiens

<400> SEQUENCE: 275
gatattacgg aagcggttat c 21

<210> SEQ ID NO 276
<211> LENGTH: 21
<212> TYPE: DNA
<213> ORGANISM: Homo sapiens

<400> SEQUENCE: 276
gcctcattac gtcacactat t 21

<210> SEQ ID NO 277
<211> LENGTH: 21
<212> TYPE: DNA
<213> ORGANISM: Homo sapiens

<400> SEQUENCE: 277
cctcattacg tcacactatt t 21

<210> SEQ ID NO 278
<211> LENGTH: 21
<212> TYPE: DNA
<213> ORGANISM: Homo sapiens

<400> SEQUENCE: 278
acgaatacca cggtcccaaa t 21

<210> SEQ ID NO 279
<211> LENGTH: 21
<212> TYPE: DNA
<213> ORGANISM: Homo sapiens

<400> SEQUENCE: 279
gtggaaacaa ggtatcaatt t 21

<210> SEQ ID NO 280
<211> LENGTH: 21
<212> TYPE: DNA
<213> ORGANISM: Homo sapiens

<400> SEQUENCE: 280
gaagtgtgct atccgggaaa g 21

<210> SEQ ID NO 281
<211> LENGTH: 21
<212> TYPE: DNA
<213> ORGANISM: Homo sapiens

<400> SEQUENCE: 281
acttgtatga gggtcatatt g 21

<210> SEQ ID NO 282
<211> LENGTH: 21
<212> TYPE: DNA
<213> ORGANISM: Homo sapiens

<400> SEQUENCE: 282
cgaatgagaa accaatccct t 21

<210> SEQ ID NO 283
<211> LENGTH: 21
<212> TYPE: DNA
<213> ORGANISM: Homo sapiens

<400> SEQUENCE: 283
gcatcaaacc tggttcgaat g 21

<210> SEQ ID NO 284
<211> LENGTH: 21
<212> TYPE: DNA
<213> ORGANISM: Homo sapiens

<400> SEQUENCE: 284
ccctgtcaac aaagtaatca a 21

<210> SEQ ID NO 285
<211> LENGTH: 21
<212> TYPE: DNA
<213> ORGANISM: Homo sapiens

<400> SEQUENCE: 285
ggaggaaaca ggcaagataa a 21

<210> SEQ ID NO 286
<211> LENGTH: 21
<212> TYPE: DNA
<213> ORGANISM: Homo sapiens

<400> SEQUENCE: 286
tgatgcggga ccagtccatt t 21

<210> SEQ ID NO 287
<211> LENGTH: 21
<212> TYPE: DNA
<213> ORGANISM: Homo sapiens

<400> SEQUENCE: 287
tgtaatgagg acaatacgga g 21

<210> SEQ ID NO 288
<211> LENGTH: 21
<212> TYPE: DNA

<213> ORGANISM: Homo sapiens

<400> SEQUENCE: 288
tcctgaccct ctgcaacatt g 21

<210> SEQ ID NO 289
<211> LENGTH: 21
<212> TYPE: DNA
<213> ORGANISM: Homo sapiens

<400> SEQUENCE: 289
tgacatggac tgcggcatca t 21

<210> SEQ ID NO 290
<211> LENGTH: 21
<212> TYPE: DNA
<213> ORGANISM: Homo sapiens

<400> SEQUENCE: 290
cgaagcatgt aatgaggaca a 21

<210> SEQ ID NO 291
<211> LENGTH: 21
<212> TYPE: DNA
<213> ORGANISM: Homo sapiens

<400> SEQUENCE: 291
gacatcagta agaagagtaa a 21

<210> SEQ ID NO 292
<211> LENGTH: 21
<212> TYPE: DNA
<213> ORGANISM: Homo sapiens

<400> SEQUENCE: 292
tgccaagtga caggttataa a 21

<210> SEQ ID NO 293
<211> LENGTH: 21
<212> TYPE: DNA
<213> ORGANISM: Homo sapiens

<400> SEQUENCE: 293
tgcaacattg tcctgggaca a 21

<210> SEQ ID NO 294
<211> LENGTH: 21
<212> TYPE: DNA
<213> ORGANISM: Homo sapiens

<400> SEQUENCE: 294
atcgtcagac tgtctagaaa t 21

<210> SEQ ID NO 295
<211> LENGTH: 21
<212> TYPE: DNA
<213> ORGANISM: Homo sapiens

<400> SEQUENCE: 295
ccgtggagaa tcacaagata t 21

<210> SEQ ID NO 296
<211> LENGTH: 21

<212> TYPE: DNA
<213> ORGANISM: Homo sapiens

<400> SEQUENCE: 296
gtttatctat tggaggttaa a 21

<210> SEQ ID NO 297
<211> LENGTH: 21
<212> TYPE: DNA
<213> ORGANISM: Homo sapiens

<400> SEQUENCE: 297
gaagagtaaa gtaaatgctg t 21

<210> SEQ ID NO 298
<211> LENGTH: 21
<212> TYPE: DNA
<213> ORGANISM: Homo sapiens

<400> SEQUENCE: 298
cgccggatgt atgtggttta a 21

<210> SEQ ID NO 299
<211> LENGTH: 21
<212> TYPE: DNA
<213> ORGANISM: Homo sapiens

<400> SEQUENCE: 299
gccggatgta tgtggtttaa t 21

<210> SEQ ID NO 300
<211> LENGTH: 21
<212> TYPE: DNA
<213> ORGANISM: Homo sapiens

<400> SEQUENCE: 300
cttggtctct cccatcatat a 21

<210> SEQ ID NO 301
<211> LENGTH: 21
<212> TYPE: DNA
<213> ORGANISM: Homo sapiens

<400> SEQUENCE: 301
acagcaactg gcaccatatc t 21

<210> SEQ ID NO 302
<211> LENGTH: 21
<212> TYPE: DNA
<213> ORGANISM: Homo sapiens

<400> SEQUENCE: 302
gataccttgg gaggccgatt t 21

<210> SEQ ID NO 303
<211> LENGTH: 21
<212> TYPE: DNA
<213> ORGANISM: Homo sapiens

<400> SEQUENCE: 303
ggccaatgag atcgtgcttc t 21

<210> SEQ ID NO 304

<211> LENGTH: 21
<212> TYPE: DNA
<213> ORGANISM: Homo sapiens

<400> SEQUENCE: 304
gtagcctttg accctcaaat c 21

<210> SEQ ID NO 305
<211> LENGTH: 21
<212> TYPE: DNA
<213> ORGANISM: Homo sapiens

<400> SEQUENCE: 305
caatggagct gctgatcaac g 21

<210> SEQ ID NO 306
<211> LENGTH: 21
<212> TYPE: DNA
<213> ORGANISM: Homo sapiens

<400> SEQUENCE: 306
gacagcaact ggcaccatat c 21

<210> SEQ ID NO 307
<211> LENGTH: 21
<212> TYPE: DNA
<213> ORGANISM: Homo sapiens

<400> SEQUENCE: 307
ttggtctctc ccatcatata c 21

<210> SEQ ID NO 308
<211> LENGTH: 21
<212> TYPE: DNA
<213> ORGANISM: Homo sapiens

<400> SEQUENCE: 308
ataccttggg aggccgattt g 21

<210> SEQ ID NO 309
<211> LENGTH: 21
<212> TYPE: DNA
<213> ORGANISM: Homo sapiens

<400> SEQUENCE: 309
cctgtcagtt tcaggacttt g 21

<210> SEQ ID NO 310
<211> LENGTH: 21
<212> TYPE: DNA
<213> ORGANISM: Homo sapiens

<400> SEQUENCE: 310
tccgcaacaa ctacatgtac g 21

<210> SEQ ID NO 311
<211> LENGTH: 21
<212> TYPE: DNA
<213> ORGANISM: Homo sapiens

<400> SEQUENCE: 311
ataagctggt agaggccttt g 21

-continued

<210> SEQ ID NO 312
<211> LENGTH: 21
<212> TYPE: DNA
<213> ORGANISM: Homo sapiens

<400> SEQUENCE: 312
cggtgccgtc atctgcatca t 21

<210> SEQ ID NO 313
<211> LENGTH: 21
<212> TYPE: DNA
<213> ORGANISM: Homo sapiens

<400> SEQUENCE: 313
caagccacac ggcatcctta t 21

<210> SEQ ID NO 314
<211> LENGTH: 21
<212> TYPE: DNA
<213> ORGANISM: Homo sapiens

<400> SEQUENCE: 314
tcaagccaca cggcatcctt a 21

<210> SEQ ID NO 315
<211> LENGTH: 21
<212> TYPE: DNA
<213> ORGANISM: Homo sapiens

<400> SEQUENCE: 315
ttggacttgc ctgaacgtct t 21

<210> SEQ ID NO 316
<211> LENGTH: 21
<212> TYPE: DNA
<213> ORGANISM: Homo sapiens

<400> SEQUENCE: 316
tttgacgggc aggatcataa a 21

<210> SEQ ID NO 317
<211> LENGTH: 21
<212> TYPE: DNA
<213> ORGANISM: Homo sapiens

<400> SEQUENCE: 317
gccaatggaa acatcaagat t 21

<210> SEQ ID NO 318
<211> LENGTH: 21
<212> TYPE: DNA
<213> ORGANISM: Homo sapiens

<400> SEQUENCE: 318
gtgtagtgac tgccattatt t 21

<210> SEQ ID NO 319
<211> LENGTH: 21
<212> TYPE: DNA
<213> ORGANISM: Homo sapiens

<400> SEQUENCE: 319
ccaaggtgtg cagcttcttc a 21

<210> SEQ ID NO 320
<211> LENGTH: 21
<212> TYPE: DNA
<213> ORGANISM: Homo sapiens

<400> SEQUENCE: 320
cctgatccgg tggctgttaa t 21

<210> SEQ ID NO 321
<211> LENGTH: 21
<212> TYPE: DNA
<213> ORGANISM: Homo sapiens

<400> SEQUENCE: 321
gggctcatca agtcgcctaa a 21

<210> SEQ ID NO 322
<211> LENGTH: 21
<212> TYPE: DNA
<213> ORGANISM: Homo sapiens

<400> SEQUENCE: 322
ccgaaaggca ttctcaagaa a 21

<210> SEQ ID NO 323
<211> LENGTH: 21
<212> TYPE: DNA
<213> ORGANISM: Homo sapiens

<400> SEQUENCE: 323
gtcgcctaaa cctctgatga a 21

<210> SEQ ID NO 324
<211> LENGTH: 21
<212> TYPE: DNA
<213> ORGANISM: Homo sapiens

<400> SEQUENCE: 324
ccgaggcgat ctgtatgatt a 21

<210> SEQ ID NO 325
<211> LENGTH: 21
<212> TYPE: DNA
<213> ORGANISM: Homo sapiens

<400> SEQUENCE: 325
gaagtctcga cagcgtgaat c 21

<210> SEQ ID NO 326
<211> LENGTH: 21
<212> TYPE: DNA
<213> ORGANISM: Homo sapiens

<400> SEQUENCE: 326
tcggaccgct gtttgacttc a 21

<210> SEQ ID NO 327
<211> LENGTH: 21
<212> TYPE: DNA
<213> ORGANISM: Homo sapiens

<400> SEQUENCE: 327
tagcagcaag attgtgattg t 21

<210> SEQ ID NO 328
<211> LENGTH: 21
<212> TYPE: DNA
<213> ORGANISM: Homo sapiens

<400> SEQUENCE: 328
agtctcgaca gcgtgaatct g 21

<210> SEQ ID NO 329
<211> LENGTH: 21
<212> TYPE: DNA
<213> ORGANISM: Homo sapiens

<400> SEQUENCE: 329
cccaaggaaa ggcatcctta a 21

<210> SEQ ID NO 330
<211> LENGTH: 21
<212> TYPE: DNA
<213> ORGANISM: Homo sapiens

<400> SEQUENCE: 330
gatggcagat actcctcaat g 21

<210> SEQ ID NO 331
<211> LENGTH: 21
<212> TYPE: DNA
<213> ORGANISM: Homo sapiens

<400> SEQUENCE: 331
gggaatggat ggcagatact c 21

<210> SEQ ID NO 332
<211> LENGTH: 21
<212> TYPE: DNA
<213> ORGANISM: Homo sapiens

<400> SEQUENCE: 332
ctccctcacc tctctagaat c 21

<210> SEQ ID NO 333
<211> LENGTH: 21
<212> TYPE: DNA
<213> ORGANISM: Homo sapiens

<400> SEQUENCE: 333
tgcaatcgtc ttcgccgtca a 21

<210> SEQ ID NO 334
<211> LENGTH: 21
<212> TYPE: DNA
<213> ORGANISM: Homo sapiens

<400> SEQUENCE: 334
cattgctgtc gctgtgttct t 21

<210> SEQ ID NO 335
<211> LENGTH: 21
<212> TYPE: DNA
<213> ORGANISM: Homo sapiens

<400> SEQUENCE: 335
acaagaatgc ctacgagaat g 21

<210> SEQ ID NO 336
<211> LENGTH: 21
<212> TYPE: DNA
<213> ORGANISM: Homo sapiens

<400> SEQUENCE: 336
ttcttggtcc ttgttgcaat c 21

<210> SEQ ID NO 337
<211> LENGTH: 21
<212> TYPE: DNA
<213> ORGANISM: Homo sapiens

<400> SEQUENCE: 337
ggagcacagt gatgatcatt g 21

<210> SEQ ID NO 338
<211> LENGTH: 21
<212> TYPE: DNA
<213> ORGANISM: Homo sapiens

<400> SEQUENCE: 338
actgctctac aggaatctac t 21

<210> SEQ ID NO 339
<211> LENGTH: 21
<212> TYPE: DNA
<213> ORGANISM: Homo sapiens

<400> SEQUENCE: 339
ctgtcaacaa ggtctaggaa a 21

<210> SEQ ID NO 340
<211> LENGTH: 21
<212> TYPE: DNA
<213> ORGANISM: Homo sapiens

<400> SEQUENCE: 340
cctcattgct gtcgctgtgt t 21

<210> SEQ ID NO 341
<211> LENGTH: 21
<212> TYPE: DNA
<213> ORGANISM: Homo sapiens

<400> SEQUENCE: 341
tctacaggaa tctactgaaa c 21

<210> SEQ ID NO 342
<211> LENGTH: 21
<212> TYPE: DNA
<213> ORGANISM: Homo sapiens

<400> SEQUENCE: 342
caagtcctat gaccctaatt t 21

<210> SEQ ID NO 343
<211> LENGTH: 21
<212> TYPE: DNA
<213> ORGANISM: Homo sapiens

<400> SEQUENCE: 343
ggtggacacc actcagtatt a 21

<210> SEQ ID NO 344
<211> LENGTH: 21
<212> TYPE: DNA
<213> ORGANISM: Homo sapiens

<400> SEQUENCE: 344
ccaactcaac atcaccgtaa a 21

<210> SEQ ID NO 345
<211> LENGTH: 21
<212> TYPE: DNA
<213> ORGANISM: Homo sapiens

<400> SEQUENCE: 345
acacaatacc acgcatattt a 21

<210> SEQ ID NO 346
<211> LENGTH: 21
<212> TYPE: DNA
<213> ORGANISM: Homo sapiens

<400> SEQUENCE: 346
ggccgcttca aatatgaaat a 21

<210> SEQ ID NO 347
<211> LENGTH: 21
<212> TYPE: DNA
<213> ORGANISM: Homo sapiens

<400> SEQUENCE: 347
ttcactagga gtggcatatt c 21

<210> SEQ ID NO 348
<211> LENGTH: 21
<212> TYPE: DNA
<213> ORGANISM: Homo sapiens

<400> SEQUENCE: 348
catctataag ggtagtcttt c 21

<210> SEQ ID NO 349
<211> LENGTH: 21
<212> TYPE: DNA
<213> ORGANISM: Homo sapiens

<400> SEQUENCE: 349
gttattacct ctcttgtttc t 21

<210> SEQ ID NO 350
<211> LENGTH: 21
<212> TYPE: DNA
<213> ORGANISM: Homo sapiens

<400> SEQUENCE: 350
gtagtctacc ctgtctattt g 21

<210> SEQ ID NO 351
<211> LENGTH: 21
<212> TYPE: DNA
<213> ORGANISM: Homo sapiens

<400> SEQUENCE: 351
gccctgtacc tttcaaccaa t 21

<210> SEQ ID NO 352
<211> LENGTH: 21
<212> TYPE: DNA
<213> ORGANISM: Homo sapiens

<400> SEQUENCE: 352
catgtcatcg agtactcttt a 21

<210> SEQ ID NO 353
<211> LENGTH: 21
<212> TYPE: DNA
<213> ORGANISM: Homo sapiens

<400> SEQUENCE: 353
caactgatgg tgtcctatat a 21

<210> SEQ ID NO 354
<211> LENGTH: 21
<212> TYPE: DNA
<213> ORGANISM: Homo sapiens

<400> SEQUENCE: 354
ccatcattga aggtggctca t 21

<210> SEQ ID NO 355
<211> LENGTH: 21
<212> TYPE: DNA
<213> ORGANISM: Homo sapiens

<400> SEQUENCE: 355
gcttcactac tcttcctgct t 21

<210> SEQ ID NO 356
<211> LENGTH: 21
<212> TYPE: DNA
<213> ORGANISM: Homo sapiens

<400> SEQUENCE: 356
cgctcgcact ttcagcaata a 21

<210> SEQ ID NO 357
<211> LENGTH: 21
<212> TYPE: DNA
<213> ORGANISM: Homo sapiens

<400> SEQUENCE: 357
gaggatgata aagacaaagt a 21

<210> SEQ ID NO 358
<211> LENGTH: 21
<212> TYPE: DNA
<213> ORGANISM: Homo sapiens

<400> SEQUENCE: 358
gctttcctca gcccattaca a 21

<210> SEQ ID NO 359
<211> LENGTH: 21
<212> TYPE: DNA
<213> ORGANISM: Homo sapiens

<400> SEQUENCE: 359
gagatgatgg tccctggaat g 21

<210> SEQ ID NO 360
<211> LENGTH: 21
<212> TYPE: DNA
<213> ORGANISM: Homo sapiens

<400> SEQUENCE: 360
tgaccacaga ggaagtcatt a 21

<210> SEQ ID NO 361
<211> LENGTH: 21
<212> TYPE: DNA
<213> ORGANISM: Homo sapiens

<400> SEQUENCE: 361
gatgccttct tggctattga t 21

<210> SEQ ID NO 362
<211> LENGTH: 21
<212> TYPE: DNA
<213> ORGANISM: Homo sapiens

<400> SEQUENCE: 362
ccatggatgg acgagtcaat g 21

<210> SEQ ID NO 363
<211> LENGTH: 21
<212> TYPE: DNA
<213> ORGANISM: Homo sapiens

<400> SEQUENCE: 363
tgacgcgata tgggcagaac t 21

<210> SEQ ID NO 364
<211> LENGTH: 21
<212> TYPE: DNA
<213> ORGANISM: Homo sapiens

<400> SEQUENCE: 364
gctaccatga ctattgaaga g 21

<210> SEQ ID NO 365
<211> LENGTH: 21
<212> TYPE: DNA
<213> ORGANISM: Homo sapiens

<400> SEQUENCE: 365
tggcaaagct ttagatatgt c 21

<210> SEQ ID NO 366
<211> LENGTH: 21
<212> TYPE: DNA
<213> ORGANISM: Homo sapiens

<400> SEQUENCE: 366
catggatgga cgagtcaatg g 21

<210> SEQ ID NO 367
<211> LENGTH: 21
<212> TYPE: DNA

<213> ORGANISM: Homo sapiens

<400> SEQUENCE: 367
cttcggttat tgtcatccat t 21

<210> SEQ ID NO 368
<211> LENGTH: 21
<212> TYPE: DNA
<213> ORGANISM: Homo sapiens

<400> SEQUENCE: 368
tgcctgtgct ctgttgtgtt g 21

<210> SEQ ID NO 369
<211> LENGTH: 21
<212> TYPE: DNA
<213> ORGANISM: Homo sapiens

<400> SEQUENCE: 369
caaattagtg agcccggtac t 21

<210> SEQ ID NO 370
<211> LENGTH: 21
<212> TYPE: DNA
<213> ORGANISM: Homo sapiens

<400> SEQUENCE: 370
gccttgtact gtgccaaata t 21

<210> SEQ ID NO 371
<211> LENGTH: 21
<212> TYPE: DNA
<213> ORGANISM: Homo sapiens

<400> SEQUENCE: 371
catgacgtgc atcatcattt g 21

<210> SEQ ID NO 372
<211> LENGTH: 21
<212> TYPE: DNA
<213> ORGANISM: Homo sapiens

<400> SEQUENCE: 372
acttcgagac ccatttagaa t 21

<210> SEQ ID NO 373
<211> LENGTH: 21
<212> TYPE: DNA
<213> ORGANISM: Homo sapiens

<400> SEQUENCE: 373
cagaagatcc cagcagtaga t 21

<210> SEQ ID NO 374
<211> LENGTH: 21
<212> TYPE: DNA
<213> ORGANISM: Homo sapiens

<400> SEQUENCE: 374
gccaccaata acttgtatat a 21

<210> SEQ ID NO 375
<211> LENGTH: 21

<212> TYPE: DNA
<213> ORGANISM: Homo sapiens

<400> SEQUENCE: 375
atagtgatca tgaaacatat c 21

<210> SEQ ID NO 376
<211> LENGTH: 21
<212> TYPE: DNA
<213> ORGANISM: Homo sapiens

<400> SEQUENCE: 376
atatgtacgc cggtcaatta g 21

<210> SEQ ID NO 377
<211> LENGTH: 21
<212> TYPE: DNA
<213> ORGANISM: Homo sapiens

<400> SEQUENCE: 377
atgctcatac atatcacata a 21

<210> SEQ ID NO 378
<211> LENGTH: 21
<212> TYPE: DNA
<213> ORGANISM: Homo sapiens

<400> SEQUENCE: 378
tcatctccac cgttgagttt a 21

<210> SEQ ID NO 379
<211> LENGTH: 21
<212> TYPE: DNA
<213> ORGANISM: Homo sapiens

<400> SEQUENCE: 379
gatctgagaa ttaacctatg g 21

<210> SEQ ID NO 380
<211> LENGTH: 21
<212> TYPE: DNA
<213> ORGANISM: Homo sapiens

<400> SEQUENCE: 380
ccatttagaa ttacggcact a 21

<210> SEQ ID NO 381
<211> LENGTH: 21
<212> TYPE: DNA
<213> ORGANISM: Homo sapiens

<400> SEQUENCE: 381
cggttcagac agtgccatta t 21

<210> SEQ ID NO 382
<211> LENGTH: 21
<212> TYPE: DNA
<213> ORGANISM: Homo sapiens

<400> SEQUENCE: 382
caccgttgag tttaactact c 21

<210> SEQ ID NO 383

<211> LENGTH: 21
<212> TYPE: DNA
<213> ORGANISM: Homo sapiens

<400> SEQUENCE: 383
gctcaataaa ggccattact c 21

<210> SEQ ID NO 384
<211> LENGTH: 21
<212> TYPE: DNA
<213> ORGANISM: Homo sapiens

<400> SEQUENCE: 384
gagaattaac ctatggcatt t 21

<210> SEQ ID NO 385
<211> LENGTH: 21
<212> TYPE: DNA
<213> ORGANISM: Homo sapiens

<400> SEQUENCE: 385
ccacagtggt cgatacatga t 21

<210> SEQ ID NO 386
<211> LENGTH: 21
<212> TYPE: DNA
<213> ORGANISM: Homo sapiens

<400> SEQUENCE: 386
cccacatcag tgcaatgtat t 21

<210> SEQ ID NO 387
<211> LENGTH: 21
<212> TYPE: DNA
<213> ORGANISM: Homo sapiens

<400> SEQUENCE: 387
cccgaggtct agaccgaatt a 21

<210> SEQ ID NO 388
<211> LENGTH: 21
<212> TYPE: DNA
<213> ORGANISM: Homo sapiens

<400> SEQUENCE: 388
tcacagtgtg tggtgatgtt c 21

<210> SEQ ID NO 389
<211> LENGTH: 21
<212> TYPE: DNA
<213> ORGANISM: Homo sapiens

<400> SEQUENCE: 389
gctgtatcta tggagcttaa a 21

<210> SEQ ID NO 390
<211> LENGTH: 21
<212> TYPE: DNA
<213> ORGANISM: Homo sapiens

<400> SEQUENCE: 390
cctatgagca aatcacattt a 21

<210> SEQ ID NO 391
<211> LENGTH: 21
<212> TYPE: DNA
<213> ORGANISM: Homo sapiens

<400> SEQUENCE: 391
aggaatgtcg gatcaagtat t 21

<210> SEQ ID NO 392
<211> LENGTH: 21
<212> TYPE: DNA
<213> ORGANISM: Homo sapiens

<400> SEQUENCE: 392
cggctaactt tgaaggaagt t 21

<210> SEQ ID NO 393
<211> LENGTH: 21
<212> TYPE: DNA
<213> ORGANISM: Homo sapiens

<400> SEQUENCE: 393
cggatgaaga aatgaacgta a 21

<210> SEQ ID NO 394
<211> LENGTH: 21
<212> TYPE: DNA
<213> ORGANISM: Homo sapiens

<400> SEQUENCE: 394
acctagtaat actcgctacc t 21

<210> SEQ ID NO 395
<211> LENGTH: 21
<212> TYPE: DNA
<213> ORGANISM: Homo sapiens

<400> SEQUENCE: 395
ctgtatctat ggagcttaaa g 21

<210> SEQ ID NO 396
<211> LENGTH: 21
<212> TYPE: DNA
<213> ORGANISM: Homo sapiens

<400> SEQUENCE: 396
agaaatgaac gtaaccgatg a 21

<210> SEQ ID NO 397
<211> LENGTH: 21
<212> TYPE: DNA
<213> ORGANISM: Homo sapiens

<400> SEQUENCE: 397
caaacaactt aaacttggag g 21

<210> SEQ ID NO 398
<211> LENGTH: 21
<212> TYPE: DNA
<213> ORGANISM: Homo sapiens

<400> SEQUENCE: 398
tgtaattcag tcgcatttat t 21

<210> SEQ ID NO 399
<211> LENGTH: 21
<212> TYPE: DNA
<213> ORGANISM: Homo sapiens

<400> SEQUENCE: 399
ggacaattct ttgacctgat g 21

<210> SEQ ID NO 400
<211> LENGTH: 21
<212> TYPE: DNA
<213> ORGANISM: Homo sapiens

<400> SEQUENCE: 400
cgaggtctag accgaattaa t 21

<210> SEQ ID NO 401
<211> LENGTH: 21
<212> TYPE: DNA
<213> ORGANISM: Homo sapiens

<400> SEQUENCE: 401
ttccgtcact tattacgatt t 21

<210> SEQ ID NO 402
<211> LENGTH: 21
<212> TYPE: DNA
<213> ORGANISM: Homo sapiens

<400> SEQUENCE: 402
ctgtggttac cagtcagctt g 21

<210> SEQ ID NO 403
<211> LENGTH: 21
<212> TYPE: DNA
<213> ORGANISM: Homo sapiens

<400> SEQUENCE: 403
gtatgtcacc acgctgctgt a 21

<210> SEQ ID NO 404
<211> LENGTH: 21
<212> TYPE: DNA
<213> ORGANISM: Homo sapiens

<400> SEQUENCE: 404
ccctcaccta ctccaagtta t 21

<210> SEQ ID NO 405
<211> LENGTH: 21
<212> TYPE: DNA
<213> ORGANISM: Homo sapiens

<400> SEQUENCE: 405
tatgagttca cggagtttat t 21

<210> SEQ ID NO 406
<211> LENGTH: 21
<212> TYPE: DNA
<213> ORGANISM: Homo sapiens

<400> SEQUENCE: 406
cgcaacccat cgctacaaga a 21

<210> SEQ ID NO 407
<211> LENGTH: 21
<212> TYPE: DNA
<213> ORGANISM: Homo sapiens

<400> SEQUENCE: 407
catcgctaca agaagaagta t 21

<210> SEQ ID NO 408
<211> LENGTH: 21
<212> TYPE: DNA
<213> ORGANISM: Homo sapiens

<400> SEQUENCE: 408
caattggagc accaagatcc c 21

<210> SEQ ID NO 409
<211> LENGTH: 21
<212> TYPE: DNA
<213> ORGANISM: Homo sapiens

<400> SEQUENCE: 409
agtgggttca tgatccgtca g 21

<210> SEQ ID NO 410
<211> LENGTH: 21
<212> TYPE: DNA
<213> ORGANISM: Homo sapiens

<400> SEQUENCE: 410
accgttatcc gctggtctga a 21

<210> SEQ ID NO 411
<211> LENGTH: 21
<212> TYPE: DNA
<213> ORGANISM: Homo sapiens

<400> SEQUENCE: 411
gatctgagga gagattcaaa t 21

<210> SEQ ID NO 412
<211> LENGTH: 21
<212> TYPE: DNA
<213> ORGANISM: Homo sapiens

<400> SEQUENCE: 412
cttaacaagg acacgaatat t 21

<210> SEQ ID NO 413
<211> LENGTH: 21
<212> TYPE: DNA
<213> ORGANISM: Homo sapiens

<400> SEQUENCE: 413
ctctgataaa gagtcataat g 21

<210> SEQ ID NO 414
<211> LENGTH: 21
<212> TYPE: DNA
<213> ORGANISM: Homo sapiens

<400> SEQUENCE: 414
cgctgctgta taagcccatc t 21

<210> SEQ ID NO 415
<211> LENGTH: 21
<212> TYPE: DNA
<213> ORGANISM: Homo sapiens

<400> SEQUENCE: 415
cttacggtca agaaatgtat g 21

<210> SEQ ID NO 416
<211> LENGTH: 21
<212> TYPE: DNA
<213> ORGANISM: Homo sapiens

<400> SEQUENCE: 416
cattaaggac agtgtgatgg t 21

<210> SEQ ID NO 417
<211> LENGTH: 21
<212> TYPE: DNA
<213> ORGANISM: Homo sapiens

<400> SEQUENCE: 417
tccgaacaca tgctgccatt t 21

<210> SEQ ID NO 418
<211> LENGTH: 21
<212> TYPE: DNA
<213> ORGANISM: Homo sapiens

<400> SEQUENCE: 418
gccaagattg acagacacct a 21

<210> SEQ ID NO 419
<211> LENGTH: 21
<212> TYPE: DNA
<213> ORGANISM: Homo sapiens

<400> SEQUENCE: 419
agactattct gcagctataa a 21

<210> SEQ ID NO 420
<211> LENGTH: 21
<212> TYPE: DNA
<213> ORGANISM: Homo sapiens

<400> SEQUENCE: 420
ccgttatact tggaaattcg a 21

<210> SEQ ID NO 421
<211> LENGTH: 21
<212> TYPE: DNA
<213> ORGANISM: Homo sapiens

<400> SEQUENCE: 421
agtatcgaat gggacttatt c 21

<210> SEQ ID NO 422
<211> LENGTH: 21
<212> TYPE: DNA
<213> ORGANISM: Homo sapiens

<400> SEQUENCE: 422
ttatattaat gccagcttag t 21

<210> SEQ ID NO 423
<211> LENGTH: 21
<212> TYPE: DNA
<213> ORGANISM: Homo sapiens

<400> SEQUENCE: 423
atgttcatga cttgagacta t 21

<210> SEQ ID NO 424
<211> LENGTH: 21
<212> TYPE: DNA
<213> ORGANISM: Homo sapiens

<400> SEQUENCE: 424
atatgatcac agtcgtgtta a 21

<210> SEQ ID NO 425
<211> LENGTH: 21
<212> TYPE: DNA
<213> ORGANISM: Homo sapiens

<400> SEQUENCE: 425
cggtggaaag aactttctaa a 21

<210> SEQ ID NO 426
<211> LENGTH: 21
<212> TYPE: DNA
<213> ORGANISM: Homo sapiens

<400> SEQUENCE: 426
ccatatctca cttccattat a 21

<210> SEQ ID NO 427
<211> LENGTH: 21
<212> TYPE: DNA
<213> ORGANISM: Homo sapiens

<400> SEQUENCE: 427
tctcctacat ggccataata g 21

<210> SEQ ID NO 428
<211> LENGTH: 21
<212> TYPE: DNA
<213> ORGANISM: Homo sapiens

<400> SEQUENCE: 428
cggtggaaag aactttctaa a 21

<210> SEQ ID NO 429
<211> LENGTH: 21
<212> TYPE: DNA
<213> ORGANISM: Homo sapiens

<400> SEQUENCE: 429
tatcgaatgg gacttattca g 21

<210> SEQ ID NO 430
<211> LENGTH: 21
<212> TYPE: DNA
<213> ORGANISM: Homo sapiens

<400> SEQUENCE: 430
cctgtcttgt tctgatggaa a 21

<210> SEQ ID NO 431
<211> LENGTH: 21
<212> TYPE: DNA
<213> ORGANISM: Homo sapiens

<400> SEQUENCE: 431
tcgctgcagt cagtgtacag g 21

<210> SEQ ID NO 432
<211> LENGTH: 21
<212> TYPE: DNA
<213> ORGANISM: Homo sapiens

<400> SEQUENCE: 432
ggccttctac ctggcttact a 21

<210> SEQ ID NO 433
<211> LENGTH: 21
<212> TYPE: DNA
<213> ORGANISM: Homo sapiens

<400> SEQUENCE: 433
ctgcaatgat tctcctagaa c 21

<210> SEQ ID NO 434
<211> LENGTH: 21
<212> TYPE: DNA
<213> ORGANISM: Homo sapiens

<400> SEQUENCE: 434
agtggtgggt tcctgcatga c 21

<210> SEQ ID NO 435
<211> LENGTH: 21
<212> TYPE: DNA
<213> ORGANISM: Homo sapiens

<400> SEQUENCE: 435
atatgccagc tagaaataag c 21

<210> SEQ ID NO 436
<211> LENGTH: 21
<212> TYPE: DNA
<213> ORGANISM: Homo sapiens

<400> SEQUENCE: 436
gtgatgatat gccagctaga a 21

<210> SEQ ID NO 437
<211> LENGTH: 21
<212> TYPE: DNA
<213> ORGANISM: Homo sapiens

<400> SEQUENCE: 437
catatttcta cagagtttac a 21

<210> SEQ ID NO 438
<211> LENGTH: 21
<212> TYPE: DNA
<213> ORGANISM: Homo sapiens

<400> SEQUENCE: 438
tcaataatga aggccagaat a 21

<210> SEQ ID NO 439
<211> LENGTH: 21
<212> TYPE: DNA
<213> ORGANISM: Homo sapiens

<400> SEQUENCE: 439
gctgccaggt tgtggtcatc a 21

<210> SEQ ID NO 440
<211> LENGTH: 21
<212> TYPE: DNA
<213> ORGANISM: Homo sapiens

<400> SEQUENCE: 440
tgatgatatg ccagctagaa a 21

<210> SEQ ID NO 441
<211> LENGTH: 21
<212> TYPE: DNA
<213> ORGANISM: Homo sapiens

<400> SEQUENCE: 441
caaggttggc aacgattctt t 21

<210> SEQ ID NO 442
<211> LENGTH: 21
<212> TYPE: DNA
<213> ORGANISM: Homo sapiens

<400> SEQUENCE: 442
gagcctgttc caaagcacat t 21

<210> SEQ ID NO 443
<211> LENGTH: 21
<212> TYPE: DNA
<213> ORGANISM: Homo sapiens

<400> SEQUENCE: 443
ccaaagcaca ttcccactga a 21

<210> SEQ ID NO 444
<211> LENGTH: 21
<212> TYPE: DNA
<213> ORGANISM: Homo sapiens

<400> SEQUENCE: 444
cattagccga gccaaagtga t 21

<210> SEQ ID NO 445
<211> LENGTH: 21
<212> TYPE: DNA
<213> ORGANISM: Homo sapiens

<400> SEQUENCE: 445
gcctccataa ttgtcaataa t 21

<210> SEQ ID NO 446
<211> LENGTH: 21
<212> TYPE: DNA

<213> ORGANISM: Homo sapiens

<400> SEQUENCE: 446
catactgtta gtcggcttga a 21

<210> SEQ ID NO 447
<211> LENGTH: 21
<212> TYPE: DNA
<213> ORGANISM: Homo sapiens

<400> SEQUENCE: 447
atgacatgca agcgcaattg g 21

<210> SEQ ID NO 448
<211> LENGTH: 21
<212> TYPE: DNA
<213> ORGANISM: Homo sapiens

<400> SEQUENCE: 448
gcctacaggt agattagatt a 21

<210> SEQ ID NO 449
<211> LENGTH: 21
<212> TYPE: DNA
<213> ORGANISM: Homo sapiens

<400> SEQUENCE: 449
agttcaattg gtgaggcata a 21

<210> SEQ ID NO 450
<211> LENGTH: 21
<212> TYPE: DNA
<213> ORGANISM: Homo sapiens

<400> SEQUENCE: 450
ctagcaaaga gagtgatatt g 21

<210> SEQ ID NO 451
<211> LENGTH: 21
<212> TYPE: DNA
<213> ORGANISM: Homo sapiens

<400> SEQUENCE: 451
cctggtttat gatttggatt t 21

<210> SEQ ID NO 452
<211> LENGTH: 21
<212> TYPE: DNA
<213> ORGANISM: Homo sapiens

<400> SEQUENCE: 452
cgggagttac aagatcaact t 21

<210> SEQ ID NO 453
<211> LENGTH: 21
<212> TYPE: DNA
<213> ORGANISM: Homo sapiens

<400> SEQUENCE: 453
ccgtgcaaag taagttacga t 21

<210> SEQ ID NO 454
<211> LENGTH: 21

<212> TYPE: DNA
<213> ORGANISM: Homo sapiens

<400> SEQUENCE: 454
gcagaaataa tgaatcgcaa a 21

<210> SEQ ID NO 455
<211> LENGTH: 21
<212> TYPE: DNA
<213> ORGANISM: Homo sapiens

<400> SEQUENCE: 455
atcaagatca gatcgtggaa g 21

<210> SEQ ID NO 456
<211> LENGTH: 21
<212> TYPE: DNA
<213> ORGANISM: Homo sapiens

<400> SEQUENCE: 456
ttcaattggt gaggcataaa t 21

<210> SEQ ID NO 457
<211> LENGTH: 21
<212> TYPE: DNA
<213> ORGANISM: Homo sapiens

<400> SEQUENCE: 457
gcagtgtctc aaattgagaa a 21

<210> SEQ ID NO 458
<211> LENGTH: 21
<212> TYPE: DNA
<213> ORGANISM: Homo sapiens

<400> SEQUENCE: 458
tgtgggatgc tacctgataa a 21

<210> SEQ ID NO 459
<211> LENGTH: 21
<212> TYPE: DNA
<213> ORGANISM: Homo sapiens

<400> SEQUENCE: 459
ctacaggtag attagattaa t 21

<210> SEQ ID NO 460
<211> LENGTH: 21
<212> TYPE: DNA
<213> ORGANISM: Homo sapiens

<400> SEQUENCE: 460
caactttcta agcagatata a 21

<210> SEQ ID NO 461
<211> LENGTH: 21
<212> TYPE: DNA
<213> ORGANISM: Homo sapiens

<400> SEQUENCE: 461
cagtatgtta ctcgtaagaa g 21

<210> SEQ ID NO 462

<211> LENGTH: 21
<212> TYPE: DNA
<213> ORGANISM: Homo sapiens

<400> SEQUENCE: 462
gcagtatgtt actcgtaaga a 21

<210> SEQ ID NO 463
<211> LENGTH: 21
<212> TYPE: DNA
<213> ORGANISM: Homo sapiens

<400> SEQUENCE: 463
tgctaagttg tttctagaac c 21

<210> SEQ ID NO 464
<211> LENGTH: 21
<212> TYPE: DNA
<213> ORGANISM: Homo sapiens

<400> SEQUENCE: 464
cgatactatg accaccgaat g 21

<210> SEQ ID NO 465
<211> LENGTH: 21
<212> TYPE: DNA
<213> ORGANISM: Homo sapiens

<400> SEQUENCE: 465
cgagaggaat ccaccaactt t 21

<210> SEQ ID NO 466
<211> LENGTH: 21
<212> TYPE: DNA
<213> ORGANISM: Homo sapiens

<400> SEQUENCE: 466
gcgatactat gaccaccgaa t 21

<210> SEQ ID NO 467
<211> LENGTH: 21
<212> TYPE: DNA
<213> ORGANISM: Homo sapiens

<400> SEQUENCE: 467
ctaacttatt gtggtgtcat g 21

<210> SEQ ID NO 468
<211> LENGTH: 21
<212> TYPE: DNA
<213> ORGANISM: Homo sapiens

<400> SEQUENCE: 468
tcttgctgga ctctgattat g 21

<210> SEQ ID NO 469
<211> LENGTH: 21
<212> TYPE: DNA
<213> ORGANISM: Homo sapiens

<400> SEQUENCE: 469
ggctagatga gggcacaatt c 21

<210> SEQ ID NO 470
<211> LENGTH: 21
<212> TYPE: DNA
<213> ORGANISM: Homo sapiens

<400> SEQUENCE: 470
gaagacaaca cgtcgcgttt a 21

<210> SEQ ID NO 471
<211> LENGTH: 21
<212> TYPE: DNA
<213> ORGANISM: Homo sapiens

<400> SEQUENCE: 471
tacggaattg catctcctat g 21

<210> SEQ ID NO 472
<211> LENGTH: 21
<212> TYPE: DNA
<213> ORGANISM: Homo sapiens

<400> SEQUENCE: 472
cacgcggaca tctatgacaa a 21

<210> SEQ ID NO 473
<211> LENGTH: 21
<212> TYPE: DNA
<213> ORGANISM: Homo sapiens

<400> SEQUENCE: 473
ttaccacata ccgcgtcatc t 21

<210> SEQ ID NO 474
<211> LENGTH: 21
<212> TYPE: DNA
<213> ORGANISM: Homo sapiens

<400> SEQUENCE: 474
ccctacagca atgtgtccaa t 21

<210> SEQ ID NO 475
<211> LENGTH: 21
<212> TYPE: DNA
<213> ORGANISM: Homo sapiens

<400> SEQUENCE: 475
gactttgtcg tccgcatgat g 21

<210> SEQ ID NO 476
<211> LENGTH: 21
<212> TYPE: DNA
<213> ORGANISM: Homo sapiens

<400> SEQUENCE: 476
agatcagtgg gacacaacag g 21

<210> SEQ ID NO 477
<211> LENGTH: 21
<212> TYPE: DNA
<213> ORGANISM: Homo sapiens

<400> SEQUENCE: 477
tggtgttcaa tcgcatacta t 21

<210> SEQ ID NO 478
<211> LENGTH: 21
<212> TYPE: DNA
<213> ORGANISM: Homo sapiens

<400> SEQUENCE: 478
gtaattacat cccagaaaca c 21

<210> SEQ ID NO 479
<211> LENGTH: 21
<212> TYPE: DNA
<213> ORGANISM: Homo sapiens

<400> SEQUENCE: 479
cggttagatg agcttgagaa a 21

<210> SEQ ID NO 480
<211> LENGTH: 21
<212> TYPE: DNA
<213> ORGANISM: Homo sapiens

<400> SEQUENCE: 480
ccagtagtag tgcctgaagt a 21

<210> SEQ ID NO 481
<211> LENGTH: 21
<212> TYPE: DNA
<213> ORGANISM: Homo sapiens

<400> SEQUENCE: 481
taacccgaat gtgcaccata a 21

<210> SEQ ID NO 482
<211> LENGTH: 21
<212> TYPE: DNA
<213> ORGANISM: Homo sapiens

<400> SEQUENCE: 482
cccaactgta accagagata c 21

<210> SEQ ID NO 483
<211> LENGTH: 21
<212> TYPE: DNA
<213> ORGANISM: Homo sapiens

<400> SEQUENCE: 483
ccactgtaga aatgacaaga a 21

<210> SEQ ID NO 484
<211> LENGTH: 21
<212> TYPE: DNA
<213> ORGANISM: Homo sapiens

<400> SEQUENCE: 484
cctccgtcgt agtattcatg t 21

<210> SEQ ID NO 485
<211> LENGTH: 21
<212> TYPE: DNA
<213> ORGANISM: Homo sapiens

<400> SEQUENCE: 485
gccagtggtg aagagacttc t 21

<210> SEQ ID NO 486
<211> LENGTH: 21
<212> TYPE: DNA
<213> ORGANISM: Homo sapiens

<400> SEQUENCE: 486
ctcggcacac ggagattcta a 21

<210> SEQ ID NO 487
<211> LENGTH: 21
<212> TYPE: DNA
<213> ORGANISM: Homo sapiens

<400> SEQUENCE: 487
gacagtatcc caaaggttat t 21

<210> SEQ ID NO 488
<211> LENGTH: 21
<212> TYPE: DNA
<213> ORGANISM: Homo sapiens

<400> SEQUENCE: 488
gagtgcgctt gtattacata g 21

<210> SEQ ID NO 489
<211> LENGTH: 21
<212> TYPE: DNA
<213> ORGANISM: Homo sapiens

<400> SEQUENCE: 489
ctaagtgata gtgcaatctt t 21

<210> SEQ ID NO 490
<211> LENGTH: 21
<212> TYPE: DNA
<213> ORGANISM: Homo sapiens

<400> SEQUENCE: 490
tgcctaagtg atagtgcaat c 21

<210> SEQ ID NO 491
<211> LENGTH: 21
<212> TYPE: DNA
<213> ORGANISM: Homo sapiens

<400> SEQUENCE: 491
tttcgagctg ctggagcact a 21

<210> SEQ ID NO 492
<211> LENGTH: 21
<212> TYPE: DNA
<213> ORGANISM: Homo sapiens

<400> SEQUENCE: 492
tcgagctgct ggagcactac g 21

<210> SEQ ID NO 493
<211> LENGTH: 21
<212> TYPE: DNA
<213> ORGANISM: Homo sapiens

<400> SEQUENCE: 493
tcgccaacgg aactgcttct t 21

<210> SEQ ID NO 494
<211> LENGTH: 21
<212> TYPE: DNA
<213> ORGANISM: Homo sapiens

<400> SEQUENCE: 494
acttctggct ggagacctca t 21

<210> SEQ ID NO 495
<211> LENGTH: 21
<212> TYPE: DNA
<213> ORGANISM: Homo sapiens

<400> SEQUENCE: 495
gcgagacctt cgactgcctt t 21

<210> SEQ ID NO 496
<211> LENGTH: 21
<212> TYPE: DNA
<213> ORGANISM: Homo sapiens

<400> SEQUENCE: 496
cgacactcac ttccgcacct t 21

<210> SEQ ID NO 497
<211> LENGTH: 21
<212> TYPE: DNA
<213> ORGANISM: Homo sapiens

<400> SEQUENCE: 497
ctacctgagt tccttcccct t 21

<210> SEQ ID NO 498
<211> LENGTH: 21
<212> TYPE: DNA
<213> ORGANISM: Homo sapiens

<400> SEQUENCE: 498
ttccgctccc actccgatta c 21

<210> SEQ ID NO 499
<211> LENGTH: 21
<212> TYPE: DNA
<213> ORGANISM: Homo sapiens

<400> SEQUENCE: 499
taacccggta ctccgtgact a 21

<210> SEQ ID NO 500
<211> LENGTH: 21
<212> TYPE: DNA
<213> ORGANISM: Homo sapiens

<400> SEQUENCE: 500
tactccgtga ctacctgagt t 21

<210> SEQ ID NO 501
<211> LENGTH: 21
<212> TYPE: DNA
<213> ORGANISM: Homo sapiens

<400> SEQUENCE: 501
cttccgctcc cactccgatt a 21

<210> SEQ ID NO 502
<211> LENGTH: 21
<212> TYPE: DNA
<213> ORGANISM: Homo sapiens

<400> SEQUENCE: 502
gcgcgacagt cgccaacgga a 21

<210> SEQ ID NO 503
<211> LENGTH: 21
<212> TYPE: DNA
<213> ORGANISM: Homo sapiens

<400> SEQUENCE: 503
tggacgcctg cggcttctat t 21

<210> SEQ ID NO 504
<211> LENGTH: 21
<212> TYPE: DNA
<213> ORGANISM: Homo sapiens

<400> SEQUENCE: 504
cgcatccctc ttaacccggt a 21

<210> SEQ ID NO 505
<211> LENGTH: 21
<212> TYPE: DNA
<213> ORGANISM: Homo sapiens

<400> SEQUENCE: 505
tacatattcc cagtatcttt g 21

<210> SEQ ID NO 506
<211> LENGTH: 21
<212> TYPE: DNA
<213> ORGANISM: Homo sapiens

<400> SEQUENCE: 506
gcgccttatt atttcttatt a 21

<210> SEQ ID NO 507
<211> LENGTH: 21
<212> TYPE: DNA
<213> ORGANISM: Homo sapiens

<400> SEQUENCE: 507
ccgtgactac ctgagttcct t 21

<210> SEQ ID NO 508
<211> LENGTH: 21
<212> TYPE: DNA
<213> ORGANISM: Homo sapiens

<400> SEQUENCE: 508
ggagggtctc tggcttcatt t 21

<210> SEQ ID NO 509
<211> LENGTH: 21
<212> TYPE: DNA
<213> ORGANISM: Homo sapiens

<400> SEQUENCE: 509
ttcgcgctca gcgtgaagat g 21

<210> SEQ ID NO 510
<211> LENGTH: 21
<212> TYPE: DNA
<213> ORGANISM: Homo sapiens

<400> SEQUENCE: 510
atccctctta acccggtact c 21

<210> SEQ ID NO 511
<211> LENGTH: 21
<212> TYPE: DNA
<213> ORGANISM: Homo sapiens

<400> SEQUENCE: 511
cgagaagatt ccgctggtac t 21

<210> SEQ ID NO 512
<211> LENGTH: 21
<212> TYPE: DNA
<213> ORGANISM: Homo sapiens

<400> SEQUENCE: 512
gctgcaggag agcggattct a 21

<210> SEQ ID NO 513
<211> LENGTH: 21
<212> TYPE: DNA
<213> ORGANISM: Homo sapiens

<400> SEQUENCE: 513
ggctaggaga ctcgccttaa a 21

<210> SEQ ID NO 514
<211> LENGTH: 21
<212> TYPE: DNA
<213> ORGANISM: Homo sapiens

<400> SEQUENCE: 514
gctaggagac tcgccttaaa t 21

<210> SEQ ID NO 515
<211> LENGTH: 21
<212> TYPE: DNA
<213> ORGANISM: Homo sapiens

<400> SEQUENCE: 515
gagagcttac tacatctatt c 21

<210> SEQ ID NO 516
<211> LENGTH: 21
<212> TYPE: DNA
<213> ORGANISM: Homo sapiens

<400> SEQUENCE: 516
gggagttcct ggatcagtat g 21

<210> SEQ ID NO 517
<211> LENGTH: 21
<212> TYPE: DNA
<213> ORGANISM: Homo sapiens

<400> SEQUENCE: 517
caagagagct tactacatct a 21

<210> SEQ ID NO 518
<211> LENGTH: 21
<212> TYPE: DNA
<213> ORGANISM: Homo sapiens

<400> SEQUENCE: 518
cagtatgatg ctccacttta a 21

<210> SEQ ID NO 519
<211> LENGTH: 21
<212> TYPE: DNA
<213> ORGANISM: Homo sapiens

<400> SEQUENCE: 519
caagctggtg caccactaca t 21

<210> SEQ ID NO 520
<211> LENGTH: 21
<212> TYPE: DNA
<213> ORGANISM: Homo sapiens

<400> SEQUENCE: 520
acctggactc ctatgagaaa g 21

<210> SEQ ID NO 521
<211> LENGTH: 21
<212> TYPE: DNA
<213> ORGANISM: Homo sapiens

<400> SEQUENCE: 521
cttcttcacg ttgagcgtca a 21

<210> SEQ ID NO 522
<211> LENGTH: 21
<212> TYPE: DNA
<213> ORGANISM: Homo sapiens

<400> SEQUENCE: 522
tcgggagttc ctggatcagt a 21

<210> SEQ ID NO 523
<211> LENGTH: 21
<212> TYPE: DNA
<213> ORGANISM: Homo sapiens

<400> SEQUENCE: 523
tgcaggagag cggattctac t 21

<210> SEQ ID NO 524
<211> LENGTH: 21
<212> TYPE: DNA
<213> ORGANISM: Homo sapiens

<400> SEQUENCE: 524
cctggtggga caataccttt g 21

<210> SEQ ID NO 525
<211> LENGTH: 21
<212> TYPE: DNA

<213> ORGANISM: Homo sapiens

<400> SEQUENCE: 525
gatcagtatg atgctccact t 21

<210> SEQ ID NO 526
<211> LENGTH: 21
<212> TYPE: DNA
<213> ORGANISM: Homo sapiens

<400> SEQUENCE: 526
tcttcacgtt gagcgtcaag a 21

<210> SEQ ID NO 527
<211> LENGTH: 21
<212> TYPE: DNA
<213> ORGANISM: Homo sapiens

<400> SEQUENCE: 527
cgcttcgact gtgtactcaa g 21

<210> SEQ ID NO 528
<211> LENGTH: 21
<212> TYPE: DNA
<213> ORGANISM: Homo sapiens

<400> SEQUENCE: 528
ggagcaaaag ggtcagaggg g 21

<210> SEQ ID NO 529
<211> LENGTH: 21
<212> TYPE: DNA
<213> ORGANISM: Homo sapiens

<400> SEQUENCE: 529
agtgggactt tggaagcttg t 21

<210> SEQ ID NO 530
<211> LENGTH: 21
<212> TYPE: DNA
<213> ORGANISM: Homo sapiens

<400> SEQUENCE: 530
catctggact gactcggaaa t 21

<210> SEQ ID NO 531
<211> LENGTH: 21
<212> TYPE: DNA
<213> ORGANISM: Homo sapiens

<400> SEQUENCE: 531
atgctgcggg tggagaaatt t 21

<210> SEQ ID NO 532
<211> LENGTH: 21
<212> TYPE: DNA
<213> ORGANISM: Homo sapiens

<400> SEQUENCE: 532
tatctgaata tttctcaagt g 21

<210> SEQ ID NO 533
<211> LENGTH: 21

<212> TYPE: DNA
<213> ORGANISM: Homo sapiens

<400> SEQUENCE: 533
tttacctgag ttagccgaaa t 21

<210> SEQ ID NO 534
<211> LENGTH: 21
<212> TYPE: DNA
<213> ORGANISM: Homo sapiens

<400> SEQUENCE: 534
gttaactcat acatcaccat t 21

<210> SEQ ID NO 535
<211> LENGTH: 21
<212> TYPE: DNA
<213> ORGANISM: Homo sapiens

<400> SEQUENCE: 535
cctataccat aactctatta c 21

<210> SEQ ID NO 536
<211> LENGTH: 21
<212> TYPE: DNA
<213> ORGANISM: Homo sapiens

<400> SEQUENCE: 536
ctcaactatg atcccattac c 21

<210> SEQ ID NO 537
<211> LENGTH: 21
<212> TYPE: DNA
<213> ORGANISM: Homo sapiens

<400> SEQUENCE: 537
agacctccaa gtcctcctgt a 21

<210> SEQ ID NO 538
<211> LENGTH: 21
<212> TYPE: DNA
<213> ORGANISM: Homo sapiens

<400> SEQUENCE: 538
gctgtggtta gacaatgtat a 21

<210> SEQ ID NO 539
<211> LENGTH: 21
<212> TYPE: DNA
<213> ORGANISM: Homo sapiens

<400> SEQUENCE: 539
tattggcata atagcgtata t 21

<210> SEQ ID NO 540
<211> LENGTH: 21
<212> TYPE: DNA
<213> ORGANISM: Homo sapiens

<400> SEQUENCE: 540
gcttgtttca tcctgaggaa a 21

<210> SEQ ID NO 541

<211> LENGTH: 21
<212> TYPE: DNA
<213> ORGANISM: Homo sapiens

<400> SEQUENCE: 541
tcctcaacta tgatcccatt a 21

<210> SEQ ID NO 542
<211> LENGTH: 21
<212> TYPE: DNA
<213> ORGANISM: Homo sapiens

<400> SEQUENCE: 542
gcagaagcta aggacgaatt t 21

<210> SEQ ID NO 543
<211> LENGTH: 21
<212> TYPE: DNA
<213> ORGANISM: Homo sapiens

<400> SEQUENCE: 543
cagaataaca ttgttcacct t 21

<210> SEQ ID NO 544
<211> LENGTH: 21
<212> TYPE: DNA
<213> ORGANISM: Homo sapiens

<400> SEQUENCE: 544
tgcccagcgc agacttaatg a 21

<210> SEQ ID NO 545
<211> LENGTH: 21
<212> TYPE: DNA
<213> ORGANISM: Homo sapiens

<400> SEQUENCE: 545
cgtgacactc tgggaaatgt t 21

<210> SEQ ID NO 546
<211> LENGTH: 21
<212> TYPE: DNA
<213> ORGANISM: Homo sapiens

<400> SEQUENCE: 546
gtgtcccacc atatctcatc c 21

<210> SEQ ID NO 547
<211> LENGTH: 21
<212> TYPE: DNA
<213> ORGANISM: Homo sapiens

<400> SEQUENCE: 547
agtagcaata ccggatcact g 21

<210> SEQ ID NO 548
<211> LENGTH: 21
<212> TYPE: DNA
<213> ORGANISM: Homo sapiens

<400> SEQUENCE: 548
gcgggaagta tctgtcatga t 21

-continued

<210> SEQ ID NO 549
<211> LENGTH: 21
<212> TYPE: DNA
<213> ORGANISM: Homo sapiens

<400> SEQUENCE: 549
agaggatgcg aggcatttcc a 21

<210> SEQ ID NO 550
<211> LENGTH: 21
<212> TYPE: DNA
<213> ORGANISM: Homo sapiens

<400> SEQUENCE: 550
ggacagagag aaggcaacgt t 21

<210> SEQ ID NO 551
<211> LENGTH: 21
<212> TYPE: DNA
<213> ORGANISM: Homo sapiens

<400> SEQUENCE: 551
agaattgggt gtacaagata c 21

<210> SEQ ID NO 552
<211> LENGTH: 21
<212> TYPE: DNA
<213> ORGANISM: Homo sapiens

<400> SEQUENCE: 552
ccacctatta tctgcaactc t 21

<210> SEQ ID NO 553
<211> LENGTH: 21
<212> TYPE: DNA
<213> ORGANISM: Homo sapiens

<400> SEQUENCE: 553
gcctctgatg tgtggatgtt t 21

<210> SEQ ID NO 554
<211> LENGTH: 21
<212> TYPE: DNA
<213> ORGANISM: Homo sapiens

<400> SEQUENCE: 554
tgcagaggat gcgaggcatt t 21

<210> SEQ ID NO 555
<211> LENGTH: 21
<212> TYPE: DNA
<213> ORGANISM: Homo sapiens

<400> SEQUENCE: 555
tggcgtgaca ctctgggaaa t 21

<210> SEQ ID NO 556
<211> LENGTH: 21
<212> TYPE: DNA
<213> ORGANISM: Homo sapiens

<400> SEQUENCE: 556
cagacttaat gaagccctga a 21

<210> SEQ ID NO 557
<211> LENGTH: 21
<212> TYPE: DNA
<213> ORGANISM: Homo sapiens

<400> SEQUENCE: 557
gtgttgtaca tcgagggtta t 21

<210> SEQ ID NO 558
<211> LENGTH: 21
<212> TYPE: DNA
<213> ORGANISM: Homo sapiens

<400> SEQUENCE: 558
ccagaacttc ggcgtacaag a 21

<210> SEQ ID NO 559
<211> LENGTH: 21
<212> TYPE: DNA
<213> ORGANISM: Homo sapiens

<400> SEQUENCE: 559
gaagtatcag cggtatcatt t 21

<210> SEQ ID NO 560
<211> LENGTH: 21
<212> TYPE: DNA
<213> ORGANISM: Homo sapiens

<400> SEQUENCE: 560
atggattgtt atcgcttata t 21

<210> SEQ ID NO 561
<211> LENGTH: 21
<212> TYPE: DNA
<213> ORGANISM: Homo sapiens

<400> SEQUENCE: 561
gcttggaaag ggtcttatta a 21

<210> SEQ ID NO 562
<211> LENGTH: 21
<212> TYPE: DNA
<213> ORGANISM: Homo sapiens

<400> SEQUENCE: 562
attgaatccc ttgagcaaat t 21

<210> SEQ ID NO 563
<211> LENGTH: 21
<212> TYPE: DNA
<213> ORGANISM: Homo sapiens

<400> SEQUENCE: 563
ccttatcaaa ccctattgaa t 21

<210> SEQ ID NO 564
<211> LENGTH: 21
<212> TYPE: DNA
<213> ORGANISM: Homo sapiens

<400> SEQUENCE: 564
ccaaagatca agaacccatt t 21

<210> SEQ ID NO 565
<211> LENGTH: 21
<212> TYPE: DNA
<213> ORGANISM: Homo sapiens

<400> SEQUENCE: 565
tagaggtaat gttctcattg a 21

<210> SEQ ID NO 566
<211> LENGTH: 21
<212> TYPE: DNA
<213> ORGANISM: Homo sapiens

<400> SEQUENCE: 566
accggattgg ttacgagata g 21

<210> SEQ ID NO 567
<211> LENGTH: 21
<212> TYPE: DNA
<213> ORGANISM: Homo sapiens

<400> SEQUENCE: 567
acctggtgca ggaccattaa c 21

<210> SEQ ID NO 568
<211> LENGTH: 21
<212> TYPE: DNA
<213> ORGANISM: Homo sapiens

<400> SEQUENCE: 568
tagactttct agccgtaaat c 21

<210> SEQ ID NO 569
<211> LENGTH: 21
<212> TYPE: DNA
<213> ORGANISM: Homo sapiens

<400> SEQUENCE: 569
ctagactttc tagccgtaaa t 21

<210> SEQ ID NO 570
<211> LENGTH: 21
<212> TYPE: DNA
<213> ORGANISM: Homo sapiens

<400> SEQUENCE: 570
cctcaggatg agtcatcaga t 21

<210> SEQ ID NO 571
<211> LENGTH: 21
<212> TYPE: DNA
<213> ORGANISM: Homo sapiens

<400> SEQUENCE: 571
cctggtataa ggtcatatta a 21

<210> SEQ ID NO 572
<211> LENGTH: 21
<212> TYPE: DNA
<213> ORGANISM: Homo sapiens

<400> SEQUENCE: 572
gctcagaatc ttattgatga t 21

<210> SEQ ID NO 573
<211> LENGTH: 21
<212> TYPE: DNA
<213> ORGANISM: Homo sapiens

<400> SEQUENCE: 573
gccctaacag tagatacatt g 21

<210> SEQ ID NO 574
<211> LENGTH: 21
<212> TYPE: DNA
<213> ORGANISM: Homo sapiens

<400> SEQUENCE: 574
cttactcaca tggcaattat t 21

<210> SEQ ID NO 575
<211> LENGTH: 21
<212> TYPE: DNA
<213> ORGANISM: Homo sapiens

<400> SEQUENCE: 575
gcacaactga agcatcactc t 21

<210> SEQ ID NO 576
<211> LENGTH: 21
<212> TYPE: DNA
<213> ORGANISM: Homo sapiens

<400> SEQUENCE: 576
gcacaagtgg atgaactgaa a 21

<210> SEQ ID NO 577
<211> LENGTH: 21
<212> TYPE: DNA
<213> ORGANISM: Homo sapiens

<400> SEQUENCE: 577
ttacggttca agagcacaaa c 21

<210> SEQ ID NO 578
<211> LENGTH: 21
<212> TYPE: DNA
<213> ORGANISM: Homo sapiens

<400> SEQUENCE: 578
taagagccta gacaaagtga t 21

<210> SEQ ID NO 579
<211> LENGTH: 21
<212> TYPE: DNA
<213> ORGANISM: Homo sapiens

<400> SEQUENCE: 579
agccatgtgt atgaagaata t 21

<210> SEQ ID NO 580
<211> LENGTH: 21
<212> TYPE: DNA
<213> ORGANISM: Homo sapiens

<400> SEQUENCE: 580

-continued tccaggagcc catacaagta a 21

<210> SEQ ID NO 581
<211> LENGTH: 21
<212> TYPE: DNA
<213> ORGANISM: Homo sapiens

<400> SEQUENCE: 581
ataaactaac ttactcacat g 21

<210> SEQ ID NO 582
<211> LENGTH: 21
<212> TYPE: DNA
<213> ORGANISM: Homo sapiens

<400> SEQUENCE: 582
gccgccacat ttcgttgtaa a 21

<210> SEQ ID NO 583
<211> LENGTH: 21
<212> TYPE: DNA
<213> ORGANISM: Homo sapiens

<400> SEQUENCE: 583
gcacttcctt atgctatgaa t 21

<210> SEQ ID NO 584
<211> LENGTH: 21
<212> TYPE: DNA
<213> ORGANISM: Homo sapiens

<400> SEQUENCE: 584
gccttaagat atgcaatgtt a 21

<210> SEQ ID NO 585
<211> LENGTH: 21
<212> TYPE: DNA
<213> ORGANISM: Homo sapiens

<400> SEQUENCE: 585
ctgaaaggaa taatggtcag a 21

<210> SEQ ID NO 586
<211> LENGTH: 21
<212> TYPE: DNA
<213> ORGANISM: Homo sapiens

<400> SEQUENCE: 586
ctccttgtaa atgatacaca a 21

<210> SEQ ID NO 587
<211> LENGTH: 21
<212> TYPE: DNA
<213> ORGANISM: Homo sapiens

<400> SEQUENCE: 587
ctttgcctgt catatagttt g 21

<210> SEQ ID NO 588
<211> LENGTH: 21
<212> TYPE: DNA
<213> ORGANISM: Homo sapiens

<400> SEQUENCE: 588
tcgagccatg tgtatgaaga a 21

<210> SEQ ID NO 589
<211> LENGTH: 21
<212> TYPE: DNA
<213> ORGANISM: Homo sapiens

<400> SEQUENCE: 589
atccctagca attacgtagt g 21

<210> SEQ ID NO 590
<211> LENGTH: 21
<212> TYPE: DNA
<213> ORGANISM: Homo sapiens

<400> SEQUENCE: 590
tggttatatc cctagcaatt a 21

<210> SEQ ID NO 591
<211> LENGTH: 21
<212> TYPE: DNA
<213> ORGANISM: Homo sapiens

<400> SEQUENCE: 591
tatgcttcac tcggcatgtt t 21

<210> SEQ ID NO 592
<211> LENGTH: 21
<212> TYPE: DNA
<213> ORGANISM: Homo sapiens

<400> SEQUENCE: 592
attccagata cggttactca a 21

<210> SEQ ID NO 593
<211> LENGTH: 21
<212> TYPE: DNA
<213> ORGANISM: Homo sapiens

<400> SEQUENCE: 593
tttaagaagg gtgaacgatt t 21

<210> SEQ ID NO 594
<211> LENGTH: 21
<212> TYPE: DNA
<213> ORGANISM: Homo sapiens

<400> SEQUENCE: 594
cacgaccaga gctcagtttg a 21

<210> SEQ ID NO 595
<211> LENGTH: 21
<212> TYPE: DNA
<213> ORGANISM: Homo sapiens

<400> SEQUENCE: 595
caggtatggt aaaccgtgaa g 21

<210> SEQ ID NO 596
<211> LENGTH: 21
<212> TYPE: DNA
<213> ORGANISM: Homo sapiens

<400> SEQUENCE: 596
ggagtggaac atgctacagt t 21

<210> SEQ ID NO 597
<211> LENGTH: 21
<212> TYPE: DNA
<213> ORGANISM: Homo sapiens

<400> SEQUENCE: 597
cctcattctc agtggtgtca a 21

<210> SEQ ID NO 598
<211> LENGTH: 21
<212> TYPE: DNA
<213> ORGANISM: Homo sapiens

<400> SEQUENCE: 598
tcgagaatca ttgcgactag a 21

<210> SEQ ID NO 599
<211> LENGTH: 21
<212> TYPE: DNA
<213> ORGANISM: Homo sapiens

<400> SEQUENCE: 599
ccaggtacaa tgatgccaga a 21

<210> SEQ ID NO 600
<211> LENGTH: 21
<212> TYPE: DNA
<213> ORGANISM: Homo sapiens

<400> SEQUENCE: 600
gcggaaagat tacttctgaa t 21

<210> SEQ ID NO 601
<211> LENGTH: 21
<212> TYPE: DNA
<213> ORGANISM: Homo sapiens

<400> SEQUENCE: 601
gctgctctgt atggtcgatt t 21

<210> SEQ ID NO 602
<211> LENGTH: 21
<212> TYPE: DNA
<213> ORGANISM: Homo sapiens

<400> SEQUENCE: 602
ccttgtatga ttatgaagct a 21

<210> SEQ ID NO 603
<211> LENGTH: 21
<212> TYPE: DNA
<213> ORGANISM: Homo sapiens

<400> SEQUENCE: 603
gccagtcatt atggagtgga a 21

<210> SEQ ID NO 604
<211> LENGTH: 2466
<212> TYPE: DNA

<213> ORGANISM: Homo sapiens

<400> SEQUENCE: 604
gtgtccggcc aagcggcgcc ctgaaggcgt gtccggccgc agcttaggct ctccgggagt 60
ccccggagag taggggcggc cggcggcgct agtcttctgg ggagcgccgg gtgcacaccg 120
gaccactgcg ggaggcctag ggccgagggc cgaggagctg gcctgcgccc ggcgaccccg 180
gcttccctcc gcagtcgccc aggcgtccct tccccctac agccgagcgg cgccgggcgc 240
aggcgcattg ggcgccccg gcagccccg cggcccgccc cgtccgctgc ccgtccgagg 300
aggcggaggg cgatgacgtc atcgagcggg gcgacgggca ttgggcgcca ttttgaaaag 360
ggaaaaaaat ccctccccgg cggcggcggc ggcggcggcg gcgccggcgg tggtggcggc 420
cccggggctg agcgctcggc tgcagcggcg cggaggccgt ctccctggtc tgccgcggtc 480
cccgcccgtc ccgccgccgg ctgccatggc aggagccgga ggcggcggct gccccgcggg 540
cggcaacgac ttccagtggt gcttctcgca ggtcaagggg gccatcgacg aggacgtggc 600
cgaagcggac atcatttcca ccgttgagtt taattactct ggagatcttc ttgcaacagg 660
agacaagggc ggcagagttg ttatttttca gcgtgaacaa gagaataaaa gccgccctca 720
ttctagggga gaatataatg tttacagcac ctttcaaagt catgaaccgg agtttgacta 780
tttgaaaagt ctagaaattg aggaaaaaat taataaaatt aggtggttac cacaacagaa 840
tgctgctcat tttctactgt ctacaaatga taaaactata aaattatgga aaataagtga 900
acgggataaa agagcagaag gttataacct gaaagacgaa gatggaagac ttcgagaccc 960
atttaggatc acggcgctac gggtcccaat attgaagccc atggatctta tggtagaagc 1020
gagtccacgg cgaatttttg caaatgctca cacatatcat ataaattcca tttcagtaaa 1080
tagtgatcat gaaacatatc tttctgcaga tgacctgaga attaatttat ggcacttaga 1140
aatcacagat agaagcttta acatcgtgga catcaagcct gctaacatgg aggagctgac 1200
cgaagtcatc actgcagccg agttccaccc gcaccagtgc aacgtgttcg tctacagcag 1260
tagcaaaggg accatccgcc tgtgtgacat gcgctcctcg gccctgtgcg acagacactc 1320
caagtttttt gaagagcctg aagatcccag cagtaggtcc ttcttctcag aaataatttc 1380
atccatatcc gatgtaaaat tcagtcatag tgggcggtac atgatgacca gagactacct 1440
gtcggtgaag gtgtgggacc tcaacatgga gagcaggccg gtggagaccc accaggtcca 1500
cgagtacctg cgcagcaagc tctgctctct ctatgagaac gactgcatct ttgacaagtt 1560
tgagtgttgc tggaacggtt cggatagcgc catcatgacc gggtcctata acaacttctt 1620
caggatgttt gatagagaca cgcggaggga tgtgaccctg gaggcctcga gagagagcag 1680
caaaccgcgc gccagcctca aaccccggaa ggtgtgtacg gggggtaagc ggaggaaaga 1740
cgagatcagt gtggacagtc tggacttcaa caagaagatc ctgcacacag cctggcaccc 1800
cgtggacaat gtcattgccg tggctgccac caataacttg tacatattcc aggacaaaat 1860
caactagaga cgcgaacgtg aggaccaagt cttgtcttgc atagttaagc cggacatttt 1920
tctgtcagag aaaaggcatc attgtccgct ccattaagaa cagtgacgca cctgctactt 1980
cccttcacag acacaggaga aagccgcctc cgctggaggc ccggtgtggt tccgcctcgg 2040
cgaggcgcga gacaggcgct gctgctcacg tggagacgct ctcgaagcag agttgacgga 2100
cactgctccc aaaaggtcat tactcagaat aaatgtattt atttcagtcc gagccttcct 2160
ttccaattta tagaccaaaa aattaacatc caagagaaaa gttattgtca gataccgctc 2220
tttctccaac tttccctctt tctctgccat cacacttggg ccttcactgc agcgtggtgt 2280
ggccaccgtc cgtgtcctct cggccttcct ccgagtccag gtggactctg tggatgtgtg 2340
gatgtggccc gagcaggctc aggcggcccc actcacccac agcatccgcc gccacccctt 2400
cgggtgtgag cgctcaataa aaacaacaca ctataaagtg tttttaaatc caaaaaaaaa 2460
aaaaaa 2466

<210> SEQ ID NO 605
<211> LENGTH: 4665
<212> TYPE: DNA
<213> ORGANISM: Homo sapiens

<400> SEQUENCE: 605
ggaaagtcca ccttccccaa caaggccagc ctgggaacat ggagtggcag cggccgcagc 60
caatgagaga gcaaacgcgc ggaaagtttg ctcaatgggc gatgtccgag ataggctgtc 120
actcaggtgg cagcggcaga ggccgggctg agacgtggcc aggggaacac ggctggctgt 180
ccaggccgtc ggggcggcag tagggtccct agcacgtcct tgccttcttg ggagctccaa 240
gcggcgggag aggcaggcgt cagtggctgc gcctccatgc ctgcgcgcgg ggcgggacgc 300
tgatggagcg cgccatcagc ccggggctgc tggtacgggc gctgctgctg ctgctgctgc 360
tgctggggct cgcggcaagg acggtggccg cggggcgcgc ccgtggcctc ccagcgccga 420
cggcggaggc ggcgttcggc ctcggggcgg ccgctgctcc cacctcagcg acgcgagtac 480
cggcggcggg cgccgtggct gcggccgagg tgactgtgga ggacgctgag gcgctgccgg 540
cagccgcggg agagcaggag cctcggggtc cggaaccaga cgatgagaca gagttgcgac 600
cgcgcggcag gtcattagta attatcagca ctttagatgg gagaattgct gccttggatc 660
ctgaaaatca tggtaaaaag cagtgggatt tggatgtggg atccggttcc ttggtgtcat 720
ccagccttag caaaccagag gtatttggga ataagatgat cattccttcc ctggatggag 780
ccctcttcca gtgggaccaa gaccgtgaaa gcatggaaac agttcctttc acagttgaat 840
cacttcttga atcttcttat aaatttggag atgatgttgt tttggttgga ggaaaatctc 900
tgactacata tggactcagt gcatatagtg gaaaggtgag gtatatctgt tcagctctgg 960
gttgtcgcca atgggatagt gacgaaatgg aacaagagga agacatcctg cttctacagc 1020
gtacccaaaa aactgttaga gctgtcggac ctcgcagtgg caatgagaag tggaatttca 1080
gtgttggcca ctttgaactt cggtatattc cagacatgga aacgagagcc ggatttattg 1140
aaagcacctt taagcccaat gagaacacag aagagtctaa aattatttca gatgtggaag 1200
aacaggaagc tgccataatg gacatagtga taaaggtttc ggttgctgac tggaaagtta 1260
tggcattcag taagaaggga ggacatctgg aatgggagta ccagtttttgt actccaattg 1320 catctgcctg gttacttaag gatgggaaag tcattcccat cagtcttttt gatgatacaa 1380
gttatacatc taatgatgat gttttagaag atgaagaaga cattgtagaa gctgccagag 1440
gagccacaga aaacagtgtt tacttgggaa tgtatagagg ccagctgtat ctgcagtcat 1500
cagtcagaat ttcagaaaag tttccttcaa gtcccaaggc tttggaatct gtcactaatg 1560
aaaacgcaat tattccttta ccaacaatca aatggaaacc cttaattcat tctccttcca 1620
gaactcctgt cttggtagga tctgatgaat ttgacaaatg tctcagtaat gataagtttt 1680
ctcatgaaga atatagtaat ggtgcacttt caatcttgca gtatccatat gataatggtt 1740
attatctacc atactacaag agggagagga acaaacgaag cacacagatt acagtcagat 1800
tcctcgacaa cccacattac aacaagaata tccgcaaaaa ggatcctgtt cttcttttac 1860
actggtggaa agaaatagtt gcaacgattt tgttttgtat catagcaaca acgtttattg 1920
tgcgcaggct tttccatcct catcctcaca ggcaaaggaa ggagtctgaa actcagtgtc 1980
aaactgaaaa taaatatgat tctgtaagtg gtgaagccaa tgacagtagc tggaatgaca 2040
taaaaaactc tggatatata tcacgatatc taactgattt tgagccaatt caatgcctgg 2100
gacgtggtgg ctttggagtt gtttttgaag ctaaaaacaa agtagatgac tgcaattatg 2160
ctatcaagag gatccgtctc cccaataggg aattggctcg ggaaaaggta atgcgagaag 2220
ttaaagcctt agccaagctt gaacacccgg gcattgttag atatttcaat gcctggctcg 2280
aagcaccacc agagaagtgg caagaaaaga tggatgaaat ttggctgaaa gatgaaagca 2340
cagactggcc actcagctct cctagcccaa tggatgcacc atcagttaaa atacgcagaa 2400
tggatccttt cgctacaaaa gaacatattg aaatcatagc tccttcacca caaagaagca 2460
ggtctttttc agtagggatt tcctgtgacc agacaagttc atctgagagc cagttctcac 2520
cactggaatt ctcaggaatg gaccatgagg acatcagtga gtcagtggat gcagcataca 2580
acctccagga cagttgcctt acagactgtg atgtggaaga tgggactatg gatggcaatg 2640
atgaggggca ctcctttgaa ctttgtcctt ctgaagcttc tccttatgta aggtcaaggg 2700
agagaacctc ctcttcaata gtatttgaag attctggctg tgataatgct tccagtaaag 2760
aagagccgaa aactaatcga ttgcatattg gcaaccattg tgctaataaa ctaactgctt 2820
tcaagcccac cagtagcaaa tcttcttctg aagctacatt gtctatttct cctccaagac 2880
caaccacttt aagtttagat ctcactaaaa acaccacaga aaaactccag cccagttcac 2940
caaaggtgta tctttacatt caaatgcagc tgtgcagaaa agaaaacctc aaagactgga 3000
tgaatggacg atgtaccata gaggagagag agaggagcgt gtgtctgcac atcttcctgc 3060
agatcgcaga ggcagtggag tttcttcaca gtaaaggact gatgcacagg gacctcaagc 3120
catccaacat attctttaca atggatgatg tggtcaaggt tggagacttt gggttagtga 3180
ctgcaatgga ccaggatgag gaagagcaga cggttctgac cccaatgcca gcttatgcca 3240
gacacacagg acaagtaggg accaaactgt atatgagccc agagcagatt catggaaaca 3300
gctattctca taaagtggac atcttttctt taggcctgat tctatttgaa ttgctgtatc 3360
cattcagcac tcagatggag agagtcagga ccttaactga tgtaagaaat ctcaaatttc 3420
caccattatt tactcagaaa tatccttgtg agtacgtgat ggttcaagac atgctctctc 3480
catcccccat ggaacgacct gaagctataa acatcattga aaatgctgta tttgaggact 3540
tggactttcc aggaaaaaca gtgctcagac agaggtctcg ctccttgagt tcatcgggaa 3600
caaaacattc aagacagtcc aacaactccc atagcccttt gccaagcaat tagccttaag 3660
ttgtgctagc aaccctaata ggtgatgcag ataatagcct acttcttaga atatgcctgt 3720
ccaaaattgc agacttgaaa agtttgttct tcgctcaatt tttttgtgga ctactttttt 3780
tatatcaaat ttaagctgga tttgggggca taacctaatt tgagccaact cctgagtttt 3840
gctatactta aggaaagggc tatctttgtt ctttgttagt ctcttgaaac tggctgctgg 3900
ccaagcttta tagccctcac catttgccta aggaggtagc agcaatccct aatatatata 3960
tatagtgaga actaaaatgg atatattttt ataatgcaga agaaggaaag tccccctgtg 4020
tggtaactgt attgttctag aaatatgctt tctagagata tgatgatttt gaaactgatt 4080
tctagaaaaa gctgactcca tttttgtccc tggcgggtaa attaggaatc tgcactattt 4140
tggaggacaa gtagcacaaa ctgtataacg gtttatgtcc gtagttttat agtcctattt 4200
gtagcattca atagctttat tccttagatg gttctagggt gggtttacag ctttttgtac 4260
ttttacctcc aataaaggga aaatgaagct ttttatgtaa attggttgaa aggtctagtt 4320
ttgggaggaa aaaagccgta gtaagaaatg gatcatatat attacaacta acttcttcaa 4380
ctatggactt tttaagccta atgaaatctt aagtgtctta tatgtaatcc tgtaggttgg 4440
tacttccccc aaactgatta taggtaacag tttaatcatc tcacttgcta acatgttttt 4500
atttttcact gtaaatatgt ttatgtttta tttataaaaa ttctgaaatc aatccatttg 4560
ggttggtggt gtacagaaca cacttaagtg tgttaacttg tgacttcttt caagtctaaa 4620
tgatttaata aaactttttt taaattaaaa aaaaaaaaaa aaaaa 4665

<210> SEQ ID NO 606
<211> LENGTH: 9604
<212> TYPE: DNA
<213> ORGANISM: Homo sapiens

<400> SEQUENCE: 606
ctcggtgagc gcgccgagga agagaggcga gcggagagtg gaggaggagg cggcggcggc 60
gggagcggtc cccaggaatg tcgctgccgc cgccaccgcc ggggccgctg ccgttgagga 120
ggagacggag gagaccgacg ttgttaggaa gatgatccct atgatcttga agatgtttct 180
gcacagaaat gagggaaata caaagaacca aatacagttc tgaaatttgg gatctgtatt 240
ttgagatgat tttattttca gaatgagaag catatctggt tacctttatg aatgtagaga 300
catgagaaga gagttatgat ggcaaaaaac aaagagcctc gtcccccatc ctataccatc 360
agtatagttg gactctctgg gactgaaaaa gacaaaggta actgtggagt tggaaagtct 420
tgtttgtgca atagatttgt acgctcaaaa gcagatgaat attatccaga gcatacttct 480
gtgcttagca ccattgactt tggaggacga gtagtaaaca atgatcactt tttgtactgg 540
ggtgacataa tacaaaatag tgaagatgga gtagaatgca aaattcatgt cattgaacaa 600
acagagttca ttgatgacca gactttcttg cctcatcgga gtacgaattt gcaaccatat 660
ataaaacgtg cagctgcatc taaattgcag tcagcagaaa aactaatgta catttgcact 720
gatcagctag gcttagaaca agactttgaa cagaagcaaa tgcctgaagg gaagctcaac 780
gtagatggat ttttattatg cattgatgta agtcaaggat gcaataggaa gtttgatgat 840
caacttaaat ttgtgaataa ccttttttgtc cagttatcaa aatcaaaaaa acctgtaata 900
atagcagcaa ctaaatgtga tgaatgcgtg gatcattatc ttagagaagt tcaggcattt 960
gcttcaaata aaaagaacct tcttgtagtg gaaacatcag cacgatttaa tgtcaacatt 1020
gaaacatgtt ttactgcact ggtacaaatg ttggataaaa ctcgtagcaa gcctaaaatt 1080
attccctatt tggatgctta taaaacacag agacaacttg ttgtcacagc aacagataag 1140
tttgaaaaac ttgtgcagac tgtgagagat tatcatgcaa cttggaaaac tgttagtaat 1200
aaattaaaaa atcatcctga ttatgaagaa tacatcaact tagagggaac aagaaaggcc 1260
agaaatacat tctcaaaaca tatagaacaa cttaaacagg aacatataag aaaaaggaga 1320
gaagagtata taaatacttt accaagagct tttaacactc ttttgccaaa tctagaagag 1380
attgaacatt tgaattggtc agaagctttg aagttaatgg aaaagagagc agatttccag 1440
ttatgttttg tggtgctaga aaaaactcct tgggatgaaa ctgaccatat agacaaaatt 1500
aatgataggc ggattccatt tgacctcctg agcactttag aagctgaaaa agtctatcag 1560
aaccatgtac agcatctgat atccgagaag aggagggtgg aaatgaagga aaaattcaaa 1620
aagactttgg aaaaaattca attcatttca ccagggcagc catgggagga agttatgtgc 1680

-continued

```
tttgttatgg aggatgaagc ctacaaatat atcactgagg ctgatagcaa agaggtatat   1740
ggtaggcatc agcgagaaat agttgaaaaa gccaaagaag agtttcaaga aatgcttttt   1800
gagcattctg aactttttta tgatttagat cttaatgcaa cacctagttc agataaaatg   1860
agtgaaattc atacagttct gagtgaagaa cctagatata aagctttaca gaaacttgca   1920
cctgataggg aatcccttct acttaagcat ataggatttg tttatcatcc cactaaagaa   1980
acatgtctta gtggccaaaa ttgtacagac attaaagtgg agcagttact tgctagtagt   2040
cttttacagt tggatcatgg ccgcttaaga ttatatcacg atagtaccaa tatagataaa   2100
gttaaccttt ttattttagg gaaggatggc cttgcccaag aactagcaaa tgagataagg   2160
acacaatcca ctgatgatga gtatgcctta gatggaaaaa tttatgaact tgatcttcgg   2220
ccggttgatg ccaaatcgcc ttactttttg agtcagttat ggactgccgc ctttaaacca   2280
catgggtgct tctgtgtatt taattccatt gagtcattga gttttattgg ggaatttatt   2340
gggaaaataa gaactgaagc ttctcagatc agaaaagata aatacatggc taatcttcca   2400
tttacattaa ttctggctaa tcagagagat tccattagta agaatctacc aattctcagg   2460
caccaagggc agcagttggc aaacaagttg caatgtcctt ttgtagatgt acctgctggt   2520
acatatcctc gtaaatttaa tgaaacccaa ataaagcaag ctctcagagg agtattggaa   2580
tcagttaaac acaatttgga tgtggtgagc ccaattcctg ccaataagga cttatcagaa   2640
gctgacttga gaattgtcat gtgcgccatg tgtggagatc catttagtgt ggatcttatt   2700
ctttcaccct tccttgattc tcattcttgc agtgctgctc aagctggaca gaataattcc   2760
ctaatgcttg ataaaatcat tggtgaaaaa aggaggcgaa tacagatcac aatattatca   2820
taccactctt caattggagt aagaaaagat gaactagttc atgggtatat attagtttac   2880
tctgcaaaac ggaaagcttc gatgggaatg cttcgagcat ttctatcaga agttcaagac   2940
accattcctg tacagctggt ggcagttact gacagccaag cagatttttt tgaaaatgag   3000
gctatcaaag agttaatgac tgaaggagaa cacattgcaa ctgagatcac tgctaaattt   3060
acagcactgt attctttatc tcagtatcat cggcaaactg aggtctttac tctgtttttt   3120
agtgatgttc tagagaaaaa aaatatgata gaaaattctt atttgtctga taatacaagg   3180
gaatcaaccc atcaaagtga agatgttttt ctaccatctc ccagagactg ttttccctat   3240
aataactacc ctgattcaga tgatgacaca gaagcaccac ctccttatag tccaattggg   3300
gatgatgtac agttgcttcc aacacctagt gaccgttcca gatatagatt agatttggaa   3360
ggaaatgagt atcctattca tagtacccca aactgtcatg accatgaacg caaccataaa   3420
gtgcctccac ctattaaacc taaaccagtt gtacctaaga caaatgtgaa aaaactcgat   3480
ccaaaccttt taaaaacaat tgaagctggt attggtaaaa atccaagaaa gcagacttcc   3540
cgggtgcctt tggcacatcc tgaagatatg gatccttcag ataactatgc ggaacccatt   3600
gatacaattt tcaaacagaa gggctattct gatgagattt atgttgtccc agatgatagt   3660
caaaatcgta ttaaaattcg aaactcattt gtaaataaca cccaaggaga tgaagaaaat   3720
gggttttctg atagaacctc aaaaagtcat ggggaacgga ggccttcaaa atacaaatat   3780
aaatctaaaa ccttgtttag taaagccaag tcatactata gaagaacaca ttcagatgcc   3840
agtgatgatg aggctttcac cacttctaaa acaaaaagaa aaggaagaca tcgtggaagt   3900
gaagaagatc cacttctttc tcctgttgaa acttggaaag gtggtattga taatcctgca   3960
atcacttctg accaggagtt agatgataag aagatgaaga agaaaaccca caaagtgaaa   4020
gaagataaaa agcagaaaaa gaaaactaag aacttcaatc caccaacacg tagaaattgg   4080
```

```
gaaagtaatt actttgggat gcccctccag gatctggtta cagctgagaa gcccatacca   4140
ctatttgttg agaaatgtgt ggaatttatt gaagatacag ggttatgtac cgaaggactc   4200
taccgtgtca gcgggaataa aactgaccaa gacaatattc aaaagcagtt tgatcaagat   4260
cataatatca atctagtgtc aatggaagta acagtaaatg ctgtagctgg agcccttaaa   4320
gctttctttg cagatctgcc agatccttta attccatatt ctcttcatcc agaactattg   4380
gaagcagcaa aaatcccgga taaaacagaa cgtcttcatg ccttgaaaga aattgttaag   4440
aaatttcatc ctgtaaacta tgatgtattc agatacgtga taacacatct aaacagggtt   4500
agtcagcaac ataaaatcaa cctaatgaca gcagacaact tatccatctg tttttggcca   4560
accttgatga gacctgattt tgaaaatcga gagtttctgt ctactactaa gattcatcaa   4620
tctgttgttg aaacattcat tcagcagtgt cagtttttct tttacaatgg agaaattgta   4680
gaaacgacaa acattgtggc tcctccacca ccttcaaacc caggacagtt ggtggaacca   4740
atggtgccac ttcagttgcc gccaccattg caacctcagc tgatacaacc acaattacaa   4800
acggatcctc ttggtattat atgagtagga agtgattgca aacaggctgg atttggacaa   4860
aaagcaaatc tagacatgca tgtttcaggg ttcagtagta tacttcatgt ttcatacaga   4920
taattcacat tcaaaattac attttctctt tgaactagat ggtattcctt attcacttac   4980
attacaaatc taagaccatg tgataagcat gactggagag gtttaatttt tataaacaaa   5040
aatagctata aagtacaaag ctgctgctgc atgcaacctt attgcaatca gtatatcatt   5100
cctgtggcaa tttctgtcac cttatattgt gaataaaatt tttctataga aattaaatga   5160
tttaaaaact cacctatatg aaacatttaa tgcttttcag cctgctttct ggctgatttt   5220
gttatttgat gtgctaattt gggcaactta atttacattc tggcagtcgg tgtagataac   5280
taaaagccca gttaagtatt ttataatttc aggctactga ggccatgctt gggatgttgt   5340
ttgaaagaaa gaaaaaatac acttgacata tttcacattt ctgtaccttc atctttactt   5400
ccaagtaaac ccgtggatga tttgatgagg gataaatgaa cctatttctt ttacacacat   5460
accaaggaca tgcttgtggc taaagtgagt tgataatgtt gtgcaaagga tagttgtcac   5520
caactcattt ctttatggtc cataatgaaa taaaaatttt gtatactgtt aattctgtaa   5580
acagatgcat gttcaaaaga tctatgatgg tcttgtaatc ttaatctaat atattttaga   5640
tattttaatt ttttccctct tggggaacac atttagtata gtgtagaaaa tacttccatg   5700
acattttcat ataaggttat ataacttttc atacataaac atgaaatttg ttgtagaaaa   5760
ttctttaaac caaacattta aatctaggac ttcaatttaa tttgttcctt gaatctattt   5820
ttatgtggcc cttaaaaaat atccaaaaaa cccattgcta atatagcaat aaaaatactt   5880
tgggtactga cagactcttt ggagtgttta tattacaaat ttgtattcat attcttttct   5940
gtgatgtgtt gtactaaaat ccaaaatggc ttttgcacca tttttaagcc aatttttttcc  6000
tttgatgttg gtaccagaat tactataagt gactgctgct tttgggggta aacattttgt   6060
tagtgaagat aaaaccagaa cactaaatta tggataaaat tttcagaata ggtggcacag   6120
gtaaatttca ctaggttata ttttgtgtag taaagaaaaa aattatttgg tcaatgttat   6180
cttaattcat actacaattt aagattatct tatgtgtatt atagtaaata gatgattttc   6240
agattcaagg ctcctaagag tttgatttgc tctgtttttt cctaaaataa atattgtctc   6300
tcccaactgt taagttctag gtattgtact tccaatttta acttcagaac caagatgttg   6360
gcatgaacca ggctgctgtt gaagtacatg tatattataa attatcttat ttgtgttata   6420
```

-continued

```
ctcttacatg ttatcttttc taagaaaaca aagtccctat tattcctatt gcaaagcaca   6480
caggaattaa gaaagtacag taatttttaa aaaaaaatcc ggtaaatgta gtattcttaa   6540
cctgttctat attacttata cctattgtct atatagcttt aatttatagt tgtcagttta   6600
actattggca tgtctggcaa agaaaattaa actttaagag ttttataaac tgtttctagg   6660
ttgctaaaga atttattttt ctactatata tggtatagac aaagcatcaa actatgtaca   6720
ggaaaaaagc ctgactattt ctatttggaa gtaggctgaa aagagaattt tcaaaactgt   6780
tcgtgtcttc agttcattct gtcataactt tgctattgta atatgtgaat accagtttat   6840
ttaagctgtt ctcttttata ctgtattaat ttaatgttca tctgcgttta gtaccatttt   6900
tgttattaaa actggcattt accgtttttc acattaaccc accttgcacc ttcccccaaa   6960
cttatctcca cttttctatg cattctatca ttgatttgac acacttcata gtgagtcatt   7020
taaatactct acgtttggtt caattaacca gtaggttaca gttattgaaa attaaagtac   7080
agtttaaagc tcagtctgtt acactgaatt gattgtgttt gtttttgcca agggtttaga   7140
tatgctttta aatattagaa acatctaaga acagaataac ataattaaac tttttctgg    7200
taagttactg gaaggtttca ctgtttaggg acctatcata tgagacttct taaaggatta   7260
aaagaatagg atagtctcat aattgtgagt aaacatcaag gcattatatt ttacaatact   7320
gaataaaatt tcatctacac acatgttgcc attgtttcat ttaaggttca gtgcttatag   7380
ttaactacaa tattggacct aacaggatct agattagcaa tataaagaag catagtggta   7440
ctctgtttca cactttcagt agatttatta gaagtcaaat tctattcaac agacacttat   7500
taggatatac aactaattta agaataaaat tccaggcaca atatattttt tttaaatggt   7560
atttgttagt agtgcttctt cccccttaaca tttacagtgt aaatactgca ggtaaccgca   7620
atctaagtta gccaaaaagc agcttttttt cccatactgt atgtaaataa tgtagacctg   7680
ggtttttttg tttatttggg tttgtttttt tttttgaggt actggaatct aattaatatc   7740
tcttaggtat caacaaaagg gaacaattgg aatgagaatt taggccttag cttccatggt   7800
gatttttagt tttttataca gtaataattg tgatgctatt tgtcaactgg atataaatac   7860
acatataatt ttaaaaagtc aaaagtgctt ttgtttcttt gtttaatgta atttttgtgc   7920
ttcacctaca ggatgctgca gtaaattaaa tatcagtgaa gcttctgatg tataaagaat   7980
gctatgaata aaacattaag aagctgtgta attttaagtt atagttgcct ctatttttac   8040
catttcattg gtaaaaatta gctaattttt ttcaagtgaa atgaaaaata aaaatataaa   8100
tttatcaata tgatggaaat cttattaagg agatgtatta ttgaattttc actgtacctg   8160
aaaaggagat tcaaaatttt ttctggggat gtatataggt gaaaatttga tttttaaat    8220
tatcaggaaa acaagataat gcacagattt ctaagactaa gatcttacct ggatgtgatt   8280
tttgagctgt ggctagacat tctttagagc cactggaaat attttgaaaa ctattctagt   8340
tatagcagag ctgctaatat taacgaatat atttgtgtct tcatggtttg tgactattag   8400
gccaaatttt gtggtatatg ttgtcagtct ggatctggtg aggtctgttc aacatgaatc   8460
tttgtgttat cttgaattta gtagtttcaa ggtacttaaa ttcttaacag tttctaattt   8520
gtttcaatac atatgggaca tggttgattt ttttactgta ttagaactct tggaagttct   8580
tagccttttc aggttatgaa atacctgaaa gtaaaatttt ctaagattta ataagggaag   8640
atactattca aatcatttc ttaggatagc atctttacat acaatgagag gattgtacaa    8700
gcattaatct catattccaa catccagtta cttgatgtga tccaagtacc ctggtctttt   8760
tgaagcagtt aaaatctaat taattaactt tgggagtctt cactattcaa ttgatcctca   8820
```

tcattgtcct atttgcatga ctccattttt tcctccacta tatgagtttt ctttgtcagg 8880
gggagaggag tgggaagagt cacagaatct catattcaca tcttaattaa attgtgtgaa 8940
attagtcttt tgtggaaatt ctgtaggcag tatgattttg aaaagctaac caatgataat 9000
tagcatttta gttaatacta aatgcataaa attataaccc ttgaaattaa tttggtgctg 9060
gcagttctgg tttagtcatt tttaccagta gttagtagta ttaagacctg cagtatatgc 9120
actttttgag tagctgtcaa ataattgtag ttgagaaaca acttgtttat tctcacaatt 9180
cagattttct attcagtttt gtctcaaata gtaagttatt gtgaacaatt taataacggc 9240
cctcctgttc tagtttgcct aatattttag ttaagattta gtgttttaac ctattttttt 9300
aagtttattt tttgtattag attttatttg aataagttat gtgggtttag taattgacct 9360
atttattcat tgcttcacta attcatccag attagtttta agtgtgtata tgtatttgct 9420
caccagatca ttttcttggg accttgaact gtgaatgttt tgtcctaacc atttaatatt 9480
ttctaggtac ttgctgcaag ttcttgaact attttaccag ctttaacttt ggggctctta 9540
gtttcttttc tccagattct tgttatttta ttttatccaa ataaatattt aggtgttcta 9600
agaa 9604

<210> SEQ ID NO 607
<211> LENGTH: 10551
<212> TYPE: DNA
<213> ORGANISM: Homo sapiens

<400> SEQUENCE: 607
cggccgggag gcggggcggg ccgtaggcaa agggaggtgg ggaggcggtg gccggcgact 60
ccccgcgccc cgctcgcccc ccggcccttc ccgcggtgct cggcctcgtt cctttcctcc 120
tccgctccct ccgtcttcca tacccgcccc gcgcggcttt cggccggcgt gcctcgcgcc 180
ctaacgggcg gctggaggcg ccaatcagcg ggcggcaggg tgccagcccc ggggctgcgc 240
cggcgaatcg gcggggcccg cggcccaggg tggcaggcgg gtctacccgc gcggccgcgg 300
cggcggagaa gcagctcgcc agccagcagc ccgccagccg ccgggaggtt cgatacaaga 360
ggctgttttc ctagcgtggc ttgctgcctt tggtaagaac atgtcgtcca tcttgccatt 420
cacgccgcca gttgtgaaga gactgctggg atggaagaag tcagctggtg ggtctggagg 480
agcaggcgga ggagagcaga atgggcagga agaaaagtgg tgtgagaaag cagtgaaaag 540
tctggtgaag aagctaaaga aaacaggacg attagatgag cttgagaaag ccatcaccac 600
tcaaaactgt aatactaaat gtgttaccat accaagcact tgctctgaaa tttggggact 660
gagtacacca aatacgatag atcagtggga tacaacaggc ctttacagct tctctgaaca 720
aaccaggtct cttgatggtc gtctccaggt atcccatcga aaaggattgc cacatgttat 780
atattgccga ttatggcgct ggcctgatct tcacagtcat catgaactca aggcaattga 840
aaactgcgaa tatgctttta atcttaaaaa ggatgaagta tgtgtaaacc cttaccacta 900
tcagagagtt gagacaccag ttttgcctcc agtattagtg ccccgacaca ccgagatcct 960
aacagaactt ccgcctctgg atgactatac tcactccatt ccagaaaaca ctaacttccc 1020
agcaggaatt gagccacaga gtaattatat tccagaaacg ccacctcctg gatatatcag 1080
tgaagatgga gaaacaagtg accaacagtt gaatcaaagt atggacacag gctctccagc 1140
agaactatct cctactactc tttcccctgt taatcatagc ttggatttac agccagttac 1200
ttactcagaa cctgcatttt ggtgttcgat agcatattat gaattaaatc agagggttgg 1260

-continued

```
agaaaccttc catgcatcac agccctcact cactgtagat ggctttacag acccatcaaa   1320
ttcagagagg ttctgcttag gtttactctc caatgttaac cgaaatgcca cggtagaaat   1380
gacaagaagg catataggaa gaggagtgcg cttatactac ataggtgggg aagtttttgc   1440
tgagtgccta agtgatagtg caatctttgt gcagagcccc aattgtaatc agagatatgg   1500
ctggcaccct gcaacagtgt gtaaaattcc accaggctgt aatctgaaga tcttcaacaa   1560
ccaggaattt gctgctcttc tggctcagtc tgttaatcag ggttttgaag ccgtctatca   1620
gctaactaga atgtgcacca taagaatgag ttttgtgaaa gggtggggag cagaataccg   1680
aaggcagacg gtaacaagta ctccttgctg gattgaactt catctgaatg gacctctaca   1740
gtggttggac aaagtattaa ctcagatggg atccccttca gtgcgttgct caagcatgtc   1800
ataaagcttc accaatcaag tcccatgaaa agacttaatg taacaactct tctgtcatag   1860
cattgtgtgt ggtccctatg gactgtttac tatccaaaag ttcaagagag aaaacagcac   1920
ttgaggtctc atcaattaaa gcaccttgtg gaatctgttt cctatatttg aatattagat   1980
gggaaaatta gtgtctagaa atactctccc attaaagagg aagagaagat tttaaagact   2040
taatgatgtc ttattgggca taaaactgag tgtcccaaag gtttattaat aacagtagta   2100
gttatgtgta caggtaatgt atcatgatcc agtatcacag tattgtgctg tttatataca   2160
tttttagttt gcatagatga ggtgtgtgtg tgcgctgctt cttgatctag gcaaaccttt   2220
ataaagttgc agtacctaat ctgttattcc cacttctctg ttatttttgt gtgtcttttt   2280
taatatataa tatatatcaa gattttcaaa ttatttagaa gcagattttc ctgtagaaaa   2340
actaattttt ctgcctttta ccaaaaataa actcttgggg gaagaaaagt ggattaactt   2400
ttgaaatcct tgaccttaat gtgttcagtg gggcttaaac agtcattctt tttgtggttt   2460
tttgtttttt tttgtttttt tttttaactg ctaaatctta ttataaggaa accatactga   2520
aaacctttcc aagcctcttt tttccattcc catttttgtc ctcataatca aaacagcata   2580
acatgacatc atcaccagta atagttgcat tgatactgct ggcaccagtt aattctggga   2640
tacagtaaga attcatatgg agaaagtccc tttgtcttat gcccaaattt caacaggaat   2700
aattggcttg tataatctag cagtctgttg atttatcctt ccacctcata aaaaatgcat   2760
aggtggcagt ataattattt tcagggatat gctagaatta cttccacata tttatccctt   2820
tttaaaaaag ctaatctata aataccgttt ttccaaaggt attttacaat atttcaacag   2880
cagaccttct gctcttcgag tagtttgatt tggtttagta accagattgc attatgaaat   2940
gggccttttg taaatgtaat tgtttctgca aaatacctag aaaagtgatg ctgaggtagg   3000
atcagcagat atgggccatc tgtttttaaa gtatgttgta ttcagtttat aaattgattg   3060
ttattctaca cataattatg aattcagaat tttaaaaatt gggggaaaag ccatttattt   3120
agcaagtttt ttagcttata agttacctgc agtctgagct gttcttaact gatcctggtt   3180
ttgtgattga caatatttca tgctctgtag tgagaggaga tttccgaaac tctgttgcta   3240
gttcattctg cagcaaataa ttattatgtc tgatgttgac tcattgcagt ttaaacattt   3300
cttcttgttt gcatcttagt agaaatggaa aataaccact cctggtcgtc ttttcataaa   3360
ttttcatatt tttgaagctg tctttggtac ttgttctttg aaatcatatc cacctgtctc   3420
tataggtatc attttcaata ctttcaacat ttggtggttt tctattgggt actccccatt   3480
ttcctatatt tgtgtgtata tgtatgtgtt catgtaaatt tggtatagta atttttttatt   3540
cattcaacaa atatttattg ttcacctgtt tgtaccagga acttttctta gtctttgggt   3600
aaaggtgaac aagacaacta cagttcctgc ctttgctgag acagcagtta cactaaccct   3660
```

taattatctt acttgtctat gaaggagata aacagggtac tgtactggag aataacagat 3720
gggatgcttc aggtaggaca tcaaggaaag cctctaagga aaggatgcat gagctaacac 3780
ctgacattaa agaagcaagc caagtgagga gccaggggag ataagcattc ctggcaaaga 3840
gaatagcatc aaatgcaaaa aggttcacac taaaggaaac tcctgattag gtattaatgc 3900
tttatacaga aacctctata caaatccaaa cttgaagatc agaatggttc tacagttcat 3960
aacattttga aggtggcctt attttgtgat agtctgcttc atgtgattct cactaacata 4020
tctccttcct caacctttgc tgtaaaaatt tcatttgcac cacatcagta ctacttaatt 4080
taacaagctt ttgttgtgta agctctcact gttttagtgc cctgctgctt gcttccagac 4140
tttgtgctgt ccagtaatta tgtcttccac tacccatctt gtgagcagag taaatgtcct 4200
aggtaatacc actatcaggc ctgtaggaga tactcagtgg agcctctgcc cttctttttc 4260
ttacttgaga acttgtaatg gtgttaggga acagttgtag gggcagaaaa caactctgaa 4320
agtggtagaa ggtcctgatc ttggtggtta ctcttgcatt actgtgttag gtcaagcagt 4380
gcctactatg ctgtttcagt agtggagcgc atctctacag ttctgatgcg atttttctgt 4440
acagtatgaa attgggactc aactctttga aaacacctat tgagcagtta tacctgttga 4500
gcagtttact tcctggttgt aattacattt gtgtgaatgt gtttgatgct ttttaacgag 4560
atgatgtttt ttgtatttta tctactgtgg cctgattttt tttttgtttt ctgcccctcc 4620
ccccatttat aggtgtggtt ttcatttttc taagtgatag aatcccctct ttgttgaatt 4680
tttgtcttta tttaaattag caacattact taggatttat tcttcacaat actgttaatt 4740
ttctaggaat gatgacctga gaaccgaatg gccatgcttt ctatcacatt tctaagatga 4800
gtaatatttt ttccagtagg ttccacagag acaccttggg ggctggctta ggggaggctg 4860
ttggagttct cactgactta gtggcatatt tattctgtac tgaagaactg catggggttt 4920
cttttggaaa gagtttcatt gctttaaaaa gaagctcaga aagtctttat aaccactggt 4980
caacgattag aaaaatataa ctggatttag gcctaccttc tggaataccg ctgattgtgc 5040
tctttttatc ctactttaaa gaagctttca tgattagatt tgagctatat cagttatacc 5100
gattatacct tataatacac attcagttag taaacattta ttgatgcctg ttgtttgccc 5160
agccactgtg atggatattg aataataaaa agatgactag gacggggccc tgacccttga 5220
gctgtgcttg gtcttgtaga ggttgtgttt tttttcctca ggacctgtca ctttggcaga 5280
aggaaatctg cctaattttt cttgaaagct aaattttctt tgtaagtttt tacaaattgt 5340
ttaataccta gttgtatttt ttaccttaag ccacattgag ttttgcttga tttgtctgtc 5400
ttttaaacac tgtcaaatgc tttccctttt gttaaaatta ttttaatttc actttttttg 5460
tgcccttgtc aatttaagac taagactttg aaggtaaaac aaacaaacaa acatcagtct 5520
tagtctcttg ctagttgaaa tcaaataaaa gaaaatatat acccagttgg tttctctacc 5580
tcttaaaagc ttcccatata tacctttaag atccttctct tttttcttta actactaaat 5640
aggttcagca tttattcagt gttagatacc ctcttcgtct gagggtggcg taggtttatg 5700
ttgggatata aagtaacaca agacaatctt cactgtacat aaaatatgtc ttcatgtaca 5760
gtctttactt taaaagctga acattccaat ttgcgccttc cctcccaagc ccctgcccac 5820
caagtatctc tttagatatc tagtctgtgg acatgaacaa tgaatacttt tttcttactc 5880
tgatcgaagg cattgatact tagacatatc aaacatttct tcctttcata tgctttactt 5940
tgctaaatct attatattca ttgcctgaat tttattcttc ctttctacct gacaacacac 6000

-continued

```
atccaggtgg tacttgctgg ttatcctctt tcttgttagc cttgtttttt gttttttttt   6060
tttttttttg agagggagtc tcgctctgtt gcccaacctg gagtgcagtg gtgcgatctt   6120
ggttcactgc aagctccgcc tcccgggttc acgccatgct tctgcctcag cctcccaagt   6180
agctgggact acaggcgccc accaccacac tcggctaatt ttttgtattt ttagtagaga   6240
cggggtttca ccgtgttggc caggatggtc tcgatctcct gacctcgtga tctgtccacc   6300
tcggcttccc aaagtgctgg gattacaggc atgagccacc gcgcccagcc tagccatatt   6360
tttatctgca tatatcagaa tgtttctctc ctttgaactt attaacaaaa aaggaacatg   6420
cttttcatac ctagagtcct aatttcttca tcatgaaggt tgctattcaa attgatcaat   6480
cattttaatt ttacaaatgg ctcaaaaatt ctgttcagta aatgtctttg tgactggcaa   6540
atggcataaa ttatgtttaa gattatgaac ttttctgaca gttgcagcca atgttttccc   6600
tacgatacca gatttccatc ttggggcata ttggattgtt gtatttaaga cagtcagaat   6660
aatgatagtg tgtggtctcc agaggtagtc agaatcctgc tattgagttc tttttatatc   6720
ttccttttca atttttattt accattttgt ttgtttagac tacactttgt agggattgag   6780
gggcaaatta tctcttggag tggaattcct gtgttttgag ccttacaacc aggaaatatg   6840
agctatacta gatagcctca tgatagcatt tacgataaga acttatctcg tgtgttcatg   6900
taatttttttg agtaggaact gttttatctt gaatattgta gctaactata tatagcagaa   6960
ctgcctcagt ctttttaaga aggaaataaa taatatatgt gtatgaattt atatatacat   7020
atacactcat agacaaactt aacagttggg gtcattctaa cagttaaaac aattgttcca   7080
ttgtttaaat ctcagatcct ggtaaaatgt tcttaatttg tctgtgtaca ttttcctttc   7140
atggacagac cattggagta cattaatttt cttaatctgc catttggcag ttcatttaat   7200
ataccatttt ttggcaactt ggtaactaag aatcacagcc aaaatttgtt aacatcaaag   7260
aaagctctgc catataccccc gttactaaat tattatacat ccagcagatt ctgggatgta   7320
ctaacttagg gttaactttg ttgttgttga taatactaga ttgctccctc tttaattctt   7380
cttctggtgc aaggttgctg cttaagttac cctgggaaat actactacaa ggtcaaattt   7440
tctagtatct tacagcctga ttgaaggtga ttcagatctt tgctcaatat aaatggattt   7500
tccaagattc tctgggccat ccttgaccca caggtgatct cgctggagta tattaactta   7560
acttcagtgc cagttggttt ggtgccatga gatccataat gaatccagaa cttcaccatt   7620
gcttagatat aagagtccct tggaagaata atgccactga tgatgggggt cagaaggtgt   7680
attaactcaa catagagggc ttttagattt ttcttcaaaa aaatttcgag aaaagtattc   7740
ttttaccctc caaacagtta acagctctta gtttctccaa atatgctctt tgatttactt   7800
atttttaatt aaagatggta atttattgaa caatgaaatc cgtaatatat tgatttaagg   7860
acaaaagtga agttttagaa ttataaaagt acttaaatat tatatatttt ccatttcata   7920
attgttttcc tttctctgtg gctttaaagt ttttgactat tttacaatgt taatcactag   7980
gtaacttgcc atatttctgg ttctatatta agttctatcc tttataatgc tgttattata   8040
aagctggttt ttagcatttg tctgtagcaa tagaaatttt actaagtctc tgttctccca   8100
gtaagttttt tcttttctca gtaagtccct aagaaaacat ttgtttgcca ctcttactat   8160
tcccaatctt ggattgttcg agctgaaaaa aaatttgatg agaaacagga ggatcctttt   8220
ctggtgaata taggttcctg ctttaagaat gtggaaatcc attgctttat ataactaata   8280
tacacacaga ttaattaaaa ttgtgagaaa taattcacac atgacaagta ggtaacatgc   8340
atgagttttg aatttttttta aaaacccaac tgtttgacaa aatatagaac ccaaattggt   8400
```

```
actttcttag accagtgtaa cctcacacct cagttttgct tttccaaccc tgacttgaaa   8460
ggcatatttg tatcttttta ttagtgatag tgaagctgtg acactaacct tttatacaaa   8520
agagtaaaga aagaaaaact acagcgatta agatgagaac agttctgcag ttgttgaact   8580
agatcacagc attgtaggca gaataaaaaa tgttcatatc tgagaatatt cctttcgcca   8640
tcttttccca aggccagacc tcctggtgga gcacagttaa aagtaacatt ctgggccttt   8700
gtaatcggag ggctgtgtct ccagctggca gcctttgttt taatatataa tgcaggactg   8760
tggaaaacag ttggcataga atattttcac ctaaaaaaga aagaaaagac atacaaaact   8820
ggattaattg caaaaagaga atacagtaaa ataccatata actggacaaa gctagaagaa   8880
cctttagaag atttgtctga aaacagattt caagagtgag cttttataca ctgctcacta   8940
atttgcttga ttactaccaa ctcttcttaa agttaacacg tttaaggtat ttctggactt   9000
cctagccttt tagcaagctt agaggaacta gccattagct agtgatgtaa aaatattttg   9060
gggactgatg cccttaaagg ttatgccctt gaaagttctt acctttctc tagtgatatt   9120
aaggaacgag tgggtagtgt tctcagggtg accagctgcc ctaaagtgcc tgggattgag   9180
ggtttccctg gatgcgggac tttccctgga tacaaaactt ttagcagagt tttgtatata   9240
tgtggatttt tctgataagt agcacatcag aggccttaac cactgcccaa aagcgattct   9300
ccattgagag tacatatctt gaacttaaga aattcatttg ctctgatttt taatcttgta   9360
aagtttttgc taaactcaaa acaagtccca ggcacaccag aaggagctga ccaccttagg   9420
tgttcttgtg atttatcctt acttccctat gttgtcatag ttgcttctaa actcagctgc   9480
actatggctg tcaacatttc tgatacttat tgggatatgt gccatccagt catttagtac   9540
tttgaatgga acatgagatt tataacacag gtaatagctg aaggtaccag tatggtggtg   9600
agactcacac ttagtgatcc agctaaggta actgatgtta taatggaaca gagaagaggc   9660
caactagata gctaagttct tctgaaccta tgtgtatatg taagtacaaa tcatgcgtcc   9720
ttatggggtt aaacttaatc tgaaatttac atttttcata gtaaaaggaa accaattgtt   9780
gcagatttct tttcttgtga ggaaatacat ggcctttgat gctctggcgt ctactgcatt   9840
tcccagtctg ttctgctcga gaagccagaa tgtgttgtta acatttttcc gtgaatgttg   9900
tgttaaaatg attaaatgca tcagccaatg gcaagtgaag gaattgggtg tcctgatgca   9960
gactgagcag tttctctcaa ttgtagcctc atactcataa ggtgcttacc agctagaaca  10020
ttgagcacgt gaggtgagat ttttttctc tgatggcatt aactttgtaa tgcaatatga  10080
tggatgcaga ccctgttctt gtttccctct ggaagtcctt agtggctgca tccttggtgc  10140
actgtgatgg agatattaaa tgtgttcttt gtgagctttc gttctatgat tgtcaaaagt  10200
acgatgtggt tcctttttta tttttattaa acaatgagct gaggctttat tacagctggt  10260
tttcaagtta aaattgttga atactgatgt ctttctccca cctacaccaa atattttagt  10320
ctatttaaag tacaaaaaaa gttctgctta agaaaacatt gcttacatgt cctgtgattt  10380
ctggtcaatt tttatatata tttgtgtgca tcatctgtat gtgctttcac tttttacctt  10440
gtttgctctt acctgtgtta acagccctgt caccgttgaa aggtggacag ttttcctagc  10500
attaaaagaa agccatttga gttgtttacc atgttaaaaa aaaaaaaaaa a           10551
```

<210> SEQ ID NO 608
<211> LENGTH: 2136
<212> TYPE: DNA
<213> ORGANISM: Homo sapiens -continued

<400> SEQUENCE: 608
gtgtgtggag gggaccctgt ggttagcagc agctatcgca gcgtcggatg ttcagagcag 60
cagaagccgg cgtcgtcgga tgttgtgttg cccgccacca tgagctacac aggctttgtc 120
cagggatctg aaaccacttt gcagtcgaca tactcggata ccagcgctca gcccacctgt 180
gattatggat atggaacttg gaactctggg acaaatagag gctacgaggg ctatggctat 240
ggctatggct atggccagga taacaccacc aactatgggt atggtatggc cacttcacac 300
tcttgggaaa tgcctagctc tgacacaaat gcaaacacta gtgcctcggg tagcgccagt 360
gccgattccg ttttatccag aattaaccag cgcttagata tggtgccgca tttggagaca 420
gacatgatgc aaggaggcgt gtacggctca ggtggagaaa ggtatgactc ttatgagtcc 480
tgcgactcga gggccgtcct gagtgagcgc gacctgtacc ggtcaggcta tgactacagc 540
gagcttgacc ctgagatgga aatggcctat gagggccaat acgatgccta ccgcgaccag 600
ttccgcatgc gtggcaacga caccttcggt cccagggcac agggctgggc ccgggatgcc 660
cggagcggcc ggccaatggc ctcaggctat gggcgcatgt gggaagaccc catgggggcc 720
cggggccagt gcatgtctgg tgcctctcgg ctgccctccc tcttctccca gaacatcatc 780
cccgagtacg gcatgttcca gggcatgcga ggtgggggcg ccttcccggg cggctcccgc 840
tttggtttcg ggtttggcaa tggcatgaag cagatgaggc ggacctggaa gacctggacc 900
acagccgact tccgaaccaa gaagaagaag agaaagcagg gcggcagtcc tgatgagcca 960
gatagcaaag ccacccgcac ggactgctcg gacaacagcg actcagacaa tgatgagggc 1020
accgaggggg aagccacaga gggccttgaa ggcaccgagg ctgtggagaa gggctccaga 1080
gtggacggag aggatgagga gggaaaagag gatgggagag aagaaggcaa agaggatcca 1140
gagaaggggg ccctaaccac ccaggatgaa aatggccaga ccaagcgcaa gttgcaggca 1200
ggcaagaaga gtcaggacaa gcagaaaaag cggcagcgag accgcatggt ggaaaggatc 1260
cagtttgtgt gttctctgtg caaataccgg accttctatg aggacgagat ggccagccat 1320
cttgacagca agttccacaa ggaacacttt aagtacgtag gcaccaagct ccctaagcag 1380
acggctgact ttctgcagga gtacgtcact aacaagacca agaagacaga ggagctccga 1440
aaaaccgtgg aggaccttga tggcctcatc caccaaatct acagagacca ggatctgacc 1500
caggaaattg ccatggagca ttttgtgaag aaggtggagg cagcccattg tgcagcctgc 1560
gacctcttca ttcccatgca gtttgggatc atccagaagc atctgaagac catggatcac 1620
aaccggaacc gcaggctcat gatggagcag tccaagaagt cctccctcat ggtggcccgc 1680
agtattctca acaacaagct catcagcaag aagctggagc gctacctgaa gggcgagaac 1740
cctttcaccg acagccccga ggaggagaag gagcaggagg aggctgaggg cggtgccctg 1800
gacgaggggg cgcagggcga agcggcaggg atctcggagg gcgcagaggg cgtgccggcg 1860
cagcctcccg tgcccccaga gccagccccc ggggccgtgt cgccgccacc gccgccgccc 1920
ccagaggagg aggaggaggg cgccgtgccc ttgctgggag ggcgctgca acgccagatc 1980
cgcggcatcc cgggcctcga cgtggaggac gacgaggagg gcggcggggg cgccccgtga 2040
cccgagctcg gggcgggcgg agcccgcgtg gccgaagctg gaaaccaaac ctaataaagt 2100
tttcccatcc caccaaaaaa aaaaaaaaaa aaaaaa 2136

<210> SEQ ID NO 609
<211> LENGTH: 1196
<212> TYPE: DNA
<213> ORGANISM: Homo sapiens

<400> SEQUENCE: 609
acctttgagc gatggcggcg tctggggaac cccagaggca gtggcaagag gaggtggcgg 60
cggtggtagt ggtgggctcc tgcatgaccg acctggtcag tcttacttct cgtttgccaa 120
aaactggaga aaccatccat ggacataagt tttttattgg ctttggaggg aaaggtgcca 180
accagtgtgt ccaagctgct cggcttggag caatgacgtc catggtgtgt aaggttggca 240
aagattcttt tggcaatgat tatatagaaa acttaaaaca gaatgatatt tctacagaat 300
ttacatatca gactaaagat gctgctacag gaactgcttc tataattgtc aataatgaag 360
gccagaatat cattgtcata gtggctggag caaatttact tttgaatacg gaggatctga 420
gggcagcagc caatgtcatt agcagagcca aagtcatggt ctgccagctc gaaataactc 480
cagcaacttc tttggaagcc ctaacaatgg cccgcaggag tggagtgaaa accttgttca 540
atccagcccc tgccattgct gacctggatc cccagttcta caccctctca gatgtgttct 600
gctgcaatga aagtgaggct gagattttaa ctggcctcac ggtgggcagc gctgcagatg 660
ctggggaggc tgcattagtg ctcttgaaaa ggggctgcca ggtggtaatc attaccttag 720
gggctgaagg atgtgtggtg ctgtcacaga cagaacctga gccaaagcac attcccacag 780
agaaagtcaa ggctgtggat accacgggtg ctggtgacag ctttgtggga gctctggcct 840
tctacctggc ttactatcca aatctgtcct tggaagacat gctcaacaga tccaatttca 900
ttgcagcagt cagtgtccag gctgcaggaa cacagtcatc ttacccttac aaaaaagacc 960
ttccgcttac tctgttttga ttgctattag tcccaaaata aatatacctg ggaataaaat 1020
gtacttgggg gtggctgctc ctggctaatg cttattagaa aatgtcctcg tcccctttct 1080
ttgcaaatat tagttctttt acgaagtcat cctcaagctt caatttattt ataacgatga 1140
ttcttttgct ttccatgcat ttgcacaaaa caaccagaat taaagattcc acaacc 1196

<210> SEQ ID NO 610
<211> LENGTH: 2992
<212> TYPE: DNA
<213> ORGANISM: Homo sapiens

<400> SEQUENCE: 610
aactgagcga ggagcaattg attaatagct cggcgagggg actcactgac tgttataata 60
acactacacc agcaactcct ggcttcccag cagccggaac acagacagga gagagtcagt 120
ggcaaataga catttttctt atttcttaaa aaacagcaac ttgtttgcta cttttatttc 180
tgttgatttt tttttcttgg tgtgtgtggt ggttgttttt aagtgtggag ggcaaaagga 240
gataccatcc caggctcagt ccaacccctc tccaaaacgg cttttctgac actccaggta 300
gcgagggagt tgggtctcca ggttgtgcga ggagcaaatg atgaccgcca aggccgtaga 360
caaaatccca gtaactctca gtggttttgt gcaccagctg tctgacaaca tctacccggt 420
ggaggacctc gccgccacgt cggtgaccat ctttcccaat gccgaactgg gaggcccctt 480
tgaccagatg aacggagtgg ccggagatgg catgatcaac attgacatga ctggagagaa 540
gaggtcgttg gatctcccat atcccagcag ctttgctccc gtctctgcac ctagaaacca 600
gaccttcact tacatgggca agttctccat tgaccctcag taccctggtg ccagctgcta 660
cccagaaggc ataatcaata ttgtgagtgc aggcatcttg caaggggtca cttccccagc 720
ttcaaccaca gcctcatcca gcgtcacctc tgcctccccc aacccactgg ccacaggacc 780
cctgggtgtg tgcaccatgt cccagaccca gcctgacctg gaccacctgt actctccgcc 840

```
accgcctcct cctccttatt ctggctgtgc aggagacctc taccaggacc cttctgcgtt    900
cctgtcagca gccaccacct ccacctcttc ctctctggcc tacccaccac ctccttccta    960
tccatccccc aagccagcca cggacccagg tctcttccca atgatcccag actatcctgg   1020
attctttcca tctcagtgcc agagagacct acatggtaca gctggcccag accgtaagcc   1080
ctttccctgc ccactggaca ccctgcgggt gccccctcca ctcactccac tctctacaat   1140
ccgtaacttt accctggggg gccccagtgc tggggtgacc ggaccagggg ccagtggagg   1200
cagcgaggga ccccggctgc ctggtagcag ctcagcagca gcagcagccg ccgccgccgc   1260
cgcctataac ccacaccacc tgccactgcg gcccattctg aggcctcgca agtaccccaa   1320
cagacccagc aagacgccgg tgcacgagag gccctacccg tgcccagcag aaggctgcga   1380
ccggcggttc tcccgctctg acgagctgac acggcacatc cgaatccaca ctgggcataa   1440
gcccttccag tgtcggatct gcatgcgcaa cttcagccgc agtgaccacc tcaccaccca   1500
tatccgcacc cacaccggtg agaagccctt cgcctgtgac tactgtggcc gaaagtttgc   1560
ccggagtgat gagaggaagc gccacaccaa gatccacctg agacagaaag agcggaaaag   1620
cagtgccccc tctgcatcgg tgccagcccc ctctacagcc tcctgctctg gggcgtgca   1680
gcctgggggt accctgtgca gcagtaacag cagcagtctt ggcggagggc cgctcgcccc   1740
ttgctcctct cggacccgga caccttgaga tgagactcag gctgatacac cagctcccaa   1800
aggtcccgga ggccctttgt ccactggagc tgcacaacaa acactaccac cctttcctgt   1860
ccctctctcc ctttgttggg caaagggctt tggtggagct agcactgccc cctttccacc   1920
tagaagcagg ttcttcctaa aacttagccc attctagtct ctcttaggtg agttgactat   1980
caacccaagg caaaggggag gctcagaagg aggtggtgtg gggacccctg gccaagaggg   2040
ctgaggtctg accctgcttt aaagggttgt ttgactaggt tttgctaccc cacttcccct   2100
tattttgacc catcacaggt ttttgaccct ggatgtcaga gttgatctaa gacgtttttct   2160
acaataggtt gggagatgct gatcccttca agtggggaca gcaaaaagac aagcaaaact   2220
gatgtgcact ttatggcttg ggactgattt gggggacatt gtacagtgag tgaagtatag   2280
cctttatgcc acactctgtg gccctaaaat ggtgaatcag agcatatcta gttgtctcaa   2340
cccttgaagc aatatgtatt ataaactcag agaacagaag tgcaatgtga tgggaggaac   2400
atagcaatat ctgctccttt tcgagttgtt tgagaaatgt aggctatttt ttcagtgtat   2460
atccactcag attttgtgta tttttgatgt acactgttct ctaaattctg aatctttggg   2520
aaaaaatgta aagcatttat gatctcagag gttaacttat ttaaggggga tgtacatata   2580
ttctctgaaa ctaggatgca tgcaattgtg ttggaagtgt ccttggtgcc ttgtgtgatg   2640
tagacaatgt tacaaggtct gcatgtaaat gggttgcctt attatggaga aaaaaatcac   2700
tccctgagtt tagtatggct gtatatttct gcctattaat atttggaatt ttttttagaa   2760
agtatatttt tgtatgcttt gttttgtgac ttaaaagtgt tacctttgta gtcaaatttc   2820
agataagaat gtacataatg ttaccggagc tgatttgttt ggtcattagc tcttaatagt   2880
tgtgaaaaaa taaatctatt ctaacgcaaa accactaact gaagttcaga taatggatgg   2940
tttgtgacta tagtgtaaat aaatactttt caacaataaa aaaaaaaaaa aa           2992
```

<210> SEQ ID NO 611
<211> LENGTH: 2756
<212> TYPE: DNA
<213> ORGANISM: Homo sapiens

<400> SEQUENCE: 611

```
agttcctgcc agtgagtccc taggcctcca tctctctccc ttgctgtacc accttcacca     60
ccatccatgc gaccccaaga gccttaatga ctctagaaga gactccaggc aggggaagct    120
gaaaggacct ttcactccct acttttggcc agggccttct gtgccacctg ccaagaccag    180
caggcctacc ctctgaagag gtccaagcaa cggaagtact actacgaagc tgcctttctg    240
gccatccttg agaaaaatag acagatggcc aaggagaggg gcctaataag ccccagtgat    300
tttgcccagc tgcaaaaata catggaatac tccaccaaaa aggtcagtga tgtcctaaag    360
ctcttcgagg atggcgagat ggctaaatat gtccaaggag atgccattgg gtacgaggga    420
ttccagcaat tcctgaaaat ctatctcgaa gtggataatg ttcccagaca cctaagcctg    480
gcactgtttc aatcctttga gactggtcac tgcttaaatg agacaaatgt gacaaaagat    540
gtggtgtgtc tcaatgatgt ttcctgctac ttttcccttc tggagggtgg tcggccagaa    600
gacaagttag aattcacctt caagctgtac gacacggaca gaaatgggat cctggacagc    660
tcagaagtgg acaaaattat cctacagatg atgcgagtgg ctgaatacct ggattgggat    720
gtgtctgagc tgaggccgat tcttcaggag atgatgaaag agattgacta tgatggcagt    780
ggctctgtct ctcaagctga gtgggtccgg gctggggcca ccaccgtgcc actgctagtg    840
ctgctgggtc tggagatgac tctgaaggac gacggacagc acatgtggag gcccaagagg    900
ttccccagac cagtctactg caatctgtgc gagtcaagca ttggtcttgg caaacaggga    960
ctgagctgta acctctgtaa gtacactgtt cacgaccagt gtgccatgaa agccctgcct   1020
tgtgaagtca gcacctatgc caagtctcgg aaggacattg gtgtccaatc acatgtgtgg   1080
gtgcgaggag gctgtgagtc cgggcgctgc gaccgctgtc agaaaaagat ccggatctac   1140
cacagtctga ccgggctgca ttgtgtatgg tgccacctag agatccacga tgactgcctg   1200
caagcggtgg gccatgagtg tgactgtggg ctgctccggg atcacatcct gcctccatct   1260
tccatctatc ccagtgtcct ggcctctgga ccggatcgta aaaatagcaa aacaagccag   1320
aagaccatgg atgatttaaa tttgagcacc tctgaggctc tgcggattga ccctgttcct   1380
aacacccacc cacttctcgt ctttgtcaat cctaagagtg gcgggaagca ggggcaaagg   1440
gtgctctgga agttccagta tatattaaac cctcgacagg tgttcaacct cctaaaggat   1500
ggtcctgaga tagggctccg attattcaag gatgttcctg atagccggat tttggtgtgt   1560
ggtggagacg gcacagtagg ctggattcta gagaccattg acaaagctaa cttgccagtt   1620
ttgcctcctg ttgctgtgtt gcccctgggt actggaaatg atctggctcg atgcctaaga   1680
tggggaggag gttatgaagg acagaatctg gcaaagatcc tcaaggattt agagatgagt   1740
aaagtggtac atatggatcg atggtctgtg gaggtgatac ctcaacaaac tgaagaaaaa   1800
agtgacccag tcccctttca aatcatcaat aactacttct ctattggcgt ggatgcctct   1860
attgctcatc gattccacat catgcgagag aaatatccgg agaagttcaa cagcagaatg   1920
aagaacaagc tatggtactt cgaatttgcc acatctgaat ccatcttctc aacatgcaaa   1980
aagctggagg agtctttgac agttgagatc tgtgggaaac cgctggatct gagcaacctg   2040
tccctagaag gcatcgcagt gctaaacatc cctagcatgc atggtggctc caacctctgg   2100
ggtgatacca ggagacccca tggggatatc tatgggatca accaggcctt aggtgctaca   2160
gctaaagtca tcaccgaccc tgatatcctg aaaacctgtg taccagacct aagtgacaag   2220
agactggaag tggttgggct ggagggtgca attgagatgg gccaaatcta taccaagctc   2280
aagaatgctg gacgtcggct ggccaagtgc tctgagatca ccttccacac cacaaaaacc   2340
```

-continued

```
cttcccatgc aaattgacgg agaaccctgg atgcagacgc cctgtacaat caagatcacc   2400

cacaagaacc agatgcccat gctcatgggc ccacccccc gctccaccaa tttctttggc   2460

ttcttgagct aagggggaca cccttggcct ccaagccagc cttgaaccca cctccctgtc   2520

cctggactct actcccgagg ctctgtacat tgctgccaca tactcctgcc agcttggggg   2580

agtgttcctt caccctcaca gtatttatta tcctgcacca cctcactgtt ccccatgcgc   2640

acacacatac acacacccca aaacacatac attgaaagtg cctcatctga ataaaatgac   2700

ttgtgtttcc cctttgggat ctgctaaaaa aaaaaaaaaa aaaaaaaaaa aaaaaa       2756
```

<210> SEQ ID NO 612
<211> LENGTH: 3976
<212> TYPE: DNA
<213> ORGANISM: Homo sapiens

<400> SEQUENCE: 612

```
ctgggtcctg tgtgtgccac aggggtgggg tgtccagcga gcggtctcct cctcctgcta     60

gtgctgctgc ggcgtcccgc ggcctccccg agtcgggcgg gaggggagag cgggtgtgga    120

tttgtcttga cggtaattgt tgcgtttcca cgtctcggag gcctgcgcgc tgggttgctc    180

cttcttcggg agcgagctgt tctcagcgat cccactccca gccggggctc cccacacaca    240

ctgggctgcg tgcgtgtgga gtgggacccg cgcacacgcg tgtctctgga cagctacggc    300

gccgaaagaa ctaaaattcc agatggcaaa ctcaatgaat ggcagaaacc ctggtggtcg    360

aggaggaaat ccccgaaaag gtcgaatttt gggtattatt gatgctattc aggatgcagt    420

tggacccccct aagcaagctg ccgcagatcg caggaccgtg gagaagactt ggaagctcat    480

ggacaaagtg gtaagactgt gccaaaatcc caaacttcag ttgaaaaata gcccaccata    540

tatacttgat attttgcctg atacatatca gcatttacga cttatattga gtaaatatga    600

tgacaaccag aaacttgccc aactcagtga gaatgagtac tttaaaatct acattgatag    660

ccttatgaaa aagtcaaaac gggcaataag actctttaaa gaaggcaagg agagaatgta    720

tgaagaacag tcacaggaca gacgaaatct cacaaaactg tcccttatct tcagtcacat    780

gctggcagaa atcaaagcaa tctttcccaa tggtcaattc cagggagata actttcgtat    840

cacaaaagca gatgctgctg aattctggag aaagtttttt ggagacaaaa ctatcgtacc    900

atggaaagta ttcagacagt gccttcatga ggtccaccag attagctctg gcctggaagc    960

aatggctcta aaatcaacaa ttgatttaac ttgcaatgat tacatttcag tttttgaatt   1020

tgatattttt accaggctgt ttcagccttg ggctctatt ttgcggaatt ggaatttctt   1080

agctgtgaca catccaggtt acatggcatt tctcacatat gatgaagtta aagcacgact   1140

acagaaatat agcaccaaac ccggaagcta tattttccgg ttaagttgca ctcgattggg   1200

acagtgggcc attggctatg tgactgggga tgggaatatc ttacagacca tacctcataa   1260

caagccctta tttcaagccc tgattgatgg cagcagggaa ggattttatc tttatcctga   1320

tgggaggagt tataatcctg atttaactgg attatgtgaa cctacacctc atgaccatat   1380

aaaagttaca caggaacaat atgaattata ttgtgaaatg ggctccactt ttcagctctg   1440

taagatttgt gcagagaatg acaaagatgt caagattgag ccttgtgggc atttgatgtg   1500

cacctcttgc cttacggcat ggcaggagtc ggatggtcag ggctgccctt tctgtcgttg   1560

tgaaataaaa ggaactgagc ccataatcgt ggaccccttt gatccaagag atgaaggctc   1620

caggtgttgc agcatcattg accccttttgg catgccgatg ctagacttgg acgacgatga   1680

tgatcgtgag gagtccttga tgatgaatcg gttggcaaac gtccgaaagt gcactgacag   1740
```

```
gcagaactca ccagtcacat caccaggatc ctctcccctt gcccagagaa gaaagccaca   1800
gcctgaccca ctccagatcc cacatctaag cctgccaccc gtgcctcctc gcctggatct   1860
aattcagaaa ggcatagtta gatctccctg tggcagccca acgggttcac caaagtcttc   1920
tccttgcatg gtgagaaaac aagataaacc actcccagca ccacctcctc ccttaagaga   1980
tcctcctcca ccgccacctg aaagacctcc accaatccca ccagacaata gactgagtag   2040
acacatccat catgtggaaa gcgtgccttc cagagacccg ccaatgcctc ttgaagcatg   2100
gtgccctcgg gatgtgtttg ggactaatca gcttgtggga tgtcgactcc taggggaggg   2160
ctctccaaaa cctggaatca cagcgagttc aaatgtcaat ggaaggcaca gtagagtggg   2220
ctctgaccca gtgcttatgc ggaaacacag acgccatgat ttgcctttag aaggagctaa   2280
ggtcttttcc aatggtcacc ttggaagtga agaatatgat gttcctcccc ggctttctcc   2340
tcctcctcca gttaccaccc tcctccctag cataaagtgt actggtccgt tagcaaattc   2400
tctttcagag aaaacaagag acccagtaga ggaagatgat gatgaataca agattccttc   2460
atcccaccct gtttccctga attcacaacc atctcattgt cataatgtaa aacctcctgt   2520
tcggtcttgt gataatggtc actgtatgct gaatggaaca catggtccat cttcagagaa   2580
gaaatcaaac atccctgact taagcatata tttaaaggga gatgtttttg attcagcctc   2640
tgatcccgtg ccattaccac ctgccaggcc tccaactcgg gacaatccaa agcatggttc   2700
ttcactcaac aggacgccct ctgattatga tcttctcatc cctccattag gtgaagatgc   2760
ttttgatgcc ctccctccat ctctcccacc tcccccacct cctgcaaggc atagtctcat   2820
tgaacattca aaacctcctg gctccagtag ccggccatcc tcaggacagg atctttttct   2880
tcttccttca gatccctttg ttgatctagc aagtggccaa gttcctttgc ctcctgctag   2940
aaggttacca ggtgaaaatg tcaaaactaa cagaacatca caggactatg atcagcttcc   3000
ttcatgttca gatggttcac aggcaccagc cagacccccct aaaccacgac cgcgcaggac   3060
tgcaccagaa attcaccaca gaaaacccca tgggcctgag gcggcattgg aaaatgtcga   3120
tgcaaaaatt gcaaaactca tgggagaggg ttatgccttt gaagaggtga agagagcctt   3180
agagatagcc cagaataatg tcgaagttgc ccggagcatc ctccgagaat ttgccttccc   3240
tcctccagta tccccacgtc taaatctata gcagccagaa ctgtagacac caaaatggaa   3300
agcaatcgat gtattccaag agtgtggaaa taaagagaac tgagatggaa ttcaagagag   3360
aagtgtctcc tcctcgtgta gcagcttgag aagaggcttg ggagtgcagc ttctcaaagg   3420
agaccgatgc ttgctcagga tgtcgacagc tgtggcttcc ttgtttttgc tagccatatt   3480
tttaaatcag ggttgaactg acaaaaataa tttaaagacg tttacttccc ttgaactttg   3540
aacctgtgaa atgctttacc ttgtttacag tttggcaaag ttgcagtttg ttcttgtttt   3600
tagtttagtt ttgttttggt gttttgatac ctgtactgtg ttcttcacag accctttgta   3660
gcgtggtcag gtctgctgta acatttccca ccaactctct tgctgtccac atcaacagct   3720
aaatcattta ttcatatgga tctctaccat ccccatgcct tgcccaggtc cagttccatt   3780
tctctcattc acaagatgct ttgaaggttc tgattttcaa ctgatcaaac taatgcaaaa   3840
aaaaaaaagt atgtattctt cactactgag tttcttcttt ggaaaccatc actattgaga   3900
gatgggaaaa acctgaatgt ataaagcatt tatttgtcaa taaactgcct tttgtaaggg   3960
gttttcacat aacata                                                  3976
```

<210> SEQ ID NO 613

<211> LENGTH: 5312
<212> TYPE: DNA
<213> ORGANISM: Homo sapiens

<400> SEQUENCE: 613
cccaggccgg ctctggcctc ctgacccaga cagcgcaggg cgcgagggat cgcgcggccg 60
agcccgggtc gcgccgctcc cagcatcggg gccgctagcc aagagttcga ggccttcccg 120
atccggatgt gatgaaaaag agcaacagag ggagaagtgt ttcaggattg taggagtgga 180
agaggggaaa gagaggcaga gagggggaag gccccctcgc aggggagccg gctggagtga 240
gctggctgga aagagggggc ggagtgcgcg gagtcagagc cgccaccgct gccgcagttg 300
ccgccactgc ggcgtctggg ctgagccgga gggaggcggg aggacgcgca ggggcggccg 360
ccgccgtcgt caggccaccg gggcgaaaat gcggccgctg ccggaggctc gctaactttc 420
cggggcggaa gaggaggagg aggaggagga aggggcttgg agcgactacg gggggatgcg 480
gagaagcagt cagttccctg cacccagcac ctcacagccc ttcctccgtg cgccctgccg 540
ggcggcgagc taggcggcag cggcgcggcg cgggctcggc ggagcggccc atgtccggcg 600
cgggcgaagc cctcgctccc gggcccgtgg ggccgcagcg cgtggccgag gcgggcggcg 660
gccagctggg ctccacagcc cagggaaaat gtgataaaga caatactgag aaagatataa 720
ctcaagctac caatagccac ttcacacatg gagagatgca agaccagtcc atttggggaa 780
atccttcgga tggtgaactc attagaaccc aacctcagcg cttgcctcag cttcagactt 840
cagcccaggt gccaagtggt gaggaaatag gcaagataaa gaacggccac acaggtctga 900
gcaatggaaa tggaattcac cacggggcca aacacggatc cgcagataat cgcaaacttt 960
cagcacctgt ttctcaaaaa atgcatagaa aaattcagtc cagcttgtct gtaaacagcg 1020
atatcagtaa gaagagcaaa gtaaatgctg tcttttccca aaagacaggc tcttcacctg 1080
aagattgttg tgtccactgt atcctggctt gcttgttctg cgaattcctg accctttgca 1140
acattgtcct gggacaagcg tcatgtggca tctgcacctc agaagcctgc tgctgttgct 1200
gtggtgacga gatgggggat gattgtaact gcccttgtga tatggactgt ggcatcatgg 1260
atgcctgttg tgaatcatca gactgcttgg aaatctgtat ggaatgctgt ggaatttgtt 1320
ttccttcata aatatttatc ttttgtttgt gttaaaactg gagagtgttt aaaaatttcc 1380
ttttgggggg aagaaaagca cattgtaaga ttctcatgaa acaacatgga atttgcactg 1440
ttaactcatt attgtaagta atctctgaaa gcctttttac tttaaccaaa tctacatggt 1500
ttaatatgtg aaattttaac tactttaact agttttataa atttcttaat atgttacaat 1560
aacttaggga cattttgaca ccccccttcc caaatgttaa atgccttctc ctttttaccg 1620
atatttctgt ttcttttaac cgttctcagg agcactttgc tccaaatata ttatttttca 1680
gtgtgtattt aaacgaggca gtttattttg atatgtatct attcatgatt gaaaggaagc 1740
agtcttggcc aggcacggtg gcttacacct gtaaccctgg cattttggga ggccaaggtg 1800
ggcagattgc ctgagctcag gagttcgaga ccagccaggg caacatggtg aaaccccatc 1860
tctactaaaa tacaaaaagt tagctgggct tggcggtgtg cgcctgtagt cccagctact 1920
caggaggctg aggcaggaga attgcttgaa cccgagaggc ggaagttgca gtgagccgag 1980
attgtgccac tgaactccaa cctgcactcc agcctgggca acagagcgag actccatctc 2040
taaataaata aataaataaa taaataaata aataaataaa taaacaaacc agtctttatt 2100
ttaaaagaaa ctttaggaaa caaacccaca taatagttgg gaaccagtgt tgatctctct 2160
cccttacctt ctccacttgt tcaacagact ctgaatgccg actgtgtgga ctctcttcct 2220

```
cagactgtgg ggacagatac aattccactc ctgtccacag gaacatgaga tttagcagac   2280
taaggagatc tgtaaagaat gaaccatacc acaaggcata ctgaagtgag gattataaga   2340
gaaataaact caaaatgctg ttggaatatg cagagaattg ctaccagaat attcagtaag   2400
gtttcaggga gaatgtggca tttgaggact ctcttagaat gagtgattca cctgctattt   2460
aaatgaatta tttagatttt tgacaaagat ttaggtggac accctaaact gtgtgtgcct   2520
ttaaccagtt aaaagaacag tgccttcagc atactttttt attagttgta ggaatacagc   2580
tttttgaaaa agctataaag tttaaattaa ctaaaaatat gcattttctt acacataatt   2640
taaatgttat catacttttt tgatgaaaac ataatgcctt agtaaaatag ctctatttaa   2700
taaagaagat tgagtactct gacacatttc atttaaatta ggaaattttt aatattaaaa   2760
tcccagtgtt ctgagttatt gaaaggcttt cttttatttt gagagcttta ggtctttttg   2820
ggatgagaac attttagttg tttagtttgt ttcttaagca gtgctatttt ttgtaaacac   2880
agataaatgg aaaccattct tttcaatgca gaagaaatct agatatcccc tactgtgacc   2940
aaatttctgt attacgattt tatgttaaat taaactaata tggcaggtta taatgatcct   3000
taagtgtaaa gaaatcagtc aattacaaga gtaattgtat agttattgag acctatagtg   3060
tgtggcttag atgaaaggga gagtaaattt tcataccatg ctctctccta ctcagtttga   3120
tctctctaaa attgtagttt ggtttgattt aatataattc ttagtagaaa ttttgaaagt   3180
atgctttggg attaataatt atttttaatt tttctggctg aatatcaaat tgatagtaac   3240
aacagaagca taattttagg aaggctttcg caaacctagc cttttaagag aggtttttaa   3300
cctgaagcat gagaatatat cacctgtggt tttcctttg agatgaaacg tagtttctag    3360
ttatatcatt acttaaaggg cttaaaaaga aaaaacttag caaacttttg aatctttctt   3420
ttattgctat ttacacatac atacacacat acaaaacctt taaattttgg gatctgaata   3480
taattctggt aaacagctgt cttcattttt ctcctctaaa gaacttaatt catttgttac   3540
ataaaatata aggaaatctt tatactattt tacagtaacc acaatctaaa tatttacata   3600
tacccaaaat taacttatgc tcatatatta ggatgtgaga atatcatctg tttatggaca   3660
catgaaacct cctaatgacc tggaattgtt agaatatttg actttttata tgcaaagttt   3720
ttcaaccaag tggtttgtct aatatttaaa catgtactgg cacaatttgt gatgaaaata   3780
ttagcacatt tgcaataatg tttctccata acagagaatg ttaatggata ccagaatttt   3840
atttttgtat ttatgttcat agtacttttc ctcttgtcta ctccagacag ttattccata   3900
aagcatttgt ataattaaaa ggaaaacaga aaaaggaaaa gtaggcaaat gtgaaaatag   3960
tttcaatata tcttatgatt tcttaatgta aaatgttttg ttgaagtata tggctatcat   4020
gactaagtgc tagaatttat agttacaggc ggtgtccttt taaatgtgga aaggctttta   4080
aaatatttta aaactggacc tgtattatcc tgaatacact attttgaaaa tttttaaaaa   4140
tgacttcttt attttgcttt accgtatgtt tatatctaat tgacatattg actaatgttt   4200
gaaagaattc aaccataagt taaaatctga aggttatctt tatcatgttt catccctgtc   4260
tgaagatttc ctagtcttct tatgtaaatc acatgactca tgtccgtaaa tgaactatga   4320
aagatatcga tcagtttatg atcattgaca tgtgatttca aaacacagtg ttcttttaaa   4380
aatctataat atgtcaaaat acaagttttt tttttttaca tcgttttagt aagttaattt   4440
catttattta ctttggagct atatttccac ttagaaaaac taaggtaatt ttacaatata   4500
tgctgagatt aaaaaccaag gtaaaaatga tcaaacatat atgaaattga gtcttagatt   4560
```

```
taatgaattt cactcgaaaa taaatgatca gaagaatttt catctaaggc atagagtggc   4620
gaaatttttg taaatgctcg cagttagcat ctaactaaaa caatacagta tgactttatt   4680
taggagaagg ctttttattt agaaaattat tttttcattt ttacagtgta tcaactgtat   4740
ccattttcct cacctggata gtcaatgtta tctgagcagt tcaaggagta accaaggcaa   4800
ccttatgtaa taactttcca ttctttatcc atacaaactc tttcagtgcc ctagattcta   4860
atgttataaa cgtcaaacat cactgcccaa cataaataag actcgagact tattaacata   4920
aataagtatc ttgccttctt gaatgctagt taaatgctta gatttaccta actgcctaat   4980
gaatcaggtt atttgttaat aagattattt ttcaaattat ttaagacctt tatgcccctt   5040
ccaattactt gtgatttgta ggcctgtagg attgttgcat ctaatctgac tggcaacaga   5100
aaatgtcatc aaatactata atatccattt tgttttcttt tgcactaata caacagaaca   5160
tatcattttt gttttaaaca atggttaata tattaatagg gtttgttcca cacttactat   5220
ttatagtttt tataatcaag cattgggtat taaaagagaa tcctttcaac ccttcatctt   5280
cgtatgctta tacaataaat tgcagtgagt gt                                 5312
```

<210> SEQ ID NO 614
<211> LENGTH: 12739
<212> TYPE: DNA
<213> ORGANISM: Homo sapiens

<400> SEQUENCE: 614

```
agggaagaag ggagaaagag agagagattt gaatatacat tgcttcaagg atgcaaaaaa     60
ttacaacctg gaaaaggctt cgagtaactt taggaaaatg agctgctgga ctcctcagtc    120
aatctgtcct ttctagtcaa tgaaaaagac agggtttgag gttccttccg aaacggggcc    180
ggctaattta gcccctccca cgagcccaag ggtctgttat atctctgttt ccttgaggac    240
ctctctcacg gagacggacc acagcaagca gaggctgggg gggggaaaga cgaggaaaga    300
ggaggaaaac aaaagctgct acttatggaa gatacaaagg agtctaacgt gaagacattt    360
tgctccaaga atatcctagc catccttggc ttctcctcta tcatagctgt gatagctttg    420
cttgctgtgg ggttgaccca gaacaaagca ttgccagaaa acgttaagta tgggattgtg    480
ctggatgcgg gttcttctca cacaagttta tacatctata agtggccagc agaaaaggag    540
aatgacacag gcgtggtgca tcaagtagaa gaatgcaggg ttaaaggtcc tggaatctca    600
aaatttgttc agaaagtaaa tgaaataggc atttacctga ctgattgcat ggaaagagct    660
agggaagtga ttccaaggtc ccagcaccaa gagacacccg tttacctggg agccacggca    720
ggcatgcggt tgctcaggat ggaaagtgaa gagttggcag acagggttct ggatgtggtg    780
gagaggagcc tcagcaacta cccctttgac ttccagggtg ccaggatcat tactggccaa    840
gaggaaggtg cctatggctg gattactatc aactatctgc tgggcaaatt cagtcagaaa    900
acaaggtggt tcagcatagt cccatatgaa accaataatc aggaaacctt tggagctttg    960
gaccttgggg gagcctctac acaagtcact tttgtacccc aaaaccagac tatcgagtcc   1020
ccagataatg ctctgcaatt tcgcctctat ggcaaggact acaatgtcta cacacatagc   1080
ttcttgtgct atgggaagga tcaggcactc tggcagaaac tggccaagga cattcaggtt   1140
gcaagtaatg aaattctcag ggacccatgc tttcatcctg gatataagaa ggtagtgaac   1200
gtaagtgacc tttacaagac cccctgcacc aagagatttg agatgactct tccattccag   1260
cagtttgaaa tccagggtat tggaaactat caacaatgcc atcaaagcat cctggagctc   1320
ttcaacacca gttactgccc ttactcccag tgtgccttca atgggatttt cttgccacca   1380
```

-continued

```
ctccaggggg attttggggc attttcagct ttttactttg tgatgaagtt tttaaacttg   1440
acatcgagaa agtctctcag gaaaaggtga ctgagatgat gaaaaagttc tgtgctcagc   1500
cttgggagga gataaaaaca tcttacgctg gagtaaagga gaagtacctg agtgaatact   1560
gcttttctgg tacctacatt ctctccctcc ttctgcaagg ctatcatttc acagctgatt   1620
cctgggagca catccatttc attggcaaga tccagggcag cgacgccggc tggactttgg   1680
gctacatgct gaacctgacc aacatgatcc cagctgagca accattgtcc acacctctct   1740
cccactccac ctatgtcttc ctcatggttc tattctccct ggtccttttc acagtggcca   1800
tcataggctt gcttatcttt cacaagcctt catatttctg gaaagatatg gtatagcaaa   1860
agcagctgaa atatgctggc tggagtgagg aaaaaaatcg tccagggagc attttcctcc   1920
atcgcagtgt tcaaggccat ccttccctgt ctgccagggc cagtcttgac gagtgtgaag   1980
cttccttggc ttttactgaa gcctttcttt tggaggtatt caatatcctt tgcctcaagg   2040
acttcggcag atactgtctc tttcatgagt ttttcccagc tacacctttc tcctttgtac   2100
tttgtgcttg tataggtttt aaagacctga cacctttcat aatctttgct ttataaaaga   2160
acaatattga ctttgtctag aagaactgag agtcttgagt cctgtgatag gaggctgagc   2220
tggctgaaag aagaatctca ggaactggtt cagttgtact ctttaagaac ccctttctct   2280
ctcctgtttg ccatccatta agaaagccat atgatgcctt tggagaaggc agacacacat   2340
tccattccca gcctgctctg tgggtaggag aatttctac agtaggcaaa tatgtgctaa    2400
agccaaagag ttttataagg aaatatatgt gctcatgcag tcaatacagt tctcaatccc   2460
acccaaagca ggtatgtcaa taaatcacat attcctaggt gatacccaaa tgctacagag   2520
tggaacactc agacctgaga tttgcaaaaa gcagatgtaa atatatgcat tcaaacatca   2580
gggcttacta tgaggtaggt ggtatataca tgtcacaaat aaaaatacag ttacaactca   2640
gggtcacaaa aaatgcatct tccaatgcat atttttatta tggtaaaata tacataaata   2700
taattcacca ttttaacatt taattcatat taaatacgta caaatcagtg acatttagta   2760
cattcacagt gttgtgccac catcaccact atttagttcc agaacatttg catcatcaat   2820
acattgtcta gagacaagac tatcctgggt aggcagaaac catagatctt ttgtgtttac   2880
agctatggaa accaactgta ccataaagat agttcactga gttttaaagc caagccacat   2940
cttatttttc caaggtttaa tttagtgaga gggcagcatt agtgtggagt ggcatgcttt   3000
tgccctatcg tggaatttac acatcagaat gtgcaggatc caagtctgaa agtgttgcca   3060
cccgtcacac aacatgggct ttgtttgctt attccatgaa gcagcagcta tagaccttac   3120
catggaaaca tgaagagacc ctgcacccct ttccttaagg attgctgcaa gagttacctg   3180
ttgagcagga ttgactggtg atgtttcatt ctgaccttgt cccaagctct ccatctctag   3240
atctggggac tgactgttga gctgatgggg aaagaaaagc tctcacacaa accggaagcc   3300
aaatgtcccc tatctcttga atgatcaagt cacttttgac aacatccagg tgaatataaa   3360
aacttaataa agctgtggaa aggaactctt aatcttcttt tctgctactt aggttaaatt   3420
cactagatct tgattaggaa tcaaaattcg aattgggaca tgttcaaatt ctttcttgtg   3480
gtagttgcct atactgtcat cgctgctgtt ggttgagcat ttgtggtgta ccacgctgtg   3540
tgctcaaggg tattacattc atcttctcat ttaatcctca caacaatctg aagaaggtag   3600
gtattacaat tcccacttca tagaaacaga aactgaggtt cagagaggtt aagtcatttg   3660
cccaaatggc tgagccaaag cctaccatgt acctaacctt tattttcttt cccgaacata   3720
```

-continued ccaggctgtc tcctcataac ttccaagcat gcacttaaaa ctccacatga atacaaggtt 3780
catgggactt ggtattcata gaaagggagg cagaaagctg gtctgttcct gataggcttg 3840
taatttaata tcattctgtt catgtgcttt ggatggaagc acatctggca tatgatgcta 3900
atcagtggtt cccatacccc tggcttccta attttaatgt ttgctcacag catagtagat 3960
tgacatcaaa tagtggccga tgatgatgaa aataaaggtc aaataagttg agccaataac 4020
agccgctttt ttccttctgt ctgcgtatac aaagcactgt catgcacaca atctattctg 4080
accctcacaa caacccataa gggtgtaaat agtatttcca ttttacaaat gaggatcaca 4140
caaactacta catggcagag cagatactcc aactcatgtc ttctggttga agcctattgc 4200
tttttctttt ctaaacactt tccctcagca agttggaatt agacttcaca agtctccttc 4260
agagaacaca aatcttttct tattccattc ctgtttggtt gcctacgtcc aatctccccc 4320
tccccagaga tgccaaaaaa aaaatccttt aaggtatttg ggagccaaac tcaacttgtt 4380
aaaatctcaa attatggaga caatcagcag acacaaccta accccaatta ttttggcagg 4440
aaggttggtt tagaggcaga tccagcaatc tgctttgggc cactctgggt ggggtaggtg 4500
aaataagatt ggtcactgtt aactaatttt aatattggat tggccattgg ttatcactga 4560
ttaccattct cccctggatt ttcacccagg actcaaaact tggttctgct aaccctgttc 4620
ctttatgagg aaccttttaa agattccttt ataaggtggg agttttttttt ctatgaacct 4680
ataggggaga aaaaagatca gcagaagtca ttactttttt tttttttttt tttttttttt 4740
gagagagagt ctcactccat tgcccaggct ggagtgcagt ggtgctatct cggctcactg 4800
caacctccgc ctcctgggtt caagcaattc tcctgcctca gcctcccgag tagctgggat 4860
tgcaggtgcc caccaccaca cccggctaat ttttgtattt ttagtaaaga cagggtttca 4920
ccatgttggc caggctggtc tccaactccc aatctcaggt gatcctattg cctcgggctc 4980
ccaaagtgct gggattacag gagtgagcca ccatgcctgg ccagaagtgg ttacttctgt 5040
agacaaaaga ataatgctac ttaatcaggc tttctgtgtg acaagaaaga gaaagaaaat 5100
aaagaagttt caattcatcc aattcttaat aagaaatatg taaataaaat tttttaaaat 5160
tacacttcat tttaatgttg tatcagtcaa ggtccctgca agagatggat ggtatggtac 5220
actcaaactg ggtaacacag gagagttttc agaaagcaac taaatccaaa atactatcaa 5280
ggaatcaata taaaaattgt taatattttt ctcatactaa attttcaaaa tattttgtgt 5340
ctattacatt tacagcacat cttaattagg actagctgtg tgttcacctc acatgtggct 5400
tgtagctacc atactggaca gcacatgtcc aaaaaaatac acgtaaagtt aaagtttaaa 5460
agacacagga actaagccct cattgtcttt cccttgggag gtagtttaaa gagctataga 5520
tgctgtaaca ttcttgctat tatttattat atatgacatt attcctaaaa aagcttttga 5580
gatcctaggt tgtattcctc aggttttgtt gccttcccat gaagatgtga aggcagggat 5640
gcctgttatt cagtccaaga tgcatgacaa gagaccttgg gaaagtttca tctggattta 5700
aagattaatt cttgatgctt acattccata ctcaaaatgt aaatttgaat attaaaataa 5760
agatgatttt ttttttggag ctagtcttgc tctgttgccc aggctggaat gcagtggcat 5820
gatcatggct cactgcagcc tcgacctccc aagctcaagc aaggctacag gtgtgcacct 5880
aagtagctag gactacaggt gtgcaccacc atgtctagct attttttttt ctgtagagac 5940
agggttttcc tatgttgtcc aggctggtct cgaactcctg ccctcaagca atcctcctgc 6000
cttggcctcc caaagtgttg agattacagg cgtaagccac tgcacctggc caagatgaat 6060
attttaatag ctcacagaac aaagtttgcc acataatgat aaaattacta tgaaaatata 6120

-continued

```
ttccctttat tgtcagttta aaagatgaac tgagtttcac ccaaactggt ctggcccctc   6180
tctgattcaa ataccaatag ttgctctgat tcaaattcca actgttagaa catgacagct   6240
gctcataact agctttgctt actaaccatg tttctttcca tttgtattag gtcctttact   6300
ttttataaca gcctcaaagt ttcatgaatt gctgcagtaa acattgattt tcatgtttgt   6360
gagtctgcaa gccagctggg cagctctact tcaggtggta agggtggatc agacctattc   6420
catatacctc ttgttctcct tgtccagtgg tttctaggga tatgttctca tgatgaaccc   6480
cgcagaggct cgtgaaagtg agaggaaact aggatgcctc ttaaggtctt ggtcaggatg   6540
gggtctcctg tcacttctgt cacaggctat tgtaagtcat atgagcaagc tcaataaaat   6600
ataaacaagt cagataaaca gtgggaggaa tggcaaagtc atatggccaa ggccatgagt   6660
gattaatttt aacacaggaa aaaagtaaag cattaaatgc gattatttaa tatacaatgt   6720
cttattaact gaaatataaa atgtgtttac tgtaaaatat aatctgttta tctcaccaaa   6780
gaaatattat ctttaaaaaa tgtcattact tctaagacat catcagtctg caacttcttt   6840
ccatagcctt aatcaggatg ctgtggcagc tcccacatta gcctcgcatt ctaaactggt   6900
agatgtccta ggaaaccata catctatgta tttttcttat tttatacgtt taggacaatg   6960
tatagctaat tacccaactt tttatttgca tacaaatcta atacaactga acacaatcag   7020
ttttatcaca ggtataatgg atttttcaat agtgaggagg tgcctccatg agccttctct   7080
ttagaaaagt ggcattcaag actcttcatt tgaagtgaag attgctatgt cttttgcatt   7140
gctctatttt acataaatta agttataaat tgacactata atcaactgac accatgatca   7200
gtgatgatga tcaccctcat cagcactaga gttgacttgt ttttataacc cctttgcatg   7260
tatgttgaat agcaaagttc atcagagaac atgtattagt caatggtaag taagatactc   7320
tcatctaaga aataacatca cctcttctaa tgaagttcta agaagagagg gaagaaaaag   7380
tcttgggagc tagtcaggga atagtgtgta tttgcaatta cctaaactga actctaccat   7440
tactcctaac ccagttcctc ctcctgtgtt ttacatgatt aatgccaccc ctgcctcaat   7500
gaaccaagat cagctccatc actgggacct ccccattctg cctgtgcaat atttttcttt   7560
tttatttctc cttctaatat tactgttatt gctccagtaa agagctgtaa tatattttac   7620
ctggactgat accaggaatg gtggtgttgc ttccaatctg ttgctgctag attaatcttt   7680
gcaaagcaca ggcttaattt cattgctgct caactaaaac cactggtggc tttccattgc   7740
ctacaaaata aagtcaacct ccccatcaga cattcaaggc tttcaatgat ccatggccgc   7800
cagctctctc caggctcata tcccactcca ctcctctgat gtttcctaca ctacactaca   7860
ctatactaca ctacagccag gtagaatgac tgttcaccca acaccactca ggttgtcttc   7920
tcaacttgga atactcttgc accttcaaag ctcatttcaa atgccccttc atttgtgaag   7980
ccttctccaa atttccaagt cagaatgtct cttccttgtg ctaccacaac cctttaactg   8040
agcctccatt agtgcactga gaccattctg ttcagtgtct gggtgaagct tcctggtgaa   8100
aaatatgtta cctatttctt tctgaaaagt tggattcagg gatattatca cggacctaag   8160
gtaatagttc tagccaacct ccctgtccac tgccaggccg actacaaacc cttctgttgc   8220
tggcgagctg gtccgcacca ctagttctgc ttcactctat ttatctcttg atgtaaccat   8280
cttctttctc caggttttaa gaaccagccc aactcctggt tccctgatga agcttttatt   8340
cccctagcca catggaactt ttcctttttg gaacatgcct ttagtttctg tgtagtttgc   8400
catgcagcac ttcattgtac acattattaa aacagaattt taaggattag aatgaacctt   8460
```

-continued

```
aaaagatcat gcatctcaaa atttaatgta catacaaatt acccagggat tttgttgaaa   8520
taaaaattat ttaattttaa ttaatataaa taattcagta ggtctggggt gaggcctgag   8580
gttttacatt tccaacaagc tgccaggtaa agccaataca tctgtccagg aatcacactt   8640
tgcgtatcaa aggtctagat gacattatca ttccaaagag tttcttttac aggctctcag   8700
atcagtgttc atccactacc tgactactgt cattcacagg cattctgttc cacagcaggc   8760
cagctaacgt ggtatttaca aagctcactc ctcttataca acaatccaag tgtttctttt   8820
gtcagttgtc tgtgccccag gagatccctc tctgccttgc cttgccctct gcctttggag   8880
accagcacct catactcagt gaaggcctgg agtgcttaag agggatttct tccagctctc   8940
ttgccctggt cttcagtgta ttagatgtat tacctccatg ctctcagtag aggcccatag   9000
gaaagagtag gtaggttatg ccagctcaca cgcatccttt aaaaatggtt tagaagttta   9060
gctggtttct tattactcct gtctatggat gtttccttct gtcactctac tagggatgaa   9120
acagctaatc atgttcaata gttacattta gattggtttt taaaaactat gattgtatta   9180
gttcgtttcc atgctgctga taaagacata tctgagactg gaaacaaaaa gggtttaatt   9240
ggacttacag ttccacatgg ctggggaggc ctcaaaatca ggtgggaggc aaaaggtact   9300
tcttacgtgg tggcatcaag agcaaaatga ggaagaagca aaagcagaaa ctcttcataa   9360
acccaccaga tcttgtggga cttattatca cgagaatagc acagaaaaga ctggcctcca   9420
tgattcaatt acctcccact gcgtccctcc cacaacatgt gggaattctg ggagatacaa   9480
ttcaagttga gatttgggtg gggacacagc caaaccatat cattcctccc tgggctcctc   9540
caaatttcat aatcctcaca tttcaaaacc aatcattcct tcccaacagt tccccaaagt   9600
cttaactcat ttcagcatta acccaaaagt ccacagtcca aagtctcatc tgagacaagg   9660
caagtccctt ccacttacaa gcctgtaaaa gcaagctagt tacctcctag atacaatggg   9720
gggtacaggt attgggtaaa tacagctgtt ccaaatgaga gaaattggcc aaaacaaagg   9780
ggttacaggg tccatgcaag tctgaaatcc agtggggcag tcaaatttta aagctccata   9840
atgatctcct ttgactccat gtctcacatt caggtcatgc tgatgcaaga gataggttcc   9900
catggtcttg tgcagctccg cccctgtggc tttgcagagt acagcctccc tcctggctgc   9960
tttctcaggc tgatgttgag tgtctgtagc ttttccaggc acaagatgca agttggtggt  10020
tgatctacca ttctggggtc taccattctg gggtctaccg ttctgggact gtggccttct  10080
tctcacagct ccactaggca gtgccccaac agggactctg tgtgggggct ctgccccaca  10140
tttcccttcc acactgccct aggagaggtt ccccatgagg gctctgcccc tgcagcaaac  10200
ttttgcctgg acatccaggt gtttccatat atattctgaa atctaggcag aggttcccaa  10260
atctcaattc ttgacatctc tgcacccaca ggctcaacat cacatggaag ctgccaatgc  10320
ttggggcctc taccctctga agccacagcc caagctctat gttggctcct ttcagccatg  10380
gctggagcag ctgggacaca gggcaccaag tccctaggct gcacacagca cagagaccct  10440
gggcccagcc cacaaaacca ctttttcctc ctgggcctct gggcctgtga tgggaggggc  10500
tgccatgaag gtctctgaca tgacctggag acattttccc catggtcttg gggattaaca  10560
ttaggctcct tgctgcttat gcaaatttct gcagccagct tgaatttctc cttaaaaaaa  10620
atgggttttt cttttctact gcatcatcag gctgcagatt ttccacattt atgctcttgt  10680
ttccctttta aaacagaatg tttttaacag cacccaagtc accttttgaa tgctttgctg  10740
cttagaaatt tattccacca gataccctaa gtcatctctc tcaagctcta agttccacaa  10800
atctctaggg caagggtgaa atgctgccag tctccttgct aaaacataac aagggtcacc  10860
```

tttacttcag ttcccaacaa ggtcttcatc tccatctgag accacctcag cctggacctt 10920
attgttcata tcactatcag tatttttgtc aatgccattc acagtctcta ggaggttcca 10980
aactttccta cattttccta tcttcttctg agccctccag attatttcaa cacccagttc 11040
caaagttgct tccacatttt cgggtatctt ttcagcaatg ccccactcta ctggtactat 11100
tagtccattt tcatgctgct gataaagaca tacctgagac tgggaacaaa aagaggttta 11160
attggactta tagttccacc tggctgggga ggcctcagaa tcatggcagg aggtgaaagg 11220
catttcttac acggcagcag caagagaaaa atgaagaagc agcaaaagca gaaacccctg 11280
ataaaaccat cagatctcgt gagacttatt cactatcaca agaatagcat gggaaagacc 11340
agcccccttg attcaattac ctccccctgg gtcctgtggg aattctggaa ggtacaattc 11400
aagttgagat ttgggtgggg acacagccaa accatatcaa tgattttgta ctttaaccag 11460
ctgaatggaa gtacaatctc ttgctatatg acacaataat tatttgcaaa atgagtaaac 11520
atatcataag gaaattattt ttacaaggtt tgaaacctga aatgcagtct attatcatac 11580
ataactaaaa atagagcctc aataaacaga ttcccagttt tgaaaatgca acatttgtac 11640
tccacattgt cagttttctt aggtatattt ataaatactc ctataaaaat gtaaagaaac 11700
acataatgta gattgctaat tttataataa cacaagttga ttttgacatc caacttatta 11760
attatgaaat gacttttggc ctagtaacaa tgaaaatggg ggcaaataca gataaatggt 11820
aattcttaga atgaactact cagcaccaat tctaagtttt tcttgatggt aaatcataat 11880
gttccctttc tcctcggttc tgcaatctat aggcatacca taattgtaat caatagctta 11940
aaaatatgtc tctctgtcct attctgtatc tgtatctctt ggatttttac ctttgcaata 12000
gtcaactgaa ccatcttctt ggagtactca tgaagatgga agtctacatg gagaatacag 12060
gatgaatcca ctctgtctcc tgcagtgaag tctgtttgaa ggatgtattt ggctgtcttc 12120
tggacaggcc attctaataa cagaaacaaa caagttattt taaaacttat tggaatattc 12180
aaatattaac caaagtagaa aaatataata cacatccatg tgcccatcac agaacttcac 12240
tgattatcat catttagcca gtcttgaaga agcaagtgct aattacaatc acaaatgaaa 12300
caagattcag acttcatgaa gagcactgcg ctataataaa agaagaaatg agcacataca 12360
ttcttttact gacagtcaaa tggtgaaggt gggcagaatc attatgtgat gcaacatggc 12420
aaaagtatac agacagtgca tccagaggaa ggcaccttgc tgaatgacta gaatggaagt 12480
aggagacatt ttgcaggccc ccttcatcct gcagggagaa ccagaaccac agcagctcta 12540
tttgcctatt cctctttaaa ttacaaagtt aaaatttggg agtagtagaa aatcaattgg 12600
ttatcttata gagtctccta gaatatttca ttggcattga gaaggtggaa aatgcaaatt 12660
atatacttta aaatgtaatt tttgcttttc acatatgctt aaagcctaaa acctcttaat 12720
aaacttcttc tgaaatata 12739

<210> SEQ ID NO 615
<211> LENGTH: 3824
<212> TYPE: DNA
<213> ORGANISM: Homo sapiens

<400> SEQUENCE: 615
ggagagtgtc tctaaggtga cactcgggtg cgcggcagca gcggcggttg caggagctcg 60
ctctccgccc gggctccggc tccgctccag ccgtccgggg ggcgccgcgg cgcgcagagc 120
gcagcacccc gactccagcc aggagccccc gcccccccgg agcgcaggag gaccccggcc 180

-continued

```
cgcctctccc aggcgcagcg cccagcatct cgctgctcct gtcgtctaag cgtcggcgtc    240
gctagggacc tgcggaaccc ggcgctcccc tccctccccg cctcgcgtcc ccggcccggg    300
cggactggag actcgaactt gagcgggtgc ccgaaaggcc gcaggagccg cgggcggaag    360
gcggccgcac gatggccgag gggcagggcg gcggagggca gcgctgggac tgggctggcg    420
gcggccgggc agccgaggag gaggtggtgc ggcggcgatg ccggcgcggg gaggaggccc    480
aggtcgcgca gccctggccc gagggttccc ggggcacggc cgctgggccc ccggtggagg    540
agcgtttccg ccagctgcac ctacgaaagc aggtgtctta caggaaagcc atcaccaagt    600
cgggcctcca gcacctggcc cccccctccgc ccacccctgg ggccccgtgc agcgagtcag    660
agcggcagat ccggagtaca gtggactgga gcgagtcagc gacatatggg gagcacatct    720
ggttcgagac caacgtgtcc ggggacttct gctacgttgg ggagcagtac tgtgtagcca    780
ggatgctgaa gtcagtgtct cgaagaaagt gcgcagcctg caagattgtg gtgcacacgc    840
cctgcatcga gcagctggag aagataaatt tccgctgtaa gccgtccttc cgtgaatcag    900
gctccaggaa tgtccgcgag ccaacctttg tacggcacca ctgggtacac agacgacgcc    960
aggacggcaa gtgtcggcac tgtgggaagg gattccagca gaagttcacc ttccacagca   1020
aggagattgt ggccatcagc tgctcgtggt gcaagcaggc ataccacagc aaggtgtcct   1080
gcttcatgct gcagcagatc gaggagccgt gctcgctggg ggtccacgca gccgtggtca   1140
tcccgcccac ctggatcctc cgcgcccgga ggccccagaa tactctgaaa gcaagcaaga   1200
agaagaagag ggcatccttc aagaggaagt ccagcaagaa agggcctgag gagggccgct   1260
ggagaccctt catcatcagg cccacccccct ccccgctcat gaagcccctg ctggtgtttg   1320
tgaaccccaa gagtgggggc aaccagggtg caaagatcat ccagtctttc ctctggtatc   1380
tcaatccccg acaagtcttc gacctgagcc agggagggcc caaggaggcg ctggagatgt   1440
accgcaaagt gcacaacctg cggatcctgg cgtgcggggg cgacggcacg gtgggctgga   1500
tcctctccac cctggaccag ctacgcctga agccgccacc ccctgttgcc atcctgcccc   1560
tgggtactgg caacgacttg gcccgaaccc tcaactgggg tgggggctac acagatgagc   1620
ctgtgtccaa gatcctctcc cacgtggagg aggggaacgt ggtacagctg gaccgctggg   1680
acctccacgc tgagcccaac cccgaggcag ggcctgagga ccgagatgaa ggcgccaccg   1740
accggttgcc cctggatgtc ttcaacaact acttcagcct gggctttgac gcccacgtca   1800
ccctggagtt ccacgagtct cgagaggcca acccagagaa attcaacagc cgctttcgga   1860
ataagatgtt ctacgccggg acagctttct ctgacttcct gatgggcagc tccaaggacc   1920
tggccaagca catccgagtg gtgtgtgatg gaatggactt gactcccaag atccaggacc   1980
tgaaacccca gtgtgttgtt ttcctgaaca tccccaggta ctgtgcgggc accatgccct   2040
ggggccaccc tggggagcac cacgactttg agccccagcg gcatgacgac ggctacctcg   2100
aggtcattgg cttcaccatg acgtcgttgg ccgcgctgca ggtgggcgga cacggcgagc   2160
ggctgacgca gtgtcgcgag gtggtgctca ccacatccaa ggccatcccg gtgcaggtgg   2220
atggcgagcc ctgcaagctt gcagcctcac gcatccgcat cgccctgcgc aaccaggcca   2280
ccatggtgca gaaggccaag cggcggagcg ccgcccccct gcacagcgac cagcagccgg   2340
tgccagagca gttgcgcatc caggtgagtc gcgtcagcat gcacgactat gaggccctgc   2400
actacgacaa ggagcagctc aaggaggcct ctgtgccgct gggcactgtg gtggtcccag   2460
gagacagtga cctagagctc tgccgtgccc acattgagag actccagcag gagcccgatg   2520
gtgctggagc caagtccccg acatgccaga aactgtcccc caagtggtgc ttcctggacg   2580
```

ccaccactgc cagccgcttc tacaggatcg accgagccca ggagcacctc aactatgtga 2640
ctgagatcgc acaggatgag atttatatcc tggaccctga gctgctgggg gcatcggccc 2700
ggcctgacct cccaaccccc acttcccctc tccccacctc accctgctca cccacgcccc 2760
ggtcactgca aggggatgct gcaccccctc aaggtgaaga gctgattgag gctgccaaga 2820
ggaacgactt ctgtaagctc caggagctgc accgagctgg gggcgacctc atgcaccgag 2880
acgagcagag tcgcacgctc ctgcaccacg cagtcagcac tggcagcaag gatgtggtcc 2940
gctacctgct ggaccacgcc cccccagaga tccttgatgc ggtggaggaa aacgggggaga 3000 cctgtttgca ccaagcagcg gccctgggcc agcgcaccat ctgccactac atcgtggagg 3060
ccggggcctc gctcatgaag acagaccagc agggcgacac tccccggcag cgggctgaga 3120
aggctcagga caccgagctg gccgcctacc tggagaaccg gcagcactac cagatgatcc 3180
agcgggagga ccaggagacg gctgtgtagc gggccgccca cgggcagcag gagggacaat 3240
gcggccaggg gacgagcgcc ttccttgccc acctcactgc cacattccag tgggacggcc 3300
acggggggac ctaggcccca gggaaagagc cccatgccgc cccctaagga gccgcccaga 3360
cctagggctg gactcaggag ctgggggggc ctcacctgtt cccctgagga ccccgccgga 3420
cccggaggct cacagggaac aagacacggc tgggttggat atgcctttgc cggggttctg 3480
gggcagggcg ctccctggcc gcagcagatg ccctcccagg agtggagggg ctggagaggg 3540
ggaggccttc gggaagaggc ttcctgggcc ccctggtctt cggccgggtc cccagccccc 3600
gctcctgccc caccccacct cctccgggct tcctcccgga aactcagcgc ctgctgcact 3660
tgcctgccct gccttgcttg gcacccgctc cggcgaccct ccccgctccc ctgtcatttc 3720
atcgcggact gtgcggcctg gggtgggggg gcgggactct cacggtgaca tgtttacagc 3780
tgggtgtgac tcagtaaagt ggattttttt ttctttaaaa aaaa 3824

<210> SEQ ID NO 616
<211> LENGTH: 2664
<212> TYPE: DNA
<213> ORGANISM: Homo sapiens

<400> SEQUENCE: 616
attggaggag cgctcccact cccaagaggc cacgcgtaga cggggcgctt catgcggaag 60
tcagcggcgt ccggtcccag cctcctctgg gagcgggcag ttggcgaccc tgcactgacc 120
cgcgtccctc cgtcccgagc ccgcgcgccc tcagagggtg cccggacaga ctgaagccat 180
ggcgattctt tttgctgttg ttgccagggg gaccactatc cttgccaaac atgcttggtg 240
tggaggaaac ttcctggagg tgacagagca gattctggct aagatacctt ctgaaaataa 300
caaactaacg tactcacatg gcaattattt gtttcattac atctgccaag acaggattgt 360
atatctttgt atcactgatg atgattttga acgttcccga gcctttaatt ttctgaatga 420
gataaagaag aggttccaga ctacttacgg ttcaagagca cagacagcac ttccatatgc 480
catgaatagc gagttctcaa gtgtcttagc tgcacagctg aagcatcact ctgagaataa 540
gggcctagac aaagtgatgg agactcaagc ccaagtggat gaactgaaag gaatcatggt 600
cagaaacata gatctggtag ctcagcgagg agaaagattg gaattattga ttgacaaaac 660
agaaaatctt gtggattctt ctgtcacctt caaaactacc agcagaaatc ttgctcgagc 720
catgtgtatg aagaacctca agctcactat tatcatcatc atcgtatcaa ttgtgttcat 780
ctatatcatt gtttcacctc tctgtggtgg atttacatgg ccaagctgtg tgaagaaata 840

-continued

```
ggaaagaaga agttaccatt aaccaaggat atgagagaac aaggagttaa aagcaatcca    900

tgtgactcaa gcctttcaca tactgacaga tggtatctgc cagtctcttc aaccctcttc    960

tcacttttta aaatcttgtt ccatgcctcc aggtttatct ttgtcttatc taccagttta   1020

ttcctgtgaa cttcagattg aaccattcat tgcagcagta gccttaaaaa ggcttttgtt   1080

tatttctttg gtttgttaac tagtgtcatc tatttagaga aacatttttg tttttaattg   1140

ctcaaagctg tcgccgctag tcttatgagc tatctactaa aactatggag aaactttgta   1200

tgtgcacaca aaagtattca agagacagta ttgctaacat ctcatcttaa tgtcttttgt   1260

tattgagaag ttttaggtgc ttcaaaacaa tataaatgga taatagttgt tatttgggga   1320

attgtaatga tgttggtgct gcttccttct aagagctcag acaagtaaag tatgaaacat   1380

tcttatttca gttagatggg gaacattttg ctagcccatt agaagcacac agaattatcc   1440

ttgtcctcct aatattgact ttcaggaata aagttcagtg tgctgatcat tcacaataca   1500

gtggatagct tgatatcttc tgttttccca ttgcagttga tttgagaaga tgaaggttta   1560

aatattgttg aaagttgcag ttttttaaat gtgttccttt ttcttctgtg aatatttagg   1620

gcaatcgtgt cgctaataga atatgtagta gagggggtgg ggaggtaaat tcctctgact   1680

tgccaaagaa aaagaaggga accacagtgg atatgctagc attttagctg tgcaaaggga   1740

ggtagtgtgg gaaaagtgtt tccattctgg gaaaagccca aaccgaatac ggtcagcagt   1800

caactccagg gtttgggctt gattcctgtt gaataatagt tttgagcatt ctttgtggtt   1860

aaataaattc ttaaatctgc ctagttttga tgaattcttt tgtgaaactt gaaagagaat   1920

agacagtatg acatatagaa ttaatacaaa acagtttaac aaccatttaa ctgcagtgta   1980

agaaaattgg actgtaatca tatcgctact ggcatctgtt atctagtatg catttctggt   2040

gtgtatctga aaggaagaca ttttctaccc tagatccaat tgcatttatt tatcaataag   2100

tgccattaaa ttgaaattat attacatttt acactttctc aatgaatgaa caaattagtc   2160

tgtagaatct agccacctgt ttagcctagt catgtgcctt gaacatatat gtgtcccata   2220

atctggctca tggtacctgt tcttctatcc aaacctttca attcatgcta cctgattcat   2280

ttatttgaca tagatcttag gcccacttga actcttttct tgtttatcta gcatagcaca   2340

aacgttttc cagtcttctt tatcaacact aatgcctctt aattgcatca gtatttccta   2400

ttggaaaata catctgttcc agaaaaacat ttggcattcc tgaataattt ccaaatgttt   2460

ttaatccaaa gaaaaaggtt taaagcttat ttccctttct tatacacacc tgaataaaat   2520

tgatgtgcat gttttaggga tcaattacct aactgttcct tggtctattt atgtataaga   2580

atgcttttta aagcacatgt ctcattttaa atgacgcaca aactgaagat gttaataaaa   2640

tttaagagta atacaatgaa aaaa                                          2664
```

<210> SEQ ID NO 617
<211> LENGTH: 8155
<212> TYPE: DNA
<213> ORGANISM: Homo sapiens

<400> SEQUENCE: 617

```
gcagagtctg cagtgcggag ggggcgggaa gtccaggccc cgcactcgat ccacgctggc     60

tccctacgga ggcccaccta ctcgaggccc accgactcct actgcaatca gtactatgcg    120

atcgtcctag agagtccatt cagctgcact tccgcctcag tatggcatca cagctgcaag    180

tgttttcgcc cccatcagtg tcgtcgagtg ccttctgcag tgcgaagaaa ctgaaaatag    240

agccctctgg ctgggatgtt tcaggacaga gtagcaacga caaatattat acccacagca    300
```

-continued

```
aaaccctccc agccacacaa gggcaagcca actcctctca ccaggtagca aatttcaaca    360
tccctgctta cgaccagggc ctcctcctcc cagctcctgc agtggagcat attgttgtaa    420
cagccgctga tagctcgggc agtgctgcta catcaacctt ccaaagcagc cagaccctga    480
ctcacagaag caacgtttct ttgcttgagc catatcaaaa atgtggattg aaacgaaaaa    540
gtgaggaagt tgacagcaac ggtagtgtgc agatcataga agaacatccc cctctcatgc    600
tgcaaaacag gactgtggtg ggtgctgctg ccacaaccac cactgtgacc acaaagagta    660
gcagttccag cggagaaggg gattaccagc tggtccagca tgagatcctt tgctctatga    720
ccaatagcta tgaagtcttg gagttcctag gccgggggac atttggacag gtggctaagt    780
gctggaagag gagcaccaag gaaattgtgg ctattaaaat cttgaagaac cacccctcct    840
atgccagaca aggacagatt gaagtgagca tcctttcccg cctaagcagt gaaaatgctg    900
atgagtataa ttttgtccgt tcatacgagt gctttcagca taagaatcac acctgccttg    960
tttttgaaat gttggagcag aacttatatg attttctaaa gcaaaacaaa tttagcccac   1020
tgccactcaa gtacatcaga ccaatcttgc agcaggtggc cacagccttg atgaagctca   1080
agagtcttgg tctgatccac gctgacctta agcctgaaaa catcatgctg gttgatccag   1140
ttcgccagcc ctaccgagtg aaggtcattg actttggttc tgctagtcac gtttccaaag   1200
ctgtgtgctc aacctactta cagtcacgtt actacagagc tcctgaaatt attcttgggt   1260
taccattttg tgaagctatt gatatgtggt cactgggctg tgtgatagct gagctgttcc   1320
tgggatggcc tctttatcct ggtgcttcag aatatgatca gattcgttat atttcacaaa   1380
cacaaggctt gccagctgaa tatcttctca gtgccggaac aaaaacaacc aggtttttca   1440
acagagatcc taatttgggg tacccactgt ggaggcttaa gacacctgaa gaacatgaac   1500
tggagactgg aataaaatca aaagaagctc ggaagtacat ttttaattgc ttagatgaca   1560
tggctcaggt gaatatgtct acagacctgg agggaacaga catgttggca gagaaggcag   1620
accgaagaga atacattgat ctgttaaaga aaatgctcac aattgatgca gataagagaa   1680
ttacccctct aaaaactctt aaccatcagt ttgtgacaat gactcacctt ttggattttc   1740
cacatagcaa tcatgttaag tcttgtttttc agaacatgga gatctgcaag cggagggttc   1800
acatgtatga tacagtgagt cagatcaaga gtcccttcac tacacatgtt gccccaaata   1860
caagcacaaa tctaaccatg agcttcagca atcagctcaa tacagtgcac aatcaggcca   1920
gtgttctagc ttccagttct actgcagcag ctgctactct ttctctggct aattcagatg   1980
tctcactact aaactaccag tcagctttgt acccatcatc tgctgcacca gttcctggag   2040
ttgcccagca gggtgtttcc ttgcagcctg gaaccaccca gatttgcact cagacagatc   2100
cattccaaca gacatttata gtatgtccac ctgcgtttca aactggacta caagcaacaa   2160
caaagcattc tggattccct gtgaggatgg ataatgctgt accgattgta ccccaggcac   2220
cagctgctca gccactacag attcagtcag gagttctcac gcagggaagc tgtacaccac   2280
taatggtagc aactctccac cctcaagtag ccaccatcac accgcagtat gcggtgccct   2340
ttactctgag ctgcgcagcc ggccggccgg cgctggttga acagactgcc gctgtactgc   2400
aggcgtggcc tggagggact cagcaaattc tcctgccttc aacttggcaa cagttgcctg   2460
ggtagctct acacaactct gtccagccca cagcaatgat tccagaggcc atggggagtg   2520
gacagcagct agctgactgg aggaatgccc actctcatgg caaccagtac agcactatca   2580
tgcagcagcc atccttgctg actaaccatg tgacattggc cactgctcag cctctgaatg   2640
```

-continued

```
ttggtgttgc ccatgttgtc agacaacaac aatccagttc cctcccttcg aagaagaata   2700
agcagtcagc tccagtctct tccaagtcct ctctagatgt tctgccttcc caagtctatt   2760
ctctggttgg gagcagtccc ctccgcacca catcttctta taattccttg gtccctgtcc   2820
aagatcagca tcagcccatc atcattccag atactcccag ccctcctgtg agtgtcatca   2880
ctatccgaag tgacactgat gaggaagagg acaacaaata caagcccagt agctctggac   2940
tgaagccaag gtctaatgtc atcagttatg tcactgtcaa tgattctcca gactctgact   3000
cttctttgag cagcccttat tccactgata ccctgagtgc tctccgaggc aatagtggat   3060
ccgttttgga ggggcctggc agagttgtgg cagatggcac tggcacccgc actatcattg   3120
tgcctccact gaaaactcag cttggtgact gcactgtagc aacccaggcc tcaggtctcc   3180
tgagcaataa gactaagcca gtcgcttcag tgagtgggca gtcatctgga tgctgtatca   3240
cccccacagg gtatcgagct caacgcgggg ggaccagtgc agcacaacca ctcaatctta   3300
gccagaacca gcagtcatcg gcggctccaa cctcacagga gagaagcagc aacccagccc   3360
cccgcaggca gcaggcgttt gtggcccctc tctcccaagc cccctacacc ttccagcatg   3420
gcagcccgct acactcgaca gggcacccac accttgcccc ggcccctgct cacctgccaa   3480
gccaggctca tctgtatacg tatgctgccc cgacttctgc tgctgcactg ggctcaacca   3540
gctccattgc tcatcttttc tccccacagg gttcctcaag gcatgctgca gcctatacca   3600
ctcaccctag cactttggtg caccaggtcc ctgtcagtgt tgggcccagc ctcctcactt   3660
ctgccagcgt ggcccctgct cagtaccaac accagtttgc cacccaatcc tacattgggt   3720
cttcccgagg ctcaacaatt tacactggat acccgctgag tcctaccaag atcagccagt   3780
attcctactt atagttggtg agcatgaggg aggaggaatc atggctacct tctcctggcc   3840
ctgcgttctt aatattgggc tatggagaga tcctccttta ccctcttgaa atttcttagc   3900
cagcaacttg ttctgcaggg gcccactgaa gcagaaggtt tttctctggg ggaacctgtc   3960
tcagtgttga ctgcattgtt gtagtcttcc caaagtttgc cctattttta aattcattat   4020
ttttgtgaca gtaattttgg tacttggaag agttcagatg cccatcttct gcagttacca   4080
aggaagagag attgttctga agttaccctc tgaaaaatat tttgtctctc tgacttgatt   4140
tctataaatg cttttaaaaa caagtgaagc ccctctttat ttcattttgt gttattgtga   4200
ttgctggtca ggaaaaatgc tgatagaagg agttgaaatc tgatgacaaa aaaagaaaaa   4260
ttactttttg tttgtttata aactcagact tgcctatttt attttaaaag cggcttacac   4320
aatctccctt ttgtttattg gacatttaaa cttacagagt ttcagttttg ttttaatgtc   4380
atattatact taatgggcaa ttgttatttt tgcaaaactg gttacgtatt actctgtgtt   4440
actattgaga ttctctcaat tgctcctgtg tttgttataa agtagtgttt aaaaggcagc   4500
tcaccatttg ctggtaactt aatgtgagag aatccatatc tgcgtgaaaa caccaagtat   4560
tctttttaaa tgaagcacca tgaattcttt tttaaattat tttttaaaag tctttctctc   4620
tctgattcag cttaaatttt tttatcgaaa aagccattaa ggtggttatt attacatggt   4680
ggtggtggtt ttattatatg caaaatctct gtctattatg agatactggc attgatgagc   4740
tttgcctaaa gattagtatg aattttcagt aatacacctc tgttttgctc atctctccct   4800
tctgttttat gtgatttgtt tggggagaaa gctaaaaaaa cctgaaacca gataagaaca   4860
tttcttgtgt atagctttta tacttcaaag tagcttcctt tgtatgccag cagcaaattg   4920
aatgctctct tattaagact tatataataa gtgcatgtag gaattgcaaa aaatatttta   4980
aaaatttatt actgaattta aaaatatttt agaagttttg taatggtggt gttttaatat   5040
```

-continued

```
tttacataat taaatatgta catattgatt agaaaaatat aacaagcaat ttttcctgct   5100
aacccaaaat gttatttgta atcaaatgtg tagtgattac acttgaattg tgtacttagt   5160
gtgtatgtga tcctccagtg ttatcccgga gatggattga tgtctccatt gtatttaaac   5220
caaaatgaac tgatacttgt tggaatgtat gtgaactaat tgcaattata ttagagcata   5280
ttactgtagt gctgaatgag caggggcatt gcctgcaagg agaggagacc cttggaattg   5340
ttttgcacag gtgtgtctgg tgaggagttt ttcagtgtgt gtctcttcct tccctttctt   5400
cctccttccc ttattgtagt gccttatatg ataatgtagt ggttaataga gtttacagtg   5460
agcttgcctt aggatggacc agcaagcccc cgtggaccct aagttgttca ccgggattta   5520
tcagaacagg attagtagct gtattgtgta atgcattgtt ctcagtttcc ctgccaacat   5580
tgaaaaataa aaacagcagc ttttctcctt taccaccacc tctacccctt tccattttgg   5640
attctcggct gagttctcac agaagcattt tccccatgtg gctctctcac tgtgcgttgc   5700
taccttgctt ctgtgagaat tcaggaagca ggtgagagga gtcaagccaa tattaaatat   5760
gcattctttt aaagtatgtg caatcacttt tagaatgaat tttttttcc ttttcccatg   5820
tggcagtcct tcctgcacat agttgacatt cctagtaaaa tatttgcttg ttgaaaaaaa   5880
catgttaaca gatgtgttta taccaaagag cctgttgtat tgcttaccat gtccccatac   5940
tatgaggaga agttttgtgg tgccgctggt gacaaggaac tcacagaaag gtttcttagc   6000
tggtgaagaa tatagagaag gaaccaaagc ctgttgagtc attgaggctt ttgaggtttc   6060
tttttaaca gcttgtatag tcttggggcc cttcaagctg tgaaattgtc cttgtactct   6120
cagctcctgc atggatctgg gtcaagtaga aggtactggg gatggggaca ttcctgccca   6180
taaaggattt ggggaaagaa gattaatcct aaaatacagg tgtgttccat ctgaattgaa   6240
aatgatatat ttgagatata attttaggac tggttctgtg tagatagaga tggtgtcaag   6300
gaggtgcagg atggagatgg gagatttcat ggagcctggt cagccagctc tgtaccaggt   6360
tgaacaccga ggagctgtca aagtatttgg agtttcttca ttgtaaggag taagggcttc   6420
caagatgggg caggtagtcc gtacagccta ccaggaacat gttgtgtttt ctttattttt   6480
taaaatcatt atattgagtt gtgttttcag cactatattg gtcaagatag ccaagcagtt   6540
tgtataattt ctgtcactag tgtcatacag ttttctggtc aacatgtgtg atctttgtgt   6600
ctcctttttg ccaagcacat tctgattttc ttgttggaac acaggtctag tttctaaagg   6660
acaaattttt tgttccttgt cttttttctg taagggacaa gatttgttgt ttttgtaaga   6720
aatgagatgc aggaaagaaa accaaatccc attcctgcac cccagtccaa taagcagata   6780
ccacttaaga taggagtcta aactccacag aaaaggataa taccaagagc ttgtattgtt   6840
accttagtca cttgcctagc agtgtgtggc tttaaaaact agagattttt cagtcttagt   6900
ctgcaaactg gcatttccga ttttccagca taaaaatcca cctgtgtctg ctgaatgtgt   6960
atgtatgtgc tcactgtggc tttagattct gtccctgggg ttagccctgt tggccctgac   7020
aggaagggag gaagcctggt gaatttagtg agcagctggc ctgggtcaca gtgacctgac   7080
ctcaaaccag cttaaggctt taagtcctct ctcagaactt ggcatttcca acttcttcct   7140
ttccgggtga gagaagaagc ggagaagggt tcagtgtagc cactctgggc tcatagggac   7200
acttggtcac tccagagttt ttaatagctc ccaggaggtg atattatttt cagtgctcag   7260
ctgaaatacc aaccccagga ataagaactc catttcaaac agttctggcc attctgagcc   7320
tgcttttgtg attgctcatc cattgtcctc cactagaggg gctaagcttg actgccctta   7380
```

-continued gccaggcaag cacagtaatg tgtgttttgt tcagcattat tatgcaaaaa ttcactagtt 7440
gagatggttt gttttaggat aggaaatgaa attgcctctc agtgacagga gtggcccgag 7500
cctgcttcct attttgattt tttttttttt taactgatag atggtgcagc atgtctacat 7560
ggttgtttgt tgctaaactt tatataatgt gtggtttcaa ttcagcttga aaaataatct 7620
cactacatgt agcagtacat tatatgtaca ttatatgtaa tgttagtatt tctgctttga 7680
atccttgata ttgcaatgga attcctactt tattaaatgt atttgatatg ctagttattg 7740
tgtgcgattt aaactttttt tgctttctcc cttttttttgg ttgtgcgctt tcttttacaa 7800
caagcctcta gaaacagata gtttctgaga attactgagc tatgtttgta atgcagatgt 7860
acttagggag tatgtaaaat aatcatttta acaaaagaaa tagatattta aaatttaata 7920
ctaactatgg gaaaagggtc cattgtgtaa aacatagttt atctttggat tcaatgtttg 7980
tctttggttt tacaaagtag cttgtatttt cagtattttc tacataatat ggtaaaatgt 8040
agagcaattg caatgcatca ataaaatggg taaattttct gacttatgtg gctgtttttg 8100
acttctgtta taggatataa aggggatcaa taaatgacat ctttgaaagt gaaaa 8155

<210> SEQ ID NO 618
<211> LENGTH: 3443
<212> TYPE: DNA
<213> ORGANISM: Homo sapiens

<400> SEQUENCE: 618
gtgctttact gcgcgctctg gtactgctgt ggctccccgt cctggtgcgg gacctgtgcc 60
ccgcgcttca gccctccccg cacagcctac tgattcccct gccgcccttg ctcacctcct 120
gctcgccatg gagtcgctgg ttttcgcgcg gcgctccggc cccactccct cggccgcaga 180
gctagcccgg ccgctggcgg aagggctgat caagtcgccc aagcccctaa tgaagaagca 240
ggcggtgaag cggcaccacc acaagcacaa cctgcggcac cgctacgagt tcctggagac 300
cctgggcaaa ggcacctacg ggaaggtgaa gaaggcgcgg gagagctcgg ggcgcctggt 360
ggccatcaag tcaatccgga aggacaaaat caaagatgag caagatctga tgcacatacg 420
gagggagatt gagatcatgt catcactcaa ccaccctcac atcattgcca tccatgaagt 480
gtttgagaac agcagcaaga tcgtgatcgt catggagtat gccagccggg gcgaccttta 540
tgactacatc agcgagcggc agcagctcag tgagcgcgaa gctaggcatt tcttccggca 600
gatcgtctct gccgtgcact attgccatca gaacagagtt gtccaccgag atctcaagct 660
ggagaacatc ctcttggatg ccaatgggaa tatcaagatt gctgacttcg gcctctccaa 720
cctctaccat caaggcaagt tcctgcagac attctgtggg agcccccctct atgcctcgcc 780 agagattgtc aatgggaagc cctacacagg cccagaggtg gacagctggt ccctgggtgt 840
tctcctctac atcctggtgc atggcaccat gccctttgat gggcatgacc ataagatcct 900
agtgaaacag atcagcaacg gggcctaccg ggagccacct aaaccctctg atgcctgtgg 960
cctgatccgg tggctgttga tggtgaaccc cacccgccgg gccaccctgg aggatgtggc 1020
cagtcactgg tgggtcaact ggggctacgc cacccgagtg ggagagcagg aggctccgca 1080
tgagggtggg caccctggca gtgactctgc ccgcgcctcc atggctgact ggctccggcg 1140
ttcctcccgc cccctcctgg agaatggggc caaggtgtgc agcttcttca agcagcatgc 1200
acctggtggg ggaagcacca cccctggcct ggagcgccag cattcgctca agaagtcccg 1260
caaggagaat gacatggccc agtctctcca cagtgacacg gctgatgaca ctgcccatcg 1320
ccctggcaag agcaacctca agctgccaaa gggcattctc aagaagaagg tgtcagcctc 1380

```
tgcagaaggg gtacaggagg accctccgga gctcagccca atccctgcga gcccagggca   1440
ggctgccccg ctgctcccca agaagggcat tctcaagaag ccccgacagc gcgagtctgg   1500
ctactactcc tctcccgagc ccagtgaatc tggggagctc ttggacgcag gcgacgtgtt   1560
tgtgagtggg gatcccaagg agcagaagcc tccgcaagct tcagggctgc tcctccatcg   1620
caaaggcatc ctcaaactca atggcaagtt ctcccagaca gccttggagc tcgcggcccc   1680
caccaccttc ggctccctgg atgaactcgc cccacctcgc cccctggccc gggccagccg   1740
accctcaggg gctgtgagcg aggacagcat cctgtcctct gagtcctttg accagctgga   1800
cttgcctgaa cggctcccag agcccccact gcggggctgt gtgtctgtgg acaacctcac   1860
ggggcttgag gagccccccct cagagggccc tggaagctgc ctgaggcgct ggcggcagga   1920
tcctttgggg gacagctgct tttccctgac agactgccag gaggtgacag cgacctaccg   1980
acaggcactg agggtctgct caaagctcac ctgagtggag taggcattgc cccagcccgg   2040
tcaggctctc agatgcagct ggttgcaccc cgaggggaga tgccttctcc cccacctccc   2100
aggacctgca tcccagctca gaaggctgag agggtttgca gtggagccct gagcagggct   2160
ggatatggga agtaggcaaa tgaaatgcgc caagggttca gtgtctgtct tcagccctgc   2220
tgaacgaaga ggatactaaa gagaggggaa cgggaatgcc cgcgacagag tccacattgc   2280
ctgtttcttg tgtacatggg ggggccacag agacctggaa agagaactct cccagggccc   2340
atctcctgca tcccatgaat actctgtaca catggtgcct tctaaggaca gctccttccc   2400
tactcattcc ctgcccaagt ggggccagac ctctttacac acacattccc gttcctacca   2460
accaccagaa ctggatggtg gcacccctaa tgtgcatgag gcatcctggg aatggtctgg   2520
agtaacgctt cgttattttt atttttattt ttatttattt atttattttt ttgagacgga   2580
gtttcgctct tggtgcccag gctagagtgc aatggcgcga tctcagctca cctcaacctc   2640
cgcctcccgg gttcaagcga ttctcctgcc tcagcctccc tagtagctgg gattacaggc   2700
gcccgccacc atgcccggct aattttgtat ttttagtaga gacagggttt ctccatgttg   2760
gtcaggctgg tctcaaactc ccgacctcag gtgatccacc cacctcggcc tcccaaagtg   2820
ctgggattac aggcgtgagc caccgcgccc cacctaaccc ttccttattt agcctaggag   2880
taagagaaca caatctctgt ttcttcaatg gttctcttcc cttttccatc ctccaaacct   2940
ggcctgagcc tcctgaagtt gctgctgtga atctgaaaga cttgaaaagc ctccgcctgc   3000
tgtgtggact tcatctcaag gggcccagcc tcctctggac tccaccttgg acctcagtga   3060
ctcagaactt ctgcctctaa gctgctctaa agtccagact atggatgtgt tctctaggcc   3120
ttcaggactc tagaatgtcc atatttattt ttatgttctt ggctttgtgt tttaggaaaa   3180
gtgaatcttg ctgttttcaa taatgtgaat gctatgttct gggaaaatcc actatgacat   3240
ctaagttttg tgtacagaga gatatttttg caactatttc cacctcctcc cacaaccccc   3300
cacactccac tccacactct tgagtctctt tacctaatgg tctctaccta atggacctcc   3360
gtggccaaaa agtaccatta aaaccagaaa ggtgattgga aaaaaaaaaa aaaaaaaaaa   3420
aaaaaaaaaa aaaaaaaaaa aaa                                           3443
```

<210> SEQ ID NO 619
<211> LENGTH: 6267
<212> TYPE: DNA
<213> ORGANISM: Homo sapiens

<400> SEQUENCE: 619

-continued

```
agctgcaagt ggcgggcgcc caggcagatg cgatccagcg gctctggggg cggcagcggt     60
ggtagcagct ggtacctccc gccgcctctg ttcggagggt cgcggggcac cgaggtgctt    120
tccggccgcc ctctggtcgg ccacccaaag ccgcgggcgc tgatgatggg tgaggagggg    180
gcggcaagat ttcgggcgcc cctgccctga acgccctcag ctgctgccgc cggggccgct    240
ccagtgcctg cgaactctga ggagccgagg cgccggtgag agcaaggacg ctgcaaactt    300
gcgcagcgcg gggctggga ttcacgccca gaagttcagc aggcagacag tccgaagcct    360
tcccgcagcg gagagatagc ttgagggtgc gcaagacggc agcctccgcc ctcggttccc    420
gcccagaccg ggcagaagag cttggaggag ccaaaaggaa cgcaaaaggc ggccaggaca    480
gcgtgcagca gctgggagcc gccgttctca gccttaaaag ttgcagagat tggaggctgc    540
cccgagaggg gacagacccc agctccgact gcggggggca ggagaggacg gtacccaact    600
gccacctccc ttcaaccata gtagttcctc tgtaccgagc gcagcgagct acagacgggg    660
gcgcggcact cggcgcggag agcgggaggc tcaaggtccc agccagtgag cccagtgtgc    720
ttgagtgtct ctggactcgc ccctgagctt ccaggtctgt ttcatttaga ctcctgctcg    780
cctccgtgca gttgggggaa agcaagagac ttgcgcgcac gcacagtcct ctggagatca    840
ggtggaagga gccgctgggt accaaggact gttcagagcc tcttcccatc tcggggagag    900
cgaagggtga ggctgggccc ggagagcagt gtaaacggcc tcctccggcg ggatgggagc    960
catcgggctc ctgtggctcc tgccgctgct gctttccacg gcagctgtgg gctccgggat   1020
ggggaccggc cagcgcgcgg gctccccagc tgcggggccg ccgctgcagc cccgggagcc   1080
actcagctac tcgcgcctgc agaggaagag tctggcagtt gacttcgtgg tgccctcgct   1140
cttccgtgtc tacgcccggg acctactgct gccaccatcc tcctcggagc tgaaggctgg   1200
caggcccgag gcccgcggct cgctagctct ggactgcgcc ccgctgctca ggttgctggg   1260
gccggcgccg gggtctcct ggaccgccgg ttcaccagcc ccggcagagg cccggacgct   1320
gtccagggtg ctgaagggcg gctccgtgcg caagctccgg cgtgccaagc agttggtgct   1380
ggagctgggc gaggaggcga tcttggaggg ttgcgtcggg ccccccgggg aggcggctgt   1440
ggggctgctc cagttcaatc tcagcgagct gttcagttgg tggattcgcc aaggcgaagg   1500
gcgactgagg atccgcctga tgcccgagaa gaaggcgtcg gaagtgggca gagagggaag   1560
gctgtccgcg gcaattcgcg cctcccagcc ccgccttctc ttccagatct tcgggactgg   1620
tcatagctcc ttggaatcac caacaaacat gccttctcct tctcctgatt attttacatg   1680
gaatctcacc tggataatga aagactcctt ccctttcctg tctcatcgca gccgatatgg   1740
tctggagtgc agctttgact tcccctgtga gctggagtat tcccctccac tgcatgacct   1800
caggaaccag agctggtcct ggcgccgcat cccctccgag gaggcctccc agatggactt   1860
gctggatggg cctggggcag agcgttctaa ggagatgccc agaggctcct ttctccttct   1920
caacacctca gctgactcca agcacaccat cctgagtccg tggatgagga gcagcagtga   1980
gcactgcaca ctggccgtct cggtgcacag gcacctgcag ccctctggaa ggtacattgc   2040
ccagctgctg ccccacaacg aggctgcaag agagatcctc ctgatgccca ctccagggaa   2100
gcatggttgg acagtgctcc agggaagaat cgggcgtcca gacaacccat ttcgagtggc   2160
cctggaatac atctccagtg gaaaccgcag cttgtctgca gtggacttct ttgccctgaa   2220
gaactgcagt gaaggaacat ccccaggctc caagatggcc ctgcagagct ccttcacttg   2280
ttggaatggg acagtcctcc agcttgggca ggcctgtgac ttccaccagg actgtgccca   2340
gggagaagat gagagccaga tgtgccggaa actgcctgtg ggtttttact gcaactttga   2400
```

```
agatggcttc tgtggctgga cccaaggcac actgtcaccc cacactcctc aatggcaggt   2460
caggacccta aaggatgccc ggttccagga ccaccaagac catgctctat tgctcagtac   2520
cactgatgtc cccgcttctg aaagtgctac agtgaccagt gctacgtttc ctgcaccgat   2580
caagagctct ccatgtgagc tccgaatgtc ctggctcatt cgtggagtct tgaggggaaa   2640
cgtgtccttg gtgctagtgg agaacaaaac cgggaaggag caaggcagga tggtctggca   2700
tgtcgccgcc tatgaaggct tgagcctgtg gcagtggatg gtgttgcctc tcctcgatgt   2760
gtctgacagg ttctggctgc agatggtcgc atggtgggga caaggatcca gagccatcgt   2820
ggcttttgac aatatctcca tcagcctgga ctgctacctc accattagcg gagaggacaa   2880
gatcctgcag aatacagcac ccaaatcaag aaacctgttt gagagaaacc caaacaagga   2940
gctgaaaccc ggggaaaatt caccaagaca gacccccatc tttgacccta cagttcattg   3000
gctgttcacc acatgtgggg ccagcgggcc ccatggcccc acccaggcac agtgcaacaa   3060
cgcctaccag aactccaacc tgagcgtgga ggtggggagc gagggccccc tgaaaggcat   3120
ccagatctgg aaggtgccag ccaccgacac ctacagcatc tcgggctacg gagctgctgg   3180
cgggaaaggc gggaagaaca ccatgatgcg gtcccacggc gtgtctgtgc tgggcatctt   3240
caacctggag aaggatgaca tgctgtacat cctggttggg cagcagggag aggacgcctg   3300
ccccagtaca aaccagttaa tccagaaagt ctgcattgga gagaacaatg tgatagaaga   3360
agaaatccgt gtgaacagaa gcgtgcatga gtgggcagga ggcggaggag gagggggtgg   3420
agccacctac gtatttaaga tgaaggatgg agtgccggtg cccctgatca ttgcagccgg   3480
aggtggtggc agggcctacg gggccaagac agacacgttc cacccagaga gactggagaa   3540
taactcctcg gttctagggc taaacggcaa ttccggagcc gcaggtggtg gaggtggctg   3600
gaatgataac acttccttgc tctgggccgg aaaatctttg caggagggtg ccaccggagg   3660
acattcctgc ccccaggcca tgaagaagtg gggggtggag acaagagggg gtttcggagg   3720
gggtggaggg gggtgctcct caggtggagg aggcggagga tatataggcg gcaatgcagc   3780
ctcaaacaat gaccccgaaa tggatgggga agatggggtt tccttcatca gtccactggg   3840
catcctgtac accccagctt taaaagtgat ggaaggccac ggggaagtga atattaagca   3900
ttatctaaac tgcagtcact gtgaggtaga cgaatgtcac atggaccctg aaagccacaa   3960
ggtcatctgc ttctgtgacc acgggacggt gctggctgag gatggcgtct cctgcattgt   4020
gtcacccacc ccggagccac acctgccact ctcgctgatc ctctctgtgg tgacctctgc   4080
cctcgtggcc gccctggtcc tggctttctc cggcatcatg attgtgtacc gccggaagca   4140
ccaggagctg caagccatgc agatggagct gcagagccct gagtacaagc tgagcaagct   4200
ccgcacctcg accatcatga ccgactacaa ccccaactac tgctttgctg gcaagacctc   4260
ctccatcagt gacctgaagg aggtgccgcg gaaaaacatc accctcattc ggggtctggg   4320
ccatggcgcc tttggggagg tgtatgaagg ccaggtgtcc ggaatgccca acgacccaag   4380
ccccctgcaa gtggctgtga agacgctgcc tgaagtgtgc tctgaacagg acgaactgga   4440
tttcctcatg gaagccctga tcatcagcaa attcaaccac cagaacattg ttcgctgcat   4500
tggggtgagc ctgcaatccc tgccccggtt catcctgctg gagctcatgg cggggggaga   4560
cctcaagtcc ttcctccgag agacccgccc tcgcccgagc cagccctcct ccctggccat   4620
gctggacctt ctgcacgtgg ctcgggacat tgcctgtggc tgtcagtatt tggaggaaaa   4680
ccacttcatc caccgagaca ttgctgccag aaactgcctc ttgacctgtc caggccctgg   4740
```

aagagtggcc aagattggag acttcgggat ggcccgagac atctacaggg cgagctacta 4800
tagaaaggga ggctgtgcca tgctgccagt taagtggatg cccccagagg ccttcatgga 4860
aggaatattc acttctaaaa cagacacatg gtcctttgga gtgctgctat gggaaatctt 4920
ttctcttgga tatatgccat accccagcaa aagcaaccag gaagttctgg agtttgtcac 4980
cagtggaggc cggatggacc cacccaagaa ctgccctggg cctgtatacc ggataatgac 5040
tcagtgctgg caacatcagc ctgaagacag gcccaacttt gccatcattt tggagaggat 5100
tgaatactgc acccaggacc cggatgtaat caacaccgct ttgccgatag aatatggtcc 5160
acttgtggaa gaggaagaga aagtgcctgt gaggcccaag gaccctgagg gggttcctcc 5220
tctcctggtc tctcaacagg caaaacggga ggaggagcgc agcccagctg ccccaccacc 5280
tctgcctacc acctcctctg gcaaggctgc aaagaaaccc acagctgcag agatctctgt 5340
tcgagtccct agagggccgg ccgtggaagg gggacacgtg aatatggcat tctctcagtc 5400
caaccctcct tcggagttgc acaaggtcca cggatccaga aacaagccca ccagcttgtg 5460
gaacccaacg tacggctcct ggtttacaga gaaacccacc aaaaagaata atcctatagc 5520
aaagaaggag ccacacgaca ggggtaacct ggggctggag ggaagctgta ctgtcccacc 5580
taacgttgca actgggagac ttccgggggc ctcactgctc ctagagccct cttcgctgac 5640
tgccaatatg aaggaggtac ctctgttcag gctacgtcac ttcccttgtg ggaatgtcaa 5700
ttacggctac cagcaacagg gcttgccctt agaagccgct actgcccctg gagctggtca 5760
ttacgaggat accattctga aaagcaagaa tagcatgaac cagcctgggc cctgagctcg 5820
gtcgcacact cacttctctt ccttgggatc cctaagaccg tggaggagag agaggcaatg 5880
gctccttcac aaaccagaga ccaaatgtca cgttttgttt tgtgccaacc tattttgaag 5940
taccaccaaa aaagctgtat tttgaaaatg ctttagaaag gttttgagca tgggttcatc 6000
ctattctttc gaaagaagaa aatatcataa aaatgagtga taaatacaag gcccagatgt 6060
ggttgcataa ggtttttatg catgtttgtt gtatacttcc ttatgcttct ttcaaattgt 6120
gtgtgctctg cttcaatgta gtcagaatta gctgcttcta tgtttcatag ttggggtcat 6180
agatgtttcc ttgccttgtt gatgtggaca tgagccattt gaggggagag ggaacggaaa 6240
taaaggagtt atttgtaatg actaaaa 6267

<210> SEQ ID NO 620
<211> LENGTH: 894
<212> TYPE: DNA
<213> ORGANISM: Homo sapiens

<400> SEQUENCE: 620
gcccgtcttc gtgtctcctc cctccctcgc cttcctcctt cctagctcct ctcctccagg 60
gccagactga gcccaggttg atttcaggcg gacaccaata gactccacag cagctccagg 120
agcccagaca ccggcggcca gaagcaaggc taggagctgc tgcagccatg tcggccctca 180
gcctcctcat tctgggcctg ctcacggcag tgccacctgc cagctgtcag caaggcctgg 240
ggaaccttca gccctggatg cagggcctta tcgcggtggc cgtgttcctg gtcctcgttg 300
caatcgcctt tgcagtcaac cacttctggt gccaggagga gccggagcct gcacacatga 360
tcctgaccgt cggaaacaag gcagatggag tcctggtggg aacagatgga aggtactctt 420
cgatggcggc cagtttcagg tccagtgagc atgagaatgc ctatgagaat gtgcccgagg 480
aggaaggcaa ggtccgcagc accccgatgt aaccttctct gtggctccaa ccccaagact 540
cccaggcaca tgggatggat gtccagtgct accacccaag ccccctcctt ctttgtgtgg 600
aatctgcaat agtgggctga ctccctccag ccccatgccg gccctacccg cccttgaagt 660
atagccagcc aaggttggag ctcagaccgt gtctaggttg gggctcggct gtggccctgg 720
ggtctcctgc tcagctcaga agagccttct ggagaggaca gtcagctgag cacctcccat 780
cctgctcaca cgtccttccc cataactatg gaaatggccc taatttctgt gaaataaaga 840
ctttttgtat ttctggggct gaggctcagc aacagcccct caggcttcca gtga 894

<210> SEQ ID NO 621
<211> LENGTH: 21
<212> TYPE: DNA
<213> ORGANISM: Homo sapiens

<400> SEQUENCE: 621
gcgctaatca cgacgcgctg t 21

<210> SEQ ID NO 622
<211> LENGTH: 21
<212> TYPE: DNA
<213> ORGANISM: Homo sapiens

<400> SEQUENCE: 622
ggaagccgac atcatctcca c 21

<210> SEQ ID NO 623
<211> LENGTH: 20
<212> TYPE: DNA
<213> ORGANISM: Homo sapiens

<400> SEQUENCE: 623
gtgagcgcgg cctttattct 20

<210> SEQ ID NO 624
<211> LENGTH: 23
<212> TYPE: DNA
<213> ORGANISM: Homo sapiens

<400> SEQUENCE: 624
ggtcgcattt tggggattat tga 23

<210> SEQ ID NO 625
<211> LENGTH: 22
<212> TYPE: DNA
<213> ORGANISM: Homo sapiens

<400> SEQUENCE: 625
tttggcacag tcttaccact tt 22

<210> SEQ ID NO 626
<211> LENGTH: 20
<212> TYPE: DNA
<213> ORGANISM: Homo sapiens

<400> SEQUENCE: 626
ctgtgaaggg aatcaaggga 20

<210> SEQ ID NO 627
<211> LENGTH: 20
<212> TYPE: DNA
<213> ORGANISM: Homo sapiens

<400> SEQUENCE: 627
tgtcgaatta ccactgctgg 20

<210> SEQ ID NO 628
<211> LENGTH: 10
<212> TYPE: PRT
<213> ORGANISM: Homo sapiens

<400> SEQUENCE: 628

Phe Phe Glu Glu Pro Glu Asp Pro Ser Ser
1 5 10

<210> SEQ ID NO 629
<211> LENGTH: 9
<212> TYPE: PRT
<213> ORGANISM: Homo sapiens

<400> SEQUENCE: 629

Gly Tyr Ser Phe Thr Thr Thr Ala Glu
1 5

<210> SEQ ID NO 630
<211> LENGTH: 24
<212> TYPE: DNA
<213> ORGANISM: Homo sapiens

<400> SEQUENCE: 630
ggatccatgg caggagctgg aggc 24

<210> SEQ ID NO 631
<211> LENGTH: 44
<212> TYPE: DNA
<213> ORGANISM: Homo sapiens

<400> SEQUENCE: 631
gctagcatta attttgtcct ggaatatata caagttattg gtgg 44

<210> SEQ ID NO 632
<211> LENGTH: 21
<212> TYPE: DNA
<213> ORGANISM: Homo sapiens

<400> SEQUENCE: 632
cccacatcag tgcaatgtat t 21

<210> SEQ ID NO 633
<211> LENGTH: 21
<212> TYPE: DNA
<213> ORGANISM: Homo sapiens

<400> SEQUENCE: 633
tccccaccaa tgtaacgtgt t 21

<210> SEQ ID NO 634
<211> LENGTH: 45
<212> TYPE: DNA
<213> ORGANISM: Homo sapiens

<400> SEQUENCE: 634
tccatcccca ccaatgtaac gtgtttgttt acagcagcag caagg 45

<210> SEQ ID NO 635
<211> LENGTH: 45
<212> TYPE: DNA
<213> ORGANISM: Homo sapiens

<400> SEQUENCE: 635
aaacaaacac gttacattgg tggggatgga actctgcggc agtga 45

<210> SEQ ID NO 636
<211> LENGTH: 21
<212> TYPE: DNA
<213> ORGANISM: Homo sapiens

<400> SEQUENCE: 636
cccgcaccag tgcaacgtgt t 21

<210> SEQ ID NO 637
<211> LENGTH: 21
<212> TYPE: DNA
<213> ORGANISM: Homo sapiens

<400> SEQUENCE: 637
tcatagtggg cggtacatga t 21

<210> SEQ ID NO 638
<211> LENGTH: 21
<212> TYPE: DNA
<213> ORGANISM: Homo sapiens

<400> SEQUENCE: 638
gagaattaat ttatggcact t 21

<210> SEQ ID NO 639
<211> LENGTH: 21
<212> TYPE: DNA
<213> ORGANISM: Homo sapiens

<400> SEQUENCE: 639
ccatttagga tcacggcgct a 21

<210> SEQ ID NO 640
<211> LENGTH: 21
<212> TYPE: DNA
<213> ORGANISM: Homo sapiens

<400> SEQUENCE: 640
gccaccaata acttgtacat a 21

<210> SEQ ID NO 641
<211> LENGTH: 21
<212> TYPE: DNA
<213> ORGANISM: Homo sapiens

<400> SEQUENCE: 641
cggttcggat agcgccatca t 21

<210> SEQ ID NO 642
<211> LENGTH: 21
<212> TYPE: DNA
<213> ORGANISM: Homo sapiens

<400> SEQUENCE: 642
tcatttccac cgttgagttt a 21

<210> SEQ ID NO 643
<211> LENGTH: 21
<212> TYPE: DNA

<213> ORGANISM: Homo sapiens

<400> SEQUENCE: 643
atgctcacac atatcatata a 21

<210> SEQ ID NO 644
<211> LENGTH: 20
<212> TYPE: DNA
<213> ORGANISM: Homo sapiens

<400> SEQUENCE: 644
cgggcaataa gactctttaa 20

<210> SEQ ID NO 645
<211> LENGTH: 22
<212> TYPE: DNA
<213> ORGANISM: Homo sapiens

<400> SEQUENCE: 645
tgcccaggtc cagttccatt tc 22

<210> SEQ ID NO 646
<211> LENGTH: 21
<212> TYPE: DNA
<213> ORGANISM: Homo sapiens

<400> SEQUENCE: 646
tcctgattta actggattat g 21

<210> SEQ ID NO 647
<211> LENGTH: 21
<212> TYPE: DNA
<213> ORGANISM: Homo sapiens

<400> SEQUENCE: 647
atcaaacatc cctgacttaa g 21

<210> SEQ ID NO 648
<211> LENGTH: 21
<212> TYPE: DNA
<213> ORGANISM: Homo sapiens

<400> SEQUENCE: 648
ctacacctca tgaccatata a 21

<210> SEQ ID NO 649
<211> LENGTH: 21
<212> TYPE: DNA
<213> ORGANISM: Homo sapiens

<400> SEQUENCE: 649
tacacctcat gaccatataa a 21

<210> SEQ ID NO 650
<211> LENGTH: 21
<212> TYPE: DNA
<213> ORGANISM: Homo sapiens

<400> SEQUENCE: 650
tcagtgagaa tgagtacttt a 21

<210> SEQ ID NO 651
<211> LENGTH: 21

<212> TYPE: DNA
<213> ORGANISM: Homo sapiens

<400> SEQUENCE: 651
cctgacttaa gcatatattt a 21

<210> SEQ ID NO 652
<211> LENGTH: 21
<212> TYPE: DNA
<213> ORGANISM: Homo sapiens

<400> SEQUENCE: 652
tctacattga tagccttatg a 21

<210> SEQ ID NO 653
<211> LENGTH: 4469
<212> TYPE: DNA
<213> ORGANISM: Homo sapiens

<400> SEQUENCE: 653
aaatgtagtc actgtcccgg aacctggggc agcggagtcc cgtgcgccct gtggtgacag 60
ctcaggaggg tgtgtgcgct cagcaggggc cagcatggac cagtctgtgg caatccagga 120
gacgctggct gagggggaat actgcgtcat cgcggtgcaa ggtgtgctgt gtgaggggga 180
cagccggcag agccgcctcc tgggactcgt gcgctaccgc ctggagcacg gcggccagga 240
acacgctctc ttcctctata cgcaccggag gatggccatt accggggacg atgtctctct 300
ggaccagata gtgccagtct cgcgggattt tacgctggaa gaagtgtccc cagatggtga 360
actctacatc cttggctcag atgtgaccgt ccagctggac acagcagagc ttagcctcgt 420
attccaactg ccctttggtt cacaaaccag gatgttcctc cacgaagttg ccagggcctg 480
tccaggcttc gattctgcga cccgggatcc tgaattcctg tggctgtctc ggtataggtg 540
cgcagagctg gagctggaga tgccaacgcc gcgcggttgt aactcggccc tagttacctg 600
gccagggtac gcgacaattg gcggaggtgg ttctaacttt gatggtttga gaccaaatgg 660
gaagggagtg cctatggacc aaagctccag ggtcaagat aaaccagaaa gcttgcaacc 720
aagacagaat aaatccaagt ccgaaattac tgacatggtt cgctcctcca ctatcacagt 780
gtcggacaag gctcatattt tatccatgca gaagtttgga ctgcgagata caattgtgaa 840
atcacatcta ctacagaaag aagaggatta cacctatatc cagaacttca ggtttttttgc 900 gggaacatac aatgtaaatg ggcagtcccc caaagaatgc ctccggctgt ggctgagcaa 960
tggtatccag gccccagatg tctattgtgt agggttccag gagcttgatc tgagtaagga 1020
agcttttttc tttcacgata ccccaaagga ggaagagtgg ttcaaagctg tgtcagaggg 1080
tcttcatcca gatgccaaat atgcaaaggt gaagcttatc cgactggttg ggattatgct 1140
gctgttatat gtcaaacagg agcatgcagc ttatatctca gaagtggaag ccgagactgt 1200
ggggacagga atcatgggga ggatgggcaa caagggaggc gtggcgatca ggttccagtt 1260
ccacaacacc agcatctgcg ttgtgaattc tcacttggca gcccacattg aagagtatga 1320
gaggaggaac caggactata aggacatttg ttctcgaatg cagttttgtc agcctgaccc 1380
aagccttccc cctctcacca tcagcaacca tgatgtgatc ttgtggctgg gggacctcaa 1440
ctacaggata gaagagctgg atgtggaaaa agtgaaaaag ctcatcgaag agaaggactt 1500
tcaaatgctg tatgcatatg atcagctgaa aattcaggtg gccgcaaaga ctgtctttga 1560
aggcttcaca gagggtgagc tcacattcca gcctacttac aagtatgata cgggctctga 1620

```
cgactgggat accagtgaga agtgccgtgc tcctgcctgg tgtgatcgga ttctctggaa   1680
agggaagaac atcactcagc tgagttacca gagccacatg gccctgaaga ccagtgacca   1740
caagcctgtc agctcagtgt ttgacatcgg ggtgagggtc gtaaatgacg agctttaccg   1800
gaagacactg gaggaaattg ttcgctccct ggataagatg gaaaatgcca acattccttc   1860
tgtgtccctg tccaagcgag agttctgttt tcagaatgtg aagtacatgc aattgaaagt   1920
agaatccttt acaattcata atggacaagt accctgtcat tttgaattca tcaacaagcc   1980
tgatgaagag tcttactgta agcagtggct gaatgccaac cccagcagag gcttcctcct   2040
gccagattct gatgttgaga ttgacttgga gctcttcgta aataagatga cagctacaaa   2100
gctcaactcg ggtgaagaca aaattgagga cattctggtt ctgcacttgg acaggggaaa   2160
ggattacttt ttgtctgtgt ctgggaacta cctgcccagc tgttttgggt ctcccattca   2220
tacactgtgt tacatgagag agccaatctt ggacctacca cttgaaacca ttagtgagct   2280
gactctgatg ccagtatgga ctggagatga tgggagccag ttggatagcc ccatggaaat   2340
ccccaaagag ctctggatga tggttgatta cctgtaccga aatgctgtcc agcaggaaga   2400
tctgtttcag caaccaggcc tgaggtcaga atttgaacat atcagggact gcttggatac   2460
tggaatgatt gataacctct ctgccagcaa tcattctgta gccgaagccc tgctgctttt   2520
cctggagagc cttccagagc ctgtcatctg ttacagcacc taccataact gcttggagtg   2580
ttctggcaac tacacagcaa gcaaacaggt catttctact ctccccatat tccacaaaaa   2640
tgtcttccac tacttgatgg cgtttttgcg agaactgctg aaaaattcag caaaaaatca   2700
tttggatgag aatattctag ctagcatatt tggcagctta ttgcttcgaa acccagctgg   2760
tcaccaaaag cttgatatga cagagaagaa gaaggctcaa gaatttattc accagttcct   2820
ctgcaaccca ctctgagcct ctctctcctc ctattttact tgaggctgcc aattaccagc   2880
cccacctgtt tcagctcaag agatgcctta agataattat gtgaggccac ttggtagcaa   2940
gaatggcagc tatttcctga gcctagtacc ccaattaagc ccaccattgg ttagcacact   3000
cagcgctgtg agtcgtgaag acacgggaga aaatccacca taataaaact gacattcaat   3060
tttcaacttt agttatttaa cacagatttt tttatttttt attttttttt attttgagac   3120
ggagttttgc tctgtcgcgc agggtggagt gcggtggcac gatctcggct cactgcaacc   3180
tctgcctcct gggtgcaagc aattatcctg cctcagcctc ccgagtagct gggactgcag   3240
gcacacactg ccacgcccag ctaatttttt gcattttagt agagacgggg tttcaccgtg   3300
ttgcccaggc tgttctaaaa ctcctgaact caggtaatct gcctgcctcg gcctccccaa   3360
gtgctaggat tacagatgtg agccaccacg cccggccttt tttttttttt tttctttttt   3420
gagatggagt ttcactcttg ttgcccaggc tggagtgcgt tggcgtggtc ttggctcact   3480
gcaacctctg cctccttggt tcaagcaatt ctcctgcctc agcctctcga gtagctggga   3540
ttataggcgt ccgccaccat gcctggctaa ttttttgtg tgtttttagt atagacacgg   3600
tttcaccatg ttggccaggc tggtctcgaa tgcctggcct caggtgatcc acctgccttg   3660
gcctcccaaa gtgctgggat tacaggcatg aaccaccacg cctggcctaa aatgttttta   3720
aataactgta cttgtactca ctcaccctac ctccagggca tagtcagtct gggctgagat   3780
ccccatgatc agatatttga tggaaagtcc tgaaaggcca atgagttgga tggcaagaat   3840
gcaggcagaa gctgctggat aaaataggct acagccacct cagatgcttt cagtgctctg   3900
tctgaggatg tgtatatgca tatgcaaact cgacccccgt tcctgcccag ataatggctc   3960
aataactctg aggctggttg ctcagcctct gagggcaata caggcattta aaaaattaaa   4020
```

```
atgaccaggc acagtggctc acgcctgtaa tctcggcact ttgggagact gaggtgggag   4080
catcacttga gaccaggagt ttgggaccag gctgggcaac acagggagac cccctctcta   4140
caaaaacatt tttaaaaaat tagctgggtg tggtgatgca tgcctgtggt cccagttact   4200
tgggaggctg acgtgggtgg ctcacttgag cacaggagtt tgaggctgca gtgacctatg   4260
accacatcac tgtacgccag cccgggtgag agagggagac cccgtctcta aaaataaaat   4320
gtaaaatcac tgaaaaaatg agtgttcggt gaaacaagtg ggattttctg ggccagcaag   4380
tcttccaaac tgtatatgat gcatcctgtc tccatgtgta atatatttta atgataaatg   4440
tatttttaac agtgaaaaaa aaaaaaaaa                                     4469
```

<210> SEQ ID NO 654
<211> LENGTH: 1216
<212> TYPE: DNA
<213> ORGANISM: Homo sapiens

<400> SEQUENCE: 654

```
ggcagctgca cggctcctgg ccccggagca tgcgcgagag ccgcccccgga gcgccccgga    60
gccccccgcc gtcccgcccg cggcgtcccg cgccccgccg ccagcgcacc cccggacgct   120
atggcccacc cctccggctg gccccttctg taggatggta gcacacaacc aggtggcagc   180
cgacaatgca gtctccacag cagcagagcc ccgacggcgg ccagaacctt cctcctcttc   240
ctcctcctcg cccgcggccc ccgcgcgccc gcggccgtgc cccgcggtcc cggccccggc   300
ccccggcgac acgcacttcc gcacattccg ttcgcacgcc gattaccggc gcatcacgcg   360
cgccagcgcg ctcctggacg cctgcggatt ctactggggg cccctgagcg tgcacggggc   420
gcacgagcgg ctgcgcgccg agcccgtggg caccttcctg gtgcgcgaca gccgccagcg   480
gaactgcttt ttcgccctta gcgtgaagat ggcctcggga cccacgagca tccgcgtgca   540
ctttcaggcc ggccgctttc acctggatgg cagccgcgag agcttcgact gcctcttcga   600
gctgctggag cactacgtgg cggcgccgcg ccgcatgctg ggggccccgc tgcgccagcg   660
ccgcgtgcgg ccgctgcagg agctgtgccg ccagcgcatc gtggccaccg tgggccgcga   720
gaacctggct cgcatccccc tcaaccccgt cctccgcgac tacctgagct ccttcccctt   780
ccagatttga ccggcagcgc ccgccgtgca cgcagcatta actgggatgc cgtgttattt   840
tgttattact tgcctggaac catgtgggta ccctccccgg cctgggttgg agggagcgga   900
tgggtgtagg ggcgaggcgc ctcccgccct cggctggaga cgaggccgca gaccccttct   960
cacctcttga gggggtcctc cccctcctgg tgctccctct gggtccccct ggttgttgta  1020
gcagcttaac tgtatctgga gccaggacct gaactcgcac ctcctacctc ttcatgttta  1080
catataccca gtatctttgc acaaaccagg ggttggggga gggtctctgg ctttattttt  1140
ctgctgtgca gaatcctatt ttatattttt taaagtcagt ttaggtaata aactttatta  1200
tgaaagtttt tttttt                                                   1216
```

<210> SEQ ID NO 655
<211> LENGTH: 3337
<212> TYPE: DNA
<213> ORGANISM: Homo sapiens

<400> SEQUENCE: 655

```
gacatcatgg gctattttta ggggttgact ggtagcagat aagtgttgag ctcgggctgg    60
ataagggctc agagttgcac tgagtgtggc tgaagcagcg aggcgggagt ggaggtgcgc   120
```

-continued

```
ggagtcaggc agacagacag acacagccag ccagccaggt cggcagtata gtccgaactg    180
caaatcttat tttcttttca ccttctctct aactgcccag agctagcgcc tgtggctccc    240
gggctggtgt ttcgggagtg tccagagagc ctggtctcca gccgcccccg ggaggagagc    300
cctgctgccc aggcgctgtt gacagcggcg gaaagcagcg gtacccacgc gcccgccggg    360
ggaagtcggc gagcggctgc agcagcaaag aactttcccg gctgggagga ccggagacaa    420
gtggcagagt cccggagcga acttttgcaa gcctttcctg cgtcttaggc ttctccacgg    480
cggtaaagac cagaaggcgg cggagagcca cgcaagagaa gaaggacgtg cgctcagctt    540
cgctcgcacc ggttgttgaa cttgggcgag cgcgagccgc ggctgccggg cgccccctcc    600
ccctagcagc ggaggagggg acaagtcgtc ggagtccggg cggccaagac ccgccgccgg    660
ccggccactg cagggtccgc actgatccgc tccgcgggga gagccgctgc tctgggaagt    720
gagttcgcct gcggactccg aggaaccgct gcgcccgaag agcgctcagt gagtgaccgc    780
gacttttcaa agccgggtag cgcgcgcgag tcgacaagta agagtgcggg aggcatctta    840
attaaccctg cgctccctgg agcgagctgg tgaggagggc gcagcgggga cgacagccag    900
cgggtgcgtg cgctcttaga gaaactttcc ctgtcaaagg ctccgggggg cgcgggtgtc    960
ccccgcttgc cagagccctg ttgcggcccc gaaacttgtg cgcgcagccc aaactaacct   1020
cacgtgaagt gacggactgt tctatgactg caaagatgga aacgaccttc tatgacgatg   1080
ccctcaacgc ctcgttcctc ccgtccgaga gcggacctta tggctacagt aaccccaaga   1140
tcctgaaaca gagcatgacc ctgaacctgg ccgacccagt gggagcctga agccgcacct   1200
ccgcgccaag aactcggacc tcctcacctc gcccgacgtg gggctgctca agctggcgtc   1260
gcccgagctg gagcgcctga taatccagtc cagcaacggg cacatcacca ccacgccgac   1320
ccccacccag ttcctgtgcc ccaagaacgt gacagatgag caggagggct tcgccgaggg   1380
cttcgtgcgc gccctggccg aactgcacag ccagaacacg ctgcccagcg tcacgtcggc   1440
ggcgcagccg gtcaacgggg caggcatggt ggctcccgcg gtagcctcgg tggcaggggg   1500
cagcggcagc ggcggcttca gcgccagcct gcacagcgag ccgccggtct acgcaaacct   1560
cagcaacttc aacccaggcg cgctgagcag cggcggcggg gcgccctcct acggcgcggc   1620
cggcctggcc tttcccgcgc aaccccagca gcagcagcag ccgccgcacc acctgcccca   1680
gcagatgccc gtgcagcacc cgcggctgca ggccctgaag gaggagcctc agacagtgcc   1740
cgagatgccc ggcgagacac cgcccctgtc cccatcgac atggagtccc aggagcggat     1800
caaggcggag aggaagcgca tgaggaaccg catcgctgcc tccaagtgcc gaaaaaggaa   1860
gctggagaga atcgcccggc tggaggaaaa agtgaaaacc ttgaaagctc agaactcgga   1920
gctggcgtcc acggccaaca tgctcaggga acaggtggca cagcttaaac agaaagtcat   1980
gaaccacgtt aacagtgggt gccaactcat gctaacgcag cagttgcaaa catttgaag   2040
agagaccgtc gggggctgag gggcaacgaa gaaaaaaaat aacacagaga gacagacttg   2100
agaacttgac aagttgcgac ggagagaaaa aagaagtgtc cgagaactaa agccaagggt   2160
atccaagttg gactgggttg cgtcctgacg gcgcccccag tgtgcacgag tgggaaggac   2220
ttggcgcgcc ctcccttggc gtggagccag ggagcggccg cctgcgggct gccccgcttt   2280
gcggacgggc tgtccccgcg cgaacggaac gttggacttt tcgttaacat tgaccaagaa   2340
ctgcatggac ctaacattcg atctcattca gtattaaagg ggggaggggg agggggttac   2400
aaactgcaat agagactgta gattgcttct gtagtactcc ttaagaacac aaagcggggg   2460
gagggttggg gaggggcggc aggagggagg tttgtgagag cgaggctgag cctacagatg   2520
```

aactctttct ggcctgcctt cgttaactgt gtatgtacat atatatattt tttaatttga 2580
tgaaagctga ttactgtcaa taaacagctt catgcctttg taagttattt cttgtttgtt 2640
tgtttgggta tcctgcccag tgttgtttgt aaataagaga tttggagcac tctgagttta 2700
ccatttgtaa taaagtatat aattttttta tgttttgttt ctgaaaattc cagaaaggat 2760
atttaagaaa atacaataaa ctattggaaa gtactcccct aacctctttt ctgcatcatc 2820
tgtagatact agctatctag gtggagttga aagagttaag aatgtcgatt aaaatcactc 2880
tcagtgcttc ttactattaa gcagtaaaaa ctgttctcta ttagacttta gaaataaatg 2940
tacctgatgt acctgatgct atggtcaggt tatactcctc ctcccccagc tatctatatg 3000
gaattgctta ccaaaggata gtgcgatgtt tcaggaggct ggaggaaggg gggttgcagt 3060
ggagagggac agcccactga gaagtcaaac atttcaaagt ttggattgta tcaagtggca 3120
tgtgctgtga ccatttataa tgttagtaga aattttacaa taggtgctta ttctcaaagc 3180
aggaattggt ggcagatttt acaaaagatg tatccttcca atttggaatc ttctctttga 3240
caattcctag ataaaaagat ggcctttgct tatgaatatt tataacagca ttcttgtcac 3300
aataaatgta ttcaaatacc aaaaaaaaaa aaaaaaa 3337

<210> SEQ ID NO 656
<211> LENGTH: 5831
<212> TYPE: DNA
<213> ORGANISM: Homo sapiens

<400> SEQUENCE: 656
cggccgcggc gacagctcca gctccggctc cggctccggc tccggctccg gctcccgcgc 60
ctgccccgct cggcccagcg cgcccgggct ccgcgccccg accccgccgc cgcgcctgcc 120
gggggcctcg ggcgcccccg ccgcccgcct cacgctgaag ttcctggccg tgctgctggc 180
cgcgggcatg ctggcgttcc tcggtgccgt catctgcatc atcgccagcg tgcccctggc 240
ggccagcccg gcgcgggcgc tgcccggcgg cgccgacaat gcttcggtcg cctcgggcgc 300
cgccgcgtcc ccgggcccgc agcggagcct gagcgcgctg cacggcgcgg gcggttcagc 360
cgggcccccc gcgctgcccg gggcacccgc ggccagcgcg cacccgctgc cgcccgggcc 420
cctgttcagc cgcttcctgt gcacgccgct ggctgctgcc tgcccgtcgg gggcccagca 480
gggggacgcg gcgggcgctg cgccgggcga gcgcgaagag ctgctgctgc tgcagagcac 540
ggccgagcag ctgcgccaga cggcgctgca gcaggaggcg cgcatccgcg ccgaccagga 600
caccatccgt gagctcaccg gcaagctggg ccgctgcgag agcggcctgc cgcgcggcct 660
ccagggcgcc gggccccgcc gcgacaccat ggccgacggg ccctgggact cgcctgcgct 720
cattctggag ctggaggacg ccgtgcgcgc cctgcgggac cgcatcgacc gcctggagca 780
ggagcttcca gcccgtgtga acctctcagc tgccccagcc ccagtctctg ctgtgcccac 840
cggcctacac tccaagatgg accagctgga ggggcagctg ctggcccagg tgctggcact 900
ggagaaggag cgtgtggccc tcagccacag cagccgccgg cagaggcagg aagtggaaaa 960
ggagttggac gtcctgcagg gtcgtgtggc tgagctggag cacgggtcct cagcctacag 1020
tcctccagat gccttcaaga tcagcatccc catccgtaac aactacatgt acgcccgcgt 1080
gcggaaggct ctgcccgagc tctacgcatt caccgcctgc atgtggctgc ggtccaggtc 1140
cagcggcacc ggccagggca ccccccttctc ctactcagtg cccgggcagg ccaacgagat 1200
tgtactgcta gaggcgggcc atgagcccat ggagctgctg atcaacgaca aggtggccca 1260

-continued

```
gctgcccctg agcctgaagg acaatggctg gcaccacatc tgcatcgcct ggaccacaag   1320
ggatggccta tggtctgcct accaggacgg ggagctgcag ggctccggtg agaacctggc   1380
tgcctggcac cccatcaagc ctcatgggat ccttatcttg ggccaggagc aggataccct   1440
gggtggccgg tttgatgcca cccaggcctt tgtcggtgac attgcccagt ttaacctgtg   1500
ggaccacgcc ctgacaccag cccaggtcct gggcattgcc aactgcactg cgccactgct   1560
gggcaacgtc cttccctggg aagacaagtt ggtggaggcc tttgggggtg caacaaaggc   1620
tgccttcgat gtctgcaagg ggagggccaa ggcatgaggg gccacctcat ccagggcccc   1680
tcccttgcct gccactttgg ggacttgagg ggggtcatat tccctcctca gcctgcccac   1740
gcactggcct tccctcctgc cccactcctg gctgtgcctc ccatttcccc tcacctgtac   1800
ccacacctcc agaatgccct gccctgcgag tgtgtcccct gtccccacct gagtggggag   1860
gagcgtctca agtgaacagt gggagcctgc ccacctggca ctgcactgga gttgtctctt   1920
accccaccct ccctgcccat caactgtatc tgatttcact aattttgaca gcacccccag   1980
tagggtagga ttgtgtatga gggggacccc actatctcag tggtgggggt ggccgcccgc   2040
ccccttgtcc cccatgcaac aggcccagtg gcttcccctt cagggccaca acaggctgta   2100
gaaggggatg acgaggacat cagaggttag acttaccctc ctccctcttt ccaccagctg   2160
ccagtcaagg gcagtgggat ctcgatggag cctccccccc cccccaccca tgcctccctc   2220
ttcctcctct ttcctcctct ctttgtgtgt agcggtttga atgttggttc catgcctggc   2280
ccagccccac ctcagtctcc aggacattcc tttcccagct ccagcctgga gggaagggga   2340
caaagacccc aggaggccaa agggctgcag tcaccccttg tgctcaccca tagtgatggc   2400
cactggtata gtcatcgctc tccctccatg ccaaggacag gacttggacc gcttcagcct   2460
gggctgggag cagccctaag gtagaggcct catggcccag gagaccccac ctctggcaga   2520
gccacattac ctaccctgtg catggtcctg gggcagcaag gaagaagctc agagggtggg   2580
gagaagcatg aagcagtgag cagagcactg ggtgagaggg agaagacctt ggttcctagc   2640
cagccctgct aatgtgctgt gtggccttct gtaagtccct gccctctctg ggcctggcct   2700
tcctcattcg tgagctgagg ccctcgcttt ggtcatttgc tctccagatt gggtgtgagc   2760
ttctctgtga ttccaggtgg atatgtgggg aaagctctgg tgaccctggg cttcgcaggg   2820
gtagatccca ggactcggca gtggatggga tgcagccagt catgggttag ggtcagcaga   2880
gactcagagt ccagggcaag gttcaaggca gactaacctc atgcatggat tgtaaaaaac   2940
cagctccctt tggatcaacc cagcctggca cccttgcctg tctgagagtg tctcaaaggg   3000
ctgatggctt cctggtcccc ttgagtcatc accagcttcc ccaagagagt gtcagaatct   3060
taagagctga gaggccgggc acggtggctc acgcctgtaa tcccagcact ttgggaggct   3120
gagacaggca gatcacttga ggtcaggagt tcgaagtcag cctggccaac gtggtgaaac   3180
cccatcttca ctaaaaatac aaaacttagc tggttaggtg gtgcatgcct gtagtcccag   3240
ctactcggga ggccgaggca gaagaatctc ttgaactgag gaggtggagg ttgcagtgag   3300
ccgagatcac gccattgcac tccagcctgg gcaacagagc aagactccat ctcaaaaaaa   3360
taataataat cttaaagatg agaaaagcca ccccatctgg caccacagct gcatcttgct   3420
tgtgagaaat ggggaagagt tcagggagga cacgtgacct gcacaggatc acagagcatg   3480
gggcagagcc aggactagag ctcagggcat ctgactccct cttcagtgtt cttccccctc   3540
catgttgcct gcccctgaag acctttgagt tcagtctaca cctaagcagg tagacatccg   3600
cgaggtcaga tgctttccaa catgacacct gaacatcttc ctttatgcaa cacccaaaca   3660
```

```
tcttggcatc cccaccccag gaagtgcggg gaggaggtta tgatccctgg gcgcttcggc   3720
agaatggaga gctgaggtgt ccctcccctg ctagtcacct accaggtgtc tgagcagctg   3780
catgctccct ggctcaagtg ggcactgtac cttttgcctg cctttttgtt ccctatctcc   3840
actccctgag gccacttagc ctgagacatg atgcaagagc tgcaggccgg ggggctcagt   3900
gccatggaag ctactccaag ttgcattgcc tcccgcgccc agatcctgct ttccatttcg   3960
agaacataaa tagattgccc agcccctcca gtacaatccc actggaagaa aaggcaatgg   4020
cgggcttcag ccagacctgc tgagacctag gttgccacgg taacagccaa agacatcaac   4080
ccaagtgctg ggtcaagtgt ctcatcatac tggcactgtt gctggggtga cggcagaatt   4140
cagaacttca atttcagtga cgccaagctt gatgtgtttc tgttattgtt ttgaagaagg   4200
tagctcttgt ggaggacttg ggagaaggat ggggtcttag gaaggaggtg acagcacttg   4260
catggtcact tgagcccaca cacacgctca accccaagtc ctttatgctt tgtcacagtg   4320
aagatgagac ctctgacgtc caagccttgt tcctgtgctg catcacccac tcagccttcc   4380
aaagggaaca ggaacaaatt tccccagcac cactgtttgg gtcccgcttt tcctatcttc   4440
tgctgcccct gagcacatcc aagcagacag ggaaagagga gtcagacatg gcccagtcac   4500
atcctgagct gctcctggct gataaccacg atggagcccg tgtttgtcct gccatctggc   4560
actgcactga gtgtggcaca ggcaccgtcc tgttgatctc acaacacagt tctaagttag   4620
gacgttcttg gctccgttag acaggtgagg aaactggggc acagagaggt gatgtcatct   4680
gcctggtgtc aatcagctag caagtgatgg agcccagatt tcaaaccaaa gggggttacg   4740
tccaggggct gagttcccac tcacctgtgt agagtgccat ctgggcacca ttgctccaga   4800
cgtgttccga cccctttccc agcccacagg gcttgaagtg aaggaacaga ggcagggggt   4860
gggccagccc cagggccagg gtccccttgg tgaagccgtg ccagggggct cagctgcttc   4920
agggaatgtg tccctcccac catgggccag agcttcagcc cttctttagc tcagctagag   4980
ttcacaggag agccaaaaaa gaaaaggaag ctgagcatct cccgagtcct gggcagggaa   5040
ggggagggaa attgctgctt ctccaactct tgcttggggc caagccctgc accagttgct   5100
tcccagctgt tatctgccag atcttcccat cttgtggcat gtggtgcccc caccaacatc   5160
ccaaggggac caatcccctt gccaccactt tgcatcacct gggaccacag atttggacag   5220
gaagggctct gagaagaggc caaagccctc attttacaga tgaggaagct gaagcccggg   5280
gaggggagcg accctcaagg ccacccagct ggacacggga gacttgagcc cagccttctg   5340
actgcattca gccctctcta ggacgcagca gcctctcccc agcactgagt ccccccctcct   5400
ttgtgtgtcc cagcaccctt ggcctgagta aacttggaaa ggggctccct cccagagaag   5460
ggactactct cttcacccct ttattccagc tgcctgccac cccagacccc cacctcccac   5520
cctgaccccc gacccctggg tggggaaggg gctcacatgg gcccaggctg agtgtgagtg   5580
agcatgtcaa gttgtctgac actgtgacat tagtgcaccc tactgacaac ccctccccag   5640
ccttgcccct ttctcctctc cctgttttgt acataaattg acatgagctg caacatgtgt   5700
gcgtgtgtgt gcgtgtgtgt gtgtgtgtat gtgtgtgtga tctgtgtcat ggttttgtta   5760
ccttttttgtt tttgtaaact tgaatgttca aaataaacat gctgtttact ctgagaaaaa   5820
aaaaaaaaaa a                                                        5831
```

<210> SEQ ID NO 657
<211> LENGTH: 2737
<212> TYPE: DNA

<213> ORGANISM: Homo sapiens

<400> SEQUENCE: 657
gcggctccga cttggactcc ctgctccgct gctgccgctt cggccccgca cgcagccagc 60
cgccagccgc ccgcccggcc cagctcccgc cgcggcccct tgccgcggtc cctctcctgg 120
tcccctcccg gttggtccgg gggtgcgcag ggggcagggc gggcgcccag gggaagctcg 180
agggacgcgc gcgcgaaggc tcctttgtgg acttcacggc cgccaacatc tgggcgcagc 240
gcgggccacc gctggccgtc tcgccgccgc gtcgccttgg ggacccgagg gggctcagcc 300
ccaaggacgg agacttcgat tcgggaccag ccccccggga tgcggtagcg gccgctgtgc 360
ggaggccgcg aagcagctgc agccgccgcc gcgcagatcc acgctggctc cgtgcgccat 420
ggtcacccac agcaagtttc ccgccgccgg gatgagccgc cccctggaca ccagcctgcg 480
cctcaagacc ttcagctcca agagcgagta ccagctggtg gtgaacgcag tgcgcaagct 540
gcaggagagc ggcttctact ggagcgcagt gaccggcggc gaggcgaacc tgctgctcag 600
tgccgagccc gccggcacct ttctgatccg cgacagctcg gaccagcgcc acttcttcac 660
gctcagcgtc aagacccagt ctgggaccaa gaacctgcgc atccagtgtg aggggggcag 720
cttctctctg cagagcgatc cccggagcac gcagcccgtg ccccgcttcg actgcgtgct 780
caagctggtg caccactaca tgccgccccc tggagccccc tccttcccct cgccacctac 840
tgaaccctcc tccgaggtgc ccgagcagcc gtctgcccag ccactccctg ggagtccccc 900
cagaagagcc tattacatct actccggggg cgagaagatc cccctggtgt tgagccggcc 960
cctctcctcc aacgtggcca ctcttcagca tctctgtcgg aagaccgtca acggccacct 1020
ggactcctat gagaaagtca cccagctgcc ggggcccatt cgggagttcc tggaccagta 1080
cgatgccccg ctttaagggg taaagggcgc aaagggcatg ggtcgggaga ggggacgcag 1140
gcccctctcc tccgtggcac atggcacaag cacaagaagc caaccaggag agagtcctgt 1200
agctctgggg ggaaagaggg cggacaggcc cctccctctg ccctctccct gcagaatgtg 1260
gcaggcggac ctggaatgtg ttggagggaa gggggagtac cacctgagtc tccagcttct 1320
ccggaggagc cagctgtcct ggtgggacga tagcaaccac aagtggattc tccttcaatt 1380
cctcagcttc ccctctgcct ccaaacaggg gacacttcgg gaatgctgaa ctaatgagaa 1440
ctgccaggga atcttcaaac tttccaacgg aacttgtttg ctctttgatt tggtttaaac 1500
ctgagctggt tgtggagcct gggaaaggtg gaagagagag aggtcctgag ggccccaggg 1560
ctgcgggctg gcgaaggaaa tggtcacacc ccccgcccac cccaggcgag gatcctggtg 1620
acatgctcct ctccctggct ccggggagaa gggcttgggg tgacctgaag ggaaccatcc 1680
tggtacccca catcctctcc tccgggacag tcaccgaaaa cacaggttcc aaagtctacc 1740
tggtgcctga gagcccaggg cccttcctcc gttttaaggg ggaagcaaca tttggagggg 1800
atggatgggc tggtcagctg gtctcctttt cctactcata ctataccttc ctgtacctgg 1860
gtggatggag cgggaggatg gaggagacgg gacatctttc acctcaggct cctggtagag 1920
aagacagggg attctactct gtgcctcctg actatgtctg gctaagagat tcgccttaaa 1980
tgctccctgt cccatggaga gggacccagc ataggaaagc cacatactca gcctggatgg 2040
gtggagaggc tgagggactc actggagggc accaagccag cccacagcca gggaagtggg 2100
gaggggggc ggaaacccat gcctcccagc tgagcactgg gaatgtcagc ccagtaagta 2160
ttggccagtc aggcgcctcg tggtcagagc agagccacca ggtcccactg ccccgagccc 2220
tgcacagccc tccctcctgc ctgggtgggg gaggctggag gtcattggag aggctggact 2280

```
gctgccaccc cgggtgctcc cgctctgcca tagcactgat cagtgacaat ttacaggaat   2340

gtagcagcga tggaattacc tggaacagtt ttttgttttt gtttttgttt ttgtttttgt   2400

gggggggggc aactaaacaa acacaaagta ttctgtgtca ggtattgggc tggacagggc   2460

agttgtgtgt tggggtggtt tttttctcta tttttttgtt tgtttcttgt tttttaataa   2520

tgtttacaat ctgcctcaat cactctgtct tttataaaga ttccacctcc agtcctctct   2580

cctcccccct actcaggccc ttgaggctat taggagatgc ttgaagaact caacaaaatc   2640

ccaatccaag tcaaactttg cacatattta tatttatatt cagaaaagaa acatttcagt   2700

aatttataat aaagagcact attttttaat gaaaaac                            2737
```

<210> SEQ ID NO 658
<211> LENGTH: 4830
<212> TYPE: DNA
<213> ORGANISM: Homo sapiens

<400> SEQUENCE: 658

```
gaggcagctc ctgtggggaa aggcgccagt gcgccgaggc ggggagtggc ggcggggtaa     60

cacctggccg aggtgactcg ttctgaagag cagcggttcc ttacaccaat cggaacgtgc    120

aggggtgggg agctggccaa tcaggcgcgg agggcggggc cgggcggggt tccacctggc    180

ggctggctct cagtcccctc gctgtagtcg cggagctgtg tctgttccca ggagtccttc    240

ggcggctgtt gtgtcgggag cctgatcgcg atggggacaa aggcgcaagt cgagaggaaa    300

ctgttgtgcc tcttcatatt ggcgatcctg ttgtgctccc tggcattggg cagtgttaca    360

gtgcactctt ctgaacctga agtcagaatt cctgagaata atcctgtgaa gttgtcctgt    420

gcctactcgg gcttttcttc tccccgtgtg gagtggaagt ttgaccaagg agacaccacc    480

agactcgttt gctataataa caagatcaca gcttcctatg aggaccgggt gaccttcttg    540

ccaactggta tcaccttcaa gtccgtgaca cgggaagaca ctgggacata cacttgtatg    600

gtctctgagg aaggcggcaa cagctatggg gaggtcaagg tcaagctcat cgtgcttgtg    660

cctccatcca agcctacagt taacatcccc tcctctgcca ccattgggaa ccgggcagtg    720

ctgacatgct cagaacaaga tggttcccca ccttctgaat acacctggtt caaagatggg    780

atagtgatgc ctacgaatcc caaaagcacc cgtgccttca gcaactcttc ctatgtcctg    840

aatcccacaa caggagagct ggtctttgat cccctgtcag cctctgatac tggagaatac    900

agctgtgagg cacggaatgg gtatgggaca cccatgactt caaatgctgt gcgcatggaa    960

gctgtggagc ggaatgtggg ggtcatcgtg gcagccgtcc ttgtaaccct gattctcctg   1020

ggaatcttgg tttttggcat ctggtttgcc tatagccgag gccactttga cagaacaaag   1080

aaagggactt cgagtaagaa ggtgatttac agccagccta gtgcccgaag tgaaggagaa   1140

ttcaaacaga cctcgtcatt cctggtgtga gcctggtcgg ctcaccgcct atcatctgca   1200

tttgccttac tcaggtgcta ccggactctg gcccctgatg tctgtagttt cacaggatgc   1260

cttatttgtc ttctacaccc cacagggccc cctacttctt cggatgtgtt tttaataatg   1320

tcagctatgt gccccatcct ccttcatgcc ctccctccct ttcctaccac tgctgagtgg   1380

cctggaactt gtttaaagtg tttattcccc atttctttga gggatcagga aggaatcctg   1440

ggtatgccat tgacttccct tctaagtaga cagcaaaaat ggcgggggtc gcaggaatct   1500

gcactcaact gcccacctgg ctggcaggga tctttgaata ggtatcttga gcttggttct   1560

gggctctttc cttgtgtact gacgaccagg gccagctgtt ctagagcggg aattagaggc   1620
```

-continued

```
tagagcggct gaaatggttg tttggtgatg acactggggt ccttccatct ctggggccca   1680
ctctcttctg tcttcccatg ggaagtgcca ctgggatccc tctgccctgt cctcctgaat   1740
acaagctgac tgacattgac tgtgtctgtg gaaaatggga gctcttgttg tggagagcat   1800
agtaaatttt cagagaactt gaagccaaaa ggatttaaaa ccgctgctct aaagaaaaga   1860
aaactggagg ctgggcgcag tggctcacgc ctataatccc agaggctgag gcaggcggat   1920
cacctgaggt caggagttca agatcagcct gaccaacatg gagaaaccct actaaaaata   1980
caaagttagc caggcatagt ggtgcatgcc tgtaatccca gctgctcagg agcctggcaa   2040
caagagcaaa actccagctc aaaaaaaaaa agaaagaaaa gaaagctgga gctggtggct   2100
taggccatca cccttccctt ggctggaact actggacaga cccttttgag atgtgcctgt   2160
ggtgctgtgg agatgtgtgt agtggtctta gctctttgtt gagcttgtgt gtgtgttgtg   2220
tagtcttagc tgtatgctga aattgggcgt gtgttggagg gcttcttagc tctttggtga   2280
gattgtattt ctatgtgttt gtatcagctg aatgttgctg gaaataaaac cttggtttgt   2340
caaggctctt ttttgtggga agtaagtagg ggaaaaggtc tttgagggtt cctaggctcc   2400
tttgtacaac aggaaaatgc ctcaaagcct tgcttcccag caacctgggg ctggttccca   2460
gtgcctggtc ctgccccttc ctggttctta tctcaaggca gagcttctga atttcaggcc   2520
ttcattccag agccctcttg tggccaggcc ttcctttgct ggaggaaggt acacagggtg   2580
aagctgatgc tgtacttggg ggatctcctt ggcctgttcc accaagtgag agaaggtact   2640
tactcttgta cctcctgttc agccaggtgc attaacagac ctccctacag ctgtaggaac   2700
tactgtccca gagctgaggc aaggggattt ctcaggtcat ttggagaaca agtgctttag   2760
tagtagttta aagtagtaac tgctactgta tttagtgggg tggaattcag aagaaatttg   2820
aagaccagat catgggtggt ctgcatgtga atgaacagga atgagccgga cagcctggct   2880
gtcattgctt tcttcctccc catttggacc cttctctgcc cttacatttt tgtttctcca   2940
tctaccacca tccaccagtc tatttattaa cttagcaaga ggacaagtaa agggccctct   3000
tggcttgatt ttgcttcttt ctttctgtgg aggatatact aagtgcgact ttgccctatc   3060
ctatttggaa atccctaaca gaattgagtt ttctattaag gatccaaaaa gaaaaacaaa   3120
atgctaatga agccatcagt caagggtcac atgccaataa acaataaatt ttccagaaga   3180
aatgaaatcc aactagacaa ataaagtaga gcttatgaaa tggttcagta aagatgagtt   3240
tgttgttttt tgttttgttt tgttttgttt ttttaaagac ggagtctcgc tctgtcaccc   3300
aggctggagt gcagtggtat gatcttggct cactgtaacc tccgcctccc gggttcaagc   3360
cattctcctg cctcagtctc ctgagtagct gggattacgg gtgcgtgcca ccatgcctgg   3420
ctaatttttg tgtttttagt agagacaggg tttcaccatg ttggtcgggc tggtctcaaa   3480
ctcctgacct cttgatccgc ctgccttggc ctcccaaagt gatgggatta cagatgtgag   3540
ccaccgtgcc tagccaagga tgagattttt aaagtatgtt tcagttctgt gtcatggttg   3600
gaagacagag taggaaggat atggaaaagg tcatggggaa gcagaggtga ttcatggctc   3660
tgtgaatttg aggtgaatgg ttccttattg tctaggccac ttgtgaagaa tatgagtcag   3720
ttattgccag ccttggaatt tacttctcta gcttacaatg gaccttttga actggaaaac   3780
accttgtctg cattcacttt aaaatgtcaa aactaatttt tataataaat gtttattttc   3840
acattgagtt tgtttaaatc ctgaagttct taccttaaga gaattgggac tcctagagtg   3900
attggacatt caaaatattc ctgatagtct tgttaattaa gagattagga tatctttcca   3960
ttaccttgat aattacgttt taatttagct tttttcattg gcctgtgttt aaatgcaaat   4020
```

```
aaccccacaa tggacatttc ctatgttaaa gtgacattta ggggataaaa aatgagagca   4080
gttccatgga ttttggtgtt tcccctgaga catgaactca gcataatctg ggataaaatg   4140
attgagtgtt aaggatgtgt ttgttgttcc tgtcgttttt ttatttttctt caaagtatac   4200
aacatggttt gatatgcaca tacatttgtg taatgattgc catggtcaat taacacatca   4260
ccatttttgt gtgtgtgtgt gtgtgtgtgt gtgagggagt cttgctccgt tgccaggctg   4320
gagtgcaatg gtacaacctt ggctcactgc aacctccacc tcctgggttc aagcaattct   4380
cttgcctcag cctcctaagt agctgggact ataggcgtgt gccaccatgc ccagctaatt   4440
tttgtatttt tagtagagac ggggtttcac catgttggcc aggatgatct cgatcccttg   4500
acctcatgat ccgcccacct cggcctccca aagtgctggg attacaggcg tgagtcactg   4560
cacccggcca catcacctcc catgttctat cttacgtatt cagaacttgt tcatcttgta   4620
actgaaagcg tgtacccttt gaccaacact gtttttcctg tcttaacagg atctacagat   4680
caaggacagg ggaggggata gtggaggaaa acggagttag tctgtttcta aatgagggga   4740
cagtatgttt cttggggcct gaggacagct taataaagta gacaaatgaa gaaaaacaac   4800
aatttgcatt aaaaaatatc caattcttta                                    4830
```

<210> SEQ ID NO 659
<211> LENGTH: 3628
<212> TYPE: DNA
<213> ORGANISM: Homo sapiens

<400> SEQUENCE: 659

```
agagcatcag caagagtagc agcgagcagc cgcgctggtg gcggcggcgc gtcgttgcag     60
ttgcgccatc tgtcaggagc ggagccggcg aggagggggc tgccgcgggc gaggaggagg    120
ggtcgccgcg agccgaaggc cttcgagacc cgcccgccgc ccggcggcga gagtagaggc    180
gaggttgttg tgcgagcggc gcgtcctctc ccgcccgggc gcgccgcgct tctcccagcg    240
caccgaggac cgcccgggcg cacacaaagc cgccgcccgc gccgcaccgc ccggcggccg    300
ccgcccgcgc cagggaggga ttcggccgcc gggccgggga caccccggcg ccgccccctc    360
ggtgctctcg gaaggcccac cggctcccgg gcccgccggg gaccccccgg agccgcctcg    420
gccgcgccgg aggagggcgg ggagaggacc atgtgagtgg gctccggagc ctcagcgccg    480
cgcagttttt ttgaagaagc aggatgctga tctaaacgtg gaaaaagacc agtcctgcct    540
ctgttgtaga agacatgtgg tgtatataaa gtttgtgatc gttggcggac attttggaat    600
ttagataatg ggctgtgtgc aatgtaagga taaagaagca acaaaactga cggaggagag    660
ggacggcagc ctgaaccaga gctctgggta ccgctatggc acagacccca cccctcagca    720
ctaccccagc ttcggtgtga cctccatccc caactacaac aacttccacg cagccggggg    780
ccaaggactc accgtctttg gaggtgtgaa ctcttcgtct catacgggga ccttgcgtac    840
gagaggagga acaggagtga cactctttgt ggccctttat gactatgaag cacggacaga    900
agatgacctg agttttcaca aaggagaaaa atttcaaata ttgaacagct cggaaggaga    960
ttggtgggaa gcccgctcct tgacaactgg agagacaggt tacattccca gcaattatgt   1020
ggctccagtt gactctatcc aggcagaaga gtggtacttt ggaaaacttg gccgaaaaga   1080
tgctgagcga cagctattgt cctttggaaa cccaagaggt acctttctta tccgcgagag   1140
tgaaaccacc aaaggtgcct attcactttc tatccgtgat tgggatgata tgaaaggaga   1200
ccatgtcaaa cattataaaa ttcgcaaact tgacaatggt ggatactaca ttaccacccg   1260
```

-continued

```
ggcccagttt gaaacacttc agcagcttgt acaacattac tcagagagag ctgcaggtct   1320
ctgctgccgc ctagtagttc cctgtcacaa agggatgcca aggcttaccg atctgtctgt   1380
caaaaccaaa gatgtctggg aaatccctcg agaatccctg cagttgatca agagactggg   1440
aaatgggcag tttggggaag tatggatggg tacctggaat ggaaacacaa aagtagccat   1500
aaagactctt aaaccaggca caatgtcccc cgaatcattc cttgaggaag cgcagatcat   1560
gaagaagctg aagcacgaca agctggtcca gctctatgca gtggtgtctg aggagcccat   1620
ctacatcgtc accgagtata tgaacaaagg aagtttactg gatttcttaa aagatggaga   1680
aggaagagct ctgaaattac caaatcttgt ggacatggca gcacaggtgg ctgcaggaat   1740
ggcttacatc gagcgcatga attatatcca tagagatctg cgatcagcaa acattctagt   1800
ggggaatgga ctcatatgca agattgctga cttcggattg gcccgattga tagaagacaa   1860
tgagtacaca gcaagacaag gtgcaaagtt ccccatcaag tggacggccc ccgaggcagc   1920
cctgtacggg aggttcacaa tcaagtctga cgtgtggtct tttggaatct tactcacaga   1980
gctggtcacc aaaggaagag tgccataccc aggcatgaac aaccgggagg tgctggagca   2040
ggtggagcga ggctacagga tgccctgccc gcaggactgc cccatctctc tgcatgagct   2100
catgatccac tgctggaaaa aggaccctga agaacgcccc acttttgagt acttgcagag   2160
cttcctggaa gactacttta ccgcgacaga gccccagtac caacctggtg aaaacctgta   2220
aggcccgggt ctgcggagag aggccttgtc ccagaggctg ccccacccct ccccattagc   2280
tttcaattcc gtagccagct gctccccagc agcggaaccg cccaggatca gattgcatgt   2340
gactctgaag ctgacgaact tccatggccc tcattaatga cacttgtccc caaatccgaa   2400
cctcctctgt gaagcattcg agacagaacc ttgttatttc tcagactttg gaaaatgcat   2460
tgtatcgatg ttatgtaaaa ggccaaacct ctgttcagtg taaatagtta ctccagtgcc   2520
aacaatccta gtgctttcct tttttaaaaa tgcaaatcct atgtgatttt aactctgtct   2580
tcacctgatt caactaaaaa aaaaaaagta ttattttcca aaagtggcct ctttgtctaa   2640
aacaataaaa tttttttca tgttttaaca aaaaccaatc aggacaggtg tttgtttttg   2700
ttttcttttt tataaatatg aatatatata atatatatgt ccctgtacat atacaatgtg   2760
ggtgctaatg tggagactgt ggccggcctg agccaccaag ctgcgggacc cagagggagg   2820
attttactgc aagtcagcat caaagcaccg gtgttattct gaaaacacca gtggcctcat   2880
ttttggcttt tgcaaagcat gaatttttc atttggattg cactttcctg gttcatgact   2940
gtacctgtag gtggttgtta ctttgactct tttcaggaac cacccccaa gctgaattta   3000
caagttctgt tagcactatt tgcttcaact tactgcgatt tgttctcaaa acttaaaaat   3060
aagcaagcaa atggctgata ctaccaagag aactggaaga tggataccac acaaacttct   3120
tgtataaaaa tatgaatgct gaaatgtttc agacattttt aatttaataa acctgtaacc   3180
acatttaagt gatctaaaac ccatagcatt gtagtcatgg caacccgcta aactttctca   3240
tgcaactaaa atttctgggg gaaatgaggg tgggggttgt acatttccca ttgtaaaata   3300
agtgttttaa atgtcctgta ctgctaacga atgactttct atatgtccag gagttctcca   3360
gtggaataac tatgcactac tttacatttc atggggatgc acaaaaacaa aaaagtatta   3420
catttttagt tgctgtttgt accaacctta aattacatat gtttaacaac aacaaatcaa   3480
aaatcctatt tctattgagt ttttaatact gactagcaac tctgaagtct taattccttt   3540
tttgttatga tttatttgtg agtttacatt tttaaattgt ttaactttct taatttagta   3600
attaaaaaga gagcatttta catttgaa                                      3628
```

<210> SEQ ID NO 660
<211> LENGTH: 5242
<212> TYPE: DNA
<213> ORGANISM: Homo sapiens

<400> SEQUENCE: 660
gccgcggcgg tggcggagac tgtggcttta agagcgtgcc gggagcccga gccccagccg 60
ggccgcgctt cgccgctgcg caccccagcg gagccaagcc ccacgctggc cggacagggc 120
cgcctgtcgc cgggctgctg agaactagcc ctagacctct gcgtgagggt tcttctgccg 180
aagacatcac cagtgtgtgg agcctgccac acccacccgc tgccaaacca cggcctttac 240
ctgtgtcttc cggtgtttcc cgtgcgaccc atcctgtggg agtgcctcgt gggctgcccc 300
agagttcacc ccacactcag cagcaccaat ggtgaagatg acaagatcga agactttcca 360
ggcatatctg ccctcctgcc accggaccta cagctgcatt cactgcagag ctcacttggc 420
caatcatgat gaactaattt ccaagtcatt ccaaggaagt caaggacgag catacctctt 480
taactcagta gttaatgtgg gctgtgggcc tgcagaagag cgagtgttgc taacaggact 540
gcatgcagtc gcagacattt actgtgaaaa ctgcaaaacc actctgggct ggaaatacga 600
acatgctttt gaaagcagcc agaaatataa agaaggcaaa tacatcattg aactagcaca 660
catgatcaag gacaatggct gggactgatt ggacagcatc tacccaaccc agtgtccacg 720
tgaacgccat tcaaccgaac attcttccca agcgtgagag agtgactgac acttggttcc 780
atccatttag ggccttgcc atccggggca tcctcccacc ctgacgccat ctttctggtg 840
accggcctct aaatcgctgt ctctctgtct ctttgctttg tatctgtttg tgagttgatc 900
ctggcttctc tctctgttct agttttggct gaaaacaaaa caacaaaagg aacagatcct 960
tgaccgcatg gcggcagccc accttggtaa gggccccagg gcccatgcga gagctgcctg 1020
atggcctctt gtcaggagag cagtggcacg ggggcgtgag gaagagggaa aggggaaact 1080
ctaagggtcc tggcgcgggg aaggggtgga agggtggagg taggaacaaa attgcgccgc 1140
tcctggagac ctgataactt aggcttgaaa taattgactt gtctaaaagg acaaagagaa 1200
aaaaaaaata cctcatgact gcattctctc tgactagaag cttctgttcc tgacaccaaa 1260
tgtgccaggt tagcaaatga gcacaagatg tggccctgat tctagttggt ggggcaaggg 1320
cctggttctc ctgggctgag tgggggagtg tcctggcagc agcgagtgac ctgggcagtg 1380
gccaggtggg tgcgatgact ctgatgcctc actcagtctc tgggcaatca tcatctttgc 1440
ctctagccac cgtagataag gtgtgaaggg actgctgttt gcaatgggct taccatccaa 1500
atatcccaaa ggctttgacc agcaaccaag taaaatcagt aattgaggag agcagggcac 1560
aaaggggctg cagtttggga gctcctgaag aaatggctca gatattgagt cagagaaata 1620
aaaagtagga tcagttagca attctaactg cccttccttc tgacccctca taagaggagt 1680
gtggtgaggg aggggactgg gtaggggtca tcccaggagg aggggtttac attggaacca 1740
gttcaggttc ggtgcatctt tcctcttcgg ttttacagtg gcttccgtgg gatcgtcaat 1800
ttcttgttct tagagtttcg ggtgtttttc tccagtcttg ttactgtaga ctgtagaaag 1860
cacgggcccc aggctctgag cttagtaata acctggctgg tagattcctc atgcccctaa 1920
ttgtcccact taggcctgaa tgtcttgcat ggagagaaat ctcctgtcag tgtggtccag 1980
cagcagggag gagttctgcc caaattccga tatcacccct tcccccatcc aagcatcctt 2040
cgattaggga agtggagagc acatccctgt aaggcccata agagaaagag gagtttgtta 2100

-continued

```
catttaatca acactgtgaa gtctgttcta cagcaattca gccattacac agtatatgac   2160
tgaaactcat ttaactgggt taatttcatt tcttagactg aatatattat tgttaagata   2220
cgtgtgcgtg ttaggtaatt ctcagcatct cctccaagta ggccgacctt ctcggaaaat   2280
tcaccctaaa agtctcacaa aagaatgagt tcatggggag attctgtaaa gtgatgaact   2340
gagatgaaag cagccaacag cccaggagct tttcagaata gcgtctgcag cagaaccagt   2400
ttccattcag agcgcgtcct tggtggaaat gctttttttgt gtgtctccac gcgctgatgg   2460
tggaatggga gccccaagac gtgtgggctt agaaatcaac ttttgttccc caaggcttct   2520
tgtccagatc tttccagtgc tttcatagcc ctgggagatc aagttgttct ccccacttta   2580
ctgcaaggta gactgaagtt cagaagaaat actgaatttc tgctcccaga agaatagttt   2640
ctctggctca caggcccaag ttctcaatga aatcgttttt taactttcac attcctaagc   2700
tggcttcccg gcacagaagc catggatttc ccctctctcc cttccccctc ctcaaggaaa   2760
tagtcttcct ttatggattt tcattggact ctttcctcag cgattgtcct ggctgtttat   2820
tgatagtcct tcccataaga aaatggggtt aaacatgggg taggtatttt gtctttcaaa   2880
ctacaaatgg aatgtggtga cataaactag acatggggtg ccctcaagtt tccaagggga   2940
ccaatgtgcc actgttcttc cttggggatg aggcctttga ctgttggatg gatcagagca   3000
ggctccagtc agaccctggt tctgaatgtt tttttttcg gtgactatcc agtgagcctt   3060
cagtgggtgc aaggcgccat acttgctgtg agagagctga gtagagtgtt ggtttttcca   3120
taactacagg gggaaaaaaa gtcattaggc tttccctttg tgtcagtgaa accaaaagtg   3180
cttcttacaa cgttcgctct gttcatgggt tgtctatcta acattgagca gcattggaga   3240
ggccacagct gagctatgga gatgctaaat taactcatgg cctcagtcag ttcattcttt   3300
aatttcctca ccaaattatt gacttagagc ataaccaaag acctcattca ttcaccccag   3360
gtgggttggg gtaattggag tttgttggtg aagtttgggg gcggggtgtt gggagtagag   3420
acagggtaag gggacgtgag aaaggaaaag gcatgaagtt ctatacctca gccagcagct   3480
gccttcgttt ggaactgaag tccagccagc agactctcta gctccatctc ccctgtgcca   3540
ccctaggtca tatgaccttg gccaccttgg agtagaccca gacccctcgg gacccgggac   3600
attagtctca ggctgctgat ggattgattt gacatgaacc aaacacagcc aaactcgata   3660
cccacaagct gtcagctgaa cctgactgag tgttcttcct gagttcacga ggataggcta   3720
gagtgcattt ttactggtgg atcagtgtgt gcgaaagaga tgaccctta taaagagatt   3780
ttcaagtgga tatatataaa agaaacagtt gcttgtaaaa tatactttg taaataatat   3840
ttaatttttt aaataatata tttggtgctg ttttctcaga tcccctgaga gcacttttta   3900
ttttcctttt aaattctatg gtttcctttg catttcttga agtatatttt aagggaaaca   3960
gtgatcacca atacatgttt tcagtttttt ttttttttaa ggtctctatc actttaatct   4020
ggatcaaggc tttgaagcaa tgcctctctg catttttttcc ccagtggaac agactctgca   4080
gtacattaat caggttgaga attgaaatat tttcttgcat cagtattggc tagaaaagaa   4140
aataaataaa accaagttaa tttagtagta acaacttaca gtgattcttc ctgttggaag   4200
aatttccaac aaatcagaat cacgttttta gttgtgcgtg tgcgcgcaca cgtgtgtaaa   4260
aagcactttc gattgtgcct cctgttttct cgagtgggga cactttaact acagtttaca   4320
cctcgggcgc ataaagtttt tcttctcttt ctctctggtt gtttctgttt ctgagtggac   4380
caacagcaga acccacgagg atttgttttg agtatggagc tgttgcgggt ttgctccttt   4440
ttcttgcttt gcgtgctcag tttttacaga ctgtaaagga gatgtgttgt ttgtgaagat   4500
```

```
ggagcagagt caaatctgtg cttctaactg agatgagagt gtattaatca cgtatcgcag   4560

ggctccagct gttttagaag ccacatcatg ttaaacatta actggtttgg attaaaagaa   4620

cattaatatt ataatacaca tatcttagtg gtaaacagct ttttttttt aaggtcagat    4680

tgcctcaggt ttagaaagag gctgagaaat caaatcttga acacaatcaa cttacatatt   4740

ttaaaggaat ctgcctcaaa tgagaaaata tgctagttat ctagatagag gaaagagata   4800

tttacttttt taaaaattaa aatagttatg aaatctggca gaaaaggtaa agcctagaag   4860

aaactatgaa agctattctc atgttaccaa attctatctg cgcatatgtt tttgtataac   4920

atttcggtga cagtgggagt cggttccctt tcccaacctg cagagactat cttccaatac   4980

agaatctgtc tatttatgct tgtgtttaca aactgtattt gttgggtttg ggtttttgtt   5040

ttctttggtg gcatttttca ggtcactttg cttctataac aaaggtaatt gttttcaaat   5100

aatttgtctt caccttttcc tgtatttgta catagtgatt cagtattaga gaaaagtgca   5160

ttgtttctgt catatttcca atctgtgttg gtgctcattt gagaaaataa aagttttcaa   5220

atattaactc ttaaaaaaaa aa                                             5242
```

<210> SEQ ID NO 661
<211> LENGTH: 3679
<212> TYPE: DNA
<213> ORGANISM: Homo sapiens

<400> SEQUENCE: 661

```
ccctcccctc ccgatcctca tccccttgcc ctcccccagc ccagggactt ttccggaaag     60

tttttatttt ccgtctgggc tctcggagaa agaagctcct ggctcagcgg ctgcaaaact    120

ttcctgctgc cgcgccgcca gcccccgccc tccgctgccc ggccctgcgc cccgccgagc    180

gatgagcgcc cctccggtcc tgcggccgcc cagtccgctg ctgcccgtgg cggcggcagc    240

tgccgcagcg gccgccgcac tggtcccagg gtccgggccc gggcccgcgc cgttcttggc    300

tcctgtcgcg gccccggtcg ggggcatctc gttccatctg cagatcggcc tgagccgtga    360

gccggtgctg ctgctgcagg actcgtccgg ggactacagc ctggcgcacg tccgcgagat    420

ggcttgctcc attgtcgacc agaagttccc tgaatgtggt ttctacggaa tgtatgataa    480

gatcctgctt tttcgccatg accctacctc tgaaaacatc cttcagctgg tgaaagcggc    540

cagtgatatc caggaaggcg atcttattga agtggtcttg tcagcttccg ccacctttga    600

agactttcag attcgtcccc acgctctctt tgttcattca tacagagctc cagctttctg    660

tgatcactgt ggagaaatgc tgtgggggct ggtacgtcaa ggtcttaaat gtgaagggtg    720

tggtctgaat taccataaga gatgtgcatt taaaataccc aacaattgca gcggtgtgag    780

gcggagaagg ctctcaaacg tttccctcac tggggtcagc accatccgca catcatctgc    840

tgaactctct acaagtgccc ctgatgagcc ccttctgcaa aaatcaccat cagagtcgtt    900

tattggtcga gagaagaggt caaattctca atcatacatt ggacgaccaa ttcaccttga    960

caagattttg atgtctaaag ttaaagtgcc gcacacattt gtcatccact cctacacccg   1020

gcccacagtg tgccagtact gcaagaagct tctgaagggg cttttcaggc agggcttgca   1080

gtgcaaagat tgcagattca actgccataa acgttgtgca ccgaaagtac caaacaactg   1140

ccttggcgaa gtgaccatta atggagattt gcttagccct ggggcagagt ctgatgtggt   1200

catggaagaa gggagtgatg acaatgatag tgaaaggaac agtgggctca tggatgatat   1260

ggaagaagca atggtccaag atgcagagat ggcaatggca gagtgccaga acgacagtgg   1320
```

-continued

```
cgagatgcaa gatccagacc cagaccacga ggacgccaac agaaccatca gtccatcaac   1380
aagcaacaat atcccactca tgagggtagt gcagtctgtc aaacacacga agaggaaaag   1440
cagcacagtc atgaaagaag gatggatggt ccactacacc agcaaggaca cgctgcggaa   1500
acggcactat tggagattgg atagcaaatg tattaccctc tttcagaatg acacaggaag   1560
caggtactac aaggaaattc ctttatctga aattttgtct ctggaaccag taaaaacttc   1620
agctttaatt cctaatgggg ccaatcctca ttgtttcgaa atcactacgg caaatgtagt   1680
gtattatgtg ggagaaaatg tggtcaatcc ttccagccca tcaccaaata acagtgttct   1740
caccagtggc gttggtgcag atgtggccag gatgtgggag atagccatcc agcatgccct   1800
tatgcccgtc attcccaagg gctcctccgt gggtacagga accaacttgc acagagatat   1860
ctctgtgagt atttcagtat caaattgcca gattcaagaa aatgtggaca tcagcacagt   1920
atatcagatt tttcctgatg aagtactggg ttctggacag tttggaattg tttatggagg   1980
aaaacatcgt aaaacaggaa gagatgtagc tattaaaatc attgacaaat tacgatttcc   2040
aacaaaacaa gaaagccagc ttcgtaatga ggttgcaatt ctacagaacc ttcatcaccc   2100
tggtgttgta aatttggagt gtatgtttga gacgcctgaa agagtgtttg ttgttatgga   2160
aaaactccat ggagacatgc tggaaatgat cttgtcaagt gaaaagggca ggttgccaga   2220
gcacataacg aagtttttaa ttactcagat actcgtggct ttgcggcacc ttcattttaa   2280
aaatatcgtt cactgtgacc tcaaaccaga aaatgtgttg ctagcctcag ctgatccttt   2340
tcctcaggtg aaactttgtg attttggttt tgcccggatc attggagaga agtctttccg   2400
gaggtcagtg gtgggtaccc ccgcttacct ggctcctgag gtcctaagga acaagggcta   2460
caatcgctct ctagacatgt ggtctgttgg ggtcatcatc tatgtaagcc taagcggcac   2520
attcccattt aatgaagatg aagacataca cgaccaaatt cagaatgcag ctttcatgta   2580
tccaccaaat ccctggaagg aaatatctca tgaagccatt gatcttatca acaatttgct   2640
gcaagtaaaa atgagaaagc gctacagtgt ggataagacc ttgagccacc cttggctaca   2700
ggactatcag acctggttag atttgcgaga gctggaatgc aaaatcgggg agcgctacat   2760
cacccatgaa agtgatgacc tgaggtggga gaagtatgca ggcgagcagg ggctgcagta   2820
ccccacacac ctgatcaatc caagtgctag ccacagtgac actcctgaga ctgaagaaac   2880
agaaatgaaa gccctcggtg agcgtgtcag catcctctga gttccatctc ctataatctg   2940
tcaaaacact gtggaactaa taaatacata cggtcaggtt taacatttgc cttgcagaac   3000
tgccattatt ttctgtcaga tgagaacaaa gctgttaaac tgttagcact gttgatgtat   3060
ctgagttgcc aagacaaatc aacagaagca tttgtatttt gtgtgaccaa ctgtgttgta   3120
ttaacaaaag ttccctgaaa cacgaaactt gttattgtga atgattcatg ttatatttaa   3180
tgcattaaac ctgtctccac tgtgcctttg caaatcagtg tttttcttac tggagcttca   3240
ttttggtaag agacagaatg tatctgtgaa gtagttctgt ttggtgtgtc ccattggtgt   3300
tgtcattgta aacaaactct tgaagagtcg attatttcca gtgttctatg aacaactcca   3360
aaacccatgt gggaaaaaaa tgaatgagga gggtagggaa taaaatccta agacacaaat   3420
gcatgaacaa gttttaatgt atagttttga atcctttgcc tgcctggtgt gcctcagtat   3480
atttaaactc aagacaatgc acctagctgt gcaagaccta gtgctcttaa gcctaaatgc   3540
cttagaaatg taaactgcca tatataacag atacatttcc ctctttctta taatactctg   3600
ttgtactatg gaaaatcagc tgctcagcaa cctttcacct ttgtgtattt ttcaataata   3660
aaaaatattc ttgtcaaaa                                                3679
```

<210> SEQ ID NO 662
<211> LENGTH: 3418
<212> TYPE: DNA
<213> ORGANISM: Homo sapiens

<400> SEQUENCE: 662
gctcgggcgc cgagtctgcg cgctgacgtc cgacgctcca ggtactttcc ccacggccga 60
cagggcttgg cgtgggggcg gggcgcggcg cgcagcgcgc atgcgccgca gcgccagcgc 120
tctccccgga tcgtgcgggg cctgagcctc tccgccggcg caggctctgc tcgcgccagc 180
tcgctcccgc agccatgccc accaccatcg agcgggagtt cgaagagttg gatactcagc 240
gtcgctggca gccgctgtac ttggaaattc gaaatgagtc ccatgactat cctcatagag 300
tggccaagtt tccagaaaac agaaatcgaa acagatacag agatgtaagc ccatatgatc 360
acagtcgtgt taaactgcaa aatgctgaga atgattatat taatgccagt ttagttgaca 420
tagaagaggc acaaaggagt tacatcttaa cacagggtcc acttcctaac acatgctgcc 480
atttctggct tatggtttgg cagcagaaga ccaaagcagt tgtcatgctg aaccgcattg 540
tggagaaaga atcggttaaa tgtgcacagt actggccaac agatgaccaa gagatgctgt 600
ttaaagaaac aggattcagt gtgaagctct tgtcagaaga tgtgaagtcg tattatacag 660
tacatctact acaattagaa aatatcaata gtggtgaaac cagaacaata tctcactttc 720
attatactac ctggccagat tttggagtcc ctgaatcacc agcttcattt ctcaatttct 780
tgtttaaagt gagagaatct ggctccttga accctgacca tgggcctgcg gtgatccact 840
gtagtgcagg cattgggcgc tctggcacct tctctctggt agacacttgt cttgttttga 900
tggaaaaagg agatgatatt aacataaaac aagtgttact gaacatgaga aaataccgaa 960
tgggtcttat tcagacccca gatcaactga gattctcata catggctata atagaaggag 1020
caaaatgtat aaagggagat tctagtatac agaaacgatg gaaagaactt tctaaggaag 1080
acttatctcc tgcctttgat cattcaccaa acaaaataat gactgaaaaa tacaatggga 1140
acagaatagg tctagaagaa gaaaaactga caggtgaccg atgtacagga ctttcctcta 1200
aaatgcaaga tacaatggag gagaacagtg agagtgctct acggaaacgt attcgagagg 1260
acagaaaggc caccacagct cagaaggtgc agcagatgaa acagaggcta aatgagaatg 1320
aacgaaaaag aaaaaggtgg ttatattggc aacctattct cactaagatg ggtttatgt 1380
cagtcatttt ggttggcgct tttgttggct ggacactgtt ttttcagcaa aatgccctat 1440
aaacaattaa ttttgcccag caagcttctg cactagtaac tgacagtgct acattaatca 1500
taggggtttg tctgcagcaa acgcctcata tcccaaaaac ggtgcagtag aatagacatc 1560
aaccagataa gtgatattta cagtcacaag cccaacatct caggactctt gactgcaggt 1620
tcctctgaac cccaaactgt aaatggctgt ctaaaataaa gacattcatg tttgttaaaa 1680
actggtaaat tttgcaactg tattcataca tgtcaaacac agtatttcac ctgaccaaca 1740
ttgagatatc ctttatcaca ggatttgttt ttggaggcta tctggatttt aacctgcact 1800
tgatataagc aataaatatt gtggttttat ctacgttatt ggaaagaaaa tgacatttaa 1860
ataatgtgtg taatgtataa tgtactattg acatgggcat caacactttt attcttaagc 1920
atttcagggt aaatatattt tataagtatc tatttaatct tttgtagtta actgtacttt 1980
ttaagagctc aatttgaaaa atctgttact aaaaaaataa attgtatgtc gattgaattg 2040
tactggatac attttccatt tttctaaaga gaagtttgat atgagcagtt agaagttgga 2100

```
ataagcaatt tctactatat attgcatttc ttttatgttt tacagttttc cccattttaa   2160

aaagaaaagc aaacaaagaa acaaaagttt ttcctaaaaa tatctttgaa ggaaaattct   2220

ccttactggg atagtcaggt aaacagttgg tcaagacttt gtaaagaaat tggtttctgt   2280

aaatcccatt attgatatgt ttatttttca tgaaaatttc aatgtagttg gggtagatta   2340

tgatttagga agcaaaagta agaagcagca ttttatgatt cataatttca gtttactaga   2400

ctgaagtttt gaagtaaaca cttttcagtt tctttctact tcaataaata gtatgattat   2460

atgcaaacct tacattgtca ttttaactta atgaatattt tttaaagcaa actgtttaat   2520

gaatttaact gctcatttga atgctagctt tcctcagatt tcaacattcc attcagtgtt   2580

taatttgtct tacttaaact tgaaattgtt gttacaaatt taattgctag gaggcatgga   2640

tagcatacat tattatggat agcatacctt atttcagtgg ttttcaaact atgctcattg   2700

gatgtccagg tgggtcaaga ggttactttc aaccacagca tctctgcctt gtctctttat   2760

atgccacata agatttctgc ataaggctta agtattttaa agggggcagt tatcatttaa   2820

aaacagtttg gtcgggcgcg gtggctcatg cctgtaatcc cagcactttg ggaggctgaa   2880

gtgggcagat cacctgaggt caggagttca agaccagcct ggccaacgtg gtgaaacacc   2940

atctctacta aaaatgcaaa aattagctgg gcatggtgga gggcacctgt aatctcagct   3000

actcaggagg ctgaggtagg agaattgctt gaacccagga gatggaggtt gcagtgagct   3060

gagatcacgt cactgcactc cagccagggc gacagagcga gactccatct caaaagaaac   3120

aaacaaaaaa aacagtttgg gccgggtgtg gtggctcacg cttgtaatcc cagcacttcg   3180

gaaggccaag gcgggcggat cacgaggtca agagatggag actgtcctgg ccaacatggt   3240

gaaatccctt ctttactaaa aatacaaaaa ttatctgggc gtggtggtgc atgcctgtag   3300

tcccagctcc ttgggaggct aaggcaggag aatcacttga acccgggagg cagaggttgc   3360

agtgagccga gattgcacca ctgcactcca gcctggcaac agagcaagac ttcgtctc     3418
```

<210> SEQ ID NO 663
<211> LENGTH: 2950
<212> TYPE: DNA
<213> ORGANISM: Homo sapiens

<400> SEQUENCE: 663

```
cggctggctg cggcggccgg ggaggccggg gaggccgcgg cgcggtcact gcgagccgag     60

ccgagccgcg ccgagccgcg ccgatcgcca tccggcctcg gcactcgcgc gcgatcccgg    120

ccggcggcgc ggcccggcgg gccaggcggc gccacagccc atggagctcg agaacatcgt    180

agcgaacacg gtgctactca aggcccggga aggtggcggt ggaaatcgca aaggcaaaag    240

caagaaatgg cggcagatgc tccagttccc tcacatcagc cagtgcgaag agctgcggct    300

cagcctcgag cgtgactatc acagcctgtg cgagcggcag cccattgggc gcctgctgtt    360

ccgagagttc tgtgccacga ggccggagct gagccgctgc gtcgccttcc tggatggggt    420

ggccgagtat gaagtgaccc cggatgacaa gcggaaggca tgtgggcggc agctaacgca    480

gaattttctg agccacacgg gtcctgacct catccctgag gtcccccggc agctggtgac    540

gaactgcacc cagcggctgg agcagggtcc ctgcaaagac cttttccagg aactcacccg    600

gctgacccac gagtacctga gcgtggcccc ttttgccgac tacctcgaca gcatctactt    660

caaccgtttc ctgcagtgga agtggctgga aaggcagcca gtgaccaaaa acaccttcag    720

gcaataccga gtcctgggca aaggtggctt tggggaggtg tgcgcctgcc aggtgcgggc    780

cacaggtaag atgtatgcct gcaagaagct agagaaaaag cggatcaaga agcggaaagg    840
```

-continued

```
ggaggccatg gcgctgaacg agaagcagat cctggagaaa gtgaacagta ggtttgtagt    900
gagcttggcc tacgcctatg agaccaagga cgcgctgtgc ctggtgctga cactgatgaa    960
cgggggcgac ctcaagttcc acatctacca catgggccag gctggcttcc ccgaagcgcg   1020
ggccgtcttc tacgccgccg agatctgctg tggcctggag gacctgcacc gggagcgcat   1080
cgtgtacagg gacctgaagc ccgagaacat cttgctggat gaccacggcc acatccgcat   1140
ctctgacctg ggactagctg tgcatgtgcc cgagggccag accatcaaag ggcgtgtggg   1200
caccgtgggt tacatggctc cggaggtggt gaagaatgaa cggtacacgt tcagccctga   1260
ctggtgggcg ctcggctgcc tcctgtacga gatgatcgca ggccagtcgc ccttccagca   1320
gaggaagaag aagatcaagc gggaggaggt ggagcggctg gtgaaggagg tccccgagga   1380
gtattccgag cgcttttccc cgcaggcccg ctcactttgc tcacagctcc tctgcaagga   1440
ccctgccgaa cgcctggggt gtcgtggggg cagtgcccgc gaggtgaagg agcacccccct   1500
ctttaagaag ctgaacttca agcggctggg agctggcatg ctggagccgc cgttcaagcc   1560
tgacccccag gccatttact gcaaggatgt tctggacatt gaacagttct ctacggtcaa   1620
gggcgtggag ctggagccta ccgaccagga cttctaccag aagtttgcca caggcagtgt   1680
gcccatcccc tggcagaacg agatggtgga gaccgagtgc ttccaagagc tgaatgtctt   1740
tgggctggat ggctcagttc ccccagacct ggactggaag ggccagccac ctgcacctcc   1800
taaaaaggga ctgctgcaga gactcttcag tcgccaagat tgctgtggaa actgcagcga   1860
cagcgaggaa gagctcccca cccgcctcta gcccccagcc cgaggccccc accagcagtt   1920
ggcggtagca gctactccga gcgccgttta cagttttgca cagtgatctt ccccattgtc   1980
cactcaagtc gtggcctggg gaacacagac ggagctgtcc ccagtgtcct ccgtccctca   2040
gcccctggcc tggctgagtt tggcagggcc tgggccatcc ctgggacaaa ggtgcgtccc   2100
ttcagctctt ctccgtggag ctcggggctt tctgtattta tgtatttgta cgaatgtata   2160
tagcgaccag agcattctta attcccgccg cagacctggc gccccccgcct tggctcctgg   2220
gggcagccag ccctggctgg gagagcggga gctggcagag gagccactgc caaactcaag   2280
gctcctctgg cccagcttgg atggctgagg gtggtcacac ccctgagcct tcagcactgt   2340
gctggccacc ccggcctctg agtaagactc gtgcctcccc ctgctgccct gggctcaggc   2400
tgctaccctc tggggcccaa agctgtccct tctcagtgct tgtcagcgct gggtctgggg   2460
cctctgtatg ccctaggcct gtgccaaagt ggccagagat tgggctgcct gtgataccca   2520
tcagcccact gccccggccg gcccagatag gtctgcctct gccttccagc tcccacagcc   2580
tggtccctga tactgggctc tgtcctgcag acacctcttt cagaaacgcc caagcccagc   2640
ccctaggagg gggtggggca tccctggtca accctcaaac attccggact cccctcataa   2700
caatagacac atgtgcccag caataatccg ccccttcctg tgtgcgcctg tggggtgcgt   2760
gcgcgcgcgt gtgtacctgt gtgggtgaag gggatagggc gaggctgtgc ctgtgcccca   2820
ggtcccagcc ctggcccttc ccagactgtg atggccatcc tggtcccagt gttagggtag   2880
catgggatta cagggccctg ttttttccat atttaaagcc aatttttatt actcgttttg   2940
tccaacgtaa                                                          2950
```

<210> SEQ ID NO 664
<211> LENGTH: 1267
<212> TYPE: DNA
<213> ORGANISM: Homo sapiens

<400> SEQUENCE: 664
cgagggctgc ttccggctgg tgcccccggg ggagacccaa cctggggcga cttcaggggt 60
gccacattcg ctaagtgctc ggagttaata gcacctcctc cgagcactcg ctcacggcgt 120
ccccttgcct ggaaagatac cgcggtccct ccagaggatt tgagggacag ggtcggaggg 180
ggctcttccg ccagcaccgg aggaagaaag aggaggggct ggctggtcac cagagggtgg 240
ggcggaccgc gtgcgctcgg cggctgcgga gagggggaga gcaggcagcg ggcggcgggg 300
agcagcatgg agccggcggc ggggagcagc atggagcctt cggctgactg gctggccacg 360
gccgcggccc ggggtcgggt agaggaggtg cgggcgctgc tggaggcggg ggcgctgccc 420
aacgcaccga atagttacgg tcggaggccg atccaggtca tgatgatggg cagcgcccga 480
gtggcggagc tgctgctgct ccacggcgcg gagcccaact gcgccgaccc cgccactctc 540
acccgacccg tgcacgacgc tgcccgggag ggcttcctgg acacgctggt ggtgctgcac 600
cgggccgggg cgcggctgga cgtgcgcgat gcctggggcc gtctgcccgt ggacctggct 660
gaggagctgg gccatcgcga tgtcgcacgg tacctgcgcg cggctgcggg ggcaccaga 720 ggcagtaacc atgcccgcat agatgccgcg gaaggtccct cagacatccc cgattgaaag 780
aaccagagag gctctgagaa acctcgggaa acttagatca tcagtcaccg aaggtcctac 840
agggccacaa ctgcccccgc cacaacccac cccgctttcg tagttttcat ttagaaaata 900
gagcttttaa aaatgtcctg ccttttaacg tagatatatg ccttccccca ctaccgtaaa 960
tgtccattta tatcattttt tatatattct tataaaaatg taaaaaagaa aaacaccgct 1020
tctgcctttt cactgtgttg gagttttctg gagtgagcac tcacgcccta agcgcacatt 1080
catgtgggca tttcttgcga gcctcgcagc ctccggaagc tgtcgacttc atgacaagca 1140
ttttgtgaac tagggaagct caggggggtt actggcttct cttgagtcac actgctagca 1200
aatggcagaa ccaaagctca aataaaaata aaataatttt cattcattca ctcaaaaaaa 1260
aaaaaaa 1267

<210> SEQ ID NO 665
<211> LENGTH: 8033
<212> TYPE: DNA
<213> ORGANISM: Homo sapiens

<400> SEQUENCE: 665
gggcgggccg gctggctggg aagatggcgg cgggaacctg ggccgccgcc gccgccgccg 60
ccgccgccgc ggagcgaacc aggggtgtcc ggggtgcgcg gtccagggcc ggggccgggc 120
catgagcgcg ccgtcctcga gtccccgagc cgcggagccc gcccgcgccc ctcgggccgc 180
cccgcgtccc tcgccatggc gcggctcgcg gactacttcg tgctggtggc gttcgggccg 240
cacccgcgcg ggagtgggga aggccagggc cagattctgc agcgcttccc agagaaggac 300
tgggaggaca acccattccc ccagggcatc gagctgtttt gccagcccag cgggtggcag 360
ctgtgtcccg agaggaatcc accgaccttc tttgttgctg tcctcaccga catcaactcc 420
gagcgccact actgcgcctg cttgaccttc tgggagccag cggagccttc acaggaaacg 480
acgcgcgtgg aggatgccac agagagggag gaagaggggg atgagggagg ccagacccac 540
ctgtctccca cagcacctgc cccatctgcc cagctgtttg caccgaagac gctggtactg 600
gtgtcgcgac tcgaccacac ggaggtgttc aggaacagcc ttggcctcat ctatgccatc 660
cacgtggagg gcctgaatgt gtgcctggag aacgtgattg ggaacctgct gacgtgcact 720
gtgcccctgg ctgggggctc gcagaggacg atctctttgg gggctggtga ccggcaggtc 780
atccagactc cactggccga ctcgctgccc gtcagccgct gcagcgtggc cctgctcttc 840
cgccagctag gcatcaccaa cgtgctgtct ttgttctgtg ccgccctcac ggagcacaag 900
gttctcttcc tgtcccggag ctaccagcgg ctcgccgatg cctgtagggg cctcctggca 960
ctgctgtttc ctctcagata cagcttcacc tatgtgccca tcctgccggc tcagctgctg 1020
gaggtcctca gcacacccac gcccttcatc attggggtca acgcggcctt ccaggcagag 1080
acccaggagc tgctcgatgt gattgttgct gatctggatg gagggacggt caccattcct 1140
gagtgtgtgc acattccacc cttgccagag ccactgcaga gtcagacgca cagtgtgctg 1200
agcatggtcc tggacccgga gctggagttg gctgacctcg ccttccctcc gcccacgaca 1260
tccacctcct ccctgaagat gcaggacaag gagctgcgcg cggtcttcct gcggctgttc 1320
gctcagctgc tgcagggcta tcgctggtgc ctgcacgtcg tgcgcatcca cccggagcct 1380
gtcatccgct tccataaggc agccttcctg ggccagcgtg ggctggtaga ggacgatttc 1440
ctgatgaagg tgctggaggg catggccttt gctggctttg tgtcagagcg tggggtccca 1500
taccgcccta cggacctgtt cgatgagctg gtggcccacg aggtggcaag gatgcgggcg 1560
gatgagaacc acccccagcg tgtcctgcgt cacgtccagg aactggcaga gcagctctac 1620
aagaacgaga acccgtaccc agccgtggcg atgcacaagg tacagaggcc cggtgagagc 1680
agccacctgc gacgggtgcc ccgacccttc ccccggctgg atgagggcac cgtgcagtgg 1740
atcgtggacc aggctgcagc caagatgcag ggtgcacccc cagctgtgaa ggccgagagg 1800
aggaccaccg tgccctcagg gccccccatg actgccatac tggagcggtg cagtgggctg 1860
catgtcaaca gcgcccggcg gctggaggtt gtgcgcaact gcatctccta cgtgtttgag 1920
gggaaaatgc ttgaggccaa gaagctgctc ccagccgtgt tgagggccct gaaggggcga 1980
gctgcccgcc gctgcctcgc ccaggagctg cacctgcatg tgcagcagaa ccgtgcggtc 2040
ctggaccacc agcagtttga ctttgtcgtc cgtatgatga actgctgcct gcaggactgc 2100
acttctctgg acgagcatgg cattgcggcg gctctgctgc ctctggtcac agccttctgc 2160
cggaagctga gcccgggggt gacgcagttt gcatacagct gtgtgcagga gcacgtggtg 2220
tggagcacgc cacagttctg ggaggccatg ttctatgggg atgtgcagac tcacatccgg 2280
gccctctacc tggagcccac ggaggacctg gccccccgccc aggaggttgg ggaggcacct 2340
tcccaggagg acgagcgctc tgccctagac gtggcttctg agcagcggcg cttgtggcca 2400
actctgagtc gtgagaagca gcaggagctg gtgcagaagg aggagagcac ggtgttcagc 2460
caggccatcc actatgccaa ccgcatgagc tacctcctcc tgcccctgga cagcagcaag 2520
agccgcctac ttcgggagcg tgccgggctg ggcgacctgg agagcgccag caacagcctg 2580
gtcaccaaca gcatggctgg cagtgtggcc gagagctatg acacggagag cggcttcgag 2640
gatgcagaga cctgcgacgt agctggggct gtggtccgct tcatcaaccg ctttgtggac 2700
aaggtctgca cggagagtgg ggtcaccagc gaccacctca aggggctgca tgtcatggtg 2760
ccagacattg tccagatgca catcgagacc ctggaggccg tgcagcggga gagccggagg 2820
ctgccgccca tccagaagcc caagctgctg cggccgcgcc tgctgccggg tgaggagtgt 2880
gtgctggacg gcctgcgcgt ctacctgctg ccggatgggc gtgaggaggg cgcgggggc 2940
agtgctgggg gaccagcatt gctcccagct gagggcgccg tcttcctcac cacgtaccgg 3000
gtcatcttca cggggatgcc cacggacccc ctggttgggg agcaggtggt ggtccgctcc 3060
ttcccggtgg ctgcgctgac caaggagaag cgcatcagcg tccagacccc tgtggaccag 3120

-continued

```
ctcctgcagg acgggctcca gctgcgctcc tgcacattcc agctgctgaa aatggccttt   3180
gacgaggagg tggggtctga cagcgccgag ctcttccgta agcagctgca taagctgcgg   3240
tacccgccgg acatcagggc cacctttgcg ttcaccttgg gctctgccca cacacctggc   3300
cggccaccgc gagtcaccaa ggacaagggt ccttccctca gaaccctgtc ccggaacctg   3360
gtcaagaacg ccaagaagac catcgggcgg cagcatgtca ctcgcaagaa gtacaacccc   3420
cccagctggg agcaccgggg ccagccgccc cctgaggacc aggaggacga gatctcagtg   3480
tcggaggagc tggagcccag cacgctgacc ccgtcctcag ccctgaagcc ctccgaccgc   3540
atgaccatga gcagcctggt ggaaagggct tgctgtcgcg actaccagcg cctcggtctg   3600
ggcaccctga gcagcagcct gagccgggcc aagtctgagc ccttccgcat ttctccggtc   3660
aaccgcatgt atgccatctg ccgcagctac ccagggctgc tgatcgtgcc ccagagtgtc   3720
caggacaacg ccctgcagcg cgtgtcccgc tgctaccgcc agaaccgctt ccccgtggtc   3780
tgctggcgca gcgggcggtc caaggcggtg ctgctgcgct ctggaggcct gcatggcaaa   3840
ggtgtcgtcg gcctcttcaa ggcccagaac gcaccttctc caggccagtc ccaggcggac   3900
tcgagtagcc tggagcagga gaagtacctg caggctgtgg tcagctccat gccccgctac   3960
gccgacgcgt cgggacgcaa cacgcttagc ggcttctcct cagcccacat gggcagtcac   4020
gttcccagcc ccagagccag ggtcaccacg ctgtccaacc ccatggcggc ctcggcctcc   4080
agacggaccg caccccgagg taagtggggc agtgtccgga ccagtggacg cagcagtggc   4140
cttggcaccg atgtgggctc ccggctagct ggcagagacg cgctggcccc accccaggcc   4200
aacgggggcc ctcccgaccc gggcttcctg cgtccgcagc gagcagccct ctatatcctt   4260
ggggacaaag cccagctcaa gggtgtgcgg tcagaccccc tgcagcagtg ggagctggtg   4320
cccattgagg tattcgaggc acggcaggtg aaggctagct tcaagaagct gctgaaagca   4380
tgtgtcccag gctgccccgc tgctgagccc agcccagcct ccttcctgcg ctcactggag   4440
gactcagagt ggctgatcca gatccacaag ctgctgcagg tgtctgtgct ggtggtggag   4500
ctcctggatt caggctcctc cgtgctggtg ggcctggagg atggctggga catcaccacc   4560
caggtggtat ccttggtgca gctgctctca gacccctttct accgcacgct ggagggcttt   4620
cgcctgctgg tggagaagga gtggctgtcc ttcggccatc gcttcagcca ccgtggagct   4680
cacaccctgg ccgggcagag cagcggcttc acacccgtct tcctgcagtt cctggactgc   4740
gtacaccagg tccacctgca gttccccatg gagtttgagt tcagccagtt ctacctcaag   4800
ttcctcggct accaccatgt gtcccgccgt ttccggacct tcctgctcga ctctgactat   4860
gagcgcattg agctggggct gctgtatgag gagaaggggg aacgcagggg ccaggtgccg   4920
tgcaggtctg tgtgggagta tgtggaccgg ctgagcaaga ggacgcctgt gttccacaat   4980
tacatgtatg cgcccgagga cgcagaggtc ctgcggccct acagcaacgt gtccaacctg   5040
aaggtgtggg acttctacac tgaggagacg ctggccgagg gccctcccta tgactgggaa   5100
ctggcccagg ggcccccctga acccccagag gaagaacggt ctgatggagg cgctccccag   5160
agcaggcgcc gcgtggtgtg gccctgttac gacagctgcc cgcgggccca gcctgacgcc   5220
atctcacgcc tgctggagga gctgcagagg ctggagacag agttgggcca acccgctgag   5280
cgctggaagg acacctggga ccgggtgaag gctgcacagc gcctcgaggg ccggccagac   5340
ggccgtggca cccctagctc cctccttgtg tccaccgcac cccaccaccg tcgctcgctg   5400
ggtgtgtacc tgcaggaggg gcccgtgggc tccaccctga gcctcagcct ggacagcgac   5460
cagagtagtg gctcaaccac atccggctcc cgtcaggctg cccgccgcag caccagcacc   5520
```

ctgtacagcc agttccagac agcagagagt gagaacaggt cctacgaggg cactctgtac 5580
aagaaggggg ccttcatgaa gccttggaag gcccgctggt tcgtgctgga caagaccaag 5640
caccagctgc gctactacga ccaccgtgtg gacacagagt gcaagggtgt catcgacttg 5700
gcggaggtgg aggctgtggc acctggcacg cccactatgg gtgcccctaa gactgtggac 5760
gagaaggcct tctttgacgt gaagacaacg cgtcgcgttt acaacttctg tgcccaggac 5820
gtgccctcgg cccagcagtg ggtggaccgg atccagagct gcctgtcgga cgcctgagcc 5880
tcccagccct gcccggctgc tctgcttccg gtcgttaccg accactaggg gtgggcaggg 5940
ccgccccggc catgtttaca gccccggccc tcgacagtat tgaggccccg agcccccagc 6000
acttgtgtgt acagccccg tccccgcccc gccccgcccg gccggcccta acttattttg 6060
gcgtcacagc tgagcaccgt gccgggaggt ggccaaggta cagcccgcaa tgggcctgta 6120
aatagtccgg ccccgtcagc gtgtgctggt ccagccagcg gctgcaggcg agtttctaga 6180
accagagtct atataaagag agaactaacg ccacgctcct gtgcctgcct tccccactcc 6240
ccggctgcct gctctcggcc tacccagagg gtcccatctg cccctatcca ggcccacctg 6300
gcgggaggtt ggcatctttc tcgtgagcct ctcctggtgc ctgggtccac ccagctcggc 6360
ctgcatgtcc ctgggagtga ctttgctctg gggcggatc gagcaggagg cttcactggg 6420
gacttgcttg attccctcca cgcctcaggg ctggtctagg ggccggcacg gctggagagg 6480
aagcccccat ccctacccag gggatgcaga agctgacctc acagaggctt gggggtgaaa 6540
gggtgggtgg tcatttgacc ccagaaggct gttgcaggtc cagaggacac ttgaggtgga 6600
cgtcagtttc tggctagacc cgagctgaag ggatggaggc cggaggcggg gggggggggg 6660
ggacagtggg ctcccagggg aatgcaggtt gaccacatct ggctcctgcc aggcaacgag 6720
cagcatctgg cagagtaagg ggccaacgcc catgggggat ggaccctctc agttcttggg 6780
aattctgccc caaaagtcct ttccctgggg tctcagaggg cccccgtcct tcccttcttg 6840
gtgtcactgt ggcccctcac tgctcttttc ctattcaaac ctgagtccca ccaggcccag 6900
ggcttcacct gctgagctgt tgtgtccttg cctgtgacga ggcctggcca ggggtgcagg 6960
agcagaaggt ggggagggtt atagacgctg caaaggccaa gagaacatct gagagtggca 7020
gctggtgacc tggccagagg ggctggtgag gggcagagaa cctggctaga ggctgggtcc 7080
ctcaggtggt cctctcaggt gggaggcgag cagcaggtgt gggtgagggg aaggttctga 7140
tgacagctgc agaggcaggg cccagtgctg gcaggtgggg ggccaagacc ctcccctggt 7200
gggacgttga agccaaggat ggccttggac cctgtcaggc ccagcatggt cccgccacct 7260
cccccacccc acaggtggtg ttgggacacc tgggcgagat gtgagggtgg gctcacttga 7320
gccactgaaa ccagccaggt cttccctcag gccggacaga tggcgcctga ccgaagttcc 7380
tggcacctgg aaaacccaca ggtcagagta aggggagaaa ggaccctgcc ctccctgttc 7440
cacgtctgtg gggggagagg acaaatgcca ggcacagggt aggcggcgag aacaaggcac 7500
tcaatgtgta gctggggcag agactcggcc tctggggagc tgagcgggtt ccctccaccc 7560
ccaaccgtgg tggaaagaca agctcgctgg ggcggggtgg gggtctggtc tccacctgcc 7620
cctcccactc agccactgag gacaaggtgg ggcccaggct tctgggaggg ggagctggca 7680
caaaaggaag tcctggggtt gatgtgtttg agcgttaggc gaagtggttc cccccatccc 7740
ccaaacggaa aaatgtcagt atttgctaag ctgtagagac ctgatgccgt gatgtggcct 7800
gttccgcctc cacccattac acggggataa cgctgggggg tggcgggccc acaaaagagg 7860
tgctggagga gactctccca cccctggccg ggccggggct ttggggccgg aaggttcaca 7920
gtacgcggtt tgtccgaacg tcacggcttt tattgggagt tgggggtttg gggtgccctg 7980
tcaggtgatc agaacattaa aaatggactc aacgtaaaaa aaaaaaaaaa aaa 8033

<210> SEQ ID NO 666
<211> LENGTH: 6133
<212> TYPE: DNA
<213> ORGANISM: Homo sapiens

<400> SEQUENCE: 666
gccgtcaggg ccccagggag cgcggggcgc cgctgctgct gttcttcggc tcggttctgt 60
ctaccgggca gcgccggggc cggcggctgc ggcggcagag gaacaggagc cgggagccgc 120
gttccgccga gagttgggca gaggagcgcc cgcgccccgg cggcgtcatg ggccccctcc 180
ccgcgcttca gagggcacca gccgcgggaa cccccgggcc tcctcgcgcc cgagcctgag 240
cgaccctcgg gttctccggc gccccctccc tcgccctatt ttttttccta ctctcgctgc 300
cgttaccgct tctgctctcc gttatggcaa cagagccacc atcccccctc cgggtcgagg 360
cgccgggccc cccagaaatg cggacctcac cggcgatcga gtccacccct gagggcaccc 420
cgcagccggc gggcggcaga ctccgcttcc tcaacggctg cgtgccccte tcgcatcagg 480 tggccgggca catgtacggg aaggacaaag tgggtatact gcaacatcca gatggcacag 540
ttttgaaaca gttacaacca cctccaaggg gcccaagaga gctggaattc tataatatgg 600
tttatgctgc tgactgtttt gatggtgttc ttctagagct acgaaaatat ttgccaaaat 660
attatggcat ctggtcacct cccactgcac caaacgattt atacctaaaa ctggaagatg 720
tgacccataa atttaataag ccctgtataa tggatgtaaa gatagggcaa aaaagctatg 780
atccttttgc ctcatctgag aagattcagc aacaggtcag caagtaccca ttaatggaag 840
agattgggtt cttggtgctt ggcatgaggg tttatcatgt tcattccgat agctatgaga 900
cagaaaacca gcattacgga agaagcttaa caaaagaaac tataaaggat ggagtctcca 960 gatttttca taatgggtac tgcttaagaa aagatgctgt tgctgccagt attcagaaga 1020
ttgagaaaat tctgcagtgg tttgaaaacc agaagcagct taatttttac gcaagttcat 1080
tactctttgt ttatgaaggt tcatctcagc caaccactac aaaattgaat gacagaactt 1140
tggcagaaaa gtttttgtcc aaaggacaac tgtcagacac agaagtacta gagtacaata 1200
ataactttca tgtgttaagt tccacagcta atggaaaaat agagtcttca gtgggcaaaa 1260
gcttgtccaa gatgtatgcg cgtcacagga aaatatatac aaaaaagcat cacagtcaga 1320
cttcattgaa agttgaaaat ctggagcaag acaatgggtg gaaaagcatg tcacaggaac 1380
atttaaatgg aaatgtactt tcccaactgg aaaaagtttt ctaccatctt cccactggtt 1440
gccaagagat tgctgaagta gaagtgcgaa tgatagattt tgctcatgtg ttccctagca 1500
acacaataga tgagggatat gtttatgggc taaagcattt aatttctgta cttcgaagta 1560
ttttagacaa ttgaatcctc tgttgcagtc tttttaaggg gtgggccaat cataatgaag 1620
aggggcagtc aatatctgca cctttaatgc tatgtaaaaa atttgtatta tgagtcgaca 1680
ttttatttgt ctttatactt ttggaagaat ggttaacttt tttataatct tactcaggaa 1740
aactaactat ttgttcatta gaaaactatg aagaataaag aaacttagga atgttaagca 1800
gggaatgtgg tggtacatgg cttaaacatc ttttttggct caagcaaaat gcaaaccatt 1860
attcagtcat taagagttta gttagctttc tgtagccaat tcatgaaatc tctgtccacc 1920
cagccttgac aatgagccat atctaaaata ttacattatt agaacaccta ccaaaatctc 1980

```
gaaagcacag gttgatgtcc ttagtattgc tatgtatgaa gttactaaaa ctggagaaaa   2040
ttctacttca gaaataagta ctgtttaggt tttatattaa aagttcagac cagcatatca   2100
aagggtgctc cttagtgaaa tgatttagaa ttgttgcatt ccaaaagcag gttttctctt   2160
taatttttac atctctctct caaaatatta tacttcatga aaaagacaat tgatgtggat   2220
gacaacaaca aagtcttgaa attaagggca cactaattgt ccttactggg gttaggggaa   2280
gagagatatt attttcaagg aacaaaatat tttcctttac aatctttcat tcatgagaaa   2340
attggaatat aaatttatta cattgtgaaa gtatcataaa ccatatacct ttgtatctaa   2400
atgcagcttc aaaaaagtaa ataattgaag ttttatttct cctctaaata acttgaattt   2460
ttttctttaa aaatttatgt atttatatgt ccccatttag ttaagtggta gtgtaaatgt   2520
atgttgttaa aaacagtttc tcagaattat agtaagcaat gaaagacaat atctaattag   2580
gttgttatca aaaatactgt gtgtaaatta gtccgtaata tagggtttgg tgcgtatcta   2640
tattcatgct tctatttcac tcttcctcaa aacagtttta tattatgttg accagtgaaa   2700
ttgtaactta atttcatggg gacaggggca gtgctacagt tcctggaaaa attagatttg   2760
tattatcttt gtttcacacc caccacctta aaaaaaaatc aactagttat ttgtcattta   2820
aaacatttaa aactttgagt cttcaaatac atttgatgtt aatgctgcca ttacttgcac   2880
ttccattcac taataacatt tctaggtagt tatcagtttt gtcatattcc tggaaaatat   2940
tttggggttg taaattcttt ctcctctttt tcttctggag ttacaaattg aatttttaaa   3000
tccgagcacc tttattgtgg tgtggagaaa attatcacaa ttttatgttt attttacctt   3060
ctcagccttc tctgagggca ctttgcaaat acctgagtcc aaacagaagt accaactaaa   3120
tgctctatga actctatcct tagtaaatct attaaacctg aataatttaa aagatcatgt   3180
tcattttgta atagcaaaat ttgattttaa tttttttattt agaattggtg tatttatcat   3240
agggacttcc aatttttctt cactttttga atggatattg gctatagttt tatgttttaa   3300
cgggaatgaa tttcaagtca taataatcag aatttttagt tttacttttt tcttttacaa   3360
tatggatttt gttgttattt ggatagtggt tcaataaatc ttaagctcag ataattaaac   3420
actattttga atcttaacaa gatactgagg ctttttttgt atgggatgat atcaacctat   3480
gtacaatgaa tttaataaac ttaagtattg tcagattttt tgcacatttt agctcaataa   3540
aatcttaatg ttcaagattt ttttatctgc atttggaaat acaattttgt aaaatcaatg   3600
tcttaccttt ttgatacaat agatcatgtt ttgtttttaa taaagcaaga agccctttta   3660
tctgttgttt ttcagggaag ggattaacat ttaattctgt ttgtttacat ttgttatcat   3720
tgttatccaa tgctcatttt atgttgcttt ataagtaggc ttaggtataa cagaataagt   3780
atctgtttat ctaatctaca tgtgactatc ttagtctctc tcggtcactt aatattatgc   3840
tgaaatttac cactgtgggg atgaatgatc gctattcacc aagtatattt gaacatgtaa   3900
atgcttaaga aataagcata atgcggatat agtttgggtt aataggattc tcatagtttt   3960
ttttccccta tgaaacataa gtaatgattt tagtgtattt cttatggaat acactcattt   4020
aaaaaggact ttaagaaatt gtggatgtga ataatacctt tctctaataa aaatttaaat   4080
tgtataatag ttttataata tttacattaa ttgatatttt aatatggata gacattgcat   4140
agattcaaat aaattaaaat caatgataaa tgctaaatat tttatctaaa tagtttttca   4200
agaaacagtt atggaaatgt gtatattaaa tggctctaat gtggagcttg tggtatttca   4260
actcagtatt cattattagt tgtgtgtctg gaaagattgt acttactttt cctctttaca   4320
```

-continued

```
ctacagtttg ctcttatggg gctctaaact gtttaactga agaaccttcg tctgtatttt   4380
gattgagcat aatttagtat tttatgattt ccaagatgat gttcttatgt ctatcaagtc   4440
tatgtatcaa atttataaca tcatttaaga aaaaggaatt tccacagata cttcagttgc   4500
aattttttgt ttcatgctac tgaaaataca tttgtttcta ggggttggaa tattatagaa   4560
gatgtaggat gaaagaaaac gatagaacaa cgaaagaatt ctgtttatga aattacagga   4620
attgtgtcca ctatggtaaa gcattgtcat tttagtacat tttctcttag tagtttggca   4680
ttttatactt taaaacttgt tttgctttaa aaattgttta taatgcttac cttctttctc   4740
cagtgccttt agtcttgatt tgatatgttt gtaccctcag ttaccctttc tattacatgt   4800
ttttgatgtt ttcatagcct aggaaacatc gattcctttt taataattgt caatctgatt   4860
atttaaagag gtaacaatta tctgttaatg ctttggaaaa acaagtaggg ttgcctttgg   4920
aggccaggct tcttagttca ttcaaaaata ttccttggat ttatgccatg tattaagcat   4980
ttttagcccc cagtattaca actgtgaacc aaacggataa ggccctaacc attttcagca   5040
ttctctttgg atggggtggg attggggact taattaaaat agagatatag aaaaataggc   5100
atctaaataa gataataagt gtggggttga aatgaagcat ctaacaatag ttgaagttag   5160
aagtaatatt ttacagtatt gtaacctcta tttaagtttg ggtattagtt acagatagca   5220
taaaaaagcc ttaatttttc actttccttg ctggcaaagg tacatttatt tagactgtcc   5280
atttaaagta atgtttaaca taaacattac tgtgaaaaac attccattac atattcccaa   5340
gcaaatgagc tgcatcttct ttactgtatt ttacaattta gtacaacagt tttaggcctc   5400
aatcttaaca tcactggtat tttaaatttg gcaatgaata tgaaattact tttgacttac   5460
agattgatta tattattact ttgaaaatgc attaatttct tagaaaagtt tggagcctct   5520
atcttttttt gagttaatac ttaaattctc attacttata ttaatagcct gtactaagtg   5580
aaaatattat ttatgcaagt aaacaagtca ctataggctt ttaagacttt tctttaattt   5640
tagattttgt catcaaagtt taaatttttt acctactgtc cacttaaata taatttaaca   5700
gtttgtaaag tgaaatagtt ttaagtatga tgtatgatgc acctgcatat aaatgaaaat   5760
ggcgtgcaca aagacacttt actatgggaa ctgtactgga agatttatga aagcatgtga   5820
aattgcacct aaaattgtgt tattagtgac tataagcagc aatgctaaat ttattgtact   5880
tgatgaatga atgtatttag tcacagttac tttggtttaa atgtataaat gtctttaggg   5940
ttttttttta aatgtgtttg taatttgtac tattgtgggg gtatacttgg actgcagggg   6000
ttattgtcaa tgtgtgattt gtgtttttat tttatagaat catctaatgt gatataccaa   6060
tttttataag tgatatttac ataattctaa taactgtata tttgacaacc tattaaaatg   6120
ttttgcattg gaa                                                      6133
```

<210> SEQ ID NO 667
<211> LENGTH: 6650
<212> TYPE: DNA
<213> ORGANISM: Homo sapiens

<400> SEQUENCE: 667

```
gctggttccc cttccgagcg tccgcgcccc gcatgcgcag tctgccccgg cggtctccgt     60
ttgtttgaac aggaaggcgg acatattagt ccctctcagc ccccctcgcc ccacccccca    120
ggcattcgcc gccgcgactc gccctttccc cggctgggac cgcagcccct cccagaagct    180
cccccatcag cagccgccgg gacccaacta tcgtcttcct cttcgcccgc tctccagcct    240
ttcctctgct aagtctccat cgggcatcga cctcgccctg ccccaccgga caccgtagca    300
```

```
gcagccccag cagcgacggg acaaaatggg agagtgaggc tgtcctgcgt ggaccagctc    360
gtggccgaga ctgatcggtg cgtcgggccg ggccgagtag agccggggac gcggggctag    420
accgtctaca gcgcctctga gcggagcggg cccggcccgt ggcccgagcg gcggccgcag    480
ctggcacagc tcctcacccg ccctttgctt tcgcctttcc tcttctccct cccttgttgc    540
ccggagggag tctccaccct gcttctcttt ctctacccgc tcctgcccat ctcgggacgg    600
ggacccctcc atggcgacgg cggccggggc ccgctagact gaagcacctc gccggagcga    660
cgaggctggt ggcgacggcg ctgtcggctg tcgtgagggg ctgccgggtg ggatgcgact    720
ttgggcgtcc gagcggctgt gggtcgctgt tgccccccggc ccggggtctg gagagcggag    780
gtcccctcag tgaggggaag acgggggaac cgggcgcacc tggtgaccct gaggttccgg    840
ctcctccgcc ccgcggctgc gaacccaccg cggaggaagt tggttgaaat tgctttccgc    900
tgctggtgct ggtaagaggg cattgtcaca gcagcagcaa catgtcgact ggggacagtt    960
ttgagactcg atttgaaaaa atggacaacc tgctgcggga tcccaaatcg gaagtgaatt   1020
cggattgttt gctggatgga ttggatgctt tggtatatga tttggatttt cctgccttaa   1080
gaaaaaacaa aaatattgac aactttttaa gcagatataa agacacaata aataaaatca   1140
gagatttacg aatgaaagct gaagattatg aagtagtgaa ggtgattggt agaggtgcat   1200
ttggagaagt tcaattggta aggcataaat ccaccaggaa ggtatatgct atgaagcttc   1260
tcagcaaatt tgaaatgata aagagatctg attctgcttt tttctgggaa gaaagggaca   1320
tcatggcttt tgccaacagt ccttgggttg ttcagctttt ttatgcattc caagatgatc   1380
gttatctcta catggtgatg gaatacatgc ctggtggaga tcttgtaaac ttaatgagca   1440
actatgatgt gcctgaaaaa tgggcacgat tctatactgc agaagtagtt cttgcattgg   1500
atgcaatcca ttccatgggt tttattcaca gagatgtgaa gcctgataac atgctgctgg   1560
ataaatctgg acatttgaag ttagcagatt ttggtacttg tatgaagatg aataaggaag   1620
gcatggtacg atgtgataca gcggttggaa cacctgatta tatttcccct gaagtattaa   1680
aatcccaagg tggtgatggt tattatggaa gagaatgtga ctggtggtcg gttggggtat   1740
ttttatacga aatgcttgta ggtgatacac ctttttatgc agattctttg gttggaactt   1800
acagtaaaat tatgaaccat aaaaattcac ttacctttcc tgatgataat gacatatcaa   1860
aagaagcaaa aaaccttatt tgtgccttcc ttactgacag ggaagtgagg ttagggcgaa   1920
atggtgtaga agaaatcaaa cgacatctct tcttcaaaaa tgaccagtgg gcttgggaaa   1980
cgctccgaga cactgtagca ccagttgtac ccgatttaag tagtgacatt gatactagta   2040
attttgatga cttggaagaa gataaaggag aggaagaaac attccctatt cctaaagctt   2100
tcgttggcaa tcaactacct tttgtaggat ttacatatta tagcaatcgt agatacttat   2160
cttcagcaaa tcctaatgat aacagaacta gctccaatgc agataaaagc ttgcaggaaa   2220
gtttgcaaaa aacaatctat aagctggaag aacagctgca taatgaaatg cagttaaaag   2280
atgaaatgga gcagaagtgc agaacctcaa acataaaact agacaagata atgaaagaat   2340
tggatgaaga gggaaatcaa agaagaaatc tagaatctac agtgtctcag attgagaagg   2400
agaaaatgtt gctacagcat agaattaatg agtaccaaag aaaagctgaa caggaaaatg   2460
agaagagaag aaatgtagaa aatgaagttt ctacattaaa ggatcagttg gaagacttaa   2520
agaaagtcag tcagaattca cagcttgcta atgagaagct gtcccagtta caaaagcagc   2580
tagaagaagc caatgactta cttaggacag aatcggacac agctgtaaga ttgaggaaga   2640
```

-continued

```
gtcacacaga gatgagcaag tcaattagtc agttagagtc cctgaacaga gagttgcaag   2700
agagaaatcg aattttagag aattctaagt cacaaacaga caaagattat taccagctgc   2760
aagctatatt agaagctgaa cgaagagaca gaggtcatga ttctgagatg attggagacc   2820
ttcaagctcg aattacatct ttacaagagg aggtgaagca tctcaaacat aatctcgaaa   2880
aagtggaagg agaaagaaaa gaggctcaag acatgcttaa tcactcagaa aaggaaaaga   2940
ataatttaga gatagattta aactacaaac ttaaatcatt acaacaacgg ttagaacaag   3000
aggtaaatga acacaaagta accaaagctc gtttaactga caaacatcaa tctattgaag   3060
aggcaaagtc tgtggcaatg tgtgagatgg aaaaaaagct gaaagaagaa agagaagctc   3120
gagagaaggc tgaaaatcgg gttgttcaga ttgagaaaca gtgttccatg ctagacgttg   3180
atctgaagca atctcagcag aaactagaac atttgactgg aaataaagaa aggatggagg   3240
atgaagttaa gaatctaacc ctgcaactgg agcaggaatc aaataagcgg ctgttgttac   3300
aaaatgaatt gaagactcaa gcatttgagg cagacaattt aaaaggttta gaaaagcaga   3360
tgaaacagga aataaatact ttattggaag caaagagatt attagaattt gagttagctc   3420
agcttacgaa acagtataga ggaaatgaag gacagatgcg ggagctacaa gatcagcttg   3480
aagctgagca atatttctcg acactttata aaacccaggt aaaggaactt aaagaagaaa   3540
ttgaagaaaa aaacagagaa aatttaaaga aaatacagga actacaaaat gaaaaagaaa   3600
ctcttgctac tcagttggat ctagcagaaa caaaagctga gtctgagcag ttggcgcgag   3660
gccttctgga agaacagtat tttgaattga cgcaagaaag caagaaagct gcttcaagaa   3720
atagacaaga gattacagat aaagatcaca ctgttagtcg gcttgaagaa gcaaacagca   3780
tgctaaccaa agatattgaa atattaagaa gagagaatga agagctaaca gagaaaatga   3840
agaaggcaga ggaagaatat aaactggaga aggaggagga gatcagtaat cttaaggctg   3900
cctttgaaaa gaatatcaac actgaacgaa cccttaaaac acaggctgtt aacaaattgg   3960
cagaaataat gaatcgaaaa gattttaaaa ttgatagaaa gaaagctaat acacaagatt   4020
tgagaaagaa agaaaaggaa aatcgaaagc tgcaactgga actcaaccaa gaaagagaga   4080
aattcaacca gatggtagtg aaacatcaga aggaactgaa tgacatgcaa gcgcaattgg   4140
tagaagaatg tgcacatagg aatgagcttc agatgcagtt ggccagcaaa gagagtgata   4200
ttgagcaatt gcgtgctaaa cttttggacc tctcggattc tacaagtgtt gctagttttc   4260
ctagtgctga tgaaactgat ggtaacctcc cagagtcaag aattgaaggt tggctttcag   4320
taccaaatag aggaaatatc aaacgatatg gctggaagaa acagtatgtt gtggtaagca   4380
gcaaaaaaat tttgttctat aatgacgaac aagataagga gcaatccaat ccatctatgg   4440
tattggacat agataaactg tttcacgtta gacctgtaac ccaaggagat gtgtatagag   4500
ctgaaactga agaaattcct aaaatattcc agatactata tgcaaatgaa ggtgaatgta   4560
gaaaagatgt agagatggaa ccagtacaac aagctgaaaa aactaatttc caaaatcaca   4620
aaggccatga gtttattcct acactctacc actttcctgc caattgtgat gcctgtgcca   4680
aacctctctg gcatgttttt aagccacccc ctgccctaga gtgtcgaaga tgccatgtta   4740
agtgccacag agatcactta gataagaaag aggacttaat ttgtccatgt aaagtaagtt   4800
atgatgtaac atcagcaaga gatatgctgc tgttagcatg ttctcaggat gaacaaaaaa   4860
aatgggtaac tcatttagta aagaaaatcc ctaagaatcc accatctggt tttgttcgtg   4920
cttcccctcg aacgctttct acaagatcca ctgcaaatca gtctttccgg aaagtggtca   4980
aaaatacatc tggaaaaact agttaaccat gtgactgagt gccctgtgga atcgtgtggg   5040
```

atgctacctg ataaaccagg cttctttaac catgcagagc agacaggctg tttctttgac 5100
acaaatatca caggcttcag ggttaagatt gctgtttttc tgtccttgct ttggcacaac 5160
acactgaggg tttttttat tgcgggtttg cctacaggta gattagatta attattacta 5220
tgtaatgcaa gtacagttgg gggaaagctt aggtagatat atttttttta aaaggtgctg 5280 ccttttgga tttataagaa aatgcctgtc agtcgtgata gaacagagtt ttcctcatat 5340
gagtaagagg aagggacttt cactttcaag tggaacagcc atcactatca agatcagctc 5400
atggaaggag taaagaaaat atctcaaaat gagacaaact gaagttttgt ttttttttta 5460
atgacttaag tttttgtgct cttgcaagac tatacaaaac tattttaaga aagcagtgat 5520
atcacttgaa cttcagtgcc ctcactgtag aatttaaaag ccttactgtt gattgcccat 5580
gttggacttg atggagaaat taaatatctt tcattatgct ttacaaaata ctgtatatgt 5640
ttcagcaagt ttggggaatg ggagaggaca aaaaaaagtt acatttaatc tatgcatttt 5700
tgccaagcca tattgagtta ttttactact agagacatta ggaaactaac tgtacaaaag 5760
aaccaagttt aaaagcattt tgtggggtac atcatttcta taattgtata atgtatttct 5820
ttgtggtttt aaatgataaa gacattaagt taacaaacat ataagaaatg tatgcactgt 5880
ttgaaatgta aattattctt agaacacttt caatgggggt tgcattgtcc ttttagtgcc 5940
ttaatttgag ataattattt tactgccatg agtaagtata gaaatttcaa aaaatgtatt 6000
ttcaaaaaat tatgtgtgtc agtgagtttt tcattgataa ttggtttaat ttaaaatatt 6060
tagaggtttg ttggactttc ataaattgag tacaatcttt gcatcaaact acctgctaca 6120
ataatgactt tataaaactg caaaaaatgt agaaggttgc accaacataa aaaggaaata 6180
tggcaataca tccatgatgt tttccagtta acataggaat taccagataa atactgttaa 6240
actcttgtcc agtaacaaga gttgattcat atggacagta tgatttattg tttatttttt 6300
taaccaaata cctcctcagt aatttataat ggctttgcag taatgtgtat cagataagaa 6360
gcactggaaa accgatcgtc tctaggatga tatgcatgtt tcaagtggta ttgaaagccg 6420
cactgatgga tatgtaataa taaacatatc tgttattaat atactaatga ctctgtgctc 6480
atttaatgag aaataaaagt aatttatgga tgggtatctt taatttttac tgcaatgtgt 6540
tttctcatgg ctgaaatgaa tggaaaacat acttcaaatt agtctctgat tgtatataaa 6600
tgtttgtgaa attccatggt tagattaaag tgtattttta aaagataaaa 6650

<210> SEQ ID NO 668
<211> LENGTH: 5324
<212> TYPE: DNA
<213> ORGANISM: Homo sapiens

<400> SEQUENCE: 668
gaacggcgat gccccagacg cggctgcagt tttcaaaccg cgactgcaag cttcggtagt 60
cctctccgct gctgtcgcca ggagtcactt cacgagaagc caggtcacaa ccgtcggccc 120
ttgtctggaa aagtaaaagt ggatcctgcc acgttcggag ctccctggcg cctcgcccgg 180
ctggagctag agaactcgtc ctgtggcggc ccccggcgtg gggcgggaca gcggccccct 240
ggagggggca gtcccgggag aacctgcggc ggccggagcg gtaaaaataa gtgactaaag 300
aagcagacct gggaatcacc taacatgtcg aggaggagat ttgattgccg aagtatttca 360
ggcctactaa ctacaactcc tcaaattcca ataaaaatgg aaaactttaa taatttctat 420
atacttacat ctaaagagct agggagagga aaatttgctg tggttagaca atgtatatca 480

-continued

```
aaatctactg gccaagaata tgctgcaaaa tttctaaaaa agagaagaag aggacaggat    540
tgtcgagcag aaattttaca cgagattgct gtgcttgaat tggcaaagtc ttgtccccgt    600
gttattaatc ttcatgaggt ctatgaaaat acaagtgaaa tcattttgat attggaatat    660
gctgcaggtg gagaaatttt cagcctgtgt ttacctgagt tggctgaaat ggtttctgaa    720
aatgatgtta tcagactcat taaacaaata cttgaaggag tttattatct acatcagaat    780
aacattgtac accttgattt aaagccacag aatatattac tgagcagcat ataccctctc    840
ggggacatta aaatagtaga ttttggaatg tctcgaaaaa tagggcatgc gtgtgaactt    900
cgggaaatca tgggaacacc agaatattta gctccagaaa tcctgaacta tgatcccatt    960
accacagcaa cagatatgtg gaatattggt ataatagcat atatgttgtt aactcacaca   1020
tcaccatttg tgggagaaga taatcaagaa acatacctca atatttctca agttaatgta   1080
gattattcgg aagaaacttt ttcatcagtt tcacagctgg ccacagactt tattcagagc   1140
cttttagtaa aaaatccaga gaaaagacca acagcagaga tatgcctttc tcattcttgg   1200
ctacagcagt gggactttga aaacttgttt caccctgaag aaacttccag ttcctctcaa   1260
actcaggatc attctgtaag gtcctctgaa gacaagactt ctaaatcctc ctgtaatgga   1320
acctgtggtg atagagaaga caaagagaat atcccagagg atagcagcat ggtttccaaa   1380
agatttcgtt tcgatgactc attacccaat ccccatgaac ttgtttcaga tttgctctgt   1440
tagcactttt ttctttgact catttggact gaatttgaaa ttttatatcc actccagtga   1500
gattatgatt tgtagcttca tatatgacat gtttatattg taaatgcact tttccatgga   1560
ataatttagg gaagtgtttt aatgttaaat tactagttgc tagcatgtta tgatttcata   1620
tcctgagata gctctgcaga taagaaaata tttaaatata tgacaaaaag taaaattgta   1680
catgtgagtt tacatgttaa tgaaataatt caacttcaaa tgaacttacc agaatgtttt   1740
gcatatcaac aaaaaaagtg gcttgagttt tattatagtt ggtgtaaact gaacacagtg   1800
aagacattgg aatttaatag gttctctctc taaggtgact cttataccat gcctctatca   1860
acataatttg tttaggaaag cagtatgaag tttaagccaa aataatttct actttataga   1920
tgctcaagag acattttaca attgaaaatg tctttcaatt acaaatattt tgaaacttcg   1980
taagattttc attctctgtg gtctgttata tgagagagat cctttaacta gagcaaagag   2040
ggagttagaa acctgatcag ggatattctt tacaagttgg agcagaggaa agagtagcat   2100
gccttcgtat tttaacgcaa atgtcttttt cctcctccca acctacttga gatctgataa   2160
ggtctggaag atggagatat ttggtatgca agtgtagagt tttttaatcc tccagaattt   2220
ctagagtaga agatacttag gtatagttaa atattctgta tttttagtca aacatattta   2280
ttaattgaat atagaagaaa atgttgacac actcagacag cttactgaat tttagatgtc   2340
ttctgcatct tagaatacaa gccagtcatt cagagttcta aaagtatgca taaaaaatta   2400
cagcaccggt aggtctatta acacagtgcc cgagtcagcg gtagcaagac tgatgtgatc   2460
ataaaacatg acatcaggct cgtctgaagt tcttgtgtga aattcctagt gagtgaggag   2520
gctcagctta aagccatctg cagagtggcc cctcattgtg gtcttttgct gggaccaatg   2580
caagagacta gggagagcaa aatgtttgct tatggctaga gactatatcc agccctaatg   2640
atggggaaag ttagtccttt tcgggtaatc ttttatgaat tttcacctga tgaccgttat   2700
attggtctgt tatcatgtta cgataactgt gatctcatga ccatgttgct gtatcagaag   2760
aaatagtttg acaaatggta acaacaacct gatgttcccc ctttagacct ttaacttctc   2820
aaaattttgg taagtttcca aattctttaa taataactta aaactttttg aataactatc   2880
```

aggtcacttt atttgaccac atggtgaatt cctttaatgt cttcagcatt tgttaaggaa 2940
aagttttctc tacttgtgtg tgtatgtgtg cacatgtgtg tatgtacagg tgtatgtata 3000
tatctataga tagatacaat acattcttta gacacttttc aagattcttt gctgtggtat 3060
attgtgctca actcaggtgc caaaggagct tttttttttt tttttttttt ttgagatgga 3120
gttttgctct gtctctcagg ctggagtgca gtggcatgat ctcagctcac ggcaacctct 3180
gcctcccggg ttcaagcaat tctcctgtct cagcctcctg agtagttggg attacaggcg 3240
catgccaccg tgcccagcta atttttgtat ttttagtaga gacggggttt caccatgttg 3300
gccaggctgg tcacaaactc ctgacttcaa gtgatccacc cgcctcggcc tcccaaagtg 3360
ctgggattac aggcgtgagc cactgcgccc ccgcccagga gctcttttct tatgacatat 3420
aaattatgac atttatattc tttatatgac tttatgttct cttcttatga catttaaatt 3480
ctttaagtag tttgttggtc caataaacta gacgttgtat aatctaaatt gagcccttgt 3540
atatctaaaa ctgatgagtt gtttctaaat tgttgattgt ccatttactt gcctttggta 3600
ttaagataat gcaagtaaag tttagtaagt cattggataa tgaaatgatt atgtttctga 3660
agaccatatt atatttttaa tttttagagg aatcatgcca tcccccaaaa aatcaagaaa 3720
tatttgaatt ttaaattata agttcatttg ttaaaagaca tttttacaaa tgtctgaaaa 3780
tcttaaaata ctttacatct acctttaagt agtagaatac agagctgtaa atttccatgc 3840
ctttttttcct gatattaagt tttatagtaa aaaagcaact agtgattgca caaagaatat 3900
aaaaatccac tctttttaca aaggtgtgaa tttaaataac gttattgatt ggaatatgaa 3960
aatagaccaa tcatttaaga gctttttagc aaatgattca attcttactc tttttctccc 4020
aagattgaaa agcataatgt atttctctaa agtaggaatc tagagagccc ctgtgagtgg 4080
acaaatgtca gtaacacttg aacacatgag aagataagtg ttatgttgtg ataatttaaa 4140
gttaaatttg ctttttgggt aggatcccta aatagatggg atttttaaat agatgatata 4200
tagatgacaa ttgcaattgt cattttaatt attttcccta cagtaaagaa cctagctctg 4260
agcagtgaaa ttgtaatggc actttaaagg aagtaagccg ttaactgttc tctagtggag 4320
cgatctccaa ctgttttggc actagggacg ggttttgtgg aagaaaattt ttccacagga 4380
ctgggggttt agggggatgg tttcaggatg attcaagtac attacattta tcattagatt 4440
ctcataagga gcatgcaacc tagatctctt gcacgtgtgg ttcacagcag gattcgagct 4500
cctttgagaa tctaatgcca tggctgatct aacaggaaac tgagctcagg cagtaatgct 4560
tggcaccgcc ccccaccttc tatgcagccc ggtcgtggcc tggggactgg ggacccctgc 4620
tctagtcagt aataaggtac ttgtgccaga atataaatca acacattgct tcctttatca 4680
aagaagtctt gttatttaaa aaaagtcaac tgagccagta tgattagtga tgtaattgat 4740
tttcattctg gcacaagcct ctttcattct ggacagctca caaatagtta atggaccatg 4800
ctttgaatag ccttcctcta agcaacattt ataaatactg atattttaga actgtttaca 4860
tttcttctgt ttatttttga attttcagtt tgatatcttg tccttattca ttgttgtata 4920
aacaactgta ctttaatttc aagtagtatt aaaagtattt cacttcagtt tggggggatt 4980
attatcaatt tataatttta taaaagtatt ttaaagaata attgtaaatt ttccataaat 5040
tacaacttcc tgccatattt tattaaataa taatcttgct taaggcatat agacagacat 5100
tattatgagt attccagtaa aaaaaatcta catcaacttg accattctgg ctaaaaatta 5160
aaaagcactt ttttatatct gtggttgtca tttgtttcaa agcatttcta aatttattgt 5220
tcttaaaagt atgtctgcat gttctagcct ttgacctagg tcatctatga accctctttg 5280
tgtctaataa acatatctgt aaaggcaaaa aaaaaaaaaa aaaa 5324

<210> SEQ ID NO 669
<211> LENGTH: 5756
<212> TYPE: DNA
<213> ORGANISM: Homo sapiens

<400> SEQUENCE: 669
taggcaggcg gctgagccgg cggcgggtgg cctgcccaac gtgtgctggg tgggagaagg 60
cgaggcgtca gcgatgctgt ctcttccgtg aggagcgcag aggaggtcgc ggcgcccggag 120 gccccagaag gctcgaaggc gccgcgggct ggggtcggtg gcttagggag cccgtccggc 180
catggtggcc gcgggtggtg gttggcgcgg ctgcgctgcg gcccggggca gtgcggagcc 240
gggacagtcg cggcgctgac gcccgcgggc cccagctgca gatatgaagc ggagccgctg 300
ccgcgaccga ccgcagccgc cgccgcccga ccgccgggag gatggagttc agcgggcagc 360
ggagctgtct cagtctttgc cgccgcgccg gcgagcgccg cccgggaggc agcggctgga 420
ggagcggacg ggccccgcgg ggcccgaggg caaggagcag gatgtagtaa ctggagttag 480
tcccctgctc ttcaggaaac tcagtaatcc tgacatattt tcatccactg gaaaagttaa 540
acttcagcga caactgagtc aggatgattg taagttatgg agaggaaacc tggccagctc 600
tctatcgggt aagcagctgc tccctttgtc cagcagtgta catagcagtg tgggacaggt 660
gacttggcag tcgtcaggag aagcatcaaa cctggttcga atgagaaacc agtcccttgg 720
acagtctgca ccttctctta ctgctggcct gaaggagttg agccttccaa gaagaggcag 780
cttttgtcgg acaagtaacc gcaagagctt gattgtgacc tctagcacat cacctacact 840
accacggcca cactcaccac tccatggcca cacaggtaac agtcctttgg acagcccccg 900
gaatttctct ccaaatgcac ctgctcactt ttcttttgtt cctgcccgta ggactgatgg 960
gcggcgctgg tctttggcct ctttgccctc ttcaggatat ggaactaaca ctcctagctc 1020
cactgtctca tcatcatgct cctcacagga aaagctgcat cagttgcctt tccagcctac 1080
agctgatgag ctgcactttt tgacgaagca tttcagcaca gagagcgtac cagatgagga 1140
aggacggcag tccccagcca tgcggcctcg ctcccggagc ctcagtcccg gacgatcccc 1200
agtatccttt gacagtgaaa taataatgat gaatcatgtt tacaaagaaa gattcccaaa 1260
ggccaccgca caaatggaag agcgactagc agagtttatt tcctccaaca ctccagacag 1320
cgtgctgccc ttggcagatg gagccctgag ctttattcat catcaggtga ttgagatggc 1380
ccgagactgc ctggataaat ctcggagtgg cctcattaca tcacaatact tctacgaact 1440
tcaagataat ttggagaaac ttttacaaga tgctcatgag cgctcagaga gctcagaagt 1500
ggcttttgtg atgcagctgg tgaaaaagct gatgattatc attgcccgcc cagcacgtct 1560
cctggaatgc ctggagtttg accctgaaga gttctaccac cttttagaag cagctgaggg 1620
ccacgccaaa gagggacaag ggattaaatg tgacattccc cgctacatcg ttagccagct 1680
gggcctcacc cgggatcccc tagaagaaat ggcccagttg agcagctgtg acagtcctga 1740
cactccagag acagatgatt ctattgaggg ccatggggca tctctgccat ctaaaaagac 1800
accctctgaa gaggacttcg agaccattaa gctcatcagc aatggcgcct atggggctgt 1860
atttctggtg cggcacaagt ccacccggca gcgctttgcc atgaagaaga tcaacaagca 1920
gaacctgatc ctacggaacc agatccagca ggccttcgtg gagcgtgaca tactgacttt 1980
cgctgagaac ccctttgtgg tcagcatgtt ctgctccttt gataccaagc gccacttgtg 2040

```
catggtgatg gagtacgttg aagggggaga ctgtgccact ctgctgaaga atattggggc   2100
cctgcctgtg gacatggtgc gtctatactt tgcggaaact gtgctggccc tggagtactt   2160
acacaactat ggcatcgtgc accgtgacct caagcctgac aacctcctaa ttacatccat   2220
ggggcacatc aagctcacgg actttggact gtccaaaatt ggcctcatga gtctgacaac   2280
gaacttgtat gagggtcata ttgaaaagga tgcccgggaa ttcctggaca agcaggtatg   2340
cgggacccca gaatacattg cgcctgaggt gatcctgcgc cagggctatg ggaagccagt   2400
ggactggtgg gccatgggca ttatcctgta tgagttcctg gtgggctgcg tccctttttt   2460
tggagatact ccggaggagc tctttgggca ggtgatcagt gatgagattg tgtggcctga   2520
gggtgatgag gcactgcccc cagacgccca ggacctcacc tccaaactgc tccaccagaa   2580
ccctctggag agacttggca caggcagtgc ctatgaggtg aagcagcacc cattctttac   2640
tggtctggac tggacaggac ttctccgcca gaaggctgaa tttattcctc agttggagtc   2700
agaggatgat actagctatt ttgacacccg ctcagagcga taccaccaca tggactcgga   2760
ggatgaggaa gaagtgagtg aggatggctg ccttgagatc cgccagttct cttcctgctc   2820
tccaaggttc aacaaggtgt acagcagcat ggagcggctc tcactgctcg aggagcgccg   2880
gacaccaccc ccgaccaagc gcagcctgag tgaggagaag gaggaccatt cagatggcct   2940
ggcagggctc aaaggccgag accggagctg ggtgattggc tcccctgaga tattacggaa   3000
gcggctgtcg gtgtctgagt catcccacac agagagtgac tcaagccctc caatgacagt   3060
gcgacgccgc tgctcaggcc tcctggatgc gcctcggttc ccggagggcc ctgaggaggc   3120
cagcagcacc ctcaggaggc aaccacagga gggtatatgg gtcctgacac cccccatctgg   3180
agagggggta tctgggcctg tcactgaaca ctcaggggag cagcggccaa agctggatga   3240
ggaagctgtt ggccggagca gtggttccag tccagctatg gagacccgag gccgtgggac   3300
ctcacagctg gctgagggag ccacagccaa ggccatcagt gacctggctg tgcgtagggc   3360
ccgccaccgg ctgctctctg ggactcaac agagaagcgc actgctcgcc ctgtcaacaa   3420
agtgatcaag tccgcctcag ccacagccct ctcactcctc attccttcgg aacaccacac   3480
ctgctccccg ttggccagcc ccatgtcccc acattctcag tcgtccaacc catcatcccg   3540
ggactcttct ccaagcaggg acttcttgcc agcccttggc agcatgaggc ctcccatcat   3600
catccaccga gctggcaaga agtatggctt caccctgcgg gccattcgcg tctacatggg   3660
tgactccgat gtctacaccg tgcaccatat ggtgtggcac gtggaggatg gaggtccggc   3720
cagtgaggca gggcttcgtc aaggtgacct catcacccat gtcaatgggg aacctgtgca   3780
tggcctggtg cacacggagg tggtagagct gatcctgaag agtggaaaca aggtggccat   3840
ttcaacaact cccctggaga acacatccat taaagtgggg ccagctcgga agggcagcta   3900
caaggccaag atggcccgaa ggagcaagag gagccgcggc aaggatgggc aagaaagcag   3960
aaaaaggagc tccctgttcc gcaagatcac caagcaagca tccctgctcc acaccagccg   4020
cagcctttct tcccttaacc gctccttgtc atcaggggag agtgggccag gctctcccac   4080
acacagccac agcctttccc cccgatctcc cactcaaggc taccgggtga cccccgatgc   4140
tgtgcattca gtgggaggga attcatcaca gagcagctcc cccagctcca gcgtgcccag   4200
ttccccagcc ggctctgggc acacacggcc cagctccctc cacggtctgg cacccaagct   4260
ccaacgccag taccgctctc cacggcgcaa gtcagcaggc agcatcccac tgtcaccact   4320
ggcccacacc ccttctcccc cacccccaac agcttcacct cagcggtccc catcgcccct   4380
```

```
gtctggccat gtagcccagg cctttcccac aaagcttcac ttgtcacctc ccctgggcag   4440
gcaactctca cggcccaaga gtgcggagcc accccgttca ccactactca agagggtgca   4500
gtcggctgag aaactggcag cagcacttgc cgcctctgag aagaagctag ccacttctcg   4560
caagcacagc cttgacctgc cccactctga actaaagaag gaactgccgc ccagggaagt   4620
gagccctctg gaggtagttg gagccaggag tgtgctgtct ggcaaggggg ccctgccagg   4680
gaagggggtg ctgcagcctg ctccctcacg ggccctaggc accctccggc aggaccgagc   4740
cgaacgacgg gagtcgctgc agaagcaaga agccattcgt gaggtggact cctcagagga   4800
cgacaccgag gaagggcctg agaacagcca gggtgcacag gagctgagct tggcacctca   4860
cccagaagtg agccagagtg tggcccctaa aggagcagga gagagtgggg aagaggatcc   4920
tttcccgtcc agagacccta ggagcctggg cccaatggtc ccaagcctat tgacagggat   4980
cacactgggg cctcccagaa tggaaagtcc cagtggtccc cacaggaggc tcgggagccc   5040
acaagccatt gaggaggctg ccagctcctc ctcagcaggc cccaacctag gtcagtctgg   5100
agccacagac cccatccctc ctgaaggttg ctggaaggcc cagcacctcc acacccaggc   5160
actaacagca ctttctccca gcacttcggg actcaccccc accagcagtt gctctcctcc   5220
cagctccacc tctgggaagc tgagcatgtg gtcctggaaa tcccttattg agggcccaga   5280
cagggcatcc ccaagcagaa aggcaaccat ggcaggtggg ctagccaacc tccaggattt   5340
ggaaaacaca actccagccc agcctaagaa cctgtctccc agggagcagg ggaagacaca   5400
gccacctagt gcccccagac tggcccatcc atcttatgag gatcccagcc agggctggct   5460
atgggagtct gagtgtgcac aagcagtgaa agaggatcca gccctgagca tcacccaagt   5520
gcctgatgcc tcaggtgaca gaaggcagga cgttccatgc cgaggctgcc ccctcaccca   5580
gaagtctgag cccagcctca ggaggggcca agaaccaggg ggccatcaaa agcatcggga   5640
tttggcattg gttccagatg agcttttaaa gcaaacatag cagttgtttg ccatttcttg   5700
cactcagacc tgtgtaatat atgctcctgg aaaccatcaa aaaaaaaaaa aaaaaa       5756
```

<210> SEQ ID NO 670
<211> LENGTH: 4373
<212> TYPE: DNA
<213> ORGANISM: Homo sapiens

<400> SEQUENCE: 670

```
agagtgggca ggccgggggt gagggctcgc gctccgggag ctgcacgggg ctgcgtggaa     60
agagcgccga gcggtggcgt cgttgtcgcc ccctcctcgt cgggaagaat cgtttggtct    120
cctgccgtgc ccggttcgta ttccctactc cctgccacga gccgccccgt ccgggatcct    180
ccacccgtcc aaagttgtga gggggcgccg ggcgtgctcg cggatcggcg gccgcgggcg    240
tgcggagggc tggacgagcc ctggagcgcc aggagaatgt gtgtgtgtcc cgggcccaga    300
cgaattggaa tcccagtcag aagttccagc ctgccactgt tctctgatgc catgccagca    360
ccaactcaac tgtttttcc tctcatccgt aactgtgaac tgagcaggat ctatggcact    420
gcatgttact gccaccacaa acatctctgt tgttcctcat cgtacattcc tcagagtcga    480
ctgagataca cacctcatcc agcatatgct accttttgca ggccaaagga gaactggtgg    540
cagtacaccc aaggaaggag atatgcttcc acaccacaga aattttacct cacacctcca    600
caagtcaata gcatccttaa agctaatgaa tacagtttca aagtgccaga atttgacggc    660
aaaaatgtca gttctatcct tggatttgac agcaatcagc tgcctgcaaa tgcaccatt    720
gaggaccgga gaagtgcagc aacctgcttg cagaccagag ggatgctttt gggggttttt    780
```

-continued

```
gatggccatg caggttgtgc ttgttcccag gcagtcagtg aaagactctt ttattatatt    840
gctgtctctt tgttacccca tgagactttg ctagagattg aaaatgcagt ggagagcggc    900
cgggcactgc tacccattct ccagtggcac aagcacccca atgattactt tagtaaggag    960
gcatccaaat tgtactttaa cagcttgagg acttactggc aagagcttat agacctcaac   1020
actggtgagt cgactgatat tgatgttaag gaggctctaa ttaatgcctt caagaggctt   1080
gataatgaca tctccttgga ggcgcaagtt ggtgatccta attcttttct caactacctg   1140
gtgcttcgag tggcattttc tggagccact gcttgtgtgg cccatgtgga tggtgttgac   1200
cttcatgtgg ccaatactgg cgatagcaga gccatgctgg gtgtgcagga agaggacggc   1260
tcatggtcag cagtcacgct gtctaatgac cacaatgctc aaaatgaaag agaactagaa   1320
cggctgaaat tggaacatcc aaagagtgag gccaagagtg tcgtgaaaca ggatcggctg   1380
cttggcttgc tgatgccatt tagggcattt ggagatgtaa agttcaaatg gagcattgac   1440
cttcaaaaga gagtgataga atctggccca gaccagttga atgacaatga atataccaag   1500
tttattcctc ctaattatca cacacctcct tatctcactg ctgagccaga ggtaacttac   1560
caccgattaa ggccacagga taagtttctg gtgttggcta ctgatgggtt gtgggagact   1620
atgcataggc aggatgtggt taggattgtg ggtgagtacc taactggcat gcatcaccaa   1680
cagccaatag ctgttggtgg ctacaaggtg actctgggac agatgcatgg ccttttaaca   1740
gaaaggagaa ccaaaatgtc ctcggtattt gaggatcaga acgcagcaac ccatctcatt   1800
cgccacgctg tgggcaacaa cgagtttggg actgttgatc atgagcgcct ctctaaaatg   1860
cttagtcttc ctgaagagct tgctcgaatg tacagagatg acattacaat cattgtagtt   1920
cagttcaatt ctcatgttgt aggggcgtat caaaaccaag aatagtgagt ggctctttca   1980
ctggcaattc tcaaatgata tacatttaaa gggcagattt tttaaaaaga tactactata   2040
ataaacattt ccagttggtc attctaagca tttacccttt tgatactcta gctagtcagg   2100
tactccaaat tgactttgca gcagggtggc agggtcagga gagtctggtc ctgcctagct   2160
cagatttcat ggcacctgca cttgaagcaa gtcacttctt tatcacaggt gtcttgaaac   2220
attagcttct tttaccaacc tgagaaaatt aggatgacct ggcaaataag atcttgaata   2280
ggccaaaagc aagtatcttg ctgtgtgtag tctcttggtt aaagtgaaga aacagtactg   2340
ttcacacctt tcttcactga gattccagtg tacatgagaa catatattta ttgcatgatt   2400
ttctagatac acagtctatg cattattcat atacatttat tttagcctaa agtggttttc   2460
aaatccagtt cttcaagcca taaatgacca agatccaagc aatctgaatt tgtttttgtg   2520
attatttgac tggaatgctt cttaagtgga ataactatac tccgttatcc acccgatttc   2580
ctaatgtaat tgaaagattt tctattttgc cacacacttg gagacaataa gggtttttag   2640
ttttatctac tcttctattg aagttaaaga aagaaaaaaa gatttttttta tttgtattaa   2700
tgaaaagctt tagtttaaaa taaggagatc cagaataaaa agaagagact gatctcttca   2760
attattgtca tctgtagcca ccagcacatc actcttatgt aatccccaaa ggcttggcat   2820
gccgtaagtg tgtggtgggt agactgctgc cggggaatcg tacttcttat ttagtaatga   2880
taagactttt cattattttt ggaattttaa agatgacata aataagttta aatatcaatt   2940
tggggagtaa ggtttaatat tgccatcggg tattgagaca ggaggaagtt tctgtttttc   3000
tccatttaga cataggtcaa ttaaaatatt tgggtttaaa atgactaaat gctttaaaca   3060
tattgtagct taagatatat gtgttaagat atatacatga gaaactttaa aaggtaacta   3120
```

```
ctgtgcatgc ctgatgctta atagaatact tagtggcatc aaatgtttgc agcagtctcc   3180
ataattatat tcagtccctt ctaatactgt atcaatgtaa atgaaataaa tatattcaaa   3240
ttggcttttt gatatgcatc aagtggcatt ttgttcctgt gtttaatagt gatctgtata   3300
cagctgtgca catattgtca tcacttattc tagcatcact gttaaggctg tgattatgtt   3360
tgatattcac ctggatttta atacaagcca atatcagctt cccattgtgt aataacttgg   3420
gtgtttagga gtcttttcac attttttggg gatatgaact agatgttcaa gaactccttc   3480
tggactgtgg atactgaatc agtgtactat tggctgcaga atttgtttca attgaaaata   3540
gactcaggaa gattgctgct cagaatatca tataatgttt attttttgag gtgtttttgt   3600
ttttatttgt gtgttttttt ttttttaagt cagcttggaa ctttttttcct gggtagtatt   3660
tgggagaggg aaaggctgta ctatatattt atttctaaat gttttgactg ggcatttttc   3720
ttttaatgaa atatgtggac tgctctagca aaccctattt tcagctacta tttgaatatt   3780
cttgaacacc accactgaag agtttcatat acaccaaata atgtctcatc tctatagtac   3840
agggaatata aaattggttt cctgtggtca tgatcaagat agtagtatta ttacacaaga   3900
aacttggtct gcagtctgga agcttgtctg ctctatagaa atgaaaatgc agcatgaagt   3960
tgacattgtg gaaatgaaag taattgggta ttagaaatct gaaagtactg tcatctaaaa   4020
gcaattgtga ttttattgta attggttgtc actgttgtac ggtgtctaga attaaagaat   4080
acatgtaaac tttcatggta tttagccttt cttaaatttt tttaaaattt aaactttcta   4140
acctatgtat tcaacttctg tatttatatt taatcagtgg ttcatgttat ataatacacc   4200
cttaactagt taaatggaat gttggtatgg tacagagtac catattgcta agaaaactgt   4260
cttataaaag atgtatatgt gtgaagacat gaaagtttaa tgtacagaat ggttggagaa   4320
atgcctatgg tgaattaaag cttcatatct gctttctgaa aaaaaaaaaa aaa          4373
```

<210> SEQ ID NO 671
<211> LENGTH: 4685
<212> TYPE: DNA
<213> ORGANISM: Homo sapiens

<400> SEQUENCE: 671

```
ggaggaggtg gagagtgagg ccgaggcgtg gggagcccgg gaactccctc ctcctgaagt     60
aacgcgtccc gggccggctc tgccgtcgtt gctgccgccg ggcgccccgg gacgaggagg    120
tggaggaggg agagggcccg cgggcctcgc ctccgccctc cgccacctcg agctgcggta    180
gcagcgactc atgagagcgc ggccggagga cagatttgat aatgggctgc attaaaagta    240
aagaaaacaa aagtccagcc attaaataca gacctgaaaa tactccagag cctgtcagta    300
caagtgtgag ccattatgga gcagaaccca ctacagtgtc accatgtccg tcatcttcag    360
caaagggaac agcagttaat ttcagcagtc tttccatgac accatttgga ggatcctcag    420
gggtaacgcc ttttggaggt gcatcttcct cattttcagt ggtgccaagt tcatatcctg    480
ctggtttaac aggtggtgtt actatatttg tggccttata tgattatgaa gctagaacta    540
cagaagacct ttcatttaag aagggtgaaa gatttcaaat aattaacaat acggaaggag    600
attggtggga agcaagatca atcgctacag gaaagaatgg ttatatcccg agcaattatg    660
tagcgcctgc agattccatt caggcagaag aatggtattt tggcaaaatg gggagaaaag    720
atgctgaaag attacttttg aatcctggaa atcaacgagg tattttctta gtaagagaga    780
gtgaaacaac taaaggtgct tattcccttt ctattcgtga ttgggatgag ataaggggtg    840
acaatgtgaa acactacaaa attaggaaac ttgacaatgg tggatactat atcacaacca    900
```

-continued

```
gagcacaatt tgatactctg cagaaattgg tgaaacacta cacagaacat gctgatggtt    960
tatgccacaa gttgacaact gtgtgtccaa ctgtgaaacc tcagactcaa ggtctagcaa   1020
aagatgcttg ggaaatccct cgagaatctt tgcgactaga ggttaaacta ggacaaggat   1080
gtttcggcga agtgtggatg ggaacatgga atggaaccac gaaagtagca atcaaaacac   1140
taaaaccagg tacaatgatg ccagaagctt tccttcaaga agctcagata atgaaaaaat   1200
taagacatga taaacttgtt ccactatatg ctgttgtttc tgaagaacca atttacattg   1260
tcactgaatt tatgtcaaaa ggaagcttat tagatttcct taaggaagga gatggaaagt   1320
atttgaagct tccacagctg gttgatatgg ctgctcagat tgctgatggt atggcatata   1380
ttgaaagaat gaactatatt caccgagatc ttcgggctgc taatattctt gtaggagaaa   1440
atcttgtgtg caaaatagca gactttggtt tagcaaggtt aattgaagac aatgaataca   1500
cagcaagaca aggtgcaaaa tttccaatca aatggacagc tcctgaagct gcactgtatg   1560
gtcggtttac aataaagtct gatgtctggt catttggaat tctgcaaaca gaactagtaa   1620
caaagggccg agtgccatat ccaggtatgg tgaaccgtga agtactagaa caagtggagc   1680
gaggatacag gatgccgtgc cctcagggct gtccagaatc cctccatgaa ttgatgaatc   1740
tgtgttggaa gaaggaccct gatgaaagac caacatttga atatattcag tccttcttgg   1800
aagactactt cactgctaca gagccacagt accagccagg agaaaattta taattcaagt   1860
agcctatttt atatgcacaa atctgccaaa atataaagaa cttgtgtaga ttttctacag   1920
gaatcaaaag aagaaaatct tctttactct gcatgttttt aatggtaaac tggaatccca   1980
gatatggttg cacaaaacca ctttttttc cccaagtatt aaactctaat gtaccaatga   2040
tgaatttatc agcgtatttc agggtccaaa caaaatagag ctaagatact gatgacagtg   2100
tgggtgacag catggtaatg aaggacagtg aggctcctgc ttatttataa atcatttcct   2160
ttcttttttt ccccaaagtc agaattgctc aaagaaaatt atttattgtt acagataaaa   2220
cttgagagat aaaaagctat accataataa aatctaaaat taaggaatat catgggacca   2280
aataattcca ttccagtttt ttaaagtttc ttgcatttat tattctcaaa agttttttct   2340
aagttaaaca gtcagtatgc aatcttaata tatgctttct tttgcatgga catgggccag   2400
gtttttcaaa aggaatataa acaggatctc aaacttgatt aaatgttaga ccacagaagt   2460
ggaatttgaa agtataatgc agtacattaa tattcatgtt catggaactg aaagaataag   2520
aactttttca cttcagtcct tttctgaaga gtttgactta gaataatgaa ggtaactaga   2580
aagtgagtta atcttgtatg aggttgcatt gattttttaa ggcaatatat aattgaaact   2640
actgtccaat caaaggggaa atgttttgat ctttagatag catgcaaagt aagacccagc   2700
attttaaaag cccttttaa aaactagact tcgtactgtg agtattgctt atatgtcctt   2760
atggggatgg gtgccacaaa tagaaaatat gaccagatca gggacttgaa tgcacttttg   2820
ctcatggtga atatagatga acagagagga aaatgtattt aaaagaaata cgagaaaaga   2880
aagtgaaagt tttacaagtt agagggatgg aaggtaatgt ttaatgttga tgtcatggag   2940
tgacagaatg gctttgctgg cactcagagc tcctcactta gctatattct gagactttga   3000
agagttataa agtataacta taaaactaat ttttcttaca cactaaatgg gtatttgttc   3060
aaaataatga agttatggct tcacattcat tgcagtggga tatggttttt atgtaaaaca   3120
tttttagaac tccagttttc aaatcatgtt tgaatctaca ttcacttttt tttgttttct   3180
tttttgagac ggagtctcgc tctgtcgccc aggctggagt gcagtggcgc gatctcggct   3240
```

-continued cactgcaagc tctgcctccc aggttcacac cattctcctg cctcagcctc ccgagtagct 3300
gggactacag gtgcccacca ccacgcctgg ctagtttttt gtatttttag tagagacgca 3360
gtttcaccgt gttagccagg atggtctcga tctcctgacc ttgtgatctg cccgcctcgg 3420
cctcccaaag tgctgggatt acaggcgtga gccaccgcgc ccagcctaca ttcacttcta 3480
aagtctatgt aatggtggtc atttttttccc ttttagaata cattaaatgg ttgatttggg 3540
gaggaaaact tattctgaat attaacggtg gtgaaaaggg gacagttttt accctaaagt 3600
gcaaaagtga aacatacaaa ataagactaa tttttaagag taactcagta atttcaaaat 3660
acagatttga atagcagcat tagtggtttg agtgtctagc aaaggaaaaa ttgatgaata 3720
aaatgaaggt ctggtgtata tgttttaaaa tactctcata tagtcacact ttaaattaag 3780
ccttatatta ggcccctcta ttttcaggat ataattctta actatcatta tttacctgat 3840
tttaatcatc agattcgaaa ttctgtgcca tggcatatat gttcaaattc aaaccatttt 3900
taaaatgtga agatggactt catgcaagtt ggcagtggtt ctggtactaa aaattgtggt 3960 tgtttttttct gtttacgtaa cctgcttagt attgacactc tctaccaaga gggtcttcct 4020
aagaagagtg ctgtcattat ttcctcttat caacaacttg tgacatgaga tttttaagg 4080 gctttatgtg aactatgata ttgtaatttt tctaagcata ttcaaaaggg tgacaaaatt 4140
acgtttatgt actaaatcta atcaggaaag taaggcagga aaagttgatg gtattcatta 4200
ggttttaact gaatggagca gttccttata taataacaat tgtatagtag ggataaaaca 4260
ctaacttaat gtgtattcat tttaaattgt tctgtatttt taaattgcca agaaaaacaa 4320
ctttgtaaat ttggagatat tttccaacag cttttcgtct tcagtgtctt aatgtggaag 4380 ttaacccctta ccaaaaaagg aagttggcaa aaacagcctt ctagcacact tttttaaatg 4440
aataatggta gcctaaactt aatattttta taaagtattg taatattgtt ttgtggataa 4500
ttgaaataaa aagttctcat tgaatgcacc tattaatcgt tttagttgct attcatattc 4560
tcattcgttt tttaaaaact gatatattct gaatttattc ttccattgag aaaaaaatgt 4620
tcagttactt gtaactactg agcagaattt aatcaatcct ttattaaatt cagaacatta 4680
ttgaa 4685

<210> SEQ ID NO 672
<211> LENGTH: 6695
<212> TYPE: DNA
<213> ORGANISM: Homo sapiens

<400> SEQUENCE: 672
gccctcgccg cccgcggcgc cccgagcgct ttgtgagcag atgcggagcc gagtggaggg 60
cgcgagccag atgcggggcg acagctgact tgctgagagg aggcggggag gcgcggagcg 120
cgcgtgtggt ccttgcgccg ctgacttctc cactggttcc tgggcaccga aagataaacc 180
tctcataatg aaggccccccg ctgtgcttgc acctggcatc ctcgtgctcc tgtttacctt 240
ggtgcagagg agcaatgggg agtgtaaaga ggcactagca aagtccgaga tgaatgtgaa 300
tatgaagtat cagcttccca acttcaccgc ggaaacaccc atccagaatg tcattctaca 360
tgagcatcac attttccttg gtgccactaa ctacatttat gttttaaatg aggaagacct 420
tcagaaggtt gctgagtaca agactgggcc tgtgctggaa cacccagatt gtttcccatg 480
tcaggactgc agcagcaaag ccaatttatc aggaggtgtt tggaaagata acatcaacat 540
ggctctagtt gtcgacacct actatgatga tcaactcatt agctgtggca gcgtcaacag 600
agggacctgc cagcgacatg tctttcccca caatcatact gctgacatac agtcggaggt 660

-continued

```
tcactgcata ttctccccac agatagaaga gcccagccag tgtcctgact gtgtggtgag    720
cgccctggga gccaaagtcc tttcatctgt aaaggaccgg ttcatcaact tctttgtagg    780
caataccata aattcttctt atttcccaga tcatccattg cattcgatat cagtgagaag    840
gctaaaggaa acgaaagatg gttttatgtt tttgacggac cagtcctaca ttgatgtttt    900
acctgagttc agagattctt accccattaa gtatgtccat gcctttgaaa gcaacaattt    960
tatttacttc ttgacggtcc aaagggaaac tctagatgct cagacttttc acacaagaat   1020
aatcaggttc tgttccataa actctggatt gcattcctac atggaaatgc ctctggagtg   1080
tattctcaca gaaaagagaa aaaagagatc cacaaagaag gaagtgttta atatacttca   1140
ggctgcgtat gtcagcaagc ctggggccca gcttgctaga caaataggag ccagcctgaa   1200
tgatgacatt cttttcgggg tgttcgcaca aagcaagcca gattctgccg aaccaatgga   1260
tcgatctgcc atgtgtgcat tccctatcaa atatgtcaac gacttcttca acaagatcgt   1320
caacaaaaac aatgtgagat gtctccagca tttttacgga cccaatcatg agcactgctt   1380
taataggaca cttctgagaa attcatcagg ctgtgaagcg cgccgtgatg aatatcgaac   1440
agagtttacc acagctttgc agcgcgttga cttattcatg ggtcaattca gcgaagtcct   1500
cttaacatct atatccacct tcattaaagg agacctcacc atagctaatc ttgggacatc   1560
agagggtcgc ttcatgcagg ttgtggtttc tcgatcagga ccatcaaccc ctcatgtgaa   1620
ttttctcctg gactcccatc cagtgtctcc agaagtgatt gtggagcata cattaaacca   1680
aaatggctac acactggtta tcactgggaa gaagatcacg aagatcccat tgaatggctt   1740
gggctgcaga catttccagt cctgcagtca atgcctctct gccccaccct ttgttcagtg   1800
tggctggtgc cacgacaaat gtgtgcgatc ggaggaatgc ctgagcggga catggactca   1860
acagatctgt ctgcctgcaa tctacaaggt tttcccaaat agtgcacccc ttgaaggagg   1920
gacaaggctg accatatgtg gctgggactt tggatttcgg aggaataata aatttgattt   1980
aaagaaaact agagttctcc ttggaaatga gagctgcacc ttgactttaa gtgagagcac   2040
gatgaataca ttgaaatgca cagttggtcc tgccatgaat aagcatttca atatgtccat   2100
aattatttca aatggccacg ggacaacaca atacagtaca ttctcctatg tggatcctgt   2160
aataacaagt atttcgccga aatacggtcc tatggctggt ggcactttac ttactttaac   2220
tggaaattac ctaaacagtg ggaattctag acacatttca attggtggaa aaacatgtac   2280
tttaaaaagt gtgtcaaaca gtattcttga atgttatacc ccagcccaaa ccatttcaac   2340
tgagtttgct gttaaattga aaattgactt agccaaccga gagacaagca tcttcagtta   2400
ccgtgaagat cccattgtct atgaaattca tccaaccaaa tcttttatta gtacttggtg   2460
gaaagaacct ctcaacattg tcagttttct attttgcttt gccagtggtg ggagcacaat   2520
aacaggtgtt gggaaaaacc tgaattcagt tagtgtcccg agaatggtca taaatgtgca   2580
tgaagcagga aggaacttta cagtggcatg tcaacatcgc tctaattcag agataatctg   2640
ttgtaccact ccttccctgc aacagctgaa tctgcaactc cccctgaaaa ccaaagcctt   2700
tttcatgtta gatgggatcc tttccaaata ctttgatctc atttatgtac ataatcctgt   2760
gtttaagcct tttgaaaagc cagtgatgat ctcaatgggc aatgaaaatg tactggaaat   2820
taagggaaat gatattgacc ctgaagcagt taaaggtgaa gtgttaaaag ttggaaataa   2880
gagctgtgag aatatacact tacattctga agccgtttta tgcacggtcc ccaatgacct   2940
gctgaaattg aacagcgagc taaatataga gtggaagcaa gcaatttctt caaccgtcct   3000
```

-continued

```
tggaaaagta atagttcaac cagatcagaa tttcacagga ttgattgctg gtgttgtctc   3060
aatatcaaca gcactgttat tactacttgg gtttttcctg tggctgaaaa agagaaagca   3120
aattaaagat ctgggcagtg aattagttcg ctacgatgca agagtacaca ctcctcattt   3180
ggataggctt gtaagtgccc gaagtgtaag cccaactaca gaaatggttt caaatgaatc   3240
tgtagactac cgagctactt ttccagaaga tcagtttcct aattcatctc agaacggttc   3300
atgccgacaa gtgcagtatc ctctgacaga catgtccccc atcctaacta gtggggactc   3360
tgatatatcc agtccattac tgcaaaatac tgtccacatt gacctcagtg ctctaaatcc   3420
agagctggtc caggcagtgc agcatgtagt gattgggccc agtagcctga ttgtgcattt   3480
caatgaagtc ataggaagag ggcattttgg ttgtgtatat catgggactt tgttggacaa   3540
tgatggcaag aaaattcact gtgctgtgaa atccttgaac agaatcactg acataggaga   3600
agtttcccaa tttctgaccg agggaatcat catgaaagat tttagtcatc ccaatgtcct   3660
ctcgctcctg ggaatctgcc tgcgaagtga agggtctccg ctggtggtcc taccatacat   3720
gaaacatgga gatcttcgaa atttcattcg aaatgagact cataatccaa ctgtaaaaga   3780
tcttattggc tttggtcttc aagtagccaa aggcatgaaa tatcttgcaa gcaaaaagtt   3840
tgtccacaga gacttggctg caagaaactg tatgctggat gaaaaattca cagtcaaggt   3900
tgctgatttt ggtcttgcca gagacatgta tgataaagaa tactatagtg tacacaacaa   3960
aacaggtgca aagctgccag tgaagtggat ggctttggaa agtctgcaaa ctcaaaagtt   4020
taccaccaag tcagatgtgt ggtcctttgg cgtgctcctc tgggagctga tgacaagagg   4080
agccccacct tatcctgacg taaacacctt tgatataact gtttacttgt tgcaagggag   4140
aagactccta caacccgaat actgcccaga ccccttatat gaagtaatgc taaaatgctg   4200
gcaccctaaa gccgaaatgc gcccatcctt ttctgaactg gtgtcccgga tatcagcgat   4260
cttctctact ttcattgggg agcactatgt ccatgtgaac gctacttatg tgaacgtaaa   4320
atgtgtcgct ccgtatcctt ctctgttgtc atcagaagat aacgctgatg atgaggtgga   4380
cacacgacca gcctccttct gggagacatc atagtgctag tactatgtca aagcaacagt   4440
ccacactttg tccaatggtt ttttcactgc ctgaccttta aaaggccatc gatattcttt   4500
gctcttgcca aaattgcact attataggac ttgtattgtt atttaaatta ctggattcta   4560
aggaatttct tatctgacag agcatcagaa ccagaggctt ggtcccacag gccacggacc   4620
aatggcctgc agccgtgaca acactcctgt catattggag tccaaaactt gaattctggg   4680
ttgaattttt taaaaatcag gtaccacttg atttcatatg ggaaattgaa gcaggaaata   4740
ttgagggctt cttgatcaca gaaaactcag aagagatagt aatgctcagg acaggagcgg   4800
cagccccaga acaggccact catttagaat tctagtgttt caaaacactt ttgtgtgttg   4860
tatggtcaat aacatttttc attactgatg gtgtcattca cccattaggt aaacattccc   4920
ttttaaatgt ttgtttgttt tttgagacag gatctcactc tgttgccagg gctgtagtgc   4980
agtggtgtga tcatagctca ctgcaacctc cacctcccag gctcaagcct cccgaatagc   5040
tgggactaca ggcgcacacc accatccccg gctaattttt gtatttttttg tagagacggg   5100
gttttgccat gttgccaagg ctggtttcaa actcctggac tcaagaaatc cacccacctc   5160
agcctcccaa agtgctagga ttacaggcat gagccactgc gcccagccct tataaatttt   5220
tgtatagaca ttcctttggt tggaagaata tttataggca atacagtcaa agtttcaaaa   5280
tagcatcaca caaaacatgt ttataaatga acaggatgta atgtacatag atgacattaa   5340
gaaaatttgt atgaaataat ttagtcatca tgaaatattt agttgtcata taaaaaccca   5400
```

ctgtttgaga atgatgctac tctgatctaa tgaatgtgaa catgtagatg ttttgtgtgt 5460
atttttttaa atgaaaactc aaaataagac aagtaatttg ttgataaata tttttaaaga 5520
taactcagca tgtttgtaaa gcaggataca ttttactaaa aggttcattg gttccaatca 5580
cagctcatag gtagagcaaa gaaagggtgg atggattgaa aagattagcc tctgtctcgg 5640
tggcaggttc ccacctcgca agcaattgga aacaaaactt ttggggagtt ttattttgca 5700
ttagggtgtg ttttatgtta agcaaaacat actttagaaa caaatgaaaa aggcaattga 5760
aaatcccagc tatttcacct agatggaata gccaccctga gcagaacttt gtgatgcttc 5820
attctgtgga attttgtgct tgctactgta tagtgcatgt ggtgtaggtt actctaactg 5880
gttttgtcga cgtaaacatt taaagtgtta tatttttat aaaaatgttt atttttaatg 5940
atatgagaaa aattttgtta ggccacaaaa acactgcact gtgaacattt tagaaaaggt 6000
atgtcagact gggattaatg acagcatgat tttcaatgac tgtaaattgc gataaggaaa 6060
tgtactgatt gccaatacac cccaccctca ttacatcatc aggacttgaa gccaagggtt 6120
aacccagcaa gctacaaaga gggtgtgtca cactgaaact caatagttga gtttggctgt 6180
tgttgcagga aaatgattat aactaaaagc tctctgatag tgcagagact taccagaaga 6240
cacaaggaat tgtactgaag agctattaca atccaaatat tgccgtttca taaatgtaat 6300
aagtaatact aattcacaga gtattgtaaa tggtggatga caaaagaaaa tctgctctgt 6360
ggaaagaaag aactgtctct accagggtca agagcatgaa cgcatcaata gaaagaactc 6420
ggggaaacat cccatcaaca ggactacaca cttgtatata cattcttgag aacactgcaa 6480
tgtgaaaatc acgtttgcta tttataaact tgtccttaga ttaatgtgtc tggacagatt 6540
gtgggagtaa gtgattcttc taagaattag atacttgtca ctgcctatac ctgcagctga 6600
actgaatggt acttcgtatg ttaatagttg ttctgataaa tcatgcaatt aaagtaaagt 6660
gatgcaacat cttgtaaaaa aaaaaaaaaa aaaaa 6695

<210> SEQ ID NO 673
<211> LENGTH: 2302
<212> TYPE: DNA
<213> ORGANISM: Homo sapiens

<400> SEQUENCE: 673
agttgctaag gaaatgactg cccgcagcgc ctggccccgc cgcgcaggcc gggcggggtc 60
tggagcggcg ccgtttccgc ttccgctccc tcacagctcc cgtcccgtta ccgcctcctg 120
gccggcctcg cgcctttcac cggcaccttg cgtcggtcgc gccgcggggc ctgctcctgc 180
cgcgcgcacc cccggggctt cggctccggc acgggtcgcg cccagctttc ctgcacctga 240
ggccgccggc cagccgccgc catgggtgcc tacctctccc agcccaacac ggtgaagtgc 300
tccggggacg gggtcggcgc cccgcgcctg ccgctgccct acggcttctc cgccatgcaa 360
ggctggcgcg tctccatgga ggatgctcac aactgtattc ctgagctgga cagtgagaca 420
gccatgtttt ctgtctacga tggacatgga ggggaggaag ttgccttgta ctgtgccaaa 480
tatcttcctg atatcatcaa agatcagaag gcctacaagg aaggcaagct acagaaggct 540
ttagaagatg ccttcttggc tattgacgcc aaattgacca ctgaagaagt cattaaagag 600
ctggcacaga ttgcagggcg acccactgag gatgaagatg aaaaagaaaa agtagctgat 660
gaagatgatg tggacaatga ggaggctgca ctgctgcatg aagaggctac catgactatt 720
gaagagctgc tgacacgcta cgggcagaac tgtcacaagg gccctcccca cagcaaatct 780

```
ggaggtggga caggcgagga accagggtcc cagggcctca atggggaggc aggacctgag    840
gactcaacta gggaaactcc ttcacaagaa aatggcccca cagccaaggc ctacacaggc    900
ttttcctcca actcggaacg tgggactgag gcaggccaag ttggtgagcc tggcattccc    960
actggtgagg ctgggccttc ctgctcttca gcctctgaca agctgcctcg agttgctaag   1020
tccaagttct ttgaggacag tgaggatgag tcagatgagg cggaggaaga agaggaagac   1080
agtgaggaat gcagcgagga agaggatggc tacagcagtg aggaggcaga gaatgaggaa   1140
gatgaggatg acaccgagga ggctgaagag gacgatgaag aagaagaaga agagatgatg   1200
gtgccaggga tggaaggcaa agaggagcct ggctctgaca gtggtacaac agcggtggtg   1260
gccctgatac gagggaagca gttgattgta gccaacgcag gagactctcg ctgtgtggta   1320
tctgaggctg gcaaagcttt agacatgtcc tatgatcaca aaccagagga tgaagtagaa   1380
ctagcacgca tcaagaatgc tggtggcaag gtcaccatgg atgggcgagt caacgggggc   1440
ctcaacctct ccagagccat tggggaccac ttctataaga gaaacaagaa cctgccacct   1500
gaggaacaga tgatttcagc ccttcctgac atcaaggtgc tgactctcac tgacgaccat   1560
gaattcatgg tcattgcctg tgatggcatc tggaatgtga tgagcagcca ggaagttgta   1620
gatttcattc aatcaaagat cagccagcgt gatgaaaatg gggagcttcg gttattgtca   1680
tccattgtgg aagagctgct ggatcagtgc ctggcaccag acacttctgg ggatggtaca   1740
gggtgtgaca acatgacctg catcatcatt tgcttcaagc cccgaaacac agcagagctc   1800
cagccagaga gtggcaagcg aaaactagag gaggtgctct ctactgaggg ggctgaagaa   1860
aatggcaaca gcgacaagaa gaagaaggcc aagcgagact agcagtcatc cagacccctg   1920
cccacctaga ctgttttctg agccctccgg acctgagact gagttttgtc tttttccttt   1980
agccttagca gtgggtatga ggtgtgcagg gggagctggg tggcttcact ccgcccattc   2040
caaagagggc tctccctcca cactgcagcc gggagcctct gctgtccttc ccagccgcct   2100
ctgctcctcg ggctcatcac cggttctgtg cctgtgctct gttgtgttgg agggaaggac   2160
tggcggttct ggtttttact ctgtgaactt tatttaagga cattcttttt tattggcggc   2220
tccatggccc tcggccgctt gcacccgctc tctgttgtac actttcaatc aacacttttt   2280
cagactaaag gccaaaacct aa                                            2302
```

<210> SEQ ID NO 674
<211> LENGTH: 874
<212> TYPE: DNA
<213> ORGANISM: Homo sapiens

<400> SEQUENCE: 674

```
ggcgtggccc ttcgagccag ctccgccccg ttgttcctgg cttgagtagg gcagagagca     60
ccgcccagca gccagtgggt tcccgcgcgt gccgagactc tgaggccttg cacccccacg    120
atcccgtacg atggccgtca agaagatcgc gatcttcggc gccactggcc agaccgggct    180
caccaccctg gcgcaggcgg tgcaagcagg ttacgaagtg acagtgctgg tgcgggactc    240
ctccaggctg ccatcagagg ggccccggcc ggcccacgtg gtagtgggag atgttctgca    300
ggcagccgat gtggacaaga ccgtggctgg gcaggacgct gtcatcgtgc tgctgggcac    360
ccgcaatgac ctcagtccca cgacagtgat gtccgagggc gcccggaaca ttgtggcagc    420
catgaaggct catggtgtgg acaaggtcgt ggcctgcacc tcggctttcc tgctctggga    480
ccctaccaag gtgcccccac gactgcaggc tgtgactgat gaccacatcc ggatgcacaa    540
ggtgctgcgg gaatcaggcc tgaagtacgt ggctgtgatg ccgccacaca taggagacca    600
```

-continued

```
gccactaact ggggcgtaca cagtgaccct ggatggacga gggccctcaa gggtcatctc    660

caaacatgac ctgggccatt tcatgctgcg ctgcctcacc accgatgagt acgacggaca    720

cagcacctac ccctcccacc agtaccagta gcactctgtc cccatctggg agggtggcat    780

tctgggacat gaggagcaaa ggaagggggc aataaatgtt gagccaagag cttcaaatta    840

ctctagagaa accgacaaaa aaaaaaaaaa aaaa                                 874
```

<210> SEQ ID NO 675
<211> LENGTH: 2927
<212> TYPE: DNA
<213> ORGANISM: Homo sapiens

<400> SEQUENCE: 675

```
ggaactcggg gtgcggccct cgccggcccc gggccagcgg ccaggtcccc gccctccgcg     60

ggatttactc ctgtcccgcc tcctcggatt tagcccaggc agcctgggag gttccgcagt    120

cgccgcttcc gccttgacca ggtggagctg gagacctggt ctctctaggg cctaccctga    180

gctcaccatc tgaaggagag tgccatcatc cttaggaact ccttctccag acatgcttcc    240

tgaggctggc tccctgtggc tactgaagct gctccgggac atccagttgg cccagtttta    300

ctggcccatc cttgaggagc ttaatgtcac tcggccagag cacttcgact ttgtaaagcc    360

tgaggacctg gacggcattg gcatgggccg gcctgcccag cgcagactgt ccgaagctct    420

gaaaaggcta cgttctgggc ctaagtctaa gaactgggtc tacaagatcc ttggaggttt    480

tgcccctgag cacaaggagc ccaccctgcc ctcggacagc ccacggcacc tccctgagcc    540

agagggggc ctcaagtgtc tgatcccaga gggtgctgtt tgcagagggg agctgctggg    600

ttcaggctgc ttcggtgtgg tgcaccgagg gctgtggacg ctgcccagtg gcaagagtgt    660

cccagtggct gtcaagtccc tccgggtagg tcccgaaggc ccgatgggca cagaactggg    720

ggacttcctg cgagaggtat cggtcatgat gaacttggag cacccacacg tgctgcgtct    780

gcacggcctt gtactgggcc agcctctgca gatggtgatg gagctggcgc cactgggctc    840

cctgcacgcg cgcctaacgg ccccggcccc gacacccccg ctgctcgtgg ccctgctctg    900

cctcttcctg cggcagctgg cgggagccat ggcgtacctg gggcccgcg ggctggtgca    960

ccgagacctc gctacgcgca acctactgct ggcgtcgccg cgcaccatca aggtggctga   1020

cttcgggctg gtgcggcctc tgggcggtgc ccggggccgc tacgtcatgg gcgggccccg   1080

ccctatcccc tacgcctggt gtgccccaga gagcctgcgc cacggagcct tctcgtctgc   1140

ctcggacgtg tggatgtttg ggtgacgct gtgggagatg ttctccgggg gcgaggaacc   1200

ctgggccggg gtcccaccgt acctcatcct gcagcggctg gaggacagag cccggctgcc   1260

taggcctccc ctctgctcca gggccctcta ctccctcgcc ttgcgctgct gggcccccca   1320

ccctgccgac cggcctagct tttcccacct ggaggggctg ctgcaagagg ccgggccttc   1380

ggaagcatgt tgtgtgaggg atgtcacaga accaggcgcc ctgaggatgg agactggtga   1440

ccccatcaca gtcatcgagg gcagctcctc tttccacagc cccgactcca caatctggaa   1500

gggccagaat ggtcgcacct tcaaagtggg cagcttccca gcctcggcag tgacgctggc   1560

agatgcgggg ggcttgccag ccacccgtcc agtccacaga ggcacccctg cccggggaga   1620

tcaacaccca ggaagcatag atggagacag aaagaaggca aatctttggg atgcgccccc   1680

agcacggggc cagaggagga acatgcccct ggagaggatg aaaggcattt ccaggagtct   1740

ggagtcagtt ctgtccctcg gtcctcgtcc cacagggggt ggttcaagcc cccctgaaat   1800
```

tcgacaagcc agagctgtgc cccagggacc tccaggcctg cctccacgcc cacctttatc 1860
ctctagctct cctcagccca gccagccctc tagggagagg cttccctggc ccaaaagaaa 1920
acccccacac aatcacccca tgggaatgcc tggagcccgt aaagccgctg ccctctctgg 1980
aggcctcttg tccgatcctg agttgcagag gaagattatg gaggtggagc tgagtgtgca 2040
tggggtcacc caccaggagt gccagacagc actaggagcc actgggggag atgtggtttc 2100
tgccatccgg aacctcaagg tagatcagct cttccacctg agtagccggt ccagagctga 2160
ctgctggcgc atcctggagc attaccagtg ggacctctca gctgccagcc gctatgtcct 2220
ggccaggccc tgagctcagc ttctgcgggc acagacacca gcatgaaaag cctaggcccc 2280
tgagggcctg gccacatggg accaagcgga accagaacaa ggtcccgaca ggggtagacg 2340
ttccacctgg ggagatccca cctgccgtag gcacatggag gaggagccca gagttgggca 2400
ctggcaaatg tctcctccct cccatgctcc ttggcttctg aaggctgaag ctcctttggc 2460
tgggccaaga aggatctagt ctgcccacta cattctcaaa caagaggact tggaggaaaa 2520
gagctgctat acatcatatg cagaggaagc ttctacgcgc tagagaggat caaggggcca 2580
cactggacca tgtgaacagc catcctgaac tgccatcagc taccacactg gactctgcag 2640
ggcagccatc ctggatgatg gaagccacca tattgacttg ggtataggc ccaaactgcc 2700 ttcgtttggt ccagggccat cgtgggtgat gacgattgct ctcttgcact caaggacatt 2760
tgatgctggt agtatggatt atgagatgga ctagcccctg ccccagccca gctctcacat 2820 tccccttgt tttttcccat accaactgct tctaccctcc cctattacat acatctttca 2880
atgtccaaaa agttacaaag tttatatgaa tgtaacatat aaaaaaa 2927

<210> SEQ ID NO 676
<211> LENGTH: 5475
<212> TYPE: DNA
<213> ORGANISM: Homo sapiens

<400> SEQUENCE: 676
actgggcgga ctccgcgccg ccggccttgt agccatttta ggaggaatcg ctggtcgcca 60
gcgaggggtg cggcttcaat ttcaataact ttattggtgg cctgatctgc agaacagcca 120
tcacatcagt ggcccttgga ggagggagcg catcgcccga ggtggtcccc gacgagctgc 180
agccatggga aacaccacca gcgaccgggt gtccggggag cgccacggcg ccaaggctgc 240
acgctccgag ggcgcaggcg gccatgcccc ggggaaggag cacaagatca tggtggggag 300
tacggacgac cccagcgtgt tcagcctccc tgactccaag ctccctgggg acaaagagtt 360
tgtatcatgg cagcaggatt tggaggactc cgtaaagccc acacagcagg cccggcccac 420
tgttatccgc tggtctgaag gaggcaagga ggtcttcatc tctgggtcct tcaacaattg 480
gagcaccaag attccactga ttaagagcca taatgacttt gttgccatcc tggacctccc 540
tgagggagag caccaataca agttctttgt ggatggacag tgggttcatg atccatcaga 600
gcctgtggtt accagtcagc ttggcacaat taacaatttg atccatgtca agaaatctga 660
ttttgaggtg ttcgatgctt taaagttaga ttctatggaa agttctgaga catcttgtag 720
agacctttcc agctcacccc cagggcctta tggtcaagaa atgtatgcgt ttcgatctga 780
ggaaagattc aaatccccac ccatccttcc tcctcatcta cttcaagtta ttcttaacaa 840
agacactaat atttcttgtg acccagcctt actccctgag cccaaccatg ttatgctgaa 900
ccatctctat gcattgtcca ttaaggacag tgtgatggtc cttagcgcaa cccatcgcta 960
caagaagaag tatgttacta ctctgctata caagcccatt tgaagggatc ccttcttgcc 1020

```
tctaaggatt caggagaagc atctcccttg catttctgga ctgaaccagt cttacctgag   1080
actggaaggc tgatttgctt tgaggctgat atgtgtgttt cagagcctct gagtaggatg   1140
ctctgctttt gcatttgatt gcagatgaga gctttatgag ttcacggaat ttattttaag   1200
aaaaaaaaat atacatatga gaagaaggta aatggaagcc tcctagcccc agctagaagt   1260
attgtttctg cctgtgggtt ttcaccaaga cctgtttggg ggcgctgcag gaataactat   1320
ataggaagat ttttcctaaa atgaaagaac agcaaactct taggatcctt gttgggtgga   1380
gattctatca ctgctacctt ggctctccaa ggaatgggct tgtgctagac cgctgcccta   1440
cttaacagct gcctcattgc aagggcagtt tttcttgcat gggttctcta tattcccaga   1500
gtatgtggca caatctgtgt tgtttatatg ataccagatg ccccacaaga acccttattc   1560
ctctcatttc acattcttcc tttaatagcc tccttcagat cccatacctg acccctctct   1620
aacacaaaac ttattgggta agtgactttg aaaagttttg tggcacctga cccaccccag   1680
acactagggc tatcagaagg tctccttttt agcccagcac aggcccaggc cactttgtcg   1740
tgtttgtttt aacttctaaa gaaaatatgt ttcagcatta taagaaaggc agaatgcaga   1800
acacctacat ttttgtttta gtttggtgcc aaggctcagg ctgtattggc aaattcccga   1860
aagttttccc actttgcctg gccctgcttc tgtcttttct ttctcagtaa acagttctga   1920
aggcaggagt ggaacccggg agtattttca tgtctttcat ccttgaaaga tttttatgtg   1980
cctgcatttt ttttttaatt aaaaaatgcc ttttcattgg tcttaagaga ccgcattgga   2040
gaatttcagg cttttgataa atgcttcttc aaagagattt tcttctctag tctagccttc   2100
cacattctta gattaatatg gccaaccctg tacacatcac tacactaaac actgctctag   2160
ataaactgct caagttcatt taactcattt gatgcaccta aaggggttcc tcattttaaa   2220
gatttgttag gccaagaagc aagagagtat tcctagtatt cccaaccatg aaaagtatca   2280
ttctttgcac caaatgttaa caaaatcatt ttgttctcct gcctcttctt tttaaaggtg   2340
tttgatgatt aagtggggtc actgaattcc atttgtggac tgaaaagtat tcaatccact   2400
tttggggttc agagataaaa catttttttcc caagtagctg gggctcttcc attttgcaga   2460
taagtcaaat aatcaacact aaaggaggct aaactgttga tgaatgagag actccctgac   2520
tgctcagatg accctagcca cactgaaagg gcacctacag gtcagtttag ctacctcctg   2580
tctttcccat gcaaagctga taacacagtt gtctttggac ttgtagacct cttggattcc   2640
aggtgtgatg gagtaaagtg tgggattgtt gttttgctgg gatgcaaata actaaatgct   2700
ttggtggtta attgctaaga gtaaatacta ctttagccat ccaaggccac cttctgcagc   2760
aaaaggcttt tgtggagaac cttttatgtt cccaaccact ttttgaatgg tgtgccattt   2820
aaaaatccag gccagatcct attataacca actctcagga tttacagcct tcagttgtac   2880
tagaattttg tttttatcca atactcatta aataagtggg ccacttagga agattcaaaa   2940
tcttggttat tacatgaagt ttgttatatt tcttgtcaac agtattgaaa tgtaatatgt   3000
atgtgttcat gtatgaaaat ttttactcca cacaggtgtt tcagtagagt ggggcaggaa   3060
aagagatctc ttcgatttct ttcaggcctg aggcttttgt gaaatgcgtc agccccctgt   3120
gacagtaggt tttgatgcta gtgatcttca gatctttctc tctggaaatg tgcagagagt   3180
gtcagtttcc caagttctga ggtaactctc agcccagatg tgaaatggga gcctaccagc   3240
tggtatagaa gggaatgggt aggaggcact gggtgctgac tcattcagca ctgtcccttt   3300
tctatactgc tgatacatcc catggttctg agaagcctta tctcagtcta tttggaagag   3360
```

```
agggaggaag agaaggaagt aacccaaagt actactcatt tatcattgta tattgattag   3420
ttaaagggat aattaattta atgctgagga gagtttgaca gattttgaaa atgagtaaag   3480
gcaaaaaaaa ttttttagc ctttattttg cttttgggaa ttttacagag tcaaagtagg   3540
cagaataaga aaatagttct tcaggagggc cgacctttaa agaacttcaa catagtttcg   3600
gaattgtggg gaagagaaga gtgactgagc tgagaagtaa taatagaata aagggttgag   3660
taacttacaa ctgaaaatga tctcttttaa aaagaaatta aatcagacac cacatggtgg   3720
tgtccttgga tctcactgta cagaattagc agtgtataac catcttctct tttcatcttg   3780
ttccaattct ctcctctttc ctttccattc tgctttaagc tcatgtgtca ggcagacttt   3840
accagagtgt cagacattac ctaaaacaca tacgttagcc atgctgctgg tatggagaaa   3900
ttccacacca tgattattag cctcctttaa gctgaatggg atttaaccat tctaggcaac   3960
acccctgaag ggcataccta acctcaatag tgttggcttt taaaacgtat gtttgtatgg   4020
tagagaaact ttgtaaaaga agaatccaag agaagtttgt gaggatccta caaacccagg   4080
cccactcact ttgctctaat tctttctagt atcttgtaga tctaatgggt ctgggataaa   4140
aactttgaaa agtgtcaata ttccatgtat gctgctgaaa tgaagttaag tttggaaaga   4200
agtgatacct ctagactggg tttatattaa tctgggatat aaatgaagaa gacatactaa   4260
tagaactcct tgcttttaat tggggaaata gggctttaat aattttgacc tcaactaaaa   4320
atgatatgca atagtctctg tgtgtgtttg aaatacattg tgttctcaga gatttctaca   4380
ttctcacgtt ctagtgattt ggggcatggg cttaatagca gatgtacagt gtattcctgc   4440
attattgtga ttccccttaa agcccagttc ttgctgtctt ctaccagggg ctgctgactc   4500
cagttaccca tggaatgcag gacctgggag gggtagccat tagggtcttt caaaactctt   4560
tggatctaag catttgtctc tccttaagtg ccaatcacaa ttggatatgg aaggactgtg   4620
atttctgcaa tgaacccaaa cttttagagt aaaaagccaa atttaaatta taagaaagaa   4680
gggaaaaaag agaaaaactc aagtctatta cttgtagagt ccaattctta gcaatggaat   4740
cgctctagga ttctagtttg ggctttgtct ggatttgctt ttctcagttg tgctttgaag   4800
tgaataagct ttgttacaaa ttaatttttt attagttcca atattagttg gagttaactt   4860
gaattgattg tatgtagcac agcacttttg cagtaagatt ggtgtgaaat actaaacact   4920
atggattttg taggtgtcag gttaaatggt caagggatac ctacattaag tcatatatta   4980
ggtattgatg atcttacttc ttttctgttc ccctgtacaa aacacttacc taacccagct   5040
tgtggtttta ggacagccaa agctcactgt tgttggttag tcctaatcac tacacgggtc   5100
tcataaatga gacttgtttg aattttggta cattggagca tgttggttgg tattacacgg   5160
cagcatttcg aatgagtgca gctctgtgtc tgtcagaaag gagagataag actactttga   5220
agggaattaa atatgtgagt cctcttttta atggtgcttt ttgtaacctt taatgctgag   5280
gtacagagct gcttttcaat atttcataaa ggagtggcag acaagagtgg attttaaagc   5340
tgttcttcaa acgtaatttg tcactggact ctgacacacc tggaaattat atgatatgat   5400
acatacagaa atgttgtggg ttttttccat aaaactttaa taaaagtatt atacagcaat   5460
aaaaaaaaaa aaaaa                                                    5475
```

<210> SEQ ID NO 677
<211> LENGTH: 10404
<212> TYPE: DNA
<213> ORGANISM: Homo sapiens

<400> SEQUENCE: 677

```
gcgccgctca cgtggtccgt ccccagcccc gtcgccggcg gaggcgggcg cgggcgcgtc     60
cctgtggcca gtcacccgga ggagttggtc gcacaattat gaaagactcg gcttctgctg    120
ctagcgccgg agctgagtta gttctgagaa ggtttccctg ggcgttcctt gtccggcggc    180
ctctgctgcc gcctccggag acgcttcccg atagatggct acaggccgcg gaggaggagg    240
aggtggagtt gctgcccttc cggagtccgc cccgtgagga gaatgtccca gaaatcctgg    300
atagaaagca ctttgaccaa gagggaatgt gtatatatta taccaagttc caaggaccct    360
cacagatgcc ttccaggatg tcaaatttgt cagcaactcg tcaggtgttt ttgtggtcgc    420
ttggtcaagc aacatgcttg ttttactgca agtcttgcca tgaaatactc agatgtgaaa    480
ttgggtgacc attttaatca ggcaatagaa gaatggtctg tggaaaagca tacagaacag    540
agcccaacgg atgcttatgg agtcataaat tttcaagggg gttctcattc ctacagagct    600
aagtatgtga ggctatcata tgacaccaaa cctgaagtca ttctgcaact tctgcttaaa    660
gaatggcaaa tggagttacc caaacttgtt atctctgtac atgggggcat gcagaaattt    720
gagcttcacc cacgaatcaa gcagttgctt ggaaaaggtc ttattaaagc tgcagttaca    780
actggagcct ggattttaac tggaggagta aacacaggtg tggcaaaaca tgttggagat    840
gccctcaaag aacatgcttc cagatcatct cgaaagattt gcactatcgg aatagctcca    900
tggggagtga ttgaaaacag aaatgatctt gttgggagag atgtggttgc tccttatcaa    960
accttattga accccctgag caaattgaat gttttgaata atctgcattc ccatttcata   1020
ttggtggatg atggcactgt tggaaagtat ggggcggaag tcagactgag aagagaactt   1080
gaaaaaacta ttaatcagca aagaattcat gctaggattg gccagggtgt ccctgtggtg   1140
gcacttatat ttgagggtgg gccaaatgtt atcctcacag ttcttgaata ccttcaggaa   1200
agccccccctg ttccagtagt tgtgtgtgaa ggaacaggca gagctgcaga tctgctagcg   1260
tatattcata aacaaacaga agaaggaggg aatcttcctg atgcagcaga gcccgatatt   1320
atttccacta tcaaaaaaac atttaacttt ggccagaatg aagcacttca tttatttcaa   1380
acactgatgg agtgcatgaa aagaaaggag cttatcactg ttttccatat tgggtcagat   1440
gaacatcaag atatagatgt agcaatactt actgcactgc taaaaggtac taatgcatct   1500
gcatttgacc agcttatcct tacattggca tgggatagag ttgacattgc caaaaatcat   1560
gtatttgttt atggacagca gtggctggtt ggatccttgg aacaagctat gcttgatgct   1620
cttgtaatgg atagagttgc atttgtaaaa cttcttattg aaaatggagt aagcatgcat   1680
aaattcctta ccattccgag actggaagaa ctttacaaca ctaaacaagg tccaactaat   1740
ccaatgctgt ttcatcttgt tcgagacgtc aaacagggaa atcttcctcc aggatataag   1800
atcactctga ttgatatagg acttgttatt gaatatctca tgggaggaac ctacagatgc   1860
acctatacta ggaaacgttt tcgattaata tataatagtc ttggtggaaa taatcggagg   1920
tctggccgaa atacctccag cagcactcct cagttgcgaa agagtcatga atcttttggc   1980
aatagggcag ataaaaagga aaaaatgagg cataaccatt tcattaagac agcacagccc   2040
taccgaccaa agattgatac agttatggaa gaaggaaaga agaaaagaac caaagatgaa   2100
attgtagaca ttgatgatcc agaaaccaag cgctttcctt atccacttaa tgaactttta   2160
atttgggctt gccttatgaa gaggcaggtc atggcccgtt ttttatggca acatggtgaa   2220
gaatcaatgg ctaaagcatt agttgcctgt aagatctatc gttcaatggc atatgaagca   2280
aagcagagtg acctggtaga tgatacttca gaagaactaa aacagtattc caatgatttt   2340
```

ggtcagttgg ccgttgaatt attagaacag tccttcagac aagatgaaac catggctatg 2400
aaattgctca cttatgaact gaagaactgg agtaattcaa cctgccttaa gttagcagtt 2460
tcttcaagac ttagaccttt tgtagctcac acctgtacac aaatgttgtt atctgatatg 2520
tggatgggaa ggctgaatat gaggaaaaat tcctggtaca aggtcatact aagcatttta 2580
gttccacctg ccatattgct gttagagtat aaaactaagg ctgaaatgtc ccatatccca 2640
caatctcaag atgctcatca gatgacaatg gatgacagcg aaaacaactt tcagaacata 2700
acagaagaga tccccatgga agtgtttaaa gaagtacgga ttttggatag taatgaagga 2760
aagaatgaga tggagataca aatgaaatca aaaaagcttc caattacgcg aaagttttat 2820
gccttttatc atgcaccaat tgtaaaattc tggtttaaca cgttggcata tttaggattt 2880
ctgatgcttt atacatttgt ggttcttgta caaatggaac agttaccttc agttcaagaa 2940
tggattgtta ttgcttatat ttttacttat gccattgaga aagtccgtga gatctttatg 3000
tctgaagctg ggaaagtaaa ccagaagatt aaagtatggt ttagtgatta cttcaacatc 3060
agtgatacaa ttgccataat ttctttcttc attggatttg gactaagatt tggagcaaaa 3120
tggaactttg caaatgcata tgataatcat gtttttgtgg ctggaagatt aatttactgt 3180
cttaacataa tattttggta tgtgcgtttg ctagattttc tagctgtaaa tcaacaggca 3240
ggaccttatg taatgatgat tggaaaaatg gtggccaata tgttctacat tgtagtgatt 3300
atggctcttg tattacttag ttttggtgtt cccagaaagg caatacttta tcctcatgaa 3360
gcaccatctt ggactcttgc taaagatata gtttttcacc catactggat gatttttggt 3420
gaagtttatg catacgaaat tgatgtgtgt gcaaatgatt ctgttatccc tcaaatctgt 3480
ggtcctggga cgtggttgac tccatttctt caagcagtct acctctttgt acagtatatc 3540
attatggtta atcttcttat tgcatttttc aacaatgtgt atttacaagt gaaggcaatt 3600
tccaatattg tatggaagta ccagcgttat cattttatta tggcttatca tgagaaacca 3660
gttctgcctc ctccacttat cattcttagc catatagttt ctctgttttg ctgcatatgt 3720
aagagaagaa agaaagataa gacttccgat ggaccaaaac ttttcttaac agaagaagat 3780
caaaagaaac ttcatgattt tgaagagcag tgtgttgaaa tgtatttcaa tgaaaaagat 3840
gacaaatttc attctgggag tgaagagaga attcgtgtca cttttgaaag agtggaacag 3900
atgtgcattc agattaaaga agttggagat cgtgtcaact acataaaaag atcattacaa 3960
tcattagatt ctcaaattgg ccatttgcaa gatctttcag ccctgacggt agatacatta 4020
aaaacactca ctgcccagaa agcgtcggaa gctagcaaag ttcataatga aatcacacga 4080
gaactgagca tttccaaaca cttggctcaa aaccttattg atgatggtcc tgtaagacct 4140
tctgtatgga aaaagcatgg tgttgtaaat acacttagct cctctcttcc tcaaggtgat 4200
cttgaaagta ataatccttt tcattgtaat attttaatga aagatgacaa agatccccag 4260
tgtaatatat ttggtcaaga cttacctgca gtaccccaga gaaaagaatt taattttcca 4320
gaggctggtt cctcttctgg tgccttattc ccaagtgctg tttcccctcc agaactgcga 4380
cagagactac atggggtaga actcttaaaa atatttaata aaaatcaaaa attaggcagt 4440
tcatctacta gcataccaca tctgtcatcc ccaccaacca aatttttgt tagtacacca 4500
tctcagccaa gttgcaaaag ccacttggaa actggaacca aagatcaaga aactgtttgc 4560
tctaaagcta cagaaggaga taatacagaa tttggagcat ttgtaggaca cagagatagc 4620
atggatttac agaggtttaa agaaacatca aacaagataa aaatactatc caataacaat 4680
acttctgaaa acactttgaa acgagtgagt tctcttgctg gatttactga ctgtcacaga 4740
acttccattc ctgttcattc aaaacaagca gaaaaaatca gtagaaggcc atctaccgaa 4800
gacactcatg aagtagattc caaagcagct ttaataccgg attggttaca agatagacca 4860
tcaaacagag aaatgccatc tgaagaagga acattaaatg gtctcacttc tccatttaag 4920
ccagctatgg atacaaatta ctattattca gctgtggaaa gaaataactt gatgaggtta 4980
tcacagagca ttccatttac acctgtgcct ccaagagggg agcctgtcac agtgtatcgt 5040
ttggaagaga gttcacccaa catactaaat aacagcatgt cttcttggtc acaactaggc 5100
ctctgtgcca aaatagagtt tttaagcaaa gaggagatgg gaggaggttt acgaagagct 5160
gtcaaagtac agtgtacctg gtcagaacat gatatcctca aatcagggca tctttatatt 5220
atcaaatctt ttcttccaga ggtggttaat acatggtcaa gtatttacaa agaagataca 5280
gttctgcatc tctgtctgag agaaattcaa caacagagag cagcacaaaa gcttacgttt 5340
gcctttaatc aaatgaaacc caaatccata ccatattctc caaggttcct tgaagttttc 5400
ctgctgtatt gccattcagc aggacagtgg tttgctgtgg aagaatgtat gactggagaa 5460
tttagaaaat acaacaataa taatggagat gagattattc caactaatac tctggaagag 5520
atcatgctag cctttagcca ctggacttac gaatatacaa gaggggagtt actggtactt 5580
gatttgcaag gtgttggtga aaatttgact gacccatctg tgataaaagc agaagaaaag 5640
agatcctgtg atatggtttt tggcccagca aatctaggag aagatgcaat taaaaacttc 5700
agagcaaaac atcactgtaa ttcttgctgt agaaagctta aacttccaga tctgaagagg 5760
aatgattata cgcctgataa aattatattt cctcaggatg agccttcaga tttgaatctt 5820
cagcctggaa attccaccaa agaatcagaa tcaactaatt ctgttcgtct gatgttataa 5880
tattaatatt actgaatcat tggttttgcc tgcacctcac agaaatgtta ctgtgtcact 5940
tttccctcgg gaggaaattg tttggtaata tagaaaggtg tatgcaagtt gaatttgctg 6000
actccagcac agttaaaagg tcaatattct tttgacctga ttaatcagtc agaaagtccc 6060
tataggatag agctggcagc tgagaaattt taaaggtaat tgataattag tatttataac 6120
tttttaaagg gctctttgta tagcagagga tctcatttga ctttgttttg atgagggtga 6180
tgctctctct tatgtggtac aataccatta accaaaggta ggtgtccatg cagattttat 6240
tggcagctgt tttattgcca ttcaactagg gaaatgaaga aatcacgcag ccttttggtt 6300
aaatggcagt caaaatttc ctcagtgtat ttagtgtgtt cagtgatgat atcactggtt 6360
cccaactaga tgcttgttgg ccacgggaag ggaaatgact tgttctaatt ctaggttcac 6420
agaggtatga gaagcctgaa ctgaagacca ttttcaagag ggacggtatt tatgaatcag 6480
ggttaggctc catatttaaa gatagagcca gttttttttt ttaaatagaa cccaaattgt 6540
gtaaaaatgt taattgggtt ttttaaacat tgttttatca agtcactgtt aagtagaaga 6600
aagccatggt aaactgatac ataacctaaa ttataaaagc agaaacctaa ctcactcgtc 6660
aagggaagtt accttttgag gaaagttaaa gtactttttt ccctatctgt atctatagca 6720
acaacccaga acttacaaac ttctccaaag attttattga ttgttatatc aaatcagaat 6780
gtaaacatga actcttgcat atatttaaaa ttgtgttgga acatttgaac atgaatgctg 6840
tttgtggtac ttaagaaatt aattcagttg gattatcatt atgtgatact ggcagattgc 6900
agtgcaacct tatgccaata aaatgtaatt taacagcccc agatattgtt gaatattcaa 6960
caataacaag aaaagctttt catctaagtt ttatgcttta atttttttc tttttttttc 7020
tttttctttt gtttccttgg tactaatttt aatttttatt tggaagggag cagtataaag 7080

-continued cttatttgta tttagtagtg tatctcatag atacagacaa ggcaagagat gataagctgt 7140
ttaaatagtg tttaatattg attgggggtg gggagaaaga aaaagtgtat tacttaaaga 7200
tactatatac gttttgtata tcattaaatc tttaaaagaa atgaaataaa tttattgttt 7260
acagatgttt agtgagttta atcattctga aaaattatct gacattttca gggtgtcaat 7320
ttgagtatca gtttttttaa atgaaccatt tgtatacctg tgcttttgat ctcctgtcct 7380
gtacaatgtt taaattaata ctgatttctt actgtcttct tagaaatctg ttttttgtta 7440
ggccaaaaaa gggcaatatg ggctgtctgt tgatttttaa ttttatattg attattttca 7500
caggattata atagtagcta tacttttttt tttttttttt tttttgagac ggagtctcgc 7560
tctgttgctt gggctggagt gcagtggtgc gatctcagct caccacaacc gccgccttcc 7620
gggtttaagt gattctcctg cctcagcctc ccgagtagct gggactacag gcacacgcca 7680
ccatgcccag ctaattttta tatttttagt agagacaggg tttcactatg ttggccagtg 7740
tggtcacaaa ctcctgacct tgtgagccac cgcacctggc tgctaacact tatttagtgc 7800
ctactgtgta ccagacatta ctctaagtat ttcacatata ttaacctact taatccttat 7860
aacaatgtta taaagaaata ggtgttatta tcctgttttg cagatttgaa agtcaaggtg 7920
ctagagaggt aaagtaacgt ccataagatt cttacgttta tttaataata agtagcaacg 7980
gtaggatttg aacccaggct ggctgccttt catctatact gtttttgttt tgttttgttt 8040
tgttttgttt tgttttgttt gtcttggtgg ggcatggtgg ctcatgcctg taatcccagc 8100
acttcgggag gccaaggcag gtggatcact tgggctcagg agtttgagac cagcctgggc 8160
aacatggcaa aatcctatct ctgctaaaaa aaaaaataca aaaattaggc caggtgcagt 8220
ggctcatgcc tgtaatccca gcactttggg aggccaaggt gggcggatca caaggtcagg 8280
agttcgagac cagcctgacc aacatagtga aaccccgtct ctactaaaaa tacaaaaaat 8340
tagctgggca tggcggtgag tgcctgtaat cccagctact caggagtctg aggcaggaga 8400
attgcttgaa cctgggaggt ggaggttgca gtgagctgag atcgtgccat tgcgctccag 8460
cctgggcaac agtgcgagac tccgtcaaaa aaaaaaaaat aactggatgt gatggtgtgc 8520
acctgtagtt ccagctactt gggagactga ggtgggagga tcacttgagc ctgggagact 8580
gaggcagcag tgagctgaga tcatgccact gctttccaac ctgggcaaca gagtgagatc 8640
ctgtctcaga aagaaaaaaa aaaaaaagac aacctcttgc tctgttgccc aggctggagt 8700
gtagtagcgt gatcatagct cactgcagcc gtaaactcct gggctcaagc aatcctcctg 8760
ccactgcctc ttgattaggt ggaaccacag gcatgcacca ccacacgtac ctaattttat 8820
atatatattt ttttattttt catttttatt tatttttgtt tttttgagtt gaagtctcac 8880
tctgttgccc aggccggagt acagtggcac aatcttggct cactgcaacc tctgcctccc 8940
aagatcaagc aattctcgtg cttcagcctc caaagtagct gagattacag gtacccacca 9000
taatgcctgg ctgattttg tatttttcgt agagacaagg tttcaccttg ttggccaggc 9060
tgatctcaaa ctcctgacct caagtgatcc acctcccccg gctacccaaa gtactgggat 9120
tataggtgtg agccaccatg cctgggtaac acccaactaa ttttaaatat atattttgta 9180
gagatggggt ctagccttgt tgcccacgct ggtctcaaat tcctgggctc aagtgatcct 9240
ctcgcctgag cttcccaaag tggtagaatt gcaggcatga attgctgcac ccagcctcat 9300
ctgtgctgtg aattatgtgc tgtattgact ctcaagcatg atgaccattg gtggtttctg 9360
taccatttcc tgttacttta ctgaaacaca cctactccat taacttcttg ggttaagtct 9420
agaaagtaac agtttacttg taaaccacat ttcttatccc caataagtat ttttttaaga 9480
ttattaaagt tcattattac taccctatga tgtgaaagtg tcatttgctt aatcttttta 9540
attttttatt ctcaacctca tcttactgaa gagaataaaa ctcttttacc atattcttaa 9600
aatgtggaat tctcggccag gtgcagtggc tcacgcctgt aattccatca ctttgggagg 9660
ccaaggtggg tggatcatct gaggtcagga gttcaagacc agcctggcca acatggtgaa 9720
accccgtctc tactaaaaat acaaaaatta tctgggtgtg gtggcgcgtg cctgtaggcc 9780
cagctactca ggaggctgag gcaggagaat tgcttgaacc caagaggtgg aggttgcagt 9840
gagcctagat tgctgccact gcactccagc ctgggtgaca gcagaactct gtctcaaaaa 9900
aaagatgtgg aattcttttc tgcaaatgtt ctctaatagt ataccttctt cagtctgtcg 9960
atatatgtat gctattattt tacaagtaat acatgttgat tgtattggaa attatagaaa 10020
agattatatt ggattgttta gaaaatattt ttaaatgtga agaaaaatat aaaaattact 10080
cccttgttcc actttcccca ctctcaagtc agactatgtt gttttcatag ttagtagcta 10140
gcagtctacc ccactagatt atatgcttca cagagggaag ggaccctcaa gacttcactg 10200
gattgagtag cacccaatac cttgcttgct gcctggtttg tgatgggcat actgtaagaa 10260
aaaaaaatct gaatgacaaa atgtttttcc ataataccag acttcctctt gaagagatgg 10320
gtcgtaatgt tgtagtctta catgcttacg tagacaatca aagcaagaat actcaataaa 10380
tggctattta ccacttgaaa gaaa 10404

<210> SEQ ID NO 678
<211> LENGTH: 2361
<212> TYPE: DNA
<213> ORGANISM: Homo sapiens

<400> SEQUENCE: 678
aaggcggaag ggtggggagg gcggcgctcg gggcgggagg cccggccggg tccgctagga 60
cagcggggcc gctgggaagt tgtgagagcg gcgctcgggg gcgcgcttgc gtgcacgagg 120
gcccgggccg cgagcagccg cggccgtccc ggtcgccacc cttagcagcg gtcgcggtcg 180
gtgccgaagc ggtgttcccc gccttagccg ctggcgcctc ccaagagagc ggccggtggg 240
ccctcgtcct gtcagtggcg tcggaggccg gcgctgcggt ggccgcgccc ttctggtgct 300
cggacaccgc tgaggagccg gggccgggca cggctggctg acggctccgg gcagctaagg 360
ctgcccgagg agaaggcggc ggccgcggcg taggcgcacg tccggcgggc tcctggagcc 420
tggaggaggc cgaggggacc atgtccggga ggcgcttcca cctctccacc accgaccgcg 480
tcatcaaagc tgtcccctttt cctccaaccc aacggcttac tttcaaggaa gtatttgaga 540
atgggaaacc taaagttgat gttttaaaaa accatttggt aaaggaagga cgactggaag 600
aggaagtagc cttaaagata atcaatgatg ggctgccat cctgaggcaa gagaagacta 660
tgatagaagt agatgctcca atcacagtat gtggtgatat tcatggacaa ttctttgacc 720
taatgaagtt atttgaagtt ggaggatcac ctagtaacac acgctacctc tttctgggtg 780
actatgtgga cagaggctat ttcagtatag agtgtgtgct gtatttatgg agtttaaaga 840
ttaatcatcc caaaacattg tttctgcttc ggggaaatca tgaatgcagg catcttacag 900
actatttcac cttcaaacag gaatgtcgaa tcaaatattc ggaacaggtg tatgatgcct 960
gtatggagac atttgactgt cttcctcttg ctgccctctt aaaccagcag tttctctgtg 1020
tacatggagg aatgtcacct gaaattactt ctttagatga cattaggaaa ttagacaggt 1080
ttacggaacc tcccgccttt ggacctgtgt gtgacctgct ttggtctgat ccctcagagg 1140

-continued

```
attatggcaa tgagaagacc ttggagcact atacccacaa cactgtccga gggtgctctt   1200

atttctacag ttaccctgca gtttgtgaat ttttgcagaa caataattta ctatcaatta   1260

tcagagccca tgaagcccaa gatgctgggt atcgaatgta caggaagagc caagccacag   1320

gctttccatc acttattaca attttctctg cccccaatta cctagatgtc tataacaata   1380

aagctgctgt gttgaaatat gaaaacaatg tcatgaatat caggcagttt aactgttctc   1440

cacaccccta ctggcttcca aactttatgg atgttttcac atggtctttg ccttttgttg   1500

gggaaaaagt cacagagatg ctggtaaatg tgctcaacat atgctctgat gacgaactga   1560

tttctgatga tgaagcagaa gatcactaca ttccaagcta tcagaaagga agcactacag   1620

ttcgtaagga gatcatcagg aataagatca gagccattgg gaagatggca cgggtctttt   1680

caattcttcg gcaagaaagt gagagtgtgc tgactctcaa gggcctgact cccacaggca   1740

cactccctct gggcgtcctc tcaggaggca agcagactat cgagacagcc acagtagaag   1800

cggtagaggc ccgggaagcc atcagagggt tctcgcttca gcacaagatc cggagttttg   1860

aagaagcgcg aggtctggac cgaattaatg agcgaatgcc accccgaaag gatagcatac   1920

acgctggtgg gccaatgaaa tctgtaacct cagcacactc acatgctgcg cacaggagcg   1980

accaagggaa gaaagcccat tcatgactta gagtcctgcc gtggctcagg tggatctaaa   2040

actcaagaac aaattctatt tatttattat tggaaaatga aaagcaactc aaaacaactt   2100

caacgtggag gtgcatttat aattcagtct gcatttattc tgtaaaaagg tggctgtttt   2160

ataaattctt ttaatttatg ttcaatatat ataaaaagtg catctgtttt gtttttccct   2220

tttttctcca taattttaag aaatgaatct gattgttgtc aacacatttg tgaagtcttg   2280

tgctataaag gggaacttcc cctaataaaa gggccttgga aacctcaaac ctgggtttct   2340

gacttgaaaa aaaaaaaaaa a                                              2361
```

<210> SEQ ID NO 679
<211> LENGTH: 24
<212> TYPE: DNA
<213> ORGANISM: Homo sapiens

<400> SEQUENCE: 679

```
cacccacatc agtgcaatgt attt                                             24
```

<210> SEQ ID NO 680
<211> LENGTH: 8
<212> TYPE: PRT
<213> ORGANISM: Homo sapiens

<400> SEQUENCE: 680

```
His Pro His Gln Cys Asn Val Phe
1               5
```

<210> SEQ ID NO 681
<211> LENGTH: 24
<212> TYPE: DNA
<213> ORGANISM: Artificial Sequence
<220> FEATURE:
<223> OTHER INFORMATION: Mutant Ppp2r2d cDNA

<400> SEQUENCE: 681

```
catccccacc aatgtaacgt gttt                                             24
```